United States Patent
Facciotti et al.

(10) Patent No.: US 7,214,853 B2
(45) Date of Patent: May 8, 2007

(54) SCHIZOCHYTRIUM PKS GENES

(75) Inventors: Daniel Facciotti, Davis, CA (US);
James George Metz, Davis, CA (US);
Michael Lassner, Davis, CA (US)

(73) Assignee: Martek Biosciences Corporation, Columbia, MD (US)

( * ) Notice: Subject to any disclaimer, the term of this patent is extended or adjusted under 35 U.S.C. 154(b) by 268 days.

(21) Appl. No.: 10/331,061

(22) Filed: Dec. 27, 2002

(65) Prior Publication Data

US 2003/0101486 A1 May 29, 2003

Related U.S. Application Data

(63) Continuation of application No. 09/231,899, filed on Jan. 14, 1999, now Pat. No. 6,566,583, which is a continuation-in-part of application No. 09/090,793, filed on Jun. 4, 1998, now Pat. No. 6,140,486.

(60) Provisional application No. 60/048,650, filed on Jun. 4, 1997.

(51) Int. Cl.
*C12N 15/82* (2006.01)
*C12N 5/04* (2006.01)
*C12N 1/20* (2006.01)
*C07H 21/04* (2006.01)

(52) U.S. Cl. .................. 800/281; 435/419; 435/252.3; 536/23.2

(58) Field of Classification Search ................ 800/281, 800/298; 435/419, 468, 252.3; 536/23.1, 536/23.2
See application file for complete search history.

(56) References Cited

U.S. PATENT DOCUMENTS

| 5,246,841 A | 9/1993 | Yazawa et al. ............. 435/134 |
| 5,639,790 A | 6/1997 | Voelker et al. ............. 514/552 |
| 5,672,491 A | 9/1997 | Khosla et al. .............. 435/148 |
| 5,683,898 A | 11/1997 | Yazawa et al. ............. 435/136 |
| 6,503,706 B1 * | 1/2003 | Abken et al. ................. 435/6 |

FOREIGN PATENT DOCUMENTS

| WO | WO 93/23545 | 11/1993 |
| WO | WO/96/21735 | 7/1996 |
| WO | WO 98/55625 | 12/1998 |

OTHER PUBLICATIONS

Brenner, *TIG*, 15(4):132-133 (1999).
Bork, *TIG*, 12(10):425-427 (1996).
Broun et al., *Science*, 282:1315-1317 (1998).
DeLong & Yayanos, *Appl. Environ. Microbiol.*, 51(4):730-737 (1986).
Doerks, *TIG*, 14(6):248-250 (1998).
Facciotti et al., *Clon. and Charac. of PUFA Genes from Marine Bac.*, 14(1998).
Hopwood & Sherman, *Annu. Rev. Genet.*, 24:37-66 (1990).
Hutchinson, *Annu. Rev. Microbiol.*, 49:201-238 (1995).
Jostensen & Landfald, *High Prev. of PUFA Produc. Bac. in Arctic Invert.*, 95-101 (1997).
Katz & Donadio, *Annu. Rev. Microbiol.*, 47:875-912 (1993).
Kyle et al., *HortScience*, 25:1523-26 (1990).
Nakahara, *Yukagaku*, 44(10):821-7 (1995).
Nasu et al., *J. Ferment. Bioeng.*, 122:467-473 (1997).
Nogi et al., *Photobac. Profundum sp. nov., A New, mod. Barophilic Ba.*, 2:1-7 (1998).
Smith et al., *Nature Biotechnol.*, 15:1222-1223 (1997).
Somerville *Am. J. Clin. Nutr.*, 58(2 supp):270S-275S (1993).
Van de Loo, *Proc. Natl. Acad. Sci. USA*, 92:6743-6747 (1995).
Watanabe et al., *J. Biochem.*, 122:467-473 (1997).
Yazawa, *Lipids*, 31(supp):S297-S300 (1996).

* cited by examiner

*Primary Examiner*—Elizabeth F. McElwain
(74) *Attorney, Agent, or Firm*—Sheridan Ross P.C.

(57) ABSTRACT

The present invention relates to compositions and methods for preparing poly-unsaturated long chain fatty acids in plants, plant parts and plant cells, such as leaves, roots, fruits and seeds. Nucleic acid sequences and constructs encoding PKS-like genes required for the poly-unsaturated long chain fatty acid production, including the genes responsible for eicosapentenoic acid production of *Shewanella putrefaciens* and novel genes associated with the production of docosahexenoic acid in *Vibrio marinus* are used to generate transgenic plants, plant parts and cells which contain and express one or more transgenes encoding one or more of the PKS-like genes associated with such long chain polyunsaturated fatty acid production. Expression of the PKS-like genes in the plant system permits the large scale production of poly-unsaturated long chain fatty acids such as eicosapentenoic acid and docosahexenoic acid for modification of the fatty acid profile of plants, plant parts and tissues. Manipulation of the fatty acid profiles allows for the production of commercial quantities of novel plant oils and products.

33 Claims, 134 Drawing Sheets

Orf6    8.3 KB - 293 kD
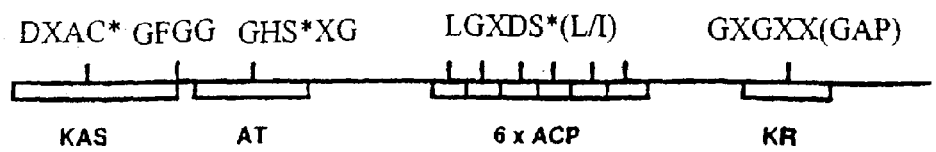
Acetate-like       FIG. 2A
Orf7    2.3 KB - 84 kD
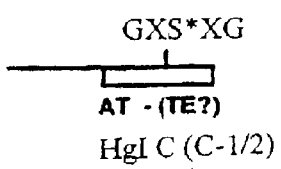
HgI C (C-1/2)
FIG. 2B
Orf3    0.8 KB - 30 kD
Het I- pantetheine transferase
FIG. 2E
Orf8    6.0 KB - 217 kD
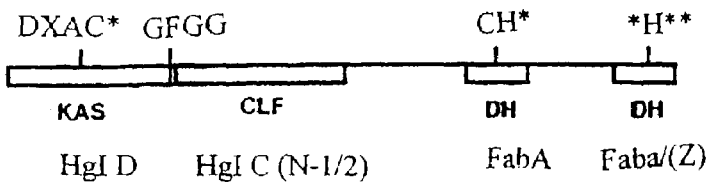
HgI D    HgI C (N-1/2)        FabA    Faba/(Z)
FIG. 2C
Orf9    1.6 KB - 59 kD
Anabeana - Orf552 homolog
FIG. 2D

| | | | | | |
|---|---|---|---|---|---|
|GATCTCTTAC|AAAGAAACTA|TCTCAATGTG|AATTTAACCT|TAATTCCGTT|TAATTACGGC 60|
|CTGATAGAGC|ATCACCCAAT|CAGCCATAAA|ACTGTAAAGT|GGGTACTCAA|AGTGGCTGG 120|
|GCGATTCTTC|TCAAATACAA|AGTGCCCAAC|CCAAGCAAAT|CCATATCCGA|TAACAGGTAA 180|
|AAGTAGCAAT|AAACCCCAGC|GCTGAGTTAG|TAATACATAA|GCGAATAATA|GGATCACTAA 240|
|ACTACTGCCG|AAATAGTGTA|ATATTCGACA|GTTTCTATGC|TGATGTTGAG|ATAAATAAAA 300|
|AGGGTAAAAT|TCAGCAAAAG|AACGATAGCG|CTTACTCATT|ACTCACACCT|CGGTAAAAAA 360|
|GCAACTCGCC|ATTAACTTGG|CCAATCGTCA|GTTGTTCTAT|CGTCTCAAAG|TTATGCCGAC 420|
|TAAATAACTC|TATATGTGCA|TTATGATTAG|CAAAAACTCC|GATACCATCA|AGATGAAGTT 480|
|GTTCATCACA|CCAACTCAAA|ACTCCGTCGA|TAAGCTTACT|GCCATAGCCC|TTGCCTTGCT 540|
|CCACATTGC|GATAGCAATA|AACTGTAAAA|TGCCACATTG|GCCACTGGT|AAGCTCTCTA 600|
|TAATCTGATT|TTCTTTGTTA|ATAAGTGCCT|GAGTTGAATA|CCAACCAGTA|CTTAACAACA 660|
|TCTTTAAACG|CCAATGCCAA|AAACGCGCTT|CACCTAAGGG|AACCTGCTGA|GTCACTATGC 720|
|AGGCTACGCC|TATCAATCTA|TCCCCAACGA|ACATACCAAT|AAGTGCTTGC|TCCTGTTGCC 780|
|AGAGCTCATT|GAGTTCTTCT|CGAATAGCCC|CGCGAAGCTT|TTGCTCATAC|TGCGCTTGAT 840|
|CACCACTAAA|AAGTGTTTCG|ATAAAAAAGG|GATCATCATG|ATAGGCGTTA|TAGAGAATAG 900|
|AGGCTGCTAT|GCGTAAATCT|TCTGCCGTGA|GATAAACTGC|ACGACACTCT|TCCATGGCTT 960|
|GATCTTCCAT|TGTTATTGTC|CTTGACCTTG|ATCACACAAC|ACCAATGTAA|CAAGACTGTA 1020|

FIG. 4A-1

| | | | | |
|---|---|---|---|---|
|TAGAAGTGCA|ATTAATAAATC|AATTCGTGCA|TTAAGCAGGT|CAGCATTTCT TTGCTAAACA 1080|
|AGCTTTATTG|GCTTTGACAA|AACTTTGCCT|AGACTTTAAC|GATAGAAATC ATAATGAAAG 1140|
|AGAAAAGCTA|CAACCTAGAG|GGGAATAATC|AAACAACTGC|TAAGATCTAG ATAATGTAAT 1200|
|AAACACCGAG|TTTATCGACC|ATACTTAGAT|AGAGTCATAG|CAACGAGAAT AGTTATGGAT 1260|
|ACAACGCCGC|AAGATCTATC|ACACCTGTTT|TTACAGCTAG|GATTAGCAAA TGATCAACCC 1320|
|GCAATTGAAC|AGTTTATCAA|TGACCATCAA|TTAGCGGACA|ATATATTGCT ACATCAAGCA 1380|
|AGCTTTTGGA|GCCCATCGCA|AAAGCACTTC|TTAATTGAGT|CATTTAATGA AGATGCCCAG 1440|
|TGGACCGAAG|TCATCGACCA|CTTAGACACC|TTATTAAGAA|AAAACTAACC ATTACAACAG 1500|
|CAACTTTAAA|TTTTGCCGTA|AGCCATCTCC|CCCCACCCCA|CAACAGCGTT GTTGCTTATG 1560|
|ACCACTGGAG|TACATTCGTC|TTTAGTCGTT|TTACCATCAC|CATGGGTACG TTGAGTGCGA 1620|
|TAAAAAGCA|CATAAACTTC|TTTATCGGCC|TGAATATAGG|CTTCGTTAAA ATCAGCTGTT 1680|
|CCCATTAAAG|TAACCACTTG|CTCTTTACTC|ATGCCTAGAG|ATATCTTTGT CAAATTGTCA 1740|
|CGGTTTTAT|CTTGAGTTTT|CTCCCAAGCA|CCGTGATTAT|CCCAGTCAGA TTCCCCATCA 1800|
|CCAACATTGA|CCACACAGCC|CGTTAGCCCT|AAGCTTGCAA|TCCCAAAACA TGCTAAACCT 1860|
|AATAATTTAT|TTTTCATTTT|AACTTCCTGT|TATGACATTA|TTTTTGCTTA GAAGAAAAGC 1920|
|AACTTACATG|CCAAAACACA|AGCTGTTGTT|TTAAATGACT|TTATTTATTA TTAGCCTTTT 1980|
|AGGATATGCC|TAGAGCAATA|ATAATTACCA|ATGTTTAAGG|AATTTGACTA ACTATGAGTC 2040|

FIG. 4A-2

```
CGATTGAGCA AGTGCTAACA GCTGCTAAAA AAATCAATGA ACAAGGTAGA GAACCAACAT 2100
TAGCATTGAT TAAAACCAAA CTTGGTAATA GCATCCCAAT GCGCGAGTTA ATCCAAGGTT 2160
TGCAACAGTT TAAGTCTATG AGTGCAGAAG AAAGACAAGC AATACCTAGC AGCTTAGCAA 2220
CAGCAAAAGA AACTCAATAT GGTCAATCAA GCTTATCTCA ATCTGAACAA GCTGATAGGA 2280
TCCTCCAGCT AGAAAACGCC CTCAATGAAT TAAGAAACGA ATTTAATGGG CTAAAAAGTC 2340
AATTTGATAA CTTACAACAA AACCTGATGA ATAAAGAGCC TGACACCAAA TGCATGTAAT 2400
TGAACTACGA TTTGAATGTT TTGATAACAC CACGATTACT GCAGCAGAAA AAGCCATTAA 2460
TGGTTTGCTT GAAGCTTATC GAGCCAATGG CCAGGTTCTA GGTCGTGAAT TTGCCGTTGC 2520
ATTTAACGAT GGTGAGTTTA AAGCACGCAT GTTAACCCCA GAAAAAAGCA GCTTATCTAA 2580
ACGCTTTAAT AGTCCTTGGG TAAATAGTGC ACTCGAAGAG CTAACCGAAG CCAAATTGCT 2640
TGCGCCACGT GAAAAGTATA TTGGCCAAGA TATTAATTCT GAAGCATTCT GCCAAGACAC 2700
ACCAAGTTGG CAGCTACTTT ACACAAGTTA TGTGCACATG AATTCCAGCA TAAGAAATGG 2760
CGACACCTTG CAGCCTATTC CACTGTATCA AATTCCAGCA ACTGCCAACG GCGATCATAA 2820
ACGAATGATC CGTTGGCAAA CAGAATGGCA AGCTTGTGAT GAATTGCAAA TGGCCGCAGC 2880
TACTAAAGCT GAATTTGCCG CACTTGAAGA GCTAACCAGT CATCAGAGTG ATCTATTTAG 2940
GCGTGGTTGG GACTTACGTG GCAGAGTCGA ATACTTGACG AAAATTCCGA CCTATTACTA 3000
TTTATACCGT GTTGGCGGTG AAAGCTTAGC AGTAGAAAAG CAGCGCTCTT GTCCTAAGTG 3060
```

FIG. 4A-3

```
TGGCAGTCAA GAATGGCTGC TCGATAAACC ATTATTGGAT ATGTTCCATT TTCGCTGTGA 3120
CACCTGCCGC ATCGTATCTA ATATCTCTTG GGACCATTTA TAACTCTTCC GAGTCTTATC 3180
ACACTAGAGT TTAGTCAGCA TAAAAATGGC GCTTATATTT CAATTAAAAG AAATATAAGC 3240
GCCATTTTCA TCGATACTAT ATATCAGCAG ACTATTTTCC GCGTAAATTA GCCCACATTA 3300
ATTTCATTCT TTGCCAGATC CCTGGATGAT CTAGTTGTGG CATCGACTCT TCAATAGGTT 3360
TAACCGCAGG TGTAACCCTT GGAGTCAATT CGTTTATAAA CTCGTTTAAA CTGTCACTTA 3420
ATTTAACGCT TTGTACTTCA CCTGGAATTT CAATCCATAC GCTGCCATCA CTATTATTAA 3480
CCGTCAACAT TTTATCTTCA TCATCAAGAA TACCAATAAA CCAAGTCGGC TCTTGCTTAA 3540
GCTTTCTCTT CATCATTAAA TGACCAATGA TGTTTTGTTG TAAGTATTCA AAATCAGTTT 3600
GATCCCACAC TTGGATTAGC TCACCTTGGC CCCATTGTGA GTCAAAAAAT AGCGGTGCAG 3660
AAAAATGACT GCCAAAAAAT GGATTAATTT CTGCAGATAA TGTCATTTCA AGTGCTGTTT 3720
CAACATTAGC AAATTCACCA GGTTGTTGAC ACACACTCAG GTACAACCGA ACTTTTGTCC ACTGCGCCAT 3780
CGGAGCCCGC TTCGGCGACA TAGGCTTGTT GATATTTAGA TTGCCATAA TATCTTGGCT 3840
GTTCACCAAG CTTATCCATG TAGGCTTGTT GATATTTAGA TAAAAAAGA TCTAAAGCAG 3900
GTAAAGAAGA CACTTAAGCC AGTTCCAAAA TCAGTTATAA TAGGGGTCTA TTTTGACATG 3960
GAAACCGTAT TGATGACACA ACATCATGAT CCCTACAGTA ACGCCCCGA ACTTTCTGAA 4020
TTAACTTTAG GAAAGTCGAC CGGTTATCAA GAGCAGTATG ATGCATCTTT ACTACAAGCG 4080
```

FIG. 4A-4

```
TGCCGCGTAA ATTAAACCGT GATGCTATCG GTCTAACCAA TGAGCTACCT TTTCATGGCT 4140
GTGATATTTG GACTGGCTAC GAACTGTCTT GGCTAAATGC TAAAGGCAAG CCAATGATTG 4200
CTATTGCAGA CTTTAACCTA AGTTTTGATA GTAAAAATCT GATCGAGTCT AAGTCGTTTA 4260
AGCTGTATTT AAACAGCTAT AACCAAACAC GATTTGATAG CGTTCAAGCG GTTCAAGAAC 4320
GTTTAACTGA AGACTTAAGC GCCTGTGCCC AAGGCACAGT TACGGTAAAA GTGATTGAAC 4380
CTAAGCAATT TAACCACCTG AGAGTGGTTG ATATGCCAGG TACCTGCATT GACGATTTAG 4440
ATATTGAAGT TGATGACTAT AGCTTTAACT CTGACTATCT CACCGACAGT GTTGATGACA 4500
AAGTCATGGT TGCTGAAACG CTAACGTCAA ACTTATTGAA ATCAAACTGC CTAATCACTT 4560
CTCAGCCTGA CTGGGGTACA GTGATGATCC GTTATCAAGG GCCTAAGATA GACCGTGAAA 4620
AGCTACTTAG ATATCTGATT TCATTTAGAC AGCACAATGA ATTTCATGAG CAGTGTGTTG 4680
AGCGTATATT TGTTGATTTA AAGCACTATT GCCAAATGTG CAAAACTTACT GTCTATGCAC 4740
GTTATACCCG CCGTGGGTGGT TTAGATATCA ACCCATATCG TAGCGACTTT GAAAACCCTG 4800
CAGAAAATCA GCGCCTAGCG AGACAGTAAT TGATTGCAGT ACCTACAAAA AACAATGCCT 4860
ATAAGCCAAG CTTATGGGCA TTTTTATATT ATCAACTTGT CATCAAACCT CAGCCGCCAA 4920
GCCTTTTAGT TTTATCGCTA AATTAAGCCG CTCTCTCAGC CAAATATTTG CAGGATTTTG 4980
CTGTAATTTA TGGCTCCACA CCATGAAATA CTCTATCGGC TCTACCGCAA AAGGTAAGTC 5040
AAATACCTGT AAGCCAAACA GCTTGGCATA TTCGTCAGTG TGGGCTTTTG ACGCGATAGC 5100
```

FIG. 4A-5

```
TAACGCATCA CTTTTTGAGG CAACCGACAT GATACTTAAT ATTGATGATT GCTCGCTGTG 5160
CATTGCCTT  GCCGGTAACA CCTGTTTAGT CAGCAAGTCG GCAACACTTA AATTGTAGCG 5220
GCGCATCTTA AAAATAATAT GCTTTTCATT AAAGTATTGC TCTTGCGTCA ACCCACCTTG 5280
GATCCTTGGG TGAGCATTTC GTGCCACACA AACTAATTTA TCCTGCATTA CTTTTTGACT 5340
CTTAAATGCC GCAGATTCTG GCAGCCAAAT ATCTAAGGCT AAATCCACCT TTTCTAGTTG 5400
TAGGTCCATC TGCAACTCTT CTTCAATGAG CGGCGGCTCA CGAAATACAA TATTAATTGC 5460
AGTGCCCTGT AACACTTGCT CAATTTGATC TTGCAAGAGT TGTATTGCCG ACTCGCTGGC 5520
ATACACATAA AAAGTTCGCT CACTTGAAGT GGGGTCAAAT GCTTCAAAGC TAGTCGCAAC 5580
TTGCTCAATT GTTGACATAG CGCCCGGAG CTGTTGATAA AGCGTCATCG CACTTGCGGT 5640
AGGTTAACT  CCCCTACCCA CTCGAGTAAA CAACTCTTCT CCAACAATAC TTTTTAGCCT 5700
CGAAATCGCA TTACTAACCG ACGACTGAGT CAAATCCAGC TCTTCTGCCG CCCGGCTAAA 5760
AGATGAGGTG CGATACACCG CAGTAAAAAC GCGAAATAAA TTAAGATCAA AAGCTTTTTG 5820
CTGCGACATA AATCAGCTAT CTCCTTATCC TTATCCTTAT CCTTATAAAA AGTTAGCTCC 5880
AGAGCACTCT AGCTCAAAAA CAACTCAGCG TATTAAGCCA ATATTTTGGG AACTCAATTA 5940
ATATTCATAA TAAAAGTATT CATAATATAA ATACCAAGTC ATAATTTAGC CCTAATTATT 6000
AATCAATTCA AGTTACCTAT ACTGGCCTCA ATTAAGCAAA TGTCTCATCA GTCTCCCTGC 6060
AACTAAATGC AATATTGAGA CATAAAGCTT TGAACTGATT CAATCTTACG AGGGTAACTT 6120
```

FIG. 4A-6

```
ATGAAACAGA CTCTAATGGC TATCTCAATC ATGTCGCTTT TTTCATTCAA TGGCTAGCA  6180
GCGCAACATG AACATGACCA CATCACTGTT GATTACGAAG GGAAAGCCGC AACAGAACAC  6240
ACCATAGCTC ACAACCAAGC TGTAGCTAAA ACACTTAACT TTGCCCGACAC GCGTGCATTT  6300
GAGCAATCGT CTAAAAATCT AGTCGCCAAG TTTGATAAAG CAACTGCCGA TATATTACGT  6360
GCCGAATTTG CTTTTATTAG CGATGAAATC CCTGACTCGG TTAACCCGTC TCTCTACCGT  6420
CAGGCTCAGC TTAATATGGT GCCTAATGGT CTGTATAAAG TGAGCGATGG CATTTACCAG  6480
GTCCGCGGTA CCGACTTATC TAACCTTACA CTTATCCGCA GTGATAACGG TTGGATAGCA  6540
TACGATGTTT TGTTAACCAA AGAAGCAGCA AAAGCCTCAC TACAATTTGC GTTAAAGAAT  6600
CTACCTAAAG ATGGCGATTT ACCCGTTGTT GCGATGATTT ACTCCCATAG CCATGCGGAC  6660
CACTTTGGCG GAGCTCGCGG TGTTCAAGAG ATGTTCCCTG ATGTCAAAGT CTACGGCTCA  6720
GATAACATCA CTAAAGAAAT TGTCGATGAG AACGTACTTG CCGGTAACGC CATGAGCCGC  6780
CGCGCAGCTT ATCAATACGG CGCAACACTG GGCAAACATG ATCACTTACG TGTTGATGCT  6840
GCGCTAGGTA AAGGTCTATC AAAAGGTGAA ATTGATGGTC TAGAGATGGT CTACACCTTA  6900
AACAGTGAAG GCAAATGGGA AACGCTGACG ATTGATGGTC TAGAGATGGT GTTTATGGAT  6960
GCCTCGGGCA CCGAAGCTGA GTCAGAAATG ATCACTTATA TTCCCTCTAA AAAAGCGCTC  7020
TGGACGGCGG AGCTTACCTA TCAAGGTATG CACAACATTT ATACGCTGCG CGGCGCTAAA  7080
GTACGTGATG CGCTCAAGTG GTCAAAAGAT ATCAACGAAA TGATCAATGC CTTTGGTCAA  7140
```

FIG. 4A-7

```
GATGTCGAAG TGCTGTTTGC CTCGCACTCT GCGCCAGTGT GGGGTAACCA AGCGATCAAC 7200
GATTTCTTAC GCCTACAGCG TGATAACTAC GGCCTAGTGC ACAATCAAAC CTTGAGACTT 7260
GCCAACGATG GTGTCGGTAT ACAAGATATT GGCGATGCGA TTCAAGACAC GATTCCAGAG 7320
TCTATCTACA AGACGTGGCA TACCACGGCA CTTATAGCCA TAACGCTAAA 7380
GCGGTTTATA ACAAGTATCT AGGCTACTTC GATATGAACC CAGCCAACCT TAATCCGCTG 7440
CCAACCAAGC AAGAATCTGC CAAGTTTGTC GAATACATGG GCGGCGCAGA TGCCGCAATT 7500
AAGCGCGCTA AAGATGATTA CGCTCAAGGT GAATACCGCT TTGTTGCAAC GGCATTAAAT 7560
AAGGTGGTGA TGGCCGAGCC AGAAAAATGAC TCCGCTCGTC AATTGCTAGC CGATACCTAT 7620
GAGCAACTTG GTTATCAAGC AGAAGGGGCT GGCTGGAGAA ACATTTACTT AACTGGCGCA 7680
CAAGAGCTAC GAGTAGGTAT TCAAGCTGGC GCGCCTAAAA CCGCATCGGC AGATGTCATC 7740
AGTGAAATGG ACATGCCGAC TCTATTTGAC TTCCTCGCGG TGAAGATTGA TAGTCAACAG 7800
GCGGCTAAGC ACGGCTTAGT TAAGATGAAT GTTATCACCC CTGATACTAA AGATATTCTC 7860
TATATTGAGC TAAGCAACGG TAACTTAAGC AACGCAGTGG TCGACAAAGA GCAAGCAGCT 7920
GACGCAAACC TTATGGTTAA TAAAGCTGAC GTTAACCGCA TCTTACTTGG CCAAGTAACC 7980
CTAAAGCGT TATTAGCCAG CGGCGATGCC AAGCTCACTG GTGATAAAAC GGCATTTAGT 8040
AAAATAGCCG ATAGCATGGT CGAGTTTACA CCTGACTTCG AAATCGTACC AACGCCTGTT 8100
AAATGAGGCA TTAATCTCAA CAAGTGCAAG CTAGACATAA AAATGGGGCG ATTAGACGCC 8160
```

FIG. 4A-8

| | | | | |
|---|---|---|---|---|
| CCATTTTTTA | TGCAATTTTG | AACTAGCTAG | TCTTAGCTGA | AGCTCGAACA | ACAGCTTTAA | 8220 |
| AATTCACTTC | TTCTGCTGCA | ATACTTATTT | GCTGACACTG | ACCAATACTC | AGTGCAAAAC | 8280 |
| GATAACTATC | ATCAAGATGG | CCCAGTAAAC | AATGCCAATT | ATCAGCAGCG | TTCATTTGCT | 8340 |
| GTTCTTTAGC | CTCAATCAAA | CCTAAAACCAG | ACTTTTGTGG | CTCAGCGTTA | GGCTTATTAG | 8400 |
| AACTCGACTC | TAGTAAAGCA | AGACCAATAT | CTTGTTTTAA | CAAAACCTGT | CGCTGATTAA | 8460 |
| GTTGATGCTC | AACCTTGTGA | TCCGCAATAG | CATCGGAAAT | ATCAACACAA | TGGCTCAAGC | 8520 |
| TTTTAGGTGC | ATTAACTCCA | AGAAAAGTTT | CGCTCAGTGC | AGAGAAGTCA | AACGCAAAAG | 8580 |
| ATTTAGCGA | TAATGCCAGC | CCAAGTCCTT | TCGCTTTAAT | GTAAGACTCC | TTGAGCGCCC | 8640 |
| ACAAATCAAA | AAAGCGGTCT | CGCTGCAAGG | CCTCTGGTAA | CGCTAACAAG | GCTCGCTTTT | 8700 |
| CTGATTCAGA | GAAATAATGA | CTAAGAATAG | AGTGGATATT | GGTGCTGTTA | CGGCAACGCT | 8760 |
| CAATGTCGAC | GCCAAACTCA | ATACTAGCAG | AGTCAGTTTC | CTCCTTGCTT | GCCTGACTGG | 8820 |
| CGCCTTTATT | ATCAGCAGTG | CAAATGCCTA | ATCTCCACTA | TGACTCACAT | 8880 |
| TAAAGTGGAC | CCCGGTTTGA | GCAAATTGCG | CATCACTCAA | TCTAGGCTTA | CCTTTGTCGC | 8940 |
| CATATTCAAA | GCGCCATTCA | TTGGGGCGTA | TTTCACTATG | TTGTGACAAT | AAAGCGCGCA | 9000 |
| AATAGCCTCT | TACCATTAAA | CCTTGAGTTT | TAGCTTCTTG | TTTAATGTAG | CGATTAACCT | 9060 |
| TAATTAACTC | ATCTTCAGGC | AGCCATGACT | TAACCAACTC | TGTAGTCTGG | TTATCGCACT | 9120 |
| CTTGTATTGT | TAACGGACAG | AAGTATAAGG | AAATCAATCG | AGAAGTTAGC | AATTTTTCAG | 9180 |

FIG. 4A-9

```
GACACTCTTT AAAGCAACAA ACATAACCCC TATTTTTACC AATTTAAGAT CAAAACTAAA 9240
GCCAAAACTA ATTGAGAATA GTGTCAAACT AGCTTTAAAG GAAAAAAATA TAAAAAGAAC 9300
ATTATACTTG TATAAATTAT TTTACACACC AAAGCCATGA TCTTCACAAA ATTAGCTCCC 9360
TCTCCCTAAA ACAAGATTGA ATAAAAAAAT AAACCTTAAC TTTCATATAG ATAAAACAAA 9420
CCAATGGGAT AAAGTATATT GAATTCATTT TTAAGGAAAA ATTCAAATTG AATTCAAGCT 9480
CTTCAGTAAA AGCATATTTT GCCGTTAGTG TGAAAAAAAA CAAATTTAAA AACCAACATA 9540
GAACAAATAA GCAGACAATA AAACCAAGGC GCAACACAAA CAACGCGCTT ACAATTTTCA 9600
CAAAAAAGCA ACAAGAGTAA CGTTTAGTAT TTGGATATGG TTATTGTAAT TGAGAATTTT 9660
ATAACAATTA TATTAAGGGA ATGAGTATGT TTTTAAATTC AAAACTTTCG CGCTCAGTCA 9720
AACTTGCCAT ATCCGCAGGC TTAACAGCCT CGCTAGCTAT GCCTGTTTTT GCAGAAGAAA 9780
CTGCTGCTGA AGAACAAATA GAAAGAGTCG CAGTGACCGG ATCGCGAATC GCTAAAGCAG 9840
AGCTAACTCA ACCAGCTCCA GTCGTCAGCC TTTCAGCCGA AGAACTGACA AAATTTGGTA 9900
ATCAAGATTT AGGTAGCGTA CTAGCAGAAT TACCTGCTAT TGGTGCAACC AACACTATTA 9960
TTGGTAATAA CAATAGCAAC TCAAGCGCAG GTGTTAGCTC AGCAGACTTG CGTCGTCTAG 10020
GTGCTAACAG AACCTTAGTA TTAGTCAACG GTAAGCGCTA CGTTGCCGGC CAACCGGGCT 10080
CAGCTGAGGT AGATTTGTCA ACTATACCAA CTAGCATGAT CTCGCGAGTT GAGATTGTAA 10140
CCGGCGGTGC TTCAGCAATT TATGGTTCGG ACGCTGTATC AGGTGTTATC AACGTTATCC 10200
```

FIG. 4A-10

```
TTAAAGAAGA CTTTGAAGGC TTTGAGTTTA ACGCACGTAC TAGCGGTTCT ACTGAAAGTG 10260
TAGGCACTCA AGAGCACTCT TTTGACATTT TGGGTGGTGC AAACGTTGCA GATGGACGTG 10320
GTAATGTAAC CTTCTACGCA GGTTATGAAC GTACAAAAGA AGTCATGGCT ACCGACATTC 10380
GCCAATTCGA TGCTTGGGGA ACAATTAAAA ACGAAGCCGA TGGTGGTGAA GATGATGGTA 10440
TTCCAGACAG ACTACGTGTA CCACGAGTTT ATTCTGAAAT GATTAATGCT ACCGGTGTTA 10500
TCAATGCATT TGGTGGTGGA ATTGGTCGCT CAACCTTTGA CAGTAACGGC AATCCTATTG 10560
CACAACAAGA ACGTGATGGG ACTAACAGCT TTGCATTTGG TTCATTCCCT AATGGCTGTG 10620
ACACATGTTT CAACACTGAA GCATACGAAA ACTATATTCC AGGGGTAGAA AGAATAAACG 10680
TTGGCTCATC ATTCAACTTT GATTTTACCG ATAACATTCA ATTTTACACT GACTTCAGAT 10740
ATGTAAAGTC AGATATTCAG CAACAATTTC AGCCTTCATT CCGTTTTTGT AACATTAATA 10800
TCAATGTTGA AGATAACGCC TTTTTGAATG ACGACTTGCG TCAGCAAATG CTCGATGCGG 10860
GTCAAACCAA TGCTAGTTTT GCCAAGTTTT TTGATGAATT AGGAAAATCGC TCAGCAGAAA 10920
ATAAACGCGA ACTTTTCCGT TACGTAGGTG GCTTTAAAGG TGGCTTTGAT ATTAGCGAAA 10980
CCATATTTGA TTACGACCTT TACTATGTTT ATGGCGAGAC TAATAACCGT CGTAAAACCC 11040
TTAATGACCT AATTCCTGAT AACTTTGTCG CAGCTGTCGA CTCTGTTATT GATCCTGATA 11100
CTGGCTTAGC AGCGTGTCGC TCACAAGTAG CAAGCGCTCA AGGCGATGAC TATACAGATC 11160
CCGCGTCTGT AAATGGTAGC GACTGTGTTG CTTATAACCC ATTTGGCATG GGTCAAGCTT 11220
```

FIG. 4A-11

| | | | | | |
|---|---|---|---|---|---|
| CAGCAGAAGC | CCGCGACTGG | GTTTCTGCTG | ATGTGACTCG | TGAAGACAAA | ATAACTCAAC | 11280
| AAGTGATTGG | TGGTACTCTC | GGTACCGATT | CTGAAGAACT | ATTTGAGCTT | CAAGGTGGTG | 11340
| CAATCGCTAT | GGTTGTTGGT | TTTGAATACC | GTGAAGAAAC | GTCTGGTTCA | ACAACCGATG | 11400
| AATTTACTAA | AGCAGGTTTC | TTGACAAGCG | CTGCAACGCC | AGATTCTTAT | GGCGAATACG | 11460
| ACGTGACTGA | GTATTTTGTT | GAGGTGAACA | TCCCAGTACT | AAAAGAATTA | CCTTTTGCAC | 11520
| ATGAGTTGAG | CTTTGACGGT | GCATACCGTA | ATGCTGATTA | CTCACATGCC | GGTAAGACTG | 11580
| AAGCATGGAA | AGCTGGTATG | TTCTACTCAC | CATTAGAGCA | ACTTGCATTA | CGTGGTACGG | 11640
| TAGGTGAAGC | AGTACGAGCA | CCAAACATTG | CAGAAGCCTT | TAGTCCACGC | TCTCCTGGTT | 11700
| TTGGCCGCGT | TTCAGATCCA | TGTGATGCAG | ATAACATTAA | TGACGATCCG | GATCGCGTGT | 11760
| CAAACTGTGC | AGCATTGGGG | ATCCCCTCCAG | GATTCCAAGC | ATCAACATCC | GTCAGTGTAG | 11820
| ATACCTTATC | TGGTGGTAAC | CCAGATCTAA | TTTGCTGACA | AACCTGAAAC | TTTACAGGTG | 11880
| GTCTTGTTTG | GACACCAACG | TTTGCTGACA | ATCTATCATT | CACTGTCGAT | TATTATGATA | 11940
| TTCAAATTGA | GGATGCTATT | TTGTCAGTAG | CCACCCAGAC | TGTGGCTGAT | AACTGTGTTG | 12000
| ACTCAACTGG | CGGACCTGAC | ACCGACTTCT | GTAGTCAAGT | TGATCGTAAT | CCAACGACCT | 12060
| ATGATATTGA | ACTTGTTCGC | TCTGGTTATC | TAAATGCCGC | GGCATTGAAT | ACCAAAGGTA | 12120
| TTGAATTTCA | AGCTGCATAC | TCATTAGATC | TAGAGTCTTT | CAACGCGCCT | GGTGAACTAC | 12180
| GCTTCAACCT | ATGGGGAAC | CAATTACTTG | AACTAGAACG | TCTTGAATTC | CAAAATCGTC | 12240

FIG. 4A-12

```
CTGATGAGAT TAATGATGAA AAAGGCGAAG TAGGTGATCC AGAGCTGCAG TTCCGCCTAG 12300
GCATCGATTA CCGTCTAGAT GATCTAAGTG TTAGCTGGAA CACGCGTTAT ATTGATAGCG 12360
TAGTAACTTA TGATGTCTCT GAAAATGGTG GCTCTCCCTGA AGATTTATAT CCAGGCCACA 12420
TAGGCTCAAT GACAACTCAT GACTTGAGCG CTACATACTA CATCAATGAG AACTTCATGA 12480
TTAACGGTGG TGTACGTAAC CTATTTGACG CACTTCCACC TGGATACACT AACGATGCGC 12540
TATATGATCT AGTTGGTCGC CGTGCATTCC TAGGTATTAA GGTAATGATG TAATTAATTA 12600
TTACGCCTCT AACTAATAAA AATGCAATCT CTTCGTAGAG ATTGCATTTT TTTATGAAAT 12660
CCAATCTTAA ACTGGTTCTC CGAGCATCTT ACGCCTTAAA AACCCCGCCC CTCAATGTAA 12720
CGCCAAAGTT AATTGCTTAC ACGCACTTAC ACAAACGAAC AATTTCATTA ACACGAGACA 12780
CAGCTCACGC TTTTTATTTT ACCCTTGATT TTACTACATA AAATTGCGTT TTAGCGCACA 12840
AGTGTTCTCC CAAGCTGGTC GTATCTGTAA TTATTCAGTC CCAGGTGATT GTATTGACCC 12900
ATAAGCTCAG GTAGTCTGCT CTGCCATTAG CTAAACAATA TTGACAAAAT GGCGATAAAA 12960
TGTGGCTTAG CGCTAAGTTC ACCGTAAGTT TTATCGGCAT TAAGTCCCAA CAGATTATTA 13020
ACGGAAACCC GCTAAACTGA TGGCAAAAAT AAATAGTGAA CACTTGGATG AAGCTACTAT 13080
TACTTCGAAT AAGTGTACGC AAACAGAGAC TGAGGCTCGG CATAGAAATG CCACTACAAC 13140
ACCTGAGATG CGCCGATTCA TACAAGAGTC GGATCTCAGT GTTAGCCAAC TGTCTAAAAT 13200
ATTAAATATC AGTGAAGCTA CCGTACGTAA GTGGCGCAAG CGTGACTCTG TCGAAAACTG 13260
```

FIG. 4A-13

```
TCCTAATACC  CCGCACCATC  TCAATACCAC  GCTAACCCCT  TTGCAAGAAT  ATGTGGTTGT  13320
GGGCCTGCGT  TATCAATTGA  AAATGCCATT  AGACAGATTG  CTCAAAGCAA  CCCAAGAGTT  13380
TATCAATCCA  AACGTGTCGC  GCTCAGGTTT  AGCAAGATGT  TTGAAGCGTT  ATGGCGTTTC  13440
ACGGGTGAGT  GATATCCAAA  GCCCACACGT  ACCAATGCGC  TACTTTAATC  AAATTCCAGT  13500
CACTCAAGGC  AGCGATGTGC  AAACCTACAC  CCTGCACTAT  GAAACGCTGG  CAAAAACCTT  13560
AGCCTTACCT  AGTACCGATG  GTGACAATGT  GGTGCAAGTG  GTGTCTCTCA  CCATTCCACC  13620
AAAGTTAACC  GAAGAAGCAC  CCAGTTTCAAT  TTTGCTCGGC  ATTGATCCTC  ATAGCGACTG  13680
GATCTATCTC  GACATATACC  AAGATGGCAA  TACACAAGCC  ACGAATAGAT  ATATGGCTTA  13740
TGTGCTAAAA  CACGGGCCAT  TCCATTTACG  AAAGTTACTC  GTGCGTAACT  ATCACACCTT  13800
TTTACAGCGC  TTTCCTGGAG  CGACGCAAAA  TCGCCGCCCC  TCTAAAGATA  TGCCTGAAAC  13860
AATCAACAAG  ACGCCTGAAA  CACAGGCACC  CAGTGGAGAC  TCATAATGAG  CCAGACCTCT  13920
AAACCTACAA  ACTCAGCAAC  TGAGCAAGCA  CAAGACTCAC  AAGCTGACTC  TCGTTTAAAT  13980
AAAGACTAA  AAGATATGCC  AATTGCTATT  GTTGGCATGG  CGAGTATTTT  TGCAAACTCT  14040
CGCTATTTGA  ATAAGTTTTG  GGACTTAATC  AGCGAAAAAA  TTGATGCGAT  TACTGAATTA  14100
CCATCAACTC  ACTGGCAGCC  TGAAGAATAT  TACGACGCAG  ATAAAACCGC  AGCAGACAAA  14160
AGCTACTGTA  AACGTGGTGG  CTTTTTGCCA  GATGTAGACT  TCAACCCAAT  GGAGTTTGGC  14220
CTGCCGCCAA  ACATTTGGA  ACTGACCGAT  TCATCGCAAC  TATTATCACT  CATCGTTGCT  14280
```

FIG. 4A-14

```
AAAGAAGTGT TGGCTGATGC TAACTTACCT GAGAATTACG ACCGCGATAA AATTGGTATC 14340
ACCTTAGGTG TCGGCGGTGG TCAAAAAATT AGCCACAGCC TAACAGGCGCG TCTGCAATAC 14400
CCAGTATTGA AGAAAGTATT CGCCAATAGC GGCATTAGTG ACACCGACAG CGAAATGCTT 14460
ATCAAGAAAT TCCAAGACCA ATATGTACAC TGGGAAGAAA ACTCGTTCCC AGGTTCACTT 14520
GGTAACGTTA TTGCGGGCCG TATCGCCAAC CGCTTCGATT TTGGCGGCAT GAACTGTGTG 14580
GTTGATGCTG CCTGTGCTGG ATCACTTGCT GCTATGCGTA TGGCGCTAAC AGAGCTAACT 14640
GAAGGTCGCT CTGAAATGAT GATCACCGGT GGTGTGTGTA CTGATAACTC ACCCTCTATG 14700
TATATGAGCT TTTCAAAAAC GCCCGCCTTT ACCACTAACG AAACCATTCA GCCATTTGAT 14760
ATCGACTCAA AAGGCATGAT GATTGGTGAA GGTATTGGCA TGGTGGCGCT AAAGCGTCTT 14820
GAAGATGCAG AGCGCGATGG CGACCGCATT TACTCTGTAA TTAAAGGTGT GGGTGCATCA 14880
TCTGACGGTA AGTTTAAATC AATCTATGCC CCTCGCCCAT CAGGCCAAGC TAAAGCACTT 14940
AACCGTGCCT ATGATGACGC AGGTTTTGCG CCGCATACCT TAGGTCTAAT TGAAGCTCAC 15000
GGAACAGGTA CTGCAGCAGG TGACGCGGCA GAGTTTGCCG GCCTTTGCTC AGTATTGCT 15060
GAAGGCAACG ATACCAAGCA ACACATTGCG CTAGGTTCAG TTAAATCACA AATTGGTCAT 15120
ACTAAATCAA CTGCAGGTAC AGCAGGTTTA ATTAAAGCTG CTCTTGCTTT GCATCACAAG 15180
GTACTGCCGC CGACCATTAA CGTTAGTCAG CCAAGCCCTA AACTTGATAT CGAAAAACTCA 15240
CCGTTTTATC TAAACACTGA GACTCGTCCA TGGTTACCAC GTGTTGATGG TACGCCGGCG 15300
```

FIG. 4A-15

```
CGCGCGGGTA TTAGCTCATT TGGTTTTGGT GGCACTAACT TCCATTTTGT ACTAGAAGAG 15360
TACAACCAAG AACACAGCCG TACTGATAGC GAAAAAGCTA AGTATCGTCA ACGCCAAGTG 15420
GCGCAAAGCT TCCTTGTTAG CGCAAGCGAT AAAGCATCGC TAATTAACGA GTTAAACGTA 15480
CTAGCAGCAT CTGCAAGCCA AGCTGAGTTT ATCCTCAAAG ATGCAGCAGC AAACTATGGC 15540
GTACGTGAGC TTGATAAAAA TGCACCACGG ATCGGTTTAG TTGCAAACAC AGCTGAAGAG 15600
TTAGCAGGCC TAATTAAGCA AGCACTTGCC AAACTAGCAG CTAGCGATGA TAACGCATGG 15660
CAGCTACCTG GTGGCACTAG CTACCGCGCC GCTGCAGTAG AAGGTAAAGT TGCCGCACTG 15720
TTTGCTGGCC AAGGTTCACA ATATCTCAAT ATGGGCCGTG ACCTTACTTG TTATTACCCA 15780
GAGATGCGTC AGCAATTTGT AACTGCAGAT AAAGTATTTG CCGCAAATGA TAAAACGCCG 15840
TTATCGCAAA CTCTGTATCC AAAGCCTGTA TTTAATAAAG ATGAATTAAA GGCTCAAGAA 15900
GCCATTTTGA CCAATACCGC CAATGCCCAA AGCGCAATTG GTGCGATTTC AATGGGTCAA 15960
TACGATTTGT TTACTGCGGC TGGCTTTAAT GCCGACATGG TTGCAGGCCA TAGCTTTGGT 16020
GAGCTAAGTG CACTGTGTGC TGCAGGTGTT ATTTCAGCTG ATGACTACTA CAAGCTGGCT 16080
TTTGCTCGTG GTGAGGCTAT GGCAACAAAA GCACCGGCTA AAGACGGCGT TGAAGCAGAT 16140
GCAGGAGCAA TGTTTGCAAT CATAACCAAG AGTGCTGCAG ACCTTGAAAC CGTTGAAGCC 16200
ACCATCGCTA AATTTGATGG GGTGAAAGTC GCTAACTATA ACGCGCCAAC GCAATCAGTA 16260
ATTGCAGGCC CAACAGCAAC TACCGCTGAT GCGGCTAAAG CGCTAACTGA GCTTGGTTAC 16320
```

FIG. 4A-16

```
AAAGCGATTA ACCTGCCAGT ATCAGGTGCA TTCCACACTG AACTTGTTGG TCACGCTCAA 16380
GCGCCATTTG CTAAAGCGAT TGACGCAGCC AAATTTACTA AAACAAGCCG AGCACTTTAC 16440
TCAAATGCAA CTGGCGGACT TTATGAAAGC ACTGCTGCAA AGATTAAAGC CTCGTTTAAG 16500
AAACATATGC TTCAATCAGT GCGCTTTACT AGCCAGCTAG AAGCCATGTA CAACGACGGC 16560
GCCCGTGTAT TTGTTGAATT TGGTCCAAAG AACATCTTAC AAAAATTAGT TCAAGGCACG 16620
CTTGTCAACA CTGAAAATGA AGTTTGCACT ATCTCTATCA ACCCTAATCC TAAAGTTGAT 16680
AGTGATCTGC AGCTTAAGCA AGCAGCAATG CAGCTAGCGG TTACTGGTGT GGTACTCAGT 16740
GAAATTGACC CATACCAAGC CGATATTGCC GCACCAGCGA AAAAGTCGCC AATGAGCATT 16800
TCGCTTAATG CTGCTAACCA TATCAGCAAA GCAACTCGCG CTAAGATGGC CAAGTCTTTA 16860
GAGACAGTA TCGTCACCTC GCAAATAGAA CATGTTATTG AAGAAAAAAT CGTTGAAGTT 16920
GAGAAACTGG TTGAAGTCGA AAAGATCGTC GAAAAAGTGG TTGAAGTAGA GAAAGTTGTT 16980
GAGGTTGAAG CTCCTGTTAA TTCAGTGCAA GCCAATGCAA TTCAAACCCG TTCAGTTGTC 17040
GCTCCAGTAA TAGAGAACCA AGTCGTGTCT AAAAACAGTA AGCCAGCAGT CCAGAGCATT 17100
AGTGGTGATG CACTCAGCAA CTTTTTTGCT GCACAGCAGC AAACCGCACA GTTGCATCAG 17160
CAGTTCTTAG CTATTCCGCA GCAATATGGT GAGACGTTCA CTACGCTGAT GACCGAGCAA 17220
GCTAAACTGG CAAGTTCTGG TGTTGCAATT CCAGAGAGTC TGCAACGCTC AATGGAGCAA 17280
TTCCACCAAC TACAAGCGCA AACACTACAA AGCCACACCC AGTTCCTTGA GATGCAAGCG 17340
```

FIG. 4A-17

```
GGTAGCAACA  TTGCAGCGTT  AAACCTACTC  AATAGCAGCC  AAGCAACTTA  CGCTCCAGCC  17400
ATTCACAATG  AAGCGATTCA  AAGCCAAGTG  GTTCAAAGCC  AAACTGCAGT  CCAGCCAGTA  17460
ATTTCAACAC  AAGTTAACCA  TGTGTCAGAG  CAGCCAACTC  AAGCTCCAGC  TCCAAAAGCG  17520
CAGCCAGCAC  CTGTGACAAC  TGCAGTTCAA  ACTGCTCCGG  CACAAGTTGT  TCGTCAAGCC  17580
GCACCAGTTC  AAGCCGCTAT  TGAACCGATT  AATACAAGTG  TTGCGACTAC  AACGCCTTCA  17640
GCCTTCAGCG  CCGAAACAGC  CCTGAGCGCA  ACAAAAGTCC  AAGCCACTAT  GCTTGAAGTG  17700
GTTGCTGAGA  AAACCGGTTA  CCCAACTGAA  ATGCTAGAGC  TTGAAATGGA  TATGGAAGCC  17760
GATTTAGGCA  TCGATTCTAT  CAAGCGTGTA  GAAATTCTTG  GCACAGTACA  AGATGAGCTA  17820
CCGGGTCTAC  CTGAGCTTAG  CCCTGAAGAT  CTAGCTGAGT  GTCGAACGCT  AGGCGAAATC  17880
GTTGACTATA  TGGGCAGTAA  ACTGCCGGCT  GAAGGCTCTA  TGAATTCTCA  GCTGTCTACA  17940
GGTTCCGCAG  CTGCGGACTCC  TGCAGCGAAT  GGTCTTTTCTG  CGGAGAAAGT  TCAAGCGACT  18000
ATGATGTCTG  TGGTTGCCGA  AAAGACTGGC  TACCCAACTG  AAATGCTAGA  GCTTGAAATG  18060
GATATGGAAG  CCGATTTAGG  CATAGATTCT  ATCAAGCGCG  TTGAAATTCT  TGGCACAGTA  18120
CAAGATGAGC  TACCTGAGCTT  AGCCCTGAAG  ATCTAGCTGA  GTGTCGTACT  18180
CTAGGCGAAA  TCGTTGACTA  TATGAACTCT  AAACTCGCTG  ACGGCTCTAA  GCTGCCGGCT  18240
GAAGGCTCTA  TGAATTCTCA  GCTGTCTACA  AGTGCCGCAG  CTGCGACTCC  TGCAGCGAAT  18300
GGTCTCTCTG  CGGAGAAAGT  TCAAGCGACT  ATGATGTCTG  TGGTTGCCGA  AAAGACTGGC  18360
```

FIG. 4A-18

```
TACCCAACTG AAATGCTAGA ACTTGAAATG GATATGGAAG CTGACCTTGG CATCGATTCA 18420
ATCAAGCGCG TTGAAATTCT TGGCACAGTA CAAGATGAGC TACCGGGTTT ACCTGAGCTA 18480
AATCCAGAAG ATTTGGCAGA GTGTCGTACT CTTGGCGAAA TCGTGACTTA TATGAACTCT 18540
AAACTCGCTG ACGGCTCTAA GCTGCCAGCT GAAGGCTCTA TGCACTATCA GCTGTCTACA 18600
AGTACCGCTG CTGCGACTCC TGTAGCGAAT GGTCTCTCTG CAGAAAAAGT TCAAGCGACC 18660
ATGATGTCTG TAGTTGCAGA TAAAACTGGC TACCCAACTG AAATGCTTGA ACTTGAAATG 18720
GATATGGAAG CCGATTTAGG TATCGATTCT ATCAAGCGCG TTGAAATTCT TGGCACAGTA 18780
CAAGATGAGC TACCGGGTTT ACCTGAGCTA AATCCAGAAG ATCTAGCAGA GTGTCGCACC 18840
CTAGGCGAAA TCGTTGACTA TATGGCAGT AAACTGCCGG CTGAAGGCTC TGCTAATACA 18900
AGTGCCGCTG CGTCTCTTAA TGTTAGTGCC GTTGCGGGCG CTCAAGCTGC TGCGACTCCT 18960
GTATCGAACG GTCTCTCTGC AGAGAAAGTG CAAAGCACTA TGATGTCAGT AGTTGCAGAA 19020
AAGACCGGCT ACCCAACTGA AATGCTAGAA CTTGGCATGG ATATGGAAGC CGATTTAGGT 19080
ATCGACTCAA TTAAACGCGT TGAGATTCTT GGCACAGTAC AAGATGAGCT ACCGGGTCTA 19140
CCAGAGCTTA ATCCTGAAGA TTTAGCTGAG TGCCGTACGC TGGGCGAAAT CGTTGACTAT 19200
ATGAACTCTA AGCTGGCTGA CGGCTCTAAG CTTCCAGCTG AAGGCTCTGC TAATACAAGT 19260
GCCACTGCTG CGACTCCCTGC AGTGAATGGT CTTTCTGCTG ACAAGGTACA GGCGACTATG 19320
ATGTCTGTAG TTGCTGAAAA GACCGGGCTAC CCAACTGAAA TGCTAGAACT TGGCATGGAT 19380
```

FIG. 4A-19

```
ATGGAAGCAG ACCTTGGTAT TGATTCTATT AAGCGGGTTG AAATTCTTGG CACAGTACAA  19440
GATGAGCTCC CAGGTTTACC TGAGCTTAAT CCTGAAGATC TCGCTGAGTG CCGCACGCTT  19500
GGCGAAATCG TTAGCTATAT GAACTCTCAA CTGGCTGATG GCTCTAAACT TTCTACAAGT  19560
GCGGCTGAAG GCTCTGCTGA TACAAGTGCT GCAAATGCTG CAAAGCCGGC AGCAATTTCG  19620
GCAGAACCAA GTGTTGAGCT TCCTCCTCAT AGCGAGGTAG CGCTAAAAAA GCTTAATGCG  19680
GCGAACAAGC TAGAAAATTG TTTCGCCGCA GACGCAAGTG TTGTGATTAA CGATGATGGT  19740
CACAACGCAG GCGTTTTAGC TGAGAAACTT ATTAAACAAG GCCTAAAAGT AGCCGTTGTG  19800
CGTTTACCGA AAGGTCAGCC TCAATCGCCA CTTTCAAGCG ATGTTGCTAG CTTTGAGCTT  19860
GCCTCAAGCC AAGAATCTGA GCTTGAAGCC AGTATCACTG CAGTTATCGC GCAGATTGAA  19920
ACTCAGGTTG GCGCTATTGG TGGCTTTATT CACTGCAAC CAGAAGCGAA TACAGAAGAG  19980
CAAACGGCAG TAAACCTAGA TGCGCAAAGT TTTACTCACG TTAGCAATGC GTTCTTGTGG  20040
GCCAAATTAT TGCAACCAAA GCTCGTTGCT GGAGCAGATG CGCGTCGCTG TTTTGTAACA  20100
GTAAGCCGTA TCGACGGGTGG CTTTGGTTAC CTAAATACTG ACGCCCTAAA AGATGCTGAG  20160
CTAAACCAAG CAGCATTAGC TGGTTTAACT AAAACCTTAA GCCATGAATG GCCACAAGTG  20220
TTCTGTGCG CGCTAGATAT TGCAACAGAT GTTGATGCAA CCCATCTTGC TGATGCAATC  20280
ACCAGTGAAC TATTTGATAG CCAAGCTCAG CTACCTGAAG TGGGCTTAAG CTTAATTGAT  20340
GGCAAAGTTA ACCGCGTAAC TCTAGTTGCT GCTGAAGCTG CAGATAAAAAC AGCAAAAGCA  20400
```

FIG. 4A-20

```
GAGCTTAACA GCACAGATAA AATCTTAGTG ACTGGTGGGG CAAAAGGGGT GACATTTGAA 20460
TGTGCACTGG CATTAGCATC TCGCAGCCAG TCTCACTTTA TCTTAGCTGG GCGCAGTGAA 20520
TTACAAGCTT TACCAAGCTG GGCTGAGGGT AAGCAAACTA GCGAGCTAAA ATCAGCTGCA 20580
ATCGCACATA TTATTCTAC  TGGTCAAAAG CCAACGCCTA AGCAAGTTGA AGCCGCTGTG 20640
TGGCCAGTGC AAAGCAGCAT TGAAATTAAT GCCGCCCTAG CCGCCTTTAA CAAAGTTGGC 20700
GCCTCAGCTG AATACGTCAG ACCGATAGCG CCGCAATCAC AGCAGCACTT 20760
AATGGTCGCT CAAATGAGAT CACCGGTCTT ATTCATGGCG CAGGTGTACT AGCCGACAAG 20820
CATATTCAAG ACAAGACTCT TGCTGAACTT GCTAAAGTTT ATGGCACTAA AGTCAACGGC 20880
CTAAAAGCGC TGCTCGCGGC ACTTGAGCCA AGCAAAATTA AATTACTTGC TATGTTCTCA 20940
TCTGCAGCAG GTTTTTACGG TAATATCGGC CAAAGCGATT ACGCGATGTC GAACGATATT 21000
CTTAACAAGG CAGGCGCTGCA GTTCACCGCT CGCAACCCAC AAGCTAAAGT CATGAGCTTT 21060
AACTGGGGTC CTTGGGATGG CGGCATGGTT AACCCAGCGC TTAAAAAGAT GTTTACCGAG 21120
CGTGGTGTGT ACGTTATTCC ACTAAAAGCA GGTGCAGAGC TATTTGCCAC TCAGCTATTG 21180
GCTGAAACTG GCGTGCAGTT GCTCATTGGT ACGTCAATGC AAGGTGGCAG CGACACTAAA 21240
GCAACTGAGA CTGCTTCTGT AAAAAAGCTT AATGCGGGTG AGGTGCTAAG TGCATCGCAT 21300
CCGCGTGCTG GTGCACAAAA AACACCACTA CAAGCTGTCA CTGCAACGCG TCTGTTAACC 21360
CCAAGTGCCA TGGTCTTCAT TGAAGATCAC CGCATTGGCG GTAACAGTGT GTTGCCAACG 21420
```

FIG. 4A-21

```
GTATGCGCCA TCGACTGGAT GCGTGAAGCG GCAAGCGACA TGCTTGGCGC TCAAGTTAAG 21480
GTACTTGATT ACAAGCTATT AAAAGGCATT GTATTGAGA  CTGATGAGCC GCAAGAGTTA 21540
ACACTTGAGC TAACGCCAGA CGATTCAGAC GAAGCTACGC TACAAGCATT AATCAGCTGT 21600
AATGGGCGTC CGCAATACAA GGCGACGCTT ATCAGTGATA ATGCCGATAT TAAGCAACTT 21660
AACAAGCAGT TTGATTTAAG CGCTAAGGCG ATTACCACAG CAAAAGAGCT TTATAGCAAC 21720
GGCACCTTGT TCCACGGTCC GCGTCTACAA GGGATCCAAT CTGTAGTGCA GTTCGATGAT 21780
CAAGGCTTAA TTGCTAAAGT CGCTCTGCCT AAGGTTGAAC TTAGCGATTG TGGTGAGTTC 21840
TTGCCCGCAAA CCCACATGGG TGGCAGTCAA CCTTTTGCTG AGGACTTGCT ATTACAAGCT 21900
ATGCTGGTTT GGGCTCGCCT TAAAAACTGGC TGCCATCAAG CATTGGTGAG 21960
TTTACCTCAT ACCAACCAAT GGCCTTTGGT GAAACTGGTA CCATAGAGCT TGAAGTGATT 22020
AAGCACAACA AACGCTCACT TGAAGCGAAT GTTGCGCTAT ATCGTGACAA CGGCGAGTTA 22080
AGTGCCATGT TTAAGTCAGC TAAAATCACC ATTAGCAAAA GCTTAAATTC AGCATTTTTA 22140
CCTGCTGTCT TAGCAAACGA CAGTGAGGCG AATTAGTGGA ACAAACGCCT AAAGCTAGTG 22200
CGATGCCGCT GCGCATCGCA CTTATCTTAC TGCCAACACC GCAGTTTGAA GTTAACTCTG 22260
TCGACCAGTC AGTATTAGCC AGCTATCAAA CACTGCAGCC TGAGCTAAAT GCCCTGCTTA 22320
ATAGTGCGCC GACACCTGAA ATGCTCAGCA TCACTATCTC AGATGATAGC GATGCAAACA 22380
GCTTTGAGTC GCAGCTAAAT GCTGCCGACCA AGGCAATTAA CAATGGCTAT ATCGTCAAGC 22440
```

FIG. 4A-22

```
TTGCTACGGC AACTCACGCT TTGTTAATGC TGCCTGCATT AAAAGCGGCG CAAATGCGGA 22500
TCCATCCTCA TGCGCAGCTT GCCGCTATGC AGCAAGCTAA ATCGACGCCA ATGAGTCAAG 22560
TATCTGGTGA GCTAAAGCTT GGCGCTAATG CGCTAAGCCT AGCTCAGACT AATGCGCTGT 22620
CTCATGCTTT AAGCCAAGCC AAGCGTAACT TAACTGATGT CAGCGTGAAT GAGTGTTTTG 22680
AGAACCTCAA AAGTGAACAG CAGTTCACAG AGGTTTATTC GCTTATTCAG CAACTTGCTA 22740
GCCGCACCCA TGTGAGAAAA GAGGTTAATC AAGGTGTGGA ACTTGGCCCT AAACAAGCCA 22800
AAAGCCACTA TTGGTTTAGC GAATTTCACC AAAACCGTGT TGCTGCCATC AACTTTATTA 22860
ATGGCCAACA AGCAACCAGC TATGTGCTTA CTCAAGGTTC AGGATTGTTA GCTGCGAAAT 22920
CAATGCTAAA CCAGCAAAGA TTAAATGTTTA TCTTGCCGGG TAACAGTCAG CAACAAATAA 22980
CCGCATCAAT AACTCAGTTA ATGCAGCAAT TAGAGCGTTT GCAGGTAACT GAGGTTAATG 23040
AGCTTTCTCT AGAATGCCAA CTAGAGCTGC TCAGCATAAT GTATGACAAC TTAGTCAACG 23100
CAGACAAACT CACTACTCGC GATAGTAAGC CCGCTTATCA GGCTGTGATT CAAGCAAGCT 23160
CTGTTAGCGC TGCAAAGCAA GAGTTAAGCG CGCTTAACGA TGCACTCACA GCGCTGTTTG 23220
CTGAGCAAAC AAACGCCACA TCAACGAATA AAGGCTTAAT CCAATACAAA ACACCGGGCGG 23280
GCAGTTACTT AACCCTAACA CCGCTTGGCA GCAACAATGA CAACGCCCAA GCGGGTCTTG 23340
CTTTTGTCTA TCCGGGTGTG GGAACGGTTT ACGCCGATAT GCTTAATGAG CTGCATCAGT 23400
ACTTCCCTGC GCTTTACGCC AAACTTGAGC GTGAAGGCGA TTTAAAGGCG ATGCTACAAG 23460
```

FIG. 4A-23

```
CAGAAGATAT CTATCATCTT GACCCTAAAC ATGCTGCCCA AATGAGCTTA GGTGACTTAG 23520
CCATTGCTGG CGTGGGGAGC AGCTACCTGT TAACTCAGCT GCTCACCGAT GAGTTTAATA 23580
TTAAGCCTAA TTTTGCATTA GGTTACTCAA TGGGTGAAGC ATCAATGTGG GCAAGCTTAG 23640
GCGTATGGCA AAACCCGCAT GCGCTGATCA GCAAAACCCA AACCGACCCG CTATTTACTT 23700
CTGCTATTTC CGGCAAATTG ACCGCGGTTA GACAAGCTTG GCAGCTTGAT GATACCGCAG 23760
CGGAAATCCA GTGGAATAGC TTTGTGGTTA GAAGTGAAGC AGCGCCGATT GAAGCCTTGC 23820
TAAAAGATTA CCCACACGCT TACCTCGCGA TTATTCAAGG GGATACCTGC GTAATCGCTG 23880
GCTGTGAAAT CCAATGTAAA GCGCTACTTG CAGCACTGGG TAAACGCGGT ATTGCAGCTA 23940
ATCGTGTAAC GGCGATGCAT ACGCAGCCTG CGATGCAAGA GCATCAAAAT GTGATGGATT 24000
TTTATCTGCA ACCGTTAAAA GCAGAGCTTC CTAGTGAAAT AAGCTTTATC AGCGCCGCTG 24060
ATTTAACTGC CAAGCAAACG GTGAGTGAGC AAGCACTTAG CAGCCAAGTC GTTGCTCAGT 24120
CTATTGCCGA CACCTTCTGC CAAACCTTGG ACTTTACCGC GCTAGTACAT CACGCCCAAC 24180
ATCAAGGCGC TAAGCTGTTT GTTGAAATTG GCGCGGATAG ACAAAACTGC ACCTTGATAG 24240
ACAAGATTGT TAAACAAGAT GGTGCCAGCA GTGTACAACA TCAACCTTGT TGCACAGTGC 24300
CTATGAACGC AAAAGGTAGC CAAGATATTA CCAGCGTGAT TAAAGCGCTT GGCCAATTAA 24360
TTAGCCATCA GGTGCCATTA TCGGTGCAAC CATTTATTGA TGGACTCAAG CGCGAGCTAA 24420
CACTTTGCCA ATTGACCAGC CAACAGCTGG CAGCACATGC AAATGTTGAC AGCAAGTTTG 24480
```

FIG. 4A-24

```
AGTCTAACCA AGACCATTTA CTTCAAGGGG AAGTCTAATG TCATTACCAG ACAATGCTTC 24540
TAACCACCTT TCTGCCAACC AGAAAGGCGC ATCTCAGGCA AGTAAAACCA GTAAGCAAAG 24600
CAAAATCGCC ATTGTCGGTT TAGCCACTCT GTATCCAGAC GCTAAAACCC CGCAAGAATT 24660
TTGGCAGAAT TTGCTGGATA AACGCGACTC TCGCAGCACC TTAACTAACG AAAAACTCGG 24720
CGCTAACAGC CAAGATTATC AAGGTGTGCA AGGCCAATCT GACCGTTTTT ATTGTAATAA 24780
AGGCGGCTAC ATTGAGAACT TCAGCTTTAA TGCTGCAGGC TACAAATTGC CGGAGCAAAG 24840
CTTAAATGGC TTGGACGACA GCTTCCTTTG GGCGCTCGAT ACTAGCCGTA ACGCACTAAT 24900
TGATGCTGGT ATTGATATCA ACGGCGCTGA TTTAAGCCGC GCAGGTGTAG TCATGGGCGC 24960
GCTGTCGTTC CCAACTACCC GCTCAAACGA TCTGTTTTTG CCAATTTATC ACAGCGCCGT 25020
TGAAAAAGCC CTGCAAGATA AACTAGGCGT AAAGGCATTT AAGCTAAGCC CAACTAATGC 25080
TCATACCGCT CGCGCGGCAA ATGAGAGCAG CCTAAATGCA GCCAATGGTG CCATTGCCCA 25140
TAACAGCTCA AAAGTGGTGG CCGATGCACT TGGCCTTGGC GGCGCACAAC TAAGCCTAGA 25200
TGCTGCCTGT GCTAGTTCGG TTTACTCATT AAAGCTTGCC TGCGATTACC TAAGCACTGG 25260
CAAAGCCGAT ATCATGCTAG CAGGCGCAGT ATCTGGCGCG GATCCTTTCT TTATTAATAT 25320
GGGATTCTCA ATCTTCCACG CCTACCCAGA CCATGGTATC TCAGTACCGT TTGATGCCAG 25380
CAGTAAAGGT TTGTTTGCTG GCGAAGGCGC TGGCGTATTA GTGCTTAAAC GTCTTGAAGA 25440
TGCCGAGCGC GACAATGACA AAATCTATGC GGTTGTTAGC GGCGTAGGTC TATCAAACGA 25500
```

FIG. 4A-25

```
CGGTAAAGGC CAGTTTGTAT TAAGCCCTAA TCCAAAAGGT CAGGTGAAGG CCTTTGAACG 25560
TGCTTATGCT GCCAGTGACA TTGAGCCAAA AGACATTGAA GTGATTGAGT GCCACGCAAC 25620
AGGCACACCG CTTGGCGATA AAATTGAGCT CACTTCAATG GAAACCTTCT TTGAAGACAA 25680
GCTGCAAGGC ACCGATGCAC CGTTAATTGG CTCAGCTAAG TCTAACTTAG GCCACCTATT 25740
AACTGCAGCG CATGCGGGGA TCATGAAGAT GATCTTCGCC ATGAAAGAAG GTTACCTGCC 25800
GCCAAGTATC AATATTAGTG ATGCTATCGC TTCGCCCGAAA AAACTCTTCG GTAAACCAAC 25860
CCTGCCTAGC ATGGTTCAAG GCTGGCCAGA TAAGCCATCG AATAATCATT TTGGTGTAAG 25920
AACCCGTCAC GCAGGCGTAT CGGTATTTGG CTTTGGTGGC TGTAACGCCC ATCTGTTGCT 25980
TGAGTCATAC AACGGCAAAG GAACAGTAAA GGCAGAAGCC ACTCAAGTAC CGCGTCAAGC 26040
TGAGCCGCTA AAAGTGGTTG GCCTTGCCTC GCACTTTGGG CCTCTTAGCA GCATTAATGC 26100
ACTCAACAAT GCTGTGACCC AAGATGGGAA TGGCTTTATC GAACTGCCGA AAAAGCGCTG 26160
GAAAGGCCTT GAAAAGCACA GTGAACTGTT AGCTGAATTT GGCTTAGCAT CTGCGCCAAA 26220
AGGTGCTTAT GTTGATAACT TCGAGCTGGA CTTTTTACGC TTTAAACTGC CGCCAAACGA 26280
AGATGACCGT TTGATCTCAC AGCAGCTAAT GCTAATGCGA AGCTGTATTA GTAACAGACG AAGCCATTCG 26340
TGATGCCAAG CTTGAGCCGG GGCAAAAAGT AGCTGTATTA GTGGCAATGG AAACTGAGCT 26400
TGAACTGCAT CAGTTCCGCG GCCGGGTTAA CTTGCATACT CAATTAGCGC AAAGTCTTGC 26460
CGCCATGGGC GTGAGTTTAT CAACGGATGA ATACCAGCCG CTTGAAGCCA TCGCCATGGA 26520
```

FIG. 4A-26

```
CAGCGTGCTT GATGCTGCCA AGCTCAATCA GTACACCAGC TTTATTGGTA ATATTATGGC  26580
GTCACGCGTG GCGTCACTAT GGGACTTTAA TGGCCCAGCC TTCACTATTT CAGCAGCAGA  26640
GCAATCTGTG AGCCGCTGTA TCGATGTGGC GCAAAACCTC ATCATGGAGG ATAACCTAGA  26700
TGCGGTGGTG ATTGCAGCGG TCGATCTCTC TGGTAGCTTT GAGCAAGTCA TTCTTAAAAA  26760
TGCCATTGCA CCTGTAGCCA TTGAGCCAAA CCTCGAAGCA AGCCTTAATC CAACATCAGC  26820
AAGCTGGAAT GTCGGTGAAG GTGCTGGCGC GGTCGTGCTT GTTAAAAATG AAGCTACATC  26880
GGGCTGCTCA TACGGCCAAA TTGATGCACT TGGCTTTGCT AAAACTGCCG AAACAGCGTT  26940
GGCTACCGAC AAGCTACTGA GCCAAACTGC CACAGACTTT AATAAGGTTA AAGTGATTGA  27000
AACTATGGCA GCGCCTGCTA GCCAAATTCA ATAGCGCCA  ATAGTTAGCT CTCAAGTGAC  27060
TCACACTGCT GCAGAGCAGC GTGTTGGTCA CTGCTTTGCT GCAGCGGGTA TGGCAAGCCT  27120
ATTACACGGC TTACTTAACT TAAATACTGT AGCCCAAACC AATAAAGCCA ATTGCGCGCT  27180
TATCAACAAT ATCAGTGAAA ACCAATTATC ACAGCTGTTG ATTAGCCAAA CAGGAGCGA  27240
ACAACAAGCA TTAACCGCGC GTTTAAGCAA TGAGCTTAAA TCCGATGCTA AACACCAACT  27300
GGTTAAGCAA GTCACCTTAG GTGGCCGTGA TATCTACCAG CATATTGTTG ATACACCGCT  27360
TGCAAGCCTT GAAAGCATTA CTCAGAAATT GGCGCAAGCG ACAGCATCGA CAGTGGTCAA  27420
CCAAGTTAAA CCTATTAAGG CCGCTGGCTC AGTCGAAATG GCTAACTCAT TCGAAACGGA  27480
AAGCTCAGCA GAGCCACAAA TAACAATTGC AGCACAACAG ACTGCAAACA TTGGCGTCAC  27540
```

FIG. 4A-27

```
CGCTCAGGCA ACCAAACGTG AATTAGGTAC CCCACCAATG ACAACAAATA CCATTGCTAA 27600
TACAGCAAAT AATTTAGACA AGACTCTTGA GACTGTTGCT GGCAATACTG TTGCTAGCAA 27660
GGTTGGCTCT GGCGACATAG TCAATTTTCA ACAGAACCAA CAATTGGCTC AACAAGCTCA 27720
CCTCGCCTTT CTTGAAAGCC GCAGTGCGGG TATGAAGGTG GCTGATGCTT TATTGAAGCA 27780
ACAGCTAGCT CAAGTAACAG GCCAAACTAT CGATAATCAG GCCCTCGATA CTCAAGCCGT 27840
CGATACTCAA ACAAGCGAGA ATGTAGCGAT TGCCGCAGAA TCACCAGTTC AAGTTACAAC 27900
ACCTGTTCAA GTTACAACAC CTGTTCAAAT CAGTGTTGTG GAGTTAAAAC CAGATCACGC 27960
TAATGTGCCA CCATACACGC CGCCAGTGCC TGCATTAAAG CCGTGTATCT GGAACTATGC 28020
CGATTTAGTT GAGTACGCAG AAGGCGATAT CGCCAAGGTA TTTGGCAGTG ATTATGCCAT 28080
TATCGACAGC TACTCGCGCC GCGTACGTCT ACCGACCACT GACTACCTGT TGGTATCGCG 28140
CGTGACCAAA CTTGATGCGA CCATCAATCA ATTTAAGCCA TGCTCAATGA CCACTGAGTA 28200
CGACATCCCT GTTGATGCGC CGTACTTAGT AGACGGACAA ATCCCCTTGGG CGGTAGCAGT 28260
AGAATCAGGC CAATGTGACT TGATGCTTAT TAGCTATCTC GGTATCGACT TTGAGAACAA 28320
AGGCGAGCGG GTTTATCGAC TACCCTCACC TTCCTAGGCG ACTTGCCACG 28380
TGGCGGAGAT ACCCTACGTT ACGACATTAA GATCAATAAC TATGCTCGCA ACGGCGACAC 28440
CCTGCTGTTC TTCTTCTCGT ATGAGTGTTT TGTTGGCGAC AAGATGATCC TCAAGATGGA 28500
TGGCGGCTGC GCTGGCTTCT TCACTGATGA AGAGCTTGCC GACGGTAAAG GCGTGATTCG 28560
```

FIG. 4A-28

```
CACAGAAGAA GAGATTAAAG CTCGCGAGCCT AGTGCAAAAG CAACGCTTTA ATCCGTTACT  28620
AGATTGTCCT AAAACCCAAT TTAGTTATGG TGATATTCAT AAGCTATTAA CTGCTGATAT  28680
TGAGGGTTGT TTTGGCCCAA GCCACAGTGG CGTCCACCAG CCGTCACTTT GTTTCGCATC  28740
TGAAAAATTC TTGATGATTG AACAAGTCAG CAAGGTTGAT CGCACTGGCG GTACTTGGGG  28800
ACTTGGCTTA ATTGAGGGTC ATAAGCAGCT TGAAGCAGAC CACTGGTACT TCCCATGTCA  28860
TTTCAAGGGC GACCAAGTGA TGGCTGGCTC GCTAATGGCT GAAGGTTGTG GCCAGTTATT  28920
GCAGTTCTAT ATGCTGCACC TTGGTATGCA TACCCAAAACT AAAAATGGTC GTTTCCAACC  28980
TCTTGAAAAC GCCTCACAGC AAGTACGCTG TCGCGGTCAA GTGCTGCCAC AATCAGGCGT  29040
GCTAACTTAC CGTATGGAAG TGACTGAAAT CGGTTTCAGT CCACGCCCAT ATGCTAAAGC  29100
TAACATCGAT ATCTTGCTTA ATGGCAAAGC GGTAGTGGAT TTCCAAAACC TAGGGGTGAT  29160
GATAAAGAG GAAGATGAGT GTACTCGTTA TCCACTTTTG ACTGAATCAA CAACGGCTAG  29220
CACTGCACAA GTAAACGCTC AAACAAGTGC GAAAAAGGTA TACAAGCCAG CATCAGTCAA  29280
TGCGCCATTA ATGGCACAAA TTCCTGATCT GACTAAAGAG CCAAACAAGG GCGTTATTCC  29340
GATTTCCCAT GTTGAAGCAC CAATTACGCC AGACTACCCG AACCGTGTAC CTGATACAGT  29400
GCCATTCACG CCGTATCACA TGTTTGAGTT TGCTACAGGC AATATCGAAA ACTGTTTCGG  29460
GCCAGAGTTC TCAATCTATC GCGGGCATGAT CCCACCACGT ACACCATGCG GTGACTTACA  29520
AGTGACCACA CGTGTGATTG AAGTTAACGG TAAGCGTGGC GACTTTAAAA AGCCATCATC  29580
```

FIG. 4A-29

```
GTGTATCGCT GAATATGAAG TGCCTGCAGA TGCGTGGTAT TTCGATAAAA ACAGCCACGG 29640
CGCAGTGATG CCATATTCAA TTTTAATGGA GATCTCACTG CAACCTAACG GCTTTATCTC 29700
AGGTTACATG GGCACAACCC TAGGCTTCCC TGGCCTTGAG CTGTTCTTCC GTAACTTAGA 29760
CGGTAGCGGT GAGTTACTAC GTGAAGTAGA TTTACGTGGT AAAACCATCC GTAACGACTC 29820
ACGTTTATTA TCAACAGTGA TGGCCGGCAC TAACATCATC CAAAGCTTTA GCTTCGAGCT 29880
AAGCACTGAC GGTGAGCCTT TCTATCGCGG CACTGCGGTA TTTGGCTATT TTAAAGGTGA 29940
CGCACTTAAA GATCAGCTAG GCCTAGATAA CGGTAAAGTC ACTCAGCCAT GGCATGTAGC 30000
TAACGGCGTT GCTGCAAGCA CTAAGGTGAA CCTGCTTGAT AAGAGCTGCC GTCACTTTAA 30060
TGCGCCAGCT AACCAGCCAC ACTATCGTCT AGCCGGTGGT CAGCTGAACT TTATCGACAG 30120
TGTTGAAATT GTTGATAATG GCGGCACCGA AGGTTTAGGT TACTTGTATG CCGAGCGCAC 30180
CATTGACCCA AGTGATTGGT TCTTCCAGTT CCACTTCCAC CAAGATCCGG TTATGCCAGG 30240
CTCCTTAGGT GTTGAAGCAA TTATTGAAAC CATGCAAGCT TACGCTATTA GTAAAGACTT 30300
GGGCGCAGAT TTCAAAAATC CTAAGTTTGG TCAGATTTTA TCGAACATCA AGTGGAAGTA 30360
TCGCGGTCAA ATCAATCCGC TGAACAAGCA GATGTCTATG GATGTCAGCA TTACTTCAAT 30420
CAAAGATGAA GACGGTAAGA AAGTCATCAC AGGTAATGCC AGCTTGAGTA AAGATGGTCT 30480
GCGCATATAC GAGGTCTTCG ATATAGCTAT CAGCATCGAA GAATCTGTAT AAATCGGAGT 30540
GACTGTCTGG CTATTTTACT CAATTTCTGT GTCAAAAGTG CTCACCTATA TTCATAGGCT 30600
```

FIG. 4A-30

```
GCGCGCTTTT TTCTGGAAAT TGAGCAAAAG TATCTGCGTC CTAACTCGAT TTATAAGAAT 30660
GGTTTAATTG AAAAGAACAA CAGCTAAGAG CCGCAAGCTC AATATAAATA ATTAAGGGTC 30720
TTACAAATAA TGAATCCTAC AGCAACTAAC GAAATGCTTT CTCCGTGGCC ATGGGCTGTG 30780
ACAGAGTCAA ATATCAGTTT TGACGTGCAA GTGATGGAAC AACAACTTAA AGATTTTAGC 30840
CGGGCATGTT ACGTGGTCAA TCATGCCGAC CACGGCTTTG GTATTGCGCA AACTGCCGAT 30900
ATCGTGACTG AACAAGCGGC AAACAGCACA GATTTACCTG TTAGTGCTTT TACTCCTGCA 30960
TTAGGTACCG AAAGCCTAGG CGACAATAAT TTCCGCCGCG TTCACGGCGT TAAATACGCT 31020
TATTACGCAG GCGCTATGGC AAACGGTATT TCATCTGAAG AGCTAGTGAT TGCCCTAGGT 31080
CAAGCTGGCA TTTTGTGTGG TTCGTTTGGA GCAGCCGGTC TTATTCCAAG TCGCGTTGAA 31140
GCGGCAATTA ACCGTATTCA AGCAGCGCTG CCAAATGGCC CTTATATGTT TAACCTTATC 31200
CATAGTCCTA GCGAGCCAGC ATTAGAGCGT GGCAGCGTAG CACAAATCGT AAAGCATAAG 31260
GTACGCACCG TTGAAGCATC AGCTTTCTTA GGTCTAACAC TTGGTAACAA CTATTACCGT 31320
GCAGCAGGAT TGAGCCGAGA CGCACAAGGT AAAGTTGTGG CAGCGCCCGC GGTTATCGCT 31380
AAAGTAAGTC GCACCGAAGT GGCTGAAAAG TTTATGATGC CAGCGCCCGC AAAAATGCTA 31440
CAAAAACTAG TTGATGACGG TTCAATTACC GCTGAGCAAA TGGAGCTGGC GCAACTTGTA 31500
CCTATGGCTG ACGACATCAC TGCAGAGGCC GATTCAGGTG GCCATACTGA TAACCGTCCA 31560
TTAGTAACAT TGCTGCCAAC CATTTTAGCG CTGAAAGAAG AAATTCAAGC TAAATACCAA 31620
```

FIG. 4A-31

```
TACGACACTC CTATTCGTGT CGGTTGTGGT GGCGGTGTGG GTACGCCTGA TGCAGCGCTG 31680
GCAACGTTTA ACATGGGCGC GGCGTATATT GTTACCGGCT CTATCAACCA AGCTTGTGTT 31740
GAAGCGGGCG CAAGTGATCA CACTCGTAAA TTACTTGCCA CCACTGAAAT GGCCGATGTG 31800
ACTATGGCAC CAGCTGCAGA TATGTTCGAG ATGGGCGTAA AACTGCAGGT GGTTAAGCGC 31860
GGCACGCTAT TCCCAATGCG CGCTAACAAG CTATATGAGA TCTACACCCG TTACGATTCA 31920
ATCGAAGCGA TCCCATTAGA CGAGCGTGAA AAGCTTGAGA AACAAGTATT CCGTCAAGC  31980
CTAGATGAAA TATGGGCAGG TACAGTGGCG CACTTTAACG AGCGCGACCC TAAGCAAATC 32040
GAACGCGCAG AGGGTAACCC TAAGCGTAAA ATGGCATTGA TTTTCCGTTG GTACTTAGGT 32100
CTTTCTAGTC GCTGGTCAAA CTCAGGCGAA GTGGGTCGTG AAATGGATTA TCAAATTTGG 32160
GCTGGCCCTG CTCTCGGTGC ATTTAACCAA TGGGCAAAAG GCAGTTACTT AGATAACTAT 32220
CAAGACCGAA ATGCCGTCGA TTTGGCAAAG CACTTAATGT ACGGCGCGGC TTACTTAAAT 32280
CGTATTAACT CGCTAACGGC TCAAGGCGTT AAAGTGCCAG CACAGTTACT TCGCTGGAAG 32340
CCAAACCAAA GAATGGCCTA ATACACTTAC AAAGCACCAG TCTAAAAAGC CACTAATCTT 32400
GATTAGTGGC TTTTTTTATT GTGGTCAATA TGAGGCTATT TAGCCCTGTAA GCCTGAAAAT 32460
ATCAGCACTC TGACTTTACA AGCAAATTAT AATTAAGGCA GGGCTCTACT CATTTATACT 32520
GCTAGCAAAC AAGCAAGTTG CCCAGTAAAA CAACAAGGTA CCTGATTTAT ATCGTCATAA 32580
AAGTTGGCTA GAGATTCGTT ATTGATCTTT ACTGATTAGA GTCGCTCTGT TTGGAAAAAG 32640
```

FIG. 4A-32

```
GTTTCTCGTT ATCATCAAAA TACACTCTCA AACCTTTAAT CAATTACAAC TTAGGCTTTC 32700
TGCGGGCATT TTTATCTTAT TTGCCACAGC TGTATTTGCC TTTAGGTTTT GGGTGCAACT 32760
ACCATTAATT GAGGCCTCAT TAGTTAAATT ATCTGAGCAA GAGCTCACCT CTTTAAATTA 32820
CGCTTTTCAG CAAATGAGAA AGCCACTACA AACCATTAAT TACGACTATG CGGTGTGGGA 32880
CAGAACCTAC AGCTATATGA AATCAAACTC AGCCGAGCGC AAAAGGTACT ATGAAAAACA 32940
TGAGTACCCA GATGATACGT TCAAGAGTTT AAAAGTCGAC GGAGTATTTA TATTCAACCG 33000
TACAAATCAG CCAGTTTTTA GTAAAGGTTT TAATCATAGA AATGATATAC CGCTGGTCTT 33060
TGAATTAACT GACTTTAAAC AACATCCACA AAACATCGCA TTATCTCCAC AAACCAAACA 33120
GGCACACCCA CCGGCAAGTA AGCCGTTAGA CTCCCCTGAT GATGTGCCTT CTACCCATGG 33180
GGTTATCGCC ACACGATACG GTCCAGCAAT TTATAGCTCT ACCAGCATTT TAAAATCTGA 33240
TCGTAGCGGC TCCCAACTTG GTTATTTAGT CTTCATTAGG TTAATTGATG AATGGTTCAT 33300
CGCTGAGCTA TCGCAATACA CTGCCGCAGG TGTTGAAATC GCTATGGCTG ATGCCGCAGA 33360
CGCACAATTA GCGAGATTAG GCGCAAACAC TAAGCTTAAT AAAGTAACCG CTACATCCGA 33420
ACGGTTAATA ACTAATGTCG ATGGTAAGCC TCTGTTGAAG TTAGTGCTTT ACCATACCAA 33480
TAACCAACCG CCGGCCGATGC TAGATTACAG TATAATAATT CTATTAGTTG AGATGTCATT 33540
TTTACTGATC CTCGCTTATT TCCTTTACTC CTACTTCTTA GTCAGGCCAG TTAGAAAGCT 33600
GGCTTCAGAT ATTAAAAAAA TGGATAAAAG TCGTGAAATT AAAAAGCTAA GGTATCACTA 33660
```

FIG. 4A-33

```
CCCTATTACT GAGCTAGTCA AAGTTGCGAC TCACTTCAAC GCCCTAATGG GGACGATTCA 33720
GGAACAAACT AAACAGCTTA ATGAACAAGT TTTTATTGAT AAATTAACCA ATATTCCCAA 33780
TCGTCGCGCT TTTGAGCAGC GACTTGAAAC CTATTGCCAA CTGCTAGCCC GGCAACAAAT 33840
TGGCTTTACT CTCATCATTG CCGATGTGGA TCATTTTAAA GAGTACAACG ATACTCTTGG 33900
GCACCTTGCT GGGGATGAAG CATTAATAAA AGTGGCACAA ACACTATCGC AACAGTTTTA 33960
CCGTGCAGAA GATATTTGTG CCCGTTTTGG TGGTGAAGAA TTTATTATGT TATTCGAGA 34020
CATACCTGAT GAGCCCTTGC AGAGAAAGCT CGATGCGATG CTGCACTCTT TTGCAGAGCT 34080
CAACCTACCT CATCCAAACT CATCAACCGC TAATTACGTT ACTGTGAGCC TTGGGGTTTG 34140
CACAGTTGTT GCTGTTGATG ATTTTGAATT TAAAAGTGAG TCGCATATTA TTGGCAGTCA 34200
GGCTGCATTA ATCGCAGATA AGGCGCTTTA TCATGCTAAA GCCTGTGGTC GTAACCAGTT 34260
GTCAAAAACT ACTATTACTG TTGATGAGAT TGAGCAATTA GAAGCAAATA AAATCGGTCA 34320
TCAAGCCTAA ACTCGTTCGA GTACTTTCCC CTAAGTCAGA GCTATTTGCC ACTTCAAGAT 34380
GTGGCTACAA GGCTTACTCT TTCAAAACCT GCATCAATAG AACACAGCAA AATACAATAA 34440
TTTAAGTCAA TTTAGCCTAT TAAACAGAGT TAATGACAGC TCATGGTCGC AACTTATTAG 34500
CTATTTCTAG CAATATAAAA ACTTATCCAT TAGTAGTAAC CAATAAAAAA ACTAATATAT 34560
AAAACTATTT AATCATTATT TTACAGATGA TTAGCTACCA CCCACCTTAA GCTGGCTATA 34620
TTCGCACTAG TAAAAATAAA CATTAGATCG GGTTCAGATC AATTTACGAG TCTCGTATAA 34680
```

FIG. 4A-34

```
AATGTACAAT AATTCACTTA ATTTAATACT GCATATTTTT ACAAGTAGAG AGCGGTGATG 34740
AAACAAAATA CGAAAGGCTT TACATTAATT GAATTAGTCA TCGTGATTAT TATTCTCGGT 34800
ATACTTGCTG CTGTGGCACT GCCGAAATTC ATCAATGTTC AAGATGACGC TAGGATCTCT 34860
GCGATGAGCG GTCAGTTTTC ATCATTTGAA AGTGCCGTAA AACTATACCA TAGCGGTTGG 34920
TTAGCCAAAG GCTACAACAC TGCGGTTGAA AAGCTCTCAG GCTTTGGCCA AGGTAATGTT 34980
GCATCAAGTG ACACAGGTTT TCCGTACTCA ACATCAGGCA CGAGTACTGA TGTGCATAAA 35040
GCTTGTGGTG AACTATGGCA TGGCATTACC GATACAGACT TCACAATTGG TGCGGTTAGT 35100
GATGGCGATC TAATGACTGC AGATGTCGAT ATTGCTTACA CCTATCGTGG TGATATGTGT 35160
ATCTATCGCG ATCTGTATTT TATTCAGCGC TCATTACCTA CTAAGGTGAT GAACTACAAA 35220
TTTAAAACTG GTGAAATAGA AATTATTGAT GCTTTCTACA ACCCTGACGG CTCAACTGGT 35280
CAATTACCAT AAATTTGGCG CTTATCTAAG TTGTACTTGC TCTGACCGAC ACAAATAATG 35340
TCGTTTCTCA GCATATATCA AAATACACAG CAAAAATTTG GGGTTAGCTA TATAGCTAAC 35400
CCCAAATCAT ATCTAACTTT ACACTGCATC TAATTCCAAA CAGTATCCAG CCAAAAGCCT 35460
AAACTATTGT TGACTCAGCG CGATGCAACA CGATGCAACA AACAAGTCTT GGATCGCAAT 35520
ACCTGAGCTA TCAAAAATGG TCACCTCATC AGCACTTTGA CGTCCTGTTG CGGACTCGTT 35580
TATCACCTGA CCAATCTCAA TTATCGGCGT ATTTCTGCTA TGTTGAAACT CACCAATAAC 35640
AATAGATTGA GAAGCAAAGT CGCAAAACAA GCGAGCATGA CTATATAGGT CAGTTGGCAA 35700
```

FIG. 4A-35

```
CTCTTGCTTA CCCACTTTAT CAGCGCCCAT TGCAGAAATA TGCGTTCCTG CTTGTACCCA 35760
CTGCGCTTCA AATAAAGGCG CTTGAGCTGT GGTTGCTGTG ATAATAATAT CTGCTTGTTC 35820
ACAAGCAGCT TGTGCATCAC AAGCTTCGGC ATTAATGCCT TTTTCTAATA AACGCTTAAC 35880
CAAGTTTTCA GTTTTGCTAG CACTACGGCC AACTACCAAT ACCTTAGTTA ATGAACGAAC 35940
CTTGCTCACT GCTAGCACTT CATATTCAGC CTGATGACCG GTACCAAAAA CAGTTAATAC 36000
CGTAGCATCT TCTCTCGCGA GGTAACTCAC TGCTACTGCA TCGGCAGCAC CAGTGCGGTA 36060
AGCATTAACG GTAGTGGCAG CAATCACCGN CTGCAACATA CCGGTTAATG GATCGAGTAA 36120
AAATACGTTA GTGCCGTGGC ATGGTAAACC ATGTTTATGG TTATCAGGCC AATAGCTGCC 36180
TGTTTTCCAG CCGACAAGGT TTGGCGTTGA AGCCGACTTT AATGAGAACA TTTCATTAAG 36240
GTTCGCGCCC TGTGCATTAA CTACCGGGAA CAAGGTTGCT TTATCATCTA CGGCAGCGAC 36300
AAACGCTTCT TTAACAGCGA TATAAGCCAG CTCATGGGAG ATGAGCTTTG ATGTTTGCGC 36360
TTCAGTTAAA TAGATCATAT TACCACCCCT GCACTCGATT CCAGATCTCA TAGCCACCAT 36420
TATCACCATC AGTATCAAAT ACATGGTACT GAGCGTGCAT TGAAGCTGTT GCACAGGCGT 36480
GGTTCGGCAA AATATGTAGA CGACTACCTA CCGGGAACTG CGCTAAATCA ATAACGCCGC 36540
CATCAACTGC TTCAATAATG CCCTGCTCTT GATTAACAGT TATAACCTGT AGACCTGATA 36600
ACACGTGACC GCTGTCGTCA CACACTAAAC CATAACCACA ATCTTTTGGC TGCTCTGCAG 36660
TACCTCTATC ACCCGAAAGA GCCATCCAAC CCGCATCAAT GAAAATCCAG TTTTTATCAG 36720
```

FIG. 4A-36

```
GATTATGACC AATAACACTG GTCACTACCG TTGCGGCAAT ATCAGTTAAC TGACACACGT 36780
TTAGCCCTGC CATGACTAAA TCGAAGAAGG TGTACACACC CGCTCTAACC TCGGTGATCC 36840
CATCAAGGTT TTGATAGCTT TGCGCTGTTG GTGTTGAACC AATACTAACG ATGTCACATT 36900
GCATACCCGC TGCGCGAATG CGTCAGCAGC TTGTACAGCC GCTGCAACTT CATTTGCGCT 36960
CGCATCAATT AATTGCTGTT TTTCAAAACA TGATATGAC TCACCAGCGT GAGTNAGTAC 37020
GCCGTGAAAA CTCGCTGCGC CAGACGTTAG TATCTGAGCA ATTTCAATCA ACTTATCGGC 37080
TTCCGGTGGA ATACCACCAC GATGGCCATC ACAATCAATT TCAATTAATG CTGGTATTTG 37140
GCAGTCATAA GAACCACAGA AATGATTTAG CTGATGCGCT TGCTCAACAC TATCAAGTAA 37200
AACTCTTGCA TTAATACCTT GGTCCAACAT TTTAGCAATA CGCGGCAACT TACCATCGGC 37260
AATACCTACT GCATAAATAA TGTCTGTGTA ACCTTTAGAT GCTAAGGCCT CGGCCTCTTT 37320
TACCGTTGAT ACAGTGACTG GTGAGTTTTT AGTGGGTAAT AAAAACTCGG CTGCTTCAAG 37380
TGATCTTAAC GTTTTAAAAT GCGGTCTTAG GTTTGCACCT AATCCTTCAA TTTTTTGGCG 37440
TAGTTGACTG AGGTTATTAA TAAATACTGG CTTATTTACA TATAAAAACG GTGTATCAAT 37500
TGCTTGATAC TGACTTTGCT GAGTCGTGGA AAGTATTTGA GTAGATGGCA TCTTTAATAT 37560
CCTAGTTCAT CAATCAATCT AACAAGTTTG ATGCCTAGCC ACAGTGGCTT GTATTCATGA 37620
TGCTTTGGAA AATGCTTATA TTCAAAGTAT TTGAAAGACA TCAAACTTCT TGTTTAATGC 37680
TCAGTATCCA CCAGCACGCA TTTATTTTAT ATTAACTATT ATCAAGATAT AGATTAGGTT 37740
```

FIG. 4A-37

```
CAAACCAAAT GATTAGTACT GAAGATCTAC GTTTTATCAG CGTAATCGCC AGTCATCGCA  37800
CCTTAGCTGA TGCCGCTAGA ACACTAAATA TCACGCCACC ATCAGTGACA TTAAGGTTGC  37860
AGCATATTGA AAAGAAACTA TCGATTAGCC TGATC                             37895
```

| | | | |
|---|---|---|---|
| MKQTLMAISI | MSLFSFNALA | AQHEHDHITV | DYEGKAATEH |
| TIAHNQAVAK | TLNFADTRAF | EQSSKNLVAK | FDKATADILR |
| AEFAFISDEI | PDSVNPSLYR | QAQLNMVPNG | YKVSDGIYQV |
| RGTDLSNLTL | IRSDNGWIAY | DVLLTKEAAK | ASLQFALKNL |
| PKDGDPVVAM | IYSHSHADHF | GGARGVQEMF | PDVKVYGSDN |
| ITKEIVDENV | LAGNAMSRRA | AYQYGATLGK | HDHGIVDAAL |
| GKGLSKGEIT | YVAPDYTLNS | EGKWETLTID | GLEMVFMDAS |
| GTEAESEMIT | YIPSKKALWT | AELTYQGMHN | IYTLRGAKVR |
| DALKWSKDIN | EMINAFGQDV | EVLFASHSAP | VWGNQAINDF |
| LRLQRDNYGL | VHNQTLRLAN | DGVGIQDIGD | AIQDTIPESI |
| YKTWHTNGYH | GTYSHNAKAV | YNKYLGYFD | MNPANLNPLP |
| TKQESAKFVE | YMGGADAAIK | RAKDDYAQGE | YRFVATALNK |
| VVMAEPENDS | ARQLLADTYE | QLGYQAEGAG | WRNIYLTGAQ |
| ELRVGIQAGA | PKTASADVIS | EMDMPTLFDF | LAVKIDSQQA |
| AKHGLVKMNV | ITPDTKDILY | IELSNGNLSN | AVVDKEQAAD |
| ANLMVNKADV | NRILLGQVTL | KALLASGDAK | LTGDKTAFSK |
| IADSMVEFTP | DFEIVPTPVK | | |

STKASARVVA KFNVEEAAIS IQQCQGISLA FRYSDDLHGL
LCHWNDAANM QQEKAEILGL GSKQPEANPK NSSSELLALG
IDQKLLVQRQ NLQHEVKHDA IADSIDVCHS LSKPANVGLF
TESLASFDFA FSKLSLALGL GKAKIYSEKL AWLDFFRDRQ
LAEPLALLAR KESESFYHSL ISHINTSNRC REIDVGFEIS
ASDTEEKSAQ SAGKNDATCI GVLLWDGSHS VNFHVGTQAF
QADSLRPKGK DGYEFRWENP RIESHQSLLA RLYGRVM
9016

GCTAGTCTTA GCTGASRTHR YSAASRAGCT CGAACAACAG CTTTAAAATT
CACTTCTTCT GCTGCAATAC TTATTTGCTG ACACTGACCA ATACTCACTG
CAAAACGATA ACTATCATCA AGATGGAAAR GVAVAAAYSH ASNVAGGAAA
ASRGNGNCYS GNGYSRAAHA RGTYRSRASA SHSCCCAGTA AACAATGCCA
ATTATCAGCA GCGTTCATTT GCTGTTCTTT AGCCTCAATC AAACCTAAAC
CAGACTTTTG TGGCTCAGCG TTAGGCTTAT TAGGYCYSHS TRASNASAAA
AASNMTGNGN GYSAAGGYGY SRYSGNRGAA ASNRYSASNS RAACTCGACT
CTAGTAAAGC AAGACCAATA TCTTGTTTTA ACAAAACCTG TCGCTGATTA
AGTTGATGCT CAACCTTGTG ATCCGCAATA GCATCGGAAA TSRSRGAAGY
ASGNYSVAGN ARGGNASNGN HSGVAYSHSA SAAAAASSRA TCAACACAAT
GGCTCAAGCT TTTAGGTGCA TTAACTCCAA GAAAAGTTTC GCTCAGTGCA
GAGAAGTCAA ACGCAAAGA TTTTAGCGAT AATGCCAGCA SVACYSHSSR
SRYSRAAASN VAGYHTHRGS RAASRHASHA AHSRYSSRAA CCAAGTCCTT
TCGCTTTAAT GTAAGACTCC TTGAGCGCCC ACAAATCAAA AAAGCGGTCT
CGCTGCAAGG CCTCTGGTAA CGCTAACAAG GCTCGCTTTT GYGYYSAAYS
TYRSRGYSAA TRASHHARGA SARGGNAAGR AAAAARGYSG CTGATTCAGA
GAAATAATGA CTAAGAATAG AGTGGATATT GGTGCTGTTA CGGCAACGCT
CAATGTCGAC GCCAAACTCA ATACTAGCAG AGTCAGTTTC SRGSRHTYRH
SSRSRHSASN THRSRASNAR GCYSARGGAS VAGYHGSRAA SRASTHRGCT
CCTTGCTTGC CTGACTGGCG CCTTTATTAT CAGCAGTGCA AATGCCTACT
AATAGCCAAT CTCCACTATG ACTCACATTA AAGTGGACCC CGGTTTGAGY
SSRAAGNSRA AGYYSASNAS AATHRCYSGY VATRASGYSR HSSRVAASNH
HSVAGYTHRG NGCAAATTGC GCATCACTCA ATCTAGGCTT ACCTTTGTCG

FIG. 4D-1

```
CCATATTCAA AGCGCCATTC ATTGGGGCGT ATTTCACTAT GTTGTGACAA
TAAAGCGCGC AAAHGNAAAS SRARGRYSGY YSASGYTYRG HARGTRGASN
RARGGSRHSG NSRAAARGAA TAGCCTCTTA CCATTAAACC TTGAGTTTTA
GCTTCTTGTT TAATGTAGCG ATTAACCTTA ATTAACTCAT CTTCAGGCAG
CCATGACTTA ACCAACTCTY RGYARGVAMT GYGNTHRYSA AGGNYSTYRA
RGASNVAYSG ASGRTRSRYS VAGTGTAGTC TGGTTATCGC ACTCTTGTAT
TGTTAACGGA CAGAAGTATA AGGAAATCAA
                                *
                              9157
```

FIG. 4D-2

9681
*MSMFLNSKLS RSVKLAISAG LTASLAMPVF AEETAAEEQI ERVAVTGSRI
AKAELTQPAP VVSLSAEELT KFGNQDLGSV LAELPAIGAT NTIIGNNNSN
SSAGVSSADL RRLGANRTLV LVNGKRYVAG QPGSAEVDLS TIPTSMISRV
EIVTGGASAI YGSDAVSGVI NVILKEDFEG FEFNARTSGS TESVGTQEHS
FDILGGANVA DGRGNVTFYA GYERTKEVMA TDIRQFDAWG TIKNEADGGE
DDGIPDRLRV PRVYSEMINA TGVINAFGGG IGRSTFDSNG NPIAQQERDG
TNSFAFGSFP NGCDTCFNTE AYENYIPGVE RINVGSSFNF DFTDNIQFYT
DFRYVKSDIQ QQFQPSFRFG NININVEDNA FLNDDLRQQM LDAGQTNASF
AKFFDELGNR SAENKRELFR YVGGFKGGFD ISETIFDYDL YVVYGETNNR
RKTLNDLIPD NFVAAVDSVI DPDTGLAACR SQVASAQGDD YTDPASVNGS
DCVAYNPFGM GQASAEARDW VSADVTREDK ITQQVIGGTL GTDSEELFEL
QGGAIAMVVG FEYREETSGS TTDEFTKAGF LTSAATPDSY GEYDVTEYFV
EVNIPVLKEL PFAHELSFDG AYRNADYSHA GKTEAWKAGM FYSPLEQLAL
RGTVGEAVRA PNIAEAFSPR SPGFGRVSDP CDADNINDDP DRVSNCAALG
IPPGFQANDN VSVDTLSGGN PDLKPETSTS FTGGLVWTPT FADNLSFTVD
YYDIQIEDAI LSVATQTVAD NCVDSTGGPD TDFCSQVDRN PTTYDIELVR
SGYLNAAALN TKGIEFQAAY SLDLESFNAP GELRFNLLGN QLLELERLEF
QNRPDEINDE KGEVGDPELQ FRLGIDYRLD DLSVSWNTRY IDSVVTYDVS
ENGGSPEDLY PGHIGSMTTH DLSATYYINE NFMINGGVRN LFDALPPGYT
NDALYDLVGR RAFLGIKVMM
                    *
                  12590

MAKINSEHLD EATITSNKCT QTETEARHRN ATTTPEMRRF IQESDLSVSQ
LSKILNISEA TVRKWRKRDS VENCPNTPHH LNTTLTPLQE YVVVGLRYQL
KMPLDRLLKA TQEFINPNVS RSGLARCLKR YGVSRVSDIQ SPHVPMRYFN
QIPVTQGSDV QTYTLHYETL AKTLALPSTD GDNVVQVVSL TIPPKLTEEA
PSSILLGIDP HSDWIYLDIY QDGNTQATNR YMAYVLKHGP FHLRKLLVRN
YHTFLQRFPG ATQNRRPSKD MPETINKTPE TQAPSGDS
13903

MSQTSKPTNS ATEQAQDSQA DSRLNKRLKD MPIAIVGMAS IFANSRYLNK
FWDLISEKID AITELPSTHW QPEEYYDADK TAADKSYCKR GGFLPDVDFN
PMEFGLPPNI LELTDSSQLL SLIVAKEVLA DANLPENYDR DKIGITLGVG
GGQKISHSLT ARLQYPVLKK VFANSGISDT DSEMLIKKFQ DQYVHWEENS
FPGSLGNVIA GRIANRFDFG GMNCVVDAAC AGSLAAMRMA LTELTEGRSE
MMITGGVCTD NSPSMYMSFS KTPAFTTNET IQPFDIDSKG MMIGEGIGMV
ALKRLEDAER DGDRIYSVIK GVGASSDGKF KSIYAPRPSG QAKALNRAYD
DAGFAPHTLG LIEAHGTGTA AGDAAEFAGL CSVFAEGNDT KQHIALGSVK
SQIGHTKSTA GTAGLIKAAL ALHHKVLPPT INVSQPSPKL DIENSPFYLN
TETRPWLPRV DGTPRRAGIS SFGFGGTNFH FVLEEYNQEH SRTDSEKAKY
RQRQVAQSFL VSASDKASLI NELNVLAASA SQAEFILKDA AANYGVRELD
KNAPRIGLVA NTAEELAGLI KQALAKLAAS DDNAWQLPGG TSYRAAAVEG
KVAALFAGQG SQYLNMGRDL TCYYPEMRQQ FVTADKVFAA NDKTPLSQTL
YPKPVFNKDE LKAQEAILTN TANAQSAIGA ISMGQYDLFT AAGFNADMVA
GHSFGELSAL CAAGVISADD YYKLAFARGE AMATKAPAKD GVEADAGAMF
AIITKSAADL ETVEATIAKF DGVKVANYNA PTQSVIAGPT ATTADAAKAL
TELGYKAINL PVSGAFHTEL VGHAQAPFAK AIDAAKFTKT SRALYSNATG
GLYESTAAKI KASFKKHMLQ SVRFTSQLEA MYNDGARVFV EFGPKNILQK
LVQGTLVNTE NEVCTISINP NPKVDSDLQL KQAAMQLAVT GVVLSEIDPY
QADIAAPAKK SPMSISLNAA NHISKATRAK MAKSLETGIV TSQIEHVIEE
KIVEVEKLVE VEKIVEKVVE VEKVVEVEAP VNSVQANAIQ TRSVVAPVIE
NQVVSKNSKP AVQSISGDAL SNFFAAQQQT AQLHQQFLAI PQQYGETFTT
LMTEQAKLAS SGVAIPESLQ RSMEQFHQLQ AQTLQSHTQF LEMQAGSNIA
ALNLLNSSQA TYAPAIHNEA IQSQVVQSQT AVQPVISTQV NHVSEQPTQA
PAPKAQPAPV TTAVQTAPAQ VVRQAAPVQA AIEPINTSVA TTTPSAFSAE

FIG. 4G-1

```
TALSATKVQA TMLEVVAEKT GYPTEMLELE MDMEADLGID SIKRVEILGT
VQDELPGLPE LSPEDLAECR TLGEIVDYMG SKLPAEGSMN SQLSTGSAAA
TPAANGLSAE KVQATMMSVV AEKTGYPTEM LELEMDMEAD LGIDSIKRVE
ILGTVQDELP GLPELSPEDL AECRTLGEIV DYMNSKLADG SKLPAEGSMN
SQLSTSAAAA TPAANGLSAE KVQATMMSVV AEKTGYPTEM LELEMDMEAD
LGIDSIKRVE ILGTVQDELP GLPELNPEDL AECRTLGEIV TYMNSKLADG
SKLPAEGSMH YQLSTSTAAA TPVANGLSAE KVQATMMSVV ADKTGYPTEM
LELEMDMEAD LGIDSIKRVE ILGTVQDELP GLPELNPEDL AECRTLGEIV
DYMGSKLPAE GSANTSAAAS LNVSAVAAFQ AAATPVSNGL SAEKVQSTMM
SVVAEKTGYP TEMLELGMDM EADLGIDSIK RVEILGTVQD ELPGLPELNP
EDLAECRTLG EIVDYMNSKL ADGSKLPAEG SANTSATAAT PAVNGLSADK
VQATMMSVVA EKTGYPTEML ELGMDMEADL GIDSIKRVEI LGTVQDELPG
LPELNPEDLA ECRTLGEIVS YMNSQLADGS KLSTSAAEGS ADTSAANAAK
PAAISAEPSV ELPPHSEVAL KKLNAANKLE NCFAADASVV INDDGHNAGV
LAEKLIKQGL KVAVVRLPKG QPQSPLSSDV ASFELASSQE SELEASITAV
IAQIETQVGA IGGFIHLQPE ANTEEQTAVN LDAQSFTHVS NAFLWAKLLQ
PKLVAGADAR RCFVTVSRID GGFGYLNTDA LKDAELNQAA LAGLTKTLSH
EWPQVFCRAL DIATDVDATH LADAITSELF DSQAQLPEVG LSLIDGKVNR
VTLVAAEAAD KTAKAELNST DKILVTGGAK GVTFECALAL ASRSQSHFIL
AGRSELQALP SWAEGKQTSE LKSAAIAHII STGQKPTPKQ VEAAVWPVQS
SIEINAALAA FNKVGASAEY VSMDVTDSAA ITAALNGRSN EITGLIHGAG
VLADKHIQDK TLAELAKVYG TKVNGLKALL AALEPSKIKL LAMFSSAAGF
YGNIGQSDYA MSNDILNKAA LQFTARNPQA KVMSFNWGPW DGGMVNPALK
```

FIG. 4G-2

```
KMFTERGVYV IPLKAGAELF ATQLLAETGV QLLIGTSMQG GSDTKATETA
SVKKLNAGEV LSASHPRAGA QKTPLQAVTA TRLLTPSAMV FIEDHRIGGN
SVLPTVCAID WMREAASDML GAQVKVLDYK LLKGIVFETD EPQELTLELT
PDDSDEATLQ ALISCNGRPQ YKATLISDNA DIKQLNKQFD LSAKAITTAK
ELYSNGTLFH GPRLQGIQSV VQFDDQGLIA KVALPKVELS DCGEFLPQTH
MGGSQPFAED LLLQAMLVWA RLKTGSASLP SSIGEFTSYQ PMAFGETGTI
ELEVIKHNKR SLEANVALYR DNGELSAMFK SAKITISKSL NSAFLPAVLA
NDSEAN
     *
 22173
```

MPLRIALILL PTPQFEVNSV DQSVLASYQT LQPELNALLN SAPTPEMLSI
TISDDSDANS FESQLNAATN AINNGYIVKL ATATHALLML PALKAAQMRI
HPHAQLAAMQ QAKSTPMSQV SGELKLGANA LSLAQTNALS HALSQAKRNL
TDVSVNECFE NLKSEQQFTE VYSLIQQLAS RTHVRKEVNQ GVELGPKQAK
SHYWFSEFHQ NRVAAINFIN GQQATSYVLT QGSGLLAAKS MLNQQRLMFI
LPGNSQQQIT ASITQLMQQL ERLQVTEVNE LSLECQLELL SIMYDNLVNA
DKLTTRDSKP AYQAVIQASS VSAAKQELSA LNDALTALFA EQTNATSTNK
GLIQYKTPAG SYLTLTPLGS NNDNAQAGLA FVYPGVGTVY ADMLNELHQY
FPALYAKLER EGDLKAMLQA EDIYHLDPKH AAQMSLGDLA IAGVGSSYLL
TQLLTDEFNI KPNFALGYSM GEASMWASLG VWQNPHALIS KTQTDPLFTS
AISGKLTAVR QAWQLDDTAA EIQWNSFVVR SEAAPIEALL KDYPHAYLAI
IQGDTCVIAG CEIQCKALLA ALGKRGIAAN RVTAMHTQPA MQEHQNVMDF
YLQPLKAELP SEISFISAAD LTAKQTVSEQ ALSSQVVAQS IADTFCQTLD
FTALVHHAQH QGAKLFVEIG ADRQNCTLID KIVKQDGASS VQHQPCCTVP
MNAKGSQDIT SVIKALGQLI SHQVPLSVQP FIDGLKRELT LCQLTSQQLA
AHANVDSKFE SNQDHLLQGE V
24515

```
MSLPDNASNH LSANQKGASQ ASKTSKQSKI AIVGLATLYP DAKTPQEFWQ
NLLDKRDSRS TLTNEKLGAN SQDYQGVQGQ SDRFYCNKGG YIENFSFNAA
GYKLPEQSLN GLDDSFLWAL DTSRNALIDA GIDINGADLS RAGVVMGALS
FPTTRSNDLF LPIYHSAVEK ALQDKLGVKA FKLSPTNAHT ARAANESSLN
AANGAIAHNS SKVVADALGL GGAQLSLDAA CASSVYSLKL ACDYLSTGKA
DIMLAGAVSG ADPFFINMGF SIFHAYPDHG ISVPFDASSK GLFAGEGAGV
LVLKRLEDAE RDNDKIYAVV SGVGLSNDGK GQFVLSPNPK GQVKAFERAY
AASDIEPKDI EVIECHATGT PLGDKIELTS METFFEDKLQ GTDAPLIGSA
KSNLGHLLTA AHAGIMKMIF AMKEGYLPPS INISDAIASP KKLFGKPTLP
SMVQGWPDKP SNNHFGVRTR HAGVSVFGFG GCNAHLLLES YNGKGTVKAE
ATQVPRQAEP LKVVGLASHF GPLSSINALN NAVTQDGNGF IELPKKRWKG
LEKHSELLAE FGLASAPKGA YVDNFELDFL RFKLPPNEDD RLISQQLMLM
RVTDEAIRDA KLEPGQKVAV LVAMETELEL HQFRGRVNLH TQLAQSLAAM
GVSLSTDEYQ ALEAIAMDSV LDAAKLNQYT SFIGNIMASR VASLWDFNGP
AFTISAAEQS VSRCIDVAQN LIMEDNLDAV VIAAVDLSGS FEQVILKNAI
APVAIEPNLE ASLNPTSASW NVGEGAGAVV LVKNEATSGC SYGQIDALGF
AKTAETALAT DKLLSQTATD FNKVKVIETM AAPASQIQLA PIVSSQVTHT
AAEQRVGHCF AAAGMASLLH GLLNLNTVAQ TNKANCALIN NISENQLSQL
LISQTASEQQ ALTARLSNEL KSDAKHQLVK QVTLGGRDIY QHIVDTPLAS
LESITQKLAQ ATASTVVNQV KPIKAAGSVE MANSFETESS AEPQITIAAQ
QTANIGVTAQ ATKRELGTPP MTTNTIANTA NNLDKTLETV AGNTVASKVG
SGDIVNFQQN QQLAQQAHLA FLESRSAGMK VADALLKQQL AQVTGQTIDN
QALDTQAVDT QTSENVAIAA ESPVQVTTPV QVTTPVQISV VELKPDHANV
PPYTPPVPAL KPCIWNYADL VEYAEGDIAK VFGSDYAIID SYSRRVRLPT
TDYLLVSRVT KLDATINQFK PCSMTTEYDI PVDAPYLVDG QIPWAVAVES
GQCDLMLISY LGIDFENKGE RVYRLLDCTL TFLGDLPRGG DTLRYDIKIN
NYARNGDTLL FFFSYECFVG DKMILKMDGG CAGFFTDEEL ADGKGVIRTE
```

FIG. 4I-1

EEIKARSLVQ KQRFNPLLDC PKTQFSYGDI HKLLTADIEG CFGPSHSGVH
QPSLCFASEK FLMIEQVSKV DRTGGTWGLG LIEGHKQLEA DHWYFPCHFK
GDQVMAGSLM AEGCGQLLQF YMLHLGMHTQ TKNGRFQPLE NASQQVRCRG
QVLPQSGVLT YRMEVTEIGF SPRPYAKANI DILLNGKAVV DFQNLGVMIK
EEDECTRYPL LTESTTASTA QVNAQTSAKK VYKPASVNAP LMAQIPDLTK
EPNKGVIPIS HVEAPITPDY PNRVPDTVPF TPYHMFEFAT GNIENCFGPE
FSIYRGMIPP RTPCGDLQVT TRVIEVNGKR GDFKKPSSCI AEYEVPADAW
YFDKNSHGAV MPYSILMEIS LQPNGFISGY MGTTLGFPGL ELFFRNLDGS
GELLREVDLR GKTIRNDSRL LSTVMAGTNI IQSFSFELST DGEPFYRGTA
VFGYFKGDAL KDQLGLDNGK VTQPWHVANG VAASTKVNLL DKSCRHFNAP
ANQPHYRLAG GQLNFIDSVE IVDNGGTEGL GYLYAERTID PSDWFFQFHF
HQDPVMPGSL GVEAIIETMQ AYAISKDLGA DFKNPKFGQI LSNIKWKYRG
QINPLNKQMS MDVSITSIKD EDGKKVITGN ASLSKDGLRI YEVFDIAISI
EESV

30730
*
MNPTATNEML SPWPWAVTES NISFDVQVME QQLKDFSRAC
YVVNHADHGF GIAQTADIVT EQAANSTDLP VSAFTPALGT
ESLGDNNFRR VHGVKYAYYA GAMANGISSE ELVIALGQAG
ILCGSFGAAG LIPSRVEAAI NRIQAALPNG PYMFNLIHSP
SEPALERGSV ELFLKHKVRT VEASAFLGLT PQIVYYRAAG
LSRDAQGKVV VGNKVIAKVS RTEVAEKFMM PAPAKMLQKL
VDDGSITAEQ MELAQLVPMA DDITAEADSG GHTDNRPLVT
LLPTILALKE EIQAKYQYDT PIRVGCGGGV GTPDAALATF
NMGAAYIVTG SINQACVEAG ASDHTRKLLA TTEMADVTMA
PAADMFEMGV KLQVVKRGTL FPMRANKLYE IYTRYDSIEA
IPLDEREKLE KQVFRSSLDE IWAGTVAHFN ERDPKQIERA
EGNPKRKMAL IFRWYLGLSS RWSNSGEVGR EMDYQIWAGP
ALGAFNQWAK GSYLDNYQDR NAVDLAKHLM YGAAYLNRIN
SLTAQGVKVP AQLLRWKPNQ RMA
                      *
                    32358

FIG. 4J

32834
*
MRKPLQTINY DYAVWDRTYS YMKSNSASAK RYYEKHEYPD
DTFKSLKVDG VFIFNRTNQP VFSKGFNHRN DIPLVFELTD
FKQHPQNIAL SPQTKQAHPP ASKPLDSPDD VPSTHGVIAT
RYGPAIYYSS TSILKSDRSG SQLGYLVFIR LIDEWFIAEL
SQYTAAGVEI AMADAADAQL ARLGANTKLN KVTATSERLI
TNVDGKPLLK LVLYHTNNQP PPMLDYSIII LLVEMSFLLI
LAYFLYSYFL VRPVRKLASD IKKMDKSREI KKLRYHYPIT
ELVKVATHFN ALMGTIQEQT KQLNEQVFID KLTNIPNRRA
FEQRLETYCQ LLARQQIGFT LIIADVDHFK EYNDTLGHLA
GDEALIKVAQ TLSQQFYRAE DICARFGGEE FIMLFRDIPD
EPLQRKLDAM LHSFAELNLP HPNSSTANYV TVSLGVCTVV
AVDDFEFKSE SHIIGSQAAL IADKALYHAK ACGRNQALSK
TTITVDEIEQ LEANKIGHQ
              *
              34327

FIG. 4K

```
AATAGATCGACTCGCAAAAGTTGCTTAAGATAGTGTCAATATAGCTTCTTATTTGTA
AATATTGTTTTTATGTGTAAACATGTTTAGTGTGTGTAAATGCTGTTAATTATCCT
TTTGGGATTGTAATAGCTGATGTTGCTGGCTAATGAGTACTTTTAGTTCGGCAATAT
CTTGCTTTAAATCGCTAACTTCAGTTTTAATTCACCCACACTTGTTGTATTTTTAA
GGCTCTCTTCCCCACCATCGACAAACCAGGATGATATGAAACCGGTAAACGTACCAA
AGAGACCGACACCTGCAGTCATGAGTAATGCCGCAATGATACGTCCGCCAGTGGTGA
CGGGGTAGTAGTCACCGTAACCAACAGTCGTTATTGTCACAAATGACCACCAAAGTG
CGTCGATGCCGTTATTGATGTTACTGCCTACTTGATCCTGTTCTAACAATAAAATAC
CGATAGCACCAAAGGTGACAAGGATGAAGGATATCGCAGATACCAGCGAAAAGGTGG
CTTTAAACCGATGTTCAAAAATCATTTTTAAGATAATTTTTGATGAGCGTATATTCT
GAATAGATCTTAATACTCTAGCGATACGAATTATGCGAATAAACTGCAGTTGCTCGA
CCATCGGAATACTCGACAGTAGGTCAATCCAACCCCATTTCATAAACTGAAATTTAT
TCTCAGCTTGGTGAAAGCGAATTACAAAGTCAGTGAAAAGAATAAGCAAATCGTAT
TATCTACGCTCGTTAATATTTCAGTGACGTTACTTGAAAAGGTAAAAATAAGTTGCA
GTAGTGATGATACGACCACATGAAGTGATAAAATAAGCATGAAAATCTGAAATGGAT
TTACATCACTGTTGTTTTGGTGCCACTTTTAAGGTTCGTTTTCACAATCTGCTGCC
TCGGTTCATTGATTTTGTTAATATAAACCTTAGTCAGTAGCAAGACAAAATATATTT
ACATCAATGTCATCGTATTATTCAACCGCGCGTCGTGTATTCAGACCAAGATCGTTG
TATATGTTAGTCATGTAGCGATGAGATTATCATGCGACAGGAGAGAATTATGTTTGT
TATTATTTTTTACGTACCTAAAGTTAATGTTGAAGAAGTAAAACAGGCGTTATTTAA
CGTCGGAGCTGGCACCATCGGTGATTATGATAGTTGTGCTTGGCAATGTTTGGGGAC
TGGGCAGTTCCAACCTTTACTTGGTAGCCAGCCACATATTGGTAAGCTAAATGAGGT
TGAATTCGTTGATGAGTTTAGAGTAGAAATGGTTTGTCGAGCAGAAAATGTAAGGGC
AGCAATAAATGCACTTATTGCTGCGCACCCTTATGAAGAACCTGCTTATCATATTCT
GCAAACATTGAATCTTGATGAGTTACCTTAAGTTAGATGCACTGCACTTAATTGGTT
CGCTGTGCTAGGTTAGCAATTAGCAATTTTGACCATGTTAGCGATAGTTTTGGCACA
```

FIG. 5-1

```
AGTGATCGATATTAAACTATCCGATTCAGATCCCATTTTTACTGCTGAATTAGGTTT
CATTACACTTGTTCTAGTGGTTTTTCCCGACAGGTGTAACTCTGTTACTTGCGTAAG
GTTGATAATCTCTACCGCATTGGCAGGAGTTACACCTGCACCAGGCATAATACTAAT
TCTACCATCTGCTTGGTTAACTAACGTTTGGATTAAGGCGCAGCCTTCTAGCGCTTG
AGCTTGTTGACCAGAGGTTAAAATACGCTCACAACCAGCAGTGATCAAGGTCTCCAA
GGCTTGTTGTGGATCATTACACAAGTCGAAAGCGCGGTGGAAGGTTACGCCGAGATC
ACGTGATGCCACCATTAAGCGTTTTAAAGCTGGCTCGTCAATATTACCATCTGCTGT
TAACGCGCCAATAACGACCCCTTGGACACCGAGTAACTTCATGAATTTGATGTCGGA
ACCATAATATCAACTTCTTGTTCGCTATATACAAAATCACCGGCGCGAGGGCGAAT
AATGGCATAAATGGGGATCGTTGCTAGATCAATAGACTTTTGTACAAAACCTGCGTT
GGCGGTCAAGCCACCTAATGCTAATGCCGAGCACAACTCAATACGATCGGCGCCAGA
TGCTTGAGCCGTCAGCAGTGATTCTATATTATCGACACATACTTCTATTGTCATTGT
CATATACTTCTCTTTAAAAAGTTTATTAAAAATAATAAAGCCAGCATAAGTCGTTTT
ATACAATATGAAAGGGGAAAAGGCGACTTAGCTCGCCTAGATCAATTATTATGGCAG
AATACTGCCGTATTGTGATTAGAAAGACAGTTTTTAAGCTCAATAGCCGTTATCGC
GTTGTTATCTACCATCGTGTAACTTTTCTGGCCTGGGTGCTTTATTAACACTGTTTC
AGTGGCTGGATTAGGGTGAAATGATTCTTTTTTCAAATCTGTTTTTTTGTATTTGAA
CGTACCTGTAATGTCTTGCTGCTCACGAAGACGTACAAATATTGGTTGCGCATAGCT
TGGTAGTGCCGCATTGACATGTTGATAGAATTCAGACGCTGAAAATTCATGAATAGG
GCAATTCAAAGTCAGCGCGACCATGCCTGCTCGGCCATCGTGATGTGGGAGCTTGAC
ACCATAAGCCACACTTTGCTCAATTTGCACAAAATCGTTAACTTGAGCTTCTACTTG
CGTCGTGGCGACATTTTCACCTTTCCAGCGGAATGTATCACCTAATCTATCCACAAA
GGAAATATGGCGATAACCTTGGTAATGAACGAGATCGCCGGTATTAAAATAACAGTC
ACCGTCTTTTAATACTGACTTAAATAGCTTTTTATTACTTTCGTTGTCATCGGTATA
ACCATCAAATGGTGAACGTTTAGTTATCTTTGTTAGCAGTAGCCCTGTTTCTCCCGT
```

FIG. 5-2

```
TTTTACTTTGGTCATTTTCCCTTTCGCATTATACACAGGTTTGTCATTGTCAATATC
ATATTGTATGACGGTAAAAGCAAGTGGAGTAACCCCCGCTGTATGCGGTAAGTTCAG
CGCATTGGAGAACACAAGATTACACTCACTGGCGCCATAGAATTCATTAATATGCTC
GATCCCAAAACGTTGTTGGAAATGATCCCAAATTTCGGGGCGTAATCCATTACCTAT
GATTTTCTTTATATTATGCTGTTTGTCTTTATTGCTAGGCGGTACATTTAATAAATA
ACGGCAGAGCTCGCCGATGTAAGTAAACGCAGTGGCATTATGAGCACGAACTTCATC
CCAAAAGCGACTTGAACTGAATTTTTCAGAAAGTGCGAGGGTTGCTGCGCTACCAAA
CACGGCGCTTAATGACACTGTCAGTGCATTGTTATCGTATAGGGGGAGTGATAAATA
CAATACATCATCAGCTGTTAAGCGTAATGATGCCATCCCCATGCCTGCCATGGATTT
AAACCAACGGTGATGGCTCATTCTTGCTGCTTTTGGCAGTCCAGTTTTTCCCGAGGT
AAAGATATAAAACGCGCAATGCTTAAGCTGTATTTGTGCTGTTGATTCAGGGTTCAA
TACTGAATATCCTGCGACTAGTGTAGATATGTTTTTATAACCATCACTCATGTCTGG
CGTTTCTAAAGCGGGTACGTAAAGACATTCTGTTGTAATGTCGATGACAAATTGGT
TTCAATATTATTAATGGCGGATGTGTATAGTTCATCTGCGATGAGTAATTTGGTATC
GACCACGCTAAGACTATGTTCGAGGATTGAATCCCGTTGTGTCGTATTTATCATACA
AGCAATCGCGCCAAGCTTGACAACTGCGAGGGCAATAATGATGGTTTCAGGCCTGTT
ATCGAGCATGATGGCGACTTTATCATTTTACCAATGCCGTATTCATGAAGGAAATG
GGCATATTGATTTGCTTGCTTATTCAATGAATCGTAACTATAACGCTGGTCTTTAAA
TTGTATTGCGATCAAGTCAGAGTTATTGACAGCTTGCTGCTCTAGTAATAAACCAAT
AGACATAAAACGTTCGGGCTTTGCTTGTTGTAAGTGCCATAAGCCTTTGATGATTGG
CTTTGGGGTTTTTAATAGATTGATGGTACTTTTCAGGAATTGTTTGCCGGTTATAAC
AGTCATAAGCTAATTCTTTTTATCAAGAAGAGGGGTTATGACACCAAATAAATGGGT
CACGCGTTGGTTTAATTTGGTTAGACTAAATGTGTTGTTTTGCTGTGATAATGCGAC
GTTCAAACAAACTTGAGAAGGTAAAAAATAGCATTTTTAAATTGAACATCAATACT
AATGTGTTGAATATCAATCAAGTTTTCTAACTGTGCGAGCACGCGTGCTTTAGCAAA
```

FIG. 5-3

```
CATGCCATGTGCTATTGCTGTTTTAAACCCCATTAGTTTCGCTGGGATAAAATGTAA
ATGGATTGGATTTGTGTCTTTGGAGATATAAGCATATTTATATACGTCAAAAGGACT
AAATTTAAACAATGAAATCGGCTCGTAAGCATAATTCGCTGGCGTATTTACTATTTT
CTCACCGCTGGAACGTTGAGATCGTTGGCACGTTTTCGCTGTTTCGTTTTCTGTAA
GAATGTCGATGTACACTCCACGCAAATTGTCCATCTACAAACACATCAATATGAGT
ATCAATGAAACGTCCTGTATCCGTTATGTACTCCTTAATTACACGACATGTGCTCGT
CAATATCGCGTTTAATGCTATCGGTTGATGTTGTGTTATGCGATTTCGATAATGGAC
TAGTCCTAATATAGATATCGGAAATTGTGTTGATGTCATGAGTTTCATCAATAATGG
AAAGATCATCACAAATGGATAAGTAACCGGTACATAGTTTGTGTTATTAAACCCACA
GCATTTAATATATTGCTTTAAATTTCGCTGATCTATTTTTTGTCCACTGATACTAAA
TTGCTCAGTACACACTTGTGTCGACCAAGTGTTCATCAGTGTTTTAACAATTGTATT
GAGCACTGCTTTCACATATAAAGCGAGATAATCGGTTGCTTTGTTAACAGTGTGAT
CTGGTTAGCGTGCATTGAAATAATTCATATAAGAGTATGTAGCATTTATGTTAATAT
TTTGTTTTGGAAGTTGAATTGGCGAATCCGTAATCGGTTTATGGCAGTTCGGTCAAA
TACTTCAGGTAAACTCGTTACTCATACCATTGATAGTGTTAAAGTGATTGACTGAAT
AAAGAATAGAGCTAAAAGTGGAAAAATTATGCAAGATGCGGGTATGTTATTACGCAT
TGCTTATGAGGCAATGAAAGAGTTAGAGGTTGATGTCATTGAAGTACTTTCTCGTTG
TAACATAAGTGAAGAAGTACTGAATGATAAGGATCTTCGCACACCTAATCATGCACA
AACACATTTTTGGCAAGTATTAGAAGACATATCACAAGATCCTAACATCGGCATTTC
ACTTGGTGAGAGAATGCCAGTGTTCACGGGGCAGGTATTACAGTATCTTTTTCTCAG
TAGTCCTACATTTGGTACTGGCTGGGAACGCGCAACAAAATACTTTCGATTAATCAG
TGATGCGGCAGTGTTTCTATCAAGATGGAAGGCTGTGAAGCGCGATTATCTGTGAA
CTTAGATGGTTTAGCGGAAGATGCGAATCGTCATTTGAATGATTGCCTAGTGATCGG
TGCATTTAAATTTTGTTTATATGTGACAGAAGGCGAATTTAAAGTAAGCAAAATAGC
CTTTGCTCATGCTCGCCCGAAAGATATTACTGCCTATACCAATGTATTTACATGTCC
```

FIG. 5-4

```
GATTGAGTTTGCTGCCGAAGATAATTATATTTATTTCGATGCTGATTTACTCGAACG
TCCTTCTTCGCATGCGGAGCCTGAGCTATTCGCCTTACACGATCAGCTTGCAAGCCG
TAAAATAGCCAAGTTAGAACTGCAAGATTTAGTGGATAAAGTACGTAAGGTTATTGC
ACAACAACTTGAGTCTGGTGTGGTGACTTTAGAAAGTATCGCCACTGAACTTGACAT
GAAACCACGTATGCTAAGAGCGAAGTTAGCTGACATTGATTATAACTTTAATCAAAT
ACTCGCTGATTTTCGTTGCGAGTTATCAAAAAACTGTTGGCGAATACGGACGAGTC
TATTGATCAGATTGTCTATCTCACTGGTTTTTCTGAACCAAGTACTTTTTATCGTGC
CTTTAAGCGCTGGGTTAAAATGACGCCAATTGAATATCGCCGTAGCAAACTCGCGGT
TAGGCATGCTAATCAACACGAGTCCTAAAAATTCGCTGCTTAGTGCATAGTGCATAG
TGCATAGTGCTAGTAAGCCAAGTACAAAGCGTTAAAGTTAAGTACTTGAGCGAACCA
TCAGACACCACTTACTAGATTAAGCACCTATTAATGATTGACCACAAATTCTGATCG
TATTGCCTGTGATCCCTGCAGCTTGAGGTTGCGCAAAAAAGCTATCGCTTCAGCAA
CATCAACTGGCTTACCACCTTGTTTTAATGAATTCATACGACGACCAGCTTCACGAA
CTGTAAATGGAATCGCTGCTGTCATTTTTGTTTCAATAAAGCCTGGTGCAACAGCAT
TAATGGTGATGTATTTGTCTGCAAGCGGAGTTTGCATTGCATCAACATAACCAATGA
CTGCGGCCTTAGACGTTGCATAATTAGTCTGACCAAAGTTACCCGCAATCCCACTCA
TCGAAGACACACAAACAATGCGGCCATAGTCGTTGAGCAGATCATCATTTAGCAGTC
GCTCATTGATTCTTTCCATTGCCGACAAGTTAATATCCATCAGTACATCCCAATGGT
TATCCGGCATACGTGCTAGCGTTTTGTCTTTTGTTACCCCGGCATTATGGACGATGA
TATCAAGCGACTGTTCTCGCACAAAGTCAGCAATGATATTTGGGGCGTCAGCAGCGG
TAATATCAGCAACAATGCTGCTACCTTTCAAGCAATGAGCTACTTTTTCAAGGTCCT
GTTTTAATGCCGGAATGTCTAAGCAAATAACATGTGCGCCATCACGGGCGAGTGTTT
CAGCAATAGCAGCCCCGATGCCACGTGATGCACCAGTGACAAGTGCTGTCTTTCCTT
GTAATGGTTTTGCCGTGTTACTTGTTTCGTTAATAACTTCGTTAATAACTTCGTTAA
```

FIG. 5-5

```
TAACTTCGTTAATAGCCCCATTAATCGAACCGGGTTTTACGTTAATAACCTGTGCTG
AGATATAGGCTGATTTTGCTGAGGTTAAGAAACGTAGCGGGGCCTCTAATAATTGCT
CACTACCAGGTTGTACATAGATAAGTTGACAGGTACTACCATTCTTGCCTATTTCTT
TGGCGACACTGCGACAAAACCCTTCTAAAGATCTTTGTACAGTCGCGTAGCTTACAT
CGTCAAGATGTTCACTCGGATGACCTAACACGATCACTCTGCTGCATGGCGAGAGCT
GCTTAATTACAGGTTGAAAAAACGATGTAATGCACTTAATTGCTTGCTGTTCTTAA
TGCCTGAGGCGTCGAAGATAATACCGTTGAAGCGATCTGTTTTAGCGATAGCATTAA
GGCTAATAGGTGTCGCGACTAAAGACGTTTGATTAAATTCAATATTAAGATCGGCTA
ACGCTGACGTGTTATTAGGATAAGAAATCGTGACTTCAGCATCTTTAAATGTGTTAA
GAATGGGTTTAATTAATTTGCTGTTGCTGGCTGCGCCGATGAGTAAGTTGCCAGAGA
TGAGATCGGTTCCCTGATCGTAGCGTGTTAACGTAACCGGTCGTGGCAGATTAAGCG
CTTTAAATAAACCTGATGTCCACTTGCCATTAGCGAGTTTTGCGTATGTATCCGTCA
TTTTCTAATCCTTGTTATAGTGAACAGTTTGAATCTCGAAGATGTACATGTGTTAAA
AATTATCTGATAGCTATGACTTATCTGCCACTACGTAATAATAAATAGACCAGTTCA
TTACATCGTTAATCGATATAGTATAACTAAATACTAAGTAAATTATAATGATAAGAC
TGTTATCGTACTCGGATCAAACTCTGATCAGCAAATAATCAAATTAGAGTTTTTATT
TTAAACTTGTATCAACAATGTTACATTAATGTATCTTACGTCTAATGTGCTACGGGC
ATATTTAAGTCACTAAATTAAAGGAATAAACCATGACAGGTCAAACAATAAGAAGAG
TAGCAATTATCGGCGGTAACCGTATCCCGTTTGCACGTTCAAATACAGCGTATTCAA
AACTAAGTAACCAAGATATGCTGACGGAAACTATCCGTGGCTTGGTGGTTAAATATA
ACCTACGTGGTGAACAACTGGGGGAAGTTGTTGCTGGTGCGGTAATTAAGCATTCTC
GTGATTTTAACTTAACACGTGAAGCCGTGCTAAGTGCAGGTCTTGCACCTGAAACGC
CTTGTTATGACATTCAACAAGCTTGTGGTACTGGTCTAGCTGCAGCTATCCAAGTAG
CAAACAAAATTGCGCTTGGTCAAATAGAAGCGGGTATTGCTGGTGGTTCTGATACGA
```

FIG. 5-6

```
CATCAGATGCACCGATTGCAGTCAGTGAAGGCATGCGTAGTGTATTACTTGAGCTTA
ATCGAGCTAAAACGGGTAAGCAACGTTTGAAAGCACTATCTCGTCTACGTCTAAAAC
ACTTTGCGCCACTAACGCCTGCAAATAAAGAGCCGCGTACCAAATGGCGATGGGCG
ATCATTGTCAAGTAACAGCGAAAGAGTGGAATATCTCACGTGAAGCACAAGATGCAT
TGGCCTGCGCAAGTCATCAAAAATTAGCTGCAGCATATGAAGAAGGTTTCTTTGATA
CGTTAGTTTCACCTATGGCCGGCTTAACGAAAGATAACGTATTACGCGCAGATACAA
CAGTTGAGAAACTGGCTAAATTGAAACCTTGTTTTGATAAAGTAAACGGCACTATGA
CGGCGGGTAACAGTACTAACCTTACCGATGGAGCATCAGCTGTATTACTTGCAAGTG
AAGAATGGGCAGCGGCACATAACTTACCAGTACAAGCTTATCTAACATTTGGTGAAA
CGGCCGCTATCGACTTCGTTGATAAGAAAGAAGGTCTGTTAATGGCGCCTGCATACG
CAGTGCCAAAAATGTTGAAGCGTGCTGGCCTTACATTACAAGACTTCGATTACTATG
AAATACATGAAGCATTTGCTGCGCAGTTATTAGCAACGCTAGCAGCTTGGGAAGACG
AAAAATTCTGTAAAGAAAAACTGGGTCTAGATGCTGCGCTTGGTTCAATTGATATGA
CCAAGTTAAACGTGAAAGGGAGTAGCTTAGCCACGGGTCACCCATTTGCCGCAACTG
GTGGTCGTGTTGTCGCTACGCTAGCGCAATTACTTGATCAGAAAGGTTCAGGTCGTG
GTTTGATCTCGATTTGTGCTGCTGGTGGTCAAGGTATCACGGCAATTTTAGAGAAAT
AAACGCACTGTTTATTATCTATTGATTAAGCTGTCCTGAGATACTGGATATTTTTAA
ATAAAACGCCAATACTGCAGAGTATTGGCGTTTTTTTGTAATACCAATTCCTATATA
ACGGTGCATTTTAAACACTTAATTTCCGGCATTGGTATCATAAAAAAGCAGCACCGA
AGTGCTGCTTGATTGTAGATTAACCTATTAAAATAGAGAGGCTAGAATTAGTCTTCG
TATGCTTCATTATGTACGCCAGCTGCACGACCCGATGGATCAGCATTGTTTTGGAAA
CTTTCATCCCAAGCTAATGCTTCTACAGTTGAACAAGCAACGGATTTACCAAACGGT
ACGCATTTCGCTGCTGAATCACCTGGGAAGTGATCTTCAAAGATGGCACGATAGTAG
TAACCTTCTTTCGTATCTGGTGTGTTAATTGGGAACTTAAATGCTGCACTTGCTAAC
ATTTGATCAGTTACCGCTTCTTCAACGTGTACTTTAAGTTGGTCAATCCAAGAATAA
```

FIG. 5-7

```
CCAACACCATCAGAGAATTGTTCTTTTTGACGCCATACAATTTCTTCAGGTAGTAAA
TCTTCAAATGCTTCTCGAATGATGTTTTTCTCAATGCGGTCGCCCGTGATCATTTTT
AGTTCAGGGTTTAGACGCATTGACGCATCAACAAATTCTTTATCTAAGAAAGGAACA
CGTGCTTCGATGCCCCAAGCTGCCATAGATTTGTTTGCACGTAAGCAATCAAACATA
TGTAATTTATTTACTTTACGTACCGTCTCTTCATGGAATTCTTTCGCATTTGGCGCT
TTGTGGAAGTACAAGTAACCACCGAACAGTTCATCAGCACCTTCACCAGAAAGCACC
ATCTTAATCCCCATGGCTTTAATTTTACGTGCCATTAGGTACATAGGGGTTGATGCA
CGAATTGTTGTTACATCGTAGGTTTCAATGTGGTAAATCACGTCGCGTAAAGCGTCG
ATACCTTCTTGCACAGTAAATTCAATTGAATGATGGATAGTACCTAAGTGATCTGCC
ACTTTTTGTGCAGCGGCTAAATCTGGAGAACCATTTAGGCCTACAGAGAAAGAGTGT
AGTTGTGGCCACCATGCTTCGGTTTTACCACCGTCTTCAATACGACGTTTTGCATAC
TGTTGGGTGATTGCTGAAATAACAGATGAATCTAACCCGCCTGATAATAATACGCCG
TAAGGTACATCACACATTAATTGACGTTTAACTGCATCTTCCAAACCTTGCTTAACA
ACGCTTTTATCACCACCATTTTGTGCAACGTTATCAAAATCTTTCCAATCACGTTGA
TAATAAGGCGTGACTACACCATCCTTACTCCACAGGTAATGACCTGCTGGGAATTCT
TCAATTTGAGTACAAATTGGCACTAGTGCTTTCATTTCAGAGGCAACATAAAAGTTA
CCGTGTTCATCATAGCCCGTATAAAGAGGGATGATACCGATATGGTCACGGCCAATC
AGGTAAGCGTCCTCTGTTTCGTCATATAAAGCGAAAGCAAAATACCATTTAGATCA
TCTAAAAATTGTGTGCCTTTTTCTTTATATAGCGCAAGTATCACTTCGCAATCTGAT
TCTGTTTGGAATTCAAAGTCTACGTTCAGCGTTTTCTTTAAATCTTTGTGGTTATAA
ATTTCACCATTAACAGCAAGTACGTGTGTCTTTTCTTCATTATATAGCGGCTGTGCA
CCATTATTTACATCGACAATAGCAAGACGTTCATGAACTAAAATAGCATTGTCACTT
GTATAGATACCTGACCAATCTGGGCCGCGGTGACGTAGTAACTTTGATAGTTCTAGT
GCTTGTTCGCGAAGAGGTTTAATGTCTGATTTGATGTCTAGAATTCCGAATATTGAG
```

FIG. 5-8

```
CACATAACTAATTCCTTCTGGGGCTGCGTCTGCAGCTAACTTTCTAAATAGTGTGTC
TAATTTGCCACATTGTAGATTTAATGCAAACATTAATGATAAACATTTATAAAAAA
TGTAATTCAATGTGGAATCGATAATTTAATGGCTTAAAAGTGAAGATCCATTAATTG
TGATGGCGAGGTGATAGACCAATGTAGACCTTAATGAATAAAGCAGGCACGATTGAA
TCCATTCAACGCAAAGTGGTACTAACTATTGTTTTAAACGTTATAAATAGTGTTTTA
AAGGTTATAAGTAAATAATTTAAAAACAATAATAATCCACATGCATTAAATTTATCA
TGATAAACCGCTATATCTCAATGGCAATTTGGGATAAGTGTAAAATATATGTAAAAT
GAATGAGTTGACTTGCTTTTTTTACACTAAGTGATGAAATTAAAGCTAGATGTCGTT
GTTAGCATTGATTAATAACGTACTAAAATACGACATCTAGTATAGAAATTTAAAAAA
CAGTTGGTTTTGATAGCATAACTGCATAAACTAATCAGCTTATTGTCTGTAATATTT
TTGTAATTTAAATAGGTTTAATAAAATTATATGTCTGATAAATATAAACCGTACGAC
CTTTCCTTTAAAAGACGTTTTTGCTGCCTAAGTTTTGGCCTGTGTGGTTCGGGGTG
TTTGCAATATACTTATTAGCTTTTATGCCAGTAAAGCCGCGTGATAAATTTGCTCGA
TTCATAGCGAAGAAATTGTTTAGTCTAAAAATGATGGCAAAGCGTAAAAGGTAGCA
AAGATCAATTTATCTATGTGCTTCCCTGAAATGGATGATACGGAACAAGACCGTATA
ATCATGGTCAATCTAGTTACTTTTGTCAAACTATCTTAAGTTATGCAGAGCCAAGT
GCGCGTAGTCGTGCTTATAACCGTGACCGTATGATAGTGCATGGTGGCGAGAATTTA
TTTCCGCTACTTGAACAAGGTAAGGCTTGTATCTTATTAGTGCCGCATAGCTTCGCT
ATTGATTTGCAGGTTTACACATTGCTTCTTATGGCGCGCCATTTTGTACTATGTTT
AACAATTCTGAGAATGAGTTGTTCGATTGGCTGATGACACGTCAACGCGCTATGTTT
GGAGGCACTGTTTATCACCGCAAGGCAGGGCTAGGGGCTCTAGTTAAATCACTTAAG
AGCGGTGAAAGCTGTTATTACTTACCTGATGAAGACCATGGACCTAAGCGTAGTGTA
TTTGCGCCTTTATTTGCGACTCAAAAAGCAACTTTACCTGTAATGGGCAAGCTAGCA
GAAAAAACAAATGCACTCGTTGTTCCTGTTTATGCGGCATATAATGAATCACTAGGT
AAATTTGAAACCTTTATTCGACCAGCAATGCAAAACTTTCCATCAGAAAGCCCAGAA
CAAGATGCAGTGATGATGAATAAAGAGATTGAAGCCTTGATTGAATGTGGTGTTGAT
```

FIG. 5-9

```
CAATATATGTGGACACTTAGATTATTGAGAACACGTCCGGACGGTAAAAAATCTAC
TAATAAAGTTTAATAAACACCATAATCTTCGTTGAATATGGTGTTTACCCCCTGAA
TACCCTCTAAATTAATAACAAAAAAGCCATTTACGTAACATCTAATGATGATTTAG
CCTGCACTTGCTTTGTTTTTAGTCTTAAGAGCCTAATAAACTTGATCTAGGTATAGA
TTCTGTCTTTCTTTACGTAACGCGATCTATTTTTTTTAACCGATAGTTGTTATAATT
AGTTTCATATGAAAGAGATATCGTTTCAGTAAAAGCTATTTCGTTTCAATAGATAAT
TTATTTATAGTCATATTTTCTGTAATGACAATCATTTTCTCATCTAGACTATAGATA
AGAATACGAATTAAGTAAGAACATTAATTTTACAAGAATATAAAATATCCCATCGGA
GCTATAAGAATGAAAAGACTAAAATTGTTTGTACAATTGGTCCAAAAACTGAATCA
GTAGAGAAACTAACAGAGCTTGTTAATGCAGGCATGAACGTTATGCGTTTAAATTTC
TCTCATGGTAACTTTGCTGAACATTCAGTGCGTATTCAAAATATCCGTCAAGTAAGT
GAAAACCTGAATAAGAAAATTGCTGTTTTACTGGATACTAAAGGTCCAGAAATCCGT
ACGATTAAACTAGAAAACGGTGACGATGTAATGTTGACCGCTGGTCAGTCATTCACG
TTTACAACAGACATTAACGTGGTAGGTAATAAAGACTGTGTTGCTGTAACATATGCT
GGTTTTGCTAAAGACCTTAATCCTGGTGCAATCATCCTTGTTGATGATGGTTTAATT
GAAATGGAAGTTGTTGCAACAACTGACACTGAAGTTAAATGTACAGTATTAAATACT
GGTGCACTTGGTGAAAATAAAGGCGTTAACTTACCTAACATCAGTGTAGGTCTACCT
GCATTGTCAGAAAAAGATAAAGCTGATTTAGCGTTTGGTTGTGAGCAAGAAGTTGAT
TTTGTTGCTGCATCATTTATTCGTAAGGCTGATGATGTAAGAGAAATTCGTGAAATC
CTATTTAATAATGGTGGCGAAAACATTCAGATTATCTCGAAAATTGAAAACCAAGAA
GGTGTAGACAATTTCGATGAAATCTTAGCTGAATCAGACGGTATCATGGTTGCTCGT
GGCGATCTCGGTGTTGAGATCCCAGTTGAAGAAGTGATCATGGCACAGAAGATGATG
ATCAAAAAATGTAATAAGCAGGTAAAGTTGTAATTACTGCAACACAAATGCTTGAT
TCAATGATCAGTAACCCACGTCCAACACGTGCAGAAGCGGGCGATGTTGCCAATGCT
GTGCTTGACGGTACCGACGCGGTAATGCTTTCTGGTGAAACTGCGAAAGGTAAATAC
```

FIG. 5-10

```
CCAGTTGAAGCTGTGTCTATCATGGCAAACATCTGTGAACGTACTGATAACTCAATG
TCTTCGGATTTAGGTGCGAACATTGTTGCTAAAAGCATGCGCATTACAGAAGCTGTG
TGTAAAGGTGCGGTAGAAACAACAGAAAATTGTGTGCTCCACTTATTGTTGTTGCA
ACTCGTGGCGGTAAATCAGCAAATCTGTTCGTAAATACTTCCCGAAAGCAAATATT
CTTGCTATCACAACAAATGAAAAGCAGCGCAACAGTTATGCCTAACTAAAGGCGTA
AGCAGCTGCATCGTTGAGCAGATTGATAGCACTGATGAGTTCTACCGTAAAGGTAAA
GAGCTTGCATTAGCAACTGGTTTAGCTAAAGAAGGCGATATCGTTGTTATGGTATCA
GGTGCGTTAGTACCATCAGGTACAACGAATACGGCATCTGTTCACCAACTTTAAGTT
GCCATATTGATATTATAAAAAGAGAGCGTATGCTCTCTTTTTTTATATCTGTAGTT
TATATGTCTGTACAAAAAAATGATAAAGAGTACATAAACTATTAATATAGCGTAATA
TATAATGATTAACGGTGATGAAAGGGTTAAATAAATGGATAGTGCTAAACATAAAAT
TGGCTTAGTCCTTTCTGGCGGTGGTGCGAAAGGTATTGCTCATCTTGGTGTATTAAA
ATACCTGTTAGAGCAAGATATAAGACCGAATGTAATTGCGGGTACAAGTGCTGGCTC
TATGGTTGGTGCACTTTATTGCTCAGGACTTGAGATTGATGACATTTTACAATTCTT
CATCGATGTAAAACCTTTTTCTTGGAAGTTTACCCGTGCCCGTGCTGGCTTTATAGA
CCCGGCAAAATTATATCCTGAAGTGCTAAAATATATCCCCGAGGATAGCTTTGAGTA
CCTTCAACCTGAATTGCGCATTGTTGCCACCAACATGTTACTCGGTAAAGAGCATAT
ATTTAAAGATGGCTCCGTGATTAATGCCTTATTAGCATCAGCCAGCTACCCTTTAGT
TTTTTCTCCGATGATCATTGACGATCAAGTGTATTCAGATGGCGGTATTGTTAATCA
TTTCCCCGTGAGTGTCATTGAAGATGATTGCGATAAAATAATCGGCGTATACGTGTC
GCCCATTCGTCAGGTCGAAGCTGACGAACTCTCGAGTATAAAAGACGTGGTATTACG
TGCGTTCACGCTGCAGGGTAGTGGTGCTGAATTAGATAAACTATCGCAATGTGATGT
GCAAATTTATCCAGAAGCGCTATTGAATTACAATACGTTTGCAACCGATGAAAAATC
ATTACGGGAGATCTACCAGATTGGTTATGATGCTGCAAAAGATCAACATGACAACCT
TATGGCATTGAAAGAAAGTATCACCACCAGCGAGGTTAAAAAGAACGTCTTTAGCAA
```

FIG. 5-11

```
ATGGTTTGGTGATAAACTTGCTAGCAACAGCGGCAAATAGCGGCCCACACGGATTTA
TACACTAGGATAATGGGCGTTAATAGCCTCACTGTCGTTGTGTGGTCTCTAATTTTA
GCTAAATCTTGTGTTATACTGACTTCCTATTAATCATAAACGATTTATCACGGTAAA
CATGACTCAAATAAATAACCCGCTTCACGGCATGACACTCGAAAAGTAATTAACAG
TCTCGTTGAACAATATGGCTGGGATGGTCTTGGATACTACATCAACATTCGTTGCTT
TACTGAAAATCCAAGTGTTAAGTCTAGTCTTAAATTTTACGTAAACCCCTTGGGC
ACGTGATAAAGTAGAAGCGCTATATATCAAAATGGTGACTGAAGGCTAACTGTCTCC
ACGCTAGCGAACCGCTGTTTATAGTTAATATAAGTACTATAAGCAGGGCTCGTTAAT
TCAGTATGTAATTAATCCTGAATACCTCCGCTTATTTCAACATTGTACTCTCTAGAT
AACACTCTCAACATTACACCTTCAACATCACAGCCTCCACATAACATCCGATGACAT
AGCCCTGTTATTTTTCACATTTATCTATATGCTATATATTTTAGCCATTTGATCAAT
TGAGTTAATTTCTGCAATGACAAAGATATACCATCATCCAGTACAAATTTATTATGA
AGATACCGACCATTCTGGTGTTGTTTACCACCCTAACTTTTTAAAATACTTTGAACG
TGCACGTGAGCATGTGATAAATAGTGACTTACTAGCAACATTGTGGAATGAACGCGG
TTTAGGTTTTGCGGTGTATAAAGCCAATATGACTTTTCAGGATGGGGTCGAATTTGC
TGAAGTGTGTGATATTCGCACTTCTTTTGTCCTAGACGGTAAGTACAAAACGATCTG
GCGCCAAGAAGTATGGCGTCCGAATGCGACTAGGGCTGCCGTTATCGGTGATATTGA
AATGGTGTGCTTAGACAAACAAAAACGTTTACAGCCCATCCCTGATGATGTGTTAGC
TGCAATGGTTAGTGAATAAATGGTTCATGCATAAATAGTTAATACATGATTCTGGCC
CGTCACGTTTACAGATAAGAGGCATCCGATGCCTCCTTCCTATTACCAATACTACTG
CTTATCCCTTTCTAACTATCTTTAGCGTCCATAACACACTGAGCATTTATTCTATTA
ATCAGTGATTGTGATTTAATTATCTTCTATATATGTAATTTAATGTAATTTCAATT
TATTTTTAGCTACATTAAGGCTTACGAATGTACGCTAAAATGAGATGTCAGACTAAT
TTTAGCTTATTAATCTGTTAGCCGTTTATATTTTATAAAGATGGGATTTAACTTAAA
```

FIG. 5-12

```
TGCAATTAATTATGGCGTAAATAGAGTGAAAACATGGCTAATATTCACTAAGTCCTG
AATTTTATATAAAGTTTAATCTGTTATTTTAGCGTTTACCTGGTCTTATCAGTGAGG
TTTATAGCCATTATTAGTGGGATTGAAGTGATTTTTAAAGCTATGTATATTATTGCA
AATATAAATTGTAACAATTAAGACTTTGGACACTTGAGTTCAATTTCGAATTGATTG
GCATAAAATTTAAAACAGCTAAATCTACCTCAATCATTTTAGCAAATGTATGCAGGT
AGATTTTTTTCGCCATTTAAGAGTACACTTGTACGCTAGGTTTTTGTTTAGTGTGCA
AATGAACGTTTTGATGAGCATTGTTTTAGAGCACAAAATAGATCCTTACAGGAGCA
ATAACGCAATGGCTAAAAGAACACCACATCGATTAAGCACGCCAAGGATGTGTTAA
GTAGTGATGATCAACAGTTAAATTCTCGCTTGCAAGAATGTCCGATTGCCATCATTG
GTATGGCATCGGTTTTTGCAGATGCTAAAAACTTGGATCAATTCTGGGATAACATCG
TTGACTCTGTGGACGCTATTATTGATGTGCCTAGCGATCGCTGGAACATTGACGACC
ATTACTCGGCTGATAAAAAAGCAGCTGACAAGACATACTGCAAACGCGGTGGTTTCA
TTCCAGAGCTTGATTTTGATCCGATGGAGTTTGGTTTACCGCCAAATATCCTCGAGT
TAACTGACATCGCTCAATTGTTGTCATTAATTGTTGCTCGTGATGTATTAAGTGATG
CTGGCATTGGTAGTGATTATGACCATGATAAAATTGGTATCACGCTGGGTGTCGGTG
GTGGTCAGAAACAAATTTCGCCATTAACGTCGCGCCTACAAGGCCCGGTATTAGAAA
AAGTATTAAAAGCCTCAGGCATTGATGAAGATGATCGCGCTATGATCATCGACAAAT
TTAAAAAAGCCTACATCGGCTGGGAAGAGAACTCATTCCCAGGCATGCTAGGTAACG
TTATTGCTGGTCGTATCGCCAATCGTTTTGATTTTGGTGGTACTAACTGTGTGGTTG
ATGCGGCATGCGCTGGCTCCCTTGCAGCTGTTAAAATGGCGATCTCAGACTTACTTG
AATATCGTTCAGAAGTCATGATATCGGGTGGTGTATGTTGTGATAACTCGCCATTCA
TGTATATGTCATTCTCGAAAACACCAGCATTTACCACCAATGATGATATCCGTCCGT
TTGATGACGATTCAAAAGGCATGCTGGTTGGTGAAGGTATTGGCATGATGGCGTTTA
AACGTCTTGAAGATGCTGAACGTGACGGCGACAAAATTTATTCTGTACTGAAAGGTA
TCGGTACATCTTCAGATGGTCGTTTCAAATCTATTTACGCTCCACGCCCAGATGGCC
AAGCAAAAGCGCTAAAACGTGCTTATGAAGATGCCGGTTTTGCCCCTGAAACATGTG
```

FIG. 5-13

```
GTCTAATTGAAGGCCATGGTACGGGTACCAAAGCGGGTGATGCCGCAGAATTTGCTG
GCTTGACCAAACACTTTGGCGCCGCCAGTGATGAAAAGCAATATATCGCCTTAGGCT
CAGTTAAATCGCAAATTGGTCATACTAAATCTGCGGCTGGCTCTGCGGGTATGATTA
AGGCGGCATTAGCGCTGCATCATAAATCTTACCTGCAACGATCCATATCGATAAAC
CAAGTGAAGCCTTGGATATCAAAACAGCCCGTTATACCTAAACAGCGAAACGCGTC
CTTGGATGCCACGTGAAGATGGTATTCCACGTCGTGCAGGTATCAGCTCATTTGGTT
TTGGCGGCACCAACTTCCATATTATTTTAGAAGAGTATCGCCCAGGTCACGATAGCG
CATATCGCTTAAACTCAGTGAGCCAAACTGTGTTGATCTCGGCAAACGACCAACAAG
GTATTGTTGCTGAGTTAAATAACTGGCGTACTAAACTGGCTGTCGATGCTGATCATC
AAGGGTTTGTATTTAATGAGTTAGTGACAACGTGGCCATTAAAAACCCCATCCGTTA
ACCAAGCTCGTTTAGGTTTTGTTGCGCGTAATGCAAATGAAGCGATCGCGATGATTG
ATACGGCATTGAAACAATTCAATGCGAACGCAGATAAAATGACATGGTCAGTACCTA
CCGGGGTTTACTATCGTCAAGCCGGTATTGATGCAACAGGTAAAGTGGTTGCGCTAT
TCTCAGGGCAAGGTTCGCAATACGTGAACATGGGTCGTGAATTAACCTGTAACTTCC
CAAGCATGATGCACAGTGCTGCGGCGATGGATAAAGAGTTCAGTGCCGCTGGTTTAG
GCCAGTTATCTGCAGTTACTTTCCCTATCCCTGTTTATACGGATGCCGAGCGTAAGC
TACAAGAAGAGCAATTACGTTTAACGCAACATGCGCAACCAGCGATTGGTAGTTTGA
GTGTTGGTCTGTTCAAAACGTTTAAGCAAGCAGGTTTTAAAGCTGATTTTGCTGCCG
GTCATAGTTTCGGTGAGTTAACCGCATTATGGGCTGCCGATGTATTGAGCGAAAGCG
ATTACATGATGTTAGCGCGTAGTCGTGGTCAAGCAATGGCTGCGCCAGAGCAACAAG
ATTTTGATGCAGGTAAGATGGCCGCTGTTGTTGGTGATCCAAAGCAAGTCGCTGTGA
TCATTGATACCCTTGATGATGTCTCTATTGCTAACTTCAACTCGAATAACCAAGTTG
TTATTGCTGGTACTACGGAGCAGGTTGCTGTAGCGGTTACAACCTTAGGTAATGCTG
GTTTCAAAGTTGTGCCACTGCCGGTATCTGCTGCGTTCCATACACCTTTAGTTCGTC
ACGCGCAAAACCATTTGCTAAAGCGGTTGATAGCGCTAAATTTAAAGCGCCAAGCA
TTCCAGTGTTTGCTAATGGCACAGGCTTGGTGCATTCAAGCAAACCGAATGACATTA
```

FIG. 5-14

```
AGAAAAACCTGAAAAACCACATGCTGGAATCTGTTCATTTCAATCAAGAAATTGACA
ACATCTATGCTGATGGTGGCCGCGTATTTATCGAATTTGGTCCAAAGAATGTATTAA
CTAAATTGGTTGAAAACATTCTCACTGAAAAATCTGATGTGACTGCTATCGCGGTTA
ATGCTAATCCTAAACAACCTGCGGACGTACAAATGCGCCAAGCTGCGCTGCAAATGG
CAGTGCTTGGTGTCGCATTAGACAATATTGACCCGTACGACGCCGTTAAGCGTCCAC
TTGTTGCGCCGAAAGCATCACCAATGTTGATGAAGTTATCTGCAGCGTCTTATGTTA
GTCCGAAAACGAAGAAAGCGTTTGCTGATGCATTGACTGATGGCTGGACTGTTAAGC
AAGCGAAAGCTGTACCTGCTGTTGTGTCACAACCACAAGTGATTGAAAGATCGTTG
AAGTTGAAAAGATAGTTGAACGCATTGTCGAAGTAGAGCGTATTGTCGAAGTAGAAA
AAATCGTCTACGTTAATGCTGACGGTTCGCTTATATCGCAAAATAATCAAGACGTTA
ACAGCGCTGTTGTTAGCAACGTGACTAATAGCTCAGTGACTCATAGCAGTGATGCTG
ACCTTGTTGCCTCTATTGAACGCAGTGTTGGTCAATTTGTTGCACACCAACAGCAAT
TATTAAATGTACATGAACAGTTTATGCAAGGTCCACAAGACTACGCGAAAACAGTGC
AGAACGTACTTGCTGCGCAGACGAGCAATGAATTACCGGAAAGTTTAGACCGTACAT
TGTCTATGTATAACGAGTTCCAATCAGAAACGCTACGTGTACATGAAACGTACCTGA
ACAATCAGACGAGCAACATGAACACCATGCTTACTGGTGCTGAAGCTGATGTGCTAG
CAACCCCAATAACTCAGGTAGTGAATACAGCCGTTGCCACTAGTCACAAGGTAGTTG
CTCCAGTTATTGCTAATACAGTGACGAATGTTGTATCTAGTGTCAGTAATAACGCGG
CGGTTGCAGTGCAAACTGTGGCATTAGCGCCTACGCAAGAAATCGCTCCAACAGTCG
CTACTACGCCAGCACCCGCATTGGTTGCTATCGTGGCTGAACCTGTGATTGTTGCGC
ATGTTGCTACAGAAGTTGCACCAATTACACCATCAGTTACACCAGTTGTCGCAACTC
AAGCGGCTATCGATGTAGCAACTATTAACAAAGTAATGTTAGAAGTTGTTGCTGATA
AAACCGGTTATCCAACGGATATGCTGGAACTGAGCATGGACATGGAAGCTGACTTAG
GTATCGACTCAATCAAACGTGTTGAGATATTAGGCGCAGTACAGGAATTGATCCCTG
ACTTACCTGAACTTAATCCTGAAGATCTTGCTGAGCTACGCACGCTTGGTGAGATTG
TCGATTACATGAATTCAAAAGCCCAGGCTGTAGCTCCTACAACAGTACCTGTAACAA
```

FIG. 5-15

```
GTGCACCTGTTTCGCCTGCATCTGCTGGTATTGATTTAGCCCACATCCAAAACGTAA
TGTTAGAAGTGGTTGCAGACAAAACCGGTTACCCAACAGACATGCTAGAACTGAGCA
TGGATATGGAAGCTGACTTAGGTATTGATTCAATCAAGCGTGTGGAAATCTTAGGTG
CAGTACAGGAGATCATAACTGATTTACCTGAGCTAAACCCTGAAGATCTTGCTGAAT
TACGCACCCTAGGTGAAATCGTTAGTTACATGCAAAGCAAAGCGCCAGTCGCTGAAA
GTGCGCCAGTGGCGACGGCTCCTGTAGCAACAAGCTCAGCACCGTCTATCGATTTGA
ACCACATTCAAACAGTGATGATGGATGTAGTTGCAGATAAGACTGGTTATCCAACTG
ACATGCTAGAACTTGGCATGGACATGGAAGCTGATTTAGGTATCGATTCAATCAAAC
GTGTGGAAATATTAGGCGCAGTGCAGGAGATCATCACTGATTTACCTGAGCTAAACC
CAGAAGACCTCGCTGAATTACGCACGCTAGGTGAAATCGTTAGTTACATGCAAAGCA
AAGCGCCAGTCGCTGAGAGTGCGCCAGTAGCGACGGCTTCTGTAGCAACAAGCTCTG
CACCGTCTATCGATTTAAACCATATCCAAACAGTGATGATGGAAGTGGTTGCAGACA
AAACCGGTTATCCAGTAGACATGTTAGAACTTGCTATGGACATGGAAGCTGACCTAG
GTATCGATTCAATCAAGCGTGTAGAAATTTTAGGTGCGGTACAGGAAATCATTACTG
ACTTACCTGAGCTTAACCCTGAAGATCTTGCTGAACTACGTACATTAGGTGAAATCG
TTAGTTACATGCAAAGCAAAGCGCCCGTAGCTGAAGCGCCTGCAGTACCTGTTGCAG
TAGAAAGTGCACCTACTAGTGTAACAAGCTCAGCACCGTCTATCGATTTAGACCACA
TCCAAAATGTAATGATGGATGTTGTTGCTGATAAGACTGGTTATCCTGCCAATATGC
TTGAATTAGCAATGGACATGGAAGCCGACCTTGGTATTGATTCAATCAAGCGTGTTG
AAATTCTAGGCGCGGTACAGGAGATCATTACTGATTTACCTGAACTAAACCCAGAAG
ACTTAGCTGAACTACGTACGTTAGAAGAAATTGTAACCTACATGCAAAGCAAGGCGA
GTGGTGTTACTGTAAATGTAGTGGCTAGCCCTGAAAATAATGCTGTATCAGATGCAT
TTATGCAAAGCAATGTGGCGACTATCACAGCGGCCGCAGAACATAAGGCGGAATTTA
AACCGGCGCCGAGCGCAACCGTTGCTATCTCTCGTCTAAGCTCTATCAGTAAAATAA
GCCAAGATTGTAAAGGTGCTAACGCCTTAATCGTAGCTGATGGCACTGATAATGCTG
```

FIG. 5-16

```
TGTTACTTGCAGACCACCTATTGCAAACTGGCTGGAATGTAACTGCATTGCAACCAA
CTTGGGTAGCTGTAACAACGACGAAAGCATTTAATAAGTCAGTGAACCTGGTGACTT
TAAATGGCGTTGATGAAACTGAAATCAACAACATTATTACTGCTAACGCACAATTGG
ATGCAGTTATCTATCTGCACGCAAGTAGCGAAATTAATGCTATCGAATACCCACAAG
CATCTAAGCAAGGCCTGATGTTAGCCTTCTTATTAGCGAAATTGAGTAAAGTAACTC
AAGCCGCTAAAGTGCGTGGCGCCTTTATGATTGTTACTCAGCAGGGTGGTTCATTAG
GTTTTGATGATATCGATTCTGCTACAAGTCATGATGTGAAAACAGACCTAGTACAAA
GCGGCTTAAACGGTTTAGTTAAGACACTGTCTCACGAGTGGGATAACGTATTCTGTC
GTGCGGTTGATATTGCTTCGTCATTAACGGCTGAACAAGTTGCAAGCCTTGTTAGTG
ATGAACTACTTGATGCTAACACTGTATTAACAGAAGTGGGTTATCAACAAGCTGGTA
AAGGCCTTGAACGTATCACGTTAACTGGTGTGGCTACTGACAGCTATGCATTAACAG
CTGGCAATAACATCGATGCTAACTCGGTATTTTAGTGAGTGGTGGCGCAAAAGGTG
TAACTGCACATTGTGTTGCTCGTATAGCTAAAGAATATCAGTCTAAGTTCATCTTAT
TGGGACGTTCAACGTTCTCAAGTGACGAACCGAGCTGGGCAAGTGGTATTACTGATG
AAGCGGCGTTAAAGAAAGCAGCGATGCAGTCTTTGATTACAGCAGGTGATAAACCAA
CACCCGTTAAGATCGTACAGCTAATCAAACCAATCCAAGCTAATCGTGAAATTGCGC
AAACCTTGTCTGCAATTACCGCTGCTGGTGGCCAAGCTGAATATGTTTCTGCAGATG
TAACTAATGCAGCAAGCGTACAAATGGCAGTCGCTCCAGCTATCGCTAAGTTCGGTG
CAATCACTGGCATCATTCATGGCGCGGGTGTGTTAGCTGACCAATTCATTGAGCAAA
AAACACTGAGTGATTTTGAGTCTGTTTACAGCACTAAAATTGACGGTTTGTTATCGC
TACTATCAGTCACTGAAGCAAGCAACATCAAGCAATTGGTATTGTTCTCGTCAGCGG
CTGGTTTCTACGGTAACCCCGGCCAGTCTGATTACTCGATTGCCAATGAGATCTTAA
ATAAAACCGCATACCGCTTTAAATCATTGCACCCACAAGCTCAAGTATTGAGCTTTA
ACTGGGGTCCTTGGGACGGTGGCATGGTAACGCCTGAGCTTAAACGTATGTTTGACC
AACGTGGTGTTTACATTATTCCACTTGATGCAGGTGCACAGTTATTGCTGAATGAAC
```

FIG. 5-17

```
TAGCCGCTAATGATAACCGTTGTCCACAAATCCTCGTGGGTAATGACTTATCTAAAG
ATGCTAGCTCTGATCAAAAGTCTGATGAAAGAGTACTGCTGTAAAAAAGCCACAAG
TTAGTCGTTTATCAGATGCTTTAGTAACTAAAAGTATCAAAGCGACTAACAGTAGCT
CTTTATCAAACAAGACTAGTGCTTTATCAGACAGTAGTGCTTTTCAGGTTAACGAAA
ACCACTTTTTAGCTGACCACATGATCAAAGGCAATCAGGTATTACCAACGGTATGCG
CGATTGCTTGGATGAGTGATGCAGCAAAAGCGACTTATAGTAACCGAGACTGTGCAT
TGAAGTATGTCGGTTTCGAAGACTATAAATTGTTTAAAGGTGTGGTTTTTGATGGCA
ATGAGGCGGCGGATTACCAAATCCAATTGTCGCCTGTGACAAGGGCGTCAGAACAGG
ATTCTGAAGTCCGTATTGCCGCAAAGATCTTTAGCCTGAAAAGTGACGGTAAACCTG
TGTTTCATTATGCAGCGACAATATTGTTAGCAACTCAGCCACTTAATGCTGTGAAGG
TAGAACTTCCGACATTGACAGAAGTGTTGATAGCAACAATAAAGTAACTGATGAAG
CACAAGCGTTATACAGCAATGGCACCTTGTTCCACGGTGAAAGTCTGCAGGGCATTA
AGCAGATATTAAGTTGTGACGACAAGGGCCTGCTATTGGCTTGTCAGATAACCGATG
TTGCAACAGCTAAGCAGGGATCCTTCCCGTTAGCTGACAACAATATCTTTGCCAATG
ATTTGGTTTATCAGGCTATGTTGGTCTGGGTGCGCAAACAATTTGGTTTAGGTAGCT
TACCTTCGGTGACAACGGCTTGGACTGTGTATCGTGAAGTGGTTGTAGATGAAGTAT
TTTATCTGCAACTTAATGTTGTTGAGCATGATCTATTGGGTTCACGCGGCAGTAAAG
CCCGTTGTGATATTCAATTGATTGCTGCTGATATGCAATTACTTGCCGAAGTGAAAT
CAGCGCAAGTCAGTGTCAGTGACATTTTGAACGATATGTCATGATCGAGTAAATAAT
AACGATAGGCGTCATGGTGAGCATGGCGTCTGCTTTCTTCATTTTTTAACATTAACA
ATATTAATAGCTAAACGCGGTTGCTTTAAACCAAGTAAACAAGTGCTTTTAGCTATT
ACTATTCCAAACAGGATATTAAGAGAATATGACGGAATTAGCTGTTATTGGTATGG
ATGCTAAATTTAGCGGACAAGACAATATTGACCGTGTGGAACGCGCTTTCTATGAAG
GTGCTTATGTAGGTAATGTTAGCCGCGTTAGTACCGAATCTAATGTTATTAGCAATG
GCGAAGAACAAGTTATTACTGCCATGACAGTTCTTAACTCTGTCAGTCTACTAGCGC
```

FIG. 5-18

```
AAACGAATCAGTTAAATATAGCTGATATCGCGGTGTTGCTGATTGCTGATGTAAAAA
GTGCTGATGATCAGCTTGTAGTCCAAATTGCATCAGCAATTGAAAACAGTGTGCGA
GTTGTGTTGTTATTGCTGATTAGGCCAAGCATTAAATCAAGTAGCTGATTTAGTTA
ATAACCAAGACTGTCCTGTGGCTGTAATTGGCATGAATAACTCGGTTAATTTATCTC
GTCATGATCTTGAATCTGTAACTGCAACAATCAGCTTTGATGAAACCTTCAATGGTT
ATAACAATGTAGCTGGGTTCGCGAGTTTACTTATCGCTTCAACTGCGTTTGCCAATG
CTAAGCAATGTTATATATACGCCAACATTAAGGGCTTCGCTCAATCGGGCGTAAATG
CTCAATTTAACGTTGGAAACATTAGCGATACTGCAAAGACCGCATTGCAGCAAGCTA
GCATAACTGCAGAGCAGGTTGGTTTGTTAGAAGTGTCAGCAGTCGCTGATTCGGCAA
TCGCATTGTCTGAAAGCCAAGGTTTAATGTCTGCTTATCATCATACGCAAACTTTGC
ATACTGCATTAAGCAGTGCCCGTAGTGTGACTGGTGAAGGCGGGTGTTTTTCACAGG
TCGCAGGTTTATTGAAATGTGTAATTGGTTTACATCAACGTTATATTCCGGCGATTA
AGATTGGCAACAACCGAGTGACAATCAAATGTCACGGTGGCGGAATTCACCATTCT
ATATGCCTGTAGATGCTCGACCTTGGTTCCCACATGCTGATGGCTCTGCACACATTG
CCGCTTATAGTTGTGTGACTGCTGACAGCTATTGTCATATTCTTTTACAAGAAAACG
TCTTACAAGAACTTGTTTTGAAAGAAACAGTCTTGCAAGATAATGACTTAACTGAAA
GCAAGCTTCAGACTCTTGAACAAAACAATCCAGTAGCTGATCTGCGCACTAATGGTT
ACTTTGCATCGAGCGAGTTAGCATTAATCATAGTACAAGGTAATGACGAAGCACAAT
TACGCTGTGAATTAGAAACTATTACAGGGCAGTTAAGTACTACTGGCATAAGTACTA
TCAGTATTAAACAGATCGCAGCAGACTGTTATGCCCGTAATGATACTAACAAAGCCT
ATAGCGCAGTGCTTATTGCCGAGACTGCTGAAGAGTTAAGCAAAGAAATAACCTTGG
CGTTTGCTGGTATCGCTAGCGTGTTTAATGAAGATGCTAAAGAATGGAAAACCCCGA
AGGGCAGTTATTTTACCGCGCAGCCTGCAAATAAACAGGCTGCTAACAGCACACAGA
ATGGTGTCACCTTCATGTACCCAGGTATTGGTGCTACATATGTTGGTTTAGGGCGTG
ATCTATTTCATCTATTCCCACAGATTTATCAGCCTGTAGCGGCTTTAGCCGATGACA
```

FIG. 5-19

```
TTGGCGAAAGTCTAAAAGATACTTTACTTAATCCACGCAGTATTAGTCGTCATAGCT
TTAAAGAACTCAAGCAGTTGGATCTGGACCTGCGCGGTAACTTAGCCAATATCGCTG
AAGCCGGTGTGGGTTTTGCTTGTGTGTTTACCAAGGTATTTGAAGAAGTCTTTGCCG
TTAAAGCTGACTTTGCTACAGGTTATAGCATGGGTGAAGTAAGCATGTATGCAGCAC
TAGGCTGCTGGCAGCAACCGGGATTGATGAGTGCTCGCCTTGCACAATCGATACCT
TTAATCATCAACTTTGCGGCGAGTTAAGAACACTACGTCAGCATTGGGGCATGGATG
ATGTAGCTAACGGTACGTTCGAGCAGATCTGGGAAACCTATACCATTAAGGCAACGA
TTGAACAGGTCGAAATTGCCTCTGCAGATGAAGATCGTGTGTATTGCACCATTATCA
ATACACCTGATAGCTTGTTGTTAGCCGGTTATCCAGAAGCCTGTCAGCGAGTCATTA
AGAATTTAGGTGTGCGTGCAATGGCATTGAATATGGCGAACGCAATTCACAGCGCGC
CAGCTTATGCCGAATACGATCATATGGTTGAGCTATACCATATGGATGTTACTCCAC
GTATTAATACCAAGATGTATTCAAGCTCATGTTATTTACCGATTCCACAACGCAGCA
AAGCGATTTCCCACAGTATTGCTAAATGTTTGTGTGATGTGGTGGATTTCCCACGTT
TGGTTAATACCTTACATGACAAAGGTGCGCGGGTATTCATTGAAATGGGTCCAGGTC
GTTCGTTATGTAGCTGGGTAGATAAGATCTTAGTTAATGGCGATGGCGATAATAAAA
AGCAAAGCCAACATGTATCTGTTCCTGTGAATGCCAAAGGCACCAGTGATGAACTTA
CTTATATTCGTGCGATTGCTAAGTTAATTAGTCATGGCGTGAATTTGAATTTAGATA
GCTTGTTTAACGGGTCAATCCTGGTTAAAGCAGGCCATATAGCAAACACGAACAAAT
AGTCAACATCGATATCTAGCGCTGGTGAGTTATACCTCATTAGTTGAAATATGGATT
TAAAGAGAGTAATTATGGAAAATATTGCAGTAGTAGGTATTGCTAATTTGTTCCCGG
GCTCACAAGCACCGGATCAATTTTGGCAGCAATTGCTTGAACAACAAGATTGCCGCA
GTAAGGCGACCGCTGTTCAAATGGGCGTTGATCCTGCTAAATATACCGCCAACAAAG
GTGACACAGATAAATTTTACTGTGTGCACGGCGGTTACATCAGTGATTTCAATTTTG
ATGCTTCAGGTTATCAACTCGATAATGATTATTTAGCCGGTTTAGATGACCTTAATC
AATGGGGCTTTATGTTACGAAACAAGCCCTTACCGATGCGGGTTATTGGGGCAGTA
```

FIG. 5-20

```
CTGCACTAGAAAACTGTGGTGTGATTTTAGGTAATTTGTCATTCCCAACTAAATCAT
CTAATCAGCTGTTTATGCCTTTGTATCATCAAGTTGTTGATAATGCCTTAAAGGCGG
TATTACATCCTGATTTTCAATTAACGCATTACACAGCACCGAAAAAACACATGCTG
ACAATGCATTAGTAGCAGGTTATCCAGCTGCATTGATCGCGCAAGCGGCGGGTCTTG
GTGGTTCACATTTTGCACTGGATGCGGCTTGTGCTTCATCTTGTTATAGCGTTAAGT
TAGCGTGTGATTACCTGCATACGGGTAAAGCCAACATGATGCTTGCTGGTGCGGTAT
CTGCAGCAGATCCTATGTTCGTAAATATGGGTTTCTCGATATTCCAAGCTTACCCAG
CTAACAATGTACATGCCCCGTTTGACCAAAATTCACAAGGTCTATTTGCCGGTGAAG
GCGCGGGCATGATGGTATTGAAACGTCAAAGTGATGCAGTACGTGATGGTGATCATA
TTTACGCCATTATTAAAGGCGGCGCATTATCGAATGACGGTAAAGGCGAGTTTGTAT
TAAGCCCGAACACCAAGGGCCAAGTATTAGTATATGAACGTGCTTATGCCGATGCAG
ATGTTGACCCGAGTACAGTTGACTATATTGAATGTCATGCAACGGGCACACCTAAGG
GTGACAATGTTGAATTGCGTTCGATGGAAACCTTTTTCAGTCGCGTAAATAACAAAC
CATTACTGGGCTCGGTTAAATCTAACCTTGGTCATTTGTTAACTGCCGCTGGTATGC
CTGGCATGACCAAAGCTATGTTAGCGCTAGGTAAAGGTCTTATTCCTGCAACGATTA
ACTTAAAGCAACCACTGCAATCTAAAAACGGTTACTTTACTGGCGAGCAAATGCCAA
CGACGACTGTGTCTTGGCCAACAACTCCGGGTGCCAAGGCAGATAAACCGCGTACCG
CAGGTGTGAGCGTATTTGGTTTTGGTGGCAGCAACGCCCATTTGGTATTACAACAGC
CAACGCAAACACTCGAGACTAATTTTAGTGTTGCTAAACCACGTGAGCCTTTGGCTA
TTATTGGTATGGACAGCCATTTTGGTAGTGCCAGTAATTTAGCGCAGTTCAAAACCT
TATTAAATAATAATCAAAATACCTTCCGTGAATTACCAGAACAACGCTGGAAAGGCA
TGGAAAGTAACGCTAACGTCATGCAGTCGTTACAATTACGCAAAGCGCCTAAAGGCA
GTTACGTTGAACAGCTAGATATTGATTTCTTGCGTTTTAAAGTACCGCCTAATGAAA
AAGATTGCTTGATCCCGCAACAGTTAATGATGATGCAAGTGGCAGACAATGCTGCGA
AAGACGGAGGTCTAGTTGAAGGTCGTAATGTTGCGGTATTAGTAGCGATGGGCATGG
```

FIG. 5-21

```
AACTGGAATTACATCAGTATCGTGGTCGCGTTAATCTAACCACCCAAATTGAAGACA
GCTTATTACAGCAAGGTATTAACCTGACTGTTGAGCAACGTGAAGAACTGACCAATA
TTGCTAAAGACGGTGTTGCCTCGGCTGCACAGCTAAATCAGTATACGAGTTTCATTG
GTAATATTATGGCGTCACGTATTTCGGCGTTATGGGATTTTTCTGGTCCTGCTATTA
CCGTATCGGCTGAAGAAACTCTGTTTATCGTTGTGTTGAATTAGCTGAAAATCTAT
TTCAAACCAGTGATGTTGAAGCCGTTATTATTGCTGCTGTTGATTTGTCTGGTTCAA
TTGAAAACATTACTTTACGTCAGCACTACGGTCCAGTTAATGAAAAGGGATCTGTAA
GTGAATGTGGTCCGGTTAATGAAAGCAGTTCAGTAACCAACAATATTCTTGATCAGC
AACAATGGCTGGTGGGTGAAGGCGCAGCGGCTATTGTCGTTAAACCGTCATCGCAAG
TCACTGCTGAGCAAGTTTATGCGCGTATTGATGCGGTGAGTTTTGCCCCTGGTAGCA
ATGCGAAAGCAATTACGATTGCAGCGGATAAAGCATTAACACTTGCTGGTATCAGTG
CTGCTGATGTAGCTAGTGTTGAAGCACATGCAAGTGGTTTTAGTGCCGAAAATAATG
CTGAAAAACCGCGTTACCGACTTTATACCCAAGCGCAAGTATCAGTTCGGTGAAAG
CCAATATTGGTCATACGTTTAATGCCTCGGGTATGGCGAGTATTATTAAAACGGCGC
TGCTGTTAGATCAGAATACGAGTCAAGATCAGAAAAGCAAACATATTGCTATTAACG
GTCTAGGTCGTGATAACAGCTGCGCGCATCTTATCTTATCGAGTTCAGCGCAAGCGC
ATCAAGTTGCACCAGCGCCTGTATCTGGTATGGCCAAGCAACGCCCACAGTTAGTTA
AAACCATCAAACTCGGTGGTCAGTTAATTAGCAACGCGATTGTTAACAGTGCGAGTT
CATCTTTACACGCTATTAAAGCGCAGTTTGCCGGTAAGCACTTAAACAAAGTTAACC
AGCCAGTGATGATGGATAACCTGAAGCCCCAAGGTATTAGCGCTCATGCAACCAATG
AGTATGTGGTGACTGGAGCTGCTAACACTCAAGCTTCTAACATTCAAGCATCTCATG
TTCAAGCGTCAAGTCATGCACAAGAGATAGCACCAAACCAAGTTCAAAATATGCAAG
CTACAGCAGCCGCTGTAAGTTCACCCCTTTCTCAACATCAACACACAGCGCAGCCCG
TAGCGGCACCGAGCGTTGTTGGAGTGACTGTGAAACATAAAGCAAGTAACCAAATTC
ATCAGCAAGCGTCTACGCATAAAGCATTTTTAGAAAGTCGTTTAGCTGCACAGAAAA
```

FIG. 5-22

```
ACCTATCGCAACTTGTTGAATTGCAAACCAAGCTGTCAATCCAAACTGGTAGTGACA
ATACATCTAACAATACTGCGTCAACAAGCAATACAGTGCTAACAAATCCTGTATCAG
CAACGCCATTAACACTTGTGTCTAATGCGCCTGTAGTAGCGACAAACCTAACCAGTA
CAGAAGCAAAAGCGCAAGCAGCTGCTACACAAGCTGGTTTTCAGATAAAAGGACCTG
TTGGTTACAACTATCCACCGCTGCAGTTAATTGAACGTTATAATAAACCAGAAACG
TGATTTACGATCAAGCTGATTTGGTTGAATTCGCTGAAGGTGATATTGGTAAGGTAT
TTGGTGCTGAATACAATATTATTGATGGCTATTCGCGTCGTGTACGTCTGCCAACCT
CAGATTACTTGTTAGTAACACGTGTTACTGAACTTGATGCCAAGGTGCATGAATACA
AGAAATCATACATGTGTACTGAATATGATGTGCCTGTTGATGCACCGTTCTTAATTG
ATGGTCAGATCCCTTGGTCTGTTGCCGTCGAATCAGGCCAGTGTGATTTGATGTTGA
TTTCATATATCGGTATTGATTTCCAAGCGAAAGGCGAACGTGTTTACCGTTTACTTG
ATTGTGAATTAACTTTCCTTGAAGAGATGGCTTTTGGTGGCGATACTTTACGTTACG
AGATCCACATTGATTCGTATGCACGTAACGGCGAGCAATTATTATTCTTCTTCCATT
ACGATTGTTACGTAGGGGATAAGAAGGTACTTATCATGCGTAATGGTTGTGCTGGTT
TCTTTACTGACGAAGAACTTTCTGATGGTAAAGGCGTTATTCATAACGACAAAGACA
AAGCTGAGTTTAGCAATGCTGTTAAATCATCATTCACGCCGTTATTACAACATAACC
GTGGTCAATACGATTATAACGACATGATGAAGTTGGTTAATGGTGATGTTGCCAGTT
GTTTTGGTCCGCAATATGATCAAGGTGGCCGTAATCCATCATTGAAATTCTCGTCTG
AGAAGTTCTTGATGATTGAACGTATTACCAAGATAGACCCAACCGGTGGTCATTGGG
GACTAGGCCTGTTAGAAGGTCAGAAAGATTTAGACCCTGAGCATTGGTATTTCCCTT
GTCACTTTAAAGGTGATCAAGTAATGGCTGGTTCGTTGATGTCGGAAGGTTGTGGCC
AAATGGCGATGTTCTTCATGCTGTCTCTTGGTATGCATACCAATGTGAACAACGCTC
GTTTCCAACCACTACCAGGTGAATCACAAACGGTACGTTGTCGTGGGCAAGTACTGC
CACAGCGCAATACCTTAACTTACCGTATGGAAGTTACTGCGATGGGTATGCATCCAC
AGCCATTCATGAAAGCTAATATTGATATTTTGCTTGACGGTAAAGTGGTTGTTGATT
```

FIG. 5-23

```
TCAAAAACTTGAGCGTGATGATCAGCGAACAAGATGAGCATTCAGATTACCCTGTAA
CACTGCCGAGTAATGTGGCGCTTAAAGCGATTACTGCACCTGTTGCGTCAGTAGCAC
CAGCATCTTCACCCGCTAACAGCGCGGATCTAGACGAACGTGGTGTTGAACCGTTTA
AGTTTCCTGAACGTCCGTTAATGCGTGTTGAGTCAGACTTGTCTGCACCGAAAGCA
AAGGTGTGACACCGATTAAGCATTTTGAAGCGCCTGCTGTTGCTGGTCATCATAGAG
TGCCTAACCAAGCACCGTTTACACCTTGGCATATGTTTGAGTTTGCGACGGGTAATA
TTTCTAACTGTTTCGGTCCTGATTTTGATGTTTATGAAGGTCGTATTCCACCTCGTA
CACCTTGTGGCGATTTACAAGTTGTTACTCAGGTTGTAGAAGTGCAGGGCGAACGTC
TTGATCTTAAAAATCCATCAAGCTGTGTAGCTGAATACTATGTACCGGAAGACGCTT
GGTACTTTACTAAAAACAGCCATGAAAACTGGATGCCTTATTCATTAATCATGGAAA
TTGCATTGCAACCAAATGGCTTTATTTCTGGTTACATGGGCACGACGCTTAAATACC
CTGAAAAGATCTGTTCTTCCGTAACCTTGATGGTAGCGGCACGTTATTAAAGCAGA
TTGATTTACGCGGCAAGACCATTGTGAATAAATCAGTCTTGGTTAGTACGGCTATTG
CTGGTGGCGCGATTATTCAAAGTTTCACGTTTGATATGTCTGTAGATGGCGAGCTAT
TTTATACTGGTAAAGCTGTATTTGGTTACTTTAGTGGTGAATCACTGACTAACCAAC
TGGGCATTGATAACGGTAAAACGACTAATGCGTGGTTTGTTGATAACAATACCCCCG
CAGCGAATATTGATGTGTTTGATTTAACTAATCAGTCATTGGCTCTGTATAAAGCGC
CTGTGGATAAACCGCATTATAAATTGGCTGGTGGTCAGATGAACTTTATCGATACAG
TGTCAGTGGTTGAAGGCGGTGGTAAAGCGGGCGTGGCTTATGTTTATGGCGAACGTA
CGATTGATGCTGATGATTGGTTCTTCCGTTATCACTTCCACCAAGATCCGGTGATGC
CAGGTTCATTAGGTGTTGAAGCTATTATTGAGTTGATGCAGACCTATGCGCTTAAAA
ATGATTTGGGTGGCAAGTTTGCTAACCCACGTTTCATTGCGCCGATGACGCAAGTTG
ATTGGAAATACCGTGGGCAAATTACGCCGCTGAATAAACAGATGTCACTGGACGTGC
ATATCACTGAGATCGTGAATGACGCTGGTGAAGTGCGAATCGTTGGTGATGCGAATC
TGTCTAAAGATGGTCTGCGTATTTATGAAGTTAAAAACATCGTTTTAAGTATTGTTG
```

FIG. 5-24

```
AAGCGTAAAGGGTCAAGTGTAACGTGCTTAAGCGCCGCATTGGTTAAAGACGCTTTG
CACGCCGTGAATCCGTCCATGGAGGCTTGGGGTTGGCATCCATGCCAACAACAGCAA
GCTTACTTTAATCAATACGGCTTGGTGTCCATTTAGACGCCTCGAACTTAGTAGTTA
ATAGACAAAATAATTTAGCTGTGGAATGAATATAGTAAGTAATCATTCGGCAGCTAC
AAAAAAGGAATTAAGAATGTCGAGTTTAGGTTTTAACAATAACAACGCAATTAACTG
GGCTTGGAAAGTAGATCCAGCGTCAGTTCATACACAAGATGCAGAAATTAAAGCAGC
TTTAATGGATCTAACTAAACCTCTCTATGTGGCGAATAATTCAGGCGTAACTGGTAT
AGCTAATCATACGTCAGTAGCAGGTGCGATCAGCAATAACATCGATGTTGATGTATT
GGCGTTTGCGCAAAAGTTAAACCCAGAAGATCTGGGTGATGATGCTTACAAGAAACA
GCACGGCGTTAAATATGCTTATCATGGCGGTGCGATGGCAAATGGTATTGCCTCGGT
TGAATTGGTTGTTGCGTTAGGTAAAGCAGGGCTGTTATGTTCATTTGGTGCTGCAGG
TCTAGTGCCTGATGCGGTTGAAGATGCAATTCGTCGTATTCAAGCTGAATTACCAAA
TGCCCTTATGCGGTTAACTTGATCCATGCACCAGCAGAAGAAGCATTAGAGCGTGG
CGCGGTTGAACGTTTCCTAAAACTTGGCGTCAAGACGGTAGAGGCTTCAGCTTACCT
TGGTTTAACTGAACACATTGTTTGGTATCGTGCTGCTGGTCTAACTAAAAACGCAGA
TGGCAGTGTTAATATCGGTAACAAGGTTATCGCTAAAGTATCGCGTACCGAAGTTGG
TCGCCGCTTTATGGAACCTGCACCGCAAAAATTACTGGATAAGTTATTAGAACAAAA
TAAGATCACCCCTGAACAAGCTGCTTTAGCGTTGCTTGTACCTATGGCTGATGATAT
TACTGGGGAAGCGGATTCTGGTGGTCATACAGATAACCGTCCGTTTTAACATTATT
ACCGACGATTATTGGTCTGCGTGATGAAGTGCAAGCGAAGTATAACTTCTCTCCTGC
ATTACGTGTTGGTGCTGGTGGTGGTATCGGAACGCCTGAAGCAGCACTCGCTGCATT
TAACATGGGCGCGGCTTATATCGTTCTGGGTTCTGTGAATCAGGCGTGTGTTGAAGC
GGGTGCATCTGAATATACTCGTAAACTGTTATCGACAGTTGAAATGGCTGATGTGAC
TATGGCACCTGCTGCAGATATGTTTGAAATGGGTGTGAAGCTGCAAGTATTAAAACG
CGGTTCTATGTTCGCGATGCGTGCGAAGAAACTGTATGACTTGTATGTGGCTTATGA
```

FIG. 5-25

```
CTCGATTGAAGATATCCCAGCTGCTGAACGTGAGAAGATTGAAAAACAAATCTTCCG
TGCAAACCTAGACGAGATTTGGGATGGCACTATCGCTTTCTTTACTGAACGCGATCC
AGAAATGCTAGCCCGTGCAACGAGTAGTCCTAAACGTAAAATGGCACTTATCTTCCG
TTGGTATCTTGGCCTTTCTTCACGCTGGTCAAACACAGGCGAGAAGGGACGTGAAAT
GGATTATCAGATTTGGGCAGGCCCAAGTTTAGGTGCATTCAACAGCTGGGTGAAAGG
TTCTTACCTTGAAGACTATACCCGCCGTGGCGCTGTAGATGTTGCTTTGCATATGCT
TAAAGGTGCTGCGTATTTACAACGTGTAAACCAGTTGAAATTGCAAGGTGTTAGCTT
AAGTACAGAATTGGCAAGTTATCGTACGAGTGATTAATGTTACTTGATGATATGTGA
ATTAATTAAAGCGCCTGAGGGCGCTTTTTTTGGTTTTTAACTCAGGTGTTGTAACTC
GAAATTGCCCCTTTCAAGTTAGATCGATTACTCACTCACAATATGTTGATATCGCAC
TTGCCATATACTTGCTCATCCAAAGCCCTATATTGATAATGGTGTTAATAGTCTTTA
ATATCCGAGTCTTTCTTCAGCATAATACTAATATAGAGACTCGACCAATGTTAAACA
CAACAAAGAATATATTCTTGTGTACTGCCTTATTATTAACGAGTGCGAGTACGACAG
CTACTACGCTAAACAATTCGATATCAGCAATTGAACAACGTATTTCTGGTCGTATCG
GTGTGGCTGTTTTAGATACGCAAAATAAACAAACGTGGGCTTACAATGGTGATGCAC
ATTTTCCGATGATGAGTACATTCAAAACCCTCGCTTGCGCGAAAATGCTAAGTGAAT
CGACAAATGGTAATCTGGATCCCAGTACTAGCTCATTGATAAAGGCTGAAGAATTAA
TCCCTTGGTCACCAGTCACTAAAACGTTTGTGAATAACACTATTACAGTGGCGAAAG
CGTGTGAAGCAACAATGCTGACCAGTGATAATACCGCGGCTAATATTGTTTTACAGT
ATATCGGAGGCCCTCAAGGCGTTACTGCATTCTTGCGAGAAATTGGTGATGAAGAGA
GTCAGTTAGATCGTATAGAACCTGAATTGAATGAAGCTAAGGTCGGAGACTTGCGTG
ATACCACGACACCGAAAGCCATAGTTACCACGCTCAACAAACTACTACTTGGTGATG
TTCTACTTGATTTGGATAAAAACCAACTTAAAACATGGATGCAAATAATAAAGTGT
CAGATCCTTTACTGCGTTCTATATTACCGCAAGGCTGGTTTATTGCCGACCGCTCAG
GTGCGGGTGGTAATGGTTCTCGAGGTATAACTGCTATGCTTTGGCACTCCGAGCGTC
```

FIG. 5-26

```
AACCGCTAATCATCAGTATTTATTTAACCGAAACTGAGTTAGCAATGGCAATGCGCA
ATGAGATTATTGTTGAGATCGGTAAGCTGATATTCAAAGAATACGCGGTGAAATAAT
AAGTTATTTTTGATAATACTTTAACGAGCGTAGCTATCGAAGTGAGGGCGTCAATT
AGACACCTTTGCTTCCCTACAAAATCTAATGTGTATTACCTCGGCTAGTACAATTG
CCCTAAGTTATTTCTGTCCAGCTTTGGCTTAGTGCAATTGCGTTAGCCAATGTGAAC
ACCAAGGGACTTTGTCGTACCATAACTACCAAGCGACTTTGTCGTTTTATCTTTTC
TTAGACAAACAGAGGTTAAATGAGTGACGCCTTCCAAATCACAGGAATGAATCCGCA
TTTCAATAAAATCTAACCCGTACCAACTCCGTACAAGTTGATCTTTAGTTGTTTAAA
ATCTATAATAAATTCAATTACGGAATTAATCCGTACAACTGGAGGTTTTATGGCTAC
TGCAAGACTTGATATCCGTTTGGATGAAGAAATCAAAGCTAAGGCTGAGAAAGCATC
AGCTTTACTCGGCTTAAAAAGTTTAACCGAATACGTTGTTCGCTTAATGGACGAAGA
TTCAACTAAAGTAGTTTCTGAGCATGAGAGTATTACCGTTGAAGCGAATGTATTCGA
CCAATTTATGGCTGCTTGTGATGAAGCGAAAGCCCCAAATAAAGCATTACTTGAAGC
CGCTGTATTTACTCAGAATGGTGAGTTTAAGTGAGTTATTCCAAACGTTTCAAAGAA
CTGGATAAATCAAAACATGACAGAGCATCATTTGACTGTGGCGAAAAGAGCTAAAT
GATTTTATCCAAACTCAAGCAGCCAAACATATGCAAGCAGGTATTAGCCGCACTCTG
GTTTTACCTGCTTCTGCGCCGTTACCAAACAAAAATATCCAATTTGCTCATTTTAT
AGTATCGCGCCAAGCTCAATTAGCCGCGATACGTTACCACAAGCAATGGCTAAAAG
TTACCACGTTATCCTATCCCTGTTTTCTTTTGGCTCAACTTGCCGTCCATAAAGAG
TTTCATGGGAGTGGGTTAGGCAAAGTTAGCTTAATTAAAGCGTTAGAGTACCTTTGG
GAATTAACTCTCACATGAGAGCTTACGCCATCGTTGTTGATTGTTAACTGAACAA
GCTGAGTCATTCTACGCTAAATATGGTTTCGACGTTCTCTGCGAAATAAATGGTCGA
GTAAGAATGTTCATATCAATGAAACAGTCAATCAGTTATTCACTTAACAGTAAGAG
TTAGTATAACAGTTGTATGAATTAAATTTATTATATTCGGTAATCTCATTGCGATCA
CGCTAGAAGTGCGAGCGGGTCAGACCGAGGCCACAATAGCAGCCGTTACGTTTAGGG
```

FIG. 5-27

```
GATGACTTAAAAAGATAACTACTACGTCAGTGGCGATCCTAGAGGATTAAAGGTTTA
TGATTCACAACATTTATTTATTGTGCTTAATTTTTTCTATCCAATATGCGCAAGCTG
TAAATATCACTGAAGTAGACTTTTATGTCAGTGATGATATCCCTAAAGATGTTGCCA
AATTAAAGATAGGTGAATCCATAACGAACTCCAGCCTTATTCTAAGTAACTCATCTA
TTCCACTCTCGCGGGAGACGGGTAACATATATTACTCTTCATCAATTGCTAACTTGA
ACTATGACTCGATAGAATTTGTTATGGCTCAATTGATGGCCGAAGATTCCAGCCTTT
ACAAGATGCTGGTAAATAGCGATAGGTTGTCCGTGCTAGTAATGACATCTTCCCAGT
CCACAGATCTCTATGGCTCGACTTACTCGGCTTATTTTCCTAATGTTGCGGTCATCG
ATTTGAATTGTGACTCGCTAACTTTAGAACATGAGCTCGGCCATCTATACGGAGCTG
AACATGAAGAAATATATGACGACTATGTCTTCTATGCTGCGATATGTGGAGACTATA
CGACTATCATGAACTCTATGCAGCCTGAAATGAAAGAAAAACAAATGATAAAGGCAT
ATTCATTCCCTGAATTAAAAGTGGATGGCTTGCAGTGCGGAAATGAAAATACGAATA
ACAAAAAGGTTATTTTAGACAATATTGGTCGGTTTAGATAGGATTGGGATATTATTC
TCATTCGGCTCTACTTAGTGCTGTTATTATGAGTGCCAGTGCTTCTATCTACGATAT
TGGTCTTAACAAGTATTTATCTATAGACGCTAAGGTGTTATGTATTTAAGGGATGTT
CAAGATGAAACTAGGTGTAAACGATGTATAGTTGTATAACATTTTTTCAACGGTTGG
AACGTTCGATTCTATCGGGTAACAAGACCGCGACGATCCGCGATAAGTCCGATAGTC
ATTACTTAGTTGGTCAGATGTTAGATGCTTGTACTCACGAAGATAATCGGAAAATGT
GTCAAATAGAAATACTGAGCATTGAATATGTGACGTTTAGTGAATTAAACCGTGCGC
ACGCCAATGCTGAAGGTTTACCGTTTTTGTTTATGCTTAAGTGGATAGTTCGAAAGA
TTTATCCGACTTCAAATGATTTATTTTTCATAAGTTTCAGAGTTGTAACTATCGATA
TCTTATAAGTCTTAGTGCACAAAACAGAACTATTTATAGCGCTCAAGAAGGCGATAA
TTTGATAATGAATTATCGCCTTGTTACTATTAAGAGACTTTAAATGACTGAGATATA
AGATATGACACGGAAGAACATATTGATCACAGGCGCAAGTTCAGGGTTGGGCCGAGG
TATGGCCATCGAATTTGCAAAATCAGGTCATAACTTAGCACTTTGTGCACGTAGACT
```

FIG. 5-28

TGATAATTTAGTTGCACTGAAAGCAGAACTCTTAGCCCTCAATCCTCACATCCAAAT

CGAAATAAAACCTCTTGATGTCAATGAACATGAACAAGTCTTCACTGTTTTCCATGA

ATTCAAAGCTGAATTTGGTACGCTTGATCGTATTATTGTTAATGCTGGATTAGGCAA

GGGTGGATCC
       *
    40138

AAATGCAATTAATTATGGCGTAAATAGAGTGAAAACATGGCTAATATTCACTAAGTC
CTGAATTTTATATAAAGTTTAATCTGTTATTTTAGCGTTTACCTGGTCTTATCAGTG
AGGTTTATAGCCATTATTAGTGGGATTGAAGTGATTTTTAAAGCTATGTATATTATT
GCAAATATAAATTGTAACAATTAAGACTTTGGACACTTGAGTTCAATTTCGAATTGA
TTGGCATAAAATTTAAAACAGCTAAATCTACCTCAATCATTTTAGCAAATGTATGCA
GGTAGATTTTTTTCGCCATTTAAGAGTACACTTGTACGCTAGGTTTTTGTTTAGTGT
GCAAATGAACGTTTTGATGAGCATTGTTTTAGAGCACAAAATAGATCCTTACAGGA
GCAATAACGCAATGGCTAAAAGAACACCACATCGATTAAGCACGCCAAGGATGTGT
TAAGTAGTGATGATCAACAGTTAAATTCTCGCTTGCAAGAATGTCCGATTGCCATCA
TTGGTATGGCATCGGTTTTTGCAGATGCTAAAAACTTGGATCAATTCTGGGATAACA
TCGTTGACTCTGTGGACGCTATTATTGATGTGCCTAGCGATCGCTGGAACATTGACG
ACCATTACTCGGCTGATAAAAAGCAGCTGACAAGACATACTGCAAACGCGGTGGTT
TCATTCCAGAGCTTGATTTTGATCCGATGGAGTTTGGTTTACCGCCAAATATCCTCG
AGTTAACTGACATCGCTCAATTGTTGTCATTAATTGTTGCTCGTGATGTATTAAGTG
ATGCTGGCATTGGTAGTGATTATGACCATGATAAAATTGGTATCACGCTGGGTGTCG
GTGGTGGTCAGAAACAAATTTCGCCATTAACGTCGCGCCTACAAGGCCCGGTATTAG
AAAAAGTATTAAAAGCCTCAGGCATTGATGAAGATGATCGCGCTATGATCATCGACA
AATTTAAAAAAGCCTACATCGGCTGGGAAGAGAACTCATTCCCAGGCATGCTAGGTA
ACGTTATTGCTGGTCGTATCGCCAATCGTTTTGATTTTGGTGGTACTAACTGTGTGG
TTGATGCGGCATGCGCTGGCTCCCTTGCAGCTGTTAAAATGGCGATCTCAGACTTAC
TTGAATATCGTTCAGAAGTCATGATATCGGGTGGTGTATGTTGTGATAACTCGCCAT
TCATGTATATGTCATTCTCGAAAACACCAGCATTTACCACCAATGATGATATCCGTC
CGTTTGATGACGATTCAAAAGGCATGCTGGTTGGTGAAGGTATTGGCATGATGGCGT
TTAAACGTCTTGAAGATGCTGAACGTGACGGCGACAAAATTTATTCTGTACTGAAAG
GTATCGGTACATCTTCAGATGGTCGTTTCAAATCTATTTACGCTCCACGCCCAGATG
GCCAAGCAAAAGCGCTAAAACGTGCTTATGAAGATGCCGGTTTTGCCCCTGAAACAT
GTGGTCTAATTGAAGGCCATGGTACGGGTACCAAAGCGGGTGATGCCGCAGAATTTG

FIG. 6-1

```
CTGGCTTGACCAAACACTTTGGCGCCGCCAGTGATGAAAAGCAATATATCGCCTTAG
GCTCAGTTAAATCGCAAATTGGTCATACTAAATCTGCGGCTGGCTCTGCGGGTATGA
TTAAGGCGGCATTAGCGCTGCATCATAAATCTTACCTGCAACGATCCATATCGATA
AACCAAGTGAAGCCTTGGATATCAAAAACAGCCCGTTATACCTAAACAGCGAAACGC
GTCCTTGGATGCCACGTGAAGATGGTATTCCACGTCGTGCAGGTATCAGCTCATTTG
GTTTTGGCGGCACCAACTTCCATATTATTTTAGAAGAGTATCGCCCAGGTCACGATA
GCGCATATCGCTTAAACTCAGTGAGCCAAACTGTGTTGATCTCGGCAAACGACCAAC
AAGGTATTGTTGCTGAGTTAAATAACTGGCGTACTAAACTGGCTGTCGATGCTGATC
ATCAAGGGTTTGTATTTAATGAGTTAGTGACAACGTGGCCATTAAAAACCCCATCCG
TTAACCAAGCTCGTTTAGGTTTTGTTGCGCGTAATGCAAATGAAGCGATCGCGATGA
TTGATACGGCATTGAAACAATTCAATGCGAACGCAGATAAAATGACATGGTCAGTAC
CTACCGGGGTTTACTATCGTCAAGCCGGTATTGATGCAACAGGTAAAGTGGTTGCGC
TATTCTCAGGGCAAGGTTCGCAATACGTGAACATGGGTCGTGAATTAACCTGTAACT
TCCCAAGCATGATGCACAGTGCTGCGGCGATGGATAAAGAGTTCAGTGCCGCTGGTT
TAGGCCAGTTATCTGCAGTTACTTTCCCTATCCCTGTTTATACGGATGCCGAGCGTA
AGCTACAAGAAGAGCAATTACGTTTAACGCAACATGCGCAACCAGCGATTGGTAGTT
TGAGTGTTGGTCTGTTCAAAACGTTTAAGCAAGCAGGTTTTAAAGCTGATTTTGCTG
CCGGTCATAGTTTCGGTGAGTTAACCGCATTATGGGCTGCCGATGTATTGAGCGAAA
GCGATTACATGATGTTAGCGCGTAGTCGTGGTCAAGCAATGGCTGCGCCAGAGCAAC
AAGATTTTGATGCAGGTAAGATGGCCGCTGTTGTTGGTGATCCAAAGCAAGTCGCTG
TGATCATTGATACCCTTGATGATGTCTCTATTGCTAACTTCAACTCGAATAACCAAG
TTGTTATTGCTGGTACTACGGAGCAGGTTGCTGTAGCGGTTACAACCTTAGGTAATG
CTGGTTTCAAAGTTGTGCCACTGCCGGTATCTGCTGCGTTCCATACACCTTTAGTTC
GTCACGCGCAAAAACCATTTGCTAAAGCGGTTGATAGCGCTAAATTTAAAGCGCCAA
GCATTCCAGTGTTTGCTAATGGCACAGGCTTGGTGCATTCAAGCAAACCGAATGACA
TTAAGAAAAACCTGAAAAACCACATGCTGGAATCTGTTCATTTCAATCAAGAAATTG
```

FIG. 6-2

ACAACATCTATGCTGATGGTGGCCGCGTATTTATCGAATTTGGTCCAAAGAATGTAT
TAACTAAATTGGTTGAAAACATTCTCACTGAAAATCTGATGTGACTGCTATCGCGG
TTAATGCTAATCCTAAACAACCTGCGGACGTACAAATGCGCCAAGCTGCGCTGCAAA
TGGCAGTGCTTGGTGTCGCATTAGACAATATTGACCCGTACGACGCCGTTAAGCGTC
CACTTGTTGCGCCGAAAGCATCACCAATGTTGATGAAGTTATCTGCAGCGTCTTATG
TTAGTCCGAAAACGAAGAAAGCGTTTGCTGATGCATTGACTGATGGCTGGACTGTTA
AGCAAGCGAAAGCTGTACCTGCTGTTGTGTCACAACCACAAGTGATTGAAAAGATCG
TTGAAGTTGAAAAGATAGTTAACGCATTGTCGAAGTAGAGCGTATTGTCGAAGTAG
AAAAAATCGTCTACGTTAATGCTGACGGTTCGCTTATATCGCAAAATAATCAAGACG
TTAACAGCGCTGTTGTTAGCAACGTGACTAATAGCTCAGTGACTCATAGCAGTGATG
CTGACCTTGTTGCCTCTATTGAACGCAGTGTTGGTCAATTTGTTGCACACCAACAGC
AATTATTAAATGTACATGAACAGTTTATGCAAGGTCCACAAGACTACGCGAAAACAG
TGCAGAACGTACTTGCTGCGCAGACGAGCAATGAATTACCGGAAAGTTTAGACCGTA
CATTGTCTATGTATAACGAGTTCCAATCAGAAACGCTACGTGTACATGAAACGTACC
TGAACAATCAGACGAGCAACATGAACACCATGCTTACTGGTGCTGAAGCTGATGTGC
TAGCAACCCCAATAACTCAGGTAGTGAATACAGCCGTTGCCACTAGTCACAAGGTAG
TTGCTCCAGTTATTGCTAATACAGTGACGAATGTTGTATCTAGTGTCAGTAATAACG
CGGCGGTTGCAGTGCAAACTGTGGCATTAGCGCCTACGCAAGAAATCGCTCCAACAG
TCGCTACTACGCCAGCACCCGCATTGGTTGCTATCGTGGCTGAACCTGTGATTGTTG
CGCATGTTGCTACAGAAGTTGCACCAATTACACCATCAGTTACACCAGTTGTCGCAA
CTCAAGCGGCTATCGATGTAGCAACTATTAACAAAGTAATGTTAGAAGTTGTTGCTG
ATAAAACCGGTTATCCAACGGATATGCTGGAACTGAGCATGGACATGGAAGCTGACT
TAGGTATCGACTCAATCAAACGTGTTGAGATATTAGGCGCAGTACAGGAATTGATCC
CTGACTTACCTGAACTTAATCCTGAAGATCTTGCTGAGCTACGCACGCTTGGTGAGA
TTGTCGATTACATGAATTCAAAAGCCCAGGCTGTAGCTCCTACAACAGTACCTGTAA

FIG. 6-3

```
CAAGTGCACCTGTTTCGCCTGCATCTGCTGGTATTGATTTAGCCCACATCCAAAACG
TAATGTTAGAAGTGGTTGCAGACAAAACCGGTTACCCAACAGACATGCTAGAACTGA
GCATGGATATGGAAGCTGACTTAGGTATTGATTCAATCAAGCGTGTGGAAATCTTAG
GTGCAGTACAGGAGATCATAACTGATTTACCTGAGCTAAACCCTGAAGATCTTGCTG
AATTACGCACCCTAGGTGAAATCGTTAGTTACATGCAAAGCAAAGCGCCAGTCGCTG
AAAGTGCGCCAGTGGCGACGGCTCCTGTAGCAACAAGCTCAGCACCGTCTATCGATT
TGAACCACATTCAAACAGTGATGATGGATGTAGTTGCAGATAAGACTGGTTATCCAA
CTGACATGCTAGAACTTGGCATGGACATGGAAGCTGATTTAGGTATCGATTCAATCA
AACGTGTGGAAATATTAGGCGCAGTGCAGGAGATCATCACTGATTTACCTGAGCTAA
ACCCAGAAGACCTCGCTGAATTACGCACGCTAGGTGAAATCGTTAGTTACATGCAAA
GCAAAGCGCCAGTCGCTGAGAGTGCGCCAGTAGCGACGGCTTCTGTAGCAACAAGCT
CTGCACCGTCTATCGATTTAAACCATATCCAAACAGTGATGATGGAAGTGGTTGCAG
ACAAAACCGGTTATCCAGTAGACATGTTAGAACTTGCTATGGACATGGAAGCTGACC
TAGGTATCGATTCAATCAAGCGTGTAGAAATTTTAGGTGCGGTACAGGAAATCATTA
CTGACTTACCTGAGCTTAACCCTGAAGATCTTGCTGAACTACGTACATTAGGTGAAA
TCGTTAGTTACATGCAAAGCAAAGCGCCCGTAGCTGAAGCGCCTGCAGTACCTGTTG
CAGTAGAAAGTGCACCTACTAGTGTAACAAGCTCAGCACCGTCTATCGATTTAGACC
ACATCCAAAATGTAATGATGGATGTTGTTGCTGATAAGACTGGTTATCCTGCCAATA
TGCTTGAATTAGCAATGGACATGGAAGCCGACCTTGGTATTGATTCAATCAAGCGTG
TTGAAATTCTAGGCGCGGTACAGGAGATCATTACTGATTTACCTGAACTAAACCCAG
AAGACTTAGCTGAACTACGTACGTTAGAAGAAATTGTAACCTACATGCAAAGCAAGG
CGAGTGGTGTTACTGTAAATGTAGTGGCTAGCCCTGAAAATAATGCTGTATCAGATG
CATTTATGCAAAGCAATGTGGCGACTATCACAGCGGCCGCAGAACATAAGGCGGAAT
TTAAACCGGCGCCGAGCGCAACCGTTGCTATCTCTCGTCTAAGCTCTATCAGTAAAA
TAAGCCAAGATTGTAAAGGTGCTAACGCCTTAATCGTAGCTGATGGCACTGATAATG
CTGTGTTACTTGCAGACCACCTATTGCAAACTGGCTGGAATGTAACTGCATTGCAAC
CAACTTGGGTAGCTGTAACAACGACGAAAGCATTTAATAAGTCAGTGAACCTGGTGA
```

FIG. 6-4

```
CTTTAAATGGCGTTGATGAAACTGAAATCAACAACATTATTACTGCTAACGCACAAT
TGGATGCAGTTATCTATCTGCACGCAAGTAGCGAAATTAATGCTATCGAATACCCAC
AAGCATCTAAGCAAGGCCTGATGTTAGCCTTCTTATTAGCGAAATTGAGTAAAGTAA
CTCAAGCCGCTAAAGTGCGTGGCGCCTTTATGATTGTTACTCAGCAGGGTGGTTCAT
TAGGTTTTGATGATATCGATTCTGCTACAAGTCATGATGTGAAAACAGACCTAGTAC
AAAGCGGCTTAAACGGTTTAGTTAAGACACTGTCTCACGAGTGGGATAACGTATTCT
GTCGTGCGGTTGATATTGCTTCGTCATTAACGGCTGAACAAGTTGCAAGCCTTGTTA
GTGATGAACTACTTGATGCTAACACTGTATTAACAGAAGTGGGTTATCAACAAGCTG
GTAAAGGCCTTGAACGTATCACGTTAACTGGTGTGGCTACTGACAGCTATGCATTAA
CAGCTGGCAATAACATCGATGCTAACTCGGTATTTTAGTGAGTGGTGGCGCAAAAG
GTGTAACTGCACATTGTGTTGCTCGTATAGCTAAAGAATATCAGTCTAAGTTCATCT
TATTGGGACGTTCAACGTTCTCAAGTGACGAACCGAGCTGGGCAAGTGGTATTACTG
ATGAAGCGGCGTTAAAGAAAGCAGCGATGCAGTCTTTGATTACAGCAGGTGATAAAC
CAACACCCGTTAAGATCGTACAGCTAATCAAACCAATCCAAGCTAATCGTGAAATTG
CGCAAACCTTGTCTGCAATTACCGCTGCTGGTGGCCAAGCTGAATATGTTTCTGCAG
ATGTAACTAATGCAGCAAGCGTACAAATGGCAGTCGCTCCAGCTATCGCTAAGTTCG
GTGCAATCACTGGCATCATTCATGGCGCGGGTGTGTTAGCTGACCAATTCATTGAGC
AAAAAACACTGAGTGATTTTGAGTCTGTTTACAGCACTAAAATTGACGGTTTGTTAT
CGCTACTATCAGTCACTGAAGCAAGCAACATCAAGCAATTGGTATTGTTCTCGTCAG
CGGCTGGTTTCTACGGTAACCCCGGCCAGTCTGATTACTCGATTGCCAATGAGATCT
TAAATAAAACCGCATACCGCTTTAAATCATTGCACCCACAAGCTCAAGTATTGAGCT
TTAACTGGGGTCCTTGGGACGGTGGCATGGTAACGCCTGAGCTTAAACGTATGTTTG
ACCAACGTGGTGTTTACATTATTCCACTTGATGCAGGTGCACAGTTATTGCTGAATG
AACTAGCCGCTAATGATAACCGTTGTCCACAAATCCTCGTGGGTAATGACTTATCTA
AAGATGCTAGCTCTGATCAAAAGTCTGATGAAAGAGTACTGCTGTAAAAAAGCCAC
AAGTTAGTCGTTTATCAGATGCTTTAGTAACTAAAAGTATCAAAGCGACTAACAGTA
```

FIG. 6-5

```
GCTCTTTATCAAACAAGACTAGTGCTTTATCAGACAGTAGTGCTTTTCAGGTTAACG
AAAACCACTTTTTAGCTGACCACATGATCAAAGGCAATCAGGTATTACCAACGGTAT
GCGCGATTGCTTGGATGAGTGATGCAGCAAAGCGACTTATAGTAACCGAGACTGTG
CATTGAAGTATGTCGGTTTCGAAGACTATAAATTGTTTAAAGGTGTGGTTTTTGATG
GCAATGAGGCGGCGGATTACCAAATCCAATTGTCGCCTGTGACAAGGGCGTCAGAAC
AGGATTCTGAAGTCCGTATTGCCGCAAGATCTTTAGCCTGAAAAGTGACGGTAAAC
CTGTGTTTCATTATGCAGCGACAATATTGTTAGCAACTCAGCCACTTAATGCTGTGA
AGGTAGAACTTCCGACATTGACAGAAAGTGTTGATAGCAACAATAAAGTAACTGATG
AAGCACAAGCGTTATACAGCAATGGCACCTTGTTCCACGGTGAAAGTCTGCAGGGCA
TTAAGCAGATATTAAGTTGTGACGACAAGGGCCTGCTATTGGCTTGTCAGATAACCG
ATGTTGCAACAGCTAAGCAGGGATCCTTCCCGTTAGCTGACAACAATATCTTTGCCA
ATGATTTGGTTTATCAGGCTATGTTGGTCTGGGTGCGCAAACAATTTGGTTTAGGTA
GCTTACCTTCGGTGACAACGGCTTGGACTGTGTATCGTGAAGTGGTTGTAGATGAAG
TATTTATCTGCAACTTAATGTTGTTGAGCATGATCTATTGGGTTCACGCGGCAGTA
AAGCCCGTTGTGATATTCAATTGATTGCTGCTGATATGCAATTACTTGCCGAAGTGA
AATCAGCGCAAGTCAGTGTCAGTGACATTTTGAACGATATGTCATGATCGAGTAAAT
AATAACGATAGGCGTCATGGTGAGCATGGCGTCTGCTTTCTTCATTTTTAACATTA
ACAATATTAATAGCTAAACGCGGTTGCTTTAAACCAAGTAAACAAGTGCTTTTAGCT
ATTACTATTCCAAACAGGATATTAAAGAGAATATGACGGAATTAGCTGTTATTGGTA
TGGATGCTAAATTTAGCGGACAAGACAATATTGACCGTGTGGAACGCGCTTTCTATG
AAGGTGCTTATGTAGGTAATGTTAGCCGCGTTAGTACCGAATCTAATGTTATTAGCA
ATGGCGAAGAACAAGTTATTACTGCCATGACAGTTCTTAACTCTGTCAGTCTACTAG
CGCAAACGAATCAGTTAAATATAGCTGATATCGCGGTGTTGCTGATTGCTGATGTAA
AAAGTGCTGATGATCAGCTTGTAGTCCAAATTGCATCAGCAATTGAAAAACAGTGTG
CGAGTTGTGTTGTTATTGCTGATTTAGGCCAAGCATTAAATCAAGTAGCTGATTTAG
```

FIG. 6-6

```
TTAATAACCAAGACTGTCCTGTGGCTGTAATTGGCATGAATAACTCGGTTAATTTAT
CTCGTCATGATCTTGAATCTGTAACTGCAACAATCAGCTTTGATGAAACCTTCAATG
GTTATAACAATGTAGCTGGGTTCGCGAGTTTACTTATCGCTTCAACTGCGTTTGCCA
ATGCTAAGCAATGTTATATATACGCCAACATTAAGGGCTTCGCTCAATCGGGCGTAA
ATGCTCAATTTAACGTTGGAAACATTAGCGATACTGCAAAGACCGCATTGCAGCAAG
CTAGCATAACTGCAGAGCAGGTTGGTTTGTTAGAAGTGTCAGCAGTCGCTGATTCGG
CAATCGCATTGTCTGAAAGCCAAGGTTTAATGTCTGCTTATCATCATACGCAAACTT
TGCATACTGCATTAAGCAGTGCCCGTAGTGTGACTGGTGAAGGCGGGTGTTTTCAC
AGGTCGCAGGTTTATTGAAATGTGTAATTGGTTTACATCAACGTTATATTCCGGCGA
TTAAAGATTGGCAACAACCGAGTGACAATCAAATGTCACGGTGGCGGAATTCACCAT
TCTATATGCCTGTAGATGCTCGACCTTGGTTCCCACATGCTGATGGCTCTGCACACA
TTGCCGCTTATAGTTGTGTGACTGCTGACAGCTATTGTCATATTCTTTTACAAGAAA
ACGTCTTACAAGAACTTGTTTTGAAAGAAACAGTCTTGCAAGATAATGACTTAACTG
AAAGCAAGCTTCAGACTCTTGAACAAAACAATCCAGTAGCTGATCTGCGCACTAATG
GTTACTTTGCATCGAGCGAGTTAGCATTAATCATAGTACAAGGTAATGACGAAGCAC
AATTACGCTGTGAATTAGAAACTATTACAGGGCAGTTAAGTACTACTGGCATAAGTA
CTATCAGTATTAAACAGATCGCAGCAGACTGTTATGCCCGTAATGATACTAACAAAG
CCTATAGCGCAGTGCTTATTGCCGAGACTGCTGAAGAGTTAAGCAAAGAAATAACCT
TGGCGTTTGCTGGTATCGCTAGCGTGTTTAATGAAGATGCTAAAGAATGGAAAACCC
CGAAGGGCAGTTATTTTACCGCGCAGCCTGCAAATAAACAGGCTGCTAACAGCACAC
AGAATGGTGTCACCTTCATGTACCCAGGTATTGGTGCTACATATGTTGGTTTAGGGC
GTGATCTATTTCATCTATTCCCACAGATTTATCAGCCTGTAGCGGCTTTAGCCGATG
ACATTGGCGAAAGTCTAAAAGATACTTTACTTAATCCACGCAGTATTAGTCGTCATA
GCTTTAAAGAACTCAAGCAGTTGGATCTGGACCTGCGCGGTAACTTAGCCAATATCG
CTGAAGCCGGTGTGGGTTTTGCTTGTGTGTTTACCAAGGTATTTGAAGAAGTCTTTG
CCGTTAAAGCTGACTTTGCTACAGGTTATAGCATGGGTGAAGTAAGCATGTATGCAG
CACTAGGCTGCTGGCAGCAACCGGGATTGATGAGTGCTCGCCTTGCACAATCGAATA
```

FIG. 6-7

```
CCTTTAATCATCAACTTTGCGGCGAGTTAAGAACACTACGTCAGCATTGGGGCATGG
ATGATGTAGCTAACGGTACGTTCGAGCAGATCTGGGAAACCTATACCATTAAGGCAA
CGATTGAACAGGTCGAAATTGCCTCTGCAGATGAAGATCGTGTGTATTGCACCATTA
TCAATACACCTGATAGCTTGTTGTTAGCCGGTTATCCAGAAGCCTGTCAGCGAGTCA
TTAAGAATTTAGGTGTGCGTGCAATGGCATTGAATATGGCGAACGCAATTCACAGCG
CGCCAGCTTATGCCGAATACGATCATATGGTTGAGCTATACCATATGGATGTTACTC
CACGTATTAATACCAAGATGTATTCAAGCTCATGTTATTTACCGATTCCACAACGCA
GCAAAGCGATTTCCCACAGTATTGCTAAATGTTTGTGTGATGTGGTGGATTTCCCAC
GTTTGGTTAATACCTTACATGACAAAGGTGCGCGGGTATTCATTGAAATGGGTCCAG
GTCGTTCGTTATGTAGCTGGGTAGATAAGATCTTAGTTAATGGCGATGGCGATAATA
AAAAGCAAAGCCAACATGTATCTGTTCCTGTGAATGCCAAAGGCACCAGTGATGAAC
TTACTTATATTCGTGCGATTGCTAAGTTAATTAGTCATGGCGTGAATTTGAATTTAG
ATAGCTTGTTTAACGGGTCAATCCTGGTTAAAGCAGGCCATATAGCAAACACGAACA
AATAGTCAACATCGATATCTAGCGCTGGTGAGTTATACCTCATTAGTTGAAATATGG
ATTTAAAGAGAGTAATTATGGAAAATATTGCAGTAGTAGGTATTGCTAATTTGTTCC
CGGGCTCACAAGCACCGGATCAATTTTGGCAGCAATTGCTTGAACAACAAGATTGCC
GCAGTAAGGCGACCGCTGTTCAAATGGGCGTTGATCCTGCTAAATATACCGCCAACA
AAGGTGACACAGATAAATTTTACTGTGTGCACGGCGGTTACATCAGTGATTTCAATT
TTGATGCTTCAGGTTATCAACTCGATAATGATTATTTAGCCGGTTTAGATGACCTTA
ATCAATGGGGGCTTTATGTTACGAAACAAGCCCTTACCGATGCGGGTTATTGGGGCA
GTACTGCACTAGAAAACTGTGGTGTGATTTTAGGTAATTTGTCATTCCCAACTAAAT
CATCTAATCAGCTGTTTATGCCTTTGTATCATCAAGTTGTTGATAATGCCTTAAAGG
CGGTATTACATCCTGATTTTCAATTAACGCATTACACAGCACCGAAAAAACACATG
CTGACAATGCATTAGTAGCAGGTTATCCAGCTGCATTGATCGCGCAAGCGGCGGGTC
TTGGTGGTTCACATTTTGCACTGGATGCGGCTTGTGCTTCATCTTGTTATAGCGTTA
AGTTAGCGTGTGATTACCTGCATACGGGTAAAGCCAACATGATGCTTGCTGGTGCGG
```

FIG. 6-8

```
TATCTGCAGCAGATCCTATGTTCGTAAATATGGGTTTCTCGATATTCCAAGCTTACC
CAGCTAACAATGTACATGCCCCGTTTGACCAAAATTCACAAGGTCTATTTGCCGGTG
AAGGCGCGGGCATGATGGTATTGAAACGTCAAAGTGATGCAGTACGTGATGGTGATC
ATATTTACGCCATTATTAAAGGCGGCGCATTATCGAATGACGGTAAAGGCGAGTTTG
TATTAAGCCCGAACACCAAGGGCCAAGTATTAGTATATGAACGTGCTTATGCCGATG
CAGATGTTGACCCGAGTACAGTTGACTATATTGAATGTCATGCAACGGGCACACCTA
AGGGTGACAATGTTGAATTGCGTTCGATGGAAACCTTTTTCAGTCGCGTAAATAACA
AACCATTACTGGGCTCGGTTAAATCTAACCTTGGTCATTTGTTAACTGCCGCTGGTA
TGCCTGGCATGACCAAAGCTATGTTAGCGCTAGGTAAAGGTCTTATTCCTGCAACGA
TTAACTTAAAGCAACCACTGCAATCTAAAAACGGTTACTTTACTGGCGAGCAAATGC
CAACGACGACTGTGTCTTGGCCAACAACTCCGGGTGCCAAGGCAGATAAACCGCGTA
CCGCAGGTGTGAGCGTATTTGGTTTTGGTGGCAGCAACGCCCATTTGGTATTACAAC
AGCCAACGCAAACACTCGAGACTAATTTTAGTGTTGCTAAACCACGTGAGCCTTTGG
CTATTATTGGTATGGACAGCCATTTTGGTAGTGCCAGTAATTTAGCGCAGTTCAAAA
CCTTATTAAATAATAATCAAAATACCTTCCGTGAATTACCAGAACAACGCTGGAAAG
GCATGGAAAGTAACGCTAACGTCATGCAGTCGTTACAATTACGCAAAGCGCCTAAAG
GCAGTTACGTTGAACAGCTAGATATTGATTTCTTGCGTTTTAAAGTACCGCCTAATG
AAAAAGATTGCTTGATCCCGCAACAGTTAATGATGATGCAAGTGGCAGACAATGCTG
CGAAAGACGGAGGTCTAGTTGAAGGTCGTAATGTTGCGGTATTAGTAGCGATGGGCA
TGGAACTGGAATTACATCAGTATCGTGGTCGCGTTAATCTAACCACCCAAATTGAAG
ACAGCTTATTACAGCAAGGTATTAACCTGACTGTTGAGCAACGTGAAGAACTGACCA
ATATTGCTAAAGACGGTGTTGCCTCGGCTGCACAGCTAAATCAGTATACGAGTTTCA
TTGGTAATATTATGGCGTCACGTATTTCGGCGTTATGGGATTTTCTGGTCCTGCTA
TTACCGTATCGGCTGAAGAAACTCTGTTTATCGTTGTGTTGAATTAGCTGAAAATC
TATTTCAAACCAGTGATGTTGAAGCCGTTATTATTGCTGCTGTTGATTTGTCTGGTT
CAATTGAAAACATTACTTTACGTCAGCACTACGGTCCAGTTAATGAAAAGGGATCTG
```

FIG. 6-9

```
TAAGTGAATGTGGTCCGGTTAATGAAAGCAGTTCAGTAACCAACAATATTCTTGATC
AGCAACAATGGCTGGTGGGTGAAGGCGCAGCGGCTATTGTCGTTAAACCGTCATCGC
AAGTCACTGCTGAGCAAGTTTATGCGCGTATTGATGCGGTGAGTTTTGCCCCTGGTA
GCAATGCGAAAGCAATTACGATTGCAGCGGATAAAGCATTAACACTTGCTGGTATCA
GTGCTGCTGATGTAGCTAGTGTTGAAGCACATGCAAGTGGTTTTAGTGCCGAAAATA
ATGCTGAAAAACCGCGTTACCGACTTTATACCCAAGCGCAAGTATCAGTTCGGTGA
AAGCCAATATTGGTCATACGTTTAATGCCTCGGGTATGGCGAGTATTATTAAAACGG
CGCTGCTGTTAGATCAGAATACGAGTCAAGATCAGAAAAGCAAACATATTGCTATTA
ACGGTCTAGGTCGTGATAACAGCTGCGCGCATCTTATCTTATCGAGTTCAGCGCAAG
CGCATCAAGTTGCACCAGCGCCTGTATCTGGTATGGCCAAGCAACGCCCACAGTTAG
TTAAAACCATCAAACTCGGTGGTCAGTTAATTAGCAACGCGATTGTTAACAGTGCGA
GTTCATCTTTACACGCTATTAAAGCGCAGTTTGCCGGTAAGCACTTAAACAAAGTTA
ACCAGCCAGTGATGATGGATAACCTGAAGCCCCAAGGTATTAGCGCTCATGCAACCA
ATGAGTATGTGGTGACTGGAGCTGCTAACACTCAAGCTTCTAACATTCAAGCATCTC
ATGTTCAAGCGTCAAGTCATGCACAAGAGATAGCACCAAACCAAGTTCAAAATATGC
AAGCTACAGCAGCCGCTGTAAGTTCACCCCTTTCTCAACATCAACACACAGCGCAGC
CCGTAGCGGCACCGAGCGTTGTTGGAGTGACTGTCAAACATAAAGCAAGTAACCAAA
TTCATCAGCAAGCGTCTACGCATAAAGCATTTTTAGAAAGTCGTTTAGCTGCACAGA
AAAACCTATCGCAACTTGTTGAATTGCAAACCAAGCTGTCAATCCAAACTGGTAGTG
ACAATACATCTAACAATACTGCGTCAACAAGCAATACAGTGCTAACAAATCCTGTAT
CAGCAACGCCATTAACACTTGTGTCTAATGCGCCTGTAGTAGCGACAAACCTAACCA
GTACAGAAGCAAAAGCGCAAGCAGCTGCTACACAAGCTGGTTTTCAGATAAAAGGAC
CTGTTGGTTACAACTATCCACCGCTGCAGTTAATTGAACGTTATAATAAACCAGAAA
ACGTGATTTACGATCAAGCTGATTTGGTTGAATTCGCTGAAGGTGATATTGGTAAGG
TATTTGGTGCTGAATACAATATTATTGATGGCTATTCGCGTCGTGTACGTCTGCCAA
CCTCAGATTACTTGTTAGTAACACGTGTTACTGAACTTGATGCCAAGGTGCATGAAT
```

FIG. 6-10

```
ACAAGAAATCATACATGTGTACTGAATATGATGTGCCTGTTGATGCACCGTTCTTAA
TTGATGGTCAGATCCCTTGGTCTGTTGCCGTCGAATCAGGCCAGTGTGATTTGATGT
TGATTTCATATATCGGTATTGATTTCCAAGCGAAAGGCGAACGTGTTTACCGTTTAC
TTGATTGTGAATTAACTTTCCTTGAAGAGATGGCTTTTGGTGGCGATACTTTACGTT
ACGAGATCCACATTGATTCGTATGCACGTAACGGCGAGCAATTATTATTCTTCTTCC
ATTACGATTGTTACGTAGGGGATAAGAAGGTACTTATCATGCGTAATGGTTGTGCTG
GTTTCTTTACTGACGAAGAACTTTCTGATGGTAAAGGCGTTATTCATAACGACAAAG
ACAAAGCTGAGTTTAGCAATGCTGTTAAATCATCATTCACGCCGTTATTACAACATA
ACCGTGGTCAATACGATTATAACGACATGATGAAGTTGGTTAATGGTGATGTTGCCA
GTTGTTTTGGTCCGCAATATGATCAAGGTGGCCGTAATCCATCATTGAAATTCTCGT
CTGAGAAGTTCTTGATGATTGAACGTATTACCAAGATAGACCCAACCGGTGGTCATT
GGGGACTAGGCCTGTTAGAAGGTCAGAAAGATTTAGACCCTGAGCATTGGTATTTCC
CTTGTCACTTTAAAGGTGATCAAGTAATGGCTGGTTCGTTGATGTCGGAAGGTTGTG
GCCAAATGGCGATGTTCTTCATGCTGTCTCTTGGTATGCATACCAATGTGAACAACG
CTCGTTTCCAACCACTACCAGGTGAATCACAAACGGTACGTTGTCGTGGGCAAGTAC
TGCCACAGCGCAATACCTTAACTTACCGTATGGAAGTTACTGCGATGGGTATGCATC
CACAGCCATTCATGAAAGCTAATATTGATATTTTGCTTGACGGTAAAGTGGTTGTTG
ATTTCAAAAACTTGAGCGTGATGATCAGCGAACAAGATGAGCATTCAGATTACCCTG
TAACACTGCCGAGTAATGTGGCGCTTAAAGCGATTACTGCACCTGTTGCGTCAGTAG
CACCAGCATCTTCACCCGCTAACAGCGCGGATCTAGACGAACGTGGTGTTGAACCGT
TTAAGTTTCCTGAACGTCCGTTAATGCGTGTTGAGTCAGACTTGTCTGCACCGAAAA
GCAAAGGTGTGACACCGATTAAGCATTTTGAAGCGCCTGCTGTTGCTGGTCATCATA
GAGTGCCTAACCAAGCACCGTTTACACCTTGGCATATGTTTGAGTTTGCGACGGGTA
ATATTTCTAACTGTTTCGGTCCTGATTTTGATGTTTATGAAGGTCGTATTCCACCTC
GTACACCTTGTGGCGATTTACAAGTTGTTACTCAGGTTGTAGAAGTGCAGGGCGAAC
GTCTTGATCTTAAAAATCCATCAAGCTGTGTAGCTGAATACTATGTACCGGAAGACG
```

FIG. 6-11

```
CTTGGTACTTTACTAAAAACAGCCATGAAAACTGGATGCCTTATTCATTAATCATGG
AAATTGCATTGCAACCAAATGGCTTTATTTCTGGTTACATGGGCACGACGCTTAAAT
ACCCTGAAAAGATCTGTTCTTCCGTAACCTTGATGGTAGCGGCACGTTATTAAAGC
AGATTGATTTACGCGGCAAGACCATTGTGAATAAATCAGTCTTGGTTAGTACGGCTA
TTGCTGGTGGCGCGATTATTCAAAGTTTCACGTTTGATATGTCTGTAGATGGCGAGC
TATTTTATACTGGTAAAGCTGTATTTGGTTACTTTAGTGGTGAATCACTGACTAACC
AACTGGGCATTGATAACGGTAAAACGACTAATGCGTGGTTTGTTGATAACAATACCC
CCGCAGCGAATATTGATGTGTTTGATTTAACTAATCAGTCATTGGCTCTGTATAAAG
CGCCTGTGGATAAACCGCATTATAAATTGGCTGGTGGTCAGATGAACTTTATCGATA
CAGTGTCAGTGGTTGAAGGCGGTGGTAAAGCGGGCGTGGCTTATGTTTATGGCGAAC
GTACGATTGATGCTGATGATTGGTTCTTCCGTTATCACTTCCACCAAGATCCGGTGA
TGCCAGGTTCATTAGGTGTTGAAGCTATTATTGAGTTGATGCAGACCTATGCGCTTA
AAAATGATTTGGGTGGCAAGTTTGCTAACCCACGTTTCATTGCGCCGATGACGCAAG
TTGATTGGAAATACCGTGGGCAAATTACGCCGCTGAATAAACAGATGTCACTGGACG
TGCATATCACTGAGATCGTGAATGACGCTGGTGAAGTGCGAATCGTTGGTGATGCGA
ATCTGTCTAAAGATGGTCTGCGTATTTATGAAGTTAAAAACATCGTTTTAAGTATTG
TTGAAGCGTAAAGGGTCAAGTGTAACGTGCTTAAGCGCCGCATTGGTTAAAGACGCT
TTGCACGCCGTGAATCCGTCCATGGAGGCTTGGGGTTGGCATCCATGCCAACAACAG
CAAGCTTACTTTAATCAATACGGCTTGGTGTCCATTTAGACGCCTCGAACTTAGTAG
TTAATAGACAAAATAATTTAGCTGTGGAATGAATATAGTAAGTAATCATTCGGCAGC
TACAAAAAAGGAATTAAGAATGTCGAGTTTAGGTTTTAACAATAACAACGCAATTAA
CTGGGCTTGGAAAGTAGATCCAGCGTCAGTTCATACACAAGATGCAGAAATTAAAGC
AGCTTTAATGGATCTAACTAAACCTCTCTATGTGGCGAATAATTCAGGCGTAACTGG
TATAGCTAATCATACGTCAGTAGCAGGTGCGATCAGCAATAACATCGATGTTGATGT
ATTGGCGTTTGCGCAAAAGTTAAACCCAGAAGATCTGGGTGATGATGCTTACAAGAA
ACAGCACGGCGTTAAATATGCTTATCATGGCGGTGCGATGGCAAATGGTATTGCCTC
```

FIG. 6-12

```
GGTTGAATTGGTTGTTGCGTTAGGTAAAGCAGGGCTGTTATGTTCATTTGGTGCTGC
AGGTCTAGTGCCTGATGCGGTTGAAGATGCAATTCGTCGTATTCAAGCTGAATTACC
AAATGGCCCTTATGCGGTTAACTTGATCCATGCACCAGCAGAAGAAGCATTAGAGCG
TGGCGCGGTTGAACGTTTCCTAAAACTTGGCGTCAAGACGGTAGAGGCTTCAGCTTA
CCTTGGTTTAACTGAACACATTGTTTGGTATCGTGCTGCTGGTCTAACTAAAAACGC
AGATGGCAGTGTTAATATCGGTAACAAGGTTATCGCTAAAGTATCGCGTACCGAAGT
TGGTCGCCGCTTTATGGAACCTGCACCGCAAAATTACTGGATAAGTTATTAGAACA
AAATAAGATCACCCCTGAACAAGCTGCTTTAGCGTTGCTTGTACCTATGGCTGATGA
TATTACTGGGGAAGCGGATTCTGGTGGTCATACAGATAACCGTCCGTTTTAACATT
ATTACCGACGATTATTGGTCTGCGTGATGAAGTGCAAGCGAAGTATAACTTCTCTCC
TGCATTACGTGTTGGTGCTGGTGGTGGTATCGGAACGCCTGAAGCAGCACTCGCTGC
ATTTAACATGGGCGCGGCTTATATCGTTCTGGGTTCTGTGAATCAGGCGTGTGTTGA
AGCGGGTGCATCTGAATATACTCGTAAACTGTTATCGACAGTTGAAATGGCTGATGT
GACTATGGCACCTGCTGCAGATATGTTTGAAATGGGTGTGAAGCTGCAAGTATTAAA
ACGCGGTTCTATGTTCGCGATGCGTGCGAAGAAACTGTATGACTTGTATGTGGCTTA
TGACTCGATTGAAGATATCCCAGCTGCTGAACGTGAGAAGATTGAAAAACAAATCTT
CCGTGCAAACCTAGACGAGATTTGGGATGGCACTATCGCTTTCTTTACTGAACGCGA
TCCAGAAATGCTAGCCCGTGCAACGAGTAGTCCTAAACGTAAAATGGCACTTATCTT
CCGTTGGTATCTTGGCCTTTCTTCACGCTGGTCAAACACAGGCGAGAAGGGACGTGA
AATGGATTATCAGATTTGGGCAGGCCCAAGTTTAGGTGCATTCAACAGCTGGGTGAA
AGGTTCTTACCTTGAAGACTATACCCGCCGTGGCGCTGTAGATGTTGCTTTGCATAT
GCTTAAAGGTGCTGCGTATTTACAACGTGTAAACCAGTTGAAATTGCAAGGTGTTAG
CTTAAGTACAGAATTGGCAAGTTATCGTACGAGTGATTAATGTTACTTGATGATATG
TGAATTAATTAAAGCGCCTGAGGGCGCTTTTTTGGTTTTTAACTCAGGTGTTGTAA
CTCGAAATTGCCCCTTTC
                *
              19227
```

FIG. 6-13

| EPA (%Fatty acids) | DHA (%Fatty acids) | 20 deg C |
|---|---|---|
| 0.00 | 0.06 | pEPAD8 |
| 0.60 | 0.70 | *4* |
| 0.64 | 0.66 | *5* |
| 0.33 | 0.22 | *6s* |
| 0.45 | 0.59 | *6l* |
| | | *23 deg C* |
| 0.02 | 0.06 | pEPAD8 |
| 0.32 | 0.62 | *4* |
| 0.27 | 0.22 | *6s* |
| 0.18 | 0.65 | *6l* |

FIGURE 16

```
AGCGAAATGC TTATCAAGAA ATTCCAAGAT CAATACATCA CTGGGAAGAA AATTCATTCC    60
CTGGTTCACT GGGTAACGTT ATTTCCGGCC GTATTGCTAA CCGCTTCGAC CTTGGTGGCA   120
TGAACTGTGT CGTTGATGCA GCATGTGCAG GCCCTCTTGC TGCATTGCGT ATGGCATTAA   180
GCGAGCTTGT TGAAGGCCGC AGCGAAATGA TGATTACAGG TGGTGTGTGT ACCGATAACT   240
CACCAACCAT GTACATGAGC TTCTCTAAAA CACCGGGCAT CACGACAAAC GAAACAATTC   300
AACCATTCGA TATTGACTCG AAAGGTATGA TGATTGGTGA AGGTATCGGT ATGATTGCGC   360
TTAAACGTCT TGAAGACGCA GAGCGTGATG GCGACCGTAT CTATTCCGTG ATTAAAGGTG   420
TTGGGTGCAT CTTCAGACGG TAATTTATTA AGAGTANTTA TGCGCNTCGT CCTGAAGGTC   480
AGGCTAAGGC ACTTAAACGT GCTTACGACG ATGCAGGTTT CGCACCGCAC ACACTTGGCT   540
TACTTGAAGC CCACGGCACA GGCACAGCAG CAGGTGATGT GGCAGAATTC AGTGGTCTTA   600
ACTCTGTATT CAGTGAAGGC AATGACGAAA AGCAACACAT CGCATTAGGT TCAGTGAAAT   660
CACAGATTGG TCACACTAAA TCAACAGCGG GTACTGCGGG TCTAATCAAA GCGTCTTTAG   720
CACTGCACCA TAAAGTACTG CCGCCAACAA TCAATGTAAC CAGCCCTAAC CCTAAACTGA   780
ATATTGAAGA CTCGCCTTTC TACCTCAATA CACAGACGCG TCCATGGATG CAACGTGTCG   840
ATGGTACACC GCGTCGTGCT GGTATTAGCT CATTTGGTTT TGGTG                  .885
```

FIG. 25

```
                            20                  40                    60
                             *                   *                     *
3-2(-VECTO   CCAAGCTAAA GCACTTAACC GTGCTTATGA AGATGCCGGT TTTGCCCCTG AAACATGTGG
             |||||||||| |||||||||| |||||||||| |||| ||||| |||||||||| ||||||||||
jmpl str +   CCAAGCTAAA GCACTTAACC GTGCCTATGA TGATGCCGGT TTTGCCCCTG AAACATGTGG
             |||||||||| |||||||||| |||| ||||| |||  ||||| |||||||||| ||||||||||
3-2(-VECTO   CCAAGCTAAA GCACTTAACC GTGCTTATGA AGATGCCGGT TTTGCCCCTG AAACATGTGG 80                 100                   120
                             *                   *                     *
3-2(-VECTO   TCTAATTGAA GGCCATGGTA CGGGTACCAA AGCGGGTGAT GCCGCAGAAT TTGCTGGCTT
             |||||||||| |||||||||| |||  ||||| | |||  |||| |||||||||| ||||||||||
jmpl str +   TCTAATTGAA GGCCATGGTA C
             |||||||||| |||||||||| |
3-2(-VECTO   TCTAATTGAA GGCCATGGTA C AGA ACGCAAAGTT GCCGCACTGT TTGGTCGCCA
                                         ||| || |||    |||||||||| | |||||||
3-2(-VECTO                               CAA AGCGGGTGAT GCCGCACTGT TTGGTCGCTT
```

FIG. 26-1

```
              140                   160                   180
               *                     *                     *
3-2(-VECTO  GACCAAACAC TTTGGGCGCCG CCAGTGATGA AAAGCAATAT ATCGCCTTAG GCTCAGTTAA jmpl str +                                              C ATTGCGCTAG GTTCAGTTAA
                                                         ||| ||||  |||||||||
3-2(-VECTO                                              T ATCGCCTTAG GCTCAGTTAA jmpl str +  AGGTTCACAA
            |||
3-2(-VECTO  GACCTAACAC 200                   220                   240
               *                     *                     *
3-2(-VECTO  ATCGCAAATT GGTCATACTA AATCTGCGGC TGGCTCTGCG GGTATGATTA AGGCGGCATT jmpl str +                                              CG GCTTCGATTT TGGCGGCATG
                                                        ||  |  | || |    ||||
3-2(-VECTO                                              CG CGTATGATTA AGGCGGCATT jmpl str +  ATCACAAATT GGTCATACTA AATCAACTGC AGGT
            ||| ||||||·|||||||||| ||||  ||||  ||
3-2(-VECTO  ATCGCAAATT GGTCATACTA AATCTGCGGC TGGC
```

FIG. 26-2

```
jmpl st +                                                              GCACTGCT GCAAGCATGA ACGCGTCGTT
                                                                       || |||  |   ||||  |||||||||
3-2(-VECTO                                                             GCTCTGCG GCTATCATTA ACGCGGCATT
                     *          *          *          *          *          *
                    260                    280                    300

3-2(-VECTO  AGCGCTGCAT CATAAAATCT TACCTGCAAC GATCCATATC GATAAACCAA GTGAAGCCTT jmpl st +   AACGGTG
            |||  ||
3-2(-VECTO  AGCGCTG jmpl st +   T
            |
3-2(-VECTO  A jmpl st +                         TCCCTGGTGC TAACCATATC AGCAAACCA
                                  | |||     ||||||||||   ||| ||
3-2(-VECTO                        TACCTGCAAC GATCCATATC GATAAACCA
                     *          *          *          *          *          *
                    320                    340                    360

3-2(-VECTO  GGATATCAAA AACAGCCCGT TATACCTAAA CAGGCGAAACG CGTCCTTGGA TGCCACGTGA
```

FIG. 26-3

```
jmpl str +                         CTCACCTT TGTATCTAAA CACTGAGACT TCGTCCATGG TTACCACGTGT
                                   |   |    ||  ||||| ||  || ||   |||||  ||  |  ||||||||
3-2(-VECTO                         CAGCCCCGT TATACCTAAA CAGCGAAACG GCGTCCTTGG ATGCCACGTGA 380                    400
                                            *                      *

3-2(-VECTO    AGATGGTATT CCACGTCGTG CAGGTATTAG CTCATTTGGT TTTGGTGGC
              |||||||||  |           |  ||| |  |||||||||  |||||||| jmpl str +    TGATGGTACG CCGCGCCGCG CGGGTATTAG CTCATTTGGT TTTGGTGGC>
              ||||||||   ||  ||  |  |  ||||||| ||||||||||  ||||||||
3-2(-VECTO    AGATGGTATT CCACGTCGTG CAGGTATTAG CTCATTTGGT TTTGGTGGC
```

FIG. 26-4

```
CGCTGCCGCCGCGTCTCGCCGCGCCGCGCCGCGCCGCCGCCGCCGCTCGCGCGCACGCC
CGCGCGTCTCGCCGCGCCTGCTGTCTCGAACGAGCTTCTCGAGAAGGCCGAGACCGTCG
TCATGGAGGTCCTCGCCGCCAAGACTGGCTACGAGACTGACATGATCGAGTCCGACATG
GAGCTCGAGACTGAGCTCGGCATTGACTCCATCAAGCGTGTCGAGATCCTCTCCGAGGT
TCAGGCCATGCTCAACGTCGAGGCCAAGGACGTCGACGCTCTCAGCCGCACTCGCACTG
TGGGTGAGGTCGTCAACGCCATGAAGGCTGAGATCGCTGGTGGCTCTGCCCCGGCGCCT
GCCGCCGCTGCCCCAGGTCCGGCTGCTGCCGCCCCTGCGCCTGCTGTCTCGAGCGAGCT
TCTCGAGAAGGCCGAGACTGTCGTCATGGAGGTCCTCGCCGCCAAGACTGGCTACGAGA
CTGACATGATTGAGTCCGACATGGAGCTCGAGACCGAGCTCGGCATTGACTCCATCAAG
CGTGTCGAGATTCTCTCCGAGGTTCAGGCCATGCTCAACGTCGAGGCCAAGGACGTCGA
CGCTCTCAGCCGCACTCGCACTGTTGGTGAGGTCGTCGATGCCATGAAGGCTGAGATCG
CTGGCAGCTCCGCCTCGGCGCCTGCCGCCGCTGCTCCTGCTCCGGCTGCTGCCGCTCCT
GCGCCCGCTGCCGCCGCCCTGCTGTCTCGAACGAGCTTCTCGAGAAAGCCGAGACTGT
CGTCATGGAGGTCCTCGCCGCCAAGACTGGCTACGAGACTGACATGATCGAGTCCGACA
TGGAGCTCGAGACTGAGCTCGGCATTGACTCCATCAAGCGTGTCGAGATCCTCTCCGAG
GTTCAGGCCATGCTCAACGTCGAGGCCAAGGACGTCGATGCCCTCAGCCGCACCCGCAC
TGTTGGCGAGGTTGTCGATGCCATGAAGGCCGAGATCGCTGGTGGCTCTGCCCCGGCGC
CTGCCGCCGCTGCCCCTGCTCCGGCTGCCGCCGCCCTGCTGTCTCGAACGAGCTTCTT
GAGAAGGCCGAGACTGTCGTCATGGAGGTCCTCGCCGCCAAGACTGGCTACGAGACCGA
CATGATCGAGTCCGACATGGAGCTCGAGACCGAGCTCGGCATTGACTCCATCAAGCGTG
TCGAGATTCTCTCCGAGGTTCAGGCCATGCTCAACGTCGAGGCCAAGGACGTCGATGCT
CTCAGCCGCACTCGCACTGTTGGCGAGGTCGTCGATGCCATGAAGGCTGAGATCGCCGG
CAGCTCCGCCCCGGCGCCTGCCGCCGCTGCTCCTGCTCCGGCTGCTGCCGCTCCTGCGC
CCGCTGCCGCTGCCCCTGCTGTCTCGAGCGAGCTTCTCGAGAAGGCCGAGACCGTCGTC
ATGGAGGTCCTCGCCGCCAAGACTGGCTACGAGACTGACATGATTGAGTCCGACATGGA
GCTCGAGACTGAGCTCGGCATTGACTCCATCAAGCGTGTCGAGATCCTCTCCGAGGTTC
AGGCCATGCTCAACGTCGAGGCCAAGGACGTCGATGCCCTCAGCCGCACCCGCACTGTT
GGCGAGGTTGTCGATGCCATGAAGGCCGAGATCGCTGGTGGCTCTGCCCCGGCGCCTGC
CGCCGCTGCCCCTGCTCCGGCTGCCGCCGCCCTGCTGTCTCGAACGAGCTTCTTGAGA
AGGCCGAGACCGTCGTCATGGAGGTCCTCGCCGCCAAGACTGGCTACGAGACCGACATG
ATCGAGTCCGACATGGAGCTCGAGACCGAGCTCGGCATTGACTCCATCAAGCGTGTCGA
GATTCTCTCCGAGGTTCAGGCCATGCTCAACGTCGAGGCCAAGGACGTCGACGCTCTCA
GCCGCACTCGCACTGTTGGCGAGGTCGTCGATGCCATGAAGGCTGAGATCGCTGGTGGC
TCTGCCCCGGCGCCTGCCGCCGCTGCTCCTGCCTCGGCTGGCGCCGCGCCTGCGGTCAA
GATTGACTCGGTCCACGGCGCTGACTGTGATGATCTTTCCCTGATGCACGCCAAGGTGG
TTGACATCCGCCGCCCGGACGAGCTCATCCTGGAGCGCCCCGAGAACCGCCCCGTTCTC
GTTGTCGATGACGGCAGCGAGCTCACCCTCGCCCTGGTCCGCGTCCTCGGCGCCTGCGC
CGTTGTCCTGACCTTTGAGGGTCTCCAGCTCGCTCAGCGCGCTGGTGCCGCTGCCATCC
GCCACGTGCTCGCCAAGGATCTTTCCGCGGAGAGCGCCGAGAAGGCCATCAAGGAGGCC
GAGCAGCGCTTTGGCGCTCTCGGCGGCTTCATCTCGCAGCAGGCGGAGCGCTTCGAGCC
CGCCGAAATCCTCGGCTTCACGCTCATGTGCGCCAAGTTCGCCAAGGCTTCCCTCTGCA
CGGCTGTGCTGGCGGCCGCCCGGCCTTTATCGGTGTGGCGCGCCTTGACGGCCGCCTC
```

FIG. 27A-1

```
GGATTCACTTCGCAGGGCACTTCTGACGCGCTCAAGCGTGCCCAGCGTGGTGCCATCTT
TGGCCTCTGCAAGACCATCGGCCTCGAGTGGTCCGAGTCTGACGTCTTTTCCCGCGGCG
TGGACATTGCTCAGGGCATGCACCCCGAGGATGCCGCCGTGGCGATTGTGCGCGAGATG
GCGTGCGCTGACATTCGCATTCGCGAGGTCGGCATTGGCGCAAACCAGCAGCGCTGCAC
GATCCGTGCCGCCAAGCTCGAGACCGGCAACCCGCAGCGCCAGATCGCCAAGGACGACG
TGCTGCTCGTTTCTGGCGGCGCTCGCGGCATCACGCCTCTTTGCATCCGGGAGATCACG
CGCCAGATCGCGGGCGGCAAGTACATTCTGCTTGGCCGCAGCAAGGTCTCTGCGAGCGA
ACCGGCATGGTGCGCTGGCATCACTGACGAGAAGGCTGTGCAAAAGGCTGCTACCCAGG
AGCTCAAGCGCGCCTTTAGCGCTGGCGAGGGCCCCAAGCCCACGCCCCGCGCTGTCACT
AAGCTTGTGGGCTCTGTTCTTGGCGCTCGCGAGGTGCGCAGCTCTATTGCTGCGATTGA
AGCGCTCGGCGGCAAGGCCATCTACTCGTCGTGCGACGTGAACTCTGCCGCCGACGTGG
CCAAGGCCGTGCGCGATGCCGAGTCCCAGCTCGGTGCCCGCGTCTCGGGCATCGTTCAT
GCCTCGGGCGTGCTCCGCGACCGTCTCATCGAGAAGAAGCTCCCCGACGAGTTCGACGC
CGTCTTTGGCACCAAGGTCACCGGTCTCGAGAACCTCCTCGCCGCCGTCGACCGCGCCA
ACCTCAAGCACATGGTCCTCTTCAGCTCGCTCGCCGGCTTCCACGGCAACGTCGGCCAG
TCTGACTACGCCATGGCCAACGAGGCCCTTAACAAGATGGGCCTCGAGCTCGCCAAGGA
CGTCTCGGTCAAGTCGATCTGCTTCGGTCCCTGGGACGGTGGCATGGTGACGCCGCAGC
TCAAGAAGCAGTTCCAGGAGATGGGCGTGCAGATCATCCCCGCGAGGGCGGCGCTGAT
ACCGTGGCGCGCATCGTGCTCGGCTCCTCGCCGGCTGAGATCCTTGTCGGCAACTGGCG
CACCCCGTCCAAGAAGGTCGGCTCGGACACCATCACCCTGCACCGCAAGATTCCGCCA
AGTCCAACCCCTTCCTCGAGGACCACGTCATCCAGGGCCGCCGCGTGCTGCCCATGACG
CTGGCCATTGGCTCGCTCGCGGAGACCTGCCTCGGCCTCTTCCCCGGCTACTCGCTCTG
GGCCATTGACGACGCCCAGCTCTTCAAGGGTGTCACTGTCGACGGCGACGTCAACTGCG
AGGTGACCCTCACCCCGTCGACGGCGCCCTCGGGCCGCGTCAACGTCCAGGCCACGCTC
AAGACCTTTTCCAGCGGCAAGCTGGTCCCGGCCTACCGCGCCGTCATCGTGCTCTCCAA
CCAGGGCGCGCCCCCGGCCAACGCCACCATGCAGCCGCCCTCGCTCGATGCCGATCCGG
CGCTCCAGGGCTCCGTCTACGACGGCAAGACCCTCTTCCACGGCCCGGCCTTCCGCGGC
ATCGATGACGTGCTCTCGTGCACCAAGAGCCAGCTTGTGGCCAAGTGCAGCGCTGTCCC
CGGCTCCGACGCCGCTCGCGGCGAGTTTGCCACGGACACTGACGCCCATGACCCCTTCG
TGAACGACCTGGCCTTTCAGGCCATGCTCGTCTGGGTGCGCCGCACGCTCGGCCAGGCT
GCGCTCCCCAACTCGATCCAGCGCATCGTCCAGCACCGCCCGGTCCCGCAGGACAAGCC
CTTCTACATTACCCTCCGCTCCAACCAGTCGGGCGGTCACTCCCAGCACAAGCACGCCC
TTCAGTTCCACAACGAGCAGGGCGATCTCTTCATTGATGTCCAGGCTTCGGTCATCGCC
ACGGACAGCCTTGCCTTCTAA
```

FIG. 27A-2

```
TGCCGTCTTTGAGGAGCATGACCCCTCCAACGCCGCCTGCACGGGCCACGACTCCATTT
CTGCGCTCTCGGCCCGCTGCGGCGGTGAAAGCAACATGCGCATCGCCATCACTGGTATG
GACGCCACCTTTGGCGCTCTCAAGGGACTCGACGCCTTCGAGCGCGCCATTTACACCGG
CGCTCACGGTGCCATCCCACTCCCAGAAAAGCGCTGGCGCTTTCTCGGCAAGGACAAGG
ACTTTCTTGACCTCTGCGGCGTCAAGGCCACCCCGCACGGCTGCTACATTGAAGATGTT
GAGGTCGACTTCCAGCGCCTCCGCACGCCCATGACCCCTGAAGACATGCTCCTCCCTCA
GCAGCTTCTGGCCGTCACCACCATTGACCGCGCCATCCTCGACTCGGGAATGAAAAGG
GTGGCAATGTCGCCGTCTTTGTCGGCCTCGGCACCGACCTCGAGCTCTACCGTCACCGT
GCTCGCGTCGCTCTCAAGGAGCGCGTCCGCCCTGAAGCCTCCAAGAAGCTCAATGACAT
GATGCAGTACATTAACGACTGCGGCACATCCACATCGTACACCTCGTACATTGGCAACC
TCGTCGCCACGCGCGTCTCGTCGCAGTGGGGCTTCACGGGCCCCTCCTTTACGATCACC
GAGGGCAACAACTCCGTCTACCGCTGCGCCGAGCTCGGCAAGTACCTCCTCGAGACCGG
CGAGGTCGATGGCGTCGTCGTTGCGGGTGTCGATCTCTGCGGCAGTGCCGAAAACCTTT
ACGTCAAGTCTCGCCGCTTCAAGGTGTCCACCTCCGATACCCCGCGCGCCAGCTTTGAC
GCCGCCGCCGATGGCTACTTTGTCGGCGAGGGCTGCGGTGCCTTTGTGCTCAAGCGTGA
GACTAGCTGCACCAAGGACGACCGTATCTACGCTTGCATGGATGCCATCGTCCCTGGCA
ACGTCCCTAGCGCCTGCTTGCGCGAGGCCCTCGACCAGGCGCGCGTCAAGCCGGGCGAT
ATCGAGATGCTCGAGCTCAGCGCCGACTCCGCCCGCCACCTCAAGGACCCGTCCGTCCT
GCCCAAGGAGCTCACTGCCGAGGAGGAAATCGGCGGCCTTCAGACGATCCTTCGTGACG
ATGACAAGCTCCCGCGCAACGTCGCAACGGGCAGTGTCAAGGCCACCGTCGGTGACACC
GGTTATGCCTCTGGTGCTGCCAGCCTCATCAAGGCTGCGCTTTGCATCTACAACCGCTA
CCTGGCCAGCAACGGCGACGACTGGGATGAACCCGCCCCTGAGGCGCCCTGGGACAGCA
CCCTCTTTGCGTGCCAGACCTCGCGCGCTTGGCTCAAGAACCCTGGCGAGCGTCGCTAT
GCGGCCGTCTCGGGCGTCTCCGAGACGCGCTCGTGCTATTCCGTGCTCCTCTCCGAAGC
CGAGGGCCACTACGAGCGCGAGAACCGCATCTCGCTCGACGAGGAGGCGCCCAAGCTCA
TTGTGCTTCGCGCCGACTCCCACGAGGAGATCCTTGGTCGCCTCGACAAGATCCGCGAG
CGCTTCTTGCAGCCCACGGGCGCCGCCCGCGCGAGTCCGAGCTCAAGGCGCAGGCCCG
CCGCATCTTCCTCGAGCTCCTCGGCGAGACCCTTGCCCAGGATGCCGCTTCTTCAGGCT
CGCAAAAGCCCCTCGCTCTCAGCCTCGTCTCCACGCCCTCCAAGCTCCAGCGCGAGGTC
GAGCTCGCGGCCAAGGGTATCCCGCGCTGCCTCAAGATGCGCCGCGATTGGAGCTCCCC
TGCTGGCAGCCGCTACGCGCCTGAGCCGCTCGCCAGCGACCGCGTCGCCTTCATGTACG
GCGAAGGTCGCAGCCCTTACTACGGCATCACCCAAGACATTCACCGCATTTGGCCCGAA
CTCCACGAGGTCATCAACGAAAAGACGAACCGTCTCTGGGCCGAAGGCGACCGCTGGGT
CATGCCGCGCGCCAGCTTCAAGTCGGAGCTCGAGAGCCAGCAGCAAGAGTTTGATCGCA
ACATGATTGAAATGTTCCGTCTTGGAATCCTCACCTCAATTGCCTTCACCAATCTGGCG
CGCGACGTTCTCAACATCACGCCCAAGGCCGCCTTTGGCCTCAGTCTTGGCGAGATTTC
CATGATTTTTGCCTTTTCCAAGAAGAACGGTCTCATCTCCGACCAGCTCACCAAGGATC
TTCGCGAGTCCGACGTGTGGAACAAGGCTCTGGCCGTTGAATTTAATGCGCTGCGCGAG
GCCTGGGGCATTCCACAGAGTGTCCCCAAGGACGAGTTCTGGCAAGGCTACATTGTGCG
CGGCACCAAGCAGGATATCGAGGCGGCCATCGCCCCGGACAGCAAGTACGTGCGCCTCA
CCATCATCAATGATGCCAACACCGCCCTCATTAGCGGCAAGCCCGACGCCTGCAAGGCT
GCGATCGCGCGTCTCGGTGGCAACATTCCTGCGCTTCCCGTGACCCAGGGCATGTGCGG
CCACTGCCCCGAGGTGGGACCTTATACCAAGGATATCGCCAAGATCCATGCCAACCTTG
```

FIG. 27B-1

```
AGTTCCCCGTTGTCGACGGCCTTGACCTCTGGACCACAATCAACCAGAAGCGCCTCGTG
CCACGCGCCACGGGCGCCAAGGACGAATGGGCCCCTTCTTCCTTTGGCGAGTACGCCGG
CCAGCTCTACGAGAAGCAGGCTAACTTCCCCCAAATCGTCGAGACCATTTACAAGCAAA
ACTACGACGTCTTTGTCGAGGTTGGGCCCAACAACCACCGTAGCACCGCAGTGCGCACC
ACGCTTGGTCCCCAGCGCAACCACCTTGCTGGCGCCATCGACAAGCAGAACGAGGATGC
TTGGACGACCATCGTCAAGCTTGTGGCTTCGCTCAAGGCCCACCTTGTTCCTGGCGTCA
CGATCTCGCCGCTGTACCACTCCAAGCTTGTGGCGGAGGCTCAGGCTTGCTACGCTGCG
CTCTGCAAGGGTGAAAAGCCCAAGAAGAACAAGTTTGTGCGCAAGATTCAGCTCAACGG
TCGCTTCAACAGCAAGGCGGACCCCATCTCCTCGGCCGATCTTGCCAGCTTTCCGCCTG
CGGACCCTGCCATTGAAGCCGCCATCTCGAGCCGCATCATGAAGCCTGTCGCTCCCAAG
TTCTACGCGCGTCTCAACATTGACGAGCAGGACGAGACCCGAGATCCGATCCTCAACAA
GGACAACGCGCCGTCTTCTTCTTCTTCTTCTTCTTCTTCTTCTTCTTCTTCTTCTTCTC
CGTCGCCTGCTCCTTCGGCCCCGTGCAAAGAAGGCTGCTCCCGCCGCGGAGACCAAG
GCTGTTGCTTCGGCTGACGCACTTCGCAGTGCCCTGCTCGATCTCGACAGTATGCTTGC
GCTGAGCTCTGCCAGTGCCTCCGGCAACCTTGTTGAGACTGCGCCTAGCGACGCCTCGG
TCATTGTGCCGCCCTGCAACATTGCGGATCTCGGCAGCCGCGCCTTCATGAAAACGTAC
GGTGTTTCGGCGCCTCTGTACACGGGCGCCATGGCCAAGGGCATTGCCTCTGCGGACCT
CGTCATTGCCGCCGGCCGCCAGGGCATCCTTGCGTCCTTTGGCGCCGGCGGACTTCCCA
TGCAGGTTGTGCGTGAGTCCATCGAAAGATTCAGGCCGCCCTGCCCAATGGCCCGTAC
GCTGTCAACCTTATCCATTCTCCCTTTGACAGCAACCTCGAAAAGGGCAATGTCGATCT
CTTCCTCGAGAAGGGTGTCACCTTTGTCGAGGCCTCGGCCTTTATGACGCTCACCCCGC
AGGTCGTGCGGTACCGCGCGGCTGGCCTCACGCGCAACGCCGACGGCTCGGTCAACATC
CGCAACCGTATCATTGGCAAGGTCTCGCGCACCGAGCTCGCCGAGATGTTCATGCGTCC
TGCGGCCGAGCACCTTCTTCAGAAGCTCATTGCTTCCGGCGAGATCAACCAGGAGCAGG
CCGAGCTCGCCCGCCGTGTTCCCGTCGCTGACGACATCGCGGTCGAAGCTGACTCGGGT
GGCCACACCGACAACCGCCCCATCCACGTCATTCTGCCCCTCATCATCAACCTTCGCGA
CCGCCTTCACCGCGAGTGCGGCTACCCGGCCAACCTTCGCGTCCGTGTGGGCGCCGGCG
GTGGCATTGGGTGCCCCAGGCGGCGCTGGCCACCTTCAACATGGGTGCCTCCTTTATT
GTCACCGGCACCGTGAACCAGGTCGCCAAGCAGTCGGGCACGTGCGACAATGTGCGCAA
GCAGCTCGCGAAGGCCACTTACTCGGACGTATGCATGGCCCCGGCTGCCGACATGTTCG
AGGAAGGCGTCAAGCTTCAGGTCCTCAAGAAGGGAACCATGTTTCCCTCGCGCGCCAAC
AAGCTCTACGAGCTCTTTTGCAAGTACGACTCGTTCGAGTCCATGCCCCCGCAGAGCT
TGCGCGCGTCGAGAAGCGCATCTTCAGCCGCGCGCTCGAAGAGGTCTGGGACGAGACCA
AAAACTTTTACATTAACCGTCTTCACAACCCGGAGAAGATCCAGCGCGCCGAGCGCGAC
CCCAAGCTCAAGATGTCGCTGTGCTTTCGCTGGTACCTGAGCCTGGCGAGCCGCTGGGC
CAACACTGGAGCTTCCGATCGCGTCATGGACTACCAGGTCTGGTGCGGTCCTGCCATTG
GTTCCTTCAACGATTTCATCAAGGGAACTTACCTTGATCCGGCCGTCGCAAACGAGTAC
CCGTGCGTCGTTCAGATTAACAAGCAGATCCTTCGTGGAGCGTGCTTCTTGCGCCGTCT
CGAAATTCTGCGCAACGCACGCCTTTCCGATGGCGCTGCCGCTCTTGTGGCCAGCATCG
ATGACACATACGTCCCGGCCGAGAAGCTGTAAGTAAGCTCTCATATATGTTAGTTGCGT
GAGACCGACACGAAGATAATATCACATACGCTTTGTTTGTTCTTTCAATTATTTGTCT
GTGCTTCATGTTGCTCCTCAGTATCTAGCTGGCGGCTCTTATCTTCTTTTAAAATATCT
GGACAAGGACAAAAACAAGAATAAAGGCGAGAAGATGTGAATTTCATTTCGACTTGAGA
```

FIG. 27B-2

```
ACTCGAAGAGCATTGATGCGGTTAGTATATGGGTATTTTCCAGACACTTTTCATCATCA
TCATCATCATCATCATTATGAAGAAGTAGTAGCTGATAAAGTAGACTCACTGTTTGCAG
CGAGAAAAAAAAAAAAAAAAAAA
```

FIG. 27B-3

```
CGAGCAGAGGCCGGCCGCGAGCCCGAGCCCGCCCCGCAGATCACTAGTACCGCTGCGGA
ATCACAGCAGCAGCAGCAGCAGCAGCAGCAGCAGCAGCAGCAGCAGCAGCCACGAGAGG
GAGATAAAGAAAAGCGGCAGAGACGATGGCGCTCCGTGTCAAGACGAACAAGAAGCCA
TGCTGGGAGATGACCAAGGAGGAGCTGACCAGCGGCAAGACCGAGGTGTTCAACTATGA
GGAACTCCTCGAGTTCGCAGAGGGCGACATCGCCAAGGTCTTCGGACCCGAGTTCGCCG
TCATCGACAAGTACCCGCGCCGCGTGCGCCTGCCCGCCCGCGAGTACCTGCTCGTGACC
CGCGTCACCCTCATGGACGCCGAGGTCAACAACTACCGCGTCGGCGCCCGCATGGTCAC
CGAGTACGATCTCCCCGTCAACGGAGAGCTCTCCGAGGGCGGAGACTGCCCCTGGGCCG
TCCTGGTCGAGAGTGGCCAGTGCGATCTCATGCTCATCTCCTACATGGGCATTGACTTC
CAGAACCAGGGCGACCGCGTCTACCGCCTGCTCAACACCACGCTCACCTTTTACGGCGT
GGCCCACGAGGGCGAGACCCTCGAGTACGACATTCGCGTCACCGGCTTCGCCAAGCGTC
TCGACGGCGGCATCTCCATGTTCTTCTTCGAGTACGACTGCTACGTCAACGGCCGCCTC
CTCATCGAGATGCGCGATGGCTGCGCCGGCTTCTTCACCAACGAGGAGCTCGACGCCGG
CAAGGGCGTCGTCTTCACCCGCGGCGACCTCGCCGCCCGCGCCAAGATCCCAAAGCAGG
ACGTCTCCCCCTACGCCGTCGCCCCTGCCTCCACAAGACCAAGCTCAACGAAAAGGAG
ATGCAGACCCTCGTCGACAAGGACTGGGCATCCGTCTTTGGCTCCAAGAACGGCATGCC
GGAAATCAACTACAAACTCTGCGCGCGTAAGATGCTCATGATTGACCGCGTCACCAGCA
TTGACCACAAGGGCGGTGTCTACGGCCTCGGTCAGCTCGTCGGTGAAAAGATCCTCGAG
CGCGACCACTGGTACTTTCCCTGCCACTTTGTCAAGGATCAGGTCATGGCCGGATCCCT
CGTCTCCGACGGCTGCAGCCAGATGCTCAAGATGTACATGATCTGGCTCGGCCTCCACC
TCACCACCGGACCCTTTGACTTCCGCCCGGTCAACGGCCACCCCAACAAGGTCCGCTGC
CGCGGCCAAATCTCCCCGCACAAGGGCAAGCTCGTCTACGTCATGGAGATCAAGGAGAT
GGGCTTCGACGAGGACAACGACCCGTACGCCATTGCCGACGTCAACATCATTGATGTCG
ACTTCGAAAAGGGCCAGGACTTTAGCCTCGACCGCATCAGCGACTACGGCAAGGGCGAC
CTCAACAAGAAGATCGTCGTCGACTTTAAGGGCATCGCTCTCAAGATGCAGAAGCGCTC
CACCAACAAGAACCCCTCCAAGGTTCAGCCCGTCTTTGCCAACGGCGCCGCCACTGTCG
GCCCCGAGGCCTCCAAGGCTTCCTCCGGCGCCAGCGCCAGCGCCAGCGCCGCCCCGGCC
AAGCCTGCCTTCAGCGCCGATGTTCTTGCGCCCAAGCCCGTTGCCCTTCCCGAGCACAT
CCTCAAGGGCGACGCCCTCGCCCCAAGGAGATGTCCTGGCACCCCATGGCCCGCATCC
CGGGCAACCCGACGCCCTCTTTTGCGCCCTCGGCCTACAAGCCGCGCAACATCGCCTTT
ACGCCCTTCCCCGGCAACCCCAACGATAACGACCACACCCCGGGCAAGATGCCGCTCAC
CTGGTTCAACATGGCCGAGTTCATGGCCGGCAAGGTCAGCATGTGCCTCGGCCCCGAGT
TCGCCAAGTTCGACGACTCGAACACCAGCCGCAGCCCCGCTTGGGACCTCGCTCTCGTC
ACCCGCGCCGTGTCTGTGTCTGACCTCAAGCACGTCAACTACCGCAACATCGACCTCGA
CCCCTCCAAGGGTACCATGGTCGGCGAGTTCGACTGCCCCGCGGACGCCTGGTTCTACA
AGGGCGCCTGCAACGATGCCCACATGCCGTACTCGATCCTCATGGAGATCGCCCTCCAG
ACCTCGGGTGTGCTCACCTCGGTGCTCAAGGCGCCCTGACCATGGAGAAGGACGACAT
CCTCTTCCGCAACCTCGACGCCAACGCCGAGTTCGTGCGCGCCGACCTCGACTACCGCG
GCAAGACTATCCGCAACGTCACCAAGTGCACTGGCTACAGCATGCTCGGCGAGATGGGC
GTCCACCGCTTCACCTTTGAGCTCTACGTCGATGATGTGCTCTTTTACAAGGGCTCGAC
CTCGTTCGGCTGGTTCGTGCCCGAGGTYTTTGCCGCCAGGCCGGCCTCGACAACGGCC
GCAAGTCGGAGCCCTGGTTCATTGAGAACAAGGTTCCGGCCTCGCAGGTCTCCTCCTTT
GACGTGCGCCCCAACGGCAGCGGCCGCACCGCCATCTTCGCCAACGCCCCCAGCGGCGC
```

```
CCAGCTCAACCGCCGCACGGACCAGGGCCAGTACCTCGACGCCGTCGACATTGTCTCCG
GCAGCGGCAAGAAGAGCCTCGGCTACGCCCACGGTTCCAAGACGGTCAACCCGAACGAC
TGGTTCTTCTCGTGCCACTTTTGGTTTGACTCGGTCATGCCCGGAAGTCTCGGTGTCGA
GTCCATGTTCCAGCTCGTCGAGGCCATCGCCGCCCACGAGGATCTCGCTGGCAAAGCAC
GGCATTGCCAACCCCACCTTTGTGCACGCCCCGGGCAAGATCAAGCTGGAAGTACCGC
GGSCAGCTCACGCCCAAGAGCAAGAAGATGGACTCGGAGGTCCACATCGTGTCCGTGGA
CGCCCACGACGGCGTTGTCGACCTCGTCGCCGACGGCTTCCTCTGGGCCGACAGCCTCC
GCGTCTACTCGGTGAGCAACATTCGCGTGCGCATCGCCTCCGGTGAGGCCCCTGCCGCC
GCCTCCTCCGCCGCCTCTGTGGGCTCCTCGGCTTCGTCCGTCGAGCGCACGCGCTCGAG
CCCCGCTGTCGCCTCCGGCCCGGCCCAGACCATCGACCTCAAGCAGCTCAAGACCGAGC
TCCTCGAGCTCGATGCCCCGCTCTACCTCTCGCAGGACCCGACCAGCGGCCAGCTCAAG
AAGCACACCGACGTGGCCTCCGGCCAGGCCACCATCGTGCAGCCCTGCACGCTCGGCGA
CCTCGGTGACCGCTCCTTCATGGAGACCTACGGCGTCGTCGCCCCGCTGTACACGGGCG
CCATGGCCAAGGGCATTGCCTCGGCGGACCTCGTCATCGCCGCCGGCAAGCGCAAGATC
CTCGGCTCCTTTGGCGCCGGCGGCCTCCCCATGCACCACGTGCGCGCCGCCCTCGAGAA
GATCCAGGCCGCCCTGCCTCAGGGCCCCTACGCCGTCAACCTCATCCACTCGCCTTTTG
ACAGCAACCTCGAGAAGGGCAACGTCGATCTCTTCCTCGAGAAGGGCGTCACTGTGGTG
GAGGCCTCGGCATTCATGACCCTCACCCCGCAGGTCGTGCGCTACCGCGCCGCCGGCCT
CTCGCGCAACGCCGACGGTTCGGTCAACATCCGCAACCGCATCATCGGCAAGGTCTCGC
GCACCGAGCTCGCCGAGATGTTCATCCGCCCGGCCCCGGAGCACCTCCTCGAGAAGCTC
ATCGCCTCGGGCGAGATCACCCAGGAGCAGGCCGAGCTCGCGCGCCGCGTTCCCGTCGC
CGACGATATCGCTGTCGAGGCTGACTCGGGCGGCCACACCGACAACCGCCCCATCCACG
TCATCCTCCCGCTCATCATCAACCTCCGCAACCGCCTGCACCGCGAGTGCGGCTACCCC
GCGCACCTCCGCGTCCGCGTTGGCGCCGGCGGTGGCGTCGGCTGCCCGCAGGCCGCCGC
CGCCGCGCTCACCATGGGCGCCGCCTTCATCGTCACCGGCACTGTCAACCAGGTCGCCA
AGCAGTCCGGCACCTGCGACAACGTGCGCAAGCAGCTCTCGCAGGCCACCTACTCGGAT
ATCTGCATGGCCCCGGCCGCCGACATGTTCGAGGAGGGCGTCAAGCTCCAGGTCCTCAA
GAAGGGAACCATGTTCCCCTCGCGCGCCAACAAGCTCTACGAGCTCTTTTGCAAGTACG
ACTCCTTCGACTCCATGCCTCCTGCCGAGCTCGAGCGCATCGAGAAGCGTATCTTCAAG
CGCGCACTCCAGGAGGTCTGGGAGGAGACCAAGGACTTTTACATTAACGGTCTCAAGAA
CCCGGAGAAGATCCAGCGCGCCGAGCACGACCCCAAGCTCAAGATGTCGCTCTGCTTCC
GCTGGTACCTTGGTCTTGCCAGCCGCTGGGCCAACATGGGCGCCCCGGACCGCGTCATG
GACTACCAGGTCTGGTGTGGCCCGGCCATTGGCGCCTTCAACGACTTCATCAAGGGCAC
CTACCTCGACCCGCTGTCTCCAACGAGTACCCTGTGTCGTCCAGATCAACCTGCAAA
TCCTCCGTGGTGCCTGCTACCTGCGCCGTCTCAACGCCCTGCGCAACGACCCGCGCATT
GACCTCGAGACCGAGGATGCTGCCTTTGTCTACGAGCCCACCAACGCGCTCTAAGAAAG
TGAACCTTGTCCTAACCCGACAGCGAATGGCGGGAGGGGCGGGCTAAAAGATCGTATT
ACATAGTATTTTTCCCCTACTCTTTGTGAAAAAAAAAAAAAAAAAAAA
```

FIG. 27C-2

RCRRVSPRRAAPPPPLARTPARLAAPAVSNELLEKAETVVMEVLAAKTGYETDMIESDM
ELETELGIDSIKRVEILSEVQAMLNVEAKDVDALSRTRTVGEVVNAMKAEIAGGSAPAP
AAAAPGPAAAAPAPAVSSELLEKAETVVMEVLAAKTGYETDMIESDMELETELGIDSIK
RVEILSEVQAMLNVEAKDVDALSRTRTVGEVVDAMKAEIAGSSASAPAAAAPAPAAAAP
APAAAAPAVSNELLEKAETVVMEVLAAKTGYETDMIESDMELETELGIDSIKRVEILSE
VQAMLNVEAKDVDALSRTRTVGEVVDAMKAEIAGGSAPAPAAAAPAPAAAAPAVSNELL
EKAETVVMEVLAAKTGYETDMIESDMELETELGIDSIKRVEILSEVQAMLNVEAKDVDA
LSRTRTVGEVVDAMKAEIAGSSAPAPAAAAPAPAAAAPAPAAAAPAVSSELLEKAETVV
MEVLAAKTGYETDMIESDMELETELGIDSIKRVEILSEVQAMLNVEAKDVDALSRTRTV
GEVVDAMKAEIAGGSAPAPAAAAPAPAAAAPAVSNELLEKAETVVMEVLAAKTGYETDM
IESDMELETELGIDSIKRVEILSEVQAMLNVEAKDVDALSRTRTVGEVVDAMKAEIAGG
SAPAPAAAAPASAGAAPAVKIDSVHGADCDDLSLMHAKVVDIRRPDELILERPENRPVL
VVDDGSELTLALVRVLGACAVVLTFEGLQLAQRAGAAAIRHVLAKDLSAESAEKAIKEA
EQRFGALGGFISQQAERFEPAEILGFTLMCAKFAKASLCTAVAGGRPAFIGVARLDGRL
GFTSQGTSDALKRAQRGAIFGLCKTIGLEWSESDVFSRGVDIAQGMHPEDAAVAIVREM
ACADIRIREVGIGANQQRCTIRAAKLETGNPQRQIAKDDVLLVSGGARGITPLCIREIT
RQIAGGKYILLGRSKVSASEPAWCAGITDEKAVQKAATQELKRAFSAGEGPKPTPRAVT
KLVGSVLGAREVRSSIAAIEALGGKAIYSSCDVNSAADVAKAVRDAESQLGARVSGIVH
ASGVLRDRLIEKKLPDEFDAVFGTKVTGLENLLAAVDRANLKHMVLFSSLAGFHGNVGQ
SDYAMANEALNKMGLELAKDVSVKSICFGPWDGGMVTPQLKKQFQEMGVQIIPREGGAD
TVARIVLGSSPAEILVGNWRTPSKKVGSDTITLHRKISAKSNPFLEDHVIQGRRVLPMT
LAIGSLAETCLGLFPGYSLWAIDDAQLFKGVTVDGDVNCEVTLTPSTAPSGRVNVQATL
KTFSSGKLVPAYRAVIVLSNQGAPPANATMQPPSLDADPALQGSVYDGKTLFHGPAFRG
IDDVLSCTKSQLVAKCSAVPGSDAARGEFATDTDAHDPFVNDLAFQAMLVWVRRTLGQA
ALPNSIQRIVQHRPVPQDKFFYITLRSNQSGGHSQHKHALQFHNEQGDLFIDVQASVIA
TDSLAF

FIG. 29A

```
AVFEEHDPSNAACTGHDSISALSARCGGESNMRIAITGMDATFGALKGLDAFERAIYTG
AHGAIPLPEKRWRFLGKDKDFLDLCGVKATPHGCYIEDVEVDFQRLRTPMTPEDMLLPQ
QLLAVTTIDRAILDSGMKKGGNVAVFVGLGTDLELYRHRARVALKERVRPEASKKLNDM
MQYINDCGTSTSYTSYIGNLVATRVSSQWGFTGPSFTITEGNNSVYRCAELGKYLLETG
EVDGVVVAGVDLCGSAENLYVKSRRFKVSTSDTPRASFDAAADGYFVGEGCGAFVLKRE
TSCTKDDRIYACMDAIVPGNVPSACLREALDQARVKPGDIEMLELSADSARHLKDPSVL
PKELTAEEEIGGLQTILRDDDKLPRNVATGSVKATVGDTGYASGAASLIKAALCIYNRY
LPSNGDDWDEPAPEAPWDSTLFACQTSRAWLKNPGERRYAAVSGVSETRSCYSVLLSEA
EGHYERENRISLDEEAPKLIVLRADSHEEILGRLDKIRERFLQPTGAAPRESELKAQAR
RIFLELLGETLAQDAASSGSQKPLALSLVSTPSKLQREVELAAKGIPRCLKMRRDWSSP
AGSRYAPEPLASDRVAFMYGEGRSPYYGITQDIHRIWPELHEVINEKTNRLWAEGDRWV
MPRASFKSELESQQQEFDRNMIEMFRLGILTSIAFTNLARDVLNITPKAAFGLSLGEIS
MIFAFSKKNGLISDQLTKDLRESDVWNKALAVEFNALREAWGIPQSVPKDEFWQGYIVR
GTKQDIEAAIAPDSKYVRLTIINDANTALISGKPDACKAAIARLGGNIPALPVTQGMCG
HCPEVGPYTKDIAKIHANLEFPVVDGLDLWTTINQKRLVPRATGAKDEWAPSSFGEYAG
QLYEKQANFPQIVETIYKQNYDVFVEVGPNNHRSTAVRTTLGPQRNHLAGAIDKQNEDA
WTTIVKLVASLKAHLVPGVTISPLYHSKLVAEAQACYAALCKGEKPKKNKFVRKIQLNG
RFNSKADPISSADLASFPPADPAIEAAISSRIMKPVAPKFYARLNIDEQDETRDPILNK
DNAPSSSSSSSSSSSSSSSPSPAPSAPVQKKAAPAAETKAVASADALRSALLDLDSMLA
LSSASASGNLVETAPSDASVIVPPCNIADLGSRAFMKTYGVSAPLYTGAMAKGIASADL
VIAAGRQGILASFGAGGLPMQVVRESIEKIQAALPNGPYAVNLIHSPFDSNLEKGNVDL
FLEKGVTFVEASAFMTLTPQVVRYRAAGLTRNADGSVNIRNRIIGKVSRTELAEMFMRP
APEHLLQKLIASGEINQEQAELARRVPVADDIAVEADSGGHTDNRPIHVILPLIINLRD
RLHRECGYPANLRVRVGAGGGIGCPQAALATFNMGASFIVTGTVNQVAKQSGTCDNVRK
QLAKATYSDVCMAPAADMFEEGVKLQVLKKGTMFPSRANKLYELFCKYDSFESMPPAEL
ARVEKRIFSRALEEVWDETKNFYINRLHNPEKIQRAERDPKLKMSLCFRWYLSLASRWA
NTGASDRVMDYQVWCGPAIGSFNDFIKGTYLDPAVANEYPCVVQINKQILRGACFLRRL
EILRNARLSDGAAALVASIDDTYVPAEKL
```

FIG. 29B

```
RAEAGREPEPAPQITSTAAESQQQQQQQQQQQQQQQPREGDKEKAAETMALRVKTNKKPCWEMT
KEELTSGKTEVFNYEELLEFAEGDIAKVFGPEFAVIDKYPRRVRLPAREYLLVTRVTLMDAEVN
NYRVGARMVTEYDLPVNGELSEGGDCPWAVLVESGQCDLMLISYMGIDFQNQCDRVYRLLNTTL
TFYGVAHEGETLEYDIRVTGFAKRLDGGISMFFFEYDCYVNGRLLIEMRDGCAGFFTNEELDAG
KGVVFTRGDLAARAKIPKQDVSPYAVAPCLHKTKLNEKEMQTLVDKDWASVFGSKNGMPEINYK
LCARKMLMIDRVTSIDHKGGVYGLGQLVGSKILERDHWYFPCHFVKDQVMAGSLVSDGCSQMLK
MYMIWLGLHLTTGPFDFRPVNGHPNKVRCRGQISPHKGKLVYVMEIKEMGFDEDNDPYAIADVN
IIDVDFEKGQDFSLDRISDYGKCDLNKKIVVDFKGIALKMQKRSTNKNPSKVQPVFANGAATVG
PEASKASSGASASASAAPAKPAFSADVLAPKPVALPEHILKGDALAPKEMSWHPMARIPGNPTP
SFAPSAYKPRNIAFTPFPGNPNDNDHTPGKMPLTWFNMAEFMAGKVSMCLGPEFAKPDDSNTSR
SPAWDLALVTRAVSVSDLKHVNYRNIDLDPSKGTMVGEFDCPADAWFYKCACNDAHMPYSILME
IALQTSGVLTSVLKAPLTMEKDDILFRNLDANAEFVRADLDYRGKTIRNVTKCTGYSMLGEMGV
HRFTFELYVDDVLFYKGSTSFGWFVPEVFAAQAGLDNGRKSEPWFIENKVPASQVSSFDVRPNG
SGRTAIFANAPSGAQLNRRTDQGQYLDAVDIVSGSGKKSLGYAHGSKTVNPNDWFFSCHFWFDS
VMPGSLGVESMFQLVEAIAAHEDLAGKARHCQPHLCARPRARSSWKYRGQLTFKSKKMDSEVHI
VSVDAHDGVVDLVADGFLWADSLRVYSVSNIRVRIASGEAPAAASSAASVGSSASSVERTRSSP
AVASGPAQTIDLKQLKTELLELDAPLYLSQDPTSGQLKKHTDVASGQATIVQPCTLGDLGDRSF
METYGVVAPLYTGAMAKGIASADLVIAAGKRKILGSFGAGGLPMHHVRAALEKIQAALPQGPYA
VNLIHSPFDSNLEKGNVDLFLEKGVTVVEASAFMTLTPQVVRYRAAGLSRNADGSVNIRNRIIG
KVSRTELAEMFIRPAPEHLLEKLIASGEITQEQAELARRVPVADDIAVEADSGGHTDNRPIHVI
LPLIINLRNRLHRECGYPAHLRVRVGAGGGVGCPQAAAAALTMGAAFIVTGTVNQVAKQSGTCD
NVRKQLSQATYSDICMAPAADMFEEGVKLQVLKKGTMFPSRANKLYELFCKYDSPDSMPPAELE
RIEKRIFKRALQEVWEETKDFYINGLKNPEKIQRAEHDPKLKMSLCFRWYLGLASRWANMGAPD
RVMDYQVWCGPAIGAFNDFIKGTYLDPAVSNEYPCVVQINLQILRGACYLRRLNALRNDPRIDL
ETEDAAFVYEPTNAL
```

FIG. 29C

SCHIZOCHYTRIUM PKS GENES

CROSS-REFERENCE TO RELATED APPLICATION

The present application is a continuation of U.S. patent application Ser. No. 09//231,899, filed Jan. 14, 1999 entitled "SCHIZOCHYTRIUM PKS GENES", now U.S. Pat. No. 6,566,583, which is a continuation-in-part of U.S. patent application Ser. No. 09/090,793, filed Jun. 4, 1998, now U.S. Pat. No. 6,140,486 which claims benefit of U.S. Provisional Application No. 60/048,650, filed Jun. 4, 1997, all of which are incorporated herein by this reference.

INTRODUCTION

1. Field of the Invention

This invention relates to modulating levels of enzymes and/or enzyme components capable of modifying long chain poly-unsaturated fatty acids (PUFAs) in a host cell, and constructs and methods for producing PUFAs in a host cell. The invention is exemplified by production of eicosapentenoic acid (EPA) using genes derived from *Shewanella putrefaciens* and *Vibrio marinus*.

2. Background

Two main families of poly-unsaturated fatty acids (PUFAs) are the ω3 fatty acids, exemplified by eicosapentenoic acid, and the ω6 fatty acids, exemplified by arachidonic acid. PUFAs are important components of the plasma membrane of the cell, where they can be found in such forms as phospholipids, and also can be found in triglycerides. PUFAs also serve as precursors to other molecules of importance in human beings and animals, including the prostacyclins, leukotrienes and prostaglandins. Long chain PUFAs of importance include docosahexenoic acid (DHA) and eicosapentenoic acid (EPA), which are found primarily in different types of fish oil, gamma-linolenic acid (GLA), which is found in the seeds of a number of plants, including evening primrose (*Oenothera biennis*), borage (*Borago officinalis*) and black currants (*Ribes nigrum*), stearidonic acid (SDA), which is found in marine oils and plant seeds, and arachidonic acid (ARA), which along with GLA is found in filamentous fungi. ARA can be purified from animal tissues including liver and adrenal gland. Several genera of marine bacteria are known which synthesize either EPA or DHA. DHA is present in human milk along with ARA.

PUFAs are necessary for proper development, particularly in the developing infant brain, and for tissue formation and repair. As an example, DHA, is an important constituent of many human cell membranes, in particular nervous cells (gray matter), muscle cells, and spermatozoa and believed to affect the development of brain functions in general and to be essential for the development of eyesight. EPA and DHA have a number of nutritional and pharmacological uses. As an example adults affected by diabetes (especially non insulin-dependent) show deficiencies and imbalances in their levels of DHA which are believed to contribute to later coronary conditions. Therefore a diet balanced in DHA may be beneficial to diabetics.

For DHA, a number of sources exist for commercial production including a variety of marine organisms, oils obtained from cold water marine fish, and egg yolk fractions. The purification of DHA from fish sources is relatively expensive due to technical difficulties, making DHA expensive and in short supply. In algae such as *Amphidinium* and *Schizochytrium* and marine fungi such as *Thraustochytrium* DHA may represent up to 48% of the fatty acid content of the cell. A few bacteria also are reported to produce DHA. These are generally deep sea bacteria such as *Vibrio marinus*. For ARA, microorganisms including the genera *Mortierella*, *Entomophthora*, *Phytium* and *Porphyridium* can be used for commercial production. Commercial sources of SDA include the genera *Trichodesma* and *Echium*. Commercial sources of GLA include evening primrose, black currants and borage. However, there are several disadvantages associated with commercial production of PUFAs from natural sources. Natural sources of PUFA, such as animals and plants, tend to have highly heterogeneous oil compositions. The oils obtained from these sources can require extensive purification to separate out one or more desired PUFA or to produce an oil which is enriched in one or more desired PUFA.

Natural sources also are subject to uncontrollable fluctuations in availability. Fish stocks may undergo natural variation or may be depleted by overfishing. Animal oils, and particularly fish oils, can accumulate environmental pollutants. Weather and disease can cause fluctuation in yields from both fish and plant sources. Cropland available for production of alternate oil-producing crops is subject to competition from the steady expansion of human populations and the associated increased need for food production on the remaining arable land. Crops which do produce PUFAs, such as borage, have not been adapted to commercial growth and may not perform well in monoculture. Growth of such crops is thus not economically competitive where more profitable and better established crops can be grown. Large-scale fermentation of organisms such as *Shewanella* also is expensive. Natural animal tissues contain low amounts of ARA and are difficult to process. Microorganisms such as *Porphyridium* and *Shewanella* are difficult to cultivate on a commercial scale.

Dietary supplements and pharmaceutical formulations containing PUFAs can retain the disadvantages of the PUFA source. Supplements such as fish oil capsules can contain low levels of the particular desired component and thus require large dosages. High dosages result in ingestion of high levels of undesired components, including contaminants. Care must be taken in providing fatty acid supplements, as overaddition may result in suppression of endogenous biosynthetic pathways and lead to competition with other necessary fatty acids in various lipid fractions in vivo, leading to undesirable results. For example, Eskimos having a diet high in ω3 fatty acids have an increased tendency to bleed (U.S. Pat. No. 4,874,603). Fish oils have unpleasant tastes and odors, which may be impossible to economically separate from the desired product, such as a food supplements. Unpleasant tastes and odors of the supplements can make such regimens involving the supplement undesirable and may inhibit compliance by the patient.

A number of enzymes have been identified as being involved in PUFA biosynthesis. Linoleic acid (LA, 18:2 Δ9, 12) is produced from oleic acid (18:1 Δ9) by a Δ12-desaturase. GLA (18:3 Δ6, 9, 12) is produced from linoleic acid (LA, 18:2 Δ9, 12) by a Δ6-desaturase. ARA (20:4 Δ5, 8, 11, 14) is produced from DGLA (20:3 Δ8, 11, 14), catalyzed by a Δ5-desaturase. Eicosapentenoic acid (EPA) is a 20 carbon, omega 3 fatty acid containing 5 double bonds (Δ5, 8, 11, 14, 17), all in the cis configuration. EPA, and the related DHA (Δ4, 7, 10, 13, 16, 19, C22:6) are produced from oleic acid by a series of elongation and desaturation reactions. Additionally, an elongase (or elongases) is required to extend the 18 carbon PUFAs out to 20 and 22 carbon chain lengths. However, animals cannot convert oleic acid (18:1 Δ9) into linoleic acid (18:2 Δ9, 12). Likewise, μ-linolenic acid (ALA, 18:3 Δ9, 12, 15) cannot be synthesized by mammals. Other eukaryotes, including fungi and plants, have enzymes which desaturate at positions Δ12 and Δ15. The major poly-unsaturated fatty acids of animals therefore are either derived from diet and/or from desaturation and elongation of linoleic acid (18:2 Δ9, 12) or μ-linolenic acid (18:3 Δ9, 12, 15).

Poly-unsaturated fatty acids are considered to be useful for nutritional, pharmaceutical, industrial, and other purposes. An expansive supply of poly-unsaturated fatty acids from natural sources and from chemical synthesis are not sufficient for commercial needs. Because a number of separate desaturase and elongase enzymes are required for fatty acid synthesis from linoleic acid (LA, 18:2 Δ9, 12), common in most plant species, to the more saturated and longer chain PUFAs, engineering plant host cells for the expression of EPA and DHA may require expression of five or six separate enzyme activities to achieve expression, at least for EPA and DHA, and for production of quantities of such PUFAs additional engineering efforts may be required, for instance the down regulation of enzymes competing for substrate, engineering of higher enzyme activities such as by mutagenesis or targeting of enzymes to plastid organelles. Therefore it is of interest to obtain genetic material involved in PUFA biosynthesis from species that naturally produce these fatty acids and to express the isolated material alone or in combination in a heterologous system which can be manipulated to allow production of commercial quantities of PUFAs.

Relevant Literature

Several genera of marine bacteria have been identified which synthesize either EPA or DHA (DeLong and Yayanos, *Applied and Environmental Microbiology* (1986) 51: 730–737). Researchers of the Sagami Chemical Research Institute have reported EPA production in *E. coli* which have been transformed with a gene cluster from the marine bacterium, *Shewanella putrefaciens*. A minimum of 5 open reading frames (ORFS) are required for fatty acid synthesis of EPA in *E. coli*. To date, extensive characterization of the functions of the proteins encoded by these genes has not been reported (Yazawa (1996) *Lipids* 31, S-297; WO 93/23545; WO 96/21735).

The protein sequence of open reading frame (ORF) 3 as published by Yazawa, U.S. Pat. No. 5,683,898 is not a functional protein. Yazawa defines the protein as initiating at the methionine codon at nucleotides 9016–9014 of the *Shewanella* PKS-like cluster (Genbank accession U73935) and ending at the stop codon at nucleotides 8185–8183 of the *Shewanella* PKS-like cluster. However, when this ORF is expressed under control of a heterologous promoter in an *E. coli* strain containing the entire PKS-like cluster except ORF 3, the recombinant cells do not produce EPA.

Polyketides are secondary metabolites the synthesis of which involves a set of enzymatic reactions analogous to those of fatty acid synthesis (see reviews: Hopwood and Sherman, *Annu. Rev. Genet.* (1990) 24: 37–66, and Katz and Donadio, in *Annual Review of Microbiology* (1993) 47: 875–912). It has been proposed to use polyketide synthases to produce novel antibiotics (Hutchinson and Fujii, *Annual Review of Microbiology* (1995) 49:201–238).

SUMMARY OF THE INVENTION

Novel compositions and methods are provided for preparation of long chain polyunsaturated fatty acids (PUFAs) using polyketide-like synthesis (PKS-like) genes in plants and plant cells. In contrast to the known and proposed methods for production of PUFAs by means of fatty acid synthesis genes, by the invention constructs and methods are provided for producing PUFAs by utilizing genes of a PKS-like system. The methods involve growing a host cell of interest transformed with an expression cassette functional in the host cell, the expression cassette comprising a transcriptional and translational initiation regulatory region, joined in reading frame 5' to a DNA sequence to a gene or component of a PKS-like system capable of modulating the production of PUFAs (PKS-like gene). An alteration in the PUFA profile of host cells is achieved by expression following introduction of a complete PKS-like system responsible for a PUFA biosynthesis into host cells. The invention finds use for example in the large scale production of DHA and EPA and for modification of the fatty acid profile of host cells and edible plant tissues and/or plant parts.

BRIEF DESCRIPTION OF THE DRAWINGS

FIG. 1 provides designations for the ORFs of the EPA gene cluster of *Shewanella*.

FIG. 2 provides the *Shewanella* PKS-like domain structure, motifs and 'Blast' matches of ORF 6 (FIG. 2A), ORF 7 (FIG. 2B), ORF 8 (FIG. 2C), ORF 9 (FIG. 2D) and ORF 3 (FIG. 2E).

FIG. 4A shows the DNA sequence (SEQ ID NO:1) for the PKS-like cluster found in *Shewanella*, containing ORF's 3–9. FIG. 4B shows the amino acid sequence (SEQ ID NO:2) of ORF 2, which is coded by nucleotides 6121–8103 of the sequence shown in FIG. 4A. FIG. 4C shows the amino acid sequence (SEQ ID NO:3) of the published, inactive ORF3, translated from the strand complementary to that shown in FIG. 4A, nucleotides 9016–8186. FIG. 4D shows the nucleotide sequence 8186–9157 (SEQ ID NO:4); its complementary strand codes for ORF 3 active in EPA synthesis. FIGS. 4E–J show the amino acid sequences (SEQ ID NOS:5–10) corresponding to ORF's 4–9, which are encoded by nucleotides 9681–12590 (SEQ ID NO:81), 13040–13903 (SEQ ID NO:82), 13906–22173 (SEQ ID NO:83), 22203–24515 (SEQ ID NO:84), 24518–30529 (SEQ ID NO:85) and 30730–32358 (SEQ ID NO:86), respectively, of FIG. 4A. FIG. 4K shows the amino acid sequence (SEQ ID NO:11) corresponding to nucleotides 32834–34327.

FIG. 5 shows the sequence (SEQ ID NO:12) for the PKS-like cluster in an approximately 40 kb DNA fragment of *Vibrio marinus*, containing ORFs 6, 7, 8 and 9. The start and last codons for each ORF are as follows: ORF 6: 17394, 25352; ORF 7: 25509, 28160; ORF 8: 28209, 34265; ORF 9: 34454, 36118.

FIG. 6 shows the sequence (SEQ ID NO:13) for an approximately 19 kb portion of the PKS-like cluster of FIG. 5 which contains the ORFs 6, 7, 8 and 9. The start and last codons for each ORF are as follows: ORF 6: 411, 8369 (SEQ ID NO:77); ORF 7: 8526, 11177 (SEQ ID NO:78); ORF 8: 11226, 17282 (SEQ ID NO:79); ORF 9: 17471, 19135 (SEQ ID NO:80).

FIG. 16 is a table of PUFA values from the ORF 8 complementation experiment, the chromatogram of which is shown in FIG. 15.

FIG. 25 shows the PCR product (SEQ ID NO:16) for SS9 Photobacter using primers in Example 1.

FIG. 26 shows probe sequences (SEQ ID NOS:17–31) resulting from PCR with primers presented in Example 1.

FIG. 27 shows the nucleotide sequence of *Schizochytrium* EST clones A. LIB 3033-047-B5, LIB3033-046-E6 and a bridging PCR product have now been assembled into a partial cDNA sequence (ORF6 homolog), B. LIB3033-046-D2 (hglc/ORF7/ORF8/ORF9 homolog), C. LIB81-015-D5, LIB81-042-B9 and a bridging PCR product have now been assembled into a partial cDNA sequence (ORF8/ORF9 homolog).

FIG. 29 shows the amino acid sequences inferred from *Schizochytrium* EST clones A. ORF6 homolog, B. hglc/ORF7/ORF8/ORF9 homolog, C. ORF8/ORF9 homolog.

DESCRIPTION OF THE PREFERRED EMBODIMENTS

Figure 1A:
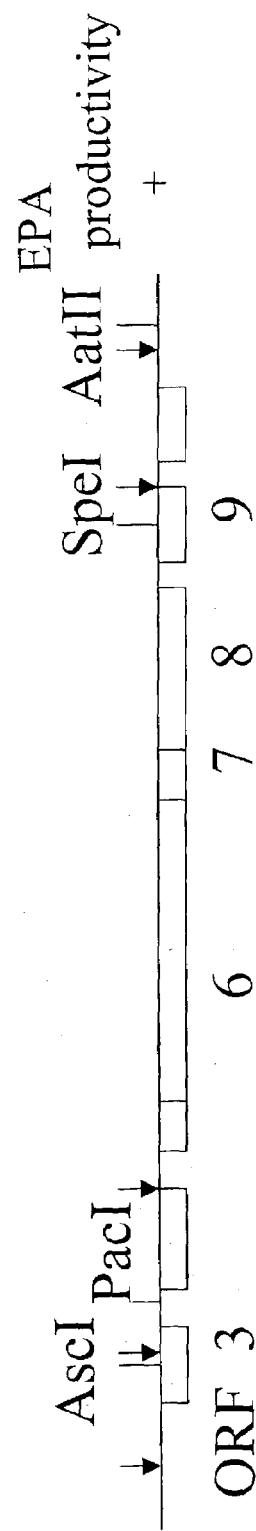
FIG. 1A shows the organization of the genes; those ORFs essential for EPA production in *E. coli* are numbered.

In accordance with the subject invention, novel DNA sequences, DNA constructs and methods are provided, which include some or all of the polyketide-like synthesis (PKS-like) pathway genes from *Shewanella*, *Vibrio*, *Schizochytrium* or other microorganisms, for modifying the poly-unsaturated long chain fatty acid content of host cells, particularly host plant cells. The present invention demonstrates that EPA synthesis genes in *Shewanella putrefaciens* constitute a polyketide-like synthesis pathway. Functions are ascribed to the *Shewanella*, *Schizochytrium* and *Vibrio* genes and methods are provided for the production of EPA and DHA in host cells. The method includes the step of transforming cells with an expression cassette comprising a DNA encoding a polypeptide capable of increasing the amount of one or more PUFA in the host cell. Desirably, integration constructs are prepared which provide for integration of the expression cassette into the genome of a host cell. Host cells are manipulated to express a sense or antisense DNA encoding a polypeptide(s) that has PKS-like gene activity. By "PKS-like gene" is intended a polypeptide which is responsible for any one or more of the functions of a PKS-like activity of interest. By "polypeptide" is meant any chain of amino acids, regardless of length or post-translational modification, for example, glycosylation or phosphorylation. Depending upon the nature of the host cell, the substrate(s) for the expressed enzyme may be produced by the host cell or may be exogenously supplied. Of particular interest is the selective control of PUFA production in plant tissues and/or plant parts such as leaves, roots, fruits and seeds. The invention can be used to synthesize EPA, DHA, and other related PUFAs in host cells.

There are many advantages to transgenic production of PUFAs. As an example, in transgenic *E. coli* as in *Shewanella*, EPA accumulates in the phospholipid fraction, specifically in the sn-2 position. It may be possible to produce a structured lipid in a desired host cell which differs substantially from that produced in either *Shewanella* or *E. coli*. Additionally transgenic production of PUFAs in particular host cells offers several advantages over purification from natural sources such as fish or plants. In transgenic plants, by utilizing a PKS-like system, fatty acid synthesis of PUFAs is achieved in the cytoplasm by a system which produces the PUFAs through de novo production of the fatty acids utilizing malonyl Co-A and acetyl Co-A as substrates. In this fashion, potential problems, such as those associated with substrate competition and diversion of normal products of fatty acid synthesis in a host to PUFA production, are avoided.

Production of fatty acids from recombinant plants provides the ability to alter the naturally occurring plant fatty acid profile by providing new synthetic pathways in the host or by suppressing undesired pathways, thereby increasing levels of desired PUFAs, or conjugated forms thereof, and decreasing levels of undesired PUFAs. Production of fatty acids in transgenic plants also offers the advantage that expression of PKS-like genes in particular tissues and/or plant parts means that greatly increased levels of desired PUFAs in those tissues and/or parts can be achieved, making recovery from those tissues more economical. Expression in a plant tissue and/or plant part presents certain efficiencies, particularly where the tissue or part is one which is easily harvested, such as seed, leaves, fruits, flowers, roots, etc. For example, the desired PUFAs can be expressed in seed; methods of isolating seed oils are well established. In addition to providing a source for purification of desired PUFAs, seed oil components can be manipulated through expression of PKS-like genes, either alone or in combination with other genes such as elongases, to provide seed oils having a particular PUFA profile in concentrated form. The concentrated seed oils then can be added to animal milks and/or synthetic or semisynthetic milks to serve as infant formulas where human nursing is impossible or undesired, or in cases of malnourishment or disease in both adults and infants.

Transgenic microbial production of fatty acids offers the advantages that many microbes are known with greatly simplified oil compositions as compared with those of higher organisms, making purification of desired components easier. Microbial production is not subject to fluctuations caused by external variables such as weather and food supply. Microbially produced oil is substantially free of contamination by environmental pollutants. Additionally, microbes can provide PUFAs in particular forms which may have specific uses. For example, *Spirulina* can provide PUFAs predominantly at the first and third positions of triglycerides; digestion by pancreatic lipases preferentially releases fatty acids from these positions. Following human or animal ingestion of triglycerides derived from *Spirulina*, these PUFAs are released by pancreatic lipases as free fatty acids and thus are directly available, for example, for infant brain development. Additionally, microbial oil production can be manipulated by controlling culture conditions, notably by providing particular substrates for microbially expressed enzymes, or by addition of compounds which suppress undesired biochemical pathways. In addition to these advantages, production of fatty acids from recombinant microbes provides the ability to alter the naturally occurring microbial fatty acid profile by providing new synthetic pathways in the host or by suppressing undesired pathways, thereby increasing levels of desired PUFAs, or conjugated forms thereof, and decreasing levels of undesired PUFAs.

Production of fatty acids in animals also presents several advantages. Expression of desaturase genes in animals can produce greatly increased levels of desired PUFAs in animal tissues, making recovery from those tissues more economical. For example, where the desired PUFAs are expressed in the breast milk of animals, methods of isolating PUFAs from animal milk are well established. In addition to providing a source for purification of desired PUFAs, animal breast milk can be manipulated through expression of desaturase genes, either alone or in combination with other human genes, to provide animal milks with a PUFA composition substantially similar to human breast milk during the different stages of infant development. Humanized animal milks could serve as infant formulas where human nursing is impossible or undesired, or in the cases of malnourishment or disease.

DNAs encoding desired PKS-like genes can be identified in a variety of ways. In one method, a source of a desired PKS-like gene, for example genomic libraries from a *Shewanella, Schizochytrium* or *Vibrio* spp., is screened with detectable enzymatically- or chemically-synthesized probes. Sources of ORFs having PKS-like genes are those organisms which produce a desired PUFA, including DHA-producing or EPA-producing deep sea bacteria growing preferentially under high pressure or at relatively low temperature. Microorgansims such as *Shewanella* which produce EPA or DHA also can be used as a source of PKS-like genes. The probes can be made from DNA, RNA, or non-naturally occurring nucleotides, or mixtures thereof. Probes can be enzymatically synthesized from DNAs of known PKS-like genes for normal or reduced-stringency hybridization methods. For discussions of nucleic acid probe design and annealing conditions, see, for example, Sambrook et al, *Molecular Cloning: A Laboratory Manual* ($2^{nd}$ ed.), Vols. 1–3, *Cold Spring Harbor Laboratory*, (1989) or *Current Protocols in Molecular Biology*, F. Ausubel et al, ed., Greene Publishing and Wiley-Interscience, New York (1987), each of which is incorporated herein by reference. Techniques for manipulation of nucleic acids encoding PUFA enzymes such as subcloning nucleic acid sequences encoding polypeptides into expression vectors, labelling probes, DNA hybridization, and the like are described generally in Sambrook, supra.

Oligonucleotide probes also can be used to screen sources and can be based on sequences of known PKS-like genes, including sequences conserved among known PKS-like genes, or on peptide sequences obtained from a desired purified protein. Oligonucleotide probes based on amino acid sequences can be degenerate to encompass the degeneracy of the genetic code, or can be biased in favor of the preferred codons of the source organism. Alternatively, a desired protein can be entirely sequenced and total synthesis of a DNA encoding that polypeptide performed.

Once the desired DNA has been isolated, it can be sequenced by known methods. It is recognized in the art that such methods are subject to errors, such that multiple sequencing of the same region is routine and is still expected to lead to measurable rates of mistakes in the resulting deduced sequence, particularly in regions having repeated domains, extensive secondary structure, or unusual base compositions, such as regions with high GC base content. When discrepancies arise, resequencing can be done and can employ special methods. Special methods can include altering sequencing conditions by using: different temperatures; different enzymes; proteins which alter the ability of oligonucleotides to form higher order structures; altered nucleotides such as ITP or methylated dGTP; different gel compositions, for example adding formamide; different primers or primers located at different distances from the problem region; or different templates such as single stranded DNAs. Sequencing of mRNA can also be employed.

For the most part, some or all of the coding sequences for the polypeptides having PKS-like gene activity are from a natural source. In some situations, however, it is desirable to modify all or a portion of the codons, for example, to enhance expression, by employing host preferred codons. Host preferred codons can be determined from the codons of highest frequency in the proteins expressed in the largest amount in a particular host species of interest. Thus, the coding sequence for a polypeptide having PKS-like gene activity can be synthesized in whole or in part. All or portions of the DNA also can be synthesized to remove any destabilizing sequences or regions of secondary structure which would be present in the transcribed mRNA. All or portions of the DNA also can be synthesized to alter the base composition to one more preferable to the desired host cell. Methods for synthesizing sequences and bringing sequences together are well established in the literature. In vitro mutagenesis and selection, site-directed mutagenesis, or other means can be employed to obtain mutations of naturally occurring PKS-like genes to produce a polypeptide having PKS-like gene activity in vivo with more desirable physical and kinetic parameters for function in the host cell, such as a longer half-life or a higher rate of production of a desired polyunsaturated fatty acid.

Of particular interest are the *Shewanella putrefaciens* ORFs and the corresponding ORFs of *Vibrio marinus* and *Schizochytrium*. The *Shewanella putrefaciens* PKS-like genes can be expressed in transgenic plants to effect biosynthesis of EPA. Other DNAs which are substantially identical in sequence to the *Shewanella putrefaciens* PKS-like genes, or which encode polypeptides which are substantially similar to PKS-like genes of *Shewanella putrefaciens* can be used, such as those identified from *Vibrio marinus* or *Schizochytrium*. By substantially identical in sequence is intended an amino acid sequence or nucleic acid sequence exhibiting in order of increasing preference at least 60%, 80%, 90% or 95% homology to the DNA sequence of the *Shewanella putrefaciens* PKS-like genes or nucleic acid sequences encoding the amino acid sequences for such genes. For polypeptides, the length of comparison sequences generally is at least 16 amino acids, preferably at least 20 amino acids, and most preferably 35 amino acids. For nucleic acids, the length of comparison sequences generally is at least 50 nucleotides, preferably at least 60 nucleotides, and more preferably at least 75 nucleotides, and most preferably, 110 nucleotides.

Homology typically is measured using sequence analysis software, for example, the Sequence Analysis software package of the Genetics Computer Group, University of Wisconsin Biotechnology Center, 1710 University Avenue, Madison, Wis. 53705, MEGAlign (DNAStar, Inc., 1228 S. Park St., Madison, Wis. 53715), and MacVector (Oxford Molecular Group, 2105 S. Bascom Avenue, Suite 200, Campbell, Calif. 95008). BLAST (National Center for Biotechnology Information (WCBI) www.ncbi.nlm.gov; FASTA (Pearson and Lipman, *Science* (1985) 227:1435–1446). Such software matches similar sequences by assigning degrees of homology to various substitutions, deletions, and other modifications. Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, *J. Mol. Biol.* (1982) 157: 105–132), or on the basis of the ability to assume similar polypeptide secondary structure (Chou and Fasman, *Adv. Enzymol.* (1978) 47: 45–148, 1978). A related protein to the probing sequence is identified when $p \geq 0.01$, preferably $p \geq 10^{-7}$ or $10^{-8}$.

Encompassed by the present invention are related PKS-like genes from the same or other organisms. Such related PKS-like genes include variants of the disclosed PKS-like ORFs that occur naturally within the same or different species of *Shewanella*, as well as homologues of the disclosed PKS-like genes from other species and evolutionarily related proteins having analogous function and activity. Also included are PKS-like genes which, although not substantially identical to the *Shewanella putrefaciens* PKS-like genes, operate in a similar fashion to produce PUFAs as part of a PKS-like system. Related PKS-like genes can be identified by their ability to function substantially the same as the disclosed PKS-like genes; that is, they can be substituted for corresponding ORFs of *Shewanella, Schizochytrium* or *Vibrio* and still effectively produce EPA or DHA. Related PKS-like genes also can be identified by screening sequence databases for sequences homologous to the disclosed PKS-like genes, by hybridization of a probe based on the disclosed PKS-like genes to a library constructed from the source organism, or by RT-PCR using mRNA from the source organism and primers based on the disclosed PKS-like gene. Thus, the phrase "PKS-like genes" refers not only to the nucleotide sequences disclosed herein, but also to other nucleic acids that are allelic or species variants of these nucleotide sequences. It is also understood that these terms include nonnatural mutations introduced by deliberate mutation using recombinant technology such as single site mutation or by excising short sections of DNA open reading frames coding for PUFA enzymes or by substituting new codons or adding new codons. Such minor alterations substantially maintain the immunoidentity of the original expression product and/or its biological activity. The biological properties of the altered PUFA enzymes can be determined by expressing the enzymes in an appropriate cell line and by determining the ability of the enzymes to synthesize PUFAs. Particular enzyme modifications considered minor would include substitution of amino acids of similar chemical properties, e.g., glutamic acid for aspartic acid or glutamine for asparagine.

When utilizing a PUFA PKS-like system from another organism, the regions of a PKS-like gene polypeptide important for PKS-like gene activity can be determined through routine mutagenesis, expression of the resulting mutant polypeptides and determination of their activities. The coding region for the mutants can include deletions, insertions and point mutations, or combinations thereof. A typical functional analysis begins with deletion mutagenesis to determine the N- and C-terminal limits of the protein necessary for function, and then internal deletions, insertions or point mutants are made in the open ready frame to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR.

Chemical mutagenesis also can be used for identifying regions of a PKS-like gene polypeptide important for activity. A mutated construct is expressed, and the ability of the resulting altered protein to function as a PKS-like gene is assayed. Such structure-function analysis can determine which regions may be deleted, which regions tolerate insertions, and which point mutations allow the mutant protein to function in substantially the same way as the native PKS-like gene. All such mutant proteins and nucleotide sequences encoding them are within the scope of the present invention. EPA is produced in *Shewanella* as the product of a PKS-like system, such that the EPA genes encode components of this system. In *Vibrio*, DHA is produced by a similar system. The enzymes which synthesize these fatty acids are encoded by a cluster of genes which are distinct from the fatty acid synthesis genes encoding the enzymes involved in synthesis of the C16 and C18 fatty acids typically found in bacteria and in plants. As the *Shewanella* EPA genes represent a PKS-like gene cluster, EPA production is, at least to some extent, independent of the typical bacterial type II FAS system. Thus, production of EPA in the cytoplasm of plant cells can be achieved by expression of the PKS-like pathway genes in plant cells under the control of appropriate plant regulatory signals.

EPA production in *E. coli* transformed with the *Shewanella* EPA genes proceeds during anaerobic growth, indicating that O$_2$-dependent desaturase reactions are not involved. Analyses of the proteins encoded by the ORFs essential for EPA production reveals the presence of domain structures characteristic of PKS-like systems. FIG. 2A shows a summary of the domains, motifs, and also key homologies detected by "BLAST" data bank searches. Because EPA is different from many of the other substances produced by PKS-like pathways, i.e., it contains 5, cis double bonds, spaced at 3 carbon intervals along the molecule, a PKS-like system for synthesis of EPA is not expected.

Figure 2F:
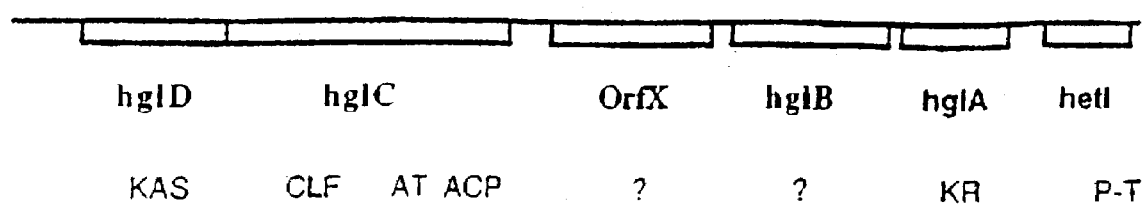
FIG. 2F shows the structure of the region of the Anabeana chromosome that is related to domains present in *Shewanella* EPA ORFs.

Further, BLAST searches using the domains present in the *Shewanella* EPA ORFs reveal that several are related to proteins encoded by a PKS-like gene cluster found in Anabeana. The structure of that region of the Anabeana chromosome is shown in FIG. 2F. The Anabeana PKS-like genes have been linked to the synthesis of a long-chain (C26), hydroxy-fatty acid found in a glycolipid layer of heterocysts. The EPA protein domains with homology to the Anabeana proteins are indicated in FIG. 2F.

ORF 6 of *Shewanella* contains a KAS domain which includes an active site motif (DXAC*), SEQ ID NO:32, as well as a "GFGG", SEQ ID NO:33, motif which is present at the end of many Type II KAS proteins (see FIG. 2A). Extended motifs are present but not shown here. Next is a malonyl-CoA:ACP acyl transferase (AT) domain. Sequences near the active site motif (GHS*XG), SEQ ID NO:34, suggest it transfers malonate rather than methylmalonate, i.e., it resembles the acetate-like ATs. Following a linker region, there is a cluster of 6 repeating domains, each ~100 amino acids in length, which are homologous to PKS-like ACP sequences. Each contains a pantetheine binding site motif (LGXDS*(L/I)), SEQ ID NOS:35 and 36. The presence of 6 such ACP domains has not been observed previously in fatty acid synthases (FAS) or PKS-like systems. Near the end of the protein is a region which shows homology to β-keto-ACP reductases (KR). It contains a pyridine nucleotide binding site motif "GXGXX(G/A/P)", SEQ ID NOS:37, 38 and 39.

The *Shewanella* ORF 8 begins with a KAS domain, including active site and ending motifs (FIG. 2C). The best match in the data banks is with the Anabeana HglD. There is also a domain which has sequence homology to the N-terminal one half of the Anabeana HglC. This region also shows weak homology to KAS proteins although it lacks the active site and ending motifs. It has the characteristics of the so-called chain length factors (CLF) of Type II PKS-like systems. ORF 8 appears to direct the production of EPA versus DHA by the PKS-like system. ORF 8 also has two domains with homology to β-hydroxyacyl-ACP dehydrases (DH). The best match for both domains is with *E. coli* FabA, a bi-functional enzyme which carries out both the dehydrase reaction and an isomerization (trans to cis) of the resulting double bond. The first DH domain contains both the active site histidine (H) and an adjacent cysteine (C) implicated in FabA catalysis. The second DH domain has the active site H but lacks the adjacent C (FIG. 2C). Blast searches with the second DH domain also show matches to FabZ, a second *E. coli* DH, which does not possess isomerase activity.

The N-terminal half of ORF 7 (FIG. 2B) has no significant matches in the data banks. The best match of the C-terminal half is with a C-terminal portion of the Anabeana HglC. This domain contains an acyl-transferase (AT) motif (GXSXG), SEQ ID NO:40. Comparison of the extended active site sequences, based on the crystal structure of the *E. coli* malonyl-CoA:ACP AT, reveals that ORF 7 lacks two residues essential for exclusion of water from the active site (*E. coli* nomenclature; Q11 and R117). These data suggest that ORF 7 may function as a thioesterase.

Figure 3:
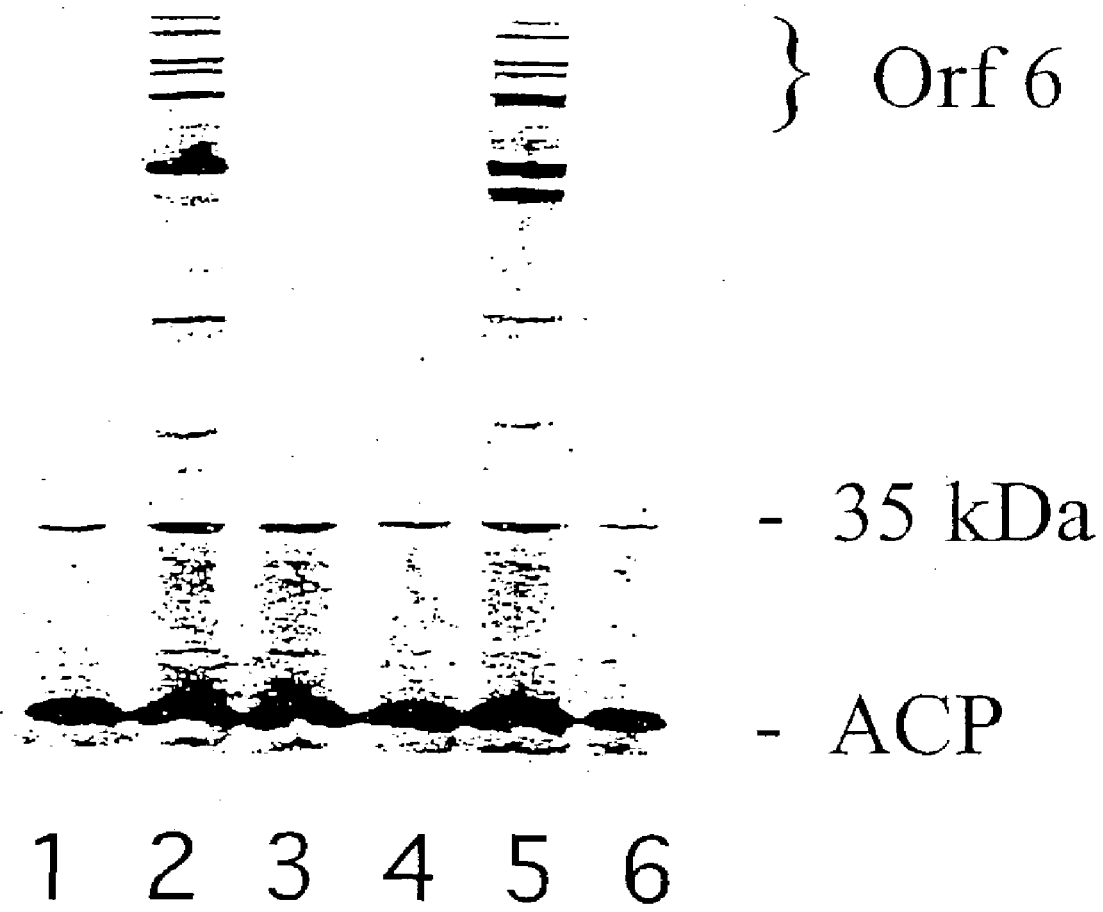
FIG. 3 shows results for pantethenylation—ORF 3 in *E. coli* strain SJ16. The image shows [$C^{14}$] β-Alanine labelled proteins from *E. coli* (strain SJ16) cells transformed with the listed plasmids. Lane 1 represents pUC19, lane 2 represents pPA-NEB (ΔORF 3), lane 3 represents pAA-Neb (EPA+), lane 4 represents ORF 6 subclone, lane 5 represents ORF 6+ORF 3 subclones, and lane 6 represents ORF 3 subclone. ACP and an unknown (but previously observed) 35 kD protein were labelled in all of the samples. The high molecular mass proteins detected in lanes 2 and 5 are full-length (largest band) and truncated products of the *Shewanella* ORF-6 gene (confirmed by Western analysis). *E. Coli* strain SJ16 is conditionally blocked in β-alanine synthesis.

ORF 9 (FIG. 2D) is homologous to an ORF of unknown function in the Anabeana Hgl cluster. It also exhibits a very weak homology to NIFA, a regulatory protein in nitrogen fixing bacteria. A regulatory role for the ORF 9 protein has not been excluded. ORF 3 (FIG. 2E) is homologous to the Anabeana HetI as well as EntD from *E. coli* and Sfp of *Bacillus*. Recently, a new enzyme family of phosphopantetheinyl transferases has been identified that includes HetI, EntD and Sfp (Lamblot RH, et al. (1996) A new enzyme superfamily—the phophopantetheinyl transferases. *Chemistry & Biology*, Vol 3, #11, 923–936 ). The data of FIG. 3 demonstrates that the presence of ORF 3 is required for addition of β-alanine (i.e. pantetheine) to the ORF 6 protein. Thus, ORF 3 encodes the phosphopantetheinyl transferase specific for the ORF 6 ACP domains. (See, Haydock SF et al (1995) Divergent sequence motifs correlated with the substrate specificity of (methyl)malonyl-CoA:acyl carrier protein transacylase domains in modular polyketide synthases, *FEBS Lett.*, 374, 246–248). Malonate is the source of the carbons utilized in the extension reactions of EPA synthesis. Additionally, malonyl-CoA rather than malonyl-ACP is the AT substrate, i.e., the AT region of ORF 6 uses malonyl Co-A.

Once the DNA sequences encoding the PKS-like genes of an organism responsible for PUFA production have been obtained, they are placed in a vector capable of replication in a host cell, or propagated in vitro by means of techniques such as PCR or long PCR. Replicating vectors can include plasmids, phage, viruses, cosmids and the like. Desirable vectors include those useful for mutagenesis of the gene of interest or for expression of the gene of interest in host cells. A PUFA synthesis enzyme or a homologous protein can be expressed in a variety of recombinantly engineered cells. Numerous expression systems are available for expression of DNA encoding a PUFA enzyme. The expression of natural or synthetic nucleic acids encoding PUFA enzyme is typically achieved by operably linking the DNA to a promoter (which is either constitutive or inducible) within an expression vector. By expression vector is meant a DNA molecule, linear or circular, that comprises a segment encoding a PUFA enzyme, operably linked to additional segments that provide for its transcription. Such additional segments include promoter and terminator sequences. An expression vector also may include one or more origins of replication, one or more selectable markers, an enhancer, a polyadenylation signal, etc. Expression vectors generally are derived from plasmid or viral DNA, and can contain elements of both. The term "operably linked" indicates that the segments are arranged so that they function in concert for their intended purposes, for example, transcription initiates in the promoter and proceeds through the coding segment to the terminator. See Sambrook et al, supra.

The technique of long PCR has made in vitro propagation of large constructs possible, so that modifications to the gene of interest, such as mutagenesis or addition of expression signals, and propagation of the resulting constructs can occur entirely in vitro without the use of a replicating vector or a host cell. In vitro expression can be accomplished, for example, by placing the coding region for the desaturase polypeptide in an expression vector designed for in vitro use and adding rabbit reticulocyte lysate and cofactors; labeled amino acids can be incorporated if desired. Such in vitro expression vectors may provide some or all of the expression signals necessary in the system used. These methods are well known in the art and the components of the system are commercially available. The reaction mixture can then be assayed directly for PKS-like enzymes for example by determining their activity, or the synthesized enzyme can be purified and then assayed.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a nucleic acid construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, integration of constructs can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus. To achieve expression in a host cell, the transformed DNA is operably associated with transcriptional and translational initiation and termination regulatory regions that are functional in the host cell.

Transcriptional and translational initiation and termination regions are derived from a variety of nonexclusive sources, including the DNA to be expressed, genes known or suspected to be capable of expression in the desired system, expression vectors, chemical synthesis The termination region can be derived from the 3' region of the gene from which the initiation region was obtained or from a different gene. A large number of termination regions are known to and have been found to be satisfactory in a variety of hosts from the same and different genera and species. The termination region usually is selected more as a matter of convenience rather than because of any particular property. When expressing more than one PKS-like ORF in the same cell, appropriate regulatory regions and expression methods should be used. Introduced genes can be propagated in the host cell through use of replicating vectors or by integration into the host genome. Where two or more genes are expressed from separate replicating vectors, it is desirable that each vector has a different means of replication. Each introduced construct, whether integrated or not, should have a different means of selection and should lack homology to the other constructs to maintain stable expression and prevent reassortment of elements among constructs. Judicious choices of regulatory regions, selection means and method of propagation of the introduced construct can be experimentally determined so that all introduced genes are expressed at the necessary levels to provide for synthesis of the desired products.

A variety of procaryotic expression systems can be used to express PUFA enzyme. Expression vectors can be constructed which contain a promoter to direct transcription, a ribosome binding site, and a transcriptional terminator. Examples of regulatory regions suitable for this purpose in *E. coli* are the promoter and operator region of the *E. coli* tryptophan biosynthetic pathway as described by Yanofsky (1984) *J. Bacteriol.*, 158:1018–1024 and the leftward promoter of phage lambda (Pλ) as described by Herskowitz and Hagen, (1980) *Ann. Rev. Genet.*, 14:399–445. The inclusion of selection markers in DNA vectors transformed in *E. coli* is also useful. Examples of such markers include genes specifying resistance to ampicillin, tetracycline, or chloramphenicol. Vectors used for expressing foreign genes in bacterial hosts generally will contain a selectable marker, such as a gene for antibiotic resistance, and a promoter which functions in the host cell. Plasmids useful for transforming bacteria include pBR322 (Bolivar, et al, (1977) *Gene* 2:95–113), the pUC plasmids (Messing, (1983) *Meth. Enzymol.* 101:20–77, Vieira and Messing, (1982) *Gene* 19:259–268), pCQV2 (Queen, ibid.), and derivatives thereof. Plasmids may contain both viral and bacterial elements. Methods for the recovery of the proteins in biologically active form are discussed in U.S. Pat. Nos. 4,966,963 and 4,999,422, which are incorporated herein by reference. See Sambrook, et al for a description of other prokaryotic expression systems.

For expression in eukaryotes, host cells for use in practicing the present invention include mammalian, avian, plant, insect, and fungal cells. As an example, for plants, the choice of a promoter will depend in part upon whether constitutive or inducible expression is desired and whether it is desirable to produce the PUFAs at a particular stage of plant development and/or in a particular tissue. Considerations for choosing a specific tissue and/or developmental stage for expression of the ORFs may depend on competing substrates or the ability of the host cell to tolerate expression of a particular PUFA. Expression can be targeted to a particular location within a host plant such as seed, leaves, fruits, flowers, and roots, by using specific regulatory sequences, such as those described in U.S. Pat. Nos. 5,463,174, 4,943,674, 5,106,739, 5,175,095, 5,420,034, 5,188,958, and 5,589,379. Where the host cell is a yeast, transcription and translational regions functional in yeast cells are provided, particularly from the host species. The transcriptional initiation regulatory regions can be obtained, for example from genes in the glycolytic pathway, such as alcohol dehydrogenase, glyceraldehyde-3-phosphate dehydrogenase (GPD), phosphoglucoisomerase, phosphoglycerate kinase, etc. or regulatable genes such as acid phosphatase, lactase, metallothionein, glucoamylase, etc. Any one of a number of regulatory sequences can be used in a particular situation, depending upon whether constitutive or induced transcription is desired, the particular efficiency of the promoter in conjunction with the open-reading frame of interest, the ability to join a strong promoter with a control region from a different promoter which allows for inducible transcription, ease of construction, and the like. Of particular interest are promoters which are activated in the presence of galactose. Galactose-inducible promoters (GAL1, GAL7, and GAL10) have been extensively utilized for high level and regulated expression of protein in yeast (Lue et al, (1987) *Mol. Cell. Biol.* 7:3446; Johnston, (1987) *Microbiol. Rev.* 51:458). Transcription from the GAL promoters is activated by the GAL4 protein, which binds to the promoter region and activates transcription when galactose is present. In the absence of galactose, the antagonist GAL80 binds to GAL4 and prevents GAL4 from activating transcription. Addition of galactose prevents GAL80 from inhibiting activation by GAL4. Preferably, the termination region is derived from a yeast gene, particularly *Saccharomyces, Schizosaccharomyces, Candida* or *Kluyveromyces*. The 3' regions of two mammalian genes, γ interferon and α2 interferon, are also known to function in yeast.

Nucleotide sequences surrounding the translational initiation codon ATG have been found to affect expression in yeast cells. If the desired polypeptide is poorly expressed in yeast, the nucleotide sequences of exogenous genes can be modified to include an efficient yeast translation initiation sequence to obtain optimal gene expression. For expression in *Saccharomyces*, this can be done by site-directed mutagenesis of an inefficiently expressed gene by fusing it in-frame to an endogenous *Saccharomyces* gene, preferably a highly expressed gene, such as the lactase gene.

As an alternative to expressing the PKS-like genes in the plant cell cytoplasm, is to target the enzymes to the chloroplast. One method to target proteins to the chloroplast entails use of leader peptides attached to the N-termini of the proteins. Commonly used leader peptides are derived from the small subunit of plant ribulose bis phosphate carboxylase. Leader sequences from other chloroplast proteins may also be used. Another method for targeting proteins to the chloroplast is to transform the chloroplast genome (Stable transformation of chloroplasts of *Chlamydomonas reinhardtii* (1 green alga) using bombardment of recipient cells with high-velocity tungsten microprojectiles coated with foreign DNA has been described. See, for example, Blowers et al *Plant Cell* (1989) 1:123–132 and Debuchy et al *EMBO J* (1989) 8:2803–2809. The transformation technique, using tungsten microprojectiles, is described by Kline et al, *Nature* (London) (1987) 327:70–73). The most common method of transforming chloroplasts involves using biolistic techniques, but other techniques developed for the purpose may also be used. (Methods for targeting foreign gene products into chloroplasts (Shrier et al *EMBO J.* (1985) 4:25–32) or mitochnodria (Boutry et al, supra) have been described. See also Tomai et al *Gen. Biol. Chem.* (1988) 263:15104–15109 and U.S. Pat. No. 4,940,835 for the use of transit peptides for translocating nuclear gene products into the chloroplast. Methods for directing the transport of proteins to the chloroplast are reviewed in Kenauf *TIBTECH* (1987) 5:40–47.

For producing PUFAs in avian species and cells, gene transfer can be performed by introducing a nucleic acid sequence encoding a PUFA enzyme into the cells following procedures known in the art. If a transgenic animal is desired, pluripotent stem cells of embryos can be provided with a vector carrying a PUFA enzyme encoding transgene and developed into adult animal (U.S. Pat. No. 5,162,215; Ono et al. (1996) *Comparative Biochemistry and Physiology A* 113(3):287–292; WO 9612793; WO 9606160). In most cases, the transgene is modified to express high levels of the PKS-like enzymes in order to increase production of PUFAs. The transgenes can be modified, for example, by providing transcriptional and/or translational regulatory regions that function in avian cells, such as promoters which direct expression in particular tissues and egg parts such as yolk. The gene regulatory regions can be obtained from a variety of sources, including chicken anemia or avian leukosis viruses or avian genes such as a chicken ovalbumin gene.

Production of PUFAs in insect cells can be conducted using baculovirus expression vectors harboring PKS-like transgenes. Baculovirus expression vectors are available from several commercial sources such as Clonetech. Methods for producing hybrid and transgenic strains of algae, such as marine algae, which contain and express a desaturase transgene also are provided. For example, transgenic marine algae can be prepared as described in U.S. Pat. No. 5,426,040. As with the other expression systems described above, the timing, extent of expression and activity of the desaturase transgene can be regulated by fitting the polypeptide coding sequence with the appropriate transcriptional and translational regulatory regions selected for a particular use. Of particular interest are promoter regions which can be induced under preselected growth conditions. For example, introduction of temperature sensitive and/or metabolite responsive mutations into the desaturase transgene coding sequences, its regulatory regions, and/or the genome of cells into which the transgene is introduced can be used for this purpose.

The transformed host cell is grown under appropriate conditions adapted for a desired end result. For host cells grown in culture, the conditions are typically optimized to produce the greatest or most economical yield of PUFAs, which relates to the selected desaturase activity. Media conditions which may be optimized include: carbon source, nitrogen source, addition of substrate, final concentration of added substrate, form of substrate added, aerobic or anaerobic growth, growth temperature, inducing agent, induction temperature, growth phase at induction, growth phase at harvest, pH, density, and maintenance of selection. Microorganisms such as yeast, for example, are preferably grown using selected media of interest, which include yeast peptone broth (YPD) and minimal media (contains amino acids, yeast nitrogen base, and ammonium sulfate, and lacks a component for selection, for example uracil). Desirably, substrates to be added are first dissolved in ethanol. Where necessary, expression of the polypeptide of interest may be induced, for example by including or adding galactose to induce expression from a GAL promoter.

When increased expression of the PKS-like gene polypeptide in a host cell which expresses PUFA from a PKS-like system is desired, several methods can be employed. Additional genes encoding the PKS-like gene polypeptide can be introduced into the host organism. Expression from the native PKS-like gene locus also can be increased through homologous recombination, for example by inserting a stronger promoter into the host genome to cause increased expression, by removing destabilizing sequences from either the mRNA or the encoded protein by deleting that information from the host genome, or by adding stabilizing sequences to the mRNA (see U.S. Pat. Nos. 4,910,141 and 5,500,365). Thus, the subject host will have at least have one copy of the expression construct and may have two or more, depending upon whether the gene is integrated into the genome, amplified, or is present on an extrachromosomal element having multiple copy numbers. Where the subject host is a yeast, four principal types of yeast plasmid vectors can be used: Yeast Integrating plasmids (YIps), Yeast Replicating plasmids (YRps), Yeast Centromere plasmids (YCps), and Yeast Episomal plasmids (YEps). YIps lack a yeast replication origin and must be propagated as integrated elements in the yeast genome. YRps have a chromosomally derived autonomously replicating sequence and are propagated as medium copy number (20 to 40), autonomously replicating, unstably segregating plasmids. YCps have both a replication origin and a centromere sequence and propagate as low copy number (10–20), autonomously replicating, stably segregating plasmids. YEps have an origin of replication from the yeast 2 μm plasmid and are propagated as high copy number, autonomously replicating, irregularly segregating plasmids. The presence of the plasmids in yeast can be ensured by maintaining selection for a marker on the plasmid. Of particular interest are the yeast vectors pYES2 (a YEp plasmid available from Invitrogen, confers uracil prototrophy and a GAL1 galactose-inducible promoter for expression), and pYX424 (a YEp plasmid having a constitutive TP1 promoter and conferring leucine prototrophy; (Alber and Kawasaki (1982). *J. Mol. & Appl. Genetics* 1:419).

Figure 1B:
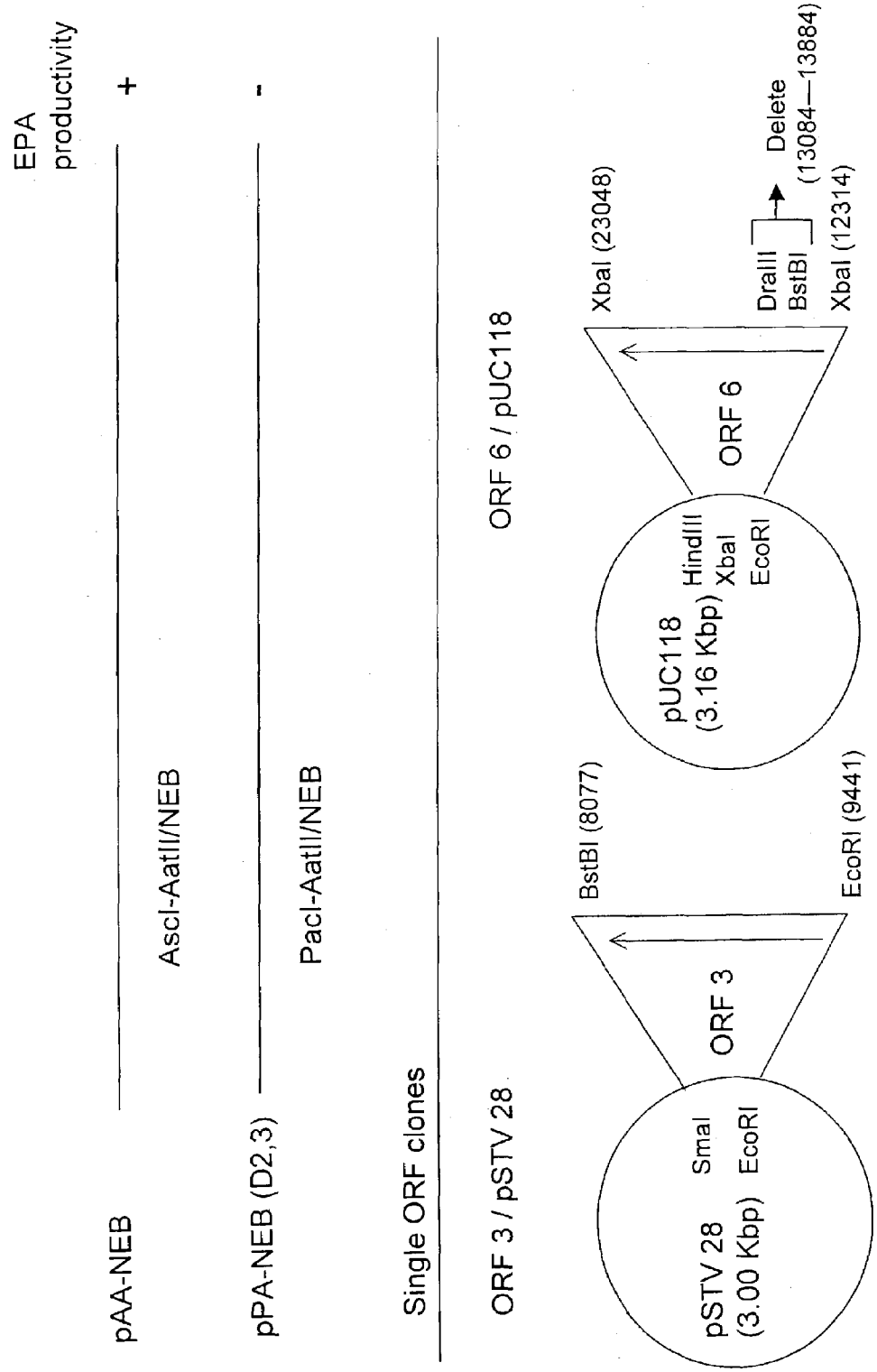
FIG. 1B shows the designations given to subclones.

The choice of a host cell is influenced in part by the desired PUFA profile of the transgenic cell, and the native profile of the host cell. Even where the host cell expresses PKS-like gene activity for one PUFA, expression of PKS-like genes of another PKS-like system can provide for production of a novel PUFA not produced by the host cell. In particular instances where expression of PKS-like gene activity is coupled with expression of an ORF 8 PKS-like gene of an organism which produces a different PUFA, it can be desirable that the host cell naturally have, or be mutated to have, low PKS-like gene activity for ORF 8. As an example, for production of EPA, the DNA sequence used encodes the polypeptide having PKS-like gene activity of an organism which produces EPA, while for production of DHA, the DNA sequences used are those from an organism which produces DHA. For use in a host cell which already expresses PKS-like gene activity it can be necessary to utilize an expression cassette which provides for overexpression of the desired PKS-like genes alone or with a construct to downregulate the activity of an existing ORF of the existing PKS-like system, such as by antisense or co-suppression. Similarly, a combination of ORFs derived from separate organisms which produce the same or different PUFAs using PKS-like systems may be used. For instance, the ORF 8 of *Vibrio* directs the expression of DHA in a host cell, even when ORFs 3, 6, 7 and 9 are from *Shewanella*, which produce EPA when coupled to ORF 8 of *Shewanella*. Therefore, for production of eicosapentanoic acid (EPA), the expression cassettes used generally include one or more cassettes which include ORFs 3, 6, 7, 8 and 9 from a PUFA-producing organism such as the marine bacterium *Shewanella putrefaciens* (for EPA production) or *Vibrio marinus* (for DHA production). ORF 8 can be used for induction of DHA production, and ORF 8 of *Vibrio* can be used in conjunction with ORFs 3, 6, 7 and 9 of *Shewanella* to produce DHA. The organization and numbering scheme of the ORFs identified in the *Shewanella* gene cluster are shown in FIG. 1A. Maps of several subclones referred to in this study are shown in FIG. 1B. For expression of a PKS-like gene polypeptide, transcriptional and translational initiation and termination regions functional in the host cell are operably linked to the DNA encoding the PKS-like gene polypeptide.

Constructs comprising the PKS-like ORFs of interest can be introduced into a host cell by any of a variety of standard techniques, depending in part upon the type of host cell. These techniques include transfection, infection, bolistic impact, electroporation, microinjection, scraping, or any other method which introduces the gene of interest into the host cell (see U.S. Pat. Nos. 4,743,548, 4,795,855, 5,068, 193, 5,188,958, 5,463,174, 5,565,346 and 5,565,347). Methods of transformation which are used include lithium acetate transformation (*Methods in Enzymology*, (1991) 194:186–187). For convenience, a host cell which has been manipulated by any method to take up a DNA sequence or construct will be referred to as "transformed" or "recombinant" herein. The subject host will have at least have one copy of the expression construct and may have two or more, depending upon whether the gene is integrated into the genome, amplified, or is present on an extrachromosomal element having multiple copy numbers.

For production of PUFAs, depending upon the host cell, the several polypeptides produced by pEPA, ORFs 3, 6, 7, 8 and 9, are introduced as individual expression constructs or can be combined into two or more cassettes which are introduced individually or co-transformed into a host cell. A standard transformation protocol is used. For plants, where less than all PKS-like genes required for PUFA synthesis have been inserted into a single plant, plants containing a complementing gene or genes can be crossed to obtain plants containing a full complement of PKS-like genes to synthesize a desired PUFA.

The PKS-like-mediated production of PUFAs can be performed in either prokaryotic or eukaryotic host cells. The cells can be cultured or formed as part or all of a host organism including an animal. Viruses and bacteriophage also can be used with appropriate cells in the production of PUFAs, particularly for gene transfer, cellular targeting and selection. Any type of plant cell can be used for host cells, including dicotyledonous plants, monocotyledonous plants, and cereals. Of particular interest are crop plants such as *Brassica, Arabidopsis*, soybean, corn, and the like. Prokaryotic cells of interest include *Eschericia, Baccillus, Lactobaccillus, cyanobacteria* and the like. Eukaryotic cells include plant cells, mammalian cells such as those of lactating animals, avian cells such as of chickens, and other cells amenable to genetic manipulation including insect, fungal, and algae cells. Examples of host animals include mice, rats, rabbits, chickens, quail, turkeys, cattle, sheep, pigs, goats, yaks, etc., which are amenable to genetic manipulation and cloning for rapid expansion of a transgene expressing population. For animals, PKS-like transgenes can be adapted for expression in target organelles, tissues and body fluids through modification of the gene regulatory regions. Of particular interest is the production of PUFAs in the breast milk of the host animal.

Examples of host microorganisms include *Saccharomyces cerevisiae*, *Saccharomyces carlsbergensis*, or other yeast such as *Candida*, *Kluyveromyces* or other fungi, for example, filamentous fungi such as *Aspergillus*, *Neurospora*, *Penicillium*, etc. Desirable characteristics of a host microorganism are, for example, that it is genetically well characterized, can be used for high level expression of the product using ultra-high density fermentation, and is on the GRAS (generally recognized as safe) list since the proposed end product is intended for ingestion by humans. Of particular interest is use of a yeast, more particularly baker's yeast (*S. cerevisiae*), as a cell host in the subject invention. Strains of particular interest are SC334 (Mat α pep4-3 prbl-1122 ura3-52 leu2-3, 112 regl-501 gal1; (Hovland et al (1989) Gene 83:57–64); BJ1995 (Yeast Genetic Stock Centre, 1021 Donner Laboratory, Berkeley, Calif. 94720), INVSC1 (Mat α hiw3Δ1 leu2 trp1-289 ura3-52 (Invitrogen, 1600 Faraday Ave., Carlsbad, Calif. 92008) and INVSC2 (Mat α his3Δ200 ura3-167; (Invitrogen). Bacterial cells also may be used as hosts. This includes *E. coli*, which can be useful in fermentation processes. Alternatively, a host such as a *Lactobacillus* species can be used as a host for introducing the products of the PKS-like pathway into a product such as yogurt.

The transformed host cell can be identified by selection for a marker contained on the introduced construct. Alternatively, a separate marker construct can be introduced with the desired construct, as many transformation techniques introduce multiple DNA molecules into host cells. Typically, transformed hosts are selected for their ability to grow on selective media. Selective media can incorporate an antibiotic or lack a factor necessary for growth of the untransformed host, such as a nutrient or growth factor. An introduced marker gene therefor may confer antibiotic resistance, or encode an essential growth factor or enzyme, and permit growth on selective media when expressed in the transformed host cell. Desirably, resistance to kanamycin and the amino glycoside G418 are of particular interest (see U.S. Pat. No. 5,034,322). For yeast transformants, any marker that functions in yeast can be used, such as the ability to grow on media lacking uracil, lencine, lysine or tryptophan.

Selection of a transformed host also can occur when the expressed marker protein can be detected, either directly or indirectly. The marker protein can be expressed alone or as a fusion to another protein. The marker protein can be one which is detected by its enzymatic activity; for example β-galactosidase can convert the substrate X-gal to a colored product, and luciferase can convert luciferin to a light-emitting product. The marker protein can be one which is detected by its light-producing or modifying characteristics; for example, the green fluorescent protein of *Aequorea victoria* fluoresces when illuminated with blue light. Antibodies can be used to detect the marker protein or a molecular tag on, for example, a protein of interest. Cells expressing the marker protein or tag can be selected, for example, visually, or by techniques such as FACS or panning using antibodies.

The PUFAs produced using the subject methods and compositions are found in the host plant tissue and/or plant part as free fatty acids and/or in conjugated forms such as acylglycerols, phospholipids, sulfolipids or glycolipids, and can be extracted from the host cell through a variety of means well-known in the art. Such means include extraction with organic solvents, sonication, supercritical fluid extraction using for example carbon dioxide, and physical means such as presses, or combinations thereof. Of particular interest is extraction with methanol and chloroform. Where appropriate, the aqueous layer can be acidified to protonate negatively charged moieties and thereby increase partitioning of desired products into the organic layer. After extraction, the organic solvents can be removed by evaporation under a stream of nitrogen. When isolated in conjugated forms, the products are enzymatically or chemically cleaved to release the free fatty acid or a less complex conjugate of interest, and are then subjected to further manipulations to produce a desired end product. Desirably, conjugated forms of fatty acids are cleaved with potassium hydroxide.

If further purification is necessary, standard methods can be employed. Such methods include extraction, treatment with urea, fractional crystallization, HPLC, fractional distillation, silica gel chromatography, high speed centrifugation or distillation, or combinations of these techniques. Protection of reactive groups, such as the acid or alkenyl groups, can be done at any step through known techniques, for example alkylation or iodination. Methods used include methylation of the fatty acids to produce methyl esters. Similarly, protecting groups can be removed at any step. Desirably, purification of fractions containing DHA and EPA is accomplished by treatment with urea and/or fractional distillation.

The uses of the subject invention are several. Probes based on the DNAs of the present invention find use in methods for isolating related molecules or in methods to detect organisms expressing PKS-like genes. When used as probes, the DNAs or oligonucleotides need to be detectable. This is usually accomplished by attaching a label either at an internal site, for example via incorporation of a modified residue, or at the 5' or 3' terminus. Such labels can be directly detectable, can bind to a secondary molecule that is detectably labeled, or can bind to an unlabelled secondary molecule and a detectably labeled tertiary molecule; this process can be extended as long as is practicable to achieve a satisfactorily detectable signal without unacceptable levels of background signal. Secondary, tertiary, or bridging systems can include use of antibodies directed against any other molecule, including labels or other antibodies, or can involve any molecules which bind to each other, for example a biotin-streptavidin/avidin system. Detectable labels typically include radioactive isotopes, molecules which chemically or enzymatically produce or alter light, enzymes which produce detectable reaction products, magnetic molecules, fluorescent molecules or molecules whose fluorescence or light-emitting characteristics change upon binding. Examples of labelling methods can be found in U.S. Pat. No. 5,011,770. Alternatively, the binding of target molecules can be directly detected by measuring the change in heat of solution on binding of a probe to a target via isothermal titration calorimetry, or by coating the probe or target on a surface and detecting the change in scattering of light from the surface produced by binding of a target or a probe, respectively, is done with the BIAcore system.

PUFAs produced by recombinant means find applications in a wide variety of areas. Supplementation of humans or animals with PUFAs in various forms can result in increased levels not only of the added PUFAs, but of their metabolic progeny as well. Complex regulatory mechanisms can make it desirable to combine various PUFAs, or to add different conjugates of PUFAs, in order to prevent, control or overcome such mechanisms to achieve the desired levels of specific PUFAs in an individual. In the present case, expression of PKS-like gene genes, or antisense PKS-like gene transcripts, can alter the levels of specific PUFAs, or derivatives thereof, found in plant parts and/or plant tissues. The PKS-like gene polypeptide coding region is expressed either by itself or with other genes, in order to produce tissues and/or plant parts containing higher proportions of desired PUFAs or containing a PUFA composition which more closely resembles that of human breast milk (Prieto et al., PCT publication WO 95/24494) than does the unmodified tissues and/or plant parts.

PUFAs, or derivatives thereof, made by the disclosed method can be used as dietary supplements for patients undergoing intravenous feeding or for preventing or treating malnutrition. For dietary supplementation, the purified PUFAs, or derivatives thereof, can be incorporated into cooking oils, fats or margarines formulated so that in normal use the recipient receives a desired amount of PUFA. The PUFAs also can be incorporated into infant formulas, nutritional supplements or other food products, and find use as anti-inflammatory or cholesterol lowering agents.

Particular fatty acids such as EPA can be used to alter the composition of infant formulas to better replicate the PUFA composition of human breast milk. The predominant triglyceride in human milk is reported to be 1,3-di-oleoyl-2-palmitoyl, with 2-palmitoyl glycerides reported as better absorbed than 2-oleoyl or 2-lineoyl glycerides (see U.S. Pat. No. 4,876,107). Typically, human breast milk has a fatty acid profile comprising from about 0.15% to about 0.36% as DHA, from about 0.03% to about 0.13% as EPA, from about 0.30% to about 0.88% as ARA, from about 0.22% to about 0.67% as DGLA, and from about 0.27% to about 1.04% as GLA. A preferred ratio of GLA:DGLA:ARA in infant formulas is from about 1:1:4 to about 1:1:1, respectively. Amounts of oils providing these ratios of PUFA can be determined without undue experimentation by one of skill in the art. PUFAs, or host cells containing them, also can be used as animal food supplements to alter an animal's tissue or milk fatty acid composition to one more desirable for human or animal consumption.

For pharmaceutical use (human or veterinary), the compositions generally are administered orally but can be administered by any route by which they may be successfully absorbed, e.g., parenterally (i.e. subcutaneously, intramuscularly or intravenously), rectally or vaginally or topically, for example, as a skin ointment or lotion. Where available, gelatin capsules are the preferred form of oral administration. Dietary supplementation as set forth above also can provide an oral route of administration. The unsaturated acids of the present invention can be administered in conjugated forms, or as salts, esters, amides or prodrugs of the fatty acids. Any pharmaceutically acceptable salt is encompassed by the present invention; especially preferred are the sodium, potassium or lithium salts. Also encompassed are the N-alkylpolyhydroxamine salts, such as N-methyl glucamine, described in PCT publication WO 96/33155. Preferred esters are the ethyl esters.

The PUFAs of the present invention can be administered alone or in combination with a pharmaceutically acceptable carrier or excipient. As solid salts, the PUFAs can also be administered in tablet form. For intravenous administration, the PUFAs or derivatives thereof can be incorporated into commercial formulations such as Intralipids. Where desired, the individual components of formulations can be individually provided in kit form, for single or multiple use. A typical dosage of a particular fatty acid is from 0.1 mg to 20 g, or even 100 g daily, and is preferably from 10 mg to 1, 2, 5 or 10 g daily as required, or molar equivalent amounts of derivative forms thereof. Parenteral nutrition compositions comprising from about 2 to about 30 weight percent fatty acids calculated as triglycerides are encompassed by the present invention. Other vitamins, and particularly fat-soluble vitamins such as vitamin A, D, E and L-carnitine optionally can be included. Where desired, a preservative such as a tocopherol can be added, typically at about 0.1% by weight.

The following examples are presented by way of illustration, not of limitation.

EXAMPLES

Example 1

The Identity of ORFs Derived from *Vibrio marinus*

Using polymerase chain reaction (PCR) with primers based on ORF 6 of *Shewanella* (Sp ORF 6) sequences (FW 5' primers CUACUACUACUACCAAGCT AAAGCACT-TAACCGTG, SEQ ID NO:41, and CUACUACUACUAA-CAGCGAAATG CTTATCAAG, SEQ ID NO:42, for *Vibrio* and SS9 respectively and 3' BW primers: CAUCAUCAU-CAUGCGACCAAAACCAAATGAGCTAATAC, SEQ ID NO:43, for both *Vibrio* and SS9) and genomic DNAs templates from *Vibrio* and a borophyllic *photobacter* producing EPA (provided by Dr. Bartlett, UC San Diego), resulted in PCR products of ca.400 bases for *Vibrio marinus* (*Vibrio*) and ca.900 bases for SS9 presenting more than 75% homology with corresponding fragments of Sp ORF 6 (see FIG. 25) as determined by direct counting of homologous amino acids.

A *Vibrio* cosmid library was then prepared and using the *Vibrio* ORF 6 PCR product as a probe (see FIG. 26); clones containing at least ORF 6 were selected by colony hybridization.

Figure 7A:
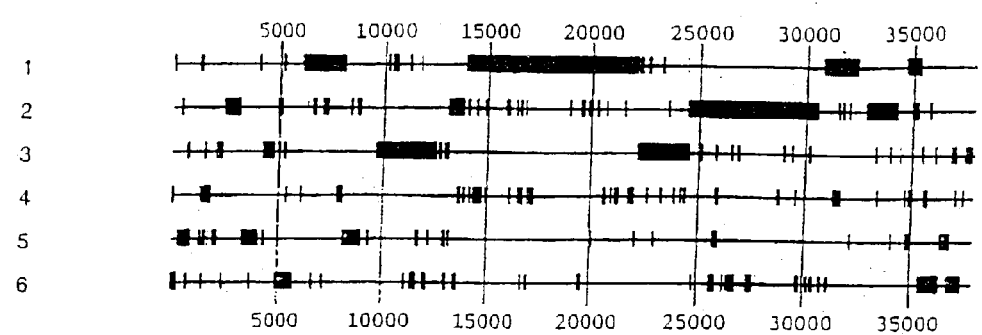
FIG. 7 shows a comparison of the PKS-like gene clusters of *Shewanella putrefaciens* and *Vibrio marinus*.
FIG. 7B is the *Vibrio marinus* operon sequence.
Figure 7B:
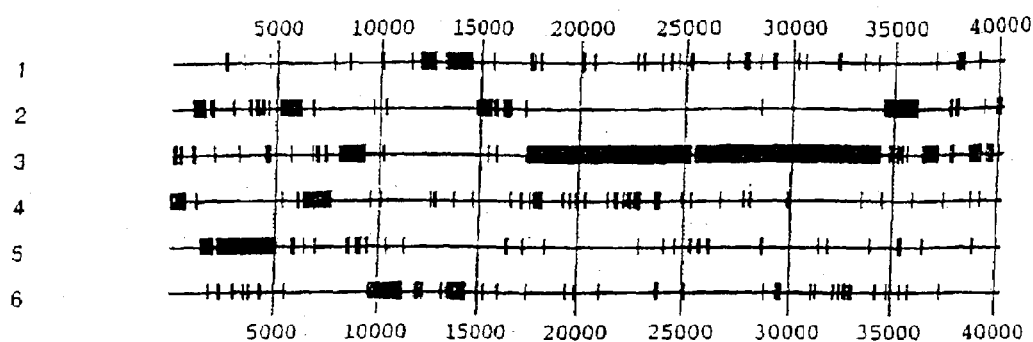

Through additional sequences of the selected cosmids such as cosmid #9 and cosmid #21, a *Vibrio* cluster (FIG. 5) with ORFs homologous to, and organized in the same sequential order (ORFs 6–9) as ORFs 6–9 of *Shewanella*, was obtained (FIG. 7). The *Vibrio* ORFs from this sequence are found at 17394 to 36115 and comprehend ORFs 6–9.

TABLE

| Vibrio operon figures | |
|---|---|
| 17394 to 25349 | length = 7956 nt |
| 25509 to 28157 | length = 2649 nt |
| 28209 to 34262 | length = 6054 nt |
| 34454 to 36115 | length = 1662 nt |

Figure 24:
FIG. 24 shows the translated DNA sequence (SEQ ID NO:14) upstream of the published ORF 3 and the corresponding amino acids for which they code (SEQ ID NO:15). The ATG start codon at position 9016 is the start codon for the protein described by Yazawa et al (1996) supra. The other arrows depict TTG or ATT codons that can also serve as start codons in bacteria. When ORF 3 is started from the published ATG codon at 9016, the protein is not functional in making EPA. When ORF 3 is initiated at the TTG codon at position 9157, the protein is capable of facilitating EPA synthesis.

The ORF designations for the *Shewanella* genes are based on those disclosed in FIG. 4, and differ from those published for the *Shewanella* cluster (Yazawa et al, U.S. Pat. No. 5,683,898). For instance, ORF 3 of FIG. 4 is read in the opposite direction from the other ORFs and is not disclosed in Yazawa et al U.S. Pat. No. 5,683,898 (See FIG. 24) for comparison with Yazawa et al U.S. Pat. No. 5,683,898.

Sequences homologous to ORF 3, were not found in the proximity of ORF 6 (17000 bases upstream of ORF 6) or of ORF 9 (ca.4000 bases downstream of ORF 9). Motifs characteristic of phosphopantethenyl transferases (Lambalot et al (1996) Current Biology 3:923–936) were absent from the Vibrio sequences screened for these motifs. In addition, there was no match to Sp ORF 3 derived probes in genomic digests of Vibrio and of SC2A Shewanella (another bacterium provided by the University of San Diego and also capable of producing EPA). Although ORF 3 may exist in Vibrio, its DNA may not be homologous to that of Sp ORF 3 and/or could be located in portions of the genome that were not sequenced.

Figure 8:
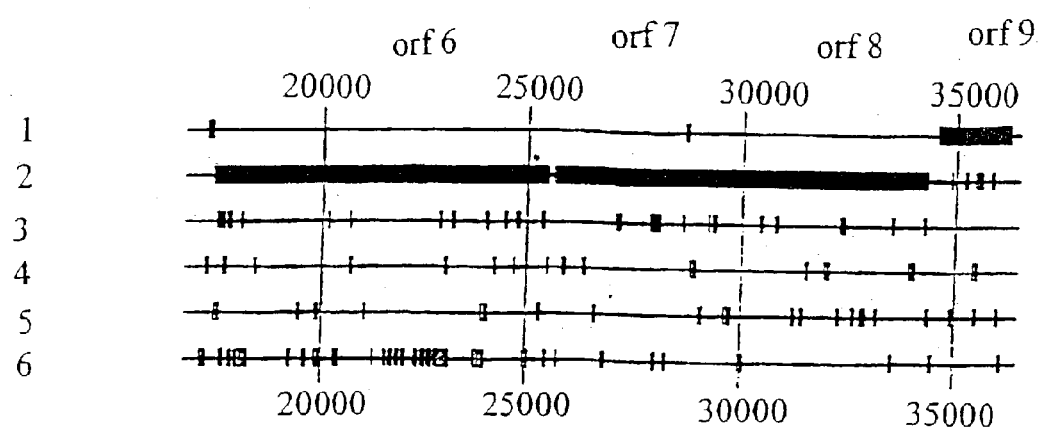
FIG. 8 is an expanded view of the PKS-like gene cluster portion of *Vibrio marinus* shown in FIG. 7B showing that ORFs 6, 7 and 8 are in reading frame 2, while ORF 9 is in reading frame 3.
Figure 9:
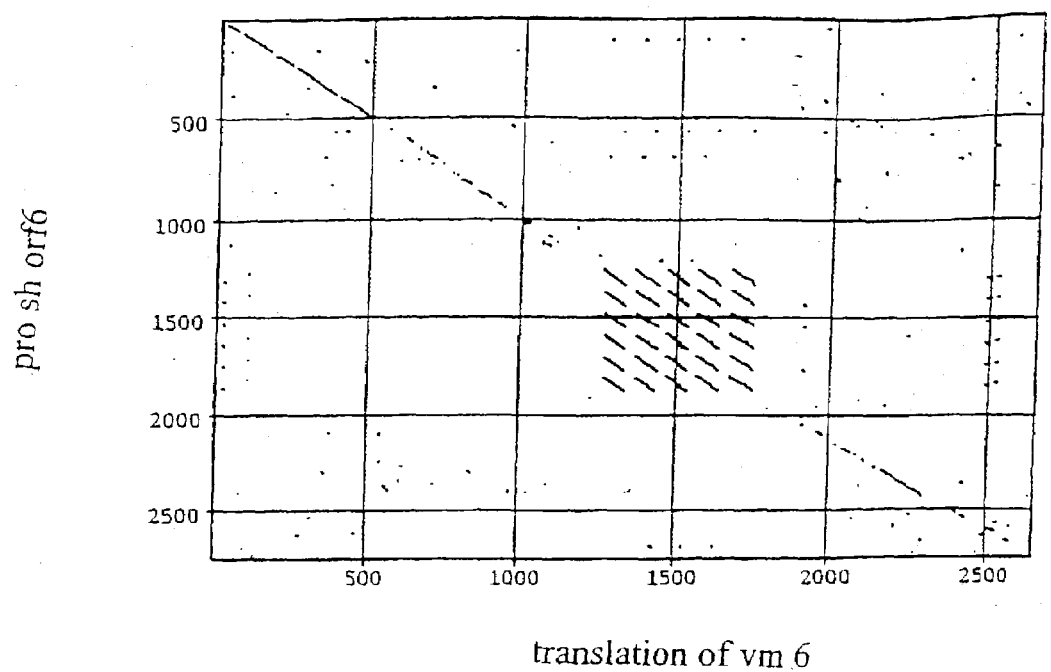
FIG. 9 demonstrates sequence homology of ORF 6 of *Shewanella putrefaciens* and *Vibrio marinus*. The *Shewanella* ORF 6 is depicted on the vertical axis, and the *Vibrio* ORF 6 is depicted on the horizontal axis. Lines indicate regions of the proteins that have a 60% identity. The repeated lines in the middle correspond to the multiple ACP domains found in ORF 6.
Figure 10:
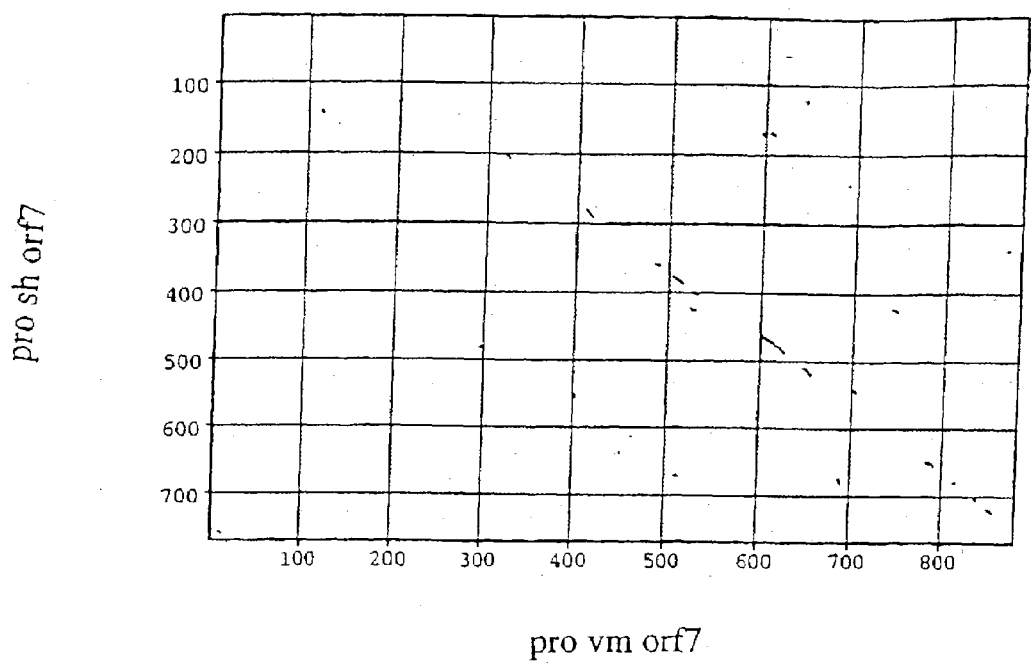
FIG. 10 demonstrates sequence homology of ORF 7 of *Shewanella putrefaciens* and *Vibrio marinus*. The *Shewanella* ORF 7 is depicted on the vertical axis, and the *Vibrio* ORF 7 is depicted on the horizontal axis. Lines indicate regions of the proteins that have a 60% identity.
Figure 11:
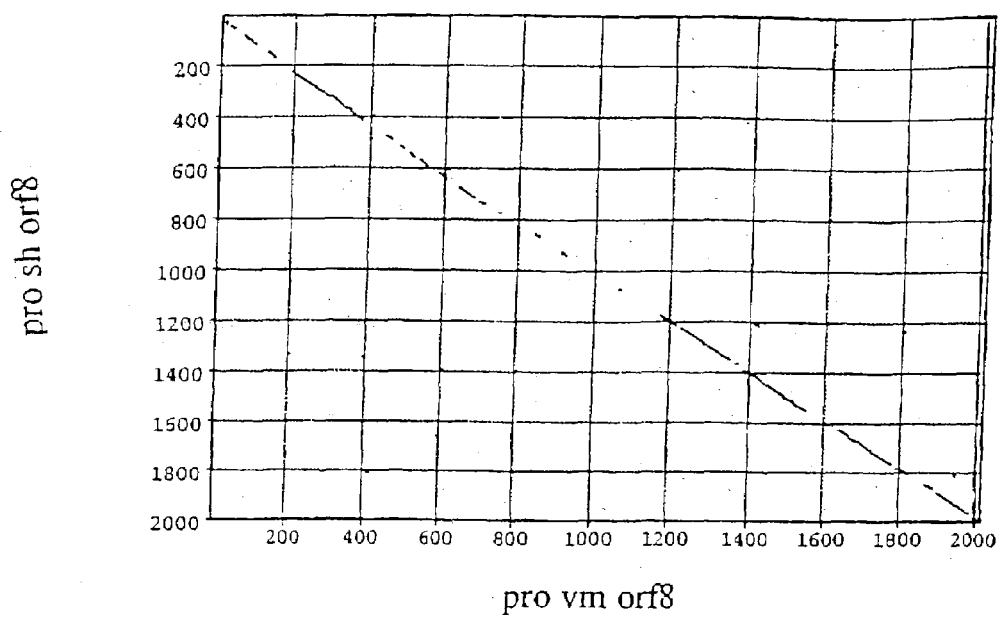
FIG. 11 demonstrates sequence homology of ORF 8 of *Shewanella putrefaciens* and *Vibrio marinus*. The *Shewanella* ORF 8 is depicted on the vertical axis, and the *Vibro*. ORF 8 is depicted on the horizontal axis. Lines indicate regions of the proteins that have a 60% identity.
Figure 12:
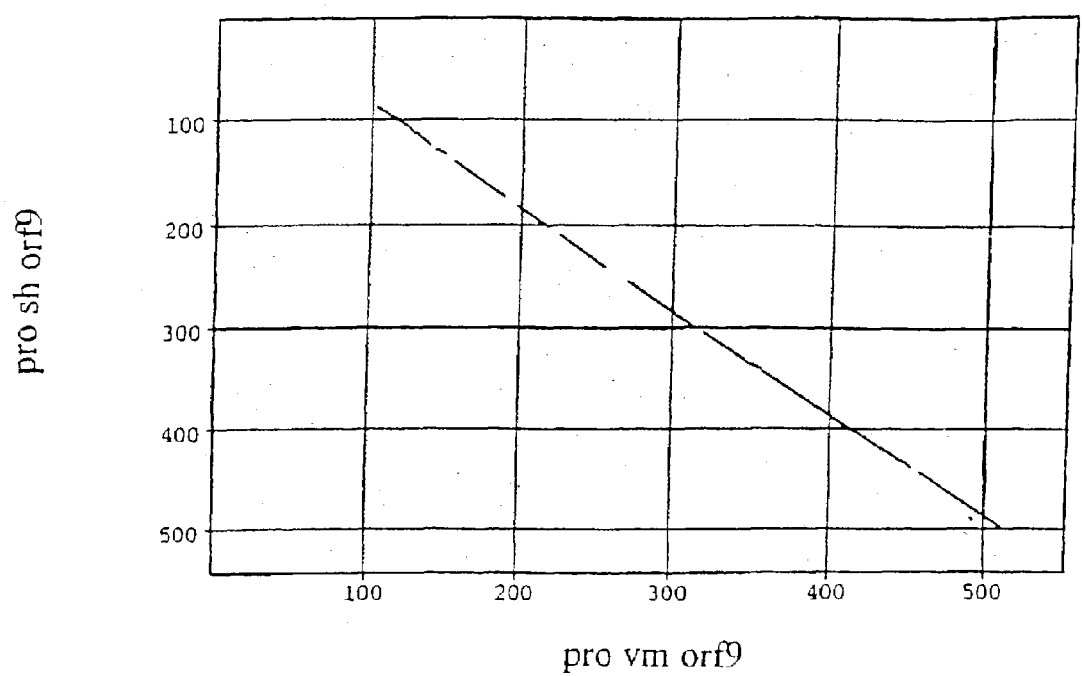
FIG. 12 demonstrates sequence homology of ORF 9 of *Shewanella putrefaciens* and *Vibrio marinus*. The *Shewanella* ORF 9 is depicted on the vertical axis, and the *Vibrio* ORF 9 is depicted on the horizontal axis. Lines indicate regions of the proteins that have a 60% identity.

FIG. 6 provides the sequence of an approximately 19 kb Vibrio clone comprising ORFs 6–9. FIGS. 7 and 8 compare the gene cluster organizations of the PKS-like systems of Vibrio marinus and Shewanella putrefacians. FIGS. 9 through 12 show the levels of sequence homology between the corresponding ORFs 6, 7, 8 and 9, respectively.

Example 2

ORF 8 Directs DHA Production

As described in example 1, DNA homologous to Sp ORF 6 was found in an unrelated species, SS9 Photobacter, which also is capable of producing EPA. Additionally, ORFs homologous to Sp ORF 6–9 were found in the DHA producing Vbrio marinus (Vibrio). From these ORFs a series of experiments was designed in which deletions in each of Sp ORFs 6–9 that suppressed EPA synthesis in E. coli (Yazawa (1996) supra) were complemented by the corresponding homologous genes from Vibrio.

Figure 13:
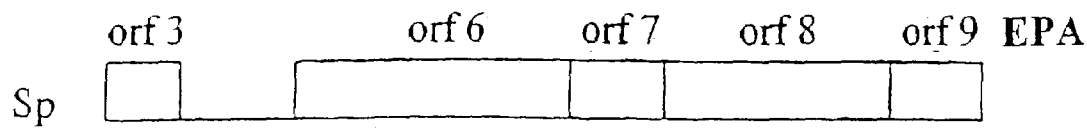
FIG. 13 is a depiction of various complementation experiments, and resulting PUFA production. On the right, is shown the longest PUFA made in the *E. coli* strain containing the *Vibrio* and *Shewanella* genes depicted on the left. The hollow boxes indicate ORFs from *Shewanella*. The solid boxes indicate ORFs from *Vibrio*.
Figure 13:
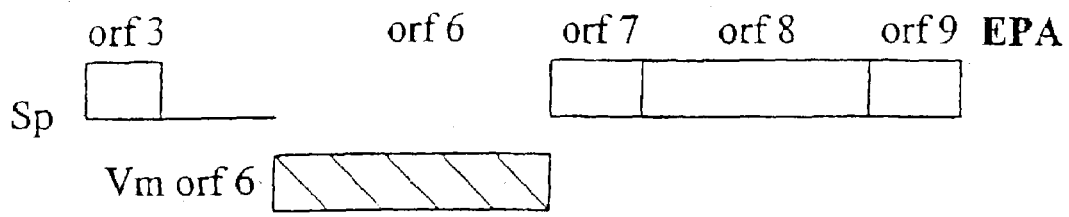
Figure 13:
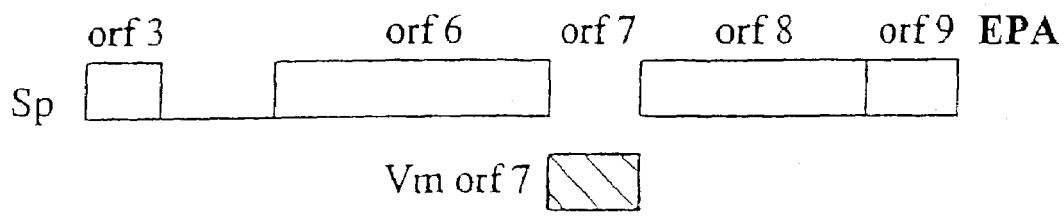
Figure 13:
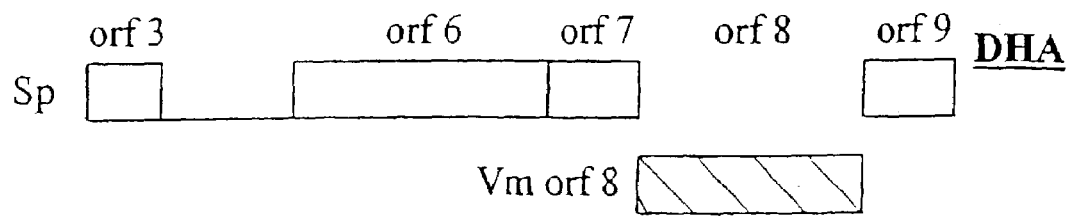

The Sp EPA cluster was used to determine if any of the Vibrio ORFs 6–9 was responsible for the production of DHA. Deletion mutants provided for each of the Sp ORFs are EPA and DHA null. Each deletion was then complemented by the corresponding Vibrio ORF expressed behind a lac promoter (FIG. 13).

Figure 14:
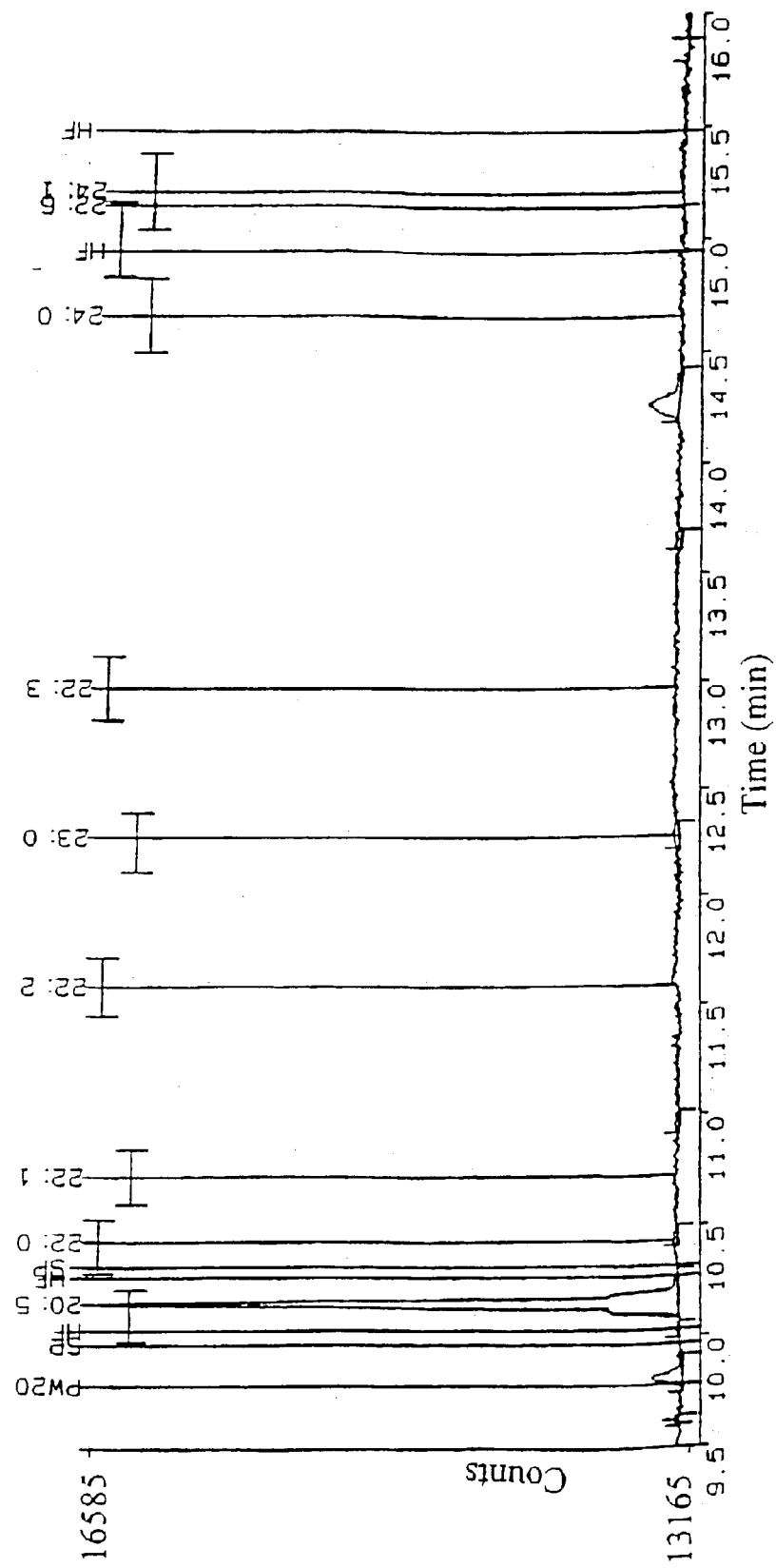
FIG. 14 is a chromatogram showing fatty acid production from complementation of pEPAD8 from *Shewanella* (deletion ORF 8) with ORF 8 from *Shewanella*, in *E. coli* Fad E-. The chromatogram presents an EPA (20:5) peak.
Figure 15:
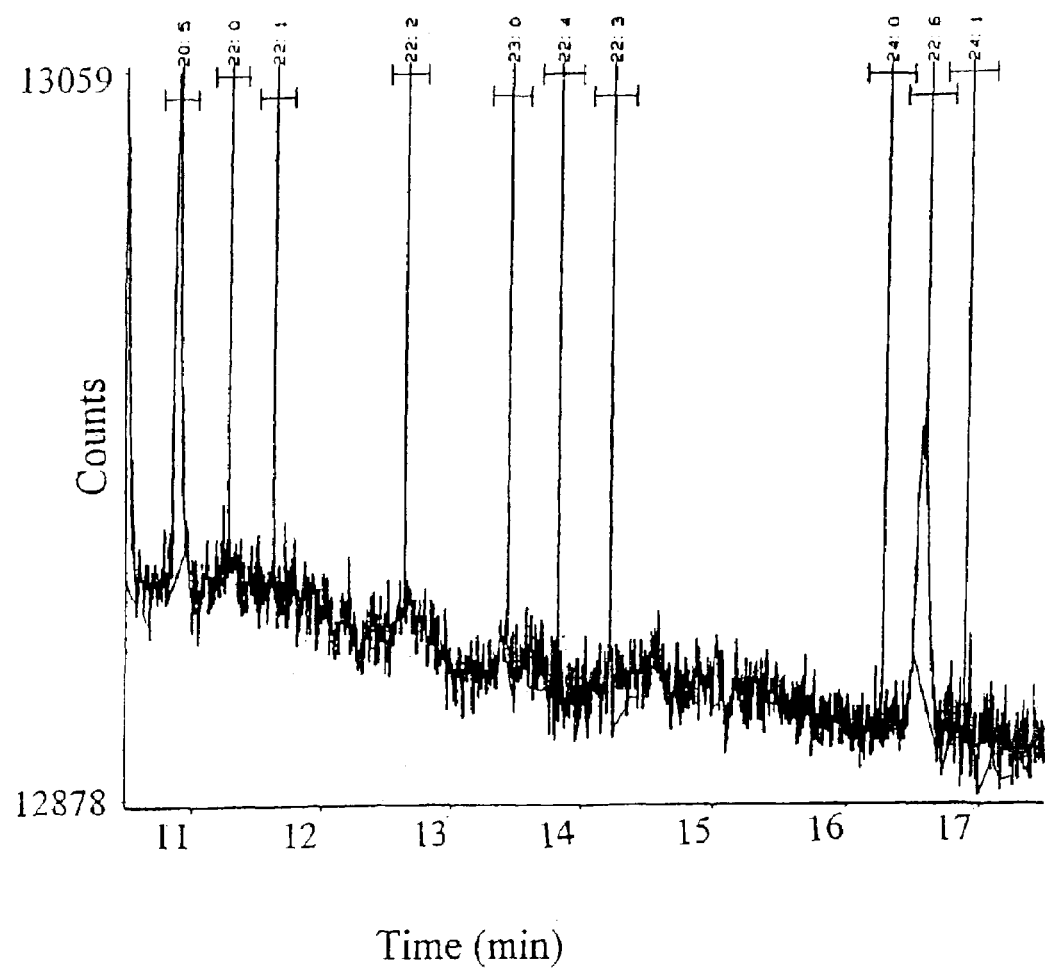
FIG. 15 is a chromatogram showing fatty acid production from complementation of pEPAD8 from *Shewanella* (deletion ORF 8) with ORF 8 from *Vibrio marinus*, in *E. coli* Fad E-. The chromatograph presents EPA (20:5) and DHA (22:6) peaks.

The complementation of a Sp ORF 6 deletion by a Vibrio ORF 6 reestablished the production of EPA. Similar results were obtained by complementing the Sp ORF 7 and ORF 9 deletions. By contrast, the complementation of a Sp ORF 8 deletion resulted in the production of C22:6. Vibrio ORF 8 therefore appears to be a key element in the synthesis of DHA. FIGS. 14 and 15 show chromatograms of fatty acid profiles from the respective complementations of Sp del ORF 6 with Vibrio ORF 6 (EPA and no DHA) and Sp del ORF 8 with Vibrio ORF 8 (DHA). FIG. 16 shows the fatty acid percentages for the ORF 8 complementation, again demonstrating that ORF 8 is responsible for DHA production.

These data show that polyketide-like synthesis genes with related or similar ORFs can be combined and expressed in a heterologous system and used to produce a distinct PUFA species in the host system, and that ORF 8 has a role in determining the ultimate chain length. The Vibrio ORFs 6, 7, 8, and 9 reestablish EPA synthesis. In the case of Vibrio ORF 8, DHA is also present (ca. 0.7%) along with EPA (ca. 0.6%) indicating that this gene plays a significant role in directing synthesis of DHA vs EPA for these systems.

Example 3

Requirements for Production of DHA

To determine how Vibrio ORFs of the cluster ORF 6–9 are used in combination with Vibrio ORF 8, some combinations of Vibrio ORF 8 with some or all of the other Vibrio ORFS 6–9 cluster were created to explain the synthesis of DHA. Vibrio ORFs 6–9 were complemented with Sp ORF 3. The results of this complementation are presented in FIGS. 16b and 16c. The significant amounts of DHA measured (greater than about 9%) and the absence of EPA suggest that no ORFs other than those of Vibrio ORFs 6–9 are required for DHA synthesis when combined with Sp ORF 3. This suggests that Sp ORF 3 plays a general function in the synthesis of bacterial PUFAs.

With respect to the DHA vs EPA production, it may be necessary to combine Vibrio ORF 8 with other Vibrio ORFs of the 6–9 cluster in order to specifically produce DHA. The roles of Vibrio ORF 9 and each of the combinations of Vibrio ORFs (6, 8), (7, 8), (8, 9), etc in the synthesis of DHA are being studied.

Example 4

Plant Expression Constructs

A cloning vector with very few restriction sites was designed to facilitate the cloning of large fragments and their subsequent manipulation. An adapter was assembled by annealing oligonucleotides with the sequences AAGC-CCGGGCTT, SEQ ID NO:44, and GTACAAGC-CCGGGCTTAGCT, SEQ ID NO:45. This adapter was ligated to the vector pBluescript II SK+ (Stratagene) after digestion of the vector with the restriction endonucleases Asp718 and SstI. The resulting vector, pCGN7769 had a single SrfI (and embedded SmaI) cloning site for the cloning of blunt ended DNA fragments.

Figure 17:
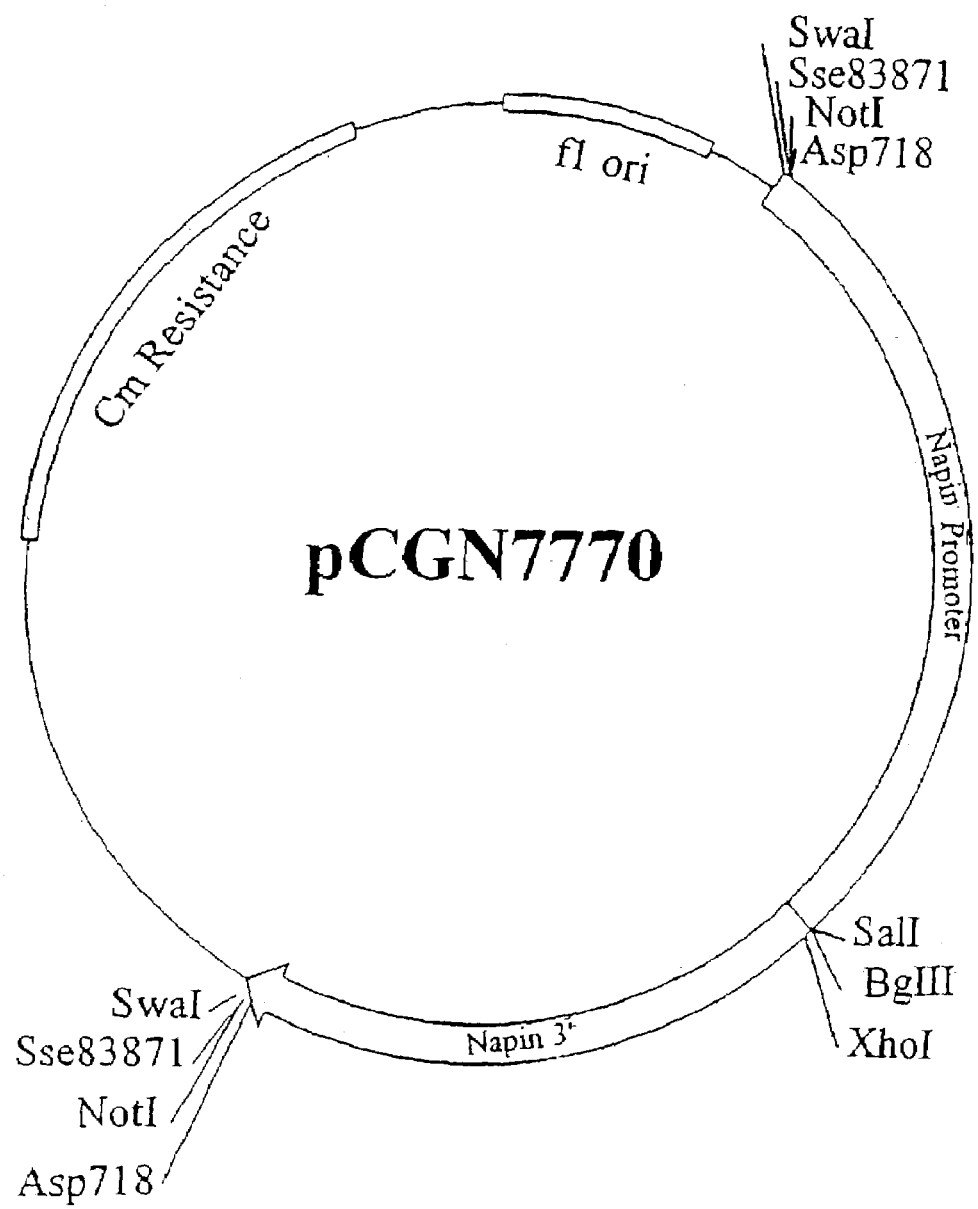
FIG. 17 is a plasmid map showing the elements of pCGN7770.

A plasmid containing the napin cassette from pCGN3223, (U.S. Pat. No. 5,639,790) was modified to make it more useful for cloning large DNA fragments containing multiple restriction sites, and to allow the cloning of multiple napin fusion genes into plant binary transformation vectors. An adapter comprised of the self annealed oligonucleotide of sequence CGCGATTTAAATGGCGCGCCCTGCAG-GCGGCCGCCTGCAGGGCGC GCCATTTAAAT, SEQ ID NO:46, was ligated into the vector pBC SK+ (Stratagene) after digestion of the vector with the restriction endonuclease BssHII to construct vector pCGN7765. Plamids pCGN3223 and pCGN7765 were digested with NotI and ligated together. The resultant vector, pCGN7770 (FIG. 17), contains the pCGN7765 backbone and the napin seed specific expression cassette from pCGN3223.

Shewanella Constructs

Genes encoding the Shewanella proteins were mutagenized to introduce suitable cloning-sites 5' and 3' ORFs using PCR. The template for the PCR reactions was DNA of the cosmid pEPA (Yazawa et al, supra). PCR reactions were performed using Pfu DNA polymerase according to the manufacturers' protocols. The PCR products were cloned into SrfI digested pCGN7769. The primers CTGCAGCTCGAGACAATGTTGATT TCCTTATACT-TCTGTCC, SEQ ID NO:47, and GGATCCA-GATCTCTAGCTAGTC TTAGCTGAAGCTCGA, SEQ ID NO:48, were used to amplify ORF 3, and to generate plasmid pCGN8520. The primers TCTAGACTCGAGA-CAATGAGCCAGACCTC TAAACCTACA, SEQ ID NO:49, and CCCGGGCTCGAGCTAATTCGCCTCACT-GTC GTTTGCT, SEQ ID NO:50, were used to amplify ORF 6, and generate plasmid pCGN7776. The primers GAATTCCTCGAGACAATGCCGCTGCGCATCG CACT-TATC, SEQ ID NO:51, and GGTACCAGATCTTTAGACT-TCCCCTTGAAG TAAATGG, SEQ ID NO:52, were used to amplify ORF 7, and generate plasmid pCGN7771. The primers GAATTCGTCGACACAATGTCATTACCA-GACAATGC TTCT, SEQ ID NO:53, and TCTAGAGTC-GACTTATACAGATTCTTCGATGCT GATAG, SEQ ID NO:54, were used to amplify ORF 8, and generate plasmid pCGN7775. The primers GAATTCGTCGACACAAT-GAATCCTACAGCAACTAACGAA, SEQ ID NO:55, and TCTAGAGGATCCTTAGGCCATTCTTTG-GTTTGGCTTC, SEQ ID NO:56, were used to amplify ORF 9, and generate plasmid pCGN7773.

The integrity of the PCR products was verified by DNA sequencing of the inserts of pCGN7771, PCGN8520, and pCGN7773. ORF 6 and ORF 8 were quite large in size. In order to avoid sequencing the entire clones, the center portions of the ORFs were replaced with restriction fragments of pEPA. The 6.6 kilobase PacI/BamHI fragment of pEPA containing the central portion of ORF 6 was ligated into PacI/BamHI digested pCGN7776 to yield pCGN7776B4. The 4.4 kilobase BamHI/BglII fragment of pEPA containing the central portion of ORF 8 was ligated into BamHI/BglII digested pCGN7775 to yield pCGN7775A. The regions flanking the pEPA fragment and the cloning junctions were verified by DNA sequencing.

Plasmid pCGN7771 was cut with XhoI and BglII and ligated to pCGN7770 after digestion with SalI and BglII. The resultant napin/ORF 7 gene fusion plasmid was designated pCGN7783. Plasmid pCGN8520 was cut with XhoI and BglII and ligated to pCGN7770 after digestion with SalI and BglII. The resultant napin/ORF 3 gene fusion plasmid was designated pCGN8528. Plasmid pCGN7773 was cut with SalI and BamHI and ligated to pCGN7770 after digestion with SalI and BglII. The resultant napin/ORF 9 gene fusion plasmid was designated pCGN7785. Plasmid pCGN7775A was cut with SalI and ligated to pCGN7770 after digestion with SalI. The resultant napin/ORF 8 gene fusion plasmid was designated pCGN7782. Plasmid pCGN7776B4 was cut with XhoI and ligated to pCGN7770 after digestion with SalI. The resultant napin/ORF 6 gene fusion plasmid was designated pCGN7786B4.

Figure 18:
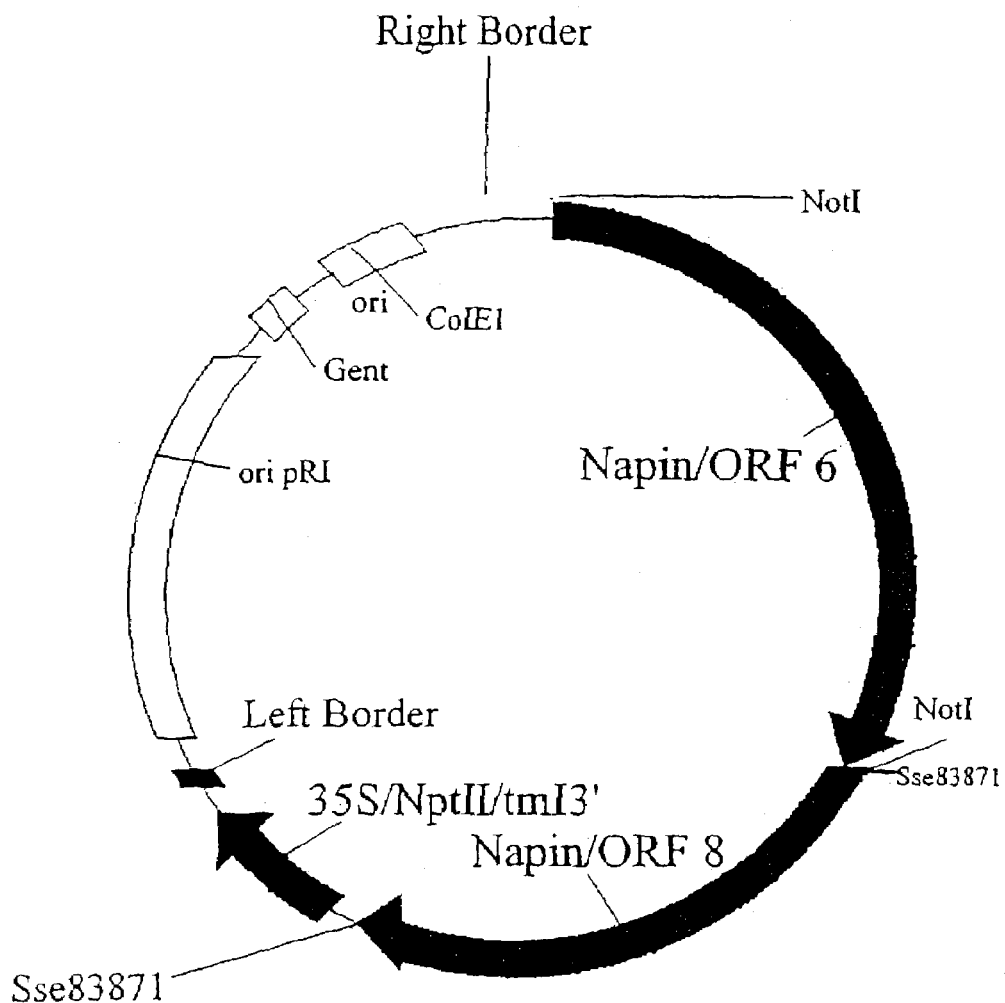
FIG. 18 is a plasmid map showing the elements of pCGN8535.

A binary vector for plant transformation, pCGN5139, was constructed from pCGN1558 (McBride and Summerfelt (1990) *Plant Molecular Biology*, 14:269–276). The polylinker of pCGN1558 was replaced as a HindIII/Asp718 fragment with a polylinker containing unique restriction endonuclease sites, AscI, PacI, XbaI, SwaI, BamHI, and NotI. The Asp718 and HindIII restriction endonuclease sites are retained in pCGN5139. PCGN5139 was digested with NotI and ligated with NotI digested pCGN7786B4. The resultant binary vector containing the napin/ORF 6 gene fusion was designated pCGN8533. Plasmid pCGN8533 was digested with Sse83871 and ligated with Sse83871 digested pCGN7782. The resultant binary vector containing the napin/ORF 6 gene fusion and the napin/ORF 8 gene fusion was designated pCGN8535 (FIG. 18).

Figure 19:
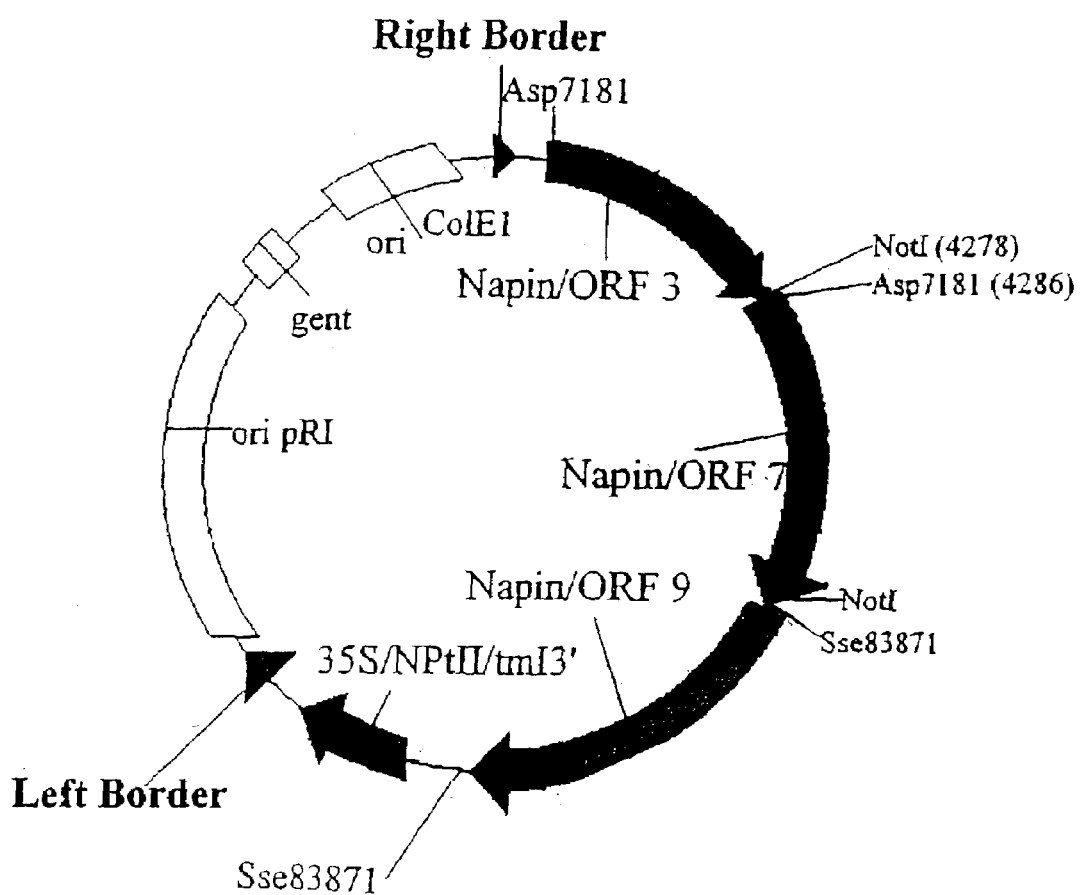
FIG. 19 is a plasmid map showing the elements of pCGN8537.
Figure 20:
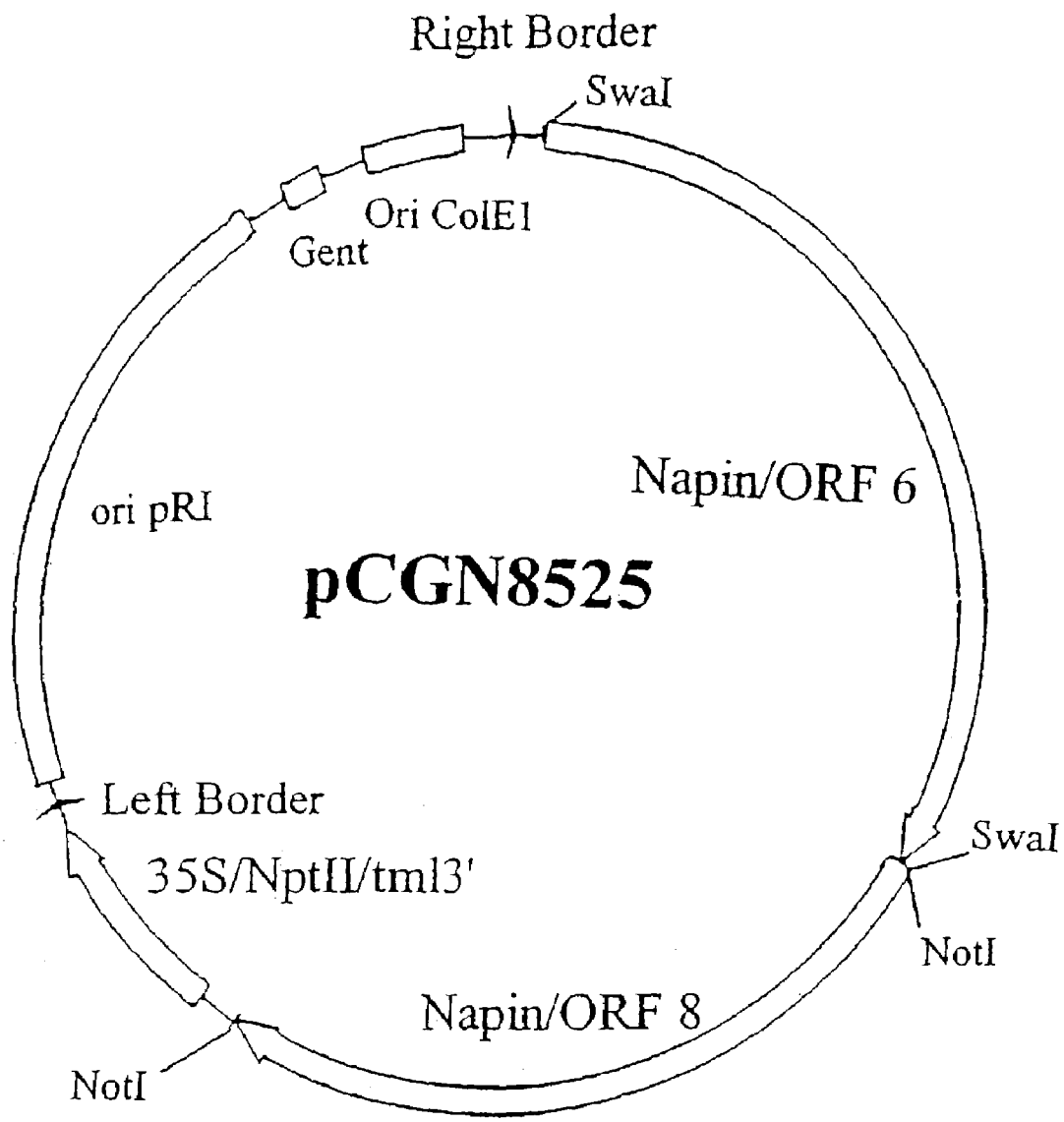
FIG. 20 is a plasmid map showing the elements of pCGN8525.
Figure 21:
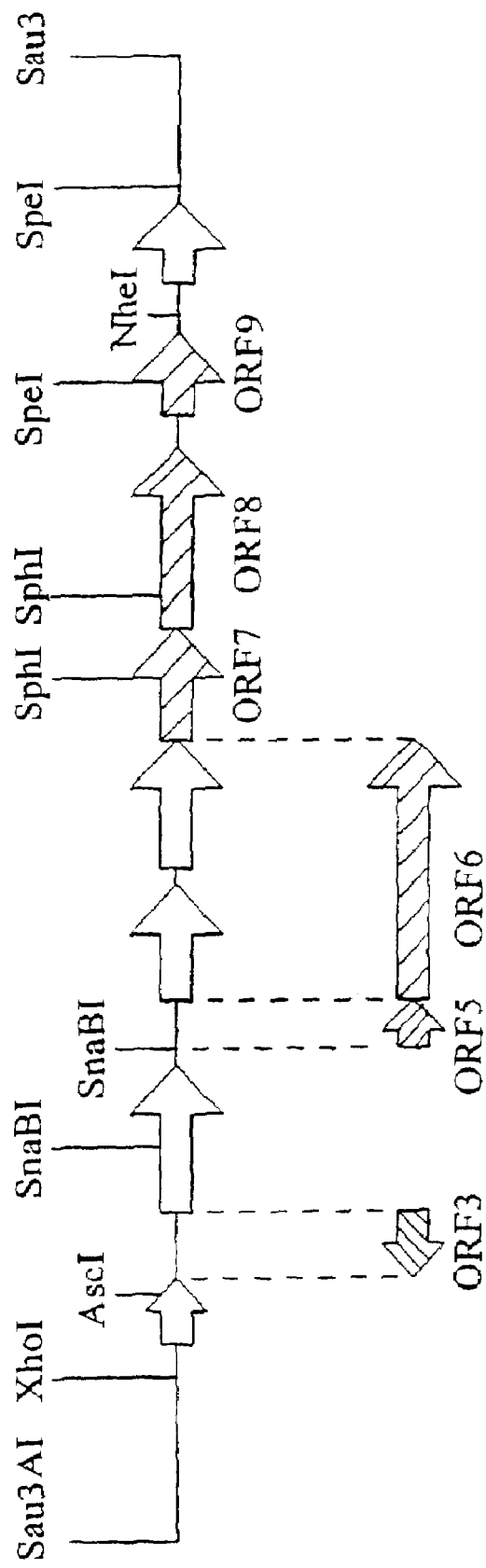
FIG. 21 is a comparison of the *Shewanella* ORFs as defined by Yazawa (1996) supra, and those disclosed in FIG. 4. When a protein starting at the leucine (TTG) codon at nucleotides 9157–9155 and ending at the stop codon at nucleotides 8185–8183 is expressed under control of a heterologous promoter in an *E. coli* strain containing the entire PKS-like cluster except ORF 3, the recombinant cells do produce EPA. Thus, the published protein sequence is likely to be wrong, and the coding sequence for the protein may start at the TTG codon at nucleotides 9157–9155 or the TTG codon at nucleotides 9172–9170. This information is critical to the expression of a functional PKS-like cluster heterologous system.

The plant binary transformation vector, pCGN5139, was digested with Asp718 and ligated with Asp718 digested pCGN8528. The resultant binary vector containing the napin/ORF 3 gene fusion was designated pCGN8532. Plasmid pCGN8532 was digested with NotI and ligated with NotI digested pCGN7783. The resultant binary vector containing the napin/ORF 3 gene fusion and the napin/ORF 7 gene fusion was designated pCGN8534. Plasmid pCGN8534 was digested with Sse83871 and ligated with Sse83871 digested pCGN7785. The resultant binary vector containing the napin/ORF 3 gene fusion, the napin/ORF 7 gene fusion and the napin/ORF 9 gene fusion was designated pCGN8537 (FIG. 19).

*Vibrio* Constructs

The *Vibrio* ORFs for plant expression were all obtained using *Vibrio* cosmid #9 as a starting molecule. *Vibrio* cosmid #9 was one of the cosmids isolated from the *Vibrio* cosmid library using the *Vibrio* ORF 6 PCR product described in Example 1.

A gene encoding *Vibrio* ORF 7 (FIG. 6) was mutagenized to introduce a SalI site upstream of the open reading frame and BamHI site downstream of the open reading frame using the PCR primers: TCTAGAGTCGACACAATGGCG-GAATTAGCTG TTATTGGT, SEQ ID NO:57, and GTC-GACGGATCCCTATTTGTTCGTGTTTGCTA TATG, SEQ ID NO:58. A gene encoding *Vibrio* ORF 9 (FIG. 6) was mutagenized to introduce a BamHI site upstream of the open reading frame and an XhoHI site downstream of the open reading frame using the PCR primers: GTCGACGGATCCA CAATGAATATAGTAAGTAATCATTCGGCA, SEQ ID NO:59, and GTCGACCTC GAGTTAATCACTCGTAC-GATAACTTGCC, SEQ ID NO:60. The restriction sites were introduced using PCR, and the integrity of the mutagenized plasmids was verified by DNA sequence. The *Vibrio* ORF 7 gene was cloned as a SalI-BamHI fragment into the napin cassette of Sal-BglI digested pCGN7770 (FIG. 17) to yield pCGN8539. The *Vibrio* ORF 9 gene was cloned as a SalI-BamHI fragment into the napin cassette of Sal-BalI digested pCGN7770 (FIG. 17) to yield pCGN8543.

Genes encoding the *Vibrio* ORF 6 and ORF 8 were mutagenized to introduce SalI sites flanking the open reading frames. The SalI sites flanking ORF 6 were introduced using PCR. The primers used were: CCCGGGTCGACA-CAATGGCTAAAAAGAACA CCACATCGA, SEQ ID NO:61, and CCCGGGTCGACTCATGACATATCGT-TCAAA ATGTCACTGA, SEQ ID NO:62. The central 7.3 kb BamHI-XhoI fragment of the PCR product was replaced with the corresponding fragment from *Vibrio* cosmid #9. The mutagenized ORF 6 were cloned into the SalI site of the napin cassette of pCGN7770 to yield plasmid pCGN8554.

The mutagenesis of ORF 8 used a different strategy. A BamHI fragment containing ORF 8 was subcloned into plasmid pHC79 to yield cosmid #9". A SalI site upstream of the coding region was introduced on and adapter comprised of the oligonucleotides TCGACATGGAAAATATTGCAG-TAGTAGGTATTGCTAATTT GTTC, SEQ ID NO:63, and CCGGGAACAAATTAGCAATACCTACTACTGCAAT ATTTTCCATG, SEQ ID NO:64. The adapter was ligated to cosmid #9" after digestion with SalI and XmaI. A SalI site was introduced downstream of the stop codon by using PCR for mutagenesis. A DNA fragment containing the stop codon was generated using cosmid #9" as a template with the primers TCAGATGAACTTTATCGATAC, SEQ ID NO:65 and TCATGAGACGTCGTCGACTTACGCT-TCAACAATACT, SEQ ID NO:66. The PCR product was digested with the restriction endonucleases ClaI and AatII and was cloned into the cosmid 9" derivative digested with the same enzymes to yield plasmid 8P3. The SalI fragment from 8P3 was cloned into SalI digested pCGN7770 to yield pCGN8515.

Figure 23:
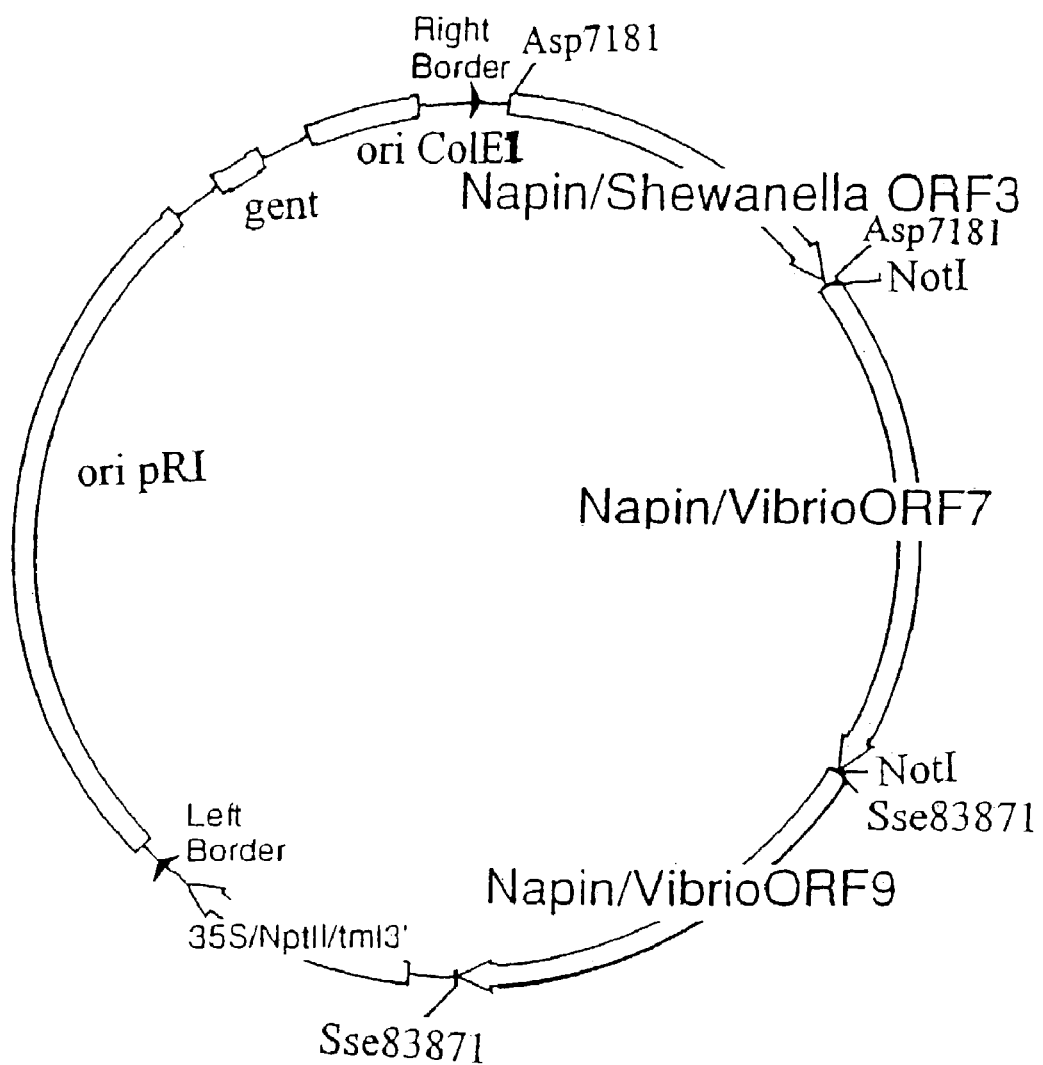
FIG. 23 is plasmid map showing the elements of pCGN8556.

PCGN8532, a binary plant transformation vector that contains a *Shewannella* ORF 3 under control of the napin promoter was digested with NotI, and a NotI fragment of pCGN8539 containing a napin *Vibrio* ORF 7 gene fusion was inserted to yield pCGN8552. Plasmid pCGN8556 (FIG. 23), which contains *Shewannella* ORF 3, and *Vibrio* ORFs 7 and 9 under control of the napin promoter was constructed by cloning the Sse8357 fragment from pCGN8543 into Sse8387 digested pCGN8552.

Figure 22:
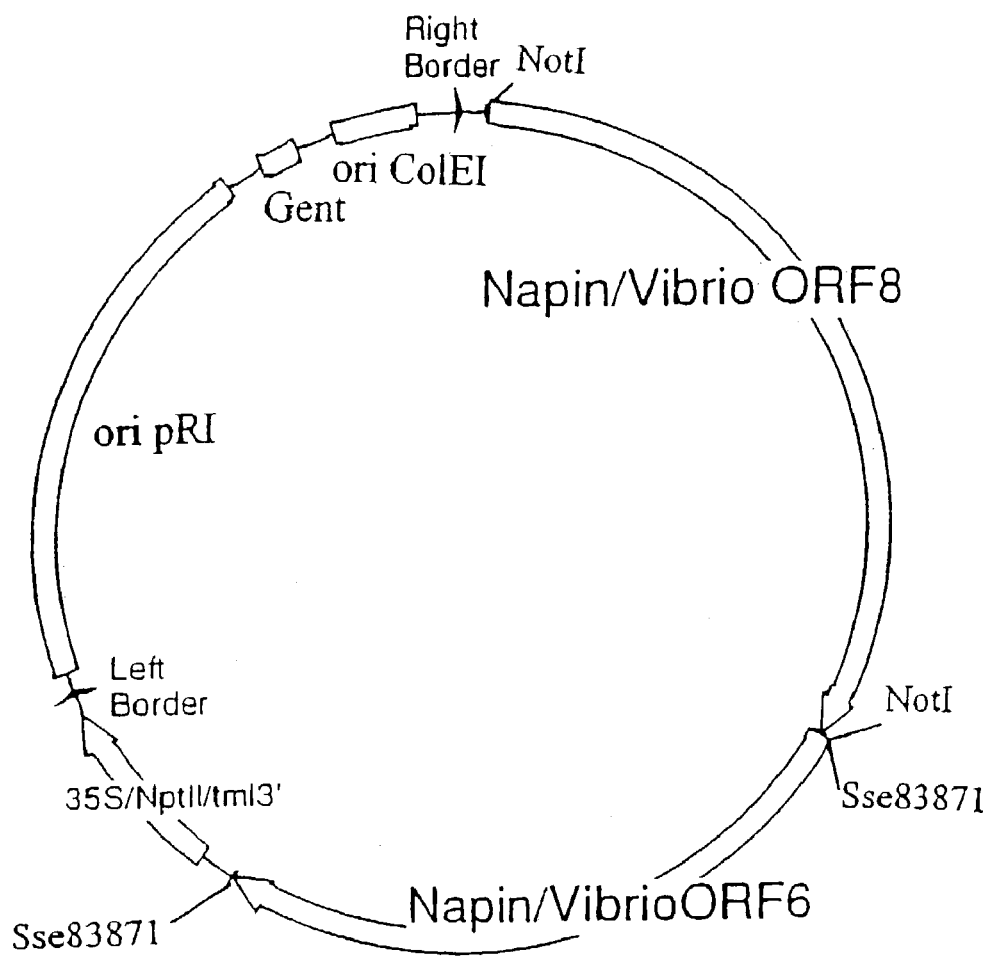
FIG. 22 is a plasmid map showing the elements of pCGN8560.

The NotI digested napin/ORF 8 gene from plasmid pCGN8515 was cloned into a NotI digested plant binary transformation vector pCGN5139 to yield pCGN8548. The Sse8387 digested napin/ORF 6 gene from pCGN8554 was subsequently cloned into the Sse8387 site of pCGN8566. The resultant binary vector containing the napin/ORF 6 gene fusion and napin/ORF 8 gene fusion was designated pCGN8560 (FIG. 22).

Example 5

Plant Transformation and PUFA Production

EPA Production

The *Shewanella* constructs pCGN8535 and pCGN8537 can be transformed into the same or separate plants. If separate plants are used, the transgenic plants can be crossed resulting in heterozygous seed which contains both constructs.

pCGN8535 and pCGN8537 are separately transformed into *Brassica napus*. Plants are selected on media containing kanamycin and transformation by full length inserts of the constructs is verified by Southern analysis. Immature seeds also can be tested for protein expression of the enzyme encoded by ORFs 3, 6, 7, 8, or 9 using western analysis, in which case, the best expressing pCGNE8535 and pCGN8537 $T_1$ transformed plants are chosen and are grown out for further experimentation and crossing. Alternatively, the $T_1$ transformed plants showing insertion by Southern are crossed to one another producing $T_2$ seed which has both insertions. In this seed, half seeds may be analyzed directly from expression of EPA in the fatty acid fraction. Remaining half-seed of events with the best EPA production are grown out and developed through conventional breeding techniques to provide *Brassica* lines for production of EPA.

Plasmids pCGN7792 and pCGN7795 also are simultaneously introduced into *Brassica napus* host cells. A standard transformation protocol is used (see for example U.S. Pat. Nos. 5,463,174 and 5,750,871, however *Agrobacteria* containing both plasmids are mixed together and incubated with *Brassica* cotyledons during the cocultivation step. Many of the resultant plants are transformed with both plasmids.

DHA Production

A plant is transformed for production of DHA by introducing pCGN8556 and pCGN8560, either into separate plants or simultaneously into the same plants as described for EPA production.

Alternatively, the *Shewanella* ORFs can be used in a concerted fashion with ORFs 6 and 8 of *Vibrio*, such as by transforming with a plant the constructs pCGN8560 and pCGN7795, allowing expression of the corresponding ORFs in a plant cell. This combination provides a PKS-like gene arrangement comprising ORFs 3, 7 and 9 of *Shewanella*, with an ORF 6 derived from *Vibrio* and also an OFR 8 derived from *Vibrio*. As described above, ORF 8 is the PKS-like gene which controls the identity of the final PUFA product. Thus, the resulting transformed plants produce DHA in plant oil.

Example 6

Transgenic Plants Containing the *Shewanella* PUFA Genes

*Brassica* Plants

Fifty-two plants cotransformed with plasmids pCGN8535 and pCGN8537 were analyzed using PCR to determine if the *Shewanella* ORFs were present in the transgenic plants. Forty-one plants contained plasmid pCGN8537, and thirty-five plants contained pCGN8535. 11 of the plants contained all five ORFs required for the synthesis of EPA. Several plants contained genes from both of the binary plasmids but appeared to be missing at least one of the ORFs. Analysis is currently being performed on approximately twenty additional plants.

Twenty-three plants transformed with pCGN8535 alone were analyzed using PCR to determine if the *Shewanella* ORFs were present in the transgenic plants. Thirteen of these plants contained both *Shewanella* ORF 6 and *Shewanella* ORF 8. Six of the plants contained only one ORF.

Nineteen plants transformed with pCGN8537 were alone analyzed using PCR to determine if the *Shewanella* ORFs were present in the transgenic plants. Eighteen of the plants contained *Shewanella* ORF 3, *Shewanella* ORF 7, and *Shewanella* ORF 9. One plant contained *Shewanella* ORFs 3 and 7.

*Arabidopsis*

More than 40 transgenic *Arabidopsis* plants cotransformed with plasmids pCGN8535 and pCGN8537 are growing in our growth chambers. PCR analysis to determine which of the ORFs are present in the plants is currently underway.

Example 7

Evidence of A PKS System of PUFA Synthesis in *Schizochytrium*

The purpose of this experiment was to identify additional sources of PKS genes. Polyunsaturated long chain fatty acids were identified in *Schizochytrium* oil. Furthermore, production of polyunsaturated fatty acids was detected in a culture of *Schizochytrium*. A freshly diluted culture of *Schizochytrium* was incubated at 24° C. in the presence of [$^{14}$C]-acetate (5 uCi/mL) for 30 min with shaking (150 rpm). The cells were then collected by centrifugation, lyophilized and subjected to a transesterification protocol that involved heating to 90° C. for 90 minutes in the presence of acidic (9% $H_2SO_4$) methanol with toluene (1 volume of toluene per two volumes of acidic methanol) as a second solvent. The resulting methylesters were extracted with an organic solvent (hexane) and separated by TLC (silica gel G, developed three times with hexane:diethyl ether (19:1)). Radioactivity on the TLC plate was detected using a scanner (AMBIS). Two prominent bands were detected on the TLC plate. These bands migrated on the TLC plate in positions expected for short chain (14 to 16 carbon), saturated methyl esters (the upper band) and with methylesters of polyunsaturated long chain (20 to 22 carbon) fatty acids (the lower band). These were also the major types of fatty acids detected by GC analysis of FAMEs of *Schizochytrium* oil.

In a parallel experiment thiolactomycin, a well known inhibitor of Type II fatty acid synthesis systems as well as several polyketide synthesis systems including EPA production by *E. coli* transformed with PKS genes derived from *Shewanella*, was added to the test tubes of varying concentrations (0, 1, 10 and 100 µg/ml) prior to addition of the *Schizochytrium* cell cultures and [$^{14}$C] acetate. Analysis of incorporation of [$^{14}$C] acetate, as described above, revealed that 100 ug/mL thiolactomycin completely blocked synthesis of polyunsaturated fatty acids, while partial inhibition of synthesis of polyunsaturated fatty acids was observed at 10 ug/mL thiolactomycin. Synthesis of the short chain saturated fatty acids was unaffected at all tested thiolactomycin concentrations. Thiolactomycin does not inhibit Type I fatty acid synthesis systems and is not toxic to mice, suggesting that it does not inhibit the elongation system leading to EPA or DHA formation. Furthermore, thiolactomycin did not inhibit the elongation system leading to PUFA synthesis in *Phaeodactylum tricornutum*. Therefore, although *Schizochytrium* is known to possess a Type I fatty acid synthesis system, the data suggested that the polyunsaturated fatty acids produced in this organism were derived from a system which was distinct from the Type I fatty acid synthesis system which produced short chain fatty acids, and from a system that was similar to the elongation/desaturation pathway found in mice and *Phaeodactylum*. The data are consistent with DHA formation being a result of a PKS pathway as found in *Vibrio marinus* and *Shewanella putrefaciens*.

Example 8

PKS Related Sequences From *Schizochytrium*

The purpose of this experiment was to identify sequences from *Schizochytrium* that encoded PKS genes. A cDNA library from *Schizochytrium* was constructed and approximately 8,000 random clones (ESTs) were sequenced. The protein sequence encoded by *Shewanella* EPA synthesis genes was compared to the predicted amino acid sequences of the *Schizochytrium* ESTs using a Smith/Waterman alignment algorithm. When the protein sequence of ORF6 (*Shewanella*) was compared with the amino acid sequences from *Schizochytrium* ESTs, 38 EST clones showed a significant degree of identity (P<0.01). When the protein sequence of ORF7 was compared by *Schizochytrium* ESTs, 4 EST clones showed significant identity (P<0.01) suggesting that the molecules were homologous. When the protein sequence of ORF8 and ORF9 were compared with the *Schizochytrium* ESTs, 7 and 14 clones respectively showed significant identity (P<0.01).

Example 9

Analysis of *Schizochytrium* cDNA Clones

Figure 28:
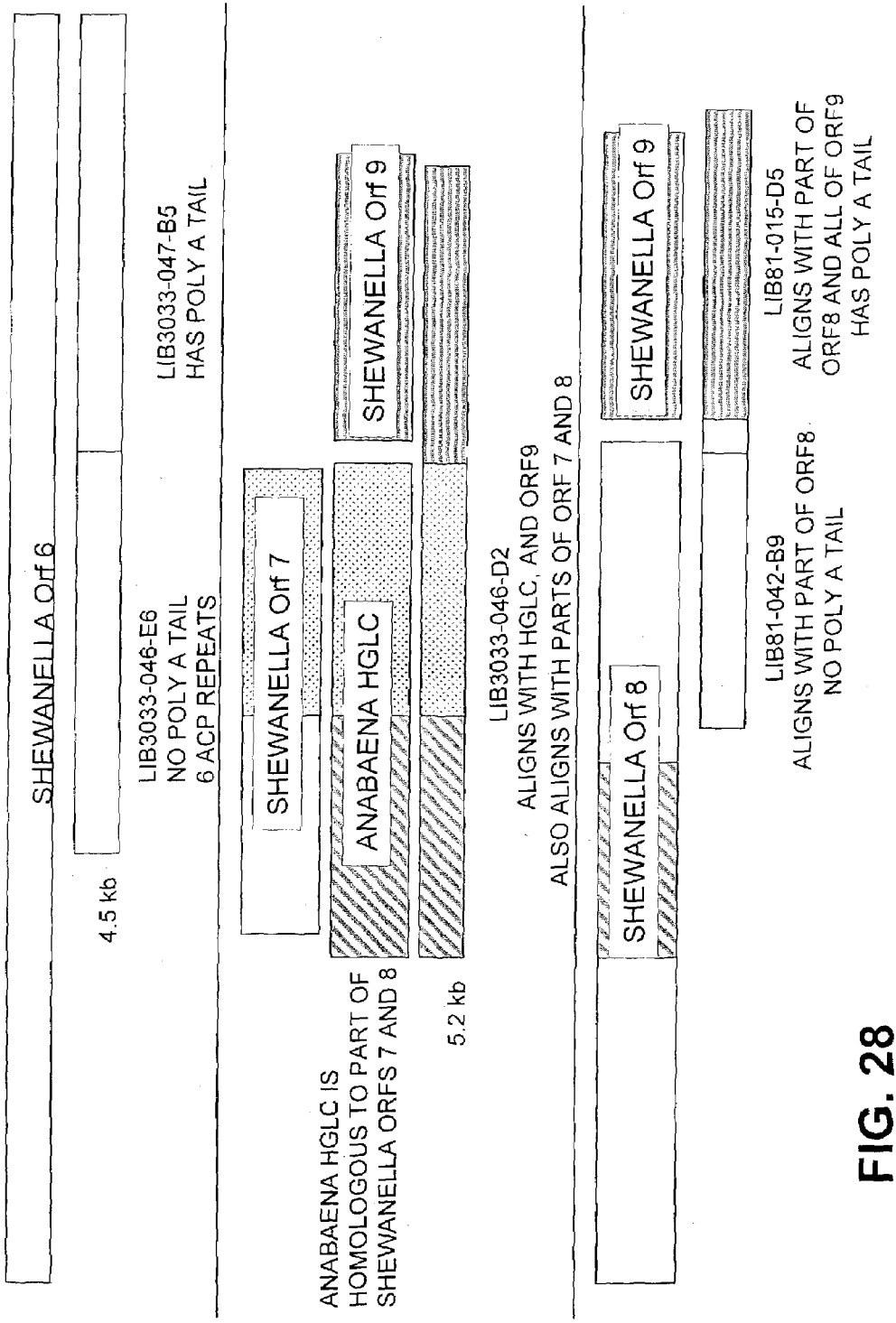
FIG. 28 shows a schematic of the similarities between *Shewanella* PKS sequences and *Schizochytrium* sequences.

Restriction enzyme analysis of the *Schizochytrium* EST clones was used to determine the longest clones, which were subsequently sequenced in their entirety. All of the EST sequences described in Example 8 were determined to be part of 5 cDNA clones. Two of the cDNA clones were homologous to *Shewanella* ORF6. LIB3033-047-B5 was homologous to the C-terminus of ORF6. The sequence of LIB3033-047-B5 could be aligned with *Shewanella* ORF6 from amino acids 2093 onwards. The open reading frame of LIB3033-047-B5 extended all the way to the 5' end of the sequence, thus this clone was not likely to be full length. LIB3033-046-E6 shared homology to the ACP domain of ORF6. It contained 6 ACP repeats. This cDNA clone did not have a poly-A-tail, and therefore, it was likely to be a partial cDNA with additional regions of the cDNA found downstream of the sequence. The PCR primers GTGATGATCTTTCCCTGATGCACGCCAAGG (SEQ ID NO:67) and AGCTCGAGACCGGCAACCCGCAGCGCCAGA (SEQ ID NO:68) were used to amplify a fragment of approximately 500 nucleotides from *Schizochytrium* genomic DNA. Primer GTGATGATCTTTCCCTGATG-CACGCCAAGG was derived from LIB3033-046-E6, and primer AGCTCGAGACCGGCAACCCGCAGCGCCAGA was derived from LIB3033-047-B5. Thus, LIB3033-046-E6 and LIB3033-047-B5 represented different portions of the same mRNA (see FIG. 28) and could be assembled into a single partial cDNA sequence (see FIG. 27A), SEQ ID NO:69, that was predicted to encode a protein with the sequence in FIG. 29A (SEQ ID NO:70). The open reading frame extended all the way to the 5' end of the sequence, thus this partial cDNA was not likely to be full length. Analysis of additional cDNA or genomic clones will allow the determination of the full extent of the mRNA represented by clones LIB3033-046-E6 and LIB3033-047-B5. It may contain condensing enzyme related domains similar to those found near the N-terminus of *Shewanella* ORF6.

cDNA clone LIB3033-047-B5 (denoted eDNA clone LIB3033-047-B5 in the form of an *E. coli* plasmid vector containing "Orf6 homolog" partial gene sequence from *Schizochytrium* sp.) was deposited with the American Type Culture Collection (ATCC), 10801 University Boulevard, Manassas, Va. 20110-2209 USA, under the terms of the Budapest Treaty on the International Recognition of the Deposit of Microorganisms for the Purposes of Patent Procedure, on Jun. 8, 2006, and assigned ATCC Accession No. PTA-7646.

One of the cDNA clones, LIB3033-046-D2, was homologous to *Shewanella* ORF9 at its 3' end. This clone was homologous to the chain length factor region of *Shewanella* ORF8 at its 5' end. This clone was also homologous to the entire open reading frame of the *Anabaena* HglC ORF. The *Anabaena* HglC ORF is homologous to the chain length factor region of *Shewanella* ORF8 and *Shewanella* ORF7. Thus this cDNA (FIG. 27B), SEQ ID NO:71, was homologous to part of *Shewanella* ORF8, *Shewanella* ORF7 and *Shewanella* ORF9 (see FIG. 28). The amino acid sequence (FIG. 29B), SEQ ID NO:72, encoded by the open reading frame of LIB3033-046-D2 extended all the way to the 5' end of the sequence; thus this clone was not likely to be full length. Analysis of additional cDNA or genomic clones will allow the determination of the full extent of the mRNA represented by LIB3033-046-E6. It may contain condensing enzyme related domains similar to those found near the N-terminus of *Shewanella* ORF8.

cDNA clone LIB3033-046-D2 (denoted cDNA clone LIB3033-046-D2 in the form of an *E. coli* plasmid vector containing "hglC/Orf7/Orf8/Orf9 homolog" gene from *Schizochytrium*) was deposited with the American Type Culture Collection (ATCC), 10801 University Boulevard, Manassas, Va. 20110-2209 USA, under the terms of the Budapest Treaty on the International Recognition of the Deposit of Microorganisms for the Purposes of Patent Procedure, on Jun. 8, 2006, and assigned ATCC Accession No. PTA-7645.

Two additional cDNA clones were homologous to *Shewanella* ORF8. LIB81-015-D5 was homologous to the C-terminus of ORF8. The 5' sequence of LIB81-015-D5 could be aligned with *Shewanella* ORF8 from amino acids 1900 onwards. The 3' end of LIB81-015-D5 could be aligned with *Shewanella* ORF9 (see FIG. 28). The amino acid sequence (FIG. 29C), SEQ ID NO:73, encoded by the open reading frame of LIB81-015-D5 extended all the way to the 5' end of the sequence; thus this clone was not likely to be full length. LIB81-042-B9 was homologous to amino acids 1150 to 1850 of *Shewanella* ORF8. LIB81-042-B9 did not have a poly-A-tail, and therefore, it was likely to be a partial cDNA with additional regions of the cDNA found downstream of the sequence. The PCR primers TACCGCG-GCAAGACTATCCGCAACGTCACC (SEQ ID NO:74) and GCCGTCGTGGGCGTCCACGGACACGATGTG (SEQ ID NO:75) were used to amplify a fragment of approximately 500 nucleotides from *Schizochytrium* genomic DNA. Primer TACCGCGGCAAGACTATCCG-CAACGTCACC was derived from LIB 81-042-B9, and primer GCCGTCGTGGGCGTCCACGGACACGATGTG was derived from LIB81-015-D5. Thus, LIB81-042- and LIB81-015-D5 represented different portions of the same mRNA and were assembled into a single partial cDNA sequence (see FIG. 27C), SEQ ID NO:76. The open reading frame of LIB81-042-B9 also extended all the way to the 5' end of the sequence, thus this clone was also not likely to be full length. Analysis of additional cDNA or genomic clones will allow the determination of the full extent of the mRNA represented by LIB81-042-B9.

cDNA clone LIB81-042-B9 (denoted cDNA clone LIB81-042-B9 in the form of an *E. coli* plasmid vector containing "Orf8 homolog" partial gene sequence from *Schizochytrium* sp.) was deposited with the American Type Culture Collection (ATCC), 10801 University Boulevard, Manassas, Va. 20110-2209 USA, under the terms of the Budapest Treaty on the International Recognition of the Deposit of Microorganisms for the Purposes of Patent Procedure, on Jun. 8, 2006, and assigned ATCC Accession No. PTA-7647.

By the present invention PKS-like genes from various organisms can now be used to transform plant cells and modify the fatty acid compositions of plant cell membranes or plant seed oils through the biosynthesis of PUFAs in the transformed plant cells. Due to the nature of the PKS-like systems, fatty acid end-products produced in the plant cells can be selected or designed to contain a number of specific chemical structures. For example, the fatty acids can comprise the following variants: Variations in the numbers of keto or hydroxyl groups at various positions along the carbon chain; variations in the numbers and types (cis or trans) of double bonds; variations in the numbers and types of branches off of the linear carbon chain (methyl, ethyl, or longer branched moieties); and variations in saturated carbons. In addition, the particular length of the end-product fatty acid can be controlled by the particular PKS-like genes utilized.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An isolated nucleic acid molecule comprising a nucleic acid sequence selected from the group consisting of:
   a) a nucleic acid sequence encoding SEQ ID NO:72, or a portion thereof having a biological activity selected from the group consisting of: chain length factor activity and acyl transferase activity; and
   b) a nucleic acid sequence encoding an amino acid sequence that is at least about 95% identical to SEQ ID NO:72, wherein said nucleic acid sequence encodes a protein having a biological activity selected from the group consisting of chain length factor activity and acyl transferase activity.

2. An oligonucleotide probe or primer consisting of at least 50 consecutive nucleotides of SEQ ID NO:71 or the complement thereof.

3. An isolated nucleic acid molecule comprising a nucleic acid sequence encoding an amino acid sequence that is at least about 95% identical to SEQ ID NO:72, wherein said nucleic acid sequence encodes a protein having a biological activity selected from the group consisting of chain length factor activity and acyl transferase activity.

4. The isolated nucleic acid molecule according to claim 3, wherein said nucleic acid sequence encodes a protein having chain length factor activity and acyl transferase activity.

5. A recombinant plant cell comprising at least one copy of a nucleic acid molecule according to claim 3.

6. The recombinant plant cell of claim 5, wherein said recombinant plant cell is a recombinant seed cell.

7. The recombinant plant cell of claim 6, wherein said recombinant seed cell is a recombinant embryo cell.

8. The recombinant plant cell of claim 5, wherein said recombinant plant cell is from a plant selected from the group consisting of *Brassica*, soybean, safflower, *Arabidopsis*, corn and sunflower.

9. A method for production of a long chain polyunsaturated fatty acid in a plant cell, said method comprising growing a plant having a plurality of recombinant plant cells as set forth in claim 5, under conditions whereby a long chain polyunsaturated fatty acid is produced by said plant cells.

10. The isolated nucleic acid molecule of claim 3, wherein said nucleic acid molecule comprises a nucleic acid sequence encoding SEQ ID NO:72.

11. The isolated nucleic acid molecule of claim 3, wherein said nucleic acid molecule comprises SEQ ID NO:71.

12. The isolated nucleic acid molecule of claim 3, wherein said nucleic acid molecule is from a *Schizochytrium*.

13. A recombinant nucleic acid molecule comprising the isolated nucleic acid molecule of claim 3.

14. A recombinant microbial cell comprising at least one copy of a recombinant nucleic acid molecule according to claim 13.

15. The recombinant microbial cell according to claim 14, wherein said cell is a eukaryotic cell.

16. The recombinant microbial cell according to claim 15, wherein said eukaryotic cell is a fungal cell or an algal cell.

17. The recombinant microbial cell according to claim 14, wherein said cell is a prokaryotic cell.

18. A method for production of a long chain polyunsaturated fatty acid in a microbial cell culture, said method comprising growing a microbial cell culture having a plurality of recombinant microbial cells as set forth in claim 14, under conditions whereby a long chain polyunsaturated fatty acid is produced by said microbial cell culture.

19. An isolated nucleic acid molecule comprising a nucleic acid sequence that is fully complementary to the nucleic acid sequence of claim 3.

20. An isolated nucleic acid molecule comprising a nucleic acid sequence encoding the amino acid sequence encoded by the plasmid LIB3033-046-D2 (ATCC Accession No. PTA-7645).

21. The isolated nucleic acid molecule of claim 20, wherein the nucleic acid molecule comprises a nucleic acid sequence of plasmid LIB3033-046-D2 (ATCC Accession No. PTA-7645) that encodes said amino acid sequence.

22. A recombinant nucleic acid molecule comprising the isolated nucleic acid molecule of claim 20.

23. A recombinant plant cell comprising at least one copy of a nucleic acid molecule according to claim 20.

24. The recombinant plant cell of claim 23, wherein said recombinant plant cell is a recombinant seed cell.

25. The recombinant plant cell of claim 24, wherein said recombinant seed cell is a recombinant embryo cell.

26. The recombinant plant cell of claim 20, wherein said recombinant plant cell is from a plant selected from the group consisting of *Brassica*, soybean, safflower, *Arabidopsis*, corn and sunflower.

27. A method for production of a long chain polyunsaturated fatty acid in a plant cell, said method comprising growing a plant having a plurality of recombinant plant cells as set forth in claim 23, under conditions whereby a long chain polyunsaturated fatty acid is produced by said plant cells.

28. A recombinant microbial cell comprising at least one copy of a recombinant nucleic acid molecule according to claim 22.

29. The recombinant microbial cell according to claim 28, wherein said cell is a eukaryotic cell.

30. The recombinant microbial cell according to claim 29, wherein said eukaryotic cell is a fungal cell or an algal cell.

31. The recombinant microbial cell according to claim 28, wherein said cell is a prokaryotic cell.

32. A method for production of a long chain polyunsaturated fatty acid in a microbial cell culture, said method comprising growing a microbial cell culture having a plurality of recombinant microbial cells as set forth in claim 28, under conditions whereby a long chain polyunsaturated fatty acid is produced by said microbial cell culture.

33. An isolated nucleic acid molecule comprising a nucleic acid sequence encoding an amino acid sequence that is at least 95% identical to the amino acid sequence encoded by the plasmid LIB3033-046-D2 (ATCC Accession No. PTA-7645), wherein the nucleic acid sequence encodes a protein having a biological activity selected from the group consisting of chain length factor activity and acyl transferase activity.

* * * * *

UNITED STATES PATENT AND TRADEMARK OFFICE
CERTIFICATE OF CORRECTION

| | |
|---|---|
| PATENT NO. | : 7,214,853 B2 |
| APPLICATION NO. | : 10/331061 |
| DATED | : May 8, 2007 |
| INVENTOR(S) | : Daniel Facciotti et al. |

It is certified that error appears in the above-identified patent and that said Letters Patent is hereby corrected as shown below:

On the Sequence Listing Section:

Col. 191-192, line 2940, please delete "c" and insert --g-- at the nucleotide position 2933 of SEQ ID NO:71, therein.

Col. 197-198, please delete "Gln" and insert --Glu-- at amino acid position 978 of SEQ ID NO:72, therein.

Signed and Sealed this

Sixteenth Day of September, 2008

JON W. DUDAS
*Director of the United States Patent and Trademark Office*

SEQUENCE LISTING

```
<160> NUMBER OF SEQ ID NOS: 86

<210> SEQ ID NO 1
<211> LENGTH: 37895
<212> TYPE: DNA
<213> ORGANISM: Shewanella putrefaciens

<400> SEQUENCE: 1
gatctcttac aaagaaacta tctcaatgtg aatttaacct taattccgtt taattacggc      60
ctgatagagc atcacccaat cagccataaa actgtaaagt gggtactcaa aggtggctgg     120
gcgattcttc tcaaatacaa agtgcccaac ccaagcaaat ccatatccga taacaggtaa     180
aagtagcaat aaacccagc gctgagttag taatacataa gcgaataata ggatcactaa      240
actactgccg aaatagtgta atattcgaca gtttctatgc tgatgttgag ataaataaaa     300
agggtaaaat tcagcaaaag aacgatagcg cttactcatt actcacacct cggtaaaaaa     360
gcaactcgcc attaacttgg ccaatcgtca gttgttctat cgtctcaaag ttatgccgac     420
taaataactc tatatgtgca ttatgattag caaaaactcc gataccatca agatgaagtt     480
gttcatcaca ccaactcaaa actgcgtcga taagcttact gccatagccc ttgccttgct     540
ccacatttgc gatagcaata aactgtaaaa tgccacattg gccacttggt aagctctcta     600
taatctgatt ttctttgtta ataagtgcct gagttgaata ccaaccagta cttaacaaca     660
tctttaaacg ccaatgccaa aaacgcgctt cacctaaggg aacctgctga gtcactatgc     720
aggctacgcc tatcaatcta tccccaacga acataccaat aagtgcttgc tcctgttgcc     780
agagctcatt gagttcttct cgaatagccc cgcgaagctt ttgctcatac tgcgcttgat     840
caccactaaa aagtgtttcg ataaaaaagg gatcatcatg ataggcgtta tagagaatag     900
aggctgctat gcgtaaatct tctgccgtga gataaactgc acgacactct tccatggctt     960
gatcttccat tgttattgtc cttgaccttg atcacacaac accaatgtaa caagactgta    1020
```

-continued

```
tagaagtgca attaataatc aattcgtgca ttaagcaggt cagcatttct ttgctaaaca    1080
agctttattg gctttgacaa aactttgcct agactttaac gatagaaatc ataatgaaag    1140
agaaaagcta aacctagag gggaataatc aaacaactgc taagatctag ataatgtaat     1200
aaacaccgag tttatcgacc atacttagat agagtcatag caacgagaat agttatggat    1260
acaacgccgc aagatctatc acacctgttt ttacagctag gattagcaaa tgatcaaccc    1320
gcaattgaac agtttatcaa tgaccatcaa ttagcggaca atatattgct acatcaagca    1380
agcttttgga gcccatcgca aaagcacttc ttaattgagt catttaatga agatgcccag    1440
tggaccgaag tcatcgacca cttagacacc ttattaagaa aaaactaacc attacaacag    1500
caactttaaa ttttgccgta agccatctcc ccccacccca aacagcgtt gttgcttatg     1560 accactggag tacattcgtc tttagtcgtt ttaccatcac catgggtacg ttgagtgcga    1620 taaaaagca cataaacttc tttatcggcc tgaatatagg cttcgttaaa atcagctgtt     1680
cccattaaag taaccacttg ctctttactc atgcctagag atatctttgt caaattgtca    1740
cggtttttat cttgagtttt ctcccaagca ccgtgattat cccagtcaga ttccccatca    1800
ccaacattga ccacacagcc cgttagccct aagcttgcaa tcccaaaaca tgctaaacct    1860
aataatttat ttttcatttt aacttcctgt tatgacatta tttttgctta gaagaaaagc    1920
aacttacatg ccaaaacaca agctgttgtt ttaaatgact ttatttatta ttagcctttt    1980
aggatatgcc tagagcaata ataattacca atgtttaagg aatttgacta actatgagtc    2040
cgattgagca agtgctaaca gctgctaaaa aaatcaatga acaaggtaga gaaccaacat    2100
tagcattgat taaaaccaaa cttggtaata gcatcccaat gcgcgagtta atccaaggtt    2160
tgcaacagtt taagtctatg agtgcagaag aaagacaagc aatacctagc agcttagcaa    2220
cagcaaaaga aactcaatat ggtcaatcaa gcttatctca atctgaacaa gctgatagga    2280
tcctccagct agaaaacgcc ctcaatgaat taagaaacga atttaatggg ctaaaaagtc    2340
aatttgataa cttacaacaa aacctgatga ataaagagcc tgacaccaaa tgcatgtaat    2400
tgaactacga tttgaatgtt ttgataacac cacgattact gcagcagaaa aagccattaa    2460
tggtttgctt gaagcttatc gagccaatgg ccaggttcta ggtcgtgaat ttgccgttgc    2520
atttaacgat ggtgagttta aagcacgcat gttaacccca gaaaaagca gcttatctaa     2580 acgctttaat agtccttggg taaatagtgc actcgaagag ctaaccgaag ccaaattgct    2640
tgcgccacgt gaaaagtata ttggccaaga tattaattct gaagcatcta gccaagacac    2700
accaagttgg cagctacttt acacaagtta tgtgcacatg tgctcaccac taagaaatgg    2760
cgacaccttg cagcctattc cactgtatca aattccagca actgccaacg gcgatcataa    2820
acgaatgatc cgttggcaaa cagaatggca agcttgtgat gaattgcaaa tggccgcagc    2880
tactaaagct gaatttgccg cacttgaaga gctaaccagt catcagagtg atctatttag    2940
gcgtggttgg gacttacgtg gcagagtcga atacttgacg aaaattccga cctattacta    3000
tttataccgt gttggcggtg aaagcttagc agtagaaaag cagcgctctt gtcctaagtg    3060
tggcagtcaa gaatggctgc tcgataaacc attattggat atgttccatt ttcgctgtga    3120
cacctgccgc atcgtatcta atatctcttg ggaccatta taactcttcc gagtcttatc      3180
acactagagt ttagtcagca taaaaatggc gcttatattt caattaaaag aaatataagc    3240
gccattttca tcgatactat atatcagcag actattttcc gcgtaaatta gcccacatta    3300
atttcattct ttgccagatc cctggatgat ctagttgtgg catcgactct tcaataggtt    3360
```

-continued

```
taaccgcagg tgtaaccctt ggagtcaatt cgtttataaa ctcgtttaaa ctgtcactta    3420
atttaacgct ttgtacttca cctggaattt caatccatac gctgccatca ctattattaa    3480
ccgtcaacat tttatcttca tcatcaagaa taccaataaa ccaagtcggc tcttgcttaa    3540
gctttctctt catcattaaa tgaccaatga tgttttgttg taagtattca aaatcagttt    3600
gatcccacac ttggattagc tcaccttggc cccattgtga gtcaaaaaat agcggtgcag    3660
aaaaatgact gccaaaaaat ggattaattt ctgcagataa tgtcatttca agtgctgttt    3720
caacattagc aaattcacca ggttgttgac gtacaaccga ttgccaaaac actgcgccat    3780
cggagcccgc ttcggcgaca acacactcag acttttgtcc ttgcgcataa tatcttggct    3840
gttcaccaag cttatccatg taggcttgtt gatatttaga taaaaaaaga tctaaagcag    3900
gtaaagaaga cacttaagcc agttccaaaa tcagttataa tagggtctta ttttgacatg    3960
gaaaccgtat tgatgacaca acatcatgat ccctacagta acgcccccga actttctgaa    4020
ttaactttag gaaagtcgac cggttatcaa gagcagtatg atgcatcttt actacaagcg    4080
tgccgcgtaa attaaaccgt gatgctatcg gtctaaccaa tgagctacct tttcatggct    4140
gtgatatttg gactggctac gaactgtctt ggctaaatgc taaaggcaag ccaatgattg    4200
ctattgcaga ctttaaccta agttttgata gtaaaaatct gatcgagtct aagtcgttta    4260
agctgtattt aaacagctat aaccaaacac gatttgatag cgttcaagcg gttcaagaac    4320
gtttaactga agacttaagc gcctgtgccc aaggcacagt tacggtaaaa gtgattgaac    4380
ctaagcaatt taaccacctg agagtggttg atatgccagg tacctgcatt gacgatttag    4440
atattgaagt tgatgactat agctttaact ctgactatct caccgacagt gttgatgaca    4500
aagtcatggt tgctgaaacg ctaacgtcaa acttattgaa atcaaactgc ctaatcactt    4560
ctcagcctga ctggggtaca gtgatgatcc gttatcaagg gcctaagata gaccgtgaaa    4620
agctacttag atatctgatt tcatttagac agcacaatga atttcatgag cagtgtgttg    4680
agcgtatatt tgttgattta aagcactatt gccaatgtgc caaacttact gtctatgcac    4740
gttatacccg ccgtggtggt ttagatatca acccatatcg tagcgacttt gaaaaccctg    4800
cagaaaatca gcgcctagcg agacagtaat tgattgcagt acctacaaaa aacaatgcct    4860
ataagccaag cttatgggca tttttatatt atcaacttgt catcaaacct cagccgccaa    4920 gcctttagt tttatcgcta aattaagccg ctctctcagc caaatatttg caggattttg    4980
ctgtaattta tggctccaca ccatgaaata ctctatcggc tctaccgcaa aaggtaagtc    5040
aaatacctgt aagccaaaca gcttggcata ttcgtcagtg tgggcttttg acgcgatagc    5100
taacgcatca cttttgagg caaccgacat catacttaat attgatgatt gctcgctgtg    5160
catttgcctt gccggtaaca cctgtttagt cagcaagtcg gcaacactta aattgtagcg    5220
gcgcatctta aaataatat gcttttcatt aaagtattgc tcttgcgtca acccaccttg    5280
gatccttggg tgagcatttc gtgccacaca aactaattta cctgcatta cttttgact    5340 cttaaatgcc gcagattctg gcagccaaat atctaaggct aaatccacct tttctagttg    5400
taggtccatc tgcaactctt cttcaatgag cggcggctca cgaaatacaa tattaattgc    5460
agtgccctgt aacacttgct caatttgatc ttgcaagagt tgtattgccg actcgctggc    5520
atacacataa aaagttcgct cacttgaagt ggggtcaaat gcttcaaagc tagtcgcaac    5580
ttgctcaatt gttgacatag cgcccgcgag ctgttgataa agcgtcatcg cacttgcggt    5640
aggtttaact cccctaccca ctcgagtaaa caactcttct ccaacaatac tttttagcct    5700
cgaaatcgca ttactaaccg acgactgagt caaatccagc tcttctgccg cccggctaaa    5760
```

```
agatgaggtg cgatacaccg cagtaaaaac gcgaaataaa ttaagatcaa aagcttttg    5820 ctgcgacata aatcagctat ctccttatcc ttatccttat ccttataaaa agttagctcc    5880
agagcactct agctcaaaaa caactcagcg tattaagcca atattttggg aactcaatta    5940
atattcataa taaaagtatt cataatataa ataccaagtc ataatttagc cctaattatt    6000
aatcaattca agttacctat actggcctca attaagcaaa tgtctcatca gtctccctgc    6060
aactaaatgc aatattgaga cataaagctt tgaactgatt caatcttacg agggtaactt    6120
atgaaacaga ctctaatggc tatctcaatc atgtcgcttt tttcattcaa tgcgctagca    6180
gcgcaacatg aacatgacca catcactgtt gattacgaag ggaaagccgc aacagaacac    6240
accatagctc acaaccaagc tgtagctaaa acacttaact ttgccgacac gcgtgcattt    6300
gagcaatcgt ctaaaaatct agtcgccaag tttgataaag caactgccga tatattacgt    6360
gccgaatttg cttttattag cgatgaaatc cctgactcgg ttaacccgtc tctctaccgt    6420
caggctcagc ttaatatggt gcctaatggt ctgtataaag tgagcgatgg catttaccag    6480
gtccgcggta ccgacttatc taaccttaca cttatccgca gtgataacgg ttggatagca    6540
tacgatgttt tgttaaccaa agaagcagca aaagcctcac tacaatttgc gttaaagaat    6600
ctacctaaag atggcgattt acccgttgtt gcgatgattt actcccatag ccatgcggac    6660
cactttggcg gagctcgcgg tgttcaagag atgttccctg atgtcaaagt ctacggctca    6720
gataacatca ctaaagaaat tgtcgatgag aacgtacttg ccggtaacgc catgagccgc    6780
cgcgcagctt atcaatacgg cgcaacactg ggcaaacatg accacggtat tgttgatgct    6840
gcgctaggta aggtctatc aaaaggtgaa atcacttacg tcgccccaga ctacaccta     6900 aacagtgaag gcaaatggga aacgctgacg attgatggtc tagagatggt gtttatggat    6960
gcctcgggca ccgaagctga gtcagaaatg atcacttata ttccctctaa aaaagcgctc    7020
tggacggcgg agcttaccta tcaaggtatg cacaacattt atacgctgcg cggcgctaaa    7080
gtacgtgatg cgctcaagtg gtcaaaagat atcaacgaaa tgatcaatgc ctttggtcaa    7140
gatgtcgaag tgctgtttgc ctcgcactct gcgccagtgt ggggtaacca agcgatcaac    7200
gatttcttac gcctacagcg tgataactac ggcctagtgc acaatcaaac cttgagactt    7260
gccaacgatg gtgtcggtat acaagatatt ggcgatgcga ttcaagacac gattccagag    7320
tctatctaca agacgtggca taccaatggt taccacggca cttatagcca taacgctaaa    7380
gcggtttata caagtatct aggctacttc gatatgaacc cagccaacct taatccgctg    7440
ccaaccaagc aagaatctgc caagtttgtc gaatacatgg gcggcgcaga tgccgcaatt    7500
aagcgcgcta agatgatta cgctcaaggt gaataccgct tgttgcaac ggcattaaat     7560 aaggtggtga tggccgagcc agaaaatgac tccgctcgtc aattgctagc cgatacctat    7620
gagcaacttg gttatcaagc agaagggggct ggctggagaa acatttactt aactggcgca    7680
caagagctac gagtaggtat tcaagctggc gcgcctaaaa ccgcatcggc agatgtcatc    7740
agtgaaatgg acatgccgac tctatttgac ttcctcgcgg tgaagattga tagtcaacag    7800
gcggctaagc acggcttagt taagatgaat gttatcaccc ctgatactaa agatattctc    7860
tatattgagc taagcaacgg taacttaagc aacgcagtgg tcgacaaaga gcaagcagct    7920
gacgcaaacc ttatggttaa taaagctgac gttaaccgca tcttacttgg ccaagtaacc    7980
ctaaaagcgt tattagccag cggcgatgcc aagctcactg gtgataaaac ggcatttagt    8040
aaaatagccg atagcatggt cgagtttaca cctgacttcg aaatcgtacc aacgcctgtt    8100
```

```
aaatgaggca ttaatctcaa caagtgcaag ctagacataa aaatggggcg attagacgcc    8160
ccatttttta tgcaattttg aactagctag tcttagctga agctcgaaca acagctttaa    8220
aattcacttc ttctgctgca atacttattt gctgacactg accaatactc agtgcaaaac    8280
gataactatc atcaagatgg cccagtaaac aatgccaatt atcagcagcg ttcatttgct    8340
gttctttagc ctcaatcaaa cctaaaccag acttttgtgg ctcagcgtta ggcttattag    8400
aactcgactc tagtaaagca agaccaatat cttgttttaa caaaacctgt cgctgattaa    8460
gttgatgctc aaccttgtga tccgcaatag catcggaaat atcaacacaa tggctcaagc    8520
ttttaggtgc attaactcca agaaaagttt cgctcagtgc agagaagtca aacgcaaaag    8580
attttagcga taatgccagc ccaagtcctt tcgctttaat gtaagactcc ttgagcgccc    8640
acaaatcaaa aaagcggtct cgctgcaagg cctctggtaa cgctaacaag gctcgctttt    8700
ctgattcaga gaaataatga ctaagaatag agtggatatt ggtgctgtta cggcaacgct    8760
caatgtcgac gccaaactca atactagcag agtcagtttc ctccttgctt gcctgactgg    8820
cgcctttatt atcagcagtg caaatgccta ctaatagcca atctccacta tgactcacat    8880
taaagtggac cccggtttga gcaaattgcg catcactcaa tctaggctta cctttgtcgc    8940
catattcaaa gcgccattca ttggggcgta tttcactatg ttgtgacaat aaagcgcgca    9000
aatagcctct taccattaaa ccttgagttt tagcttcttg tttaatgtag cgattaacct    9060
taattaactc atcttcaggc agccatgact taaccaactc tgtagtctgg ttatcgcact    9120
cttgtattgt taacggacag aagtataagg aaatcaatcg agaagttagc aattttcag    9180 gacactcttt aaagcaacaa ataaccccc tatttttacc aatttaagat caaaactaaa    9240
gccaaaacta attgagaata gtgtcaaact agctttaaag gaaaaaaata taaaagaac    9300 attatacttg tataaattat tttacacacc aaagccatga tcttcacaaa attagctccc    9360
tctccctaaa acaagattga ataaaaaaat aaaccttaac tttcatatag ataaaacaaa    9420
ccaatgggat aaagtatatt gaattcattt ttaaggaaaa attcaaattg aattcaagct    9480
cttcagtaaa agcatatttt gccgttagtg tgaaaaaaaa caaatttaaa aaccaacata    9540
gaacaaataa gcagacaata aaaccaaggc gcaacacaaa caacgcgctt acaattttca    9600
caaaaaagca acaagagtaa cgtttagtat ttggatatgg ttattgtaat tgagaatttt    9660
ataacaatta tattaaggga atgagtatgt ttttaaattc aaaactttcg cgctcagtca    9720
aacttgccat atccgcaggc ttaacagcct cgctagctat gcctgttttt gcagaagaaa    9780
ctgctgctga agaacaaata gaaagagtcg cagtgaccgg atcgcgaatc gctaaagcag    9840
agctaactca accagctcca gtcgtcagcc tttcagccga agaactgaca aaatttggta    9900
atcaagattt aggtagcgta ctagcagaat tacctgctat tggtgcaacc aacactatta    9960
ttggtaataa caatagcaac tcaagcgcag gtgttagctc agcagacttg cgtcgtctag   10020
gtgctaacag aaccttagta ttagtcaacg gtaagcgcta cgttgccggc caaccgggct   10080
cagctgaggt agatttgtca actataccaa ctagcatgat ctcgcgagtt gagattgtaa   10140
ccggcggtgc ttcagcaatt tatggttcgg acgctgtatc aggtgttatc aacgttatcc   10200
ttaaagaaga ctttgaaggc tttgagttta acgcacgtac tagcggttct actgaaagtg   10260
taggcactca agagcactct tttgacattt ggggtggtgc aaacgttgca gatgacgtg    10320 gtaatgtaac cttctacgca ggttatgaac gtacaaaaga agtcatggct accgacattc   10380
gccaattcga tgcttgggga acaattaaaa acgaagccga tggtggtgaa gatgatggta   10440
ttccagacag actacgtgta ccacgagttt attctgaaat gattaatgct accggtgtta   10500
```

```
tcaatgcatt tggtggtgga attggtcgct caacctttga cagtaacggc aatcctattg    10560
cacaacaaga acgtgatggg actaacagct ttgcatttgg ttcattccct aatggctgtg    10620
acacatgttt caacactgaa gcatacgaaa actatattcc aggggtagaa agaataaacg    10680
ttggctcatc attcaacttt gattttaccg ataacattca attttacact gacttcagat    10740
atgtaaagtc agatattcag caacaatttc agccttcatt ccgttttggt aacattaata    10800
tcaatgttga agataacgcc ttttttgaatg acgacttgcg tcagcaaatg ctcgatgcgg    10860
gtcaaaccaa tgctagtttt gccaagtttt ttgatgaatt aggaaatcgc tcagcagaaa    10920
ataaacgcga acttttccgt tacgtaggtg gctttaaagg tggctttgat attagcgaaa    10980
ccatatttga ttacgacctt tactatgttt atggcgagac taataaccgt cgtaaaaccc    11040
ttaatgacct aattcctgat aactttgtcg cagctgtcga ctctgttatt gatcctgata    11100
ctggcttagc agcgtgtcgc tcacaagtag caagcgctca aggcgatgac tatacagatc    11160
ccgcgtctgt aaatggtagc gactgtgttg cttataaccc atttggcatg ggtcaagctt    11220
cagcagaagc ccgcgactgg gtttctgctg atgtgactcg tgaagacaaa ataactcaac    11280
aagtgattgg tggtactctc ggtaccgatt ctgaagaact atttgagctt caaggtggtg    11340
caatcgctat ggttgttggt tttgaatacc gtgaagaaac gtctggttca acaaccgatg    11400
aatttactaa agcaggtttc ttgacaagcg ctgcaacgcc agattcttat ggcgaatacg    11460
acgtgactga gtattttgtt gaggtgaaca tcccagtact aaaagaatta cctttttgcac    11520 atgagttgag ctttgacggt gcataccgta atgctgatta ctcacatgcc ggtaagactg    11580
aagcatggaa agctgtatg ttctactcac cattagagca acttgcatta cgtggtacgg    11640
taggtgaagc agtacgagca ccaaacattg cagaagcctt tagtccacgc tctcctggtt    11700
ttggccgcgt ttcagatcca tgtgatgcag ataacattaa tgacgatccg gatcgcgtgt    11760
caaactgtgc agcattgggg atccctccag gattccaagc taatgataac gtcagtgtag    11820
ataccttatc tggtggtaac ccagatctaa aacctgaaac atcaacatcc tttacaggtg    11880
gtcttgtttg gacaccaacg tttgctgaca atctatcatt cactgtcgat tattatgata    11940
ttcaaattga ggatgctatt ttgtcagtag ccacccagac tgtggctgat aactgtgttg    12000
actcaactgg cggacctgac accgacttct gtagtcaagt tgatcgtaat ccaacgacct    12060
atgatattga acttgttcgc tctggttatc taaatgccgc ggcattgaat accaaaggta    12120
ttgaatttca agctgcatac tcattagatc tagagtcttt caacgcgcct ggtgaactac    12180
gcttcaacct attggggaac caattacttg aactagaacg tcttgaattc caaaatcgtc    12240
ctgatgagat taatgatgaa aaaggcgaag taggtgatcc agagctgcag ttccgcctag    12300
gcatcgatta ccgtctagat gatctaagtg ttagctggaa cacgcgttat attgatagcg    12360
tagtaactta tgatgtctct gaaaatggtg gctctcctga agatttatat ccaggccaca    12420
taggctcaat gacaactcat gacttgagcg ctacatacta catcaatgag aacttcatga    12480
ttaacggtgg tgtacgtaac ctatttgacg cacttccacc tggatacact aacgatgcgc    12540
tatatgatct agttggtcgc cgtgcattcc taggtattaa ggtaatgatg taattaatta    12600
ttacgcctct aactaataaa aatgcaatct cttcgtagag attgcatttt tttatgaaat    12660
ccaatcttaa actggttctc cgagcatctt acgccttaaa aaccccgccc ctcaatgtaa    12720
cgccaaagtt aattgcttac acgcacttac acaaacgaac aatttcatta acacgagaca    12780
cagctcacgc ttttttatttt acccttgatt ttactacata aaattgcgtt ttagcgcaca    12840
```

-continued

```
agtgttctcc caagctggtc gtatctgtaa ttattcagtc ccaggtgatt gtattgaccc    12900
ataagctcag gtagtctgct ctgccattag ctaaacaata ttgacaaaat ggcgataaaa    12960
tgtggcttag cgctaagttc accgtaagtt ttatcggcat taagtcccaa cagattatta    13020
acggaaaccc gctaaactga tggcaaaaat aaatagtgaa cacttggatg aagctactat    13080
tacttcgaat aagtgtacgc aaacagagac tgaggctcgg catagaaatg ccactacaac    13140
acctgagatg cgccgattca tacaagagtc ggatctcagt gttagccaac tgtctaaaat    13200
attaaatatc agtgaagcta ccgtacgtaa gtggcgcaag cgtgactctg tcgaaaactg    13260
tcctaatacc ccgcaccatc tcaataccac gctaaccct ttgcaagaat atgtggttgt     13320
gggcctgcgt tatcaattga aaatgccatt agacagattg ctcaaagcaa cccaagagtt    13380
tatcaatcca aacgtgtcgc gctcaggttt agcaagatgt tgaagcgtt atggcgtttc     13440
acgggtgagt gatatccaaa gcccacacgt accaatgcgc tactttaatc aaattccagt    13500
cactcaaggc agcgatgtgc aaacctacac cctgcactat gaaacgctgg caaaaacctt    13560
agccttacct agtaccgatg gtgacaatgt ggtgcaagtg gtgtctctca ccattccacc    13620
aaagttaacc gaagaagcac ccagttcaat tttgctcggc attgatcctc atagcgactg    13680
gatctatctc gacatatacc aagatggcaa tacacaagcc acgaatagat atatggctta    13740
tgtgctaaaa cacgggccat tccatttacg aaagttactc gtgcgtaact atcacacctt    13800
tttacagcgc tttcctggag cgacgcaaaa tcgccgcccc tctaaagata tgcctgaaac    13860
aatcaacaag acgcctgaaa cacaggcacc cagtggagac tcataatgag ccagacctct    13920
aaacctacaa actcagcaac tgagcaagca caagactcac aagctgactc tcgtttaaat    13980
aaacgactaa aagatatgcc aattgctatt gttggcatgg cgagtatttt tgcaaactct    14040
cgctatttga ataagttttg ggacttaatc agcgaaaaaa ttgatgcgat tactgaatta    14100
ccatcaactc actggcagcc tgaagaatat tacgacgcag ataaaaccgc agcagacaaa    14160
agctactgta aacgtggtgg ctttttgcca gatgtagact tcaacccaat ggagtttggc    14220
ctgccgccaa acattttgga actgaccgat tcatcgcaac tattatcact catcgttgct    14280
aaagaagtgt tggctgatgc taacttacct gagaattacg accgcgataa aattggtatc    14340
accttaggtg tcggcggtgg tcaaaaaatt agccacagcc taacagcgcg tctgcaatac    14400
ccagtattga agaaagtatt cgccaatagc ggcattagtg acaccgacag cgaaatgctt    14460
atcaagaaat tccaagacca atatgtacac tgggaagaaa actcgttccc aggttcactt    14520
ggtaacgtta ttgcgggccg tatcgccaac cgcttcgatt ttgcgggcat gaactgtgtg    14580
gttgatgctg cctgtgctgg atcacttgct gctatgcgta tggcgctaac agagctaact    14640
gaaggtcgct ctgaaatgat gatcaccggt ggtgtgtgta ctgataactc accctctatg    14700
tatatgagct tttcaaaaac gcccgccttt accactaacg aaaccattca gccatttgat    14760
atcgactcaa aaggcatgat gattggtgaa ggtattggca tggtggcgct aaagcgtctt    14820
gaagatgcag agcgcgatgg cgaccgcatt tactctgtaa ttaaaggtgt gggtgcatca    14880
tctgacggta agtttaaatc aatctatgcc cctcgcccat caggccaagc taaagcactt    14940
aaccgtgcct atgatgacgc aggttttgcg ccgcatacct aggtctaat tgaagctcac     15000
ggaacaggta ctgcagcagg tgacgcggca gagtttgccg gcctttgctc agtatttgct    15060
gaaggcaacg ataccaagca acacattgcg ctaggttcag ttaaatcaca aattggtcat    15120
actaaatcaa ctgcaggtac agcaggttta attaaagctg ctcttgcttt gcatcacaag    15180
gtactgccgc cgaccattaa cgttagtcag ccaagcccta aacttgatat cgaaaactca    15240
```

```
ccgttttatc taaacactga gactcgtcca tggttaccac gtgttgatgg tacgccgcgc    15300
cgcgcgggta ttagctcatt tggttttggt ggcactaact tccattttgt actagaagag    15360
tacaaccaag aacacagccg tactgatagc gaaaaagcta agtatcgtca acgccaagtg    15420
gcgcaaagct tccttgttag cgcaagcgat aaagcatcgc taattaacga gttaaacgta    15480
ctagcagcat ctgcaagcca agctgagttt atcctcaaag atgcagcagc aaactatggc    15540
gtacgtgagc ttgataaaaa tgcaccacgg atcggtttag ttgcaaacac agctgaagag    15600
ttagcaggcc taattaagca agcacttgcc aaactagcag ctagcgatga taacgcatgg    15660
cagctacctg gtggcactag ctaccgcgcc gctgcagtag aaggtaaagt tgccgcactg    15720
tttgctggcc aaggttcaca atatctcaat atgggccgtg accttacttg ttattaccca    15780
gagatgcgtc agcaatttgt aactgcagat aaagtatttg ccgcaaatga taaaacgccg    15840
ttatcgcaaa ctctgtatcc aaagcctgta tttaataaag atgaattaaa ggctcaagaa    15900
gccattttga ccaataccgc caatgcccaa agcgcaattg gtgcgatttc aatgggtcaa    15960
tacgatttgt ttactgcggc tggctttaat gccgacatgg ttgcaggcca tagctttggt    16020
gagctaagtg cactgtgtgc tgcaggtgtt atttcagctg atgactacta caagctggct    16080
tttgctcgtg gtgaggctat ggcaacaaaa gcaccggcta agacggcgt tgaagcagat    16140
gcaggagcaa tgtttgcaat cataaccaag agtgctgcag accttgaaac cgttgaagcc    16200
accatcgcta aatttgatgg ggtgaaagtc gctaactata cgcgccaac gcaatcagta    16260
attgcaggcc caacagcaac taccgctgat gcggctaaag cgctaactga gcttggttac    16320
aaagcgatta acctgccagt atcaggtgca ttccacactg aacttgttgg tcacgctcaa    16380
gcgccatttg ctaaagcgat tgacgcagcc aaatttacta aaacaagccg agcactttac    16440
tcaaatgcaa ctggcggact ttatgaaagc actgctgcaa agattaaagc ctcgtttaag    16500
aaacatatgc ttcaatcagt gcgctttact agccagctag aagccatgta caacgacggc    16560
gcccgtgtat tgttgaatt tggtccaaag aacatcttac aaaaattagt tcaaggcacg    16620
cttgtcaaca ctgaaaatga gtttgcact atctctatca accctaatcc taaagttgat    16680
agtgatctgc agcttaagca agcagcaatg cagctagcgg ttactggtgt ggtactcagt    16740
gaaattgacc cataccaagc cgatattgcc gcaccagcaa aaagtcgcc aatgagcatt    16800
tcgcttaatg ctgctaacca tatcagcaaa gcaactcgcg ctaagatggc caagtctta    16860
gagacaggta tcgtcacctc gcaaatagaa catgttattg aagaaaaaat cgttgaagtt    16920
gagaaactgg ttgaagtcga aaagatcgtc gaaaaagtgg ttgaagtaga aaagttgtt    16980
gaggttgaag ctcctgttaa ttcagtgcaa gccaatgcaa ttcaaacccg ttcagttgtc    17040
gctccagtaa tagagaacca agtcgtgtct aaaaacagta agccagcagt ccagagcatt    17100
agtggtgatg cactcagcaa cttttttgct gcacagcagc aaaccgcaca gttgcatcag    17160
cagttcttag ctattccgca gcaatatggt gagacgttca ctacgctgat gaccgagcaa    17220
gctaaactgg caagttctgg tgttgcaatt ccagagagtc tgcaacgctc aatggagcaa    17280
ttccaccaac tacaagcgca aacactacaa agccacaccc agttccttga gatgcaagcg    17340
ggtagcaaca ttgcagcgtt aaacctactc aatagcagcc aagcaactta cgctccagcc    17400
attcacaatg aagcgattca aagccaagtg gttcaaagcc aaactgcagt ccagccagta    17460
atttcaacac aagttaacca tgtgtcagag cagccaactc aagctccagc tccaaaagcg    17520
cagccagcac ctgtgacaac tgcagttcaa actgctccgg cacaagttgt tcgtcaagcc    17580
```

```
gcaccagttc aagccgctat tgaaccgatt aatacaagtg ttgcgactac aacgccttca    17640
gccttcagcg ccgaaacagc cctgagcgca acaaaagtcc aagccactat gcttgaagtg    17700
gttgctgaga aaaccggtta cccaactgaa atgctagagc ttgaaatgga tatggaagcc    17760
gatttaggca tcgattctat caagcgtgta gaaattcttg gcacagtaca agatgagcta    17820
ccgggtctac ctgagcttag ccctgaagat ctagctgagt gtcgaacgct aggcgaaatc    17880
gttgactata tgggcagtaa actgccggct gaaggctcta tgaattctca gctgtctaca    17940
ggttccgcag ctgcgactcc tgcagcgaat ggtctttctg cggagaaagt tcaagcgact    18000
atgatgtctg tggttgccga aaagactggc tacccaactg aaatgctaga gcttgaaatg    18060
gatatggaag ccgatttagg catagattct atcaagcgcg ttgaaattct tggcacagta    18120
caagatgagc taccgggtct acctgagctt agccctgaag atctagctga gtgtcgtact    18180
ctaggcgaaa tcgttgacta tatgaactct aaactcgctg acggctctaa gctgccggct    18240
gaaggctcta tgaattctca gctgtctaca agtgccgcag ctgcgactcc tgcagcgaat    18300
ggtctctctg cggagaaagt tcaagcgact atgatgtctg tggttgccga aaagactggc    18360
tacccaactg aaatgctaga acttgaaatg gatatggaag ctgaccttgg catcgattca    18420
atcaagcgcg ttgaaattct tggcacagta caagatgagc taccgggttt acctgagcta    18480
aatccagaag atttggcaga gtgtcgtact cttggcgaaa tcgtgactta tatgaactct    18540
aaactcgctg acggctctaa gctgccagct gaaggctcta tgcactatca gctgtctaca    18600
agtaccgctg ctgcgactcc tgtagcgaat ggtctctctg cagaaaaagt tcaagcgacc    18660
atgatgtctg tagttgcaga taaaactggc tacccaactg aaatgcttga acttgaaatg    18720
gatatggaag ccgatttagg tatcgattct atcaagcgcg ttgaaattct tggcacagta    18780
caagatgagc taccgggttt acctgagcta aatccagaag atctagcaga gtgtcgcacc    18840
ctaggcgaaa tcgttgacta tatgggcagt aaactgccgg ctgaaggctc tgctaataca    18900
agtgccgctg cgtctcttaa tgttagtgcc gttgcggcgc tcaagctgc tgcgactcct    18960 gtatcgaacg gtctctctgc agagaaagtc aaagcacta tgatgtcagt agttgcagaa    19020
aagaccggct acccaactga aatgctagaa cttggcatgg atatggaagc cgatttaggt    19080
atcgactcaa ttaaacgcgt tgagattctt ggcacagtac aagatgagct accgggtcta    19140
ccagagctta atcctgaaga tttagctgag tgccgtacgc tgggcgaaat cgttgactat    19200
atgaactcta agctggctga cggctctaag cttccagctg aaggctctgc taatacaagt    19260
gccactgctg cgactcctgc agtgaatggt ctttctgctg acaaggtaca ggcgactatg    19320
atgtctgtag ttgctgaaaa gaccggctac ccaactgaaa tgctagaact tggcatggat    19380
atggaagcag accttggtat tgattctatt aagcgcgttg aaattcttgg cacagtacaa    19440
gatgagctcc caggtttacc tgagcttaat cctgaagatc tcgctgagtg ccgcacgctt    19500
ggcgaaatcg ttagctatat gaactctcaa ctggctgatg gctctaaact ttctacaagt    19560
gcggctgaag gctctgctga tacaagtgct gcaaatgctg caaagccggc agcaatttcg    19620
gcagaaccaa gtgttgagct tcctcctcat agcgaggtag cgctaaaaaa gcttaatgcg    19680
gcgaacaagc tagaaaattg tttcgccgca gacgcaagtg ttgtgattaa cgatgatggt    19740
cacaacgcag gcgtttagc tgagaaactt attaaacaag gcctaaaagt agccgttgtg    19800
cgtttaccga aggtcagcc tcaatcgcca ctttcaagcg atgttgctag ctttgagctt    19860
gcctcaagcc aagaatctga gcttgaagcc agtatcactg cagttatcgc gcagattgaa    19920
actcaggttg gcgctattgg tggctttatt cacttgcaac cagaagcgaa tacagaagag    19980
```

-continued

```
caaacggcag taaacctaga tgcgcaaagt tttactcacg ttagcaatgc gttcttgtgg    20040
gccaaattat tgcaaccaaa gctcgttgct ggagcagatg cgcgtcgctg ttttgtaaca    20100
gtaagccgta tcgacggtgg ctttggttac ctaaatactg acgccctaaa agatgctgag    20160
ctaaaccaag cagcattagc tggtttaact aaaaccttaa gccatgaatg ccacaagtg     20220 ttctgtcgcg cgctagatat tgcaacagat gttgatgcaa cccatcttgc tgatgcaatc    20280
accagtgaac tatttgatag ccaagctcag ctacctgaag tgggcttaag cttaattgat    20340
ggcaaagtta accgcgtaac tctagttgct gctgaagctg cagataaaac agcaaaagca    20400
gagcttaaca gcacagataa aatcttagtg actggtgggg caaaagggt gacatttgaa     20460 tgtgcactgg cattagcatc tcgcagccag tctcactttta tcttagctgg gcgcagtgaa   20520
ttacaagctt taccaagctg ggctgagggt aagcaaacta gcgagctaaa atcagctgca    20580
atcgcacata tttattctac tggtcaaaag ccaacgccta agcaagttga agccgctgtg    20640
tggccagtgc aaagcagcat tgaaattaat gccgccctag ccgcctttaa caaagttggc    20700
gcctcagctg aatacgtcag catggatgtt accgatagcg ccgcaatcac agcagcactt    20760
aatggtcgct caaatgagat caccggtctt attcatggcg caggtgtact agccgacaag    20820
catattcaag acaagactct tgctgaactt gctaaagttt atggcactaa agtcaacggc    20880
ctaaaagcgc tgctcgcggc acttgagcca agcaaaatta aattacttgc tatgttctca    20940
tctgcagcag ttttttacgg taatatcggc caaagcgatt acgcgatgtc gaacgatatt    21000
cttaacaagg cagcgctgca gttcaccgct cgcaacccac aagctaaagt catgagcttt    21060
aactggggtc cttgggatgg cggcatggtt aacccagcgc ttaaaaagat gtttaccgag    21120
cgtggtgtgt acgttattcc actaaaagca ggtgcagagc tatttgccac tcagctattg    21180
gctgaaactg gcgtgcagtt gctcattggt acgtcaatgc aaggtggcag cgacactaaa    21240
gcaactgaga ctgcttctgt aaaaaagctt aatgcgggtg aggtgctaag tgcatcgcat    21300
ccgcgtgctg gtgcacaaaa aacaccacta caagctgtca ctgcaacgcg tctgttaacc    21360
ccaagtgcca tggtcttcat tgaagatcac cgcattggcg gtaacagtgt gttgccaacg    21420
gtatgcgcca tcgactggat gcgtgaagcg gcaagcgaca tgcttggcgc tcaagttaag    21480
gtacttgatt acaagctatt aaaaggcatt gtatttgaga ctgatgagcc gcaagagtta    21540
acacttgagc taacgccaga cgattcagac gaagctacgc tacaagcatt aatcagctgt    21600
aatgggcgtc cgcaatacaa ggcgacgctt atcagtgata tgccgatat taagcaactt     21660 aacaagcagt ttgatttaag cgctaaggcg attaccacag caaaagagct ttatagcaac    21720
ggcaccttgt tccacggtcc gcgtctacaa gggatccaat ctgtagtgca gttcgatgat    21780
caaggcttaa ttgctaaagt cgctctgcct aaggttgaac ttagcgattg tggtgagttc    21840
ttgccgcaaa cccacatggg tggcagtcaa cctttttgctg aggacttgct attacaagct   21900
atgctggttt gggctcgcct taaaactggc tcggcaagtt tgccatcaag cattggtgag    21960
tttacctcat accaaccaat ggcctttggt gaaactggta ccatagagct tgaagtgatt    22020
aagcacaaca aacgctcact tgaagcgaat gttgcgctat atcgtgacaa cggcgagtta    22080
agtgccatgt ttaagtcagc taaaatcacc attagcaaaa gcttaaattc agcatttta    22140 cctgctgtct tagcaaacga cagtgaggcg aattagtgga acaaacgcct aaagctagtg    22200
cgatgccgct gcgcatcgca cttatcttac tgccaacacc gcagtttgaa gttaactctg    22260
tcgaccagtc agtattagcc agctatcaaa cactgcagcc tgagctaaat gccctgctta    22320
```

```
atagtgcgcc gacacctgaa atgctcagca tcactatctc agatgatagc gatgcaaaca    22380
gctttgagtc gcagctaaat gctgcgacca acgcaattaa caatggctat atcgtcaagc    22440
ttgctacggc aactcacgct tgttaatgc tgcctgcatt aaaagcggcg caaatgcgga     22500
tccatcctca tgcgcagctt gccgctatgc agcaagctaa atcgacgcca atgagtcaag    22560
tatctggtga gctaaagctt ggcgctaatg cgctaagcct agctcagact aatgcgctgt    22620
ctcatgcttt aagccaagcc aagcgtaact taactgatgt cagcgtgaat gagtgttttg    22680
agaacctcaa aagtgaacag cagttcacag aggtttattc gcttattcag caacttgcta    22740
gccgcaccca tgtgagaaaa gaggttaatc aaggtgtgga acttggccct aaacaagcca    22800
aaagccacta ttggtttagc gaatttcacc aaaaccgtgt tgctgccatc aactttatta    22860
atggccaaca agcaaccagc tatgtgctta ctcaaggttc aggattgtta gctgcgaaat    22920
caatgctaaa ccagcaaaga ttaatgttta tcttgccggg taacagtcag caacaaataa    22980
ccgcatcaat aactcagtta atgcagcaat tagagcgttt gcaggtaact gaggttaatg    23040
agctttctct agaatgccaa ctagagctgc tcagcataat gtatgacaac ttagtcaacg    23100
cagacaaact cactactcgc gatagtaagc ccgcttatca ggctgtgatt caagcaagct    23160
ctgttagcgc tgcaaagcaa gagttaagcg cgcttaacga tgcactcaca gcgctgtttg    23220
ctgagcaaac aaacgccaca tcaacgaata aaggcttaat ccaatacaaa acaccggcgg    23280
gcagttactt aaccctaaca ccgcttggca gcaacaatga caacgcccaa gcgggtcttg    23340
cttttgtcta tccgggtgtg ggaacggttt acgccgatat gcttaatgag ctgcatcagt    23400
acttccctgc gctttacgcc aaacttgagc gtgaaggcga tttaaaggcg atgctacaag    23460
cagaagatat ctatcatctt gaccctaaac atgctgccca aatgagctta ggtgacttag    23520
ccattgctgg cgtggggagc agctacctgt taactcagct gctcaccgat gagtttaata    23580
ttaagcctaa ttttgcatta ggttactcaa tgggtgaagc atcaatgtgg gcaagcttag    23640
gcgtatggca aaacccgcat gcgctgatca gcaaaaccca aaccgacccg ctatttactt    23700
ctgctatttc cggcaaattg accgcggtta gacaagcttg gcagcttgat gataccgcag    23760
cggaaatcca gtggaatagc tttgtggtta gaagtgaagc agcgccgatt gaagccttgc    23820
taaaagatta cccacacgct tacctcgcga ttattcaagg ggatacctgc gtaatcgctg    23880
gctgtgaaat ccaatgtaaa gcgctacttg cagcactggg taaacgcggt attgcagcta    23940
atcgtgtaac ggcgatgcat acgcagcctg cgatgcaaga gcatcaaaat gtgatggatt    24000
tttatctgca accgttaaaa gcagagcttc ctagtgaaat aagctttatc agcgccgctg    24060
atttaactgc caagcaaacg gtgagtgagc aagcacttag cagccaagtc gttgctcagt    24120
ctattgccga caccttctgc aaaaccttgg actttaccgc gctagtacat cacgcccaac    24180
atcaaggcgc taagctgttt gttgaaattg gcgcggatag acaaaactgc accttgatag    24240
acaagattgt taaacaagat ggtgccagca gtgtacaaca tcaaccttgt tgcacagtgc    24300
ctatgaacgc aaaaggtagc caagatatta ccagcgtgat taaagcgctt ggccaattaa    24360
ttagccatca ggtgccatta tcggtgcaac catttattga tggactcaag cgcgagctaa    24420
cactttgcca attgaccagc caacagctgg cagcacatgc aaatgttgac agcaagtttg    24480
agtctaacca agaccatttta cttcaagggg aagtctaatg tcattaccag acaatgcttc    24540
taaccacctt tctgccaacc agaaaggcgc atctcaggca agtaaaacca gtaagcaaag    24600
caaaatcgcc attgtcggtt tagccactct gtatccagac gctaaaaccc cgcaagaatt    24660
ttggcagaat ttgctggata aacgcgactc tcgcagcacc ttaactaacg aaaaactcgg    24720
```

-continued

| | |
|---|---|
| cgctaacagc caagattatc aaggtgtgca aggccaatct gaccgttttt attgtaataa | 24780 |
| aggcggctac attgagaact tcagcttta tgctgcaggc tacaaattgc cggagcaaag | 24840 |
| cttaaatggc ttggacgaca gcttcctttg ggcgctcgat actagccgta acgcactaat | 24900 |
| tgatgctggt attgatatca acggcgctga tttaagccgc gcaggtgtag tcatgggcgc | 24960 |
| gctgtcgttc ccaactaccc gctcaaacga tctgttttg ccaatttatc acagcgccgt | 25020 |
| tgaaaaagcc ctgcaagata actaggcgt aaaggcattt aagctaagcc caactaatgc | 25080 |
| tcataccgct cgcgcggcaa atgagagcag cctaaatgca gccaatggtg ccattgccca | 25140 |
| taacagctca aaagtggtgg ccgatgcact tggccttggc ggcgcacaac taagcctaga | 25200 |
| tgctgcctgt gctagttcgg tttactcatt aaagcttgcc tgcgattacc taagcactgg | 25260 |
| caaagccgat atcatgctag caggcgcagt atctggcgcg gatccttct ttattaatat | 25320 |
| gggattctca atcttccacg cctacccaga ccatggtatc tcagtaccgt ttgatgccag | 25380 |
| cagtaaaggt ttgtttgctg cgaaggcgc tggcgtatta gtgcttaaac gtcttgaaga | 25440 |
| tgccgagcgc gacaatgaca aaatctatgc ggttgttagc ggcgtaggtc tatcaaacga | 25500 |
| cggtaaaggc cagtttgtat taagccctaa tccaaaaggt caggtgaagg cctttgaacg | 25560 |
| tgcttatgct gccagtgaca ttgagccaaa agacattgaa gtgattgagt gccacgcaac | 25620 |
| aggcacaccg cttggcgata aaattgagct cacttcaatg gaaaccttct ttgaagacaa | 25680 |
| gctgcaaggc accgatgcac cgttaattgg ctcagctaag tctaacttag gccacctatt | 25740 |
| aactgcagcg catgcgggga tcatgaagat gatcttcgcc atgaaagaag gttacctgcc | 25800 |
| gccaagtatc aatattagtg atgctatcgc ttcgccgaaa aaactcttcg gtaaaccaac | 25860 |
| cctgccatagc atggttcaag gctggccaga taagccatcg aataatcatt ttggtgtaag | 25920 |
| aacccgtcac gcaggcgtat cggtattgg cttggtggc tgtaacgccc atctgttgct | 25980 |
| tgagtcatac aacggcaaag gaacagtaaa ggcagaagcc actcaagtac gcgtcaagc | 26040 |
| tgagccgcta aaagtggttg gccttgcctc gcactttggg cctcttagca gcattaatgc | 26100 |
| actcaacaat gctgtgaccc aagatgggaa tggctttatc gaactgccga aaaagcgctg | 26160 |
| gaaaggcctt gaaaagcaca gtgaactgtt agctgaattt ggcttagcat ctgcgccaaa | 26220 |
| aggtgcttat gttgataact tcgagctgga ctttttacgc tttaaactgc cgccaaacga | 26280 |
| agatgaccgt ttgatctcac agcagctaat gctaatgcga gtaacagacg aagccattcg | 26340 |
| tgatgccaag cttgagccgg ggcaaaaagt agctgtatta gtggcaatgg aaactgagct | 26400 |
| tgaactgcat cagttccgcg gccgggttaa cttgcatact caattagcgc aaagtcttgc | 26460 |
| cgccatgggc gtgagtttat caacggatga ataccaagcg cttgaagcca tcgccatgga | 26520 |
| cagcgtgctt gatgctgcca agctcaatca gtacaccagc tttattggta atattatggc | 26580 |
| gtcacgcgtg gcgtcactat gggacttta tggcccagcc ttcactattt cagcagcaga | 26640 |
| gcaatctgtg agccgctgta tcgatgtggc gcaaaacctc atcatggagg ataacctaga | 26700 |
| tgcggtggtg attgcagcgg tcgatctctc tggtagcttt gagcaagtca ttcttaaaaa | 26760 |
| tgccattgca cctgtagcca ttgagccaaa cctcgaagca agccttaatc caacatcagc | 26820 |
| aagctggaat gtcggtgaag gtgctggcgc ggtcgtgctt gttaaaaatg aagctacatc | 26880 |
| gggctgctca tacggccaaa ttgatgcact tggctttgct aaaactgccg aaacagcgtt | 26940 |
| ggctaccgac aagctactga gccaaactgc cacagacttt aataaggtta aagtgattga | 27000 |
| aactatggca gcgcctgcta gccaaattca attagcgcca atagttagct ctcaagtgac | 27060 |

-continued

```
tcacactgct gcagagcagc gtgttggtca ctgctttgct gcagcgggta tggcaagcct    27120
attacacggc ttacttaact taaatactgt agcccaaacc aataaagcca attgcgcgct    27180
tatcaacaat atcagtgaaa accaattatc acagctgttg attagccaaa cagcgagcga    27240
acaacaagca ttaaccgcgc gtttaagcaa tgagcttaaa tccgatgcta acaccaact     27300
ggttaagcaa gtcaccttag gtggccgtga tatctaccag catattgttg ataccgct      27360
tgcaagcctt gaaagcatta ctcagaaatt ggcgcaagcg acagcatcga cagtggtcaa    27420
ccaagttaaa cctattaagg ccgctggctc agtcgaaatg gctaactcat tcgaaacgga    27480
aagctcagca gagccacaaa taacaattgc agcacaacga actgcaaaca ttggcgtcac    27540
cgctcaggca accaaacgtg aattaggtac cccaccaatg acaacaaata ccattgctaa    27600
tacagcaaat aatttagaca agactcttga gactgttgct ggcaatactg ttgctagcaa    27660
ggttggctct ggcgacatag tcaattttca acagaaccaa caattggctc aacaagctca    27720
cctcgccttt cttgaaagcc gcagtgcggg tatgaaggtg gctgatgctt tattgaagca    27780
acagctagct caagtaacag gccaaactat cgataatcag gccctcgata ctcaagccgt    27840
cgatactcaa acaagcgaga atgtagcgat gccgcagaa tcaccagttc aagttacaac     27900
acctgttcaa gttacaacac ctgttcaaat cagtgttgtg gagttaaaac cagatcacgc    27960
taatgtgcca ccatacacgc cgccagtgcc tgcattaaag ccgtgtatct ggaactatgc    28020
cgatttagtt gagtacgcag aaggcgatat cgccaaggta tttggcagtg attatgccat    28080
tatcgacagc tactcgcgcc gcgtacgtct accgaccact gactacctgt tggtatcgcg    28140
cgtgaccaaa cttgatgcga ccatcaatca atttaagcca tgctcaatga ccactgagta    28200
cgacatccct gttgatgcgc cgtacttagt agacggacaa atcccttggg cggtagcagt    28260
agaatcaggc caatgtgact tgatgcttat tagctatctc ggtatcgact ttgagaacaa    28320
aggcgagcgg gtttatcgac tactcgattg taccctcacc ttcctaggcg acttgccacg    28380
tggcggagat accctacgtt acgacattaa gatcaataac tatgctcgca acggcgacac    28440
cctgctgttc ttcttctcgt atgagtgttt tgttggcgac aagatgatcc tcaagatgga    28500
tggcggctgc gctggcttct tcactgatga agagcttgcc gacggtaaag gcgtgattcg    28560
cacagaagaa gagattaaag ctcgcagcct agtgcaaaag caacgcttta atccgttact    28620
agattgtcct aaaacccaat ttagttatgg tgatattcat aagctattaa ctgctgatat    28680
tgagggttgt tttggcccaa gccacagtgg cgtccaccag ccgtcacttt gtttcgcatc    28740
tgaaaaattc ttgatgattg aacaagtcag caaggttgat cgcactggcg gtacttgggg    28800
acttggctta attgagggtc ataagcagct gaagcagac cactggtact tcccatgtca     28860
tttcaagggc gaccaagtga tggctggctc gctaatggct gaaggttgtg gccagttatt    28920
gcagttctat atgctgcacc ttggtatgca tacccaaact aaaaatggtc gtttccaacc    28980
tcttgaaaac gcctcacagc aagtacgctg tcgcggtcaa gtgctgccac aatcaggcgt    29040
gctaacttac cgtatggaag tgactgaaat cggtttcagt ccacgcccat atgctaaagc    29100
taacatcgat atcttgctta atggcaaagc ggtagtggat ttccaaaacc tagggtgat    29160
gataaaagag gaagatgagt gtactcgtta tccactttg actgaatcaa caacggctag    29220
cactgcacaa gtaaacgctc aaacaagtgc gaaaaggta tacaagccag catcagtcaa     29280
tgcgccatta atggcacaaa ttcctgatct gactaaagag ccaaacaagg cgttattcc     29340
gatttcccat gttgaagcac caattacgcc agactacccg aaccgtgtac ctgatacagt    29400
gccattcacg ccgtatcaca tgtttgagtt tgctacaggc aatatcgaaa actgtttcgg    29460
```

-continued

```
gccagagttc tcaatctatc gcggcatgat cccaccacgt acaccatgcg gtgacttaca      29520
agtgaccaca cgtgtgattg aagttaacgg taagcgtggc gactttaaaa agccatcatc      29580
gtgtatcgct gaatatgaag tgcctgcaga tgcgtggtat ttcgataaaa acagccacgg      29640
cgcagtgatg ccatattcaa ttttaatgga gatctcactg caacctaacg gctttatctc      29700
aggttacatg gcacaaccc taggcttccc tggccttgag ctgttcttcc gtaacttaga      29760
cggtagcggt gagttactac gtgaagtaga tttacgtggt aaaaccatcc gtaacgactc      29820
acgtttatta tcaacagtga tggccggcac taacatcatc caaagcttta gcttcgagct      29880
aagcactgac ggtgagcctt tctatcgcgg cactgcggta tttggctatt ttaaaggtga      29940
cgcacttaaa gatcagctag gcctagataa cggtaaagtc actcagccat ggcatgtagc      30000
taacggcgtt gctgcaagca ctaaggtgaa cctgcttgat aagagctgcc gtcactttaa      30060
tgcgccagct aaccagccac actatcgtct agccggtggt cagctgaact ttatcgacag      30120
tgttgaaatt gttgataatg gcggcaccga aggtttaggt tacttgtatg ccgagcgcac      30180
cattgaccca agtgattggt tcttccagtt ccacttccac caagatccgg ttatgccagg      30240
ctccttaggt gttgaagcaa ttattgaaac catgcaagct tacgctatta gtaaagactt      30300
gggcgcagat ttcaaaaatc ctaagtttgg tcagatttta tcgaacatca agtggaagta      30360
tcgcggtcaa atcaatccgc tgaacaagca gatgtctatg gatgtcagca ttacttcaat      30420
caaagatgaa gacggtaaga agtcatcac aggtaatgcc agcttgagta agatggtct      30480 gcgcatatac gaggtcttcg atatagctat cagcatcgaa gaatctgtat aaatcggagt      30540
gactgtctgg ctattttact caatttctgt gtcaaaagtg ctcacctata ttcataggct      30600
gcgcgctttt ttctggaaat tgagcaaaag tatctgcgtc ctaactcgat ttataagaat      30660
ggtttaattg aaaagaacaa cagctaagag ccgcaagctc aatataaata attaagggtc      30720
ttacaaataa tgaatcctac agcaactaac gaaatgcttt ctccgtggcc atgggctgtg      30780
acagagtcaa atatcagttt tgacgtgcaa gtgatggaac aacaacttaa agattttagc      30840
cgggcatgtt acgtggtcaa tcatgccgac cacggctttg gtattgcgca aactgccgat      30900
atcgtgactg aacaagcggc aaacagcaca gatttacctg ttagtgcttt tactcctgca      30960
ttaggtaccg aaagcctagg cgacaataat tccgccgcg ttcacggcgt taaatacgct      31020
tattacgcag gcgctatggc aaacggtatt tcatctgaag agctagtgat tgccctaggt      31080
caagctggca ttttgtgtgg ttcgtttgga gcagccggtc ttattccaag tcgcgttgaa      31140
gcggcaatta accgtattca agcagcgctg ccaaatggcc cttatatgtt taaccttatc      31200
catagtccta gcgagccagc attagagcgt ggcagcgtag agctattttt aaagcataag      31260
gtacgcaccg ttgaagcatc agctttctta ggtctaacac cacaaatcgt ctattaccgt      31320
gcagcaggat tgagccgaga cgcacaaggt aaagttgtgg ttggtaacaa ggttatcgct      31380
aaagtaagtc gcaccgaagt ggctgaaaag tttatgatgc cagcgcccgc aaaaatgcta      31440
caaaaactag ttgatgacgg ttcaattacc gctgagcaaa tggagctggc gcaacttgta      31500
cctatggctg acgacatcac tgcagaggcc gattcaggtg gccatactga taccgtcca      31560 ttagtaacat tgctgccaac catttttagcg ctgaaagaag aaattcaagc taaataccaa      31620
tacgacactc ctattcgtgt cggttgtggt ggcggtgtgg gtacgcctga tgcagcgctg      31680
gcaacgttta acatgggcgc ggcgtatatt gttaccggct ctatcaacca agcttgtgtt      31740
gaagcgggcg caagtgatca cactcgtaaa ttacttgcca ccactgaaat ggccgatgtg      31800
```

```
actatggcac cagctgcaga tatgttcgag atgggcgtaa aactgcaggt ggttaagcgc   31860
ggcacgctat tcccaatgcg cgctaacaag ctatatgaga tctacacccg ttacgattca   31920
atcgaagcga tcccattaga cgagcgtgaa aagcttgaga acaagtatt ccgctcaagc    31980 ctagatgaaa tatgggcagg tacagtggcg cactttaacg agcgcgaccc taagcaaatc   32040
gaacgcgcag agggtaaccc taagcgtaaa atggcattga ttttccgttg gtacttaggt   32100 cttctagtc gctggtcaaa ctcaggcgaa gtgggtcgtg aaatggatta tcaaatttgg    32160
gctggccctg ctctcggtgc atttaaccaa tgggcaaaag gcagttactt agataactat   32220
caagaccgaa atgccgtcga tttggcaaag cacttaatgt acggcgcggc ttacttaaat   32280
cgtattaact cgctaacggc tcaaggcgtt aaagtgccag cacagttact tcgctggaag   32340
ccaaaccaaa gaatggccta atacacttac aaagcaccag tctaaaaagc cactaatctt   32400
gattagtggc ttttttttatt gtggtcaata tgaggctatt tagcctgtaa gcctgaaaat   32460
atcagcactc tgactttaca agcaaattat aattaaggca gggctctact catttatact   32520
gctagcaaac aagcaagttg cccagtaaaa caacaaggta cctgatttat atcgtcataa   32580
aagttggcta gagattcgtt attgatcttt actgattaga gtcgctctgt ttggaaaaag   32640
gtttctcgtt atcatcaaaa tacactctca aacctttaat caattacaac ttaggctttc   32700
tgcgggcatt tttatcttat ttgccacagc tgtatttgcc tttaggtttt gggtgcaact   32760
accattaatt gaggcctcat tagttaaatt atctgagcaa gagctcacct ctttaaatta   32820
cgcttttcag caaatgagaa agccactaca aaccattaat tacgactatg cggtgtggga   32880
cagaacctac agctatatga aatcaaactc agcgagcgct aaaaggtact atgaaaaaca   32940
tgagtaccca gatgatacgt tcaagagttt aaaagtcgac ggagtattta tattcaaccg   33000
tacaaatcag ccagttttta gtaaaggttt taatcataga aatgatatac cgctggtctt   33060
tgaattaact gactttaaac aacatccaca aaacatcgca ttatctccac aaaccaaaca   33120
ggcacaccca ccggcaagta agccgttaga ctcccctgat gatgtgcctt ctacccatgg   33180
ggttatcgcc acacgatacg gtccagcaat ttatagctct accagcattt taaaatctga   33240
tcgtagcggc tcccaacttg gttatttagt cttcattagg ttaattgatg aatggttcat   33300
cgctgagcta tcgcaataca ctgccgcagg tgttgaaatc gctatggctg atgccgcaga   33360
cgcacaatta gcgagattag cgcaaacac taagcttaat aaagtaaccg ctacatccga   33420
acggttaata actaatgtcg atggtaagcc tctgttgaag ttagtgcttt accataccaa   33480
taaccaaccg ccgccgatgc tagattacag tataataatt ctattagttg agatgtcatt   33540
tttactgatc ctcgcttatt tcctttactc ctacttctta gtcaggccag ttagaaagct   33600
ggcttcagat attaaaaaaa tggataaaag tcgtgaaatt aaaaagctaa ggtatcacta   33660
ccctattact gagctagtca aagttgcgac tcacttcaac gccctaatgg ggacgattca   33720
ggaacaaact aaacagctta atgaacaagt ttttattgat aaattaacca atattcccaa   33780
tcgtcgcgct tttgagcagc gacttgaaac ctattgccaa ctgctagccc ggcaacaaat   33840
tggctttact ctcatcattg ccgatgtgga tcattttaaa gagtacaacg atactcttgg   33900
gcaccttgct ggggatgaag cattaataaa agtggcacaa acactatcgc aacagtttta   33960
ccgtgcagaa gatatttgtg cccgttttgg tggtgaagaa tttattatgt tatttcgaga   34020
catacctgat gagcccttgc agagaaagct cgatgcgatg ctgcactctt ttgcagagct   34080
caacctacct catccaaact catcaaccgc taattacgtt actgtgagcc ttggggtttt   34140
cacagttgtt gctgttgatg attttgaatt taaaagtgag tcgcatatta ttggcagtca   34200
```

```
ggctgcatta atcgcagata aggcgcttta tcatgctaaa gcctgtggtc gtaaccagtt   34260
gtcaaaaact actattactg ttgatgagat tgagcaatta gaagcaaata aaatcggtca   34320
tcaagcctaa actcgttcga gtactttccc ctaagtcaga gctatttgcc acttcaagat   34380
gtggctacaa ggcttactct ttcaaaacct gcatcaatag aacacagcaa aatacaataa   34440
tttaagtcaa tttagcctat taaacagagt taatgacagc tcatggtcgc aacttattag   34500
ctatttctag caatataaaa acttatccat tagtagtaac caataaaaaa actaatatat   34560
aaaactattt aatcattatt ttacagatga ttagctacca cccaccttaa gctggctata   34620
ttcgcactag taaaaataaa cattagatcg ggttcagatc aatttacgag tctcgtataa   34680
aatgtacaat aattcactta atttaatact gcatattttt acaagtagag agcggtgatg   34740
aaacaaaata cgaaaggctt tacattaatt gaattagtca tcgtgattat tattctcggt   34800
atacttgctg ctgtggcact gccgaaattc atcaatgttc aagatgacgc taggatctct   34860
gcgatgagcg gtcagttttc atcatttgaa agtgccgtaa aactatacca tagcggttgg   34920
ttagccaaag gctacaacac tgcggttgaa aagctctcag gctttggcca aggtaatgtt   34980
gcatcaagtg acacaggttt tccgtactca acatcaggca cgagtactga tgtgcataaa   35040
gcttgtggtg aactatggca tggcattacc gatacagact tcacaattgg tgcggttagt   35100
gatggcgatc taatgactgc agatgtcgat attgcttaca cctatcgtgg tgatatgtgt   35160
atctatcgcg atctgtattt tattcagcgc tcattaccta ctaaggtgat gaactacaaa   35220
tttaaaactg gtgaaataga aattattgat gctttctaca accctgacgg ctcaactggt   35280
caattaccat aaatttggcg cttatctaag ttgtacttgc tctgaccgac acaaataatg   35340
tcgtttctca gcatatatca aaatacacag caaaaatttg gggttagcta tatagctaac   35400
cccaaatcat atctaacttt acactgcatc taattccaaa cagtatccag ccaaaagcct   35460
aaactattgt tgactcagcg ctaaaatatg cgatgcaaca aacaagtctt ggatcgcaat   35520
acctgagcta tcaaaaatgg tcacctcatc agcactttga cgtcctgttg cggactcgtt   35580
tatcacctga ccaatctcaa ttatcggcgt atttctgcta tgttgaaact caccaataac   35640
aatagattga gaagcaaagt cgcaaaacaa gcgagcatga ctatataggt cagttggcaa   35700
ctcttgctta cccactttat cagcgcccat tgcagaaata tgcgttcctg cttgtaccca   35760
ctgcgcttca aataaaggcg cttgagctgt ggttgctgtg ataataatat ctgcttgttc   35820
acaagcagct tgtgcatcac aagcttcggc attaatgcct tttctaata aacgcttaac   35880 caagttttca gttttgctag cactacggcc aactaccaat accttagtta atgaacgaac   35940
cttgctcact gctagcactt catattcagc ctgatgaccg gtaccaaaaa cagttaatac   36000
cgtagcatct tctctcgcga ggtaactcac tgctactgca tcggcagcac cagtgcggta   36060
agcattaacg gtagtggcag caatcaccgn ctgcaacata ccggttaatg gatcgagtaa   36120
aaatacgtta gtgccgtggc atggtaaacc atgtttatgg ttatcaggcc aatagctgcc   36180
tgttttccag ccgacaaggt ttggcgttga agccgacttt aatgagaaca tttcattaag   36240
gttcgcgccc tgtgcattaa ctaccgggaa caaggttgct ttatcatcta cggcagcgac   36300
aaacgcttct ttaacagcga tataagccag ctcatgggag atgagctttg atgtttcgc   36360 ttcagttaaa tagatcatat taccacccct gcactcgatt ccagatctca tagccaccat   36420
tatcaccatc agtatcaaat acatggtact gagcgtgcat tgaagctgtt gcacaggcgt   36480
ggttcggcaa aatatgtaga cgactaccta ccgggaactg cgctaaatca ataacgccgc   36540
```

-continued

```
catcaactgc ttcaataatg ccgtgctctt gattaacagt tataacctgt agacctgata    36600
acacgtgacc gctgtcgtca cacactaaac cataaccaca atcttttggc tgctctgcag    36660
tacctctatc acccgaaaga gccatccaac ccgcatcaat gaaaatccag tttttatcag    36720
gattatgacc aataacactg gtcactaccg ttgcggcaat atcagttaac tgacacacgt    36780
ttagccctgc catgactaaa tcgaagaagg tgtacacacc cgctctaacc tcggtgatcc    36840
catcaaggtt ttgatagctt tgcgctgttg gtgttgaacc aatactaacg atgtcacatt    36900 gcataccgc tgcgcgaatg cgtcagcagc ttgtacagcc gctgcaactt cattttgcgc    36960
cgcatcaatt aattgctgtt tttcaaaaca ttgatatgac tcaccagcgt gagtnagtac    37020
gccgtgaaaa ctcgctgcgc cagacgttag tatctgagca atttcaatca acttatcggc    37080
ttccggtgga ataccaccac gatggccatc acaatcaatt tcaattaatg ctggtatttg    37140
gcagtcataa gaaccacaga atgatttag ctgatgcgct tgctcaacac tatcaagtaa    37200
aactcttgca ttaataccctt ggtccaacat tttagcaata cgcggcaact taccatcggc    37260 aataccctact gcataaataa tgtctgtgta acctttagat gctaaggcct cggcctcttt    37320
taccgttgat acagtgactg gtgagttttt agtgggtaat aaaaactcgg ctgcttcaag    37380
tgatcttaac gttttaaaat gcggtcttag gtttgcacct aatccttcaa ttttttggcg    37440
tagttgactg aggttattaa taaatactgg cttatttaca tataaaaacg gtgtatcaat    37500
tgcttgatac tgactttgct gagtcgtgga aagtatttga gtagatggca tctttaatat    37560
cctagttcat caatcaatct aacaagtttg atgcctagcc acagtggctt gtattcatga    37620
tgctttggaa aatgcttata ttcaaagtat ttgaaagaca tcaaacttct tgtttaatgc    37680
tcagtatcca ccagcacgca tttattttat attaactatt atcaagatat agattaggtt    37740
caaaccaaat gattagtact gaagatctac gttttatcag cgtaatcgcc agtcatcgca    37800
ccttagctga tgccgctaga acactaaata tcacgccacc atcagtgaca ttaaggttgc    37860
agcatattga aaagaaacta tcgattagcc tgatc    37895
```

<210> SEQ ID NO 2
<211> LENGTH: 654
<212> TYPE: PRT
<213> ORGANISM: Shewanella putrefaciens

<400> SEQUENCE: 2

```
Met Lys Gln Thr Leu Met Ala Ile Ser Ile Met Ser Leu Phe Ser Phe
  1               5                  10                  15

Asn Ala Leu Ala Ala Gln His Glu His Asp His Ile Thr Val Asp Tyr
             20                  25                  30

Glu Gly Lys Ala Ala Thr Glu His Thr Ile Ala His Asn Gln Ala Val
         35                  40                  45

Ala Lys Thr Leu Asn Phe Ala Asp Thr Arg Ala Phe Glu Gln Ser Ser
     50                  55                  60

Lys Asn Leu Val Ala Lys Phe Asp Lys Ala Thr Ala Asp Ile Leu Arg
 65                  70                  75                  80

Ala Glu Phe Ala Phe Ile Ser Asp Glu Ile Pro Asp Ser Val Asn Pro
                 85                  90                  95

Ser Leu Tyr Arg Gln Ala Gln Leu Asn Met Val Pro Asn Gly Tyr Lys
            100                 105                 110

Val Ser Asp Gly Ile Tyr Gln Val Arg Gly Thr Asp Leu Ser Asn Leu
        115                 120                 125

Thr Leu Ile Arg Ser Asp Asn Gly Trp Ile Ala Tyr Asp Val Leu Leu
```

-continued

```
            130                 135                 140
Thr Lys Glu Ala Ala Lys Ala Ser Leu Gln Phe Ala Leu Lys Asn Leu
145                 150                 155                 160

Pro Lys Asp Gly Asp Pro Val Val Ala Met Ile Tyr Ser His Ser His
                165                 170                 175

Ala Asp His Phe Gly Gly Ala Arg Gly Val Gln Glu Met Phe Pro Asp
                180                 185                 190

Val Lys Val Tyr Gly Ser Asp Asn Ile Thr Lys Glu Ile Val Asp Glu
            195                 200                 205

Asn Val Leu Ala Gly Asn Ala Met Ser Arg Arg Ala Ala Tyr Gln Tyr
210                 215                 220

Gly Ala Thr Leu Gly Lys His Asp His Gly Ile Val Asp Ala Ala Leu
225                 230                 235                 240

Gly Lys Gly Leu Ser Lys Gly Glu Ile Thr Tyr Val Ala Pro Asp Tyr
                245                 250                 255

Thr Leu Asn Ser Glu Gly Lys Trp Glu Thr Leu Thr Ile Asp Gly Leu
                260                 265                 270

Glu Met Val Phe Met Asp Ala Ser Gly Thr Glu Ala Glu Ser Glu Met
            275                 280                 285

Ile Thr Tyr Ile Pro Ser Lys Lys Ala Leu Trp Thr Ala Glu Leu Thr
290                 295                 300

Tyr Gln Gly Met His Asn Ile Tyr Thr Leu Arg Gly Ala Lys Val Arg
305                 310                 315                 320

Asp Ala Leu Lys Trp Ser Lys Asp Ile Asn Glu Met Ile Asn Ala Phe
                325                 330                 335

Gly Gln Asp Val Glu Val Leu Phe Ala Ser His Ser Ala Pro Val Trp
                340                 345                 350

Gly Asn Gln Ala Ile Asn Asp Phe Leu Arg Leu Gln Arg Asp Asn Tyr
            355                 360                 365

Gly Leu Val His Asn Gln Thr Leu Arg Leu Ala Asn Asp Gly Val Gly
            370                 375                 380

Ile Gln Asp Ile Gly Asp Ala Ile Gln Asp Thr Ile Pro Glu Ser Ile
385                 390                 395                 400

Tyr Lys Thr Trp His Thr Asn Gly Tyr His Gly Thr Tyr Ser His Asn
                405                 410                 415

Ala Lys Ala Val Tyr Asn Lys Tyr Leu Gly Tyr Phe Asp Met Asn Pro
                420                 425                 430

Ala Asn Leu Asn Pro Leu Pro Thr Lys Gln Glu Ser Ala Lys Phe Val
                435                 440                 445

Glu Tyr Met Gly Gly Ala Asp Ala Ala Ile Lys Arg Ala Lys Asp Asp
            450                 455                 460

Tyr Ala Gln Gly Glu Tyr Arg Phe Val Ala Thr Ala Leu Asn Lys Val
465                 470                 475                 480

Val Met Ala Glu Pro Glu Asn Asp Ser Ala Arg Gln Leu Leu Ala Asp
                485                 490                 495

Thr Tyr Glu Gln Leu Gly Tyr Gln Ala Glu Gly Ala Gly Trp Arg Asn
                500                 505                 510

Ile Tyr Leu Thr Gly Ala Gln Glu Leu Arg Val Gly Ile Gln Ala Gly
            515                 520                 525

Ala Pro Lys Thr Ala Ser Ala Asp Val Ile Ser Glu Met Asp Met Pro
            530                 535                 540

Thr Leu Phe Asp Phe Leu Ala Val Lys Ile Asp Ser Gln Gln Ala Ala
545                 550                 555                 560
```

```
Lys His Gly Leu Val Lys Met Asn Val Ile Thr Pro Asp Thr Lys Asp
                565                 570                 575

Ile Leu Tyr Ile Glu Leu Ser Asn Gly Asn Leu Ser Asn Ala Val Val
            580                 585                 590

Asp Lys Glu Gln Leu Met Val Asn Lys Ala Asp Val Asn Arg Ile Leu
        595                 600                 605

Leu Gly Gln Val Thr Leu Lys Ala Leu Leu Ala Ser Gly Asp Ala Lys
    610                 615                 620

Leu Thr Gly Asp Lys Thr Ala Phe Ser Lys Ile Ala Asp Ser Met Val
625                 630                 635                 640

Glu Phe Thr Pro Asp Phe Glu Ile Val Pro Thr Pro Val Lys
                645                 650

<210> SEQ ID NO 3
<211> LENGTH: 277
<212> TYPE: PRT
<213> ORGANISM: Shewanella putrefaciens

<400> SEQUENCE: 3

Ser Thr Lys Ala Ser Ala Arg Val Val Ala Lys Phe Asn Val Glu Glu
1               5                   10                  15

Ala Ala Ile Ser Ile Gln Gln Cys Gln Gly Ile Ser Leu Ala Phe Arg
            20                  25                  30

Tyr Ser Asp Asp Leu His Gly Leu Leu Cys His Trp Asn Asp Ala Ala
        35                  40                  45

Asn Met Gln Gln Glu Lys Ala Glu Ile Leu Gly Leu Gly Ser Lys Gln
    50                  55                  60

Pro Glu Ala Asn Pro Lys Asn Ser Ser Glu Leu Leu Ala Leu Gly
65                  70                  75                  80

Ile Asp Gln Lys Leu Leu Val Gln Arg Gln Asn Leu Gln His Glu Val
                85                  90                  95

Lys His Asp Ala Ile Ala Asp Ser Ile Asp Val Cys His Ser Leu Ser
            100                 105                 110

Lys Pro Ala Asn Val Gly Leu Phe Thr Glu Ser Leu Ala Ser Phe Asp
        115                 120                 125

Phe Ala Phe Ser Lys Leu Ser Leu Ala Leu Gly Leu Gly Lys Ala Lys
    130                 135                 140

Ile Tyr Ser Glu Lys Leu Ala Trp Leu Asp Phe Phe Arg Asp Arg Gln
145                 150                 155                 160

Leu Ala Glu Pro Leu Ala Leu Leu Ala Arg Lys Glu Ser Glu Ser Phe
                165                 170                 175

Tyr His Ser Leu Ile Ser His Ile Asn Thr Ser Asn Arg Cys Arg Glu
            180                 185                 190

Ile Asp Val Gly Phe Glu Ile Ser Ala Ser Asp Thr Glu Glu Lys Ser
        195                 200                 205

Ala Gln Ser Ala Gly Lys Asn Asp Ala Thr Cys Ile Gly Val Leu Leu
    210                 215                 220

Trp Asp Gly Ser His Ser Val Asn Phe His Val Gly Thr Gln Ala Phe
225                 230                 235                 240

Gln Ala Asp Ser Leu Arg Pro Lys Gly Lys Asp Gly Tyr Glu Phe Arg
                245                 250                 255

Trp Glu Asn Pro Arg Ile Glu Ser His Gln Ser Leu Leu Ala Arg Leu
            260                 265                 270

Tyr Gly Arg Val Met
        275
```

-continued

275

<210> SEQ ID NO 4
<211> LENGTH: 1480
<212> TYPE: DNA
<213> ORGANISM: Shewanella putrefaciens

<400> SEQUENCE: 4

```
gctagtctta gctgasrthr ysaasragct cgaacaacag ctttaaaatt cacttcttct     60
gctgcaatac ttatttgctg acactgacca atactcagtg caaaacgata actatcatca    120
agatggaaar gvavaaaysh asnvaggaaa asrgngncys gngysraaha rgtyrsrasa    180
shscccagta aacaatgcca attatcagca gcgttcattt gctgttcttt agcctcaatc    240
aaacctaaac cagacttttg tggctcagcg ttaggcttat taggycyshs trasnasaaa    300
aasnmtgngn gysaaggygy srysgnrgaa asnrysasns raactcgact ctagtaaagc    360
aagaccaata tcttgtttta acaaaacctg tcgctgatta agttgatgct caaccttgtg    420
atccgcaata gcatcggaaa tsrsrgaagy asgnysvagn arggnasngn hsgvayshsa    480
saaaaassra tcaacacaat ggctcaagct tttaggtgca ttaactccaa gaaaagtttc    540
gctcagtgca gagaagtcaa acgcaaaaga ttttagcgat aatgccagca svacyshssr    600
srysraaasn vagyhthrgs raasrhasha ahsryssraa ccaagtcctt tcgctttaat    660
gtaagactcc ttgagcgccc acaaatcaaa aaagcggtct cgctgcaagg cctctggtaa    720
cgctaacaag gctcgctttt gygyysaays tyrsrgysaa trashharga sarggnaagr    780
aaaaargysg ctgattcaga gaaataatga ctaagaatag agtggatatt ggtgctgtta    840
cggcaacgct caatgtcgac gccaaactca atactagcag agtcagtttc srgsrhtyrh    900
ssrsrhsasn thrsrasnar gcysarggas vagyhgsraa srasthrgct ccttgcttgc    960
ctgactggcg cctttattat cagcagtgca aatgcctact aatagccaat ctccactatg   1020
actcacatta aagtggaccc cggtttgagy ssraagnsra agyysasnas aathrcysgy   1080
vatrasgysr hssrvaasnh hsvagythrg ngcaaattgc gcatcactca atctaggctt   1140
acctttgtcg ccatattcaa agcgccattc attggggcgt atttcactat gttgtgacaa   1200
taaagcgcgc aaahgnaaas srargrysgy ysasgytyrg hargtrgasn rarggsrhsg   1260
nsraaargaa tagcctctta ccattaaacc ttgagtttta gcttcttgtt taatgtagcg   1320
attaacctta attaactcat cttcaggcag ccatgactta accaactcty rgyargvamt   1380
gygnthrysa aggnystyra rgasnvaysg asgrtrsrys vagtgtagtc tggttatcgc   1440
actcttgtat tgttaacgga cagaagtata aggaaatcaa                         1480
```

<210> SEQ ID NO 5
<211> LENGTH: 970
<212> TYPE: PRT
<213> ORGANISM: Shewanella putrefaciens

<400> SEQUENCE: 5

```
Met Ser Met Phe Leu Asn Ser Lys Leu Ser Arg Ser Val Lys Leu Ala
1               5                   10                  15

Ile Ser Ala Gly Leu Thr Ala Ser Leu Ala Met Pro Val Phe Ala Glu
            20                  25                  30

Glu Thr Ala Ala Glu Glu Gln Ile Glu Arg Val Ala Val Thr Gly Ser
        35                  40                  45

Arg Ile Ala Lys Ala Glu Leu Thr Gln Pro Ala Pro Val Val Ser Leu
    50                  55                  60
```

```
Ser Ala Glu Glu Leu Thr Lys Phe Gly Asn Gln Asp Leu Gly Ser Val
 65                  70                  75                  80

Leu Ala Glu Leu Pro Ala Ile Gly Ala Thr Asn Thr Ile Ile Gly Asn
                 85                  90                  95

Asn Asn Ser Asn Ser Ser Ala Gly Val Ser Ser Ala Asp Leu Arg Arg
            100                 105                 110

Leu Gly Ala Asn Arg Thr Leu Val Leu Val Asn Gly Lys Arg Tyr Val
            115                 120                 125

Ala Gly Gln Pro Gly Ser Ala Glu Val Asp Leu Ser Thr Ile Pro Thr
            130                 135                 140

Ser Met Ile Ser Arg Val Glu Ile Val Thr Gly Gly Ala Ser Ala Ile
145                 150                 155                 160

Tyr Gly Ser Asp Ala Val Ser Gly Val Ile Asn Val Ile Leu Lys Glu
                165                 170                 175

Asp Phe Glu Gly Phe Glu Phe Asn Ala Arg Thr Ser Gly Ser Thr Glu
                180                 185                 190

Ser Val Gly Thr Gln Glu His Ser Phe Asp Ile Leu Gly Gly Ala Asn
            195                 200                 205

Val Ala Asp Gly Arg Gly Asn Val Thr Phe Tyr Ala Gly Tyr Glu Arg
            210                 215                 220

Thr Lys Glu Val Met Ala Thr Asp Ile Arg Gln Phe Asp Ala Trp Gly
225                 230                 235                 240

Thr Ile Lys Asn Glu Ala Asp Gly Gly Glu Asp Asp Gly Ile Pro Asp
                245                 250                 255

Arg Leu Arg Val Pro Arg Val Tyr Ser Glu Met Ile Asn Ala Thr Gly
            260                 265                 270

Val Ile Asn Ala Phe Gly Gly Ile Gly Arg Ser Thr Phe Asp Ser
            275                 280                 285

Asn Gly Asn Pro Ile Ala Gln Gln Glu Arg Asp Gly Thr Asn Ser Phe
290                 295                 300

Ala Phe Gly Ser Phe Pro Asn Gly Cys Asp Thr Cys Phe Asn Thr Glu
305                 310                 315                 320

Ala Tyr Glu Asn Tyr Ile Pro Gly Val Glu Arg Ile Asn Val Gly Ser
                325                 330                 335

Ser Phe Asn Phe Asp Phe Thr Asp Asn Ile Gln Phe Tyr Thr Asp Phe
            340                 345                 350

Arg Tyr Val Lys Ser Asp Ile Gln Gln Gln Phe Gln Pro Ser Phe Arg
            355                 360                 365

Phe Gly Asn Ile Asn Ile Asn Val Glu Asp Asn Ala Phe Leu Asn Asp
370                 375                 380

Asp Leu Arg Gln Gln Met Leu Asp Ala Gly Gln Thr Asn Ala Ser Phe
385                 390                 395                 400

Ala Lys Phe Phe Asp Glu Leu Gly Asn Arg Ser Ala Glu Asn Lys Arg
                405                 410                 415

Glu Leu Phe Arg Tyr Val Gly Phe Lys Gly Gly Phe Asp Ile Ser
                420                 425                 430

Glu Thr Ile Phe Asp Tyr Asp Leu Tyr Tyr Val Tyr Gly Glu Thr Asn
            435                 440                 445

Asn Arg Arg Lys Thr Leu Asn Asp Leu Ile Pro Asp Asn Phe Val Ala
            450                 455                 460

Ala Val Asp Ser Val Ile Asp Pro Asp Thr Gly Leu Ala Ala Cys Arg
465                 470                 475                 480
```

```
Ser Gln Val Ala Ser Ala Gln Gly Asp Asp Tyr Thr Asp Pro Ala Ser
            485                 490                 495

Val Asn Gly Ser Asp Cys Val Ala Tyr Asn Pro Phe Gly Met Gly Gln
            500                 505                 510

Ala Ser Ala Glu Ala Arg Asp Trp Val Ser Ala Asp Val Thr Arg Glu
            515                 520                 525

Asp Lys Ile Thr Gln Gln Val Ile Gly Gly Thr Leu Gly Thr Asp Ser
            530                 535                 540

Glu Glu Leu Phe Glu Leu Gln Gly Gly Ala Ile Ala Met Val Val Gly
545                 550                 555                 560

Phe Glu Tyr Arg Glu Thr Ser Gly Ser Thr Thr Asp Glu Phe Thr
                565                 570                 575

Lys Ala Gly Phe Leu Thr Ser Ala Ala Thr Pro Asp Ser Tyr Gly Glu
            580                 585                 590

Tyr Asp Val Thr Glu Tyr Phe Val Glu Val Asn Ile Pro Val Leu Lys
            595                 600                 605

Glu Leu Pro Phe Ala His Glu Leu Ser Phe Asp Gly Ala Tyr Arg Asn
            610                 615                 620

Ala Asp Tyr Ser His Ala Gly Lys Thr Glu Ala Trp Lys Ala Gly Met
625                 630                 635                 640

Phe Tyr Ser Pro Leu Glu Gln Leu Ala Leu Arg Gly Thr Val Gly Glu
            645                 650                 655

Ala Val Arg Ala Pro Asn Ile Ala Glu Ala Phe Ser Pro Arg Ser Pro
            660                 665                 670

Gly Phe Gly Arg Val Ser Asp Pro Cys Asp Ala Asp Asn Ile Asn Asp
            675                 680                 685

Asp Pro Asp Arg Val Ser Asn Cys Ala Ala Leu Gly Ile Pro Pro Gly
            690                 695                 700

Phe Gln Ala Asn Asp Asn Val Ser Val Asp Thr Leu Ser Gly Gly Asn
705                 710                 715                 720

Pro Asp Leu Lys Pro Glu Thr Ser Thr Ser Phe Thr Gly Gly Leu Val
            725                 730                 735

Trp Thr Pro Thr Phe Ala Asp Asn Leu Ser Phe Thr Val Asp Tyr Tyr
            740                 745                 750

Asp Ile Gln Ile Glu Asp Ala Ile Leu Ser Val Ala Thr Gln Thr Val
            755                 760                 765

Ala Asp Asn Cys Val Asp Ser Thr Gly Gly Pro Asp Thr Asp Phe Cys
770                 775                 780

Ser Gln Val Asp Arg Asn Pro Thr Thr Tyr Asp Ile Glu Leu Val Arg
785                 790                 795                 800

Ser Gly Tyr Leu Asn Ala Ala Leu Asn Thr Lys Gly Ile Glu Phe
            805                 810                 815

Gln Ala Ala Tyr Ser Leu Asp Leu Glu Ser Phe Asn Ala Pro Gly Glu
            820                 825                 830

Leu Arg Phe Asn Leu Leu Gly Asn Gln Leu Leu Glu Leu Glu Arg Leu
            835                 840                 845

Glu Phe Gln Asn Arg Pro Asp Glu Ile Asn Asp Glu Lys Gly Glu Val
            850                 855                 860

Gly Asp Pro Glu Leu Gln Phe Arg Leu Gly Ile Asp Tyr Arg Leu Asp
865                 870                 875                 880

Asp Leu Ser Val Ser Trp Asn Thr Arg Tyr Ile Asp Ser Val Val Thr
                885                 890                 895

Tyr Asp Val Ser Glu Asn Gly Gly Ser Pro Glu Asp Leu Tyr Pro Gly
```

```
                        900             905             910
His Ile Gly Ser Met Thr Thr His Asp Leu Ser Ala Thr Tyr Tyr Ile
            915                 920                 925

Asn Glu Asn Phe Met Ile Asn Gly Val Arg Asn Leu Phe Asp Ala
        930                 935                 940

Leu Pro Pro Gly Tyr Thr Asn Asp Ala Leu Tyr Asp Leu Val Gly Arg
945                 950                 955                 960

Arg Ala Phe Leu Gly Ile Lys Val Met Met
                965                 970

<210> SEQ ID NO 6
<211> LENGTH: 288
<212> TYPE: PRT
<213> ORGANISM: Shewanella putrefaciens

<400> SEQUENCE: 6

Met Ala Lys Ile Asn Ser Glu His Leu Asp Glu Ala Thr Ile Thr Ser
1               5                   10                  15

Asn Lys Cys Thr Gln Thr Glu Thr Glu Ala Arg His Arg Asn Ala Thr
            20                  25                  30

Thr Thr Pro Glu Met Arg Arg Phe Ile Gln Glu Ser Asp Leu Ser Val
        35                  40                  45

Ser Gln Leu Ser Lys Ile Leu Asn Ile Ser Glu Ala Thr Val Arg Lys
    50                  55                  60

Trp Arg Lys Arg Asp Ser Val Glu Asn Cys Pro Asn Thr Pro His His
65                  70                  75                  80

Leu Asn Thr Thr Leu Thr Pro Leu Gln Glu Tyr Val Val Gly Leu
                85                  90                  95

Arg Tyr Gln Leu Lys Met Pro Leu Asp Arg Leu Leu Lys Ala Thr Gln
                100                 105                 110

Glu Phe Ile Asn Pro Asn Val Ser Arg Ser Gly Leu Ala Arg Cys Leu
            115                 120                 125

Lys Arg Tyr Gly Val Ser Arg Val Ser Asp Ile Gln Ser Pro His Val
130                 135                 140

Pro Met Arg Tyr Phe Asn Gln Ile Pro Val Thr Gln Gly Ser Asp Val
145                 150                 155                 160

Gln Thr Tyr Thr Leu His Tyr Glu Thr Leu Ala Lys Thr Leu Ala Leu
                165                 170                 175

Pro Ser Thr Asp Gly Asp Asn Val Val Gln Val Val Ser Leu Thr Ile
            180                 185                 190

Pro Pro Lys Leu Thr Glu Glu Ala Pro Ser Ser Ile Leu Leu Gly Ile
        195                 200                 205

Asp Pro His Ser Asp Trp Ile Tyr Leu Asp Ile Tyr Gln Asp Gly Asn
    210                 215                 220

Thr Gln Ala Thr Asn Arg Tyr Met Ala Tyr Val Leu Lys His Gly Pro
225                 230                 235                 240

Phe His Leu Arg Lys Leu Leu Val Arg Asn Tyr His Thr Phe Leu Gln
                245                 250                 255

Arg Phe Pro Gly Ala Thr Gln Asn Arg Arg Pro Ser Lys Asp Met Pro
            260                 265                 270

Glu Thr Ile Asn Lys Thr Pro Glu Thr Gln Ala Pro Ser Gly Asp Ser
        275                 280                 285

<210> SEQ ID NO 7
<211> LENGTH: 2756
```

<212> TYPE: PRT
<213> ORGANISM: Shewanella putrefaciens

<400> SEQUENCE: 7

```
Met Ser Gln Thr Ser Lys Pro Thr Asn Ser Ala Thr Glu Gln Ala Gln
 1               5                  10                  15

Asp Ser Gln Ala Asp Ser Arg Leu Asn Lys Arg Leu Lys Asp Met Pro
             20                  25                  30

Ile Ala Ile Val Gly Met Ala Ser Ile Phe Ala Asn Ser Arg Tyr Leu
         35                  40                  45

Asn Lys Phe Trp Asp Leu Ile Ser Glu Lys Ile Asp Ala Ile Thr Glu
 50                  55                  60

Leu Pro Ser Thr His Trp Gln Pro Glu Tyr Tyr Asp Ala Asp Lys
 65                  70                  75                  80

Thr Ala Ala Asp Lys Ser Tyr Cys Lys Arg Gly Phe Leu Pro Asp
                 85                  90                  95

Val Asp Phe Asn Pro Met Glu Phe Gly Leu Pro Pro Asn Ile Leu Glu
                100                 105                 110

Leu Thr Asp Ser Ser Gln Leu Leu Ser Leu Ile Val Ala Lys Glu Val
            115                 120                 125

Leu Ala Asp Ala Asn Leu Pro Glu Asn Tyr Asp Arg Asp Lys Ile Gly
130                 135                 140

Ile Thr Leu Gly Val Gly Gly Gln Lys Ile Ser His Ser Leu Thr
145                 150                 155                 160

Ala Arg Leu Gln Tyr Pro Val Leu Lys Lys Val Phe Ala Asn Ser Gly
                165                 170                 175

Ile Ser Asp Thr Asp Ser Glu Met Leu Ile Lys Lys Phe Gln Asp Gln
            180                 185                 190

Tyr Val His Trp Glu Glu Asn Ser Phe Pro Gly Ser Leu Gly Asn Val
        195                 200                 205

Ile Ala Gly Arg Ile Ala Asn Arg Phe Asp Phe Gly Met Asn Cys
    210                 215                 220

Val Val Asp Ala Ala Cys Ala Gly Ser Leu Ala Ala Met Arg Met Ala
225                 230                 235                 240

Leu Thr Glu Leu Thr Glu Gly Arg Ser Glu Met Met Ile Thr Gly Gly
                245                 250                 255

Val Cys Thr Asp Asn Ser Pro Ser Met Tyr Met Ser Phe Ser Lys Thr
            260                 265                 270

Pro Ala Phe Thr Thr Asn Glu Thr Ile Gln Pro Phe Asp Ile Asp Ser
        275                 280                 285

Lys Gly Met Met Ile Gly Glu Gly Ile Gly Met Val Ala Leu Lys Arg
    290                 295                 300

Leu Glu Asp Ala Glu Arg Asp Gly Asp Arg Ile Tyr Ser Val Ile Lys
305                 310                 315                 320

Gly Val Gly Ala Ser Ser Asp Gly Lys Phe Lys Ser Ile Tyr Ala Pro
                325                 330                 335

Arg Pro Ser Gly Gln Ala Lys Ala Leu Asn Arg Ala Tyr Asp Asp Ala
            340                 345                 350

Gly Phe Ala Pro His Thr Leu Gly Leu Ile Glu Ala His Gly Thr Gly
        355                 360                 365

Thr Ala Ala Gly Asp Ala Ala Glu Phe Ala Gly Leu Cys Ser Val Phe
    370                 375                 380

Ala Glu Gly Asn Asp Thr Lys Gln His Ile Ala Leu Gly Ser Val Lys
385                 390                 395                 400
```

```
Ser Gln Ile Gly His Thr Lys Ser Thr Ala Gly Thr Ala Gly Leu Ile
                405                 410                 415
Lys Ala Ala Leu Ala Leu His His Lys Val Leu Pro Thr Ile Asn
            420                 425                 430
Val Ser Gln Pro Ser Pro Lys Leu Asp Ile Glu Asn Ser Pro Phe Tyr
            435                 440                 445
Leu Asn Thr Glu Thr Arg Pro Trp Leu Pro Arg Val Asp Gly Thr Pro
        450                 455                 460
Arg Arg Ala Gly Ile Ser Ser Phe Gly Phe Gly Thr Asn Phe His
465                 470                 475                 480
Phe Val Leu Glu Glu Tyr Asn Gln Glu His Ser Arg Thr Asp Ser Glu
                485                 490                 495
Lys Ala Lys Tyr Arg Gln Arg Gln Val Ala Gln Ser Phe Leu Val Ser
                500                 505                 510
Ala Ser Asp Lys Ala Ser Leu Ile Asn Glu Leu Asn Val Leu Ala Ala
            515                 520                 525
Ser Ala Ser Gln Ala Glu Phe Ile Leu Lys Asp Ala Ala Asn Tyr
        530                 535                 540
Gly Val Arg Glu Leu Asp Lys Asn Ala Pro Arg Ile Gly Leu Val Ala
545                 550                 555                 560
Asn Thr Ala Glu Glu Leu Ala Gly Leu Ile Lys Gln Ala Leu Ala Lys
                565                 570                 575
Leu Ala Ala Ser Asp Asp Asn Ala Trp Gln Leu Pro Gly Gly Thr Ser
            580                 585                 590
Tyr Arg Ala Ala Ala Val Glu Gly Lys Val Ala Ala Leu Phe Ala Gly
                595                 600                 605
Gln Gly Ser Gln Tyr Leu Asn Met Gly Arg Asp Leu Thr Cys Tyr Tyr
            610                 615                 620
Pro Glu Met Arg Gln Gln Phe Val Thr Ala Asp Lys Val Phe Ala Ala
625                 630                 635                 640
Asn Asp Lys Thr Pro Leu Ser Gln Thr Leu Tyr Pro Lys Pro Val Phe
                645                 650                 655
Asn Lys Asp Glu Leu Lys Ala Gln Glu Ala Ile Leu Thr Asn Thr Ala
                660                 665                 670
Asn Ala Gln Ser Ala Ile Gly Ala Ile Ser Met Gly Gln Tyr Asp Leu
            675                 680                 685
Phe Thr Ala Ala Gly Phe Asn Ala Asp Met Val Ala Gly His Ser Phe
        690                 695                 700
Gly Glu Leu Ser Ala Leu Cys Ala Ala Gly Val Ile Ser Ala Asp Asp
705                 710                 715                 720
Tyr Tyr Lys Leu Ala Phe Ala Arg Gly Glu Ala Met Ala Thr Lys Ala
                725                 730                 735
Pro Ala Lys Asp Gly Val Glu Ala Asp Ala Gly Ala Met Phe Ala Ile
            740                 745                 750
Ile Thr Lys Ser Ala Ala Asp Leu Glu Thr Val Glu Ala Thr Ile Ala
        755                 760                 765
Lys Phe Asp Gly Val Lys Val Ala Asn Tyr Asn Ala Pro Thr Gln Ser
        770                 775                 780
Val Ile Ala Gly Pro Thr Ala Thr Thr Ala Asp Ala Ala Lys Ala Leu
785                 790                 795                 800
Thr Glu Leu Gly Tyr Lys Ala Ile Asn Leu Pro Val Ser Gly Ala Phe
                805                 810                 815
```

-continued

```
His Thr Glu Leu Val Gly His Ala Gln Ala Pro Phe Ala Lys Ala Ile
            820                 825                 830

Asp Ala Ala Lys Phe Thr Lys Thr Ser Arg Ala Leu Tyr Ser Asn Ala
            835                 840                 845

Thr Gly Gly Leu Tyr Glu Ser Thr Ala Ala Lys Ile Lys Ala Ser Phe
            850                 855                 860

Lys Lys His Met Leu Gln Ser Val Arg Phe Thr Ser Gln Leu Glu Ala
865                 870                 875                 880

Met Tyr Asn Asp Gly Ala Arg Val Phe Val Glu Phe Gly Pro Lys Asn
                885                 890                 895

Ile Leu Gln Lys Leu Val Gln Gly Thr Leu Val Asn Thr Glu Asn Glu
            900                 905                 910

Val Cys Thr Ile Ser Ile Asn Pro Asn Pro Lys Val Asp Ser Asp Leu
            915                 920                 925

Gln Leu Lys Gln Ala Ala Met Gln Leu Ala Val Thr Gly Val Val Leu
            930                 935                 940

Ser Glu Ile Asp Pro Tyr Gln Ala Asp Ile Ala Ala Pro Ala Lys Lys
945                 950                 955                 960

Ser Pro Met Ser Ile Ser Leu Asn Ala Ala Asn His Ile Ser Lys Ala
            965                 970                 975

Thr Arg Ala Lys Met Ala Lys Ser Leu Glu Thr Gly Ile Val Thr Ser
            980                 985                 990

Gln Ile Glu His Val Ile Glu Glu Lys Ile Val Glu Val Glu Lys Leu
            995                 1000                1005

Val Glu Val Glu Lys Ile Val Glu Lys Val Val Glu Val Glu Lys Val
        1010                1015                1020

Val Glu Val Glu Ala Pro Val Asn Ser Val Gln Ala Asn Ala Ile Gln
1025                1030                1035                1040

Thr Arg Ser Val Val Ala Pro Val Ile Glu Asn Gln Val Val Ser Lys
                1045                1050                1055

Asn Ser Lys Pro Ala Val Gln Ser Ile Ser Gly Asp Ala Leu Ser Asn
            1060                1065                1070

Phe Phe Ala Ala Gln Gln Gln Thr Ala Gln Leu His Gln Gln Phe Leu
        1075                1080                1085

Ala Ile Pro Gln Gln Tyr Gly Glu Thr Phe Thr Thr Leu Met Thr Glu
        1090                1095                1100

Gln Ala Lys Leu Ala Ser Ser Gly Val Ala Ile Pro Glu Ser Leu Gln
1105                1110                1115                1120

Arg Ser Met Glu Gln Phe His Gln Leu Gln Ala Gln Thr Leu Gln Ser
                1125                1130                1135

His Thr Gln Phe Leu Glu Met Gln Ala Gly Ser Asn Ile Ala Ala Leu
        1140                1145                1150

Asn Leu Leu Asn Ser Ser Gln Ala Thr Tyr Ala Pro Ala Ile His Asn
        1155                1160                1165

Glu Ala Ile Gln Ser Gln Val Val Gln Ser Gln Thr Ala Val Gln Pro
    1170                1175                1180

Val Ile Ser Thr Gln Val Asn His Val Ser Glu Gln Pro Thr Gln Ala
1185                1190                1195                1200

Pro Ala Pro Lys Ala Gln Pro Ala Pro Val Thr Thr Ala Val Gln Thr
                1205                1210                1215

Ala Pro Ala Gln Val Val Arg Gln Ala Ala Pro Val Gln Ala Ala Ile
            1220                1225                1230

Glu Pro Ile Asn Thr Ser Val Ala Thr Thr Thr Pro Ser Ala Phe Ser
```

-continued

```
            1235                1240                1245
Ala Glu Thr Ala Leu Ser Ala Thr Lys Val Gln Ala Thr Met Leu Glu
        1250                1255                1260
Val Val Ala Glu Lys Thr Gly Tyr Pro Thr Glu Met Leu Glu Leu Glu
1265                1270                1275                1280
Met Asp Met Glu Ala Asp Leu Gly Ile Asp Ser Ile Lys Arg Val Glu
            1285                1290                1295
Ile Leu Gly Thr Val Gln Asp Glu Leu Pro Gly Leu Pro Glu Leu Ser
        1300                1305                1310
Pro Glu Asp Leu Ala Glu Cys Arg Thr Leu Gly Glu Ile Val Asp Tyr
        1315                1320                1325
Met Gly Ser Lys Leu Pro Ala Glu Gly Ser Met Asn Ser Gln Leu Ser
        1330                1335                1340
Thr Gly Ser Ala Ala Thr Pro Ala Ala Asn Gly Leu Ser Ala Glu
1345                1350                1355                1360
Lys Val Gln Ala Thr Met Met Ser Val Val Ala Glu Lys Thr Gly Tyr
            1365                1370                1375
Pro Thr Glu Met Leu Glu Leu Glu Met Asp Met Glu Ala Asp Leu Gly
        1380                1385                1390
Ile Asp Ser Ile Lys Arg Val Glu Ile Leu Gly Thr Val Gln Asp Glu
            1395                1400                1405
Leu Pro Gly Leu Pro Glu Leu Ser Pro Glu Asp Leu Ala Glu Cys Arg
    1410                1415                1420
Thr Leu Gly Glu Ile Val Asp Tyr Met Asn Ser Lys Leu Ala Asp Gly
1425                1430                1435                1440
Ser Lys Leu Pro Ala Glu Gly Ser Met Asn Ser Gln Leu Ser Thr Ser
                1445                1450                1455
Ala Ala Ala Ala Thr Pro Ala Ala Asn Gly Leu Ser Ala Glu Lys Val
                1460                1465                1470
Gln Ala Thr Met Met Ser Val Val Ala Glu Lys Thr Gly Tyr Pro Thr
        1475                1480                1485
Glu Met Leu Glu Leu Glu Met Asp Met Glu Ala Asp Leu Gly Ile Asp
        1490                1495                1500
Ser Ile Lys Arg Val Glu Ile Leu Gly Thr Val Gln Asp Glu Leu Pro
1505                1510                1515                1520
Gly Leu Pro Glu Leu Asn Pro Glu Asp Leu Ala Glu Cys Arg Thr Leu
            1525                1530                1535
Gly Glu Ile Val Thr Tyr Met Asn Ser Lys Leu Ala Asp Gly Ser Lys
            1540                1545                1550
Leu Pro Ala Glu Gly Ser Met His Tyr Gln Leu Ser Thr Ser Thr Ala
        1555                1560                1565
Ala Ala Thr Pro Val Ala Asn Gly Leu Ser Ala Glu Lys Val Gln Ala
    1570                1575                1580
Thr Met Met Ser Val Val Ala Asp Lys Thr Gly Tyr Pro Thr Glu Met
1585                1590                1595                1600
Leu Glu Leu Glu Met Asp Met Glu Ala Asp Leu Gly Ile Asp Ser Ile
                1605                1610                1615
Lys Arg Val Glu Ile Leu Gly Thr Val Gln Asp Glu Leu Pro Gly Leu
            1620                1625                1630
Pro Glu Leu Asn Pro Glu Asp Leu Ala Glu Cys Arg Thr Leu Gly Glu
        1635                1640                1645
Ile Val Asp Tyr Met Gly Ser Lys Leu Pro Ala Glu Gly Ser Ala Asn
    1650                1655                1660
```

-continued

```
Thr Ser Ala Ala Ala Ser Leu Asn Val Ser Ala Val Ala Ala Pro Gln
1665                1670                1675                1680

Ala Ala Ala Thr Pro Val Ser Asn Gly Leu Ser Ala Glu Lys Val Gln
            1685                1690                1695

Ser Thr Met Met Ser Val Val Ala Glu Lys Thr Gly Tyr Pro Thr Glu
            1700                1705                1710

Met Leu Glu Leu Gly Met Asp Met Glu Ala Asp Leu Gly Ile Asp Ser
            1715                1720                1725

Ile Lys Arg Val Glu Ile Leu Gly Thr Val Gln Asp Glu Leu Pro Gly
1730                1735                1740

Leu Pro Glu Leu Asn Pro Glu Asp Leu Ala Glu Cys Arg Thr Leu Gly
1745                1750                1755                1760

Glu Ile Val Asp Tyr Met Asn Ser Lys Leu Ala Asp Gly Ser Lys Leu
            1765                1770                1775

Pro Ala Glu Gly Ser Ala Asn Thr Ser Ala Thr Ala Ala Thr Pro Ala
            1780                1785                1790

Val Asn Gly Leu Ser Ala Asp Lys Val Gln Ala Thr Met Met Ser Val
            1795                1800                1805

Val Ala Glu Lys Thr Gly Tyr Pro Thr Glu Met Leu Glu Leu Gly Met
    1810                1815                1820

Asp Met Glu Ala Asp Leu Gly Ile Asp Ser Ile Lys Arg Val Glu Ile
1825                1830                1835                1840

Leu Gly Thr Val Gln Asp Glu Leu Pro Gly Leu Pro Glu Leu Asn Pro
            1845                1850                1855

Glu Asp Leu Ala Glu Cys Arg Thr Leu Gly Glu Ile Val Ser Tyr Met
            1860                1865                1870

Asn Ser Gln Leu Ala Asp Gly Ser Lys Leu Ser Thr Ser Ala Ala Glu
            1875                1880                1885

Gly Ser Ala Asp Thr Ser Ala Ala Asn Ala Ala Lys Pro Ala Ala Ile
    1890                1895                1900

Ser Ala Glu Pro Ser Val Glu Leu Pro Pro His Ser Glu Val Ala Leu
1905                1910                1915                1920

Lys Lys Leu Asn Ala Ala Asn Lys Leu Glu Asn Cys Phe Ala Ala Asp
            1925                1930                1935

Ala Ser Val Val Ile Asn Asp Asp Gly His Asn Ala Gly Val Leu Ala
            1940                1945                1950

Glu Lys Leu Ile Lys Gln Gly Leu Lys Val Ala Val Arg Leu Pro
            1955                1960                1965

Lys Gly Gln Pro Gln Ser Pro Leu Ser Ser Asp Val Ala Ser Phe Glu
    1970                1975                1980

Leu Ala Ser Ser Gln Glu Ser Glu Leu Glu Ala Ser Ile Thr Ala Val
1985                1990                1995                2000

Ile Ala Gln Ile Glu Thr Gln Val Gly Ala Ile Gly Phe Ile His
            2005                2010                2015

Leu Gln Pro Glu Ala Asn Thr Glu Glu Gln Thr Ala Val Asn Leu Asp
            2020                2025                2030

Ala Gln Ser Phe Thr His Val Ser Asn Ala Phe Leu Trp Ala Lys Leu
    2035                2040                2045

Leu Gln Pro Lys Leu Val Ala Gly Ala Asp Ala Arg Arg Cys Phe Val
    2050                2055                2060

Thr Val Ser Arg Ile Asp Gly Gly Phe Gly Tyr Leu Asn Thr Asp Ala
2065                2070                2075                2080
```

-continued

Leu Lys Asp Ala Glu Leu Asn Gln Ala Ala Leu Ala Gly Leu Thr Lys
        2085                2090                2095

Thr Leu Ser His Glu Trp Pro Gln Val Phe Cys Arg Ala Leu Asp Ile
        2100                2105                2110

Ala Thr Asp Val Asp Ala Thr His Leu Ala Asp Ala Ile Thr Ser Glu
        2115                2120                2125

Leu Phe Asp Ser Gln Ala Gln Leu Pro Glu Val Gly Leu Ser Leu Ile
        2130                2135                2140

Asp Gly Lys Val Asn Arg Val Thr Leu Val Ala Ala Glu Ala Ala Asp
2145                2150                2155                2160

Lys Thr Ala Lys Ala Glu Leu Asn Ser Thr Asp Lys Ile Leu Val Thr
        2165                2170                2175

Gly Gly Ala Lys Gly Val Thr Phe Glu Cys Ala Leu Ala Leu Ala Ser
        2180                2185                2190

Arg Ser Gln Ser His Phe Ile Leu Ala Gly Arg Ser Glu Leu Gln Ala
        2195                2200                2205

Leu Pro Ser Trp Ala Glu Gly Lys Gln Thr Ser Glu Leu Lys Ser Ala
        2210                2215                2220

Ala Ile Ala His Ile Ile Ser Thr Gly Gln Lys Pro Thr Pro Lys Gln
2225                2230                2235                2240

Val Glu Ala Ala Val Trp Pro Val Gln Ser Ser Ile Glu Ile Asn Ala
        2245                2250                2255

Ala Leu Ala Ala Phe Asn Lys Val Gly Ala Ser Ala Glu Tyr Val Ser
        2260                2265                2270

Met Asp Val Thr Asp Ser Ala Ala Ile Thr Ala Ala Leu Asn Gly Arg
        2275                2280                2285

Ser Asn Glu Ile Thr Gly Leu Ile His Gly Ala Gly Val Leu Ala Asp
        2290                2295                2300

Lys His Ile Gln Asp Lys Thr Leu Ala Glu Leu Ala Lys Val Tyr Gly
2305                2310                2315                2320

Thr Lys Val Asn Gly Leu Lys Ala Leu Leu Ala Ala Leu Glu Pro Ser
        2325                2330                2335

Lys Ile Lys Leu Leu Ala Met Phe Ser Ser Ala Ala Gly Phe Tyr Gly
        2340                2345                2350

Asn Ile Gly Gln Ser Asp Tyr Ala Met Ser Asn Asp Ile Leu Asn Lys
        2355                2360                2365

Ala Ala Leu Gln Phe Thr Ala Arg Asn Pro Gln Ala Lys Val Met Ser
        2370                2375                2380

Phe Asn Trp Gly Pro Trp Asp Gly Gly Met Val Asn Pro Ala Leu Lys
2385                2390                2395                2400

Lys Met Phe Thr Glu Arg Gly Val Tyr Val Ile Pro Leu Lys Ala Gly
        2405                2410                2415

Ala Glu Leu Phe Ala Thr Gln Leu Leu Ala Glu Thr Gly Val Gln Leu
        2420                2425                2430

Leu Ile Gly Thr Ser Met Gln Gly Gly Ser Asp Thr Lys Ala Thr Glu
        2435                2440                2445

Thr Ala Ser Val Lys Lys Leu Asn Ala Gly Glu Val Leu Ser Ala Ser
        2450                2455                2460

His Pro Arg Ala Gly Ala Gln Lys Thr Pro Leu Gln Ala Val Thr Ala
2465                2470                2475                2480

Thr Arg Leu Leu Thr Pro Ser Ala Met Val Phe Ile Glu Asp His Arg
        2485                2490                2495

Ile Gly Gly Asn Ser Val Leu Pro Thr Val Cys Ala Ile Asp Trp Met

-continued

```
                2500                2505                2510

Arg Glu Ala Ala Ser Asp Met Leu Gly Ala Gln Val Lys Val Leu Asp
        2515                2520                2525

Tyr Lys Leu Leu Lys Gly Ile Val Phe Glu Thr Asp Glu Pro Gln Glu
        2530                2535                2540

Leu Thr Leu Glu Leu Thr Pro Asp Asp Ser Asp Glu Ala Thr Leu Gln
2545                2550                2555                2560

Ala Leu Ile Ser Cys Asn Gly Arg Pro Gln Tyr Lys Ala Thr Leu Ile
            2565                2570                2575

Ser Asp Asn Ala Asp Ile Lys Gln Leu Asn Lys Gln Phe Asp Leu Ser
        2580                2585                2590

Ala Lys Ala Ile Thr Thr Ala Lys Glu Leu Tyr Ser Asn Gly Thr Leu
        2595                2600                2605

Phe His Gly Pro Arg Leu Gln Gly Ile Gln Ser Val Gln Phe Asp
        2610                2615                2620

Asp Gln Gly Leu Ile Ala Lys Val Ala Leu Pro Lys Val Glu Leu Ser
2625                2630                2635                2640

Asp Cys Gly Glu Phe Leu Pro Gln Thr His Met Gly Gly Ser Gln Pro
            2645                2650                2655

Phe Ala Glu Asp Leu Leu Gln Ala Met Leu Val Trp Ala Arg Leu
        2660                2665                2670

Lys Thr Gly Ser Ala Ser Leu Pro Ser Ser Ile Gly Glu Phe Thr Ser
        2675                2680                2685

Tyr Gln Pro Met Ala Phe Gly Glu Thr Gly Thr Ile Glu Leu Glu Val
        2690                2695                2700

Ile Lys His Asn Lys Arg Ser Leu Glu Ala Asn Val Ala Leu Tyr Arg
2705                2710                2715                2720

Asp Asn Gly Glu Leu Ser Ala Met Phe Lys Ser Ala Lys Ile Thr Ile
            2725                2730                2735

Ser Lys Ser Leu Asn Ser Ala Phe Leu Pro Ala Val Leu Ala Asn Asp
        2740                2745                2750

Ser Glu Ala Asn
        2755

<210> SEQ ID NO 8
<211> LENGTH: 771
<212> TYPE: PRT
<213> ORGANISM: Shewanella putrefaciens

<400> SEQUENCE: 8

Met Pro Leu Arg Ile Ala Leu Ile Leu Leu Pro Thr Pro Gln Phe Glu
1               5                   10                  15

Val Asn Ser Val Asp Gln Ser Val Leu Ala Ser Tyr Gln Thr Leu Gln
                20                  25                  30

Pro Glu Leu Asn Ala Leu Leu Asn Ser Ala Pro Thr Pro Glu Met Leu
            35                  40                  45

Ser Ile Thr Ile Ser Asp Asp Ser Asp Ala Asn Ser Phe Glu Ser Gln
        50                  55                  60

Leu Asn Ala Ala Thr Asn Ala Ile Asn Asn Gly Tyr Ile Val Lys Leu
65                  70                  75                  80

Ala Thr Ala Thr His Ala Leu Leu Met Leu Pro Ala Leu Lys Ala Ala
                85                  90                  95

Gln Met Arg Ile His Pro His Ala Gln Leu Ala Ala Met Gln Gln Ala
            100                 105                 110
```

-continued

```
Lys Ser Thr Pro Met Ser Gln Val Ser Gly Glu Leu Lys Leu Gly Ala
    115                 120                 125

Asn Ala Leu Ser Leu Ala Gln Thr Asn Ala Leu Ser His Ala Leu Ser
130                 135                 140

Gln Ala Lys Arg Asn Leu Thr Asp Val Ser Val Asn Glu Cys Phe Glu
145                 150                 155                 160

Asn Leu Lys Ser Glu Gln Gln Phe Thr Glu Val Tyr Ser Leu Ile Gln
                165                 170                 175

Gln Leu Ala Ser Arg Thr His Val Arg Lys Glu Val Asn Gln Gly Val
            180                 185                 190

Glu Leu Gly Pro Lys Gln Ala Lys Ser His Tyr Trp Phe Ser Glu Phe
        195                 200                 205

His Gln Asn Arg Val Ala Ala Ile Asn Phe Ile Asn Gly Gln Gln Ala
    210                 215                 220

Thr Ser Tyr Val Leu Thr Gln Gly Ser Gly Leu Leu Ala Ala Lys Ser
225                 230                 235                 240

Met Leu Asn Gln Gln Arg Leu Met Phe Ile Leu Pro Gly Asn Ser Gln
                245                 250                 255

Gln Gln Ile Thr Ala Ser Ile Thr Gln Leu Met Gln Gln Leu Glu Arg
            260                 265                 270

Leu Gln Val Thr Glu Val Asn Glu Leu Ser Leu Glu Cys Gln Leu Glu
        275                 280                 285

Leu Leu Ser Ile Met Tyr Asp Asn Leu Val Asn Ala Asp Lys Leu Thr
    290                 295                 300

Thr Arg Asp Ser Lys Pro Ala Tyr Gln Ala Val Ile Gln Ala Ser Ser
305                 310                 315                 320

Val Ser Ala Ala Lys Gln Glu Leu Ser Ala Leu Asn Asp Ala Leu Thr
                325                 330                 335

Ala Leu Phe Ala Glu Gln Thr Asn Ala Thr Ser Thr Asn Lys Gly Leu
            340                 345                 350

Ile Gln Tyr Lys Thr Pro Ala Gly Ser Tyr Leu Thr Leu Thr Pro Leu
        355                 360                 365

Gly Ser Asn Asn Asp Asn Ala Gln Ala Gly Leu Ala Phe Val Tyr Pro
    370                 375                 380

Gly Val Gly Thr Val Tyr Ala Asp Met Leu Asn Glu Leu His Gln Tyr
385                 390                 395                 400

Phe Pro Ala Leu Tyr Ala Lys Leu Glu Arg Glu Gly Asp Leu Lys Ala
                405                 410                 415

Met Leu Gln Ala Glu Asp Ile Tyr His Leu Asp Pro Lys His Ala Ala
            420                 425                 430

Gln Met Ser Leu Gly Asp Leu Ala Ile Ala Gly Val Gly Ser Ser Tyr
        435                 440                 445

Leu Leu Thr Gln Leu Leu Thr Asp Glu Phe Asn Ile Lys Pro Asn Phe
    450                 455                 460

Ala Leu Gly Tyr Ser Met Gly Glu Ala Ser Met Trp Ala Ser Leu Gly
465                 470                 475                 480

Val Trp Gln Asn Pro His Ala Leu Ile Ser Lys Thr Gln Thr Asp Pro
                485                 490                 495

Leu Phe Thr Ser Ala Ile Ser Gly Lys Leu Thr Ala Val Arg Gln Ala
            500                 505                 510

Trp Gln Leu Asp Asp Thr Ala Ala Glu Ile Gln Trp Asn Ser Phe Val
        515                 520                 525

Val Arg Ser Glu Ala Ala Pro Ile Glu Ala Leu Leu Lys Asp Tyr Pro
```

-continued

```
                530                 535                 540
His Ala Tyr Leu Ala Ile Ile Gln Gly Asp Thr Cys Val Ile Ala Gly
545                 550                 555                 560

Cys Glu Ile Gln Cys Lys Ala Leu Leu Ala Leu Gly Lys Arg Gly
                565                 570                 575

Ile Ala Ala Asn Arg Val Thr Ala Met His Thr Gln Pro Ala Met Gln
                580                 585                 590

Glu His Gln Asn Val Met Asp Phe Tyr Leu Gln Pro Leu Lys Ala Glu
                595                 600                 605

Leu Pro Ser Glu Ile Ser Phe Ile Ser Ala Ala Asp Leu Thr Ala Lys
610                 615                 620

Gln Thr Val Ser Glu Gln Ala Leu Ser Ser Gln Val Val Ala Gln Ser
625                 630                 635                 640

Ile Ala Asp Thr Phe Cys Gln Thr Leu Asp Phe Thr Ala Leu Val His
                645                 650                 655

His Ala Gln His Gln Gly Ala Lys Leu Phe Val Glu Ile Gly Ala Asp
                660                 665                 670

Arg Gln Asn Cys Thr Leu Ile Asp Lys Ile Val Lys Gln Asp Gly Ala
                675                 680                 685

Ser Ser Val Gln His Gln Pro Cys Cys Thr Val Pro Met Asn Ala Lys
690                 695                 700

Gly Ser Gln Asp Ile Thr Ser Val Ile Lys Ala Leu Gly Gln Leu Ile
705                 710                 715                 720

Ser His Gln Val Pro Leu Ser Val Gln Pro Phe Ile Asp Gly Leu Lys
                725                 730                 735

Arg Glu Leu Thr Leu Cys Gln Leu Thr Ser Gln Gln Leu Ala Ala His
                740                 745                 750

Ala Asn Val Asp Ser Lys Phe Glu Ser Asn Gln Asp His Leu Leu Gln
                755                 760                 765

Gly Glu Val
    770
```

<210> SEQ ID NO 9
<211> LENGTH: 2004
<212> TYPE: PRT
<213> ORGANISM: Shewanella putrefaciens

<400> SEQUENCE: 9

```
Met Ser Leu Pro Asp Asn Ala Ser Asn His Leu Ser Ala Asn Gln Lys
1               5                   10                  15

Gly Ala Ser Gln Ala Ser Lys Thr Ser Lys Gln Ser Lys Ile Ala Ile
                20                  25                  30

Val Gly Leu Ala Thr Leu Tyr Pro Asp Ala Lys Thr Pro Gln Glu Phe
            35                  40                  45

Trp Gln Asn Leu Leu Asp Lys Arg Asp Ser Arg Ser Thr Leu Thr Asn
        50                  55                  60

Glu Lys Leu Gly Ala Asn Ser Gln Asp Tyr Gln Gly Val Gln Gly Gln
65                  70                  75                  80

Ser Asp Arg Phe Tyr Cys Asn Lys Gly Gly Tyr Ile Glu Asn Phe Ser
                85                  90                  95

Phe Asn Ala Ala Gly Tyr Lys Leu Pro Glu Gln Ser Leu Asn Gly Leu
                100                 105                 110

Asp Asp Ser Phe Leu Trp Ala Leu Asp Thr Ser Arg Asn Ala Leu Ile
            115                 120                 125
```

-continued

```
Asp Ala Gly Ile Asp Ile Asn Gly Ala Asp Leu Ser Arg Ala Gly Val
130                 135                 140

Val Met Gly Ala Leu Ser Phe Pro Thr Thr Arg Ser Asn Asp Leu Phe
145                 150                 155                 160

Leu Pro Ile Tyr His Ser Ala Val Glu Lys Ala Leu Gln Asp Lys Leu
                165                 170                 175

Gly Val Lys Ala Phe Lys Leu Ser Pro Thr Asn Ala His Thr Ala Arg
                180                 185                 190

Ala Ala Asn Glu Ser Ser Leu Asn Ala Ala Asn Gly Ala Ile Ala His
                195                 200                 205

Asn Ser Ser Lys Val Val Ala Asp Ala Leu Gly Leu Gly Gly Ala Gln
210                 215                 220

Leu Ser Leu Asp Ala Ala Cys Ala Ser Ser Val Tyr Ser Leu Lys Leu
225                 230                 235                 240

Ala Cys Asp Tyr Leu Ser Thr Gly Lys Ala Asp Ile Met Leu Ala Gly
                245                 250                 255

Ala Val Ser Gly Ala Asp Pro Phe Phe Ile Asn Met Gly Phe Ser Ile
                260                 265                 270

Phe His Ala Tyr Pro Asp His Gly Ile Ser Val Pro Phe Asp Ala Ser
                275                 280                 285

Ser Lys Gly Leu Phe Ala Gly Glu Gly Ala Gly Val Leu Val Leu Lys
290                 295                 300

Arg Leu Glu Asp Ala Glu Arg Asp Asn Asp Lys Ile Tyr Ala Val Val
305                 310                 315                 320

Ser Gly Val Gly Leu Ser Asn Asp Gly Lys Gly Gln Phe Val Leu Ser
                325                 330                 335

Pro Asn Pro Lys Gly Gln Val Lys Ala Phe Glu Arg Ala Tyr Ala Ala
                340                 345                 350

Ser Asp Ile Glu Pro Lys Asp Ile Glu Val Ile Glu Cys His Ala Thr
                355                 360                 365

Gly Thr Pro Leu Gly Asp Lys Ile Glu Leu Thr Ser Met Glu Thr Phe
370                 375                 380

Phe Glu Asp Lys Leu Gln Gly Thr Asp Ala Pro Leu Ile Gly Ser Ala
385                 390                 395                 400

Lys Ser Asn Leu Gly His Leu Leu Thr Ala Ala His Ala Gly Ile Met
                405                 410                 415

Lys Met Ile Phe Ala Met Lys Glu Gly Tyr Leu Pro Pro Ser Ile Asn
                420                 425                 430

Ile Ser Asp Ala Ile Ala Ser Pro Lys Lys Leu Phe Gly Lys Pro Thr
                435                 440                 445

Leu Pro Ser Met Val Gln Gly Trp Pro Asp Lys Pro Ser Asn Asn His
450                 455                 460

Phe Gly Val Arg Thr Arg His Ala Gly Val Ser Val Phe Gly Phe Gly
465                 470                 475                 480

Gly Cys Asn Ala His Leu Leu Leu Glu Ser Tyr Asn Gly Lys Gly Thr
                485                 490                 495

Val Lys Ala Glu Ala Thr Gln Val Pro Arg Gln Ala Glu Pro Leu Lys
                500                 505                 510

Val Val Gly Leu Ala Ser His Phe Gly Pro Leu Ser Ser Ile Asn Ala
                515                 520                 525

Leu Asn Asn Ala Val Thr Gln Asp Gly Asn Gly Phe Ile Glu Leu Pro
530                 535                 540

Lys Lys Arg Trp Lys Gly Leu Glu Lys His Ser Glu Leu Leu Ala Glu
```

-continued

```
                545                 550                 555                 560
Phe Gly Leu Ala Ser Ala Pro Lys Gly Ala Tyr Val Asp Asn Phe Glu
                565                 570                 575
Leu Asp Phe Leu Arg Phe Lys Leu Pro Pro Asn Glu Asp Asp Arg Leu
                580                 585                 590
Ile Ser Gln Gln Leu Met Leu Met Arg Val Thr Asp Glu Ala Ile Arg
                595                 600                 605
Asp Ala Lys Leu Glu Pro Gly Gln Lys Val Ala Val Leu Val Ala Met
                610                 615                 620
Glu Thr Glu Leu Glu Leu His Gln Phe Arg Gly Arg Val Asn Leu His
625                 630                 635                 640
Thr Gln Leu Ala Gln Ser Leu Ala Ala Met Gly Val Ser Leu Ser Thr
                645                 650                 655
Asp Glu Tyr Gln Ala Leu Glu Ala Ile Ala Met Asp Ser Val Leu Asp
                660                 665                 670
Ala Ala Lys Leu Asn Gln Tyr Thr Ser Phe Ile Gly Asn Ile Met Ala
                675                 680                 685
Ser Arg Val Ala Ser Leu Trp Asp Phe Asn Gly Pro Ala Phe Thr Ile
                690                 695                 700
Ser Ala Glu Gln Ser Val Ser Arg Cys Ile Asp Val Ala Gln Asn
705                 710                 715                 720
Leu Ile Met Glu Asp Asn Leu Asp Ala Val Ile Ala Ala Val Asp
                725                 730                 735
Leu Ser Gly Ser Phe Glu Gln Val Ile Leu Lys Asn Ala Ile Ala Pro
                740                 745                 750
Val Ala Ile Glu Pro Asn Leu Glu Ala Ser Leu Asn Pro Thr Ser Ala
                755                 760                 765
Ser Trp Asn Val Gly Glu Gly Ala Gly Ala Val Val Leu Val Lys Asn
770                 775                 780
Glu Ala Thr Ser Gly Cys Ser Tyr Gly Gln Ile Asp Ala Leu Gly Phe
785                 790                 795                 800
Ala Lys Thr Ala Glu Thr Ala Leu Ala Thr Asp Lys Leu Leu Ser Gln
                805                 810                 815
Thr Ala Thr Asp Phe Asn Lys Val Lys Val Ile Glu Thr Met Ala Ala
                820                 825                 830
Pro Ala Ser Gln Ile Gln Leu Ala Pro Ile Val Ser Ser Gln Val Thr
                835                 840                 845
His Thr Ala Ala Glu Gln Arg Val Gly His Cys Phe Ala Ala Ala Gly
                850                 855                 860
Met Ala Ser Leu Leu His Gly Leu Leu Asn Leu Asn Thr Val Ala Gln
865                 870                 875                 880
Thr Asn Lys Ala Asn Cys Ala Leu Ile Asn Asn Ile Ser Glu Asn Gln
                885                 890                 895
Leu Ser Gln Leu Leu Ile Ser Gln Thr Ala Ser Glu Gln Gln Ala Leu
                900                 905                 910
Thr Ala Arg Leu Ser Asn Glu Leu Lys Ser Asp Ala Lys His Gln Leu
                915                 920                 925
Val Lys Gln Val Thr Leu Gly Gly Arg Asp Ile Tyr Gln His Ile Val
                930                 935                 940
Asp Thr Pro Leu Ala Ser Leu Glu Ser Ile Thr Gln Lys Leu Ala Gln
945                 950                 955                 960
Ala Thr Ala Ser Thr Val Val Asn Gln Val Lys Pro Ile Lys Ala Ala
                965                 970                 975
```

```
Gly Ser Val Glu Met Ala Asn Ser Phe Glu Thr Glu Ser Ser Ala Glu
            980                 985                 990

Pro Gln Ile Thr Ile Ala Ala Gln Gln Thr Ala Asn Ile Gly Val Thr
            995                 1000                1005

Ala Gln Ala Thr Lys Arg Glu Leu Gly Thr Pro Pro Met Thr Thr Asn
    1010                1015                1020

Thr Ile Ala Asn Thr Ala Asn Asn Leu Asp Lys Thr Leu Glu Thr Val
1025                1030                1035                1040

Ala Gly Asn Thr Val Ala Ser Lys Val Gly Ser Gly Asp Ile Val Asn
            1045                1050                1055

Phe Gln Gln Asn Gln Gln Leu Ala Gln Gln Ala His Leu Ala Phe Leu
            1060                1065                1070

Glu Ser Arg Ser Ala Gly Met Lys Val Ala Asp Ala Leu Leu Lys Gln
            1075                1080                1085

Gln Leu Ala Gln Val Thr Gly Gln Thr Ile Asp Asn Gln Ala Leu Asp
            1090                1095                1100

Thr Gln Ala Val Asp Thr Gln Thr Ser Glu Asn Val Ala Ile Ala Ala
1105                1110                1115                1120

Glu Ser Pro Val Gln Val Thr Thr Pro Val Gln Val Thr Thr Pro Val
            1125                1130                1135

Gln Ile Ser Val Val Glu Leu Lys Pro Asp His Ala Asn Val Pro Pro
            1140                1145                1150

Tyr Thr Pro Pro Val Pro Ala Leu Lys Pro Cys Ile Trp Asn Tyr Ala
            1155                1160                1165

Asp Leu Val Glu Tyr Ala Glu Gly Asp Ile Ala Lys Val Phe Gly Ser
    1170                1175                1180

Asp Tyr Ala Ile Ile Asp Ser Tyr Ser Arg Arg Val Arg Leu Pro Thr
1185                1190                1195                1200

Thr Asp Tyr Leu Leu Val Ser Arg Val Thr Lys Leu Asp Ala Thr Ile
            1205                1210                1215

Asn Gln Phe Lys Pro Cys Ser Met Thr Thr Glu Tyr Asp Ile Pro Val
            1220                1225                1230

Asp Ala Pro Tyr Leu Val Asp Gly Gln Ile Pro Trp Ala Val Ala Val
            1235                1240                1245

Glu Ser Gly Gln Cys Asp Leu Met Leu Ile Ser Tyr Leu Gly Ile Asp
            1250                1255                1260

Phe Glu Asn Lys Gly Glu Arg Val Tyr Arg Leu Leu Asp Cys Thr Leu
1265                1270                1275                1280

Thr Phe Leu Gly Asp Leu Pro Arg Gly Gly Asp Thr Leu Arg Tyr Asp
            1285                1290                1295

Ile Lys Ile Asn Asn Tyr Ala Arg Asn Gly Asp Thr Leu Leu Phe Phe
            1300                1305                1310

Phe Ser Tyr Glu Cys Phe Val Gly Asp Lys Met Ile Leu Lys Met Asp
            1315                1320                1325

Gly Gly Cys Ala Gly Phe Phe Thr Asp Glu Leu Ala Asp Gly Lys
    1330                1335                1340

Gly Val Ile Arg Thr Glu Glu Ile Lys Ala Arg Ser Leu Val Gln
1345                1350                1355                1360

Lys Gln Arg Phe Asn Pro Leu Leu Asp Cys Pro Lys Thr Gln Phe Ser
            1365                1370                1375

Tyr Gly Asp Ile His Lys Leu Leu Thr Ala Asp Ile Glu Gly Cys Phe
            1380                1385                1390
```

```
Gly Pro Ser His Ser Gly Val His Gln Pro Ser Leu Cys Phe Ala Ser
        1395                1400                1405
Glu Lys Phe Leu Met Ile Glu Gln Val Ser Lys Val Asp Arg Thr Gly
    1410                1415                1420
Gly Thr Trp Gly Leu Gly Leu Ile Glu Gly His Lys Gln Leu Glu Ala
1425                1430                1435                1440
Asp His Trp Tyr Phe Pro Cys His Phe Lys Gly Asp Gln Val Met Ala
            1445                1450                1455
Gly Ser Leu Met Ala Glu Gly Cys Gly Gln Leu Leu Gln Phe Tyr Met
        1460                1465                1470
Leu His Leu Gly Met His Thr Gln Thr Lys Asn Gly Arg Phe Gln Pro
    1475                1480                1485
Leu Glu Asn Ala Ser Gln Gln Val Arg Cys Arg Gly Gln Val Leu Pro
1490                1495                1500
Gln Ser Gly Val Leu Thr Tyr Arg Met Glu Val Thr Glu Ile Gly Phe
1505                1510                1515                1520
Ser Pro Arg Pro Tyr Ala Lys Ala Asn Ile Asp Ile Leu Leu Asn Gly
            1525                1530                1535
Lys Ala Val Val Asp Phe Gln Asn Leu Gly Val Met Ile Lys Glu Glu
        1540                1545                1550
Asp Glu Cys Thr Arg Tyr Pro Leu Leu Thr Glu Ser Thr Thr Ala Ser
    1555                1560                1565
Thr Ala Gln Val Asn Ala Gln Thr Ser Ala Lys Lys Val Tyr Lys Pro
1570                1575                1580
Ala Ser Val Asn Ala Pro Leu Met Ala Gln Ile Pro Asp Leu Thr Lys
1585                1590                1595                1600
Glu Pro Asn Lys Gly Val Ile Pro Ile Ser His Val Glu Ala Pro Ile
            1605                1610                1615
Thr Pro Asp Tyr Pro Asn Arg Val Pro Asp Thr Val Pro Phe Thr Pro
        1620                1625                1630
Tyr His Met Phe Glu Phe Ala Thr Gly Asn Ile Glu Asn Cys Phe Gly
    1635                1640                1645
Pro Glu Phe Ser Ile Tyr Arg Gly Met Ile Pro Pro Arg Thr Pro Cys
1650                1655                1660
Gly Asp Leu Gln Val Thr Thr Arg Val Ile Glu Val Asn Gly Lys Arg
1665                1670                1675                1680
Gly Asp Phe Lys Lys Pro Ser Ser Cys Ile Ala Glu Tyr Glu Val Pro
            1685                1690                1695
Ala Asp Ala Trp Tyr Phe Asp Lys Asn Ser His Gly Ala Val Met Pro
        1700                1705                1710
Tyr Ser Ile Leu Met Glu Ile Ser Leu Gln Pro Asn Gly Phe Ile Ser
    1715                1720                1725
Gly Tyr Met Gly Thr Thr Leu Gly Phe Pro Gly Leu Glu Leu Phe Phe
1730                1735                1740
Arg Asn Leu Asp Gly Ser Gly Glu Leu Leu Arg Glu Val Asp Leu Arg
1745                1750                1755                1760
Gly Lys Thr Ile Arg Asn Asp Ser Arg Leu Leu Ser Thr Val Met Ala
            1765                1770                1775
Gly Thr Asn Ile Ile Gln Ser Phe Ser Phe Glu Leu Ser Thr Asp Gly
        1780                1785                1790
Glu Pro Phe Tyr Arg Gly Thr Ala Val Phe Gly Tyr Phe Lys Gly Asp
    1795                1800                1805
Ala Leu Lys Asp Gln Leu Gly Leu Asp Asn Gly Lys Val Thr Gln Pro
```

-continued

```
            1810                1815                1820
Trp His Val Ala Asn Gly Val Ala Ala Ser Thr Lys Val Asn Leu Leu
1825                1830                1835                1840

Asp Lys Ser Cys Arg His Phe Asn Ala Pro Ala Asn Gln Pro His Tyr
                1845                1850                1855

Arg Leu Ala Gly Gly Gln Leu Asn Phe Ile Asp Ser Val Glu Ile Val
                1860                1865                1870

Asp Asn Gly Gly Thr Glu Gly Leu Gly Tyr Leu Tyr Ala Glu Arg Thr
                1875                1880                1885

Ile Asp Pro Ser Asp Trp Phe Phe Gln Phe His Phe His Gln Asp Pro
                1890                1895                1900

Val Met Pro Gly Ser Leu Gly Val Glu Ala Ile Ile Glu Thr Met Gln
1905                1910                1915                1920

Ala Tyr Ala Ile Ser Lys Asp Leu Gly Ala Asp Phe Lys Asn Pro Lys
                1925                1930                1935

Phe Gly Gln Ile Leu Ser Asn Ile Lys Trp Lys Tyr Arg Gly Gln Ile
                1940                1945                1950

Asn Pro Leu Asn Lys Gln Met Ser Met Asp Val Ser Ile Thr Ser Ile
                1955                1960                1965

Lys Asp Glu Asp Gly Lys Lys Val Ile Thr Gly Asn Ala Ser Leu Ser
                1970                1975                1980

Lys Asp Gly Leu Arg Ile Tyr Glu Val Phe Asp Ile Ala Ile Ser Ile
1985                1990                1995                2000

Glu Glu Ser Val

<210> SEQ ID NO 10
<211> LENGTH: 543
<212> TYPE: PRT
<213> ORGANISM: Shewanella putrefaciens

<400> SEQUENCE: 10

Met Asn Pro Thr Ala Thr Asn Glu Met Leu Ser Pro Trp Pro Trp Ala
  1               5                  10                  15

Val Thr Glu Ser Asn Ile Ser Phe Asp Val Gln Val Met Glu Gln Gln
                 20                  25                  30

Leu Lys Asp Phe Ser Arg Ala Cys Tyr Val Val Asn His Ala Asp His
             35                  40                  45

Gly Phe Gly Ile Ala Gln Thr Ala Asp Ile Val Thr Glu Gln Ala Ala
         50                  55                  60

Asn Ser Thr Asp Leu Pro Val Ser Ala Phe Thr Pro Ala Leu Gly Thr
 65                  70                  75                  80

Glu Ser Leu Gly Asp Asn Asn Phe Arg Arg Val His Gly Val Lys Tyr
                 85                  90                  95

Ala Tyr Tyr Ala Gly Ala Met Ala Asn Gly Ile Ser Ser Glu Glu Leu
                100                 105                 110

Val Ile Ala Leu Gly Gln Ala Gly Ile Leu Cys Gly Ser Phe Gly Ala
            115                 120                 125

Ala Gly Leu Ile Pro Ser Arg Val Glu Ala Ala Ile Asn Arg Ile Gln
        130                 135                 140

Ala Ala Leu Pro Asn Gly Pro Tyr Met Phe Asn Leu Ile His Ser Pro
145                 150                 155                 160

Ser Glu Pro Ala Leu Glu Arg Gly Ser Val Glu Leu Phe Leu Lys His
                165                 170                 175

Lys Val Arg Thr Val Glu Ala Ser Ala Phe Leu Gly Leu Thr Pro Gln
```

```
                    180                 185                 190
Ile Val Tyr Tyr Arg Ala Ala Gly Leu Ser Arg Asp Ala Gln Gly Lys
            195                 200                 205
Val Val Val Gly Asn Lys Val Ile Ala Lys Val Ser Arg Thr Glu Val
210                 215                 220
Ala Glu Lys Phe Met Met Pro Ala Pro Ala Lys Met Leu Gln Lys Leu
225                 230                 235                 240
Val Asp Asp Gly Ser Ile Thr Ala Glu Gln Met Glu Leu Ala Gln Leu
                245                 250                 255
Val Pro Met Ala Asp Asp Ile Thr Ala Glu Ala Asp Ser Gly Gly His
            260                 265                 270
Thr Asp Asn Arg Pro Leu Val Thr Leu Leu Pro Thr Ile Leu Ala Leu
        275                 280                 285
Lys Glu Glu Ile Gln Ala Lys Tyr Gln Tyr Asp Thr Pro Ile Arg Val
    290                 295                 300
Gly Cys Gly Gly Gly Val Gly Thr Pro Asp Ala Ala Leu Ala Thr Phe
305                 310                 315                 320
Asn Met Gly Ala Ala Tyr Ile Val Thr Gly Ser Ile Asn Gln Ala Cys
                325                 330                 335
Val Glu Ala Gly Ala Ser Asp His Thr Arg Lys Leu Leu Ala Thr Thr
            340                 345                 350
Glu Met Ala Asp Val Thr Met Ala Pro Ala Ala Asp Met Phe Glu Met
        355                 360                 365
Gly Val Lys Leu Gln Val Val Lys Arg Gly Thr Leu Phe Pro Met Arg
    370                 375                 380
Ala Asn Lys Leu Tyr Glu Ile Tyr Thr Arg Tyr Asp Ser Ile Glu Ala
385                 390                 395                 400
Ile Pro Leu Asp Glu Arg Glu Lys Leu Glu Lys Gln Val Phe Arg Ser
                405                 410                 415
Ser Leu Asp Glu Ile Trp Ala Gly Thr Val Ala His Phe Asn Glu Arg
            420                 425                 430
Asp Pro Lys Gln Ile Glu Arg Ala Glu Gly Asn Pro Lys Arg Lys Met
        435                 440                 445
Ala Leu Ile Phe Arg Trp Tyr Leu Gly Leu Ser Ser Arg Trp Ser Asn
    450                 455                 460
Ser Gly Glu Val Gly Arg Glu Met Asp Tyr Gln Ile Trp Ala Gly Pro
465                 470                 475                 480
Ala Leu Gly Ala Phe Asn Gln Trp Ala Lys Gly Ser Tyr Leu Asp Asn
                485                 490                 495
Tyr Gln Asp Arg Asn Ala Val Asp Leu Ala Lys His Leu Met Tyr Gly
            500                 505                 510
Ala Ala Tyr Leu Asn Arg Ile Asn Ser Leu Thr Ala Gln Gly Val Lys
        515                 520                 525
Val Pro Ala Gln Leu Leu Arg Trp Lys Pro Asn Gln Arg Met Ala
    530                 535                 540

<210> SEQ ID NO 11
<211> LENGTH: 499
<212> TYPE: PRT
<213> ORGANISM: Shewanella putrefaciens

<400> SEQUENCE: 11

Met Arg Lys Pro Leu Gln Thr Ile Asn Tyr Asp Tyr Ala Val Trp Asp
1               5                   10                  15
```

```
Arg Thr Tyr Ser Tyr Met Lys Ser Asn Ser Ala Ser Ala Lys Arg Tyr
             20                  25                  30

Tyr Glu Lys His Glu Tyr Pro Asp Asp Thr Phe Lys Ser Leu Lys Val
             35                  40                  45

Asp Gly Val Phe Ile Phe Asn Arg Thr Asn Gln Pro Val Phe Ser Lys
 50                  55                  60

Gly Phe Asn His Arg Asn Asp Ile Pro Leu Val Phe Glu Leu Thr Asp
 65                  70                  75                  80

Phe Lys Gln His Pro Gln Asn Ile Ala Leu Ser Pro Gln Thr Lys Gln
                 85                  90                  95

Ala His Pro Pro Ala Ser Lys Pro Leu Asp Ser Pro Asp Val Pro
                 100                 105                 110

Ser Thr His Gly Val Ile Ala Thr Arg Tyr Gly Pro Ala Ile Tyr Tyr
             115                 120                 125

Ser Ser Thr Ser Ile Leu Lys Ser Asp Arg Ser Gly Ser Gln Leu Gly
 130                 135                 140

Tyr Leu Val Phe Ile Arg Leu Ile Asp Glu Trp Phe Ile Ala Glu Leu
145                 150                 155                 160

Ser Gln Tyr Thr Ala Ala Gly Val Glu Ile Ala Met Ala Asp Ala Ala
                 165                 170                 175

Asp Ala Gln Leu Ala Arg Leu Gly Ala Asn Thr Lys Leu Asn Lys Val
             180                 185                 190

Thr Ala Thr Ser Glu Arg Leu Ile Thr Asn Val Asp Gly Lys Pro Leu
             195                 200                 205

Leu Lys Leu Val Leu Tyr His Thr Asn Asn Gln Pro Pro Met Leu
 210                 215                 220

Asp Tyr Ser Ile Ile Ile Leu Leu Val Glu Met Ser Phe Leu Leu Ile
225                 230                 235                 240

Leu Ala Tyr Phe Leu Tyr Ser Tyr Phe Leu Val Arg Pro Val Arg Lys
                 245                 250                 255

Leu Ala Ser Asp Ile Lys Lys Met Asp Lys Ser Arg Glu Ile Lys Lys
             260                 265                 270

Leu Arg Tyr His Tyr Pro Ile Thr Glu Leu Val Lys Val Ala Thr His
             275                 280                 285

Phe Asn Ala Leu Met Gly Thr Ile Gln Glu Gln Thr Lys Gln Leu Asn
 290                 295                 300

Glu Gln Val Phe Ile Asp Lys Leu Thr Asn Ile Pro Asn Arg Arg Ala
305                 310                 315                 320

Phe Glu Gln Arg Leu Glu Thr Tyr Cys Gln Leu Ala Arg Gln Gln
                 325                 330                 335

Ile Gly Phe Thr Leu Ile Ile Ala Asp Val Asp His Phe Lys Glu Tyr
             340                 345                 350

Asn Asp Thr Leu Gly His Leu Ala Gly Asp Glu Ala Leu Ile Lys Val
             355                 360                 365

Ala Gln Thr Leu Ser Gln Gln Phe Tyr Arg Ala Glu Asp Ile Cys Ala
 370                 375                 380

Arg Phe Gly Gly Glu Glu Phe Ile Met Leu Phe Arg Asp Ile Pro Asp
385                 390                 395                 400

Glu Pro Leu Gln Arg Lys Leu Asp Ala Met Leu His Ser Phe Ala Glu
                 405                 410                 415

Leu Asn Leu Pro His Pro Asn Ser Ser Thr Ala Asn Tyr Val Thr Val
             420                 425                 430

Ser Leu Gly Val Cys Thr Val Val Ala Val Asp Asp Phe Glu Phe Lys
```

|     |     |     |     |     |     |     |     |     |     |     |     |
| --- | --- | --- | --- | --- | --- | --- | --- | --- | --- | --- | --- |
|     |     | 435 |     |     |     | 440 |     |     |     | 445 |     |
| Ser | Glu | Ser | His | Ile | Ile | Gly | Ser | Gln | Ala | Ala | Leu | Ile | Ala | Asp | Lys |
|     | 450 |     |     |     |     | 455 |     |     |     |     | 460 |
| Ala | Leu | Tyr | His | Ala | Lys | Ala | Cys | Gly | Arg | Asn | Gln | Ala | Leu | Ser | Lys |
| 465 |     |     |     |     | 470 |     |     |     |     | 475 |     |     |     |     | 480 |
| Thr | Thr | Ile | Thr | Val | Asp | Glu | Ile | Glu | Gln | Leu | Glu | Ala | Asn | Lys | Ile |
|     |     |     | 485 |     |     |     |     | 490 |     |     |     |     | 495 |

Gly His Gln

```
<210> SEQ ID NO 12
<211> LENGTH: 40138
<212> TYPE: DNA
<213> ORGANISM: Vibrio marinus

<400> SEQUENCE: 12
aatagatcga ctcgcaaaag ttgcttaaga tagtgtcaat atagcttctt atttgtaaat      60
attgtttttt atgtgtaaac atgtttagtg tgtgtaaatg ctgttaatta tcctttgggg    120
attgtaatag ctgatgttgc tggctaatga gtacttttag ttcggcaata tcttgcttta    180
aatcgctaac ttcagttttt aattcaccca cacttgttgt atttttaagg ctctcttccc    240
caccatcgac aaaccaggat gatatgaaac cggtaaacgt accaaagaga ccgacacctg    300
cagtcatgag taatgccgca atgatacgtc cgccagtggt gacggggtag tagtcaccgt    360
aaccaacagt cgttattgtc acaaatgacc accaaagtgc gtcgatgccg ttattgatgt    420
tactgcctac ttgatcctgt tctaacaata aataccgat agcaccaaag gtgacaagga     480
tgaaggatat cgcagatacc agcgaaaagg tggctttaaa ccgatgttca aaaatcattt    540
ttaagataat ttttgatgag cgtatattct gaatagatct taatactcta gcgatacgaa    600
ttatgcgaat aaactgcagt tgctcgacca tcggaatact cgacagtagg tcaatccaac    660
cccatttcat aaactgaaat ttattctcag cttggtgaaa gcgaattaca aagtcagtga    720
aaagaataa gcaaatcgta ttatctacgc tcgttaatat ttcagtgacg ttacttgaaa     780
aggtaaaaat aagttgcagt agtgatgata cgaccacatg aagtgataaa ataagcatga    840
aaatctgaaa tggatttaca tcactgttgt ttttggtgcc acttttaagg ttcgttttca    900
caatctgctg cctcggttca ttgattttgt taatataaac cttagtcagt agcaagacaa    960
aatatattta catcaatgtc atcgtattat tcaaccgcgc gtcgtgtatt cagaccaaga   1020
tcgttgtata tgttagtcat gtagcgatga gattatcatg cgacaggaga gaattatgtt   1080
tgttattatt ttttacgtac ctaaagttaa tgttgaagaa gtaaacagg cgttatttaa    1140
cgtcggagct ggcaccatcg gtgattatga tagttgtgct tggcaatgtt tggggactgg   1200
gcagttccaa cctttacttg gtagccagcc acatattggt aagctaaatg aggttgaatt   1260
cgttgatgag tttagagtag aaatggtttg tcgagcagaa aatgtaaggg cagcaataaa   1320
tgcacttatt gctgcgcacc cttatgaaga acctgcttat catattctgc aaacattgaa   1380
tcttgatgag ttaccttaag ttagatgcac tgcacttaat tggttcgctg tgctaggtta   1440
gcaattagca atttttgacca tgttagcgat agttttggca caagtgatcg atattaaact   1500
atccgattca gatcccattt ttactgctga attaggtttc attacacttg ttctagtggt   1560
ttttcccgac aggtgtaact ctgttacttg cgtaaggttg ataatctcta ccgcattggc   1620
aggagttaca cctgcaccag gcataatact aattctacca tctgcttggt taactaacgt   1680
ttggattaag gcgcagcctt ctagcgcttg agcttgttga ccagaggtta aaatacgctc   1740
```

```
acaaccagca gtgatcaagg tctccaaggc ttgttgtgga tcattacaca agtcgaaagc    1800
gcggtggaag gttacgccga gatcacgtga tgccaccatt aagcgtttta aagctggctc    1860
gtcaatatta ccatctgctg ttaacgcgcc aataacgacc ccttggacac cgagtaactt    1920
catgaatttg atgtcggaaa ccataatatc aacttcttgt tcgctatata caaaatcacc    1980
ggcgcgaggg cgaataatgg cataaatggg gatcgttgct agatcaatag acttttgtac    2040
aaaacctgcg ttggcggtca agccacctaa tgctaatgcc gagcacaact caatacgatc    2100
ggcgccagat gcttgagccg tcagcagtga ttctatatta tcgacacata cttctattgt    2160
cattgtcata tacttctctt taaaaagttt attaaaaata ataaagccag cataagtcgt    2220
tttatacaat atgaaagggg aaaaggcgac ttagctcgcc tagatcaatt attatggcag    2280
aatactgccg tattgtgatt agaaagacag ttttttaagc tcaatagccg ttatcgcgtt    2340
gttatctacc atcgtgtaac ttttctggcc tgggtgcttt attaacactg tttcagtggc    2400
tggattaggg tgaaatgatt cttttttcaa atctgttttt ttgtatttga acgtacctgt    2460
aatgtcttgc tgctcacgaa gacgtacaaa tattggttgc gcatagcttg gtagtgccgc    2520
attgacatgt tgatagaatt cagacgctga aaattcatga ataggcaat tcaaagtcag    2580 cgcgaccatg cctgctcggc catcgtgatg tgggagcttg acaccataag ccacactttg    2640
ctcaatttgc acaaaatcgt taacttgagc ttctacttgc gtcgtggcga cattttcacc    2700
tttccagcgg aatgtatcac ctaatctatc cacaaaggaa atatggcgat aaccttggta    2760
atgaacgaga tcgccggtat taaaataaca gtcaccgtct tttaatactg acttaaaatag    2820 cttttttatta ctttcgttgt catcggtata accatcaaat ggtgaacgtt tagttatctt    2880
tgttagcagt agccctgttt ctcccgtttt tactttggtc attttccctt tcgcattata    2940
cacaggtttg tcattgtcaa tatcatattg tatgacggta aaagcaagtg gagtaaccccc    3000 cgctgtatgc ggtaagttca gcgcattgga gaacacaaga ttacactcac tggcgccata    3060
gaattcatta atatgctcga tcccaaaacg ttgttggaaa tgatcccaaa tttcggggcg    3120
taatccatta cctatgattt tctttatatt atgctgtttg tctttattgc taggcggtac    3180
atttaataaa taacggcaga gctcgccgat gtaagtaaac gcagtggcat tatgagcacg    3240
aacttcatcc caaaagcgac ttgaactgaa ttttcagaa agtgcgaggg ttgctgcgct    3300
accaaacacg gcgcttaatg acactgtcag tgcattgtta tggtataggg ggagtgataa    3360
atacaataca tcatcagctg ttaagcgtaa tgatgccatc cccatgcctg ccatggattt    3420
aaaccaacgg tgatggctca ttcttgctgc ttttggcagt ccagttttttc ccgaggtaaa    3480 gatataaaac gcgcaatgct taagctgtat ttgtgctgtt gattcagggt tcaatactga    3540
atatcctgcg actagtgtag atatgttttt ataaccatca ctcatgtctg gcgtttctaa    3600
agcgggtacg taaagacat tctgttgtaa tgtcgatgac aaattggttt caatattatt    3660
aatggcggat gtgtatagtt catctgcgat gagtaatttg gtatcgacca cgctaagact    3720
atgttcgagg attgaatccc gttgtgtcgt atttatcata caagcaatcg cgccaagctt    3780
gacaactgcg agggcaataa tgatggtttc aggcctgtta tcgagcatga tggcgacttt    3840
atcattttta ccaatgccgt attcatgaag gaaatgggca tattgatttg cttgcttatt    3900
caatgaatcg taactataac gctggtcttt aaattgtatt gcgatcaagt cagagttatt    3960
gacagcttgc tgctctagta ataaaccaat agacataaaa cgttcgggct ttgcttgttg    4020
taagtgccat aagcctttga tgattggctt tggggttttt aatagattga tggtactttt    4080
caggaattgt ttgccggtta taacagtcat aagctaattc ttttttatcaa gaagaggggt    4140
```

```
tatgacacca aataaatggg tcacgcgttg gtttaatttg gttagactaa atgtgttgtt      4200
ttgctgtgat aatgcgacgt tcaaacaaac ttgagaaggt aaaaaaatag cattttaaa       4260 ttgaacatca atactaatgt gttgaatatc aatcaagttt tctaactgtg cgagcacgcg      4320
tgctttagca aacatgccat gtgctattgc tgttttaaac cccattagtt tcgctgggat      4380
aaaatgtaaa tggattggat ttgtgtcttt ggagatataa gcatatttat atacgtcaaa      4440
aggactaaat ttaaacaatg aaatcggctc gtaagcataa ttcgctggcg tatttactat      4500
tttctcaccg ctggaacgtt gagatcgttg gcacgttttt cgctgtttcg ttttctgtaa      4560
gaatgtcgat gtacactccc acgcaaattg tccatctaca aacacatcaa tatgagtatc      4620
aatgaaacgt cctgtatccg ttatgtactc cttaattaca cgacatgtgc tcgtcaatat      4680
cgcgtttaat gctatcggtt gatgttgtgt tatgcgattt cgataatgga ctagtcctaa      4740
tatagatatc ggaaattgtg ttgatgtcat gagtttcatc aataatgaaa agatcatcac      4800
aaatggataa gtaaccggta catagtttgt gttattaaac ccacagcatt taatatattg      4860
ctttaaattt cgctgatcta ttttttgtcc actgatacta aattgctcag tacacacttg      4920
tgtcgaccaa gtgttcatca gtgttttaac aattgtattg accactgctt tcacatataa      4980
aagcgagata atcggttgct ttgttaacag tgtgatctgg ttagcgtgca ttgaaataat      5040
tcatataaga gtatgtagca tttatgttaa tattttgttt tggaagttga attggcgaat      5100
ccgtaatcgg tttatggcag ttcggtcaaa tacttcaggt aaactcgtta ctcataccat      5160
tgatagtgtt aaagtgattg actgaataaa gaatagagct aaaagtggaa aaattatgca      5220
agatgcgggt atgttattac gcattgctta tgaggcaatg aaagagttag aggttgatgt      5280
cattgaagta cttctctcgtt gtaacataag tgaagaagta ctgaatgata aggatcttcg      5340
cacacctaat catgcacaaa cacattttttg gcaagtatta aagacatat cacaagatcc      5400 taacatcggc atttcacttg gtgagagaat gccagtgttc acggggcagg tattacagta      5460 tcttttttctc agtagtccta catttggtac tggctgggaa cgcgcaacaa aatactttcg      5520
attaatcagt gatgcggcga gtgtttctat caagatggaa ggctgtgaag cgcgattatc      5580
tgtgaactta gatggtttag cggaagatgc gaatcgtcat ttgaatgatt gcctagtgat      5640
cggtgcattt aaattttgtt tatatgtgac agaaggcgaa tttaaagtaa gcaaaatagc      5700 cttttgctcat gctcgcccga agatattac tgcctatacc aatgtattta catgtccgat      5760
tgagtttgct gccgaagata attatattta tttcgatgct gatttactcg aacgtccttc      5820
ttcgcatgcg gagcctgagc tattcgcctt acacgatcag cttgcaagcc gtaaaatagc      5880
caagttagaa ctgcaagatt tagtggataa agtacgtaag gttattgcac aacaacttga      5940
gtctggtgtg gtgactttag aaagtatcgc cactgaactt gacatgaaac cacgtatgct      6000
aagagcgaag ttagctgaca ttgattataa ctttaatcaa atactcgctg attttcgttg      6060
cgagttatca aaaaaactgt tggcgaatac ggacgagtct attgatcaga ttgtctatct      6120
cactggtttt tctgaaccaa gtactttta tcgtgccttt aagcgctggg ttaaaatgac      6180
gccaattgaa tatcgccgta gcaaactcgc ggttaggcat gctaatcaac acgagtccta      6240
aaaattcgct gcttagtgca tagtgcatag tgcatagtgc tagtaagcca agtacaaagc      6300
gttaaagtta agtacttgag cgaaccatca gacaccactt actagattaa gcacctatta      6360
atgattgacc acaaattctg atcgtattgc ctgtgatccc tgcagcttga ggttgcgcaa      6420
aaaaagctat cgcttcagca acatcaactg gcttaccacc ttgttttaat gaattcatac      6480
```

```
gacgaccagc ttcacgaact gtaaatggaa tcgctgctgt cattttttgtt tcaataaagc   6540 ctggtgcaac agcattaatg gtgatgtatt tgtctgcaag cggagtttgc attgcatcaa   6600
cataaccaat gactgcggcc ttagacgttg cataattagt ctgaccaaag ttacccgcaa   6660
tcccactcat cgaagacaca caaacaatgc ggccatagtc gttgagcaga tcatcattta   6720
gcagtcgctc attgattctt tccattgccg acaagttaat atccatcagt acatcccaat   6780
ggttatccgg catacgtgct agcgttttgt cttttgttac cccggcatta tggacgatga   6840
tatcaagcga ctgttctcgc acaaagtcag caatgatatt tggggcgtca gcagcggtaa   6900
tatcagcaac aatgctgcta cctttcaagc aatgagctac tttttcaagg tcctgtttta   6960
atgccggaat gtctaagcaa ataacatgtg cgccatcacg ggcgagtgtt tcagcaatag   7020
cagccccgat gccacgtgat gcaccagtga caagtgctgc tttccttgt aatggttttg    7080 ccgtgttact tgtttcgtta ataacttcgt taataacttc gttataact cgttaatag     7140 ccccattaat cgaaccgggt tttacgttaa taacctgtgc tgagatatag gctgattttg   7200
ctgaggttaa gaaacgtagc ggggcctcta ataattgctc actaccaggt tgtacataga   7260
taagttgaca ggtactacca ttcttgccta tttctttggc gacactgcga caaacccctt   7320
ctaaagatct ttgtacagtc gcgtagctta catcgtcaag atgttcactc ggatgaccta   7380
acacgatcac tctgctgcat ggcgagagct gcttaattac aggttgaaaa aaacgatgta   7440
atgcacttaa ttgcttgctg ttcttaatgc ctgaggcgtc gaagataata ccgttgaagc   7500
gatctgtttt agcgatagca ttaaggctaa taggtgtcgc gactaaagac gtttgattaa   7560
attcaatatt aagatcggct aacgctgacg tgttattagg ataagaaatc gtgacttcag   7620
catctttaaa tgtgttaaga atgggtttaa ttaatttgct gttgctggct gcgccgatga   7680
gtaagttgcc agagatgaga tcggttccct gatcgtagcg tgttaacgta accggtcgtg   7740
gcagattaag cgctttaaat aaacctgatg tccacttgcc attagcgagt tttgcgtatg   7800
tatccgtcat tttctaatcc ttgttatagt gaacagtttg aatctcgaag atgtacatgt   7860
gttaaaaatt atctgatagc tatgacttat ctgccactac gtaataataa atagaccagt   7920
tcattacatc gttaatcgat atagtataac taaatactaa gtaaattata atgataagac   7980
tgttatcgta ctcggatcaa actctgatca gcaaataatc aaattagagt ttttattta   8040 aacttgtatc aacaatgtta cattaatgta tcttacgtct aatgtgctac gggcatattt   8100
aagtcactaa attaaaggaa taaaccatga caggtcaaac aataagaaga gtagcaatta   8160
tcggcggtaa ccgtatcccg tttgcacgtt caaatacagc gtattcaaaa ctaagtaacc   8220
aagatatgct gacggaaact atccgtggct tggtggttaa atataaccta cgtggtgaac   8280
aactggggga agttgttgct ggtgcggtaa ttaagcattc tcgtgatttt aacttaacac   8340
gtgaagccgt gctaagtgca ggtcttgcac ctgaaacgcc ttgttatgac attcaacaag   8400
cttgtggtac tggtctagct gcagctatcc aagtagcaaa caaaattgcg cttggtcaaa   8460
tagaagcggg tattgctggt ggttctgata cgacatcaga tgcaccgatt gcagtcagtg   8520
aaggcatgcg tagtgtatta cttgagctta atcgagctaa aacgggtaag caacgtttga   8580
aagcactatc tcgtctacgt ctaaaacact ttgcgccact aacgcctgca aataaagagc   8640
cgcgtaccaa aatggcgatg ggcgatcatt gtcaagtaac agcgaaagag tggaatatct   8700
cacgtgaagc acaagatgca ttggcctgcg caagtcatca aaaattagct gcagcatatg   8760
aagaaggttt ctttgatacg ttagtttcac ctatggccgg cttaacgaaa gataacgtat   8820
tacgcgcaga tacaacagtt gagaaactgg ctaaattgaa accttgtttt gataaagtaa   8880
```

```
acggcactat gacggcgggt aacagtacta accttaccga tggagcatca gctgtattac    8940
ttgcaagtga agaatgggca gcggcacata acttaccagt acaagcttat ctaacatttg    9000
gtgaaacggc cgctatcgac ttcgttgata agaaagaagg tctgttaatg gcgcctgcat    9060
acgcagtgcc aaaaatgttg aagcgtgctg gccttacatt acaagacttc gattactatg    9120
aaatacatga agcatttgct gcgcagttat tagcaacgct agcagcttgg gaagacgaaa    9180
aattctgtaa agaaaaactg ggtctagatg ctgcgcttgg ttcaattgat atgaccaagt    9240
taaacgtgaa agggagtagc ttagccacgg gtcacccatt tgccgcaact ggtggtcgtg    9300
ttgtcgctac gctagcgcaa ttacttgatc agaaaggttc aggtcgtggt ttgatctcga    9360
tttgtgctgc tggtggtcaa ggtatcacgg caattttaga gaaataaacg cactgtttat    9420
tatctattga ttaagctgtc ctgagatact ggatattttt aaataaaacg ccaatactgc    9480
agagtattgg cgttttttttg taataccaat tcctatataa cggtgcattt taaacactta    9540
atttccggca ttggtatcat aaaaaagcag caccgaagtg ctgcttgatt gtagattaac    9600
ctattaaaat agagaggcta gaattagtct tcgtatgctt cattatgtac gccagctgca    9660
cgacccgatg gatcagcatt gttttggaaa ctttcatccc aagctaatgc ttctacagtt    9720
gaacaagcaa cggatttacc aaacggtacg catttcgctg ctgaatcacc tgggaagtga    9780
tcttcaaaga tggcacgata gtagtaacct tctttcgtat ctggtgtgtt aattgggaac    9840
ttaaatgctg cacttgctaa catttgatca gttaccgctt cttcaacgtg tactttaagt    9900
tggtcaatcc aagaataacc aacaccatca gagaattgtt ctttttgacg ccatacaatt    9960
tcttcaggta gtaaatcttc aaatgcttct cgaatgatgt ttttctcaat gcggtcgccc   10020
gtgatcattt ttagttcagg gtttagacgc attgacgcat caacaaattc tttatctaag   10080
aaaggaacac gtgcttcgat gccccaagct gccatagatt tgtttgcacg taagcaatca   10140
aacatatgta atttatttac tttacgtacc gtctcttcat ggaattcttt cgcatttggc   10200
gctttgtgga agtacaagta accaccgaac agttcatcag caccttcacc agaaagcacc   10260
atcttaatcc ccatggcttt aattttacgt gccattaggt acatagggg tgatgcacga   10320
attgttgtta catcgtaggt ttcaatgtgg taaatcacgt cgcgtaaagc gtcgataacct   10380
tcttgcacag taaattcaat tgaatgatg atagtaccta agtgatctgc cacttttgt   10440
gcagcggcta atctggaga accatttagg cctacagaga aagagtgtag ttgtggccac   10500
catgcttcgg ttttaccacc gtcttcaata cgacgttttg catactgttg ggtgattgct   10560
gaaataacag atgaatctaa cccgcctgat aataatacgc cgtaaggtac atcacacatt   10620
aattgacgtt taactgcatc ttccaaacct tgcttaacaa cgcttttatc accaccattt   10680
tgtgcaacgt tatcaaaatc tttccaatca cgttgataat aaggcgtgac tacaccatcc   10740
ttactccaca gtaatgacc tgctgggaat tcttcaattt gagtacaaat tggcactagt   10800
gctttcattt cagaggcaac ataaaagtta ccgtgttcat catagcccgt ataagaggg    10860
atgataccga tatggtcacg gccaatcagg taagcgtcct ctgtttcgtc atataaagcg   10920
aaagcaaaaa taccatttag atcatctaaa aattgtgtgc cttttctttt atatagcgca   10980
agtatcactt cgcaatctga ttctgttggg aattcaaagt ctacgttcag cgttttcttt   11040
aaatctttgt ggttataaat ttcaccatta acagcaagta cgtgtgtctt ttcttcatta   11100
tatagcggct gtgcaccatt atttacatcg acaatagcaa gacgttcatg aactaaaata   11160
gcattgtcac ttgtatagat acctgaccaa tctgggccgc ggtgacgtag taactttgat   11220
```

```
agttctagtg cttgttcgcg aagaggttta atgtctgatt tgatgtctag aattccgaat    11280
attgagcaca taactaattc cttctgggc tgcgtctgca gctaacttc taaatagtgt     11340 gtctaatttg ccacattgta gatttaatgc aaacattaat gataaaacat ttataaaaaa    11400
tgtaattcaa tgtggaatcg ataatttaat ggcttaaaag tgaagatcca ttaattgtga    11460
tggcgaggtg atagaccaat gtagacctta atgaataaag caggcacgat tgaatccatt    11520
caacgcaaag tggtactaac tattgttta aacgttataa atagtgtttt aaaggttata    11580
agtaaataat ttaaaaacaa taataatcca catgcattaa atttatcatg ataaaccgct    11640
atatctcaat ggcaatttgg gataagtgta aatatatgt aaaatgaatg agttgacttg     11700
ctttttttac actaagtgat gaaattaaag ctagatgtcg ttgttagcat tgattaataa    11760
cgtactaaaa tacgacatct agtatagaaa tttaaaaaac agttggtttt gatagcataa    11820
ctgcataaac taatcagctt attgtctgta atatttttgt aatttaaata ggtttaataa    11880
aattatatgt ctgataaata taaaccgtac gacctttcct ttaaaagac gttttgctg      11940 cctaagtttt ggcctgtgtg gttcggggtg tttgcaatat acttattagc ttttatgcca    12000
gtaaagccgc gtgataaatt tgctcgattc atagcgaaga aattgtttag tctaaaaatg    12060
atggcaaagc gtaaaaggt agcaaagatc aatttatcta tgtgcttccc tgaaatggat     12120
gatacggaac aagaccgtat aatcatggtc aatctagtta cttttgtca aactatctta     12180 agttatgcag agccaagtgc gcgtagtcgt gcttataacc gtgaccgtat gatagtgcat    12240
ggtggcgaga atttatttcc gctacttgaa caaggtaagg cttgtatctt attagtgccg    12300
catagcttcg ctattgattt tgcaggttta cacattgctt cttatggcgc gccattttgt    12360
actatgttta acaattctga gaatgagttg ttcgattggc tgatgacacg tcaacgcgct    12420
atgtttggag gcactgttta tcaccgcaag gcagggctag gggctctagt taaatcactt    12480
aagagcggtg aaagctgtta ttacttacct gatgaagacc atggacctaa gcgtagtgta    12540
tttgcgcctt tatttgcgac tcaaaaagca actttacctg taatgggcaa gctagcagaa    12600
aaaacaaatg cactcgttgt tcctgtttat gcggcatata atgaatcact aggtaaattt    12660
gaaaccttta ttcgaccagc aatgcaaaac tttccatcag aaagcccaga acaagatgca    12720
gtgatgatga ataaagagat tgaagccttg attgaatgtg gtgttgatca atatatgtgg    12780
acacttagat tattgagaac acgtccggac ggtaaaaaaa tctactaata aagttaaata    12840
aacaccataa tcttcgttga atatggtgtt taccccctg aatacccct aaattaataa      12900 caaaaaaagc catttacgta acatctaatg atgatttagc ctgcacttgc tttgttttta   12960
gtcttaagag cctaataaac ttgatctagg tatagattct gtctttcttt acgtaacgcg    13020
atctattttt tttaaccgat agttgttata attagtttca tatgaaagag atatcgtttc    13080
agtaaaagct atttcgtttc aatagataat ttatttatag tcatattttc tgtaatgaca    13140
atcattttct catctagact atagataaga atacgaatta agtaagaaca ttaattttac    13200
aagaatataa aatatccat cggagctata agaatgaaaa agactaaaat tgtttgtaca     13260
attggtccaa aaactgaatc agtagagaaa ctaacagagc ttgttaatgc aggcatgaac    13320
gttatgcgtt taaatttctc tcatggtaac tttgctgaac attcagtgcg tattcaaaat    13380
atccgtcaag taagtgaaaa cctgaataag aaaattgctg ttttactgga tactaaaggt    13440
ccagaaatcc gtacgattaa actagaaaac ggtgacgatg taatgttgac cgctggtcag    13500
tcattcacgt ttcaacagca cattaacgtg gtaggtaata aagactgtgt tgctgtaaca    13560
tatgctggtt ttgctaaaga ccttaatcct ggtgcaatca tccttgttga tgatggttta    13620
```

```
attgaaatgg aagttgttgc aacaactgac actgaagtta aatgtacagt attaaatact    13680
ggtgcacttg gtgaaaataa aggcgttaac ttacctaaca tcagtgtagg tctacctgca    13740
ttgtcagaaa aagataaagc tgatttagcg tttggttgtg agcaagaagt tgattttgtt    13800
gctgcatcat ttattcgtaa ggctgatgat gtaagagaaa ttcgtgaaat cctatttaat    13860
aatggtggcg aaaacattca gattatctcg aaaattgaaa accaagaagg tgtagacaat    13920
ttcgatgaaa tcttagctga atcagacggt atcatggttg ctcgtggcga tctcggtgtt    13980
gagatcccag ttgaagaagt gatcatggca cagaagatga tgatcaaaaa atgtaataaa    14040
gcaggtaaag ttgtaattac tgcaacacaa atgcttgatt caatgatcag taacccacgt    14100
ccaacacgtg cagaagcggg cgatgttgcc aatgctgtgc ttgacggtac cgacgcggta    14160
atgctttctg gtgaaactgc gaaaggtaaa tacccagttg aagctgtgtc tatcatggca    14220
aacatctgtg aacgtactga taactcaatg tcttcggatt taggtgcgaa cattgttgct    14280
aaaagcatgc gcattacaga agctgtgtgt aaaggtgcgg tagaaacaac agaaaaattg    14340
tgtgctccac ttattgttgt tgcaactcgt ggcggtaaat cagcaaaatc tgttcgtaaa    14400
tacttcccga aagcaaatat tcttgctatc acaacaaatg aaaaagcagc gcaacagtta    14460
tgcctaacta aaggcgtaag cagctgcatc gttgagcaga ttgatagcac tgatgagttc    14520
taccgtaaag gtaaagagct tgcattagca actggtttag ctaaagaagg cgatatcgtt    14580
gttatggtat caggtgcgtt agtaccatca ggtacaacga atacggcatc tgttcaccaa    14640
ctttaagttg ccatattgat attataaaaa agagagcgta tgctctcttt ttttatatct    14700
gtagtttata tgtctgtaca aaaaatgat aaagagtaca taaactatta atatagcgta    14760
atatataatg attaacggtg atgaaagggt taaataaatg gatagtgcta aacataaaat    14820
tggcttagtc ctttctggcg gtggtgcgaa aggtattgct catcttggtg tattaaaata    14880
cctgttagag caagatataa gaccgaatgt aattgcgggt acaagtgctg gctctatggt    14940
tggtgcactt tattgctcag gacttgagat tgatgacatt ttacaattct tcatcgatgt    15000 aaaaccttt tcttggaagt ttacccgtgc ccgtgctggc tttatagacc cggcaaaatt    15060
atatcctgaa gtgctaaaat atatccccga ggatagcttt gagtaccttc aacctgaatt    15120
gcgcattgtt gccaccaaca tgttactcgg taaagagcat atatttaaag atggctccgt    15180
gattaatgcc ttattagcat cagccagcta ccctttagtt ttttctccga tgatcattga    15240
cgatcaagtg tattcagatg gcggtattgt taatcatttc cccgtgagtg tcattgaaga    15300
tgattgcgat aaaataatcg gcgtatacgt gtcgcccatt cgtcaggtcg aagctgacga    15360
actctcgagt ataaaagacg tggtattacg tgcgttcacg ctgcagggta gtggtgctga    15420
attagataaa ctatcgcaat gtgatgtgca aatttatcca gaagcgctat tgaattacaa    15480 tacgttttgca accgatgaaa atcattacg ggagatctac cagattggtt atgatgctgc    15540
aaaagatcaa catgacaacc ttatggcatt gaaagaaagt atcaccacca gcgaggttaa    15600
aaagaacgtc tttagcaaat ggtttggtga taaacttgct agcaacagcg gcaaatagcg    15660
gcccacacgg atttatacac taggataatg ggcgttaata gcctcactgt cgttgtgtgg    15720
tctctaattt tagctaaatc ttgtgttata ctgacttcct attaatcata acgatttat    15780 cacggtaaac atgactcaaa taaataaccc gcttcacggc atgacactcg aaaaagtaat    15840
taacagtctc gttgaacaat atggctggga tggtcttgga tactacatca acattcgttg    15900
ctttactgaa aatccaagtg ttaagtctag tcttaaattt ttacgtaaaa cccctttggc    15960
```

```
acgtgataaa gtagaagcgc tatatatcaa aatggtgact gaaggctaac tgtctccacg    16020
ctagcgaacc gctgtttata gttaatataa gtactataag cagggctcgt taattcagta    16080
tgtaattaat cctgaatacc tccgcttatt tcaacattgt actctctaga taacactctc    16140
aacattacac cttcaacatc acagcctcca cataacatcc gatgacatag ccctgttatt    16200
tttcacattt atctatatgc tatatatttt agccatttga tcaattgagt taatttctgc    16260
aatgacaaag atataccatc atccagtaca aatttattat gaagataccg accattctgg    16320
tgttgtttac caccctaact tttttaaaata ctttgaacgt gcacgtgagc atgtgataaa    16380
tagtgactta ctagcaacat gtggaatga acgcggttta ggttttgcgg tgtataaagc    16440
caatatgact tttcaggatg gggtcgaatt tgctgaagtg tgtgatattc gcacttcttt    16500
tgtcctagac ggtaagtaca aaacgatctg gcgccaagaa gtatggcgtc cgaatgcgac    16560
tagggctgcc gttatcggtg atattgaaat ggtgtgctta gacaaacaaa aacgtttaca    16620
gcccatccct gatgatgtgt tagctgcaat ggttagtgaa taaatggttc atgcataaat    16680
agttaataca tgattctggc ccgtcacgtt tacagataag aggcatccga tgcctccttc    16740
ctattaccaa tactactgct tatcccttc taactatctt tagcgtccat aacacactga    16800
gcatttattc tattaatcag tgattgtgat ttaattatct tctatatatg taatttaatg    16860
taattttcaa tttatttta gctacattaa ggcttacgaa tgtacgctaa aatgagatgt    16920
cagactaatt ttagcttatt aatctgttag ccgtttatat tttataaaga tgggatttaa    16980
cttaaatgca attaattatg gcgtaaatag agtgaaaaca tggctaatat tcactaagtc    17040
ctgaatttta tataaagttt aatctgttat tttagcgttt acctggtctt atcagtgagg    17100
tttatagcca ttattagtgg gattgaagtg atttttaaag ctatgtatat tattgcaaat    17160
ataaattgta acaattaaga cttttggacac ttgagttcaa tttcgaattg attggcataa    17220
aatttaaaac agctaaatct acctcaatca ttttagcaaa tgtatgcagg tagatttttt    17280
tcgccattta agagtacact tgtacgctag ttttttgttt agtgtgcaaa tgaacgtttt    17340
gatgagcatt gttttagag cacaaaatag atccttacag gagcaataac gcaatggcta    17400
aaaagaacac cacatcgatt aagcacgcca aggatgtgtt aagtagtgat gatcaacagt    17460
taaattctcg cttgcaagaa tgtccgattg ccatcattgg tatggcatcg gtttttgcag    17520
atgctaaaaa cttggatcaa ttctgggata acatcgttga ctctgtggac gctattattg    17580
atgtgcctag cgatcgctgg aacattgacg accattactc ggctgataaa aaagcagctg    17640
acaagacata ctgcaaacgc ggtggtttca ttccagagct tgattttgat ccgatggagt    17700
ttggtttacc gccaaatatc ctcgagttaa ctgacatcgc tcaattgttg tcattaattg    17760
ttgctcgtga tgtattaagt gatgctggca ttggtagtga ttatgaccat gataaaattg    17820
gtatcacgct gggtgtcggt ggtggtcaga acaaatttc gccattaacg tcgcgcctac    17880
aaggcccggt attagaaaaa gtattaaaag cctcaggcat tgatgaagat gatcgcgcta    17940
tgatcatcga caaatttaaa aaagcctaca tcggctggga agagaactca ttcccaggca    18000
tgctaggtaa cgttattgct ggtcgtatcg ccaatcgttt tgattttggt ggtactaact    18060
gtgtggttga tgcggcatgc gctggctccc ttgcagctgt taaaatggcg atctcagact    18120
tacttgaata tcgttcagaa gtcatgatat cgggtggtgt atgttgtgat aactcgccat    18180
tcatgtatat gtcattctcg aaaacaccag catttaccac caatgatgat atccgtccgt    18240
ttgatgacga ttcaaaaggc atgctggttg gtgaaggtat tggcatgatg gcgtttaaac    18300
gtcttgaaga tgctgaacgt gacggcgaca aaatttattc tgtactgaaa ggtatcggta    18360
```

```
catcttcaga tggtcgtttc aaatctattt acgctccacg cccagatggc caagcaaaag    18420
cgctaaaacg tgcttatgaa gatgccggtt ttgcccctga acatgtggt ctaattgaag    18480 gccatggtac gggtaccaaa gcgggtgatg ccgcagaatt tgctggcttg accaaacact    18540
ttggcgccgc cagtgatgaa aagcaatata tcgccttagg ctcagttaaa tcgcaaattg    18600
gtcatactaa atctgcggct ggctctgcgg tatgattaa gcggcatta gcgctgcatc    18660 ataaaatctt acctgcaacg atccatatcg ataaaccaag tgaagccttg gatatcaaaa    18720
acagcccgtt atacctaaac agcgaaacgc gtccttggat gccacgtgaa gatggtattc    18780
cacgtcgtgc aggtatcagc tcatttggtt ttggcggcac caacttccat attattttag    18840
aagagtatcg cccaggtcac gatagcgcat atcgcttaaa ctcagtgagc caaactgtgt    18900
tgatctcggc aaacgaccaa caaggtattg ttgctgagtt aaataactgg cgtactaaac    18960
tggctgtcga tgctgatcat caaggggtttg tatttaatga gttagtgaca acgtggccat    19020
taaaaacccc atccgttaac caagctcgtt taggttttgt tgcgcgtaat gcaaatgaag    19080
cgatcgcgat gattgatacg gcattgaaac aattcaatgc gaacgcagat aaaatgacat    19140
ggtcagtacc taccggggtt tactatcgtc aagccggtat tgatgcaaca ggtaaagtgg    19200
ttgcgctatt ctcagggcaa ggttcgcaat acgtgaacat gggtcgtgaa ttaacctgta    19260
acttcccaag catgatgcac agtgctgcgg cgatggataa agagttcagt gccgctggtt    19320
taggccagtt atctgcagtt actttcccta tccctgttta tacggatgcc gagcgtaagc    19380
tacaagaaga gcaattacgt ttaacgcaac atgcgcaacc agcgattggt agtttgagtg    19440
ttggtctgtt caaaacgttt aagcaagcag ttttaaagc tgattttgct gccggtcata    19500 gtttcgtga gttaaccgca ttatgggctg ccgatgtatt gagcgaaagc gattacatga    19560
tgttagcgcg tagtcgtggt caagcaatgg ctgcgccaga gcaacaagat tttgatgcag    19620
gtaagatggc cgctgttgtt ggtgatccaa agcaagtcgc tgtgatcatt gatacccttg    19680
atgatgtctc tattgctaac ttcaactcga ataaccaagt tgttattgct ggtactacgg    19740
agcaggttgc tgtagcggtt acaaccttag gtaatgctgg tttcaaagtt gtgccactgc    19800
cggtatctgc tgcgttccat acacctttag ttcgtcacgc gcaaaaacca tttgctaaag    19860
cggttgatag cgctaaattt aaagcgccaa gcattccagt gtttgctaat ggcacaggct    19920
tggtgcattc aagcaaaccg aatgacatta agaaaaacct gaaaaaccac atgctggaat    19980
ctgttcattt caatcaagaa attgacaaca tctatgctga tggtggccgc gtatttatcg    20040
aatttggtcc aaagaatgta ttaactaaat tggttgaaaa cattctcact gaaaaatctg    20100
atgtgactgc tatcgcggtt aatgctaatc ctaaacaacc tgcggacgta caaatgcgcc    20160
aagctgcgct gcaaatggca gtgcttggtg tcgcattaga caatattgac ccgtacgacg    20220
ccgttaagcg tccacttgtt gcgccgaaag catcaccaat gttgatgaag ttatctgcag    20280
cgtcttatgt tagtccgaaa acgaagaaag cgtttgctga tgcattgact gatggctgga    20340
ctgttaagca agcgaaagct gtacctgctg ttgtgtcaca accacaagtg attgaaaaga    20400
tcgttgaagt tgaaaagata gttgaacgca ttgtcgaagt agagcgtatt gtcgaagtag    20460
aaaaaatcgt ctacgttaat gctgacggtt cgcttatatc gcaaaataat caagacgtta    20520
acagcgctgt tgttagcaac gtgactaata gctcagtgac tcatagcagt gatgctgacc    20580
ttgttgcctc tattgaacgc agtgttggtc aatttgttgc acaccaacag caattattaa    20640
atgtacatga acagtttatg caaggtccac aagactacgc gaaaacagtg cagaacgtac    20700
```

```
ttgctgcgca gacgagcaat gaattaccgg aaagtttaga ccgtacattg tctatgtata   20760
acgagttcca atcagaaacg ctacgtgtac atgaaacgta cctgaacaat cagacgagca   20820
acatgaacac catgcttact ggtgctgaag ctgatgtgct agcaaccca ataactcagg    20880 tagtgaatac agccgttgcc actagtcaca aggtagttgc tccagttatt gctaatacag   20940
tgacgaatgt tgtatctagt gtcagtaata acgcggcggt tgcagtgcaa actgtggcat   21000
tagcgcctac gcaagaaatc gctccaacag tcgctactac gccagcaccc gcattggttg   21060
ctatcgtggc tgaacctgtg attgttgcgc atgttgctac agaagttgca ccaattacac   21120
catcagttac accagttgtc gcaactcaag cggctatcga tgtagcaact attaacaaag   21180
taatgttaga agttgttgct gataaaaccg gttatccaac ggatatgctg gaactgagca   21240
tggacatgga agctgactta ggtatcgact caatcaaacg tgttgagata ttaggcgcag   21300
tacaggaatt gatccctgac ttacctgaac ttaatcctga agatcttgct gagctacgca   21360
cgcttggtga gattgtcgat tacatgaatt caaaagccca ggctgtagct cctacaacag   21420
tacctgtaac aagtgcacct gtttcgcctg catctgctgg tattgattta gcccacatcc   21480
aaaacgtaat gttagaagtg gttgcagaca aaaccggtta cccaacagac atgctagaac   21540
tgagcatgga tatggaagct gacttaggta ttgattcaat caagcgtgtg gaaatcttag   21600
gtgcagtaca ggagatcata actgatttac ctgagctaaa ccctgaagat cttgctgaat   21660 tacgcacccct aggtgaaatc gttagttaca tgcaaagcaa agcgccagtc gctgaaagtg   21720
cgccagtggc gacggctcct gtagcaacaa gctcagcacc gtctatcgat ttgaaccaca   21780
ttcaaacagt gatgatggat gtagttgcag ataagactgg ttatccaact gacatgctag   21840
aacttggcat ggacatggaa gctgatttag gtatcgattc aatcaaacgt gtggaaatat   21900
taggcgcagt gcaggagatc atcactgatt tacctgagct aaacccagaa gacctcgctg   21960
aattacgcac gctaggtgaa atcgttagtt acatgcaaag caaagcgcca gtcgctgaga   22020
gtgcgccagt agcgacggct tctgtagcaa caagctctgc accgtctatc gatttaaacc   22080
atatccaaac agtgatgatg gaagtggttg cagacaaaac cggttatcca gtagacatgt   22140
tagaacttgc tatggacatg gaagctgacc taggtatcga ttcaatcaag cgtgtagaaa   22200
ttttaggtgc ggtacaggaa atcattactg acttacctga gcttaaccct gaagatcttg   22260
ctgaactacg tacattaggt gaaatcgtta gttacatgca aagcaaagcg cccgtagctg   22320
aagcgcctgc agtacctgtt gcagtagaaa gtgcacctac tagtgtaaca agctcagcac   22380
cgtctatcga tttagaccac atccaaaatg taatgatgga tgttgttgct gataagactg   22440
gttatcctgc caatatgctt gaattagcaa tggacatgga agccgacctt ggtattgatt   22500
caatcaagcg tgttgaaatt ctaggcgcgg tacaggagat cattactgat ttacctgaac   22560
taaacccaga agacttagct gaactacgta cgttagaaga aattgtaacc tacatgcaaa   22620
gcaaggcgag tggtgttact gtaaatgtag tggctagccc tgaaaataat gctgtatcag   22680
atgcatttat gcaaagcaat gtggcgacta tcacagcggc cgcagaacat aaggcggaat   22740
ttaaaccggc gccgagcgca accgttgcta tctctcgtct aagctctatc agtaaaataa   22800
gccaagattg taaaggtgct aacgccttaa tcgtagctga tggcactgat aatgctgtgt   22860
tacttgcaga ccaccctattg caaactggct ggaatgtaac tgcattgcaa ccaacttggg   22920
tagctgtaac aacgacgaaa gcatttaata agtcagtgaa cctggtgact ttaaatggcg   22980
ttgatgaaac tgaaatcaac aacattatta ctgctaacgc acaattggat gcagttatct   23040
atctgcacgc aagtagcgaa attaatgcta tcgaataccc acaagcatct aagcaaggcc   23100
```

```
tgatgttagc cttcttatta gcgaaattga gtaaagtaac tcaagccgct aaagtgcgtg    23160
gcgcctttat gattgttact cagcagggtg gttcattagg ttttgatgat atcgattctg    23220
ctacaagtca tgatgtgaaa acagacctag tacaaagcgg cttaaacggt ttagttaaga    23280
cactgtctca cgagtgggat aacgtattct gtcgtgcggt tgatattgct tcgtcattaa    23340
cggctgaaca agttgcaagc cttgttagtg atgaactact tgatgctaac actgtattaa    23400
cagaagtggg ttatcaacaa gctggtaaag gccttgaacg tatcacgtta actggtgtgg    23460
ctactgacag ctatgcatta acagctggca ataacatcga tgctaactcg gtattttag    23520 tgagtggtgg cgcaaaaggt gtaactgcac attgtgttgc tcgtatagct aaagaatatc    23580
agtctaagtt catcttattg ggacgttcaa cgttctcaag tgacgaaccg agctgggcaa    23640
gtggtattac tgatgaagcg gcgttaaaga aagcagcgat gcagtctttg attacagcag    23700
gtgataaacc aacacccgtt aagatcgtac agctaatcaa accaatccaa gctaatcgtg    23760
aaattgcgca aaccttgtct gcaattaccg ctgctggtgg ccaagctgaa tatgtttctg    23820
cagatgtaac taatgcagca agcgtacaaa tggcagtcgc tccagctatc gctaagttcg    23880
gtgcaatcac tggcatcatt catggcgcgg gtgtgttagc tgaccaattc attgagcaaa    23940
aaacactgag tgattttgag tctgtttaca gcactaaaat tgacggtttg ttatcgctac    24000
tatcagtcac tgaagcaagc aacatcaagc aattggtatt gttctcgtca gcggctggtt    24060
tctacggtaa ccccggccag tctgattact cgattgccaa tgagatctta aataaaaccg    24120
cataccgctt taaatcattg cacccacaag ctcaagtatt gagctttaac tggggtcctt    24180
gggacggtgg catggtaacg cctgagctta acgtatgtt tgaccaacgt ggtgtttaca    24240
ttattccact tgatgcaggt gcacagttat tgctgaatga actagccgct aatgataacc    24300
gttgtccaca aatcctcgtg ggtaatgact tatctaaaga tgctagctct gatcaaaagt    24360
ctgatgaaaa gagtactgct gtaaaaaagc cacaagttag tcgtttatca gatgctttag    24420
taactaaaag tatcaaagcg actaacagta gctctttatc aaacaagact agtgctttat    24480
cagacagtag tgcttttcag gttaacgaaa accactttt agctgaccac atgatcaaag    24540
gcaatcaggt attaccaacg gtatgcgcga ttgcttggat gagtgatgca gcaaaagcga    24600
cttatagtaa ccgagactgt gcattgaagt atgtcggttt cgaagactat aaattgttta    24660
aaggtgtggt ttttgatggc aatgaggcgg cggattacca aatccaattg tcgcctgtga    24720
caagggcgtc agaacaggat tctgaagtcc gtattgccgc aaagatcttt agcctgaaaa    24780
gtgacggtaa acctgtgttt cattatgcag cgacaatatt gttagcaact cagccactta    24840
atgctgtgaa ggtagaactt ccgacattga cagaaagtgt tgatagcaac aataaagtaa    24900
ctgatgaagc acaagcgtta tacagcaatg gcaccttgtt ccacggtgaa agtctgcagg    24960
gcattaagca gatattaagt tgtgacgaca agggcctgct attggcttgt cagataaccg    25020
atgttgcaac agctaagcag ggatccttcc cgttagctga caacaatatc tttgccaatg    25080
atttggttta tcaggctatg ttggtctggg tgcgcaaaca atttggttta ggtagcttac    25140
cttcggtgac aacggcttgg actgtgtatc gtgaagtggt tgtagatgaa gtattttatc    25200
tgcaacttaa tgttgttgag catgatctat tgggttcacg cggcagtaaa gcccgttgtg    25260
atattcaatt gattgctgct gatatgcaat tacttgccga agtgaaatca gcgcaagtca    25320
gtgtcagtga cattttgaac gatatgtcat gatcgagtaa ataataacga taggcgtcat    25380
ggtgagcatg gcgtctgctt tcttcatttt ttaacattaa caatattaat agctaaacgc    25440
```

```
ggttgcttta aaccaagtaa acaagtgctt ttagctatta ctattccaaa caggatatta   25500
aagagaatat gacggaatta gctgttattg gtatggatgc taaatttagc ggacaagaca   25560
atattgaccg tgtggaacgc gcttttctatg aaggtgctta tgtaggtaat gttagccgcg   25620
ttagtaccga atctaatgtt attagcaatg gcgaagaaca agttattact gccatgacag   25680
ttcttaactc tgtcagtcta ctagcgcaaa cgaatcagtt aaatatagct gatatcgcgg   25740
tgttgctgat tgctgatgta aaaagtgctg atgatcagct tgtagtccaa attgcatcag   25800
caattgaaaa acagtgtgcg agttgtgttg ttattgctga tttaggccaa gcattaaatc   25860
aagtagctga tttagttaat aaccaagact gtcctgtggc tgtaattggc atgaataact   25920
cggttaattt atctcgtcat gatcttgaat ctgtaactgc aacaatcagc tttgatgaaa   25980
ccttcaatgg ttataacaat gtagctgggt tcgcgagttt acttatcgct tcaactgcgt   26040
ttgccaatgc taagcaatgt tatatatacg ccaacattaa gggcttcgct caatcgggcg   26100
taaatgctca atttaacgtt ggaaacatta gcgatactgc aaagaccgca ttgcagcaag   26160
ctagcataac tgcagagcag gttggtttgt tagaagtgtc agcagtcgct gattcggcaa   26220
tcgcattgtc tgaaagccaa ggtttaatgt ctgcttatca tcatacgcaa actttgcata   26280
ctgcattaag cagtgcccgt agtgtgactg gtgaaggcgg gtgttttttca caggtcgcag   26340 gtttattgaa atgtgtaatt ggtttacatc aacgttatat tccggcgatt aaagattggc   26400
aacaaccgag tgacaatcaa atgtcacggt ggcggaattc accattctat atgcctgtag   26460
atgctcgacc ttggttccca catgctgatg gctctgcaca cattgccgct tatagttgtg   26520
tgactgctga cagctattgt catattcttt tacaagaaaa cgtcttacaa gaacttgttt   26580
tgaaagaaac agtcttgcaa gataatgact taactgaaag caagcttcag actcttgaac   26640
aaaacaatcc agtagctgat ctgcgcacta atggttactt tgcatcgagc gagttagcat   26700
taatcatagt acaaggtaat gacgaagcac aattacgctg tgaattagaa actattacag   26760
ggcagttaag tactactggc ataagtacta tcagtattaa acagatcgca gcagactgtt   26820
atgcccgtaa tgatactaac aaagcctata gcgcagtgct tattgccgag actgctgaag   26880
agttaagcaa agaaataacc ttggcgtttg ctggtatcgc tagcgtgttt aatgaagatg   26940
ctaaagaatg gaaaaccccg aagggcagtt attttaccgc gcagcctgca aataaacagg   27000
ctgctaacag cacacagaat ggtgtcacct tcatgtaccc aggtattggt gctacatatg   27060
ttggtttagg gcgtgatcta tttcatctat tcccacagat ttatcagcct gtagcggctt   27120
tagccgatga cattggcgaa agtctaaaag atactttact taatccacgc agtattagtc   27180
gtcatagctt taaagaactc aagcagttgg atctggacct gcgcggtaac ttagccaata   27240
tcgctgaagc cggtgtgggt tttgcttgtg tgttaccaa ggtatttgaa gaagtctttg   27300
ccgttaaagc tgactttgct acaggttata gcatgggtga agtaagcatg tatgcagcac   27360
taggctgctg gcagcaaccg ggattgatga gtgctcgcct tgcacaatcg aataccttta   27420
atcatcaact ttgcggcgag ttaagaacac tacgtcagca ttggggcatg gatgatgtag   27480
ctaacggtac gttcgagcag atctgggaaa cctataccat taaggcaacg attgaacagg   27540
tcgaaattgc ctctgcagat gaagatcgtg tgtattgcac cattatcaat acacctgata   27600
gcttgttgtt agccggttat ccagaagcct gtcagcgagt cattaagaat ttaggtgtgc   27660
gtgcaatggc attgaatatg gcgaacgcaa ttcacagcgc gccagcttat gccgaatacg   27720
atcatatggt tgagctatac catatggatg ttactccacg tattaatacc aagatgtatt   27780
caagctcatg ttatttaccg attccacaac gcagcaaagc gatttcccac agtattgcta   27840
```

-continued

```
aatgtttgtg tgatgtggtg gatttcccac gtttggttaa taccttacat gacaaaggtg   27900
cgcgggtatt cattgaaatg ggtccaggtc gttcgttatg tagctgggta gataagatct   27960
tagttaatgg cgatggcgat aataaaaagc aaagccaaca tgtatctgtt cctgtgaatg   28020
ccaaaggcac cagtgatgaa cttacttata ttcgtgcgat tgctaagtta attagtcatg   28080
gcgtgaattt gaatttagat agcttgttta acgggtcaat cctggttaaa gcaggccata   28140
tagcaaacac gaacaaatag tcaacatcga tatctagcgc tggtgagtta tacctcatta   28200
gttgaaatat ggatttaaag agagtaatta tggaaaatat tgcagtagta ggtattgcta   28260
atttgttccc gggctcacaa gcaccggatc aattttggca gcaattgctt gaacaacaag   28320
attgccgcag taaggcgacc gctgttcaaa tgggcgttga tcctgctaaa tataccgcca   28380
acaaaggtga cacagataaa ttttactgtg tgcacggcgg ttacatcagt gatttcaatt   28440
ttgatgcttc aggttatcaa ctcgataatg attatttagc cggtttagat gaccttaatc   28500
aatgggggct ttatgttacg aaacaagccc ttaccgatgc gggttattgg ggcagtactg   28560
cactagaaaa ctgtggtgtg attttaggta atttgtcatt cccaactaaa tcatctaatc   28620
agctgtttat gcctttgtat catcaagttg ttgataatgc cttaaaggcg gtattacatc   28680
ctgattttca attaacgcat tacacagcac cgaaaaaaac acatgctgac aatgcattag   28740
tagcaggtta tccagctgca ttgatcgcgc aagcggcggg tcttggtggt tcacattttg   28800
cactggatgc ggcttgtgct tcatcttgtt atagcgttaa gttagcgtgt gattacctgc   28860
atacgggtaa agccaacatg atgcttgctg gtgcggtatc tgcagcagat cctatgttcg   28920
taaatatggg tttctcgata ttccaagctt acccagctaa caatgtacat gccccgtttg   28980
accaaaattc acaaggtcta tttgccggtg aaggcgcggg catgatggta ttgaaacgtc   29040
aaagtgatgc agtacgtgat ggtgatcata tttacgccat tattaaaggc ggcgcattat   29100
cgaatgacgg taaaggcgag tttgtattaa gcccgaacac caagggccaa gtattagtat   29160
atgaacgtgc ttatgccgat gcagatgttg acccgagtac agttgactat attgaatgtc   29220
atgcaacggg cacacctaag ggtgacaatg ttgaattgcg ttcgatggaa acctttttca   29280
gtcgcgtaaa taacaaacca ttactgggct cggttaaatc taaccttggt catttgttaa   29340
ctgccgctgg tatgcctggc atgaccaaag ctatgttagc gctaggtaaa ggtcttattc   29400
ctgcaacgat taacttaaag caaccactgc aatctaaaaa cggttacttt actggcgagc   29460
aaatgccaac gacgactgtg tcttggccaa caactccggg tgccaaggca gataaaccgc   29520
gtaccgcagg tgtgagcgta tttggttttg gtggcagcaa cgcccatttg gtattacaac   29580
agccaacgca aacactcgag actaatttta gtgttgctaa accacgtgag cctttggcta   29640
ttattggtat ggacagccat tttggtagtg ccagtaattt agcgcagttc aaaaccttat   29700
taaataataa tcaaaatacc ttccgtgaat taccagaaca acgctggaaa ggcatggaaa   29760
gtaacgctaa cgtcatgcag tcgttacaat tacgcaaagc gcctaaaggc agttacgttg   29820
aacagctaga tattgatttc ttgcgttttta aagtaccgcc taatgaaaaa gattgcttga   29880
tcccgcaaca gttaatgatg atgcaagtgg cagacaatgc tgcgaaagac ggaggtctag   29940
ttgaaggtcg taatgttgcg gtattagtag cgatgggcat ggaactggaa ttacatcagt   30000
atcgtggtcg cgttaatcta accacccaaa ttgaagacag cttattacag caaggtatta   30060
acctgactgt tgagcaacgt gaagaactga ccaatattgc taaagacggt gttgcctcgg   30120
ctgcacagct aaatcagtat acgagtttca ttggtaatat tatggcgtca cgtatttcgg   30180
```

```
cgttatggga ttttttctggt cctgctatta ccgtatcggc tgaagaaaac tctgtttatc   30240
gttgtgttga attagctgaa aatctatttc aaaccagtga tgttgaagcc gttattattg   30300
ctgctgttga tttgtctggt tcaattgaaa acattacttt acgtcagcac tacggtccag   30360
ttaatgaaaa gggatctgta agtgaatgtg gtccggttaa tgaaagcagt tcagtaacca   30420
acaatattct tgatcagcaa caatggctgg tgggtgaagg cgcagcggct attgtcgtta   30480
aaccgtcatc gcaagtcact gctgagcaag tttatgcgcg tattgatgcg gtgagttttg   30540
cccctggtag caatgcgaaa gcaattacga ttgcagcgga taaagcatta acacttgctg   30600
gtatcagtgc tgctgatgta gctagtgttg aagcacatgc aagtggtttt agtgccgaaa   30660
ataatgctga aaaaccgcg ttaccgactt tatacccaag cgcaagtatc agttcggtga   30720
aagccaatat tggtcatacg tttaatgcct cgggtatggc gagtattatt aaaacggcgc   30780
tgctgttaga tcagaatacg agtcaagatc agaaaagcaa acatattgct attaacggtc   30840
taggtcgtga taacagctgc gcgcatctta tcttatcgag ttcagcgcaa gcgcatcaag   30900
ttgcaccagc gcctgtatct ggtatggcca agcaacgccc acagttagtt aaaaccatca   30960
aactcggtgg tcagttaatt agcaacgcga ttgttaacag tgcgagttca tctttacacg   31020
ctattaaagc gcagtttgcc ggtaagcact aaacaaagt taaccagcca gtgatgatgg   31080
ataacctgaa gccccaaggt attagcgctc atgcaaccaa tgagtatgtg gtgactggag   31140
ctgctaacac tcaagcttct aacattcaag catctcatgt tcaagcgtca agtcatgcac   31200
aagagatagc accaaaccaa gttcaaaata tgcaagctac agcagccgct gtaagttcac   31260 cccttttctca acatcaacac acagcgcagc ccgtagcggc accgagcgtt gttggagtga   31320
ctgtgaaaca taaagcaagt aaccaaattc atcagcaagc gtctacgcat aaagcatttt   31380
tagaaagtcg tttagctgca cagaaaaacc tatcgcaact tgttgaattg caaaccaagc   31440
tgtcaatcca aactggtagt gacaatacat ctaacaatac tgcgtcaaca agcaatacag   31500
tgctaacaaa tcctgtatca gcaacgccat taacacttgt gtctaatgcg cctgtagtag   31560
cgacaaacct aaccagtaca gaagcaaaag cgcaagcagc tgctacacaa gctggttttc   31620
agataaaagg acctgttggt tacaactatc caccgctgca gttaattgaa cgttataata   31680
aaccagaaaa cgtgatttac gatcaagctg atttggttga attcgctgaa ggtgatattg   31740
gtaaggtatt tggtgctgaa tacaaatatta ttgatggcta ttcgcgtcgt gtacgtctgc   31800
caacctcaga ttacttgtta gtaacacgtg ttactgaact tgatgccaag gtgcatgaat   31860
acaagaaatc atacatgtgt actgaatatg atgtgcctgt tgatgcaccg ttcttaattg   31920
atggtcagat cccttggtct gttgccgtcg aatcaggcca gtgtgatttg atgttgattt   31980
catatatcgg tattgatttc caagcgaaag gcgaacgtgt ttaccgttta cttgattgtg   32040 aattaactttt ccttgaagag atggctttttg gtggcgatac tttacgttac gagatccaca   32100
ttgattcgta tgcacgtaac ggcgagcaat tattattctt cttccattac gattgttacg   32160 tagggataa gaaggtactt atcatgcgta atggttgtgc tggtttctttt actgacgaag   32220 aactttctga tggtaaaggc gttattcata acgacaaaga caaagctgag tttagcaatg   32280
ctgttaaatc atcattcacg ccgttattac aacataaccg tggtcaatac gattataacg   32340
acatgatgaa gttggttaat ggtgatgttg ccagttgttt tggtccgcaa tatgatcaag   32400
gtggccgtaa tccatcattg aaattctcgt ctgagaagtt cttgatgatt gaacgtatta   32460
ccaagataga cccaaccggt ggtcattggg gactaggcct gttagaaggt cagaaagatt   32520
tagaccctga gcattggtat ttcccttgtc acttttaaagg tgatcaagta atggctggtt   32580
```

```
cgttgatgtc ggaaggttgt ggccaaatgg cgatgttctt catgctgtct cttggtatgc    32640
ataccaatgt gaacaacgct cgtttccaac cactaccagg tgaatcacaa acggtacgtt    32700
gtcgtgggca agtactgcca cagcgcaata ccttaactta ccgtatggaa gttactgcga    32760
tgggtatgca tccacagcca ttcatgaaag ctaatattga tattttgctt gacggtaaag    32820
tggttgttga tttcaaaaac ttgagcgtga tgatcagcga acaagatgag cattcagatt    32880
accctgtaac actgccgagt aatgtggcgc ttaaagcgat tactgcacct gttgcgtcag    32940
tagcaccagc atcttcaccc gctaacagcg cggatctaga cgaacgtggt gttgaaccgt    33000
ttaagtttcc tgaacgtccg ttaatgcgtg ttgagtcaga cttgtctgca ccgaaaagca    33060
aaggtgtgac accgattaag cattttgaag cgcctgctgt tgctggtcat catagagtgc    33120
ctaaccaagc accgtttaca ccttggcata tgtttgagtt tgcgacgggt aatatttcta    33180
actgtttcgg tcctgatttt gatgtttatg aaggtcgtat tccacctcgt acaccttgtg    33240
gcgatttaca agttgttact caggttgtag aagtgcaggg cgaacgtctt gatcttaaaa    33300
atccatcaag ctgtgtagct gaatactatg taccggaaga cgcttggtac tttactaaaa    33360
acagccatga aaactggatg ccttattcat taatcatgga aattgcattg caaccaaatg    33420
gctttatttc tggttacatg ggcacgacgc ttaaataccc tgaaaaagat ctgttcttcc    33480
gtaaccttga tggtagcggc acgttattaa agcagattga tttacgcggc aagaccattg    33540
tgaataaatc agtcttggtt agtacggcta ttgctggtgg cgcgattatt caaagtttca    33600
cgtttgatat gtctgtagat ggcgagctat tttatactgg taaagctgta tttggttact    33660
ttagtggtga atcactgact aaccaactgg gcattgataa cggtaaaacg actaatgcgt    33720
ggtttgttga taacaatacc cccgcagcga atattgatgt gtttgattta actaatcagt    33780
cattggctct gtataaagcg cctgtggata aaccgcatta taaattggct ggtggtcaga    33840
tgaactttat cgatacagtg tcagtggttg aaggcggtgg taaagcgggc gtggcttatg    33900
tttatggcga acgtacgatt gatgctgatg attggttctt ccgttatcac ttccaccaag    33960
atccggtgat gccaggttca ttaggtgttg aagctattat tgagttgatg cagacctatg    34020
cgcttaaaaa tgatttgggt ggcaagtttg ctaacccacg tttcattgcg ccgatgacgc    34080
aagttgattg gaaataccgt gggcaaatta cgccgctgaa taaacagatg tcactggacg    34140
tgcatatcac tgagatcgtg aatgacgctg gtgaagtgcg aatcgttggt gatgcgaatc    34200
tgtctaaaga tggtctgcgt atttatgaag ttaaaaacat cgttttaagt attgttgaag    34260
cgtaaagggt caagtgtaac gtgcttaagc gccgcattgg ttaaagacgc tttgcacgcc    34320
gtgaatccgt ccatggaggc ttggggttgg catccatgcc aacaacagca agcttacttt    34380
aatcaatacg gcttggtgtc catttagacg cctcgaactt agtagttaat agacaaaata    34440
atttagctgt ggaatgaata tagtaagtaa tcattcggca gctacaaaaa aggaattaag    34500
aatgtcgagt ttaggttttta acaataacaa cgcaattaac tgggcttgga agtagatcc    34560 agcgtcagtt catacacaag atgcagaaat taaagcagct ttaatggatc taactaaacc    34620
tctctatgtg gcgaataatt caggcgtaac tggtatagct aatcatacgt cagtagcagg    34680
tgcgatcagc aataacatcg atgttgatgt attggcgttt gcgcaaaagt taaacccaga    34740
agatctgggt gatgatgctt acaagaaaca gcacggcgtt aaatatgctt atcatggcgg    34800
tgcgatggca aatggtattg cctcggttga attggttgtt gcgttaggta agcagggct    34860 gttatgttca tttggtgctg caggtctagt gcctgatgcg gttgaagatg caattcgtcg    34920
```

```
tattcaagct gaattaccaa atggcccttta tgcggttaac ttgatccatg caccagcaga   34980
agaagcatta gagcgtggcg cggttgaacg tttcctaaaa cttggcgtca agacggtaga   35040
ggcttcagct taccttggtt taactgaaca cattgtttgg tatcgtgctg ctggtctaac   35100
taaaaacgca gatggcagtg ttaatatcgg taacaaggtt atcgctaaag tatcgcgtac   35160
cgaagttggt cgccgcttta tggaacctgc accgcaaaaa ttactggata agttattaga   35220
acaaaataag atcacccctg aacaagctgc tttagcgttg cttgtaccta tggctgatga   35280
tattactggg gaagcggatt ctggtggtca tacagataac cgtccgtttt taacattatt   35340
accgacgatt attggtctgc gtgatgaagt gcaagcgaag tataacttct ctcctgcatt   35400
acgtgttggt gctggtggtg gtatcggaac gcctgaagca gcactcgctg catttaacat   35460
gggcgcggct tatatcgttc tgggttctgt gaatcaggcg tgtgttgaag cgggtgcatc   35520
tgaatatact cgtaaactgt tatcgacagt tgaaatggct gatgtgacta tggcacctgc   35580
tgcagatatg tttgaaatgg gtgtgaagct gcaagtatta aaacgcggtt ctatgttcgc   35640
gatgcgtgcg aagaaactgt atgacttgta tgtggcttat gactcgattg aagatatccc   35700
agctgctgaa cgtgagaaga ttgaaaaaca aatcttccgt gcaaacctag acgagatttg   35760
ggatggcact atcgctttct ttactgaacg cgatccagaa atgctagccc gtgcaacgag   35820
tagtcctaaa cgtaaaatgg cacttatctt ccgttggtat cttggccttt cttcacgctg   35880
gtcaaacaca ggcgagaagg gacgtgaaat ggattatcag atttgggcag cccaagttt   35940 aggtgcattc aacagctggg tgaaaggttc ttaccttgaa gactataccc gccgtggcgc   36000
tgtagatgtt gctttgcata tgcttaaagg tgctgcgtat ttacaacgtg taaaccagtt   36060
gaaattgcaa ggtgttagct taagtacaga attggcaagt tatcgtacga gtgattaatg   36120
ttacttgatg atatgtgaat taattaaagc gcctgagggc gcttttttg gttttaact   36180 caggtgttgt aactcgaaat tgccccttc aagttagatc gattactcac tcacaatatg   36240
ttgatatcgc acttgccata tacttgctca tccaaagccc tatattgata atggtgttaa   36300
tagtctttaa tatccgagtc tttcttcagc ataatactaa tatagagact cgaccaatgt   36360
taaacacaac aaagaatata ttcttgtgta ctgccttatt attaacgagt gcgagtacga   36420
cagctactac gctaaacaat tcgatatcag caattgaaca acgtatttct ggtcgtatcg   36480
gtgtggctgt tttagatacg caaaataaac aaacgtgggc ttacaatggt gatgcacatt   36540
ttccgatgat gagtacattc aaaaccctcg cttgcgcgaa aatgctaagt gaatcgacaa   36600
atggtaatct ggatcccagt actagctcat tgataaaggc tgaagaatta atcccttggt   36660
caccagtcac taaaacgttt gtgaataaca ctattacagt ggcgaaagcg tgtgaagcaa   36720
caatgctgac cagtgataat accgcggcta atattgtttt acagtatatc ggaggccctc   36780
aaggcgttac tgcattcttg cgagaaattg gtgatgaaga gagtcagtta gatcgtatag   36840
aacctgaatt gaatgaagct aaggtcggag acttgcgtga taccacgaca ccgaaagcca   36900
tagttaccac gctcaacaaa ctactacttg gtgatgttct acttgatttg gataaaaacc   36960
aacttaaaac atggatgcaa aataataaag tgtcagatcc tttactgcgt tctatattac   37020
cgcaaggctg gtttattgcc gaccgctcag gtgcgggtgg taatggttct cgaggtataa   37080
ctgctatgct ttggcactcc gagcgtcaac cgctaatcat cagtatttat ttaaccgaaa   37140
ctgagttagc aatggcaatg cgcaatgaga ttattgttga gatcggtaag ctgatattca   37200
aagaatacgc ggtgaaataa taagttattt tttgataata cttttaacgag cgtagcatc   37260 gaagtgaggg cgtcaattag acacctttgc ttccccctaca aaatctaatg tgtattaccct   37320
```

```
cggctagtac aattgcccta agttatttct gtccagcttt ggcttagtgc aattgcgtta    37380
gccaatgtga acaccaaggg actttgtcgt accataacta ccaagcgact ttgtcgtttt    37440
tatcttttct tagacaaaca gaggttaaat gagtgacgcc ttccaaatca caggaatgaa    37500
tccgcatttc aataaaatct aacccgtacc aactccgtac aagttgatct ttagttgttt    37560
aaaatctata ataaattcaa ttacggaatt aatccgtaca actggaggtt ttatggctac    37620
tgcaagactt gatatccgtt tggatgaaga atcaaagct aaggctgaga agcatcagc      37680 tttactcggc ttaaaaagtt taaccgaata cgttgttcgc ttaatggacg aagattcaac    37740
taaagtagtt tctgagcatg agagtattac cgttgaagcg aatgtattcg accaatttat    37800
ggctgcttgt gatgaagcga aagccccaaa taaagcatta cttgaagccg ctgtatttac    37860
tcagaatggt gagtttaagt gagttattcc aaacgtttca aagaactgga taaatcaaaa    37920
catgacagag catcatttga ctgtggcgaa aaagagctaa atgattttat ccaaactcaa    37980
gcagccaaac atatgcaagc aggtattagc cgcactctgg ttttacctgc ttctgcgccg    38040
ttaccaaaca aaaatatcc aatttgctca ttttatagta tcgcgccaag ctcaattagc      38100
cgcgatacgt taccacaagc aatggctaaa aagttaccac gttatcctat ccctgttttt    38160
cttttggctc aacttgccgt ccataaagag tttcatggga gtgggttagg caaagttagc    38220
ttaattaaag cgttagagta cctttgggaa attaactctc acatgagagc ttacgccatc    38280
gttgttgatt gtttaactga acaagctgag tcattctacg ctaaatatgg tttcgacgtt    38340
ctctgcgaaa taaatggtcg agtaagaatg ttcatatcaa tgaaaacagt caatcagtta    38400
ttcacttaac agtaagagtt agtataacag ttgtatgaat taaatttatt atattcggta    38460
atctcattgc gatcacgcta gaagtgcgag cgggtcagac cgaggccaca atagcagccg    38520
ttacgtttag gggatgactt aaaaagataa ctactacgtc agtggcgatc ctagaggatt    38580
aaaggtttat gattcacaac atttatttat tgtgcttaat ttttctatc caatatgcgc     38640 aagctgtaaa tatcactgaa gtagactttt atgtcagtga tgatatccct aaagatgttg    38700
ccaaattaaa gataggtgaa tccataacga actccagcct tattctaagt aactcatcta    38760
ttccactctc gcgggagacg ggtaacatat attactcttc atcaattgct aacttgaact    38820
atgactcgat agaatttgtt atggctcaat tgatggccga agattccagc ctttacaaga    38880
tgctggtaaa tagcgatagg ttgtccgtgc tagtaatgac atcttcccag tccacagatc    38940
tctatggctc gacttactcg gcttattttc ctaatgttgc ggtcatcgat ttgaattgtg    39000
actcgctaac tttagaacat gagctcggcc atctatacgg agctgaacat aagaaatat    39060 atgacgacta tgtcttctat gctgcgatat gtggagacta tacgactatc atgaactcta    39120
tgcagcctga aatgaaagaa aaacaaatga taaaggcata ttcattccct gaattaaaag    39180
tggatggctt gcagtgcgga aatgaaaata cgaataacaa aaaggttatt ttagacaata    39240
ttggtcggtt tagataggat tgggatatta ttctcattcg gctctactta gtgctgttat    39300
tatgagtgcc agtgcttcta tctacgatat tggtcttaac aagtatttat ctatagacgc    39360
taaggtgtta tgtatttaag ggatgttcaa gatgaaacta ggtgtaaacg atgtatagtt    39420
gtataacatt ttttcaacgg ttggaacgtt cgattctatc gggtaacaag accgcgacga    39480
tccgcgataa gtccgatagt cattacttag ttggtcagat gttagatgct tgtactcacg    39540
aagataatcg gaaatgtgt caaatagaaa tactgagcat tgaatatgtg acgtttagtg      39600
aattaaaccg tgcgcacgcc aatgctgaag gtttaccgtt tttgtttatg cttaagtgga    39660
```

```
tagttcgaaa gatttatccg acttcaaatg atttattttt cataagtttc agagttgtaa     39720
ctatcgatat cttataagtc ttagtgcaca aaacagaact atttatagcg ctcaagaagg     39780
cgataatttg ataatgaatt atcgccttgt tactattaag agactttaaa tgactgagat     39840
ataagatatg acacggaaga acatattgat cacaggcgca agttcagggt tgggccgagg     39900
tatggccatc gaatttgcaa aatcaggtca taacttagca cttgtgcac gtagacttga      39960 taatttagtt gcactgaaag cagaactctt agccctcaat cctcacatcc aaatcgaaat     40020
aaaacctctt gatgtcaatg aacatgaaca agtcttcact gttttccatg aattcaaagc     40080
tgaatttggt acgcttgatc gtattattgt taatgctgga ttaggcaagg gtggatcc       40138

<210> SEQ ID NO 13
<211> LENGTH: 19227
<212> TYPE: DNA
<213> ORGANISM: Vibrio marinus

<400> SEQUENCE: 13
aaatgcaatt aattatggcg taaatagagt gaaaacatgg ctaatattca ctaagtcctg       60
aattttatat aaagtttaat ctgttatttt agcgtttacc tggtcttatc agtgaggttt      120
atagccatta ttagtgggat tgaagtgatt tttaaagcta tgtatattat tgcaaatata      180
aattgtaaca attaagactt tggacacttg agttcaattt cgaattgatt ggcataaaat      240
ttaaaacagc taaatctacc tcaatcattt tagcaaatgt atgcaggtag attttttttcg     300 ccatttaaga gtacacttgt acgctaggtt tttgtttagt gtgcaaatga acgttttgat      360
gagcattgtt tttagagcac aaaatagatc cttacaggag caataacgca atggctaaaa      420
agaacaccac atcgattaag cacgccaagg atgtgttaag tagtgatgat caacagttaa      480
attctcgctt gcaagaatgt ccgattgcca tcattggtat ggcatcggtt tttgcagatg      540
ctaaaaactt ggatcaattc tgggataaca tcgttgactc tgtggacgct attattgatg      600
tgcctagcga tcgctggaac attgacgacc attactcggc tgataaaaaa gcagctgaca      660
agacatactg caaacgcggt ggtttcattc cagagcttga ttttgatccg atggagtttg      720
gtttaccgcc aaatatcctc gagttaactg acatcgctca attgttgtca ttaattgttg      780
ctcgtgatgt attaagtgat gctggcattg gtagtgatta tgaccatgat aaaattggta      840
tcacgctggg tgtcggtggt ggtcagaaac aaatttcgcc attaacgtcg cgcctacaag      900
gcccggtatt agaaaaagta ttaaaagcct caggcattga tgaagatgat cgcgctatga      960
tcatcgacaa atttaaaaaa gcctacatcg gctgggaaga gaactcattc ccaggcatgc     1020
taggtaacgt tattgctggt cgtatcgcca atcgttttga ttttggtggt actaactgtg     1080
tggttgatgc ggcatgcgct ggctcccttg cagctgttaa aatggcgatc tcagacttac     1140
ttgaatatcg ttcagaagtc atgatatcgg gtggtgtatg ttgtgataac tcgccattca     1200
tgtatatgtc attctcgaaa acaccagcat ttaccaccaa tgatgatatc cgtccgtttg     1260
atgacgattc aaaaggcatg ctggttggtg aaggtattgg catgatggcg tttaaacgtc     1320
ttgaagatgc tgaacgtgac ggcgacaaaa tttattctgt actgaaaggt atcggtacat     1380
cttcagatgg tcgtttcaaa tctatttacg ctccacgccc agatggccaa gcaaaagcgc     1440
taaaacgtgc ttatgaagat gccggttttt cccctgaaac atgtggtcta attgaaggcc     1500
atggtacggg taccaaagcg ggtgatgccg cagaatttgc tggcttgacc aaacactttg     1560
gcgccgccag tgatgaaaag caatatatcg ccttaggctc agttaaatcg caaattggtc     1620
atactaaatc tgcggctggc tctgcgggta tgattaaggc ggcattagcg ctgcatcata     1680
```

-continued

```
aaatcttacc tgcaacgatc catatcgata aaccaagtga agccttggat atcaaaaaca    1740
gcccgttata cctaaacagc gaaacgcgtc cttggatgcc acgtgaagat ggtattccac    1800
gtcgtgcagg tatcagctca tttggttttg gcggcaccaa cttccatatt attttagaag    1860
agtatcgccc aggtcacgat agcgcatatc gcttaaactc agtgagccaa actgtgttga    1920
tctcggcaaa cgaccaacaa ggtattgttg ctgagttaaa taactggcgt actaaactgg    1980
ctgtcgatgc tgatcatcaa gggtttgtat ttaatgagtt agtgacaacg tggccattaa    2040
aaacccatc cgttaaccaa gctcgtttag gttttgttgc gcgtaatgca aatgaagcga    2100
tcgcgatgat tgatacggca ttgaaacaat tcaatgcgaa cgcagataaa atgacatggt    2160
cagtacctac cggggtttac tatcgtcaag ccggtattga tgcaacaggt aaagtggttg    2220
cgctattctc agggcaaggt tcgcaatacg tgaacatggg tcgtgaatta acctgtaact    2280
tcccaagcat gatgcacagt gctgcggcga tggataaaga gttcagtgcc gctggtttag    2340
gccagttatc tgcagttact ttccctatcc ctgtttatac ggatgccgag cgtaagctac    2400
aagaagagca attacgttta acgcaacatg cgcaaccagc gattggtagt ttgagtgttg    2460
gtctgttcaa aacgtttaag caagcaggtt ttaaagctga ttttgctgcc ggtcatagtt    2520
tcggtgagtt aaccgcatta tgggctgccg atgtattgag cgaaagcgat tacatgatgt    2580
tagcgcgtag tcgtggtcaa gcaatggctg cgccagagca acaagatttt gatgcaggta    2640
agatggccgc tgttgttggt gatccaaagc aagtcgctgt gatcattgat acccttgatg    2700
atgtctctat tgctaacttc aactcgaata accaagttgt tattgctggt actacggagc    2760
aggttgctgt agcggttaca accttaggta atgctggttt caaagttgtg ccactgccgg    2820
tatctgctgc gttccataca ccttagttc gtcacgcgca aaaccatt gctaaagcgg    2880
ttgatagcgc taaatttaaa gcgccaagca ttccagtgtt tgctaatggc acaggcttgg    2940
tgcattcaag caaaccgaat gacattaaga aaaacctgaa aaaccacatg ctggaatctg    3000
ttcatttcaa tcaagaaatt gacaacatct atgctgatgg tggccgcgta tttatcgaat    3060
ttggtccaaa gaatgtatta actaaattgg ttgaaaacat tctcactgaa aaatctgatg    3120
tgactgctat cgcggttaat gctaatccta acaacctgc ggacgtacaa atgcgccaag    3180
ctgcgctgca aatggcagtg cttggtgtcg cattagacaa tattgacccg tacgacgccg    3240
ttaagcgtcc acttgttgcg ccgaaagcat caccaatgtt gatgaagtta tctgcagcgt    3300
cttatgttag tccgaaaacg aagaaagcgt ttgctgatgc attgactgat ggctggactg    3360
ttaagcaagc gaaagctgta cctgctgttg tgtcacaacc acaagtgatt gaaaagatcg    3420
ttgaagttga aaagatagtt gaacgcattg tcgaagtaga gcgtattgtc gaagtagaaa    3480
aaatcgtcta cgttaatgct gacggttcgc ttatatcgca aaataatcaa gacgttaaca    3540
gcgctgttgt tagcaacgtg actaatagct cagtgactca tagcagtgat gctgaccttg    3600
ttgcctctat tgaacgcagt gttggtcaat tgttgcaca ccaacagcaa ttattaaatg    3660
tacatgaaca gtttatgcaa ggtccacaag actacgcgaa aacagtgcag aacgtacttg    3720
ctgcgcagac gagcaatgaa ttaccggaaa gtttagaccg tacattgtct atgtataacg    3780
agttccaatc agaaacgcta cgtgtacatg aaacgtacct gaacaatcag acgagcaaca    3840
tgaacaccat gcttactggt gctgaagctg atgtgctagc aaccccaata actcaggtag    3900
tgaatacagc cgttgccact agtcacaagg tagttgctcc agttattgct aatacagtga    3960
cgaatgttgt atctagtgtc agtaataacg cggcggttgc agtgcaaact gtggcattag    4020
```

-continued

```
cgcctacgca agaaatcgct ccaacagtcg ctactacgcc agcacccgca ttggttgcta    4080
tcgtggctga acctgtgatt gttgcgcatg ttgctacaga agttgcacca attacaccat    4140
cagttacacc agttgtcgca actcaagcgg ctatcgatgt agcaactatt aacaaagtaa    4200
tgttagaagt tgttgctgat aaaaccggtt atccaacgga tatgctggaa ctgagcatgg    4260
acatggaagc tgacttaggt atcgactcaa tcaaacgtgt tgagatatta ggcgcagtac    4320
aggaattgat ccctgactta cctgaactta atcctgaaga tcttgctgag ctacgcacgc    4380
ttggtgagat tgtcgattac atgaattcaa aagcccaggc tgtagctcct acaacagtac    4440
ctgtaacaag tgcacctgtt tcgcctgcat ctgctggtat tgatttagcc cacatccaaa    4500
acgtaatgtt agaagtggtt gcagacaaaa ccggttaccc aacagacatg ctagaactga    4560
gcatggatat ggaagctgac ttaggtattg attcaatcaa gcgtgtggaa atcttaggtg    4620
cagtacagga gatcataact gatttacctg agctaaaccc tgaagatctt gctgaattac    4680
gcaccctagg tgaaatcgtt agttacatgc aaagcaaagc gccagtcgct gaaagtgcgc    4740
cagtggcgac ggctcctgta gcaacaagct cagcaccgtc tatcgatttg aaccacattc    4800
aaacagtgat gatggatgta gttgcagata agactggtta tccaactgac atgctagaac    4860
ttggcatgga catggaagct gatttaggta tcgattcaat caaacgtgtg gaaatattag    4920
gcgcagtgca ggagatcatc actgatttac ctgagctaaa cccagaagac ctcgctgaat    4980
tacgcacgct aggtgaaatc gttagttaca tgcaaagcaa agcgccagtc gctgagagtg    5040
cgccagtagc gacggcttct gtagcaacaa gctctgcacc gtctatcgat ttaaaccata    5100
tccaaacagt gatgatggaa gtggttgcag acaaaaccgg ttatccagta gacatgttag    5160
aacttgctat ggacatggaa gctgacctag gtatcgattc aatcaagcgt gtagaaattt    5220
taggtgcggt acaggaaatc attactgact tacctgagct taaccctgaa gatcttgctg    5280
aactacgtac attaggtgaa atcgttagtt acatgcaaag caaagcgccc gtagctgaag    5340
cgcctgcagt acctgttgca gtagaaagtg cacctactag tgtaacaagc tcagcaccgt    5400
ctatcgattt agaccacatc caaaatgtaa tgatggatgt tgttgctgat aagactggtt    5460
atcctgccaa tatgcttgaa ttagcaatgg acatggaagc cgaccttggt attgattcaa    5520
tcaagcgtgt tgaaattcta ggcgcggtac aggagatcat tactgattta cctgaactaa    5580
acccagaaga cttagctgaa ctacgtacgt tagaagaaat tgtaacctac atgcaaagca    5640
aggcgagtgg tgttactgta aatgtagtgg ctagccctga aaataatgct gtatcagatg    5700
catttatgca aagcaatgtg gcgactatca cagcggccgc agaacataag gcggaattta    5760
aaccggcgcc gagcgcaacc gttgctatct ctcgtctaag ctctatcagt aaaataagcc    5820
aagattgtaa aggtgctaac gccttaatcg tagctgatgg cactgataat gctgtgttac    5880
ttgcagacca cctattgcaa actggctgga atgtaactgc attgcaacca acttgggtag    5940
ctgtaacaac gacgaaagca tttaataagt cagtgaacct ggtgactta aatggcgttg    6000 atgaaactga atcaacaac attattactg ctaacgcaca attggatgca gttatctatc    6060
tgcacgcaag tagcgaaatt aatgctatcg aatacccaca agcatctaag caaggcctga    6120
tgttagcctt cttattagcg aaattgagta agtaactca agccgctaaa gtgcgtggcg    6180 ccttttatgat tgttactcag cagggtggtt cattaggttt tgatgatatc gattctgcta    6240
caagtcatga tgtgaaaaca gacctagtac aaagcggctt aaacggttta gttaagacac    6300
tgtctcacga gtgggataac gtattctgtc gtgcggttga tattgcttcg tcattaacgg    6360
ctgaacaagt tgcaagcctt gttagtgatg aactacttga tgctaacact gtattaacag    6420
```

```
aagtgggtta tcaacaagct ggtaaaggcc ttgaacgtat cacgttaact ggtgtggcta   6480
ctgacagcta tgcattaaca gctggcaata acatcgatgc taactcggta tttttagtga   6540
gtggtggcgc aaaaggtgta actgcacatt gtgttgctcg tatagctaaa gaatatcagt   6600
ctaagttcat cttattggga cgttcaacgt tctcaagtga cgaaccgagc tgggcaagtg   6660
gtattactga tgaagcggcg ttaaagaaag cagcgatgca gtctttgatt acagcaggtg   6720
ataaaccaac acccgttaag atcgtacagc taatcaaacc aatccaagct aatcgtgaaa   6780
ttgcgcaaac cttgtctgca attaccgctg ctggtggcca agctgaatat gtttctgcag   6840
atgtaactaa tgcagcaagc gtacaaatgg cagtcgctcc agctatcgct aagttcggtg   6900
caatcactgg catcattcat ggcgcgggtg tgttagctga ccaattcatt gagcaaaaaa   6960
cactgagtga ttttgagtct gtttacagca ctaaaattga cggtttgtta tcgctactat   7020
cagtcactga agcaagcaac atcaagcaat tggtattgtt ctcgtcagcg gctggtttct   7080
acggtaaccc cggccagtct gattactcga ttgccaatga gatcttaaat aaaaccgcat   7140
accgctttaa atcattgcac ccacaagctc aagtattgag ctttaactgg ggtccttggg   7200
acggtggcat ggtaacgcct gagcttaaac gtatgtttga ccaacgtggt gtttacatta   7260
ttccacttga tgcaggtgca cagttattgc tgaatgaact agccgctaat gataaccgtt   7320
gtccacaaat cctcgtgggt aatgactat ctaaagatgc tagctctgat caaaagtctg   7380
atgaaaagag tactgctgta aaaaagccac aagttagtcg tttatcagat gctttagtaa   7440
ctaaaagtat caaagcgact aacagtagct ctttatcaaa caagactagt gctttatcag   7500
acagtagtgc ttttcaggtt aacgaaaacc acttttagc tgaccacatg atcaaaggca   7560
atcaggtatt accaacggta tgcgcgattg cttggatgag tgatgcagca aaagcgactt   7620
atagtaaccg agactgtgca ttgaagtatg tcggtttcga agactataaa ttgtttaaag   7680
gtgtggtttt tgatggcaat gaggcggcgg attaccaaat ccaattgtcg cctgtgacaa   7740
gggcgtcaga acaggattct gaagtccgta ttgccgcaaa gatctttagc ctgaaaagtg   7800
acggtaaacc tgtgtttcat tatgcagcga caatattgtt agcaactcag ccacttaatg   7860
ctgtgaaggt agaacttccg acattgacag aaagtgttga tagcaacaat aaagtaactg   7920
atgaagcaca agcgttatac agcaatggca ccttgttcca cggtgaaagt ctgcagggca   7980
ttaagcagat attaagttgt gacgacaagg gcctgctatt ggcttgtcag ataaccgatg   8040
ttgcaacagc taagcaggga tccttcccgt tagctgacaa caatatcttt gccaatgatt   8100
tggtttatca ggctatgttg gtctgggtgc gcaaacaatt tggtttaggt agcttacctt   8160
cggtgacaac ggcttggact gtgtatcgtg aagtggttgt agatgaagta ttttatctgc   8220
aacttaatgt tgttgagcat gatctattgg gttcacgcgg cagtaaagcc cgttgtgata   8280
ttcaattgat tgctgctgat atgcaattac ttgccgaagt gaaatcagcg caagtcagtg   8340
tcagtgacat tttgaacgat atgtcatgat cgagtaaata ataacgatag cgtcatggt   8400 gagcatggcg tctgctttct tcattttta acattaacaa tattaatagc taaacgcggt   8460
tgctttaaac caagtaaaca agtgcttta gctattacta ttccaaacag gatattaaag   8520
agaatatgac ggaattagct gttattggta tggatgctaa atttagcgga caagacaata   8580
ttgaccgtgt ggaacgcgct ttctatgaag gtgcttatgt aggtaatgtt agccgcgtta   8640
gtaccgaatc taatgttatt agcaatggca agaacaagt tattactgcc atgacagttc   8700
ttaactctgt cagtctacta gcgcaaacga atcagttaaa tatagctgat atcgcggtgt   8760
```

-continued

```
tgctgattgc tgatgtaaaa agtgctgatg atcagcttgt agtccaaatt gcatcagcaa    8820
ttgaaaaaca gtgtgcgagt tgtgttgtta ttgctgattt aggccaagca ttaaatcaag    8880
tagctgattt agttaataac caagactgtc ctgtggctgt aattggcatg ataactcgg     8940
ttaatttatc tcgtcatgat cttgaatctg taactgcaac aatcagcttt gatgaaacct    9000
tcaatggtta taacaatgta gctgggttcg cgagtttact tatcgcttca actgcgtttg    9060
ccaatgctaa gcaatgttat atatacgcca acattaaggg cttcgctcaa tcgggcgtaa    9120
atgctcaatt taacgttgga aacattagcg atactgcaaa gaccgcattg cagcaagcta    9180
gcataactgc agagcaggtt ggtttgttag aagtgtcagc agtcgctgat tcggcaatcg    9240
cattgtctga aagccaaggt ttaatgtctg cttatcatca tacgcaaaact ttgcatactg    9300
cattaagcag tgcccgtagt gtgactggtg aaggcgggtg ttttcacag gtcgcaggtt     9360
tattgaaatg tgtaattggt ttacatcaac gttatattcc ggcgattaaa gattggcaac    9420
aaccgagtga caatcaaatg tcacggtggc ggaattcacc attctatatg cctgtagatg    9480
ctcgaccttg gttcccacat gctgatggct ctgcacacat tgccgcttat agttgtgtga    9540
ctgctgacag ctattgtcat attcttttac aagaaaacgt cttacaagaa cttgttttga    9600
aagaaacagt cttgcaagat aatgacttaa ctgaaagcaa gcttcagact cttgaacaaa    9660
acaatccagt agctgatctg cgcactaatg gttactttgc atcgagcgag ttagcattaa    9720
tcatagtaca aggtaatgac gaagcacaat tacgctgtga attagaaact attacagggc    9780
agttaagtac tactggcata agtactatca gtattaaaca gatcgcagca gactgttatg    9840
cccgtaatga tactaacaaa gcctatagcg cagtgcttat tgccgagact gctgaagagt    9900
taagcaaaga aataaccttg gcgtttgctg gtatcgctag cgtgtttaat gaagatgcta    9960
agaatggaa accccgaag ggcagttatt ttaccgcgca gcctgcaaat aaacaggctg      10020
ctaacagcac acagaatggt gtcaccttca tgtacccagg tattggtgct acatatgttg    10080
gtttagggcg tgatctatt catctattcc cacagattta tcagcctgta gcggctttag     10140
ccgatgacat tggcgaaagt ctaaaagata ctttacttaa tccacgcagt attagtcgtc    10200
atagctttaa agaactcaag cagttggatc tggacctgcg cggtaactta gccaatatcg    10260
ctgaagccgg tgtgggtttt gcttgtgtgt ttaccaaggt atttgaagaa gtctttgccg    10320
ttaaagctga ctttgctaca ggttatagca tgggtgaagt aagcatgtat gcagcactag    10380
gctgctggca gcaaccggga ttgatgagtg ctcgccttgc acaatcgaat acctttaatc    10440
atcaactttg cggcgagtta agaacactac gtcagcattg gggcatggat gatgtagcta    10500
acggtacgtt cgagcagatc tgggaaacct ataccattaa ggcaacgatt gaacaggtcg    10560
aaattgcctc tgcagatgaa gatcgtgtgt attgcaccat tatcaataca cctgatagct    10620
tgttgttagc cggttatcca gaagcctgtc agcgagtcat taagaattta ggtgtgcgtg    10680
caatggcatt gaatatggcg aacgcaattc acagcgcgcc agcttatgcc gaatacgatc    10740
atatggttga gctataccat atggatgtta ctccacgtat taataccaag atgtattcaa    10800
gctcatgtta tttaccgatt ccacaacgca gcaaagcgat ttcccacagt attgctaaat    10860
gtttgtgtga tgtggtggat ttcccacgtt tggttaatac cttacatgac aaaggtgcgc    10920
gggtattcat tgaaatgggt ccaggtcgtt cgttatgtag ctgggtagat aagatcttag    10980
ttaatggcga tggcgataat aaaaagcaaa gccaacatgt atctgttcct gtgaatgcca    11040
aaggcaccag tgatgaactt acttatattc gtgcgattgc taagttaatt agtcatggcg    11100
tgaatttgaa tttagatagc ttgtttaacg ggtcaatcct ggttaaagca ggccatatag    11160
```

-continued

```
caaacacgaa caaatagtca acatcgatat ctagcgctgg tgagttatac ctcattagtt    11220
gaaatatgga tttaaagaga gtaattatgg aaaatattgc agtagtaggt attgctaatt    11280
tgttcccggg ctcacaagca ccggatcaat tttggcagca attgcttgaa caacaagatt    11340
gccgcagtaa ggcgaccgct gttcaaatgg gcgttgatcc tgctaaatat accgccaaca    11400
aaggtgacac agataaattt tactgtgtgc acggcggtta catcagtgat ttcaattttg    11460
atgcttcagg ttatcaactc gataatgatt atttagccgg tttagatgac cttaatcaat    11520
gggggcttta tgttacgaaa caagcccttta ccgatgcggg ttattgggc agtactgcac    11580 tagaaaactg tggtgtgatt ttaggtaatt tgtcattccc aactaaatca tctaatcagc    11640
tgtttatgcc tttgtatcat caagttgttg ataatgcctt aaaggcggta ttacatcctg    11700
attttcaatt aacgcattac acagcaccga aaaaaacaca tgctgacaat gcattagtag    11760
caggttatcc agctgcattg atcgcgcaag cggcgggtct tggtggttca cattttgcac    11820
tggatgcggc ttgtgcttca tcttgttata gcgttaagtt agcgtgtgat tacctgcata    11880
cgggtaaagc caacatgatg cttgctggtg cggtatctgc agcagatcct atgttcgtaa    11940
atatgggttt ctcgatattc caagcttacc cagctaacaa tgtacatgcc ccgtttgacc    12000
aaaattcaca aggtctattt gccggtgaag gcgcgggcat gatggtattg aaacgtcaaa    12060
gtgatgcagt acgtgatggt gatcatattt acgccattat taaaggcggc gcattatcga    12120
atgacggtaa aggcgagttt gtattaagcc cgaacaccaa gggccaagta ttagtatatg    12180
aacgtgctta tgccgatgca gatgttgacc cgagtacagt tgactatatt gaatgtcatg    12240
caacgggcac acctaagggt gacaatgttg aattgcgttc gatggaaacc ttttttcagtc    12300 gcgtaaaataa caaaccatta ctgggctcgg ttaaatctaa ccttggtcat tgttaactg    12360 ccgctggtat gcctggcatg accaaagcta tgttagcgct aggtaaaggt cttattcctg    12420
caacgattaa cttaaagcaa ccactgcaat ctaaaaacgg ttactttact ggcgagcaaa    12480
tgccaacgac gactgtgtct tggccaacaa ctccgggtgc caaggcagat aaaccgcgta    12540
ccgcaggtgt gagcgtattt ggttttggtg gcagcaacgc ccatttggta ttacaacagc    12600
caacgcaaac actcgagact aatttttagtg ttgctaaacc acgtgagcct ttggctatta    12660
ttggtatgga cagccatttt ggtagtgcca gtaatttagc gcagttcaaa accttattaa    12720
ataataatca aaataccttc cgtgaattac cagaacaacg ctggaaaggc atggaaagta    12780
acgctaacgt catgcagtcg ttacaattac gcaaagcgcc taaaggcagt tacgttgaac    12840
agctagatat tgatttcttg cgttttaaag taccgcctaa tgaaaaagat tgcttgatcc    12900
cgcaacagtt aatgatgatg caagtggcag acaatgctgc gaaagacgga ggtctagttg    12960
aaggtcgtaa tgttgcggta ttagtagcga tgggcatgga actggaatta catcagtatc    13020
gtggtcgcgt taatctaacc acccaaattg aagacagctt attacagcaa ggtattaacc    13080
tgactgttga gcaacgtgaa gaactgacca atattgctaa agacggtgtt gcctcggctg    13140
cacagctaaa tcagtatacg agtttcattg gtaatattat ggcgtcacgt atttcggcgt    13200
tatgggattt ttctggtcct gctattaccg tatcggctga agaaaactct gtttatcgtt    13260
gtgttgaatt agctgaaaat ctatttcaaa ccagtgatgt tgaagccgtt attattgctg    13320
ctgttgattt gtctggttca attgaaaaca ttactttacg tcagcactac ggtccagtta    13380
atgaaaaggg atctgtaagt gaatgtggtc cggttaatga aagcagttca gtaaccaaca    13440
atattcttga tcagcaacaa tggctggtgg gtgaaggcgc agcggctatt gtcgttaaac    13500
```

```
cgtcatcgca agtcactgct gagcaagttt atgcgcgtat tgatgcggtg agttttgccc   13560
ctggtagcaa tgcgaaagca attacgattg cagcggataa agcattaaca cttgctggta   13620
tcagtgctgc tgatgtagct agtgttgaag cacatgcaag tggttttagt gccgaaaata   13680
atgctgaaaa aaccgcgtta ccgactttat acccaagcgc aagtatcagt tcggtgaaag   13740
ccaatattgg tcatacgttt aatgcctcgg gtatggcgag tattattaaa acggcgctgc   13800
tgttagatca gaatacgagt caagatcaga aaagcaaaca tattgctatt aacggtctag   13860
gtcgtgataa cagctgcgcg catcttatct tatcgagttc agcgcaagcg catcaagttg   13920
caccagcgcc tgtatctggt atggccaagc aacgcccaca gttagttaaa accatcaaac   13980
tcggtggtca gttaattagc aacgcgattg ttaacagtgc gagttcatct ttacacgcta   14040
ttaaagcgca gtttgccggt aagcacttaa acaaagttaa ccagccagtg atgatggata   14100
acctgaagcc ccaaggtatt agcgctcatg caaccaatga gtatgtggtg actggagctg   14160
ctaacactca agcttctaac attcaagcat ctcatgttca agcgtcaagt catgcacaag   14220
agatagcacc aaaccaagtt caaaatatgc aagctacagc agccgctgta agttcacccc   14280
tttctcaaca tcaacacaca gcgcagcccg tagcggcacc gagcgttgtt ggagtgactg   14340
tgaaacataa agcaagtaac caaattcatc agcaagcgtc tacgcataaa gcattttag   14400 aaagtcgttt agctgcacag aaaaacctat cgcaacttgt tgaattgcaa accaagctgt   14460
caatccaaac tggtagtgac aatacatcta acaatactgc gtcaacaagc aatacagtgc   14520
taacaaatcc tgtatcagca acgccattaa cacttgtgtc taatgcgcct gtagtagcga   14580
caaacctaac cagtacagaa gcaaaagcgc aagcagctgc tacacaagct ggttttcaga   14640
taaaaggacc tgttggttac aactatccac cgctgcagtt aattgaacgt tataataaac   14700
cagaaaacgt gatttacgat caagctgatt tggttgaatt cgctgaaggt gatattggta   14760
aggtatttgg tgctgaatac aatattattg atggctattc gcgtcgtgta cgtctgccaa   14820
cctcagatta cttgttagta acacgtgtta ctgaacttga tgccaaggtg catgaataca   14880
agaaatcata catgtgtact gaatatgatg tgcctgttga tgcaccgttc ttaattgatg   14940
gtcagatccc ttggtctgtt gccgtcgaat caggccagtg tgatttgatg ttgatttcat   15000
atatcggtat tgatttccaa gcgaaaggcg aacgtgttta ccgtttactt gattgtgaat   15060
taactttcct tgaagagatg gcttttggtg gcgatacttt acgttacgag atccacattg   15120
attcgtatgc acgtaacggc gagcaattat tattcttctt ccattacgat tgttacgtag   15180
gggataagaa ggtacttatc atgcgtaatg gttgtgctgg tttctttact gacgaagaac   15240
tttctgatgg taaaggcgtt attcataacg acaaagacaa agctgagttt agcaatgctg   15300
ttaaatcatc attcacgccg ttattacaac ataaccgtgg tcaatacgat tataacgaca   15360
tgatgaagtt ggttaatggt gatgttgcca gttgttttgg tccgcaatat gatcaaggtg   15420
gccgtaatcc atcattgaaa ttctcgtctg agaagttctt gatgattgaa cgtattacca   15480
agatagaccc aaccggtggt cattgggac taggcctgtt agaaggtcag aaagatttag   15540
accctgagca ttggtatttc ccttgtcact ttaaggtga tcagtaatg gctggttcgt   15600 tgatgtcgga aggttgtggc caaatggcga tgttcttcat gctgtctctt ggtatgcata   15660
ccaatgtgaa caacgctcgt ttccaaccac taccaggtga atcacaaacg gtacgttgtc   15720
gtgggcaagt actgccacag cgcaatacct taacttaccg tatggaagtt actgcgatgg   15780
gtatgcatcc acagccattc atgaaagcta atattgatat tttgcttgac ggtaaagtgg   15840
ttgttgattt caaaaacttg agcgtgatga tcagcgaaca agatgagcat tcagattacc   15900
```

```
ctgtaacact gccgagtaat gtggcgctta aagcgattac tgcacctgtt gcgtcagtag    15960
caccagcatc ttcacccgct aacagcgcgg atctagacga acgtggtgtt gaaccgttta    16020
agtttcctga acgtccgtta atgcgtgttg agtcagactt gtctgcaccg aaaagcaaag    16080
gtgtgacacc gattaagcat tttgaagcgc ctgctgttgc tggtcatcat agagtgccta    16140
accaagcacc gtttacacct tggcatatgt ttgagtttgc gacgggtaat atttctaact    16200
gtttcggtcc tgattttgat gtttatgaag tcgtattcc acctcgtaca ccttgtggcg    16260
atttacaagt tgttactcag gttgtagaag tgcagggcga acgtcttgat cttaaaaatc    16320
catcaagctg tgtagctgaa tactatgtac cggaagacgc ttggtacttt actaaaaaca    16380
gccatgaaaa ctggatgcct tattcattaa tcatggaaat tgcattgcaa ccaaatggct    16440
ttatttctgg ttacatgggc acgacgctta aatacctga aaagatctg ttcttccgta    16500 accttgatgg tagcggcacg ttattaaagc agattgattt acgcggcaag accattgtga    16560
ataaatcagt cttggttagt acggctattg ctggtggcgc gattattcaa agtttcacgt    16620
ttgatatgtc tgtagatggc gagctatttt atactggtaa agctgtattt ggttacttta    16680
gtggtgaatc actgactaac caactgggca ttgataacgg taaaacgact aatgcgtggt    16740
ttgttgataa caataccccc gcagcgaata ttgatgtgtt tgatttaact aatcagtcat    16800
tggctctgta taaagcgcct gtggataaac cgcattataa attggctggt ggtcagatga    16860
actttatcga tacagtgtca gtggttgaag gcggtggtaa agcgggcgtg gcttatgttt    16920
atggcgaacg tacgattgat gctgatgatt ggttcttccg ttatcacttc caccaagatc    16980
cggtgatgcc aggttcatta ggtgttgaag ctattattga gttgatgcag acctatgcgc    17040
ttaaaaatga tttgggtggc aagtttgcta acccacgttt cattgcgccg atgacgcaag    17100
ttgattggaa ataccgtggg caaattacgc cgctgaataa acagatgtca ctggacgtgc    17160
atatcactga gatcgtgaat gacgctggtg aagtgcgaat cgttggtgat gcgaatctgt    17220
ctaaagatgg tctgcgtatt tatgaagtta aaaacatcgt tttaagtatt gttgaagcgt    17280
aaagggtcaa gtgtaacgtg cttaagcgcc gcattggtta aagacgcttt gcacgccgtg    17340
aatccgtcca tggaggcttg gggttggcat ccatgccaac aacagcaagc ttactttaat    17400
caatacggct tggtgtccat ttagacgcct cgaacttagt agttaataga caaataatt    17460 tagctgtgga atgaatatag taagtaatca ttcggcagct acaaaaaagg aattaagaat    17520
gtcgagttta ggttttaaca ataacaacgc aattaactgg gcttggaaag tagatccagc    17580
gtcagttcat acacaagatg cagaaattaa agcagcttta atggatctaa ctaaacctct    17640
ctatgtggcg aataattcag gcgtaactgg tatagctaat catacgtcag tagcaggtgc    17700
gatcagcaat aacatcgatg ttgatgtatt ggcgtttgcg caaaagttaa acccagaaga    17760
tctgggtgat gatgcttaca agaaacagca cggcgttaaa tatgcttatc atggcggtgc    17820
gatggcaaat ggtattgcct cggttgaatt ggttgttgcg ttaggtaaag cagggctgtt    17880
atgttcattt ggtgctgcag gtctagtgcc tgatgcggtt gaagatgcaa ttcgtcgtat    17940
tcaagctgaa ttaccaaatg gcccttatgc ggttaacttg atccatgcac cagcagaaga    18000
agcattagag cgtggcgcgg ttgaacgttt cctaaaactt ggcgtcaaga cggtagaggc    18060
ttcagcttac cttggtttaa ctgaacacat tgtttggtat cgtgctgctg gtctaactaa    18120
aaacgcagat ggcagtgtta atatcggtaa caaggttatc gctaaagtat cgcgtaccga    18180
agttggtcgc cgctttatgg aacctgcacc gcaaaaatta ctggataagt tattagaaca    18240
```

```
aaataagatc acccctgaac aagctgcttt agcgttgctt gtacctatgg ctgatgatat    18300
tactggggaa gcggattctg gtggtcatac agataaccgt ccgttttaa cattattacc     18360 gacgattatt ggtctgcgtg atgaagtgca agcgaagtat aacttctctc ctgcattacg    18420
tgttggtgct ggtggtggta tcggaacgcc tgaagcagca ctcgctgcat ttaacatggg    18480
cgcggcttat atcgttctgg gttctgtgaa tcaggcgtgt gttgaagcgg gtgcatctga    18540
atatactcgt aaactgttat cgacagttga atggctgat gtgactatgg cacctgctgc     18600
agatatgttt gaaatgggtg tgaagctgca agtattaaaa cgcggttcta tgttcgcgat    18660
gcgtgcgaag aaactgtatg acttgtatgt ggcttatgac tcgattgaag atatcccagc    18720
tgctgaacgt gagaagattg aaaaacaaat cttccgtgca aacctagacg agatttggga    18780
tggcactatc gctttctta ctgaacgcga tccagaaatg ctagcccgtg caacgagtag     18840
tcctaaacgt aaaatggcac ttatcttccg ttggtatctt ggcctttctt cacgctggtc    18900
aaacacaggc gagaagggac gtgaaatgga ttatcgatt tgggcaggcc caagtttagg     18960
tgcattcaac agctgggtga aggttctta ccttgaagac tatcccgcc gtggcgctgt      19020 agatgttgct ttgcatatgc ttaaaggtgc tgcgtattta caacgtgtaa accagttgaa    19080
attgcaaggt gttagcttaa gtacagaatt ggcaagttat cgtacgagtg attaatgtta    19140
cttgatgata tgtgaattaa ttaaagcgcc tgagggcgct ttttttggtt tttaactcag    19200
gtgttgtaac tcgaaattgc ccctttc                                        19227

<210> SEQ ID NO 14
<211> LENGTH: 217
<212> TYPE: DNA
<213> ORGANISM: Shewanella putrefaciens

<400> SEQUENCE: 14
attggtaaaa ataggggtta tgtttgttgc tttaaagagt gtcctgaaaa attgctaact      60
tctcgattga tttccttata cttctgtccg ttaacaatac aagagtgcga taaccagact    120
acagagttgg ttaagtcatg gctgcctgaa gatgagttaa ttaaggttaa tcgctacatt    180
aaacaagaag ctaaaactca aggtttaatg gtaagag                             217

<210> SEQ ID NO 15
<211> LENGTH: 72
<212> TYPE: PRT
<213> ORGANISM: Shewanella putrefaciens

<400> SEQUENCE: 15

Ile Gly Lys Asn Arg Gly Tyr Val Cys Cys Phe Lys Glu Cys Pro Glu
1               5                   10                  15

Lys Leu Leu Thr Ser Arg Leu Ile Ser Leu Tyr Phe Cys Pro Leu Thr
            20                  25                  30

Ile Gln Glu Cys Asp Asn Gln Thr Thr Glu Leu Val Lys Ser Trp Leu
        35                  40                  45

Pro Glu Asp Glu Leu Ile Lys Val Asn Arg Tyr Ile Lys Gln Glu Ala
    50                  55                  60

Lys Thr Gln Gly Leu Met Val Arg
65                  70

<210> SEQ ID NO 16
<211> LENGTH: 885
<212> TYPE: DNA
<213> ORGANISM: Shewanella putrefaciens
```

```
<400> SEQUENCE: 16
agcgaaatgc ttatcaagaa attccaagat caatacatca ctgggaagaa aattcattcc      60
ctggttcact gggtaacgtt atttccggcc gtattgctaa ccgcttcgac cttggtggca    120
tgaactgtgt cgttgatgca gcatgtgcag gccctcttgc tgcattgcgt atggcattaa    180
gcgagcttgt tgaaggccgc agcgaaatga tgattacagg tggtgtgtgt accgataact    240
caccaaccat gtacatgagc ttctctaaaa caccggcatt cacgacaaac gaaacaattc    300
aaccattcga tattgactcg aaaggtatga tgattggtga aggtatcggt atgattgcgc    360
ttaaacgtct tgaagacgca gagcgtgatg gcgaccgtat ctattccgtg attaaaggtg    420
ttgggtgcat cttcagacgg taatttatta agagtantta tgcgcntcgt cctgaaggtc    480
aggctaaggc acttaaacgt gcttacgacg atgcaggttt cgcaccgcac acacttggct    540
tacttgaagc ccacggcaca ggcacagcag caggtgatgt ggcagaattc agtggtctta    600
actctgtatt cagtgaaggc aatgacgaaa agcaacacat cgcattaggt tcagtgaaat    660
cacagattgg tcacactaaa tcaacagcgg gtactgcggg tctaatcaaa gcgtctttag    720
cactgcacca taaagtactg ccgccaacaa tcaatgtaac cagccctaac cctaaactga    780
atattgaaga ctcgcctttc tacctcaata cacagacgcg tccatggatg caacgtgtcg    840
atggtacacc gcgtcgtgct ggtattagct catttggttt tggtg                    885

<210> SEQ ID NO 17
<211> LENGTH: 409
<212> TYPE: DNA
<213> ORGANISM: Shewanella putrefaciens

<400> SEQUENCE: 17
ccaagctaaa gcacttaacc gtgcttatga agatgccggt tttgcccctg aaacatgtgg      60
tctaattgaa ggccatggta cgggtaccaa agcgggtgat gccgcagaat tgctggctt     120 gaccaaacac tttggcgccg ccagtgatga aaagcaatat atcgccttag ctcagttaa    180 atcgcaaatt ggtcatacta atctgcggc tggctctgcg gtatgatta aggcggcatt     240 agcgctgcat cataaaatct tacctgcaac gatccatatc gataaaccaa gtgaagcctt    300
ggatatcaaa aacagcccgt tatacctaaa cagcgaaacg cgtccttgga tgccacgtga    360
agatggtatt ccacgtcgtg caggtattag ctcatttggt tttggtggc                  409

<210> SEQ ID NO 18
<211> LENGTH: 81
<212> TYPE: DNA
<213> ORGANISM: Artificial Sequence
<220> FEATURE:
<223> OTHER INFORMATION: Description of Artificial Sequence: SYNTHETIC

<400> SEQUENCE: 18
ccaagctaaa gcacttaacc gtgcctatga tgatgccggt tttgcccctg aaacatgtgg      60
tctaattgaa ggccatggta c                                                81

<210> SEQ ID NO 19
<211> LENGTH: 81
<212> TYPE: DNA
<213> ORGANISM: Artificial Sequence
<220> FEATURE:
<223> OTHER INFORMATION: Description of Artificial Sequence: SYNTHETIC

<400> SEQUENCE: 19
ccaagctaaa gcacttaacc gtgcttatga agatgccggt tttgcccctg aaacatgtgg      60
```
tctaattgaa ggccatggta c                                        81

<210> SEQ ID NO 20
<211> LENGTH: 43
<212> TYPE: DNA
<213> ORGANISM: Artificial Sequence
<220> FEATURE:
<223> OTHER INFORMATION: Description of Artificial Sequence: SYNTHETIC

<400> SEQUENCE: 20
agaacgcaaa gttgccgcac tgtttggtcg ccaaggttca caa                 43

<210> SEQ ID NO 21
<211> LENGTH: 43
<212> TYPE: DNA
<213> ORGANISM: Artificial Sequence
<220> FEATURE:
<223> OTHER INFORMATION: Description of Artificial Sequence: SYNTHETIC

<400> SEQUENCE: 21
caaagcgggt gatgccgcac tgtttggtcg cttgacctaa cac                 43

<210> SEQ ID NO 22
<211> LENGTH: 55
<212> TYPE: DNA
<213> ORGANISM: Artificial Sequence
<220> FEATURE:
<223> OTHER INFORMATION: Description of Artificial Sequence: SYNTHETIC

<400> SEQUENCE: 22
cattgcgcta ggttcagtta aatcacaaat tggtcatact aaatcaactg caggt     55

<210> SEQ ID NO 23
<211> LENGTH: 55
<212> TYPE: DNA
<213> ORGANISM: Artificial Sequence
<220> FEATURE:
<223> OTHER INFORMATION: Description of Artificial Sequence: SYNTHETIC

<400> SEQUENCE: 23
tatcgcctta ggctcagtta aatcgcaaat tggtcatact aaatctgcgg ctggc     55

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: SYNTHETIC

<400> SEQUENCE: 24
cggcttcgat tttggcggca tgaacggtg                                 29

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: SYNTHETIC

<400> SEQUENCE: 25
cgcgtatgat taaggcggca ttagcgctg                                 29

<210> SEQ ID NO 26
<211> LENGTH: 28
<212> TYPE: DNA

```
<213> ORGANISM: Artificial Sequence
<220> FEATURE:
<223> OTHER INFORMATION: Description of Artificial Sequence: SYNTHETIC

<400> SEQUENCE: 26
gcactgctgc aagcatgaac gcgtcgtt                                      28

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: SYNTHETIC

<400> SEQUENCE: 27
gctctgcggc tatcattaac gcggcatt                                      28

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: SYNTHETIC

<400> SEQUENCE: 28
tccctggtgc taaccatatc agcaaacca                                     29

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: SYNTHETIC

<400> SEQUENCE: 29
tacctgcaac gatccatatc gataaacca                                     29

<210> SEQ ID NO 30
<211> LENGTH: 98
<212> TYPE: DNA
<213> ORGANISM: Artificial Sequence
<220> FEATURE:
<223> OTHER INFORMATION: Description of Artificial Sequence: SYNTHETIC

<400> SEQUENCE: 30
ctcacctttg tatctaaaca ctgagacttc gtccatggtt accacgtgtt gatggtacgc    60
cgcgccgcgc gggtattagc tcatttggtt ttggtggc                            98

<210> SEQ ID NO 31
<211> LENGTH: 98
<212> TYPE: DNA
<213> ORGANISM: Artificial Sequence
<220> FEATURE:
<223> OTHER INFORMATION: Description of Artificial Sequence: SYNTHETIC

<400> SEQUENCE: 31
cagcccgtta tacctaaaca gcgaaacggc gtccttggat gccacgtgaa gatggtattc    60
cacgtcgtgc aggtattagc tcatttggtt ttggtggc                            98

<210> SEQ ID NO 32
<211> LENGTH: 4
<212> TYPE: PRT
<213> ORGANISM: Shewanella putrefaciens

<400> SEQUENCE: 32
```

Asp Xaa Ala Cys
1

<210> SEQ ID NO 33
<211> LENGTH: 4
<212> TYPE: PRT
<213> ORGANISM: Shewanella putrefaciens

<400> SEQUENCE: 33

Gly Phe Gly Gly
1

<210> SEQ ID NO 34
<211> LENGTH: 5
<212> TYPE: PRT
<213> ORGANISM: Shewanella putrefaciens

<400> SEQUENCE: 34

Gly His Ser Xaa Gly
1               5

<210> SEQ ID NO 35
<211> LENGTH: 6
<212> TYPE: PRT
<213> ORGANISM: Shewanella putrefaciens

<400> SEQUENCE: 35

Leu Gly Xaa Asp Ser Leu
1               5

<210> SEQ ID NO 36
<211> LENGTH: 6
<212> TYPE: PRT
<213> ORGANISM: Shewanella putrefaciens

<400> SEQUENCE: 36

Leu Gly Xaa Asp Ser Ile
1               5

<210> SEQ ID NO 37
<211> LENGTH: 6
<212> TYPE: PRT
<213> ORGANISM: Shewanella putrefaciens

<400> SEQUENCE: 37

Gly Xaa Gly Xaa Xaa Gly
1               5

<210> SEQ ID NO 38
<211> LENGTH: 6
<212> TYPE: PRT
<213> ORGANISM: Shewanella putrefaciens

<400> SEQUENCE: 38

Gly Xaa Gly Xaa Xaa Ala
1               5

<210> SEQ ID NO 39
<211> LENGTH: 6
<212> TYPE: PRT
<213> ORGANISM: 'Axial Seamount' polynoid polychaete

<400> SEQUENCE: 39

Gly Xaa Gly Xaa Xaa Pro

<210> SEQ ID NO 40
<211> LENGTH: 5
<212> TYPE: PRT
<213> ORGANISM: Shewanella putrefaciens

<400> SEQUENCE: 40

Gly Xaa Ser Xaa Gly
 1               5

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: synthetic

<400> SEQUENCE: 41
cuacuacuac uaccaagcta aagcacuuaa ccgtg                          35

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: synthetic

<400> SEQUENCE: 42
cuacuacuac uaacagcgaa atgcttatca ag                             32

<210> SEQ ID NO 43
<211> LENGTH: 38
<212> TYPE: DNA
<213> ORGANISM: Artificial Sequence
<220> FEATURE:
<223> OTHER INFORMATION: Description of Artificial Sequence: synthetic

<400> SEQUENCE: 43
cuacuacuac uagcgaccaa aaccaaatga gctaatac                       38

<210> SEQ ID NO 44
<211> LENGTH: 12
<212> TYPE: DNA
<213> ORGANISM: Artificial Sequence
<220> FEATURE:
<223> OTHER INFORMATION: Description of Artificial Sequence: synthetic

<400> SEQUENCE: 44
aagcccgggc tt                                                   12

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: synthetic

<400> SEQUENCE: 45
gtacaagccc gggcttagct                                           20

<210> SEQ ID NO 46
<211> LENGTH: 56
<212> TYPE: DNA
<213> ORGANISM: Artificial Sequence
<220> FEATURE:

-continued

<223> OTHER INFORMATION: Description of Artificial Sequence: synthetic

<400> SEQUENCE: 46
cgcgatttaa atggcgcgcc ctgcaggcgg ccgcctgcag ggcgcgccat ttaaat    56

<210> SEQ ID NO 47
<211> LENGTH: 41
<212> TYPE: DNA
<213> ORGANISM: Artificial Sequence
<220> FEATURE:
<223> OTHER INFORMATION: Description of Artificial Sequence: synthetic

<400> SEQUENCE: 47
ctgcagctcg agacaatgtt gatttcctta tacttctgtc c    41

<210> SEQ ID NO 48
<211> LENGTH: 37
<212> TYPE: DNA
<213> ORGANISM: Artificial Sequence
<220> FEATURE:
<223> OTHER INFORMATION: Description of Artificial Sequence: synthetic

<400> SEQUENCE: 48
ggatccagat ctctagctag tcttagctga agctcga    37

<210> SEQ ID NO 49
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 49
tctagactcg agacaatgag ccagacctct aaacctaca    39

<210> SEQ ID NO 50
<211> LENGTH: 37
<212> TYPE: DNA
<213> ORGANISM: Artificial Sequence
<220> FEATURE:
<223> OTHER INFORMATION: Description of Artificial Sequence: synthetic

<400> SEQUENCE: 50
cccgggctcg agctaattcg cctcactgtc gtttgct    37

<210> SEQ ID NO 51
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 51
gaattcctcg agacaatgcc gctgcgcatc gcacttatc    39

<210> SEQ ID NO 52
<211> LENGTH: 37
<212> TYPE: DNA
<213> ORGANISM: Artificial Sequence
<220> FEATURE:
<223> OTHER INFORMATION: Description of Artificial Sequence: synthetic

<400> SEQUENCE: 52
ggtaccagat ctttagactt ccccttgaag taaatgg    37

<210> SEQ ID NO 53
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 53
gaattcgtcg acacaatgtc attaccagac aatgcttct                    39

<210> SEQ ID NO 54
<211> LENGTH: 38
<212> TYPE: DNA
<213> ORGANISM: Artificial Sequence
<220> FEATURE:
<223> OTHER INFORMATION: Description of Artificial Sequence: synthetic

<400> SEQUENCE: 54
tctagagtcg acttatacag attcttcgat gctgatag                     38

<210> SEQ ID NO 55
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 55
gaattcgtcg acacaatgaa tcctacagca actaacgaa                    39

<210> SEQ ID NO 56
<211> LENGTH: 37
<212> TYPE: DNA
<213> ORGANISM: Artificial Sequence
<220> FEATURE:
<223> OTHER INFORMATION: Description of Artificial Sequence: synthetic

<400> SEQUENCE: 56
tctagaggat ccttaggcca ttctttggtt tggcttc                      37

<210> SEQ ID NO 57
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 57
tctagagtcg acacaatggc ggaattagct gttattggt                    39

<210> SEQ ID NO 58
<211> LENGTH: 36
<212> TYPE: DNA
<213> ORGANISM: Artificial Sequence
<220> FEATURE:
<223> OTHER INFORMATION: Description of Artificial Sequence: synthetic

<400> SEQUENCE: 58
gtcgacggat ccctatttgt tcgtgtttgc tatatg                       36

<210> SEQ ID NO 59
<211> LENGTH: 42
<212> TYPE: DNA
<213> ORGANISM: Artificial Sequence
<220> FEATURE:
<223> OTHER INFORMATION: Description of Artificial Sequence: synthetic

```
<400> SEQUENCE: 59
gtcgacggat ccacaatgaa tatagtaagt aatcattcgg ca                    42

<210> SEQ ID NO 60
<211> LENGTH: 37
<212> TYPE: DNA
<213> ORGANISM: Artificial Sequence
<220> FEATURE:
<223> OTHER INFORMATION: Description of Artificial Sequence: synthetic

<400> SEQUENCE: 60
gtcgacctcg agttaatcac tcgtacgata acttgcc                          37

<210> SEQ ID NO 61
<211> LENGTH: 39
<212> TYPE: DNA
<213> ORGANISM: Artificial Sequence
<220> FEATURE:
<223> OTHER INFORMATION: Description of Artificial Sequence: synthetic

<400> SEQUENCE: 61
cccgggtcga cacaatggct aaaaagaaca ccacatcga                        39

<210> SEQ ID NO 62
<211> LENGTH: 40
<212> TYPE: DNA
<213> ORGANISM: Artificial Sequence
<220> FEATURE:
<223> OTHER INFORMATION: Description of Artificial Sequence: synthetic

<400> SEQUENCE: 62
cccgggtcga ctcatgacat atcgttcaaa atgtcactga                       40

<210> SEQ ID NO 63
<211> LENGTH: 44
<212> TYPE: DNA
<213> ORGANISM: Artificial Sequence
<220> FEATURE:
<223> OTHER INFORMATION: Description of Artificial Sequence: synthetic

<400> SEQUENCE: 63
tcgacatgga aaatattgca gtagtaggta ttgctaattt gttc                  44

<210> SEQ ID NO 64
<211> LENGTH: 44
<212> TYPE: DNA
<213> ORGANISM: Artificial Sequence
<220> FEATURE:
<223> OTHER INFORMATION: Description of Artificial Sequence: synthetic

<400> SEQUENCE: 64
ccgggaacaa attagcaata cctactactg caatattttc catg                  44

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: synthetic

<400> SEQUENCE: 65
tcagatgaac tttatcgata c                                           21

<210> SEQ ID NO 66
<211> LENGTH: 36
```

```
<212> TYPE: DNA
<213> ORGANISM: Artificial Sequence
<220> FEATURE:
<223> OTHER INFORMATION: Description of Artificial Sequence: synthetic

<400> SEQUENCE: 66
tcatgagacg tcgtcgactt acgcttcaac aatact                                 36

<210> SEQ ID NO 67
<211> LENGTH: 30
<212> TYPE: DNA
<213> ORGANISM: Schizochytrium aggregatum

<400> SEQUENCE: 67
gtgatgatct ttccctgatg cacgccaagg                                        30

<210> SEQ ID NO 68
<211> LENGTH: 30
<212> TYPE: DNA
<213> ORGANISM: Schizochytrium aggregatum

<400> SEQUENCE: 68
agctcgagac cggcaacccg cagcgccaga                                        30

<210> SEQ ID NO 69
<211> LENGTH: 4446
<212> TYPE: DNA
<213> ORGANISM: Schizochytrium aggregatum

<400> SEQUENCE: 69
cgctgccgcc gcgtctcgcc gcgccgcgcc gcgccgccgc cgccgctcgc gcgcacgccc        60
gcgcgtctcg ccgcgcctgc tgtctcgaac gagcttctcg agaaggccga gaccgtcgtc       120
atggaggtcc tcgccgccaa gactggctac gagactgaca tgatcgagtc cgacatggag       180
ctcgagactg agctcggcat tgactccatc aagcgtgtcg agatcctctc cgaggttcag       240
gccatgctca acgtcgaggc caaggacgtc gacgctctca gccgcactcg cactgtgggt       300
gaggtcgtca acgccatgaa ggctgagatc gctggtggct ctgccccggc gcctgccgcc       360
gctgccccag gtccggctgc tgccgcccct gcgcctgctg tctcgagcga gcttctcgag       420
aaggccgaga ctgtcgtcat ggaggtcctc gccgccaaga ctggctacga gactgacatg       480
attgagtccg acatggagct cgagaccgag ctcggcattg actccatcaa gcgtgtcgag       540
attctctccg aggttcaggc catgctcaac gtcgaggcca aggacgtcga cgctctcagc       600
cgcactcgca ctgttggtga ggtcgtcgat gccatgaagg ctgagatcgc tggcagctcc       660
gcctcggcgc ctgccgccgc tgctcctgct ccggctgctg ccgctcctgc gcccgctgcc       720
gccgcccctg ctgtctcgaa cgagcttctc gagaaagccg agactgtcgt catggaggtc       780
ctcgccgcca agactggcta cgagactgac atgatcgagt ccgacatgga gctcgagact       840
gagctcggca ttgactccat caagcgtgtc gagatcctct ccgaggttca ggccatgctc       900
aacgtcgagg ccaaggacgt cgatgccctc agccgcaccc gcactgttgg cgaggttgtc       960
gatgccatga aggccgagat cgctggtggc tctgccccgg cgcctgccgc cgctgcccct      1020
gctccggctg ccgccgcccc tgctgtctcg aacgagcttc ttgagaaggc cgagactgtc      1080
gtcatggagg tcctcgccgc caagactggc tacgagacca catgatcga gtccgacatg      1140 gagctcgaga ccgagctcgg cattgactcc atcaagcgtg tcgagattct ctccgaggtt      1200
caggccatgc tcaacgtcga ggccaaggac gtcgatgctc tcagccgcac tcgcactgtt      1260
```

```
ggcgaggtcg tcgatgccat gaaggctgag atcgccggca gctccgcccc ggcgcctgcc    1320
gccgctgctc ctgctccggc tgctgccgct cctgcgcccg ctgccgctgc ccctgctgtc    1380
tcgagcgagc ttctcgagaa ggccgagacc gtcgtcatgg aggtcctcgc cgccaagact    1440
ggctacgaga ctgacatgat tgagtccgac atggagctcg agactgagct cggcattgac    1500
tccatcaagc gtgtcgagat cctctccgag gttcaggcca tgctcaacgt cgaggccaag    1560
gacgtcgatg ccctcagccg cacccgcact gttggcgagg ttgtcgatgc catgaaggcc    1620
gagatcgctg gtggctctgc cccggcgcct gccgccgctg ccctgctcc ggctgccgcc     1680 gcccctgctg tctcgaacga gcttcttgag aaggccgaga ccgtcgtcat ggaggtcctc    1740
gccgccaaga ctggctacga gaccgacatg atcgagtccg acatggagct cgagaccgag    1800
ctcggcattg actccatcaa gcgtgtcgag attctctccg aggttcaggc catgctcaac    1860
gtcgaggcca aggacgtcga cgctctcagc cgcactcgca ctgttggcga ggtcgtcgat    1920
gccatgaagc tgagatcgc tggtggctct gccccggcgc ctgccgccgc tgctcctgcc     1980
tcggctggcg ccgcgcctgc ggtcaagatt gactcggtcc acggcgctga ctgtgatgat    2040
ctttccctga tgcacgccaa ggtggttgac atccgccgcc cggacgagct catcctggag    2100
cgccccgaga accgccccgt tctcgttgtc gatgacggca gcgagctcac cctcgccctg    2160
gtccgcgtcc tcggcgcctg cgccgttgtc ctgacctttg agggtctcca gctcgctcag    2220
cgcgctggtg ccgctgccat ccgccacgtg ctcgccaagg atctttccgc ggagagcgcc    2280
gagaaggcca tcaaggaggc cgagcagcgc tttggcgctc tcggcggctt catctcgcag    2340
caggcggagc gcttcgagcc cgccgaaatc ctcggcttca cgctcatgtg cgccaagttc    2400
gccaaggctt ccctctgcac ggctgtggct ggcggccgcc cggcctttat cggtgtggcg    2460
cgccttgacg gccgcctcgg attcacttcg cagggcactt ctgacgcgct caagcgtgcc    2520
cagcgtggtg ccatctttgg cctctgcaag accatcggcc tcgagtggtc cgagtctgac    2580
gtcttttccc gcggcgtgga cattgctcag ggcatgcacc ccgaggatgc cgccgtggcg    2640
attgtgcgcg agatggcgtg cgctgacatt cgcattcgcg aggtcggcat tggcgcaaac    2700
cagcagcgct gcacgatccg tgccgccaag ctcgagaccg gcaacccgca gcgccagatc    2760
gccaaggacg acgtgctgct cgtttctggc ggcgctcgcg gcatcacgcc tctttgcatc    2820
cgggagatca cgcgccagat cgcgggcggc aagtacattc tgcttggccg cagcaaggtc    2880
tctgcgagcg aaccggcatg gtgcgctggc atcactgacg agaaggctgt gcaaaaggct    2940
gctacccagg agctcaagcg cgcctttagc gctggcgagg gccccaagcc cacgccccgc    3000
gctgtcacta gcttgtggg ctctgttctt ggcgctcgcg aggtgcgcag ctctattgct     3060
gcgattgaag cgctcggcgg caaggccatc tactcgtcgt gcgacgtgaa ctctgccgcc    3120
gacgtggcca aggccgtgcg cgatgccgag tcccagctcg gtgcccgcgt ctcgggcatc    3180
gttcatgcct cggcgtgct ccgcgaccgt ctcatcgaga agaagctccc cgacgagttc      3240
gacgccgtct ttggcaccaa ggtcaccggt ctcgagaacc tcctcgccgc cgtcgaccgc    3300
gccaacctca gcacatggt cctcttcagc tcgctcgccg gcttccacgg caacgtcggc      3360
cagtctgact acgccatggc caacgaggcc cttaacaaga tgggcctcga gctcgccaag    3420
gacgtctcgg tcaagtcgat ctgcttcggt ccctgggacg tggcatggt gacgccgcag      3480 ctcaagaagc agttccagga gatgggcgtg cagatcatcc ccgcgagggg cggcgctgat    3540
accgtggcgc gcatcgtgct cggctcctcg ccggctgaga tccttgtcgg caactggcgc    3600
accccgtcca agaaggtcgg ctcggacacc atcaccctgc accgcaagat tccgccaag     3660
```

-continued

| | |
|---|---|
| tccaacccct tcctcgagga ccacgtcatc cagggccgcc gcgtgctgcc catgacgctg | 3720 |
| gccattggct cgctcgcgga gacctgcctc ggcctcttcc ccggctactc gctctgggcc | 3780 |
| attgacgacg cccagctctt caagggtgtc actgtcgacg gcgacgtcaa ctgcgaggtg | 3840 |
| accctcaccc cgtcgacggc gccctcgggc cgcgtcaacg tccaggccac gctcaagacc | 3900 |
| ttttccagcg gcaagctggt cccggcctac gcgcgccgtca tcgtgctctc caaccagggc | 3960 |
| gcgccccccgg ccaacgccac catgcagccg ccctcgctcg atgccgatcc ggcgctccag | 4020 |
| ggctccgtct acgacggcaa gaccctcttc cacggcccgg ccttccgcgg catcgatgac | 4080 |
| gtgctctcgt gcaccaagag ccagcttgtg gccaagtgca gcgctgtccc cggctccgac | 4140 |
| gccgctcgcg gcgagtttgc cacggacact gacgcccatg acccttcgt gaacgacctg | 4200 |
| gcctttcagg ccatgctcgt ctgggtgcgc cgcacgctcg gccaggctgc gctccccaac | 4260 |
| tcgatccagc gcatcgtcca gcaccgcccg gtcccgcagg acaagcccctt ctacattacc | 4320 |
| ctccgctcca accagtcggg cggtcactcc cagcacaagc acgcccttca gttccacaac | 4380 |
| gagcagggcg atctcttcat tgatgtccag gcttcggtca tcgccacgga cagccttgcc | 4440 |
| ttctaa | 4446 |

<210> SEQ ID NO 70
<211> LENGTH: 1481
<212> TYPE: PRT
<213> ORGANISM: Schizochytrium aggregatum

<400> SEQUENCE: 70

```
Arg Cys Arg Arg Val Ser Pro Arg Arg Ala Ala Pro Pro Pro Pro Leu
  1               5                  10                  15

Ala Arg Thr Pro Ala Arg Leu Ala Ala Pro Ala Val Ser Asn Glu Leu
             20                  25                  30

Leu Glu Lys Ala Glu Thr Val Val Met Glu Val Leu Ala Ala Lys Thr
         35                  40                  45

Gly Tyr Glu Thr Asp Met Ile Glu Ser Asp Met Glu Leu Glu Thr Glu
     50                  55                  60

Leu Gly Ile Asp Ser Ile Lys Arg Val Glu Ile Leu Ser Glu Val Gln
 65                  70                  75                  80

Ala Met Leu Asn Val Glu Ala Lys Asp Val Asp Ala Leu Ser Arg Thr
                 85                  90                  95

Arg Thr Val Gly Glu Val Val Asn Ala Met Lys Ala Glu Ile Ala Gly
            100                 105                 110

Gly Ser Ala Pro Ala Pro Ala Ala Ala Pro Gly Pro Ala Ala Ala
        115                 120                 125

Ala Pro Ala Pro Ala Val Ser Ser Glu Leu Leu Glu Lys Ala Glu Thr
    130                 135                 140

Val Val Met Glu Val Leu Ala Ala Lys Thr Gly Tyr Glu Thr Asp Met
145                 150                 155                 160

Ile Glu Ser Asp Met Glu Leu Glu Thr Glu Leu Gly Ile Asp Ser Ile
                165                 170                 175

Lys Arg Val Glu Ile Leu Ser Glu Val Gln Ala Met Leu Asn Val Glu
            180                 185                 190

Ala Lys Asp Val Asp Ala Leu Ser Arg Thr Arg Thr Val Gly Glu Val
        195                 200                 205

Val Asp Ala Met Lys Ala Glu Ile Ala Gly Ser Ser Ala Ser Ala Pro
    210                 215                 220
```

```
Ala Ala Ala Ala Pro Ala Pro Ala Ala Ala Pro Ala Pro Ala Ala
225                 230                 235                 240

Ala Ala Pro Ala Val Ser Asn Glu Leu Leu Glu Lys Ala Glu Thr Val
            245                 250                 255

Val Met Glu Val Leu Ala Ala Lys Thr Gly Tyr Glu Thr Asp Met Ile
        260                 265                 270

Glu Ser Asp Met Glu Leu Glu Thr Glu Leu Gly Ile Asp Ser Ile Lys
        275                 280                 285

Arg Val Glu Ile Leu Ser Glu Val Gln Ala Met Leu Asn Val Glu Ala
        290                 295                 300

Lys Asp Val Asp Ala Leu Ser Arg Thr Arg Thr Val Gly Glu Val Val
305                 310                 315                 320

Asp Ala Met Lys Ala Glu Ile Ala Gly Gly Ser Ala Pro Ala Pro Ala
                325                 330                 335

Ala Ala Ala Pro Ala Pro Ala Ala Ala Pro Ala Val Ser Asn Glu
            340                 345                 350

Leu Leu Glu Lys Ala Glu Thr Val Val Met Glu Val Leu Ala Ala Lys
        355                 360                 365

Thr Gly Tyr Glu Thr Asp Met Ile Glu Ser Asp Met Glu Leu Glu Thr
        370                 375                 380

Glu Leu Gly Ile Asp Ser Ile Lys Arg Val Glu Ile Leu Ser Glu Val
385                 390                 395                 400

Gln Ala Met Leu Asn Val Glu Ala Lys Asp Val Asp Ala Leu Ser Arg
            405                 410                 415

Thr Arg Thr Val Gly Glu Val Val Asp Ala Met Lys Ala Glu Ile Ala
        420                 425                 430

Gly Ser Ser Ala Pro Ala Pro Ala Ala Ala Pro Ala Pro Ala Ala
            435                 440                 445

Ala Ala Pro Ala Pro Ala Ala Ala Pro Ala Val Ser Ser Glu Leu
        450                 455                 460

Leu Glu Lys Ala Glu Thr Val Val Met Glu Val Leu Ala Ala Lys Thr
465                 470                 475                 480

Gly Tyr Glu Thr Asp Met Ile Glu Ser Asp Met Glu Leu Glu Thr Glu
            485                 490                 495

Leu Gly Ile Asp Ser Ile Lys Arg Val Glu Ile Leu Ser Glu Val Gln
        500                 505                 510

Ala Met Leu Asn Val Glu Ala Lys Asp Val Asp Ala Leu Ser Arg Thr
        515                 520                 525

Arg Thr Val Gly Glu Val Val Asp Ala Met Lys Ala Glu Ile Ala Gly
        530                 535                 540

Gly Ser Ala Pro Ala Pro Ala Ala Ala Pro Ala Pro Ala Ala Ala
545                 550                 555                 560

Ala Pro Ala Val Ser Asn Glu Leu Leu Glu Lys Ala Glu Thr Val Val
            565                 570                 575

Met Glu Val Leu Ala Ala Lys Thr Gly Tyr Glu Thr Asp Met Ile Glu
        580                 585                 590

Ser Asp Met Glu Leu Glu Thr Glu Leu Gly Ile Asp Ser Ile Lys Arg
        595                 600                 605

Val Glu Ile Leu Ser Glu Val Gln Ala Met Leu Asn Val Glu Ala Lys
        610                 615                 620

Asp Val Asp Ala Leu Ser Arg Thr Arg Thr Val Gly Glu Val Val Asp
625                 630                 635                 640

Ala Met Lys Ala Glu Ile Ala Gly Gly Ser Ala Pro Ala Pro Ala Ala
```

-continued

```
                645                 650                 655
Ala Ala Pro Ala Ser Ala Gly Ala Pro Ala Val Lys Ile Asp Ser
                660                 665                 670
Val His Gly Ala Asp Cys Asp Leu Ser Leu Met His Ala Lys Val
                675                 680                 685
Val Asp Ile Arg Arg Pro Asp Glu Leu Ile Leu Glu Arg Pro Glu Asn
                690                 695                 700
Arg Pro Val Leu Val Asp Asp Gly Ser Glu Leu Thr Leu Ala Leu
705                 710                 715                 720
Val Arg Val Leu Gly Ala Cys Ala Val Val Leu Thr Phe Glu Gly Leu
                725                 730                 735
Gln Leu Ala Gln Arg Ala Gly Ala Ala Ile Arg His Val Leu Ala
                740                 745                 750
Lys Asp Leu Ser Ala Glu Ser Ala Glu Lys Ala Ile Lys Glu Ala Glu
                755                 760                 765
Gln Arg Phe Gly Ala Leu Gly Gly Phe Ile Ser Gln Gln Ala Glu Arg
                770                 775                 780
Phe Glu Pro Ala Glu Ile Leu Gly Phe Thr Leu Met Cys Ala Lys Phe
785                 790                 795                 800
Ala Lys Ala Ser Leu Cys Thr Ala Val Ala Gly Gly Arg Pro Ala Phe
                805                 810                 815
Ile Gly Val Ala Arg Leu Asp Gly Arg Leu Gly Phe Thr Ser Gln Gly
                820                 825                 830
Thr Ser Asp Ala Leu Lys Arg Ala Gln Arg Gly Ala Ile Phe Gly Leu
                835                 840                 845
Cys Lys Thr Ile Gly Leu Glu Trp Ser Glu Ser Asp Val Phe Ser Arg
                850                 855                 860
Gly Val Asp Ile Ala Gln Gly Met His Pro Glu Asp Ala Ala Val Ala
865                 870                 875                 880
Ile Val Arg Glu Met Ala Cys Ala Asp Ile Arg Ile Arg Glu Val Gly
                885                 890                 895
Ile Gly Ala Asn Gln Gln Arg Cys Thr Ile Arg Ala Ala Lys Leu Glu
                900                 905                 910
Thr Gly Asn Pro Gln Arg Gln Ile Ala Lys Asp Asp Val Leu Leu Val
                915                 920                 925
Ser Gly Gly Ala Arg Gly Ile Thr Pro Leu Cys Ile Arg Glu Ile Thr
                930                 935                 940
Arg Gln Ile Ala Gly Gly Lys Tyr Ile Leu Leu Gly Arg Ser Lys Val
945                 950                 955                 960
Ser Ala Ser Glu Pro Ala Trp Cys Ala Gly Ile Thr Asp Glu Lys Ala
                965                 970                 975
Val Gln Lys Ala Ala Thr Gln Glu Leu Lys Arg Ala Phe Ser Ala Gly
                980                 985                 990
Glu Gly Pro Lys Pro Thr Pro Arg Ala Val Thr Lys Leu Val Gly Ser
                995                 1000                1005
Val Leu Gly Ala Arg Glu Val Arg Ser Ser Ile Ala Ala Ile Glu Ala
        1010                1015                1020
Leu Gly Gly Lys Ala Ile Tyr Ser Ser Cys Asp Val Asn Ser Ala Ala
1025                1030                1035                1040
Asp Val Ala Lys Ala Val Arg Asp Ala Glu Ser Gln Leu Gly Ala Arg
                1045                1050                1055
Val Ser Gly Ile Val His Ala Ser Gly Val Leu Arg Asp Arg Leu Ile
                1060                1065                1070
```

-continued

```
Glu Lys Lys Leu Pro Asp Glu Phe Asp Ala Val Phe Gly Thr Lys Val
        1075                1080                1085

Thr Gly Leu Glu Asn Leu Leu Ala Ala Val Asp Arg Ala Asn Leu Lys
        1090                1095                1100

His Met Val Leu Phe Ser Ser Leu Ala Gly Phe His Gly Asn Val Gly
1105                1110                1115                1120

Gln Ser Asp Tyr Ala Met Ala Asn Glu Ala Leu Asn Lys Met Gly Leu
                1125                1130                1135

Glu Leu Ala Lys Asp Val Ser Val Lys Ser Ile Cys Phe Gly Pro Trp
            1140                1145                1150

Asp Gly Gly Met Val Thr Pro Gln Leu Lys Lys Gln Phe Gln Glu Met
            1155                1160                1165

Gly Val Gln Ile Ile Pro Arg Glu Gly Ala Asp Thr Val Ala Arg
        1170                1175                1180

Ile Val Leu Gly Ser Ser Pro Ala Glu Ile Leu Val Gly Asn Trp Arg
1185                1190                1195                1200

Thr Pro Ser Lys Lys Val Gly Ser Asp Thr Ile Thr Leu His Arg Lys
            1205                1210                1215

Ile Ser Ala Lys Ser Asn Pro Phe Leu Glu Asp His Val Ile Gln Gly
            1220                1225                1230

Arg Arg Val Leu Pro Met Thr Leu Ala Ile Gly Ser Leu Ala Glu Thr
        1235                1240                1245

Cys Leu Gly Leu Phe Pro Gly Tyr Ser Leu Trp Ala Ile Asp Asp Ala
        1250                1255                1260

Gln Leu Phe Lys Gly Val Thr Val Asp Gly Asp Val Asn Cys Glu Val
1265                1270                1275                1280

Thr Leu Thr Pro Ser Thr Ala Pro Ser Gly Arg Val Asn Val Gln Ala
                1285                1290                1295

Thr Leu Lys Thr Phe Ser Ser Gly Lys Leu Val Pro Ala Tyr Arg Ala
            1300                1305                1310

Val Ile Val Leu Ser Asn Gln Gly Ala Pro Pro Ala Asn Ala Thr Met
        1315                1320                1325

Gln Pro Pro Ser Leu Asp Ala Asp Pro Ala Leu Gln Gly Ser Val Tyr
        1330                1335                1340

Asp Gly Lys Thr Leu Phe His Gly Pro Ala Phe Arg Gly Ile Asp Asp
1345                1350                1355                1360

Val Leu Ser Cys Thr Lys Ser Gln Leu Val Ala Lys Cys Ser Ala Val
                1365                1370                1375

Pro Gly Ser Asp Ala Ala Arg Gly Glu Phe Ala Thr Asp Thr Asp Ala
        1380                1385                1390

His Asp Pro Phe Val Asn Asp Leu Ala Phe Gln Ala Met Leu Val Trp
        1395                1400                1405

Val Arg Arg Thr Leu Gly Gln Ala Ala Leu Pro Asn Ser Ile Gln Arg
        1410                1415                1420

Ile Val Gln His Arg Pro Val Pro Gln Asp Lys Pro Phe Tyr Ile Thr
1425                1430                1435                1440

Leu Arg Ser Asn Gln Ser Gly Gly His Ser Gln His Lys His Ala Leu
            1445                1450                1455

Gln Phe His Asn Glu Gln Gly Asp Leu Phe Ile Asp Val Gln Ala Ser
            1460                1465                1470

Val Ile Ala Thr Asp Ser Leu Ala Phe
        1475                1480
```

-continued

<210> SEQ ID NO 71
<211> LENGTH: 5215
<212> TYPE: DNA
<213> ORGANISM: Schizochytrium aggregatum

<400> SEQUENCE: 71

| | | | | | |
|---|---|---|---|---|---|
| tgccgtcttt | gaggagcatg | acccctccaa | cgccgcctgc | acgggccacg | actccatttc | 60 |
| tgcgctctcg | gcccgctgcg | gcggtgaaag | caacatgcgc | atcgccatca | ctggtatgga | 120 |
| cgccaccttt | ggcgctctca | agggactcga | cgccttcgag | cgcgccattt | acaccggcgc | 180 |
| tcacggtgcc | atcccactcc | cagaaaagcg | ctggcgcttt | ctcggcaagg | acaaggactt | 240 |
| tcttgacctc | tgcggcgtca | aggccacccc | gcacggctgc | tacattgaag | atgttgaggt | 300 |
| cgacttccag | cgcctccgca | cgcccatgac | ccctgaagac | atgctcctcc | ctcagcagct | 360 |
| tctggccgtc | accaccattg | accgcgccat | cctcgactcg | ggaatgaaaa | agggtggcaa | 420 |
| tgtcgccgtc | tttgtcggcc | tcggcaccga | cctcgagctc | taccgtcacc | gtgctcgcgt | 480 |
| cgctctcaag | gagcgcgtcc | gccctgaagc | ctccaagaag | ctcaatgaca | tgatgcagta | 540 |
| cattaacgac | tgcggcacat | ccacatcgta | cacctcgtac | attggcaacc | tcgtcgccac | 600 |
| gcgcgtctcg | tcgcagtggg | gcttcacggg | cccctccttt | acgatcaccg | agggcaacaa | 660 |
| ctccgtctac | cgctgcgccg | agctcggcaa | gtacctcctc | gagaccggcg | aggtcgatgg | 720 |
| cgtcgtcgtt | gcgggtgtcg | atctctgcgg | cagtgccgaa | aacctttacg | tcaagtctcg | 780 |
| ccgcttcaag | gtgtccacct | ccgatacccc | gcgcgccagc | tttgacgccg | ccgccgatgg | 840 |
| ctactttgtc | ggcgagggct | gcggtgcctt | tgtgctcaag | cgtgagacta | gctgcaccaa | 900 |
| ggacgaccgt | atctacgctt | gcatggatgc | catcgtccct | ggcaacgtcc | ctagcgcctg | 960 |
| cttgcgcgag | gccctcgacc | aggcgcgcgt | caagccgggc | gatatcgaga | tgctcgagct | 1020 |
| cagcgccgac | tccgcccgcc | acctcaagga | cccgtccgtc | ctgcccaagg | agctcactgc | 1080 |
| cgaggaggaa | atcggcggcc | ttcagacgat | ccttcgtgac | gatgacaagc | tcccgcgcaa | 1140 |
| cgtcgcaacg | ggcagtgtca | aggccaccgt | cggtgacacc | ggttatgcct | ctggtgctgc | 1200 |
| cagcctcatc | aaggctgcgc | tttgcatcta | caaccgctac | ctgcccagca | acggcgacga | 1260 |
| ctgggatgaa | cccgcccctg | aggcgccctg | ggacagcacc | ctctttgcgt | gccagacctc | 1320 |
| gcgcgcttgg | ctcaagaacc | ctggcgagcg | tcgctatgcg | gccgtctcgg | gcgtctccga | 1380 |
| gacgcgctcg | tgctattccg | tgctcctctc | cgaagccgag | ggccactacg | agcgcgagaa | 1440 |
| ccgcatctcg | ctcgacgagg | aggcgcccaa | gctcattgtg | cttcgcgccg | actcccacga | 1500 |
| ggagatcctt | ggtcgcctcg | acaagatccg | cgagcgcttc | ttgcagccca | cgggcgccgc | 1560 |
| cccgcgcgag | tccgagctca | aggcgcaggc | ccgccgcatc | ttcctcgagc | tcctcggcga | 1620 |
| gacccttgcc | caggatgccg | cttcttcagg | ctcgcaaaag | cccctcgctc | tcagcctcgt | 1680 |
| ctccacgccc | tccaagctcc | agcgcgaggt | cgagctcgcg | gccaagggta | tcccgcgctg | 1740 |
| cctcaagatg | cgccgcgatt | ggagctcccc | tgctggcagc | cgctacgcgc | ctgagccgct | 1800 |
| cgccagcgac | cgcgtcgcct | tcatgtacgg | cgaaggtcgc | agcccttact | acggcatcac | 1860 |
| ccaagacatt | caccgcattt | ggcccgaact | ccacgaggtc | atcaacgaaa | agacgaaccg | 1920 |
| tctctgggcc | gaaggcgacc | gctgggtcat | gccgcgcgcc | agcttcaagt | cggagctcga | 1980 |
| gagccagcag | caagagtttg | atcgcaacat | gattgaaatg | ttccgtcttg | gaatcctcac | 2040 |
| ctcaattgcc | ttcaccaatc | tggcgcgcga | cgttctcaac | atcacgccca | aggccgcctt | 2100 |
| tggcctcagt | cttggcgaga | tttccatgat | ttttgccttt | tccaagaaga | acggtctcat | 2160 |

-continued

```
ctccgaccag ctcaccaagg atcttcgcga gtccgacgtg tggaacaagg ctctggccgt    2220
tgaatttaat gcgctgcgcg aggcctgggg cattccacag agtgtcccca aggacgagtt    2280
ctggcaaggc tacattgtgc gcggcaccaa gcaggatatc gaggcggcca tcgcccggga    2340
cagcaagtac gtgcgcctca ccatcatcaa tgatgccaac accgccctca ttagcggcaa    2400
gcccgacgcc tgcaaggctg cgatcgcgcg tctcggtggc aacattcctg cgcttcccgt    2460
gacccagggc atgtgcggcc actgccccga ggtgggacct tataccaagg atatcgccaa    2520
gatccatgcc aaccttgagt tccccgttgt cgacggcctt gacctctgga ccacaatcaa    2580
ccagaagcgc ctcgtgccac gcgccacggg cgccaaggac gaatgggccc cttcttcctt    2640
tggcgagtac gccggccagc tctacgagaa gcaggctaac ttcccccaaa tcgtcgagac    2700
catttacaag caaaactacg acgtctttgt cgaggttggg cccaacaacc accgtagcac    2760
cgcagtgcgc accacgcttg gtccccagcg caaccaccTt gctggcgcca tcgacaagca    2820
gaacgaggat gcttggacga ccatcgtcaa gcttgtggct cgctcaaggg cccaccttgt    2880
tcctggcgtc acgatctcgc cgctgtacca ctccaagctt gtggcggagg ctcaggcttg    2940
ctacgctgcg ctctgcaagg gtgaaaagcc caagaagaac aagtttgtgc gcaagattca    3000
gctcaacggt cgcttcaaca gcaaggcgga ccccatctcc tcggccgatc ttgccagctt    3060
tccgcctgcg gaccctgcca ttgaagccgc catctcgagc cgcatcatga agcctgtcgc    3120
tcccaagttc tacgcgcgtc tcaacattga cgagcaggac gagacccgag atccgatcct    3180
caacaaggac aacgcgccgt cttcttcttc ttcttcttct tcttcttctt cttcttcttc    3240
ttctccgtcg cctgctcctt cggccccgt gcaaaagaag gctgctcccg ccgcggagac    3300
caaggctgtt gcttcggctg acgcacttcg cagtgccctg ctcgatctcg acagtatgct    3360
tgcgctgagc tctgccagtg cctccggcaa ccttgttgag actgcgccta gcgacgcctc    3420
ggtcattgtg ccgccctgca acattgcgga tctcggcagc cgcgccttca tgaaaacgta    3480
cggtgtttcg gcgcctctgt acacgggcgc catggccaag gcattgcct ctgcggacct    3540 cgtcattgcc gccggccgcc agggcatcct tgcgtccttt ggcgccggcg gacttcccat    3600
gcaggttgtg cgtgagtcca tcgaaaagat tcaggccgcc ctgcccaatg gcccgtacgc    3660
tgtcaacctt atccattctc cctttgacag caacctcgaa aagggcaatg tcgatctctt    3720
cctcgagaag ggtgtcacct tgtcgaggc ctcggccttt atgacgctca ccccgcaggt    3780
cgtgcggtac cgcgcggctg gcctcacgcg caacgccgac ggctcggtca acatccgcaa    3840
ccgtatcatt ggcaaggtct cgcgcaccga gctcgccgag atgttcatgc gtcctgcgcc    3900
cgagcacctc cttcagaagc tcattgcttc cggcgagatc aaccaggagc aggccgagct    3960
cgcccgccgt gttcccgtcg ctgacgacat cgcggtcgaa gctgactcgg gtggccacac    4020
cgacaaccgc cccatccacg tcattctgcc cctcatcatc aaccttcgcg accgccttca    4080
ccgcgagtgc ggctacccgg ccaaccttcg cgtccgtgtg ggcgccggcg gtggcattgg    4140
gtgcccccag gcgcgctgg ccaccttcaa catgggtgcc tcctttattg tcaccggcac    4200
cgtgaaccag gtcgccaagc agtcgggcac gtgcgacaat gtgcgcaagc agctcgcgaa    4260
ggccacttac tcggacgtat gcatggcccc ggctgccgac atgttcgagg aaggcgtcaa    4320
gcttcaggtc ctcaagaagg gaaccatgtt tccctcgcgc gccaacaagc tctacgagct    4380
cttttgcaag tacgactcgt tcgagtccat gccccccgca gagcttgcgc gcgtcgagaa    4440
gcgcatcttc agccgcgcgc tcgaagaggt ctgggacgag accaaaaaact tttacattaa    4500
```

-continued

```
ccgtcttcac aacccggaga agatccagcg cgccgagcgc gacccccaagc tcaagatgtc   4560
gctgtgcttt cgctggtacc tgagcctggc gagccgctgg gccaacactg gagcttccga   4620
tcgcgtcatg gactaccagg tctggtgcgg tcctgccatt ggttccttca acgatttcat   4680
caagggaact taccttgatc cggccgtcgc aaacgagtac ccgtgcgtcg ttcagattaa   4740
caagcagatc cttcgtggag cgtgcttctt gcgccgtctc gaaattctgc gcaacgcacg   4800
cctttccgat ggcgctgccg ctcttgtggc cagcatcgat gacacatacg tcccggccga   4860
gaagctgtaa gtaagctctc atatatgtta gttgcgtgag accgacacga agataatatc   4920
acatacgctt ttgtttgttc tttcaattat ttgtctgtgc ttcatgttgc tcctcagtat   4980
ctagctggcg gctcttatct tcttttaaaa tatctggaca aggacaaaaa caagaataaa   5040
ggcgagaaga tgtgaatttc atttcgactt gagaactcga agagcattga tgcggttagt   5100
atatgggtat tttccagaca cttttcatca tcatcatcat catcatcatt atgaagaagt   5160
agtagctgat aaagtagact cactgtttgc agcgagaaaa aaaaaaaaaa aaaaa        5215
```

<210> SEQ ID NO 72
<211> LENGTH: 1622
<212> TYPE: PRT
<213> ORGANISM: Schizochytrium aggregatum

<400> SEQUENCE: 72

```
Ala Val Phe Glu Glu His Asp Pro Ser Asn Ala Ala Cys Thr Gly His
 1               5                  10                  15

Asp Ser Ile Ser Ala Leu Ser Ala Arg Cys Gly Gly Glu Ser Asn Met
            20                  25                  30

Arg Ile Ala Ile Thr Gly Met Asp Ala Thr Phe Gly Ala Leu Lys Gly
        35                  40                  45

Leu Asp Ala Phe Glu Arg Ala Ile Tyr Thr Gly Ala His Gly Ala Ile
    50                  55                  60

Pro Leu Pro Glu Lys Arg Trp Arg Phe Leu Lys Asp Lys Asp Phe
 65                  70                  75                  80

Leu Asp Leu Cys Gly Val Lys Ala Thr Pro His Gly Cys Tyr Ile Glu
                85                  90                  95

Asp Val Glu Val Asp Phe Gln Arg Leu Arg Thr Pro Met Thr Pro Glu
            100                 105                 110

Asp Met Leu Leu Pro Gln Gln Leu Leu Ala Val Thr Thr Ile Asp Arg
        115                 120                 125

Ala Ile Leu Asp Ser Gly Met Lys Lys Gly Gly Asn Val Ala Val Phe
    130                 135                 140

Val Gly Leu Gly Thr Asp Leu Glu Leu Tyr Arg His Arg Ala Arg Val
145                 150                 155                 160

Ala Leu Lys Glu Arg Val Arg Pro Glu Ala Ser Lys Lys Leu Asn Asp
                165                 170                 175

Met Met Gln Tyr Ile Asn Asp Cys Gly Thr Ser Thr Ser Tyr Thr Ser
            180                 185                 190

Tyr Ile Gly Asn Leu Val Ala Thr Arg Val Ser Ser Gln Trp Gly Phe
        195                 200                 205

Thr Gly Pro Ser Phe Thr Ile Thr Glu Gly Asn Asn Ser Val Tyr Arg
    210                 215                 220

Cys Ala Glu Leu Gly Lys Tyr Leu Leu Glu Thr Gly Glu Val Asp Gly
225                 230                 235                 240

Val Val Val Ala Gly Val Asp Leu Cys Gly Ser Ala Glu Asn Leu Tyr
                245                 250                 255
```

```
Val Lys Ser Arg Arg Phe Lys Val Ser Thr Ser Asp Thr Pro Arg Ala
            260                 265                 270

Ser Phe Asp Ala Ala Ala Asp Gly Tyr Phe Val Gly Glu Gly Cys Gly
            275                 280                 285

Ala Phe Val Leu Lys Arg Glu Thr Ser Cys Thr Lys Asp Asp Arg Ile
            290                 295                 300

Tyr Ala Cys Met Asp Ala Ile Val Pro Gly Asn Val Pro Ser Ala Cys
305                 310                 315                 320

Leu Arg Glu Ala Leu Asp Gln Ala Arg Val Lys Pro Gly Asp Ile Glu
            325                 330                 335

Met Leu Glu Leu Ser Ala Asp Ser Ala Arg His Leu Lys Asp Pro Ser
            340                 345                 350

Val Leu Pro Lys Glu Leu Thr Ala Glu Glu Ile Gly Gly Leu Gln
            355                 360                 365

Thr Ile Leu Arg Asp Asp Asp Lys Leu Pro Arg Asn Val Ala Thr Gly
            370                 375                 380

Ser Val Lys Ala Thr Val Gly Asp Thr Gly Tyr Ala Ser Gly Ala Ala
385                 390                 395                 400

Ser Leu Ile Lys Ala Ala Leu Cys Ile Tyr Asn Arg Tyr Leu Pro Ser
            405                 410                 415

Asn Gly Asp Asp Trp Asp Glu Pro Ala Pro Glu Ala Pro Trp Asp Ser
            420                 425                 430

Thr Leu Phe Ala Cys Gln Thr Ser Arg Ala Trp Leu Lys Asn Pro Gly
            435                 440                 445

Glu Arg Arg Tyr Ala Ala Val Ser Gly Val Ser Glu Thr Arg Ser Cys
450                 455                 460

Tyr Ser Val Leu Leu Ser Glu Ala Glu Gly His Tyr Glu Arg Glu Asn
465                 470                 475                 480

Arg Ile Ser Leu Asp Glu Glu Ala Pro Lys Leu Ile Val Leu Arg Ala
            485                 490                 495

Asp Ser His Glu Glu Ile Leu Gly Arg Leu Asp Lys Ile Arg Glu Arg
            500                 505                 510

Phe Leu Gln Pro Thr Gly Ala Ala Pro Arg Glu Ser Glu Leu Lys Ala
            515                 520                 525

Gln Ala Arg Arg Ile Phe Leu Glu Leu Leu Gly Glu Thr Leu Ala Gln
            530                 535                 540

Asp Ala Ala Ser Ser Gly Ser Gln Lys Pro Leu Ala Leu Ser Leu Val
545                 550                 555                 560

Ser Thr Pro Ser Lys Leu Gln Arg Glu Val Glu Leu Ala Ala Lys Gly
            565                 570                 575

Ile Pro Arg Cys Leu Lys Met Arg Arg Asp Trp Ser Ser Pro Ala Gly
            580                 585                 590

Ser Arg Tyr Ala Pro Glu Pro Leu Ala Ser Asp Arg Val Ala Phe Met
            595                 600                 605

Tyr Gly Glu Gly Arg Ser Pro Tyr Tyr Gly Ile Thr Gln Asp Ile His
            610                 615                 620

Arg Ile Trp Pro Glu Leu His Glu Val Ile Asn Glu Lys Thr Asn Arg
625                 630                 635                 640

Leu Trp Ala Glu Gly Asp Arg Trp Val Met Pro Arg Ala Ser Phe Lys
            645                 650                 655

Ser Glu Leu Glu Ser Gln Gln Gln Glu Phe Asp Arg Asn Met Ile Glu
            660                 665                 670
```

-continued

```
Met Phe Arg Leu Gly Ile Leu Thr Ser Ile Ala Phe Thr Asn Leu Ala
            675                 680                 685

Arg Asp Val Leu Asn Ile Thr Pro Lys Ala Ala Phe Gly Leu Ser Leu
            690                 695                 700

Gly Glu Ile Ser Met Ile Phe Ala Phe Ser Lys Lys Asn Gly Leu Ile
705                 710                 715                 720

Ser Asp Gln Leu Thr Lys Asp Leu Arg Glu Ser Asp Val Trp Asn Lys
                725                 730                 735

Ala Leu Ala Val Glu Phe Asn Ala Leu Arg Glu Ala Trp Gly Ile Pro
            740                 745                 750

Gln Ser Val Pro Lys Asp Glu Phe Trp Gln Gly Tyr Ile Val Arg Gly
            755                 760                 765

Thr Lys Gln Asp Ile Glu Ala Ala Ile Ala Pro Asp Ser Lys Tyr Val
            770                 775                 780

Arg Leu Thr Ile Ile Asn Asp Ala Asn Thr Ala Leu Ile Ser Gly Lys
785                 790                 795                 800

Pro Asp Ala Cys Lys Ala Ala Ile Ala Arg Leu Gly Gly Asn Ile Pro
                805                 810                 815

Ala Leu Pro Val Thr Gln Gly Met Cys Gly His Cys Pro Glu Val Gly
            820                 825                 830

Pro Tyr Thr Lys Asp Ile Ala Lys Ile His Ala Asn Leu Glu Phe Pro
            835                 840                 845

Val Val Asp Gly Leu Asp Leu Trp Thr Thr Ile Asn Gln Lys Arg Leu
            850                 855                 860

Val Pro Arg Ala Thr Gly Ala Lys Asp Glu Trp Ala Pro Ser Ser Phe
865                 870                 875                 880

Gly Glu Tyr Ala Gly Gln Leu Tyr Glu Lys Gln Ala Asn Phe Pro Gln
                885                 890                 895

Ile Val Glu Thr Ile Tyr Lys Gln Asn Tyr Asp Val Phe Val Glu Val
                900                 905                 910

Gly Pro Asn Asn His Arg Ser Thr Ala Val Arg Thr Thr Leu Gly Pro
            915                 920                 925

Gln Arg Asn His Leu Ala Gly Ala Ile Asp Lys Gln Asn Glu Asp Ala
            930                 935                 940

Trp Thr Thr Ile Val Lys Leu Val Ala Ser Leu Lys Ala His Leu Val
945                 950                 955                 960

Pro Gly Val Thr Ile Ser Pro Leu Tyr His Ser Lys Leu Val Ala Glu
                965                 970                 975

Ala Gln Ala Cys Tyr Ala Ala Leu Cys Lys Gly Glu Lys Pro Lys Lys
                980                 985                 990

Asn Lys Phe Val Arg Lys Ile Gln Leu Asn Gly Arg Phe Asn Ser Lys
            995                 1000                1005

Ala Asp Pro Ile Ser Ser Ala Asp Leu Ala Ser Phe Pro Ala Asp
    1010                1015                1020

Pro Ala Ile Glu Ala Ala Ile Ser Ser Arg Ile Met Lys Pro Val Ala
    1025                1030                1035                1040

Pro Lys Phe Tyr Ala Arg Leu Asn Ile Asp Glu Gln Asp Glu Thr Arg
                1045                1050                1055

Asp Pro Ile Leu Asn Lys Asp Asn Ala Pro Ser Ser Ser Ser Ser
    1060                1065                1070

Ser Ser Ser Ser Ser Ser Ser Ser Pro Ser Pro Ala Pro Ser Ala
    1075                1080                1085

Pro Val Gln Lys Lys Ala Ala Pro Ala Ala Glu Thr Lys Ala Val Ala
```

```
                1090                1095                1100
Ser Ala Asp Ala Leu Arg Ser Ala Leu Leu Asp Leu Asp Ser Met Leu
1105                1110                1115                1120

Ala Leu Ser Ser Ala Ser Ala Ser Gly Asn Leu Val Glu Thr Ala Pro
                1125                1130                1135

Ser Asp Ala Ser Val Ile Val Pro Pro Cys Asn Ile Ala Asp Leu Gly
                1140                1145                1150

Ser Arg Ala Phe Met Lys Thr Tyr Gly Val Ser Ala Pro Leu Tyr Thr
                1155                1160                1165

Gly Ala Met Ala Lys Gly Ile Ala Ser Ala Asp Leu Val Ile Ala Ala
1170                1175                1180

Gly Arg Gln Gly Ile Leu Ala Ser Phe Gly Ala Gly Leu Pro Met
1185                1190                1195                1200

Gln Val Val Arg Glu Ser Ile Glu Lys Ile Gln Ala Ala Leu Pro Asn
                1205                1210                1215

Gly Pro Tyr Ala Val Asn Leu Ile His Ser Pro Phe Asp Ser Asn Leu
                1220                1225                1230

Glu Lys Gly Asn Val Asp Leu Phe Leu Glu Lys Gly Val Thr Phe Val
                1235                1240                1245

Glu Ala Ser Ala Phe Met Thr Leu Thr Pro Gln Val Val Arg Tyr Arg
                1250                1255                1260

Ala Ala Gly Leu Thr Arg Asn Ala Asp Gly Ser Val Asn Ile Arg Asn
1265                1270                1275                1280

Arg Ile Ile Gly Lys Val Ser Arg Thr Glu Leu Ala Glu Met Phe Met
                1285                1290                1295

Arg Pro Ala Pro Glu His Leu Leu Gln Lys Leu Ile Ala Ser Gly Glu
                1300                1305                1310

Ile Asn Gln Glu Gln Ala Glu Leu Ala Arg Arg Val Pro Val Ala Asp
                1315                1320                1325

Asp Ile Ala Val Glu Ala Asp Ser Gly Gly His Thr Asp Asn Arg Pro
                1330                1335                1340

Ile His Val Ile Leu Pro Leu Ile Ile Asn Leu Arg Asp Arg Leu His
1345                1350                1355                1360

Arg Glu Cys Gly Tyr Pro Ala Asn Leu Arg Val Arg Val Gly Ala Gly
                1365                1370                1375

Gly Gly Ile Gly Cys Pro Gln Ala Ala Leu Ala Thr Phe Asn Met Gly
                1380                1385                1390

Ala Ser Phe Ile Val Thr Gly Thr Val Asn Gln Val Ala Lys Gln Ser
                1395                1400                1405

Gly Thr Cys Asp Asn Val Arg Lys Gln Leu Ala Lys Ala Thr Tyr Ser
                1410                1415                1420

Asp Val Cys Met Ala Pro Ala Ala Asp Met Phe Glu Glu Gly Val Lys
1425                1430                1435                1440

Leu Gln Val Leu Lys Lys Gly Thr Met Phe Pro Ser Arg Ala Asn Lys
                1445                1450                1455

Leu Tyr Glu Leu Phe Cys Lys Tyr Asp Ser Phe Glu Ser Met Pro Pro
                1460                1465                1470

Ala Glu Leu Ala Arg Val Glu Lys Arg Ile Phe Ser Arg Ala Leu Glu
                1475                1480                1485

Glu Val Trp Asp Glu Thr Lys Asn Phe Tyr Ile Asn Arg Leu His Asn
                1490                1495                1500

Pro Glu Lys Ile Gln Arg Ala Glu Arg Asp Pro Lys Leu Lys Met Ser
1505                1510                1515                1520
```

-continued

```
Leu Cys Phe Arg Trp Tyr Leu Ser Leu Ala Ser Arg Trp Ala Asn Thr
            1525                1530                1535

Gly Ala Ser Asp Arg Val Met Asp Tyr Gln Val Trp Cys Gly Pro Ala
        1540                1545                1550

Ile Gly Ser Phe Asn Asp Phe Ile Lys Gly Thr Tyr Leu Asp Pro Ala
        1555                1560                1565

Val Ala Asn Glu Tyr Pro Cys Val Val Gln Ile Asn Lys Gln Ile Leu
        1570                1575                1580

Arg Gly Ala Cys Phe Leu Arg Arg Leu Glu Ile Leu Arg Asn Ala Arg
1585                1590                1595                1600

Leu Ser Asp Gly Ala Ala Leu Val Ala Ser Ile Asp Asp Thr Tyr
        1605                1610                1615

Val Pro Ala Glu Lys Leu
        1620

<210> SEQ ID NO 73
<211> LENGTH: 1551
<212> TYPE: PRT
<213> ORGANISM: Schizochytrium aggregatum

<400> SEQUENCE: 73

Arg Ala Glu Ala Gly Arg Glu Pro Glu Pro Ala Pro Gln Ile Thr Ser
1               5                   10                  15

Thr Ala Ala Glu Ser Gln Gln Gln Gln Gln Gln Gln Gln Gln Gln Gln
            20                  25                  30

Gln Gln Gln Gln Pro Arg Glu Gly Asp Lys Glu Lys Ala Ala Glu Thr
        35                  40                  45

Met Ala Leu Arg Val Lys Thr Asn Lys Lys Pro Cys Trp Glu Met Thr
    50                  55                  60

Lys Glu Glu Leu Thr Ser Gly Lys Thr Glu Val Phe Asn Tyr Glu Glu
65              70                  75                  80

Leu Leu Glu Phe Ala Glu Gly Asp Ile Ala Lys Val Phe Gly Pro Glu
            85                  90                  95

Phe Ala Val Ile Asp Lys Tyr Pro Arg Arg Val Arg Leu Pro Ala Arg
            100                 105                 110

Glu Tyr Leu Leu Val Thr Arg Val Thr Leu Met Asp Ala Glu Val Asn
        115                 120                 125

Asn Tyr Arg Val Gly Ala Arg Met Val Thr Glu Tyr Asp Leu Pro Val
130             135                 140

Asn Gly Glu Leu Ser Glu Gly Gly Asp Cys Pro Trp Ala Val Leu Val
145                 150                 155                 160

Glu Ser Gly Gln Cys Asp Leu Met Leu Ile Ser Tyr Met Gly Ile Asp
            165                 170                 175

Phe Gln Asn Gln Gly Asp Arg Val Tyr Arg Leu Leu Asn Thr Thr Leu
        180                 185                 190

Thr Phe Tyr Gly Val Ala His Glu Gly Glu Thr Leu Glu Tyr Asp Ile
    195                 200                 205

Arg Val Thr Gly Phe Ala Lys Arg Leu Asp Gly Ile Ser Met Phe
    210                 215                 220

Phe Phe Glu Tyr Asp Cys Tyr Val Asn Gly Arg Leu Leu Ile Glu Met
225                 230                 235                 240

Arg Asp Gly Cys Ala Gly Phe Phe Thr Asn Glu Glu Leu Asp Ala Gly
            245                 250                 255

Lys Gly Val Val Phe Thr Arg Gly Asp Leu Ala Ala Arg Ala Lys Ile
```

-continued

```
                    260                 265                 270
Pro Lys Gln Asp Val Ser Pro Tyr Ala Val Ala Pro Cys Leu His Lys
        275                 280                 285
Thr Lys Leu Asn Glu Lys Glu Met Gln Thr Leu Val Asp Lys Asp Trp
        290                 295                 300
Ala Ser Val Phe Gly Ser Lys Asn Gly Met Pro Glu Ile Asn Tyr Lys
305                 310                 315                 320
Leu Cys Ala Arg Lys Met Leu Met Ile Asp Arg Val Thr Ser Ile Asp
                325                 330                 335
His Lys Gly Gly Val Tyr Gly Leu Gly Gln Leu Val Gly Glu Lys Ile
                340                 345                 350
Leu Glu Arg Asp His Trp Tyr Phe Pro Cys His Phe Val Lys Asp Gln
                355                 360                 365
Val Met Ala Gly Ser Leu Val Ser Asp Gly Cys Ser Gln Met Leu Lys
        370                 375                 380
Met Tyr Met Ile Trp Leu Gly Leu His Leu Thr Thr Gly Pro Phe Asp
385                 390                 395                 400
Phe Arg Pro Val Asn Gly His Pro Asn Lys Val Arg Cys Arg Gly Gln
                405                 410                 415
Ile Ser Pro His Lys Gly Lys Leu Val Tyr Val Met Glu Ile Lys Glu
                420                 425                 430
Met Gly Phe Asp Glu Asp Asn Asp Pro Tyr Ala Ile Ala Asp Val Asn
                435                 440                 445
Ile Ile Asp Val Asp Phe Glu Lys Gly Gln Asp Phe Ser Leu Asp Arg
        450                 455                 460
Ile Ser Asp Tyr Gly Lys Gly Asp Leu Asn Lys Lys Ile Val Val Asp
465                 470                 475                 480
Phe Lys Gly Ile Ala Leu Lys Met Gln Lys Arg Ser Thr Asn Lys Asn
                485                 490                 495
Pro Ser Lys Val Gln Pro Val Phe Ala Asn Gly Ala Ala Thr Val Gly
                500                 505                 510
Pro Glu Ala Ser Lys Ala Ser Ser Gly Ala Ser Ala Ser Ala Ser Ala
                515                 520                 525
Ala Pro Ala Lys Pro Ala Phe Ser Ala Asp Val Leu Ala Pro Lys Pro
        530                 535                 540
Val Ala Leu Pro Glu His Ile Leu Lys Gly Asp Ala Leu Ala Pro Lys
545                 550                 555                 560
Glu Met Ser Trp His Pro Met Ala Arg Ile Pro Gly Asn Pro Thr Pro
                565                 570                 575
Ser Phe Ala Pro Ser Ala Tyr Lys Pro Arg Asn Ile Ala Phe Thr Pro
                580                 585                 590
Phe Pro Gly Asn Pro Asn Asp Asn Asp His Thr Pro Gly Lys Met Pro
                595                 600                 605
Leu Thr Trp Phe Asn Met Ala Glu Phe Met Ala Gly Lys Val Ser Met
        610                 615                 620
Cys Leu Gly Pro Glu Phe Ala Lys Phe Asp Asp Ser Asn Thr Ser Arg
625                 630                 635                 640
Ser Pro Ala Trp Asp Leu Ala Leu Val Thr Arg Ala Val Ser Val Ser
                645                 650                 655
Asp Leu Lys His Val Asn Tyr Arg Asn Ile Asp Leu Asp Pro Ser Lys
                660                 665                 670
Gly Thr Met Val Gly Glu Phe Asp Cys Pro Ala Asp Ala Trp Phe Tyr
                675                 680                 685
```

-continued

```
Lys Gly Ala Cys Asn Asp Ala His Met Pro Tyr Ser Ile Leu Met Glu
    690                 695                 700
Ile Ala Leu Gln Thr Ser Gly Val Leu Thr Ser Val Leu Lys Ala Pro
705                 710                 715                 720
Leu Thr Met Glu Lys Asp Asp Ile Leu Phe Arg Asn Leu Asp Ala Asn
                725                 730                 735
Ala Glu Phe Val Arg Ala Asp Leu Asp Tyr Arg Gly Lys Thr Ile Arg
            740                 745                 750
Asn Val Thr Lys Cys Thr Gly Tyr Ser Met Leu Gly Glu Met Gly Val
                755                 760                 765
His Arg Phe Thr Phe Glu Leu Tyr Val Asp Asp Val Leu Phe Tyr Lys
            770                 775                 780
Gly Ser Thr Ser Phe Gly Trp Phe Val Pro Glu Val Phe Ala Ala Gln
785                 790                 795                 800
Ala Gly Leu Asp Asn Gly Arg Lys Ser Glu Pro Trp Phe Ile Glu Asn
                805                 810                 815
Lys Val Pro Ala Ser Gln Val Ser Ser Phe Asp Val Arg Pro Asn Gly
            820                 825                 830
Ser Gly Arg Thr Ala Ile Phe Ala Asn Ala Pro Ser Gly Ala Gln Leu
                835                 840                 845
Asn Arg Arg Thr Asp Gln Gly Gln Tyr Leu Asp Ala Val Asp Ile Val
            850                 855                 860
Ser Gly Ser Gly Lys Lys Ser Leu Gly Tyr Ala His Gly Ser Lys Thr
865                 870                 875                 880
Val Asn Pro Asn Asp Trp Phe Phe Ser Cys His Phe Trp Phe Asp Ser
                885                 890                 895
Val Met Pro Gly Ser Leu Gly Val Glu Ser Met Phe Gln Leu Val Glu
            900                 905                 910
Ala Ile Ala Ala His Glu Asp Leu Ala Gly Lys Ala Arg His Cys Gln
            915                 920                 925
Pro His Leu Cys Ala Arg Pro Arg Ala Arg Ser Ser Trp Lys Tyr Arg
    930                 935                 940
Gly Gln Leu Thr Pro Lys Ser Lys Lys Met Asp Ser Glu Val His Ile
945                 950                 955                 960
Val Ser Val Asp Ala His Asp Gly Val Val Asp Leu Val Ala Asp Gly
                965                 970                 975
Phe Leu Trp Ala Asp Ser Leu Arg Val Tyr Ser Val Ser Asn Ile Arg
            980                 985                 990
Val Arg Ile Ala Ser Gly Glu Ala Pro Ala Ala Ser Ser Ala Ala
            995                 1000                1005
Ser Val Gly Ser Ser Ala Ser Ser Val Glu Arg Thr Arg Ser Ser Pro
    1010                1015                1020
Ala Val Ala Ser Gly Pro Ala Gln Thr Ile Asp Leu Lys Gln Leu Lys
1025                1030                1035                1040
Thr Glu Leu Leu Glu Leu Asp Ala Pro Leu Tyr Leu Ser Gln Asp Pro
                1045                1050                1055
Thr Ser Gly Gln Leu Lys Lys His Thr Asp Val Ala Ser Gly Gln Ala
                1060                1065                1070
Thr Ile Val Gln Pro Cys Thr Leu Gly Asp Leu Gly Asp Arg Ser Phe
            1075                1080                1085
Met Glu Thr Tyr Gly Val Val Ala Pro Leu Tyr Thr Gly Ala Met Ala
    1090                1095                1100
```

-continued

Lys Gly Ile Ala Ser Ala Asp Leu Val Ile Ala Ala Gly Lys Arg Lys
1105                1110                1115                1120

Ile Leu Gly Ser Phe Gly Ala Gly Leu Pro Met His His Val Arg
           1125                1130                1135

Ala Ala Leu Glu Lys Ile Gln Ala Leu Pro Gln Gly Pro Tyr Ala
           1140                1145                1150

Val Asn Leu Ile His Ser Pro Phe Asp Ser Asn Leu Glu Lys Gly Asn
           1155                1160                1165

Val Asp Leu Phe Leu Glu Lys Gly Val Thr Val Glu Ala Ser Ala
1170                1175                1180

Phe Met Thr Leu Thr Pro Gln Val Val Arg Tyr Arg Ala Ala Gly Leu
1185                1190                1195                1200

Ser Arg Asn Ala Asp Gly Ser Val Asn Ile Arg Asn Arg Ile Ile Gly
           1205                1210                1215

Lys Val Ser Arg Thr Glu Leu Ala Glu Met Phe Ile Arg Pro Ala Pro
           1220                1225                1230

Glu His Leu Leu Glu Lys Leu Ile Ala Ser Gly Glu Ile Thr Gln Glu
           1235                1240                1245

Gln Ala Glu Leu Ala Arg Arg Val Pro Val Ala Asp Asp Ile Ala Val
           1250                1255                1260

Glu Ala Asp Ser Gly Gly His Thr Asp Asn Arg Pro Ile His Val Ile
1265                1270                1275                1280

Leu Pro Leu Ile Ile Asn Leu Arg Asn Arg Leu His Arg Glu Cys Gly
           1285                1290                1295

Tyr Pro Ala His Leu Arg Val Arg Val Gly Ala Gly Gly Val Gly
           1300                1305                1310

Cys Pro Gln Ala Ala Ala Ala Leu Thr Met Gly Ala Ala Phe Ile
           1315                1320                1325

Val Thr Gly Thr Val Asn Gln Val Ala Lys Gln Ser Gly Thr Cys Asp
           1330                1335                1340

Asn Val Arg Lys Gln Leu Ser Gln Ala Thr Tyr Ser Asp Ile Cys Met
1345                1350                1355                1360

Ala Pro Ala Ala Asp Met Phe Glu Glu Gly Val Lys Leu Gln Val Leu
           1365                1370                1375

Lys Lys Gly Thr Met Phe Pro Ser Arg Ala Asn Lys Leu Tyr Glu Leu
           1380                1385                1390

Phe Cys Lys Tyr Asp Ser Phe Asp Ser Met Pro Pro Ala Glu Leu Glu
           1395                1400                1405

Arg Ile Glu Lys Arg Ile Phe Lys Arg Ala Leu Gln Glu Val Trp Glu
           1410                1415                1420

Glu Thr Lys Asp Phe Tyr Ile Asn Gly Leu Lys Asn Pro Glu Lys Ile
1425                1430                1435                1440

Gln Arg Ala Glu His Asp Pro Lys Leu Lys Met Ser Leu Cys Phe Arg
           1445                1450                1455

Trp Tyr Leu Gly Leu Ala Ser Arg Trp Ala Asn Met Gly Ala Pro Asp
           1460                1465                1470

Arg Val Met Asp Tyr Gln Val Trp Cys Gly Pro Ala Ile Gly Ala Phe
           1475                1480                1485

Asn Asp Phe Ile Lys Gly Thr Tyr Leu Asp Pro Ala Val Ser Asn Glu
           1490                1495                1500

Tyr Pro Cys Val Val Gln Ile Asn Leu Gln Ile Leu Arg Gly Ala Cys
1505                1510                1515                1520

Tyr Leu Arg Arg Leu Asn Ala Leu Arg Asn Asp Pro Arg Ile Asp Leu

|   | 1525 |   |   |   | 1530 |   |   |   |   | 1535 |   |
|---|---|---|---|---|---|---|---|---|---|---|---|
| Glu | Thr | Glu | Asp | Ala | Ala | Phe | Val | Tyr | Glu | Pro | Thr | Asn | Ala | Leu |
|   |   | 1540 |   |   |   |   | 1545 |   |   |   | 1550 |

<210> SEQ ID NO 74
<211> LENGTH: 30
<212> TYPE: DNA
<213> ORGANISM: Schizochytrium aggregatum

<400> SEQUENCE: 74
taccgcggca agactatccg caacgtcacc                                      30

<210> SEQ ID NO 75
<211> LENGTH: 30
<212> TYPE: DNA
<213> ORGANISM: Schizochytrium aggregatum

<400> SEQUENCE: 75
gccgtcgtgg gcgtccacgg acacgatgtg                                      30

<210> SEQ ID NO 76
<211> LENGTH: 4767
<212> TYPE: DNA
<213> ORGANISM: Schizochytrium aggregatum

<400> SEQUENCE: 76

```
cgagcagagg ccggccgcga gcccgagccc gcgccgcaga tcactagtac cgctgcggaa      60
tcacagcagc agcagcagca gcagcagcag cagcagcagc agcagcagcc acgagaggga     120
gataaagaaa aagcggcaga gacgatggcg ctccgtgtca agacgaacaa gaagccatgc     180
tgggagatga ccaaggagga gctgaccagc ggcaagaccg aggtgttcaa ctatgaggaa     240
ctcctcgagt tcgcagaggg cgacatcgcc aaggtcttcg acccgagtt cgccgtcatc      300
gacaagtacc cgcgccgcgt gcgcctgccc gcccgcgagt acctgctcgt gacccgcgtc     360
accctcatgg acgccgaggt caacaactac cgcgtcggcg cccgcatggt caccgagtac     420
gatctccccg tcaacggaga gctctccgag ggcgagact gccccctggc cgtcctggtc      480
gagagtggcc agtgcgatct catgctcatc tcctacatgg gcattgactt ccagaaccag     540
ggcgaccgcg tctaccgcct gctcaacacc acgctcacct tttacggcgt ggcccacgag     600
ggcgagaccc tcgagtacga cattcgcgtc accggcttcg ccaagcgtct cgacggcggc     660
atctccatgt tcttcttcga gtacgactgc tacgtcaacg gccgcctcct catcgagatg     720
cgcgatggct gcgccggctt cttcaccaac gaggagctcg acgccggcaa gggcgtcgtc     780
ttcacccgcg cgcgacctcgc cgcccgcgcc aagatcccaa gcaggacgt ctcccccta c     840
gccgtcgccc cctgcctcca caagaccaag ctcaacgaaa aggagatgca gaccctcgtc     900
gacaaggact gggcatccgt ctttggctcc aagaacggca tgccggaaat caactacaaa     960
ctctgcgcgc gtaagatgct catgattgac cgcgtcacca gcattgacca caagggcggt    1020
gtctacggcc tcggtcagct cgtcggtgaa aagatcctcg agcgcgacca ctggtacttt    1080
ccctgccact tgtcaaggga tcaggtcatg gccggatccc tcgtctccga cggctgcagc    1140
cagatgctca agatgtacat gatctggctc ggcctccacc tcaccaccgg accctttgac    1200
ttccgcccgg tcaacggcca ccccaacaag gtccgctgcc gcggccaaat ctcccgcac     1260
aagggcaagc tcgtctacgt catggagatc aaggagatgg gcttgacga ggacaacgac    1320
ccgtacgcca ttgccgacgt caacatcatt gatgtcgact tcgaaaaggg ccaggacttt    1380
```

```
agcctcgacc gcatcagcga ctacggcaag ggcgacctca acaagaagat cgtcgtcgac    1440
tttaagggca tcgctctcaa gatgcagaag cgctccacca caagaaccc ctccaaggtt     1500 cagcccgtct ttgccaacgg cgccgccact gtcggcccg aggcctccaa ggcttcctcc     1560
ggcgccagcg ccagcgccag cgccgccccg gccaagcctg ccttcagcgc cgatgttctt    1620
gcgcccaagc ccgttgccct tcccgagcac atcctcaagg gcgacgccct cgccccccaag   1680 gagatgtcct ggcaccccat ggcccgcatc ccgggcaacc cgacgccctc ttttgcgccc    1740
tcggcctaca agccgcgcaa catcgccttt acgcccttcc ccggcaaccc caacgataac    1800
gaccacaccc cgggcaagat gccgctcacc tggttcaaca tggccgagtt catgccggc    1860 aaggtcagca tgtgcctcgg ccccgagttc gccaagttcg acgactcgaa caccagccgc   1920
agccccgctt gggacctcgc tctcgtcacc cgcgccgtgt ctgtgtctga cctcaagcac   1980
gtcaactacc gcaacatcga cctcgacccc tccaagggta ccatggtcgg cgagttcgac   2040
tgccccgcgg acgcctggtt ctacaagggc gcctgcaacg atgcccacat gccgtactcg   2100
atcctcatgg agatcgccct ccagacctcg ggtgtgctca cctcggtgct caaggcgccc   2160
ctgaccatgg agaaggacga catcctcttc cgcaacctcg acgccaacgc cgagttcgtg   2220
cgcgccgacc tcgactaccg cggcaagact atccgcaacg tcaccaagtg cactggctac   2280
agcatgctcg gcgagatggg cgtccaccgc ttcacctttg agctctacgt cgatgatgtg   2340
ctcttttaca agggctcgac ctcgttcggc tggttcgtgc ccgaggtytt tgccgcccag   2400
gccggcctcg acaacggccg caagtcggag ccctggttca ttgagaacaa ggttccggcc   2460
tcgcaggtct cctcctttga cgtgcgcccc aacggcagcg gccgcaccgc catcttcgcc   2520
aacgccccca gcgcgccca gctcaaccgc cgcacggacc agggccagta cctcgacgcc   2580
gtcgacattg tctccggcag cggcaagaag agcctcggct acgcccacgg ttccaagacg   2640
gtcaacccga cgactggtt cttctcgtgc cacttttggt ttgactcggt catgcccgga   2700
agtctcggtg tcgagtccat gttccagctc gtcgaggcca tcgccgccca cgaggatctc   2760
gctggcaaag cacggcattg ccaaccccac ctttgtgcac gccccggcc aagatcaagc    2820 tggaagtacc gcggscagct cacgcccaag agcaagaaga tggactcgga ggtccacatc   2880
gtgtccgtgg acgcccacga cggcgttgtc gacctcgtcg ccgacggctt cctctgggcc   2940
gacagcctcc gcgtctactc ggtgagcaac attcgcgtgc gcatcgcctc cggtgaggcc   3000
cctgccgccg cctcctccgc cgcctctgtg ggcctcctcg gcttcgtccgt cgagcgcacg   3060 cgctcgagcc ccgctgtcgc ctccggcccg gcccagacca tcgacctcaa gcagctcaag   3120
accgagctcc tcgagctcga tgccccgctc tacctctcgc aggacccgac cagcggccag   3180
ctcaagaagc acaccgacgt ggcctccggc caggccacca tcgtgcagcc ctgcacgctc   3240
ggcgacctcg gtgaccgctc cttcatggag acctacggcg tcgtcgcccc gctgtacacg   3300
ggcgccatgc ccaagggcat tgcctcggcg gacctcgtca tcgccgccgg caagcgcaag   3360
atcctcggct cctttggcgc cggcggcctc cccatgcacc acgtgcgcgc cgccctcgag   3420
aagatccagg ccgccctgcc tcagggcccc tacgccgtca acctcatcca ctcgcctttt    3480
gacagcaacc tcgagaaggg caacgtcgat ctcttcctcg agaagggcgt cactgtggtg   3540
gaggcctcgg cattcatgac cctcaccccg caggtcgtgc gctaccgcgc cgccggcctc   3600
tcgcgcaacg ccgacggttc ggtcaacatc cgcaaccgca tcatcggcaa ggtctcgcgc   3660
accgagctcg ccgagatgtt catccgcccg gccccgagc acctcctcga aagctcatc    3720 gcctcgggcg agatcaccca ggagcaggcc gagctcgcgc gccgcgttcc cgtcgccgac   3780
```

-continued

```
gatatcgctg tcgaggctga ctcgggcggc cacaccgaca accgccccat ccacgtcatc    3840
ctcccgctca tcatcaacct ccgcaaccgc ctgcaccgcg agtgcggcta ccccgcgcac    3900
ctccgcgtcc gcgttggcgc cggcggtggc gtcggctgcc cgcaggccgc cgccgccgcg    3960
ctcaccatgg gcgccgcctt catcgtcacc ggcactgtca accaggtcgc caagcagtcc    4020
ggcacctgcg acaacgtgcg caagcagctc tcgcaggcca cctactcgga tatctgcatg    4080
gccccggccg ccgacatgtt cgaggagggc gtcaagctcc aggtcctcaa gaagggaacc    4140
atgttcccct cgcgcgccaa caagctctac gagctctttt gcaagtacga ctccttcgac    4200
tccatgcctc ctgccgagct cgagcgcatc gagaagcgta tcttcaagcg cgcactccag    4260
gaggtctggg aggagaccaa ggacttttac attaacggtc tcaagaaccc ggagaagatc    4320
cagcgcgccg agcacgaccc caagctcaag atgtcgctct gcttccgctg gtaccttggt    4380
cttgccagcc gctgggccaa catgggcgcc ccggaccgcg tcatggacta ccaggtctgg    4440
tgtggcccgg ccattggcgc cttcaacgac ttcatcaagg gcacctacct cgaccccgct    4500
gtctccaacg agtaccccct gtcgtccag atcaacctgc aaatcctccg tggtgcctgc    4560
tacctgcgcc gtctcaacgc cctgcgcaac gacccgcgca ttgacctcga gaccgaggat    4620
gctgcctttg tctacgagcc caccaacgcg ctctaagaaa gtgaaccttg tcctaacccg    4680
acagcgaatg gcgggagggg gcgggctaaa agatcgtatt acatagtatt tttcccctac    4740
tctttgtgaa aaaaaaaaa aaaaaaa                                        4767
```

<210> SEQ ID NO 77
<211> LENGTH: 7959
<212> TYPE: DNA
<213> ORGANISM: Vibrio marinus

<400> SEQUENCE: 77

```
atggctaaaa agaacaccac atcgattaag cacgccaagg atgtgttaag tagtgatgat      60
caacagttaa attctcgctt gcaagaatgt ccgattgcca tcattggtat ggcatcggtt     120
tttgcagatg ctaaaaactt ggatcaattc tgggataaca tcgttgactc tgtgacgct     180 attattgatg tgcctagcga tcgctggaac attgacgacc attactcggc tgataaaaaa     240
gcagctgaca agacatactg caaacgcggt ggtttcattc cagagcttga ttttgatccg     300
atggagtttg gtttaccgcc aaatatcctc gagttaactg acatcgctca attgttgtca     360
ttaattgttg ctcgtgatgt attaagtgat gctggcattg gtagtgatta tgaccatgat     420
aaaattggta tcacgctggg tgtcggtggt ggtcagaaac aaatttcgcc attaacgtcg     480
cgcctacaag gccccggtatt agaaaaagta ttaaaagcct caggcattga tgaagatgat     540
cgcgctatga tcatcgacaa atttaaaaaa gcctacatcg gctgggaaga gaactcattc     600
ccaggcatgc taggtaacgt tattgctggt cgtatcgcca atcgttttga ttttggtggt     660
actaactgtg tggttgatgc ggcatgcgct ggctcccttg cagctgttaa aatggcgatc     720
tcagacttac ttgaatatcg ttcagaagtc atgatatcgg tggtgtatg ttgtgataac     780 tcgccattca tgtatatgtc attctcgaaa acaccagcat ttaccaccaa tgatgatatc     840
cgtccgtttg atgacgattc aaaaggcatg ctggttggtg aagtattgg catgatggcg     900 tttaaacgtc ttgaagatgt tgaacgtgac ggcgacaaaa tttattctgt actgaaaggt     960
atcggtacat cttcgatgg tcgtttcaaa tctatttacg ctcccgcc agatggccaa    1020 gcaaaagcgc taaaacgtgc ttatgaagat gccggttttg cccctgaaac atgtggtcta    1080
```

```
attgaaggcc atggtacggg taccaaagcg ggtgatgccg cagaatttgc tggcttgacc      1140
aaacactttg gcgccgccag tgatgaaaag caatatatcg ccttaggctc agttaaatcg      1200
caaattggtc atactaaatc tgcggctggc tctgcgggta tgattaaggc ggcattagcg      1260
ctgcatcata aaatcttacc tgcaacgatc catatcgata aaccaagtga agccttggat      1320
atcaaaaaca gcccgttata cctaaacagc gaaacgcgtc cttggatgcc acgtgaagat      1380
ggtattccac gtcgtgcagg tatcagctca tttggttttg gcggcaccaa cttccatatt      1440
attttagaag agtatcgccc aggtcacgat agcgcatatc gcttaaactc agtgagccaa      1500
actgtgttga tctcggcaaa cgaccaacaa ggtattgttg ctgagttaaa taactggcgt      1560
actaaactgg ctgtcgatgc tgatcatcaa gggtttgtat ttaatgagtt agtgacaacg      1620
tggccattaa aaaccccatc cgttaaccaa gctcgtttag gttttgttgc gcgtaatgca      1680
aatgaagcga tcgcgatgat tgatacggca ttgaaacaat tcaatgcgaa cgcagataaa      1740
atgacatggt cagtacctac cggggtttac tatcgtcaag ccggtattga tgcaacaggt      1800
aaagtggttg cgctattctc agggcaaggt tcgcaatacg tgaacatggg tcgtgaatta      1860
acctgtaact tcccaagcat gatgcacagt gctgcggcga tggataaaga gttcagtgcc      1920
gctggtttag gccagttatc tgcagttact ttccctatcc ctgtttatac ggatgccgag      1980
cgtaagctac aagaagagca attacgttta acgaacatg cgcaaccagc gattggtagt      2040
ttgagtgttg gtctgttcaa aacgtttaag caagcaggtt ttaaagctga ttttgctgcc      2100
ggtcatagtt tcggtgagtt aaccgcatta tgggctgccg atgtattgag cgaaagcgat      2160
tacatgatgt tagcgcgtag tcgtggtcaa gcaatggctg cgccagagca caagattttt      2220
gatgcaggta agatggccgc tgttgttggt gatccaaagc aagtcgctgt gatcattgat      2280
acccttgatg atgtctctat tgctaacttc aactcgaata accaagttgt tattgctggt      2340
actacggagc aggttgctgt agcggttaca accttaggta atgctggttt caaagttgtg      2400
ccactgccgg tatctgctgc gttccataca cctttagttc gtcacgcgca aaaaccattt      2460
gctaaagcgg ttgatagcgc taaatttaaa gcgccaagca ttccagtgtt tgctaatggc      2520
acaggcttgg tgcattcaag caaaccgaat gacattaaga aaaacctgaa aaaccacatg      2580
ctggaatctg ttcatttcaa tcaagaaatt gacaacatct atgctgatgg tggccgcgta      2640
tttatcgaat ttggtccaaa gaatgtatta actaaattgg ttgaaaacat tctcactgaa      2700
aaatctgatg tgactgctat cgcggttaat gctaatccta acaacctgc ggacgtacaa      2760 atgcgccaag ctgcgctgca aatggcagtg cttggtgtcg cattagacaa tattgacccg      2820
tacgacgccg ttaagcgtcc acttgttgcg ccgaaagcat caccaatgtt gatgaagtta      2880
tctgcagcgt cttatgttag tccgaaaacg aagaaagcgt ttgctgatgc attgactgat      2940
ggctggactg ttaagcaagc gaaagctgta cctgctgttg tgtcacaacc acaagtgatt      3000
gaaaagatcg ttgaagttga aaagatagtt gaacgcattg tcgaagtaga gcgtattgtc      3060
gaagtagaaa aaatcgtcta cgttaatgct gacggttcgc ttatatcgca aaataatcaa      3120
gacgttaaca gcgctgttgt tagcaacgtg actaatagct cagtgactca tagcagtgat      3180
gctgaccttg ttgcctctat tgaacgcagt gttggtcaat tgttgcaca ccaacagcaa      3240 ttattaaatg tacatgaaca gtttatgcaa ggtccacaag actacgcgaa aacagtgcag      3300
aacgtacttg ctgcgcagac gagcaatgaa ttaccggaaa gtttagaccg tacattgtct      3360
atgtataacg agttccaatc agaaacgcta cgtgtacatg aaacgtacct gaacaatcag      3420
acgagcaaca tgaacaccat gcttactggt gctgaagctg atgtgctagc aaccccaata      3480
```

```
actcaggtag tgaatacagc cgttgccact agtcacaagg tagttgctcc agttattgct   3540
aatacagtga cgaatgttgt atctagtgtc agtaataacg cggcggttgc agtgcaaact   3600
gtggcattag cgcctacgca agaaatcgct ccaacagtcg ctactacgcc agcacccgca   3660
ttggttgcta tcgtggctga acctgtgatt gttgcgcatg ttgctacaga agttgcacca   3720
attacaccat cagttacacc agttgtcgca actcaagcgg ctatcgatgt agcaactatt   3780
aacaaagtaa tgttagaagt tgttgctgat aaaaccggtt atccaacgga tatgctggaa   3840
ctgagcatgg acatggaagc tgacttaggt atcgactcaa tcaaacgtgt tgagatatta   3900
ggcgcagtac aggaattgat ccctgactta cctgaactta atcctgaaga tcttgctgag   3960
ctacgcacgc ttggtgagat tgtcgattac atgaattcaa aagcccaggc tgtagctcct   4020
acaacagtac ctgtaacaag tgcacctgtt tcgcctgcat ctgctggtat tgatttagcc   4080
cacatccaaa acgtaatgtt agaagtggtt gcagacaaaa ccggttaccc aacagacatg   4140
ctagaactga gcatggatat ggaagctgac ttaggtattg attcaatcaa gcgtgtggaa   4200
atcttaggtg cagtacagga gatcataact gatttacctg agctaaaccc tgaagatctt   4260
gctgaattac gcaccctagg tgaaatcgtt agttacatgc aaagcaaagc gccagtcgct   4320
gaaagtgcgc cagtggcgac ggctcctgta gcaacaagct cagcaccgtc tatcgatttg   4380
aaccacattc aaacagtgat gatggatgta gttgcagata agactggtta tccaactgac   4440
atgctagaac ttggcatgga catgaaagct gatttaggta tcgattcaat caaacgtgtg   4500
gaaatattag gcgcagtgca ggagatcatc actgatttac ctgagctaaa cccagaagac   4560
ctcgctgaat tacgcacgct aggtgaaatc gttagttaca tgcaaagcaa agcgccagtc   4620
gctgagagtg cgccagtagc gacggcttct gtagcaacaa gctctgcacc gtctatcgat   4680
ttaaaccata tccaaacagt gatgatggaa gtggttgcag acaaaaccgg ttatccagta   4740
gacatgttag aacttgctat ggacatggaa gctgacctag gtatcgattc aatcaagcgt   4800
gtagaaattt aggtgcggt acaggaaatc attactgact tacctgagct taaccctgaa   4860
gatcttgctg aactacgtac attaggtgaa atcgttagtt acatgcaaag caaagcgccc   4920
gtagctgaag cgcctgcagt acctgttgca gtagaaagtg cacctactag tgtaacaagc   4980
tcagcaccgt ctatcgattt agaccacatc caaaatgtaa tgatgatgt tgttgctgat   5040 aagactggtt atcctgccaa tatgcttgaa ttagcaatgg acatggaagc cgaccttggt   5100
attgattcaa tcaagcgtgt tgaaattcta ggcgcggtac aggagatcat tactgattta   5160
cctgaactaa acccagaaga cttagctgaa ctacgtacgt tagaagaaat tgtaacctac   5220
atgcaaagca aggcgagtgg tgttactgta aatgtagtgg ctagccctga aaataatgct   5280
gtatcagatg catttatgca aagcaatgtg gcgactatca cagcggccgc agaacataag   5340
gcggaattta aaccggcgcc gagcgcaacc gttgctatct ctcgtctaag ctctatcagt   5400
aaaataagcc aagattgtaa aggtgctaac gccttaatcg tagctgatgg cactgataat   5460
gctgtgttac ttgcagacca cctattgcaa actggctgga atgtaactgc attgcaacca   5520
acttgggtag ctgtaacaac gacgaaagca tttaataagt cagtgaacct ggtgactta   5580 aatggcgttg atgaaactga atcaacaac attattactg ctaacgcaca attggatgca   5640
gttatctatc tgcacgcaag tagcgaaatt aatgctatcg aatacccaca agcatctaag   5700
caaggcctga tgttagcctt cttattagcg aaattgagta agtaactca agccgctaaa   5760 gtgcgtggcg cctttatgat tgttactcag cagggtggtt cattaggttt tgatgatatc   5820
```

| | | | | |
|---|---|---|---|---|
| gattctgcta | caagtcatga | tgtgaaaaca | gacctagtac | aaagcggctt aaacggttta | 5880 |
| gttaagacac | tgtctcacga | gtgggataac | gtattctgtc | gtgcggttga tattgcttcg | 5940 |
| tcattaacgg | ctgaacaagt | tgcaagcctt | gttagtgatg | aactacttga tgctaacact | 6000 |
| gtattaacag | aagtgggtta | tcaacaagct | ggtaaaggcc | ttgaacgtat cacgttaact | 6060 |
| ggtgtggcta | ctgacagcta | tgcattaaca | gctggcaata | acatcgatgc taactcggta | 6120 |
| tttttagtga | gtggtggcgc | aaaaggtgta | actgcacatt | gtgttgctcg tatagctaaa | 6180 |
| gaatatcagt | ctaagttcat | cttattggga | cgttcaacgt | tctcaagtga cgaaccgagc | 6240 |
| tgggcaagtg | gtattactga | tgaagcggcg | ttaaagaaag | cagcgatgca gtctttgatt | 6300 |
| acagcaggtg | ataaaccaac | acccgttaag | atcgtacagc | taatcaaacc aatccaagct | 6360 |
| aatcgtgaaa | ttgcgcaaac | cttgtctgca | attaccgctg | ctggtggcca agctgaatat | 6420 |
| gtttctgcag | atgtaactaa | tgcagcaagc | gtacaaatgg | cagtcgctcc agctatcgct | 6480 |
| aagttcggtg | caatcactgg | catcattcat | ggcgcgggtg | tgttagctga ccaattcatt | 6540 |
| gagcaaaaaa | cactgagtga | ttttgagtct | gtttacagca | ctaaaattga cggtttgtta | 6600 |
| tcgctactat | cagtcactga | agcaagcaac | atcaagcaat | tggtattgtt ctcgtcagcg | 6660 |
| gctggtttct | acggtaaccc | cggccagtct | gattactcga | ttgccaatga gatcttaaat | 6720 |
| aaaaccgcat | accgctttaa | atcattgcac | ccacaagctc | aagtattgag ctttaactgg | 6780 |
| ggtccttggg | acggtggcat | ggtaacgcct | gagcttaaac | gtatgtttga ccaacgtggt | 6840 |
| gtttacatta | ttccacttga | tgcaggtgca | cagttattgc | tgaatgaact agccgctaat | 6900 |
| gataaccgtt | gtccacaaat | cctcgtgggt | aatgacttat | ctaaagatgc tagctctgat | 6960 |
| caaaagtctg | atgaaaagag | tactgctgta | aaaaagccac | aagttagtcg tttatcagat | 7020 |
| gctttagtaa | ctaaaagtat | caaagcgact | aacagtagct | ctttatcaaa caagactagt | 7080 |
| gctttatcag | acagtagtgc | ttttcaggtt | aacgaaaacc | acttttttagc tgaccacatg | 7140 |
| atcaaaggca | atcaggtatt | accaacggta | tgcgcgattg | cttggatgag tgatgcagca | 7200 |
| aaagcgactt | atagtaaccg | agactgtgca | ttgaagtatg | tcggtttcga agactataaa | 7260 |
| ttgtttaaag | gtgtggtttt | tgatggcaat | gaggcggcgg | attaccaaat ccaattgtcg | 7320 |
| cctgtgacaa | gggcgtcaga | acaggattct | gaagtccgta | ttgccgcaaa gatctttagc | 7380 |
| ctgaaaagtg | acggtaaacc | tgtgtttcat | tatgcagcga | caatattgtt agcaactcag | 7440 |
| ccacttaatg | ctgtgaaggt | agaacttccg | acattgacag | aaagtgttga tagcaacaat | 7500 |
| aaagtaactg | atgaagcaca | agcgttatac | agcaatggca | ccttgttcca cggtgaaagt | 7560 |
| ctgcagggca | ttaagcagat | attaagttgt | gacgacaagg | gcctgctatt ggcttgtcag | 7620 |
| ataaccgatg | ttgcaacagc | taagcaggga | tccttcccgt | tagctgacaa caatatcttt | 7680 |
| gccaatgatt | tggtttatca | ggctatgttg | gtctgggtgc | gcaaacaatt tggtttaggt | 7740 |
| agcttacctt | cggtgcacaac | ggcttggact | gtgtatcgtg | aagtggttgt agatgaagta | 7800 |
| ttttatctgc | aacttaatgt | tgttgagcat | gatctattgg | gttcacgcgg cagtaaagcc | 7860 |
| cgttgtgata | ttcaattgat | tgctgctgat | atgcaattac | ttgccgaagt gaaatcagcg | 7920 |
| caagtcagtg | tcagtgacat | tttgaacgat | atgtcatga | | 7959 |

<210> SEQ ID NO 78
<211> LENGTH: 2652
<212> TYPE: DNA
<213> ORGANISM: Vibrio marinus

<400> SEQUENCE: 78

-continued

| | | | | |
|---|---|---|---|---|
| atgacggaat | tagctgttat | tggtatggat | gctaaattta | gcggacaaga caatattgac | 60 |
| cgtgtggaac | gcgctttcta | tgaaggtgct | tatgtaggta | atgttagccg cgttagtacc | 120 |
| gaatctaatg | ttattagcaa | tggcgaagaa | caagttatta | ctgccatgac agttcttaac | 180 |
| tctgtcagtc | tactagcgca | aacgaatcag | ttaaatatag | ctgatatcgc ggtgttgctg | 240 |
| attgctgatg | taaaaagtgc | tgatgatcag | cttgtagtcc | aaattgcatc agcaattgaa | 300 |
| aaacagtgtg | cgagttgtgt | tgttattgct | gatttaggcc | aagcattaaa tcaagtagct | 360 |
| gatttagtta | ataaccaaga | ctgtcctgtg | gctgtaattg | gcatgaataa ctcggttaat | 420 |
| ttatctcgtc | atgatcttga | atctgtaact | gcaacaatca | gctttgatga aaccttcaat | 480 |
| ggttataaca | atgtagctgg | gttcgcgagt | ttacttatcg | cttcaactgc gtttgccaat | 540 |
| gctaagcaat | gttatatata | cgccaacatt | aagggcttcg | ctcaatcggg cgtaaatgct | 600 |
| caatttaacg | ttgaaacat | tagcgatact | gcaaagaccg | cattgcagca agctagcata | 660 |
| actgcagagc | aggttggttt | gttagaagtg | tcagcagtcg | ctgattcggc aatcgcattg | 720 |
| tctgaaagcc | aaggtttaat | gtctgcttat | catcatacgc | aaactttgca tactgcatta | 780 |
| agcagtgccc | gtagtgtgac | tggtgaaggc | gggtgttttt | cacaggtcgc aggtttattg | 840 |
| aaatgtgtaa | ttggtttaca | tcaacgttat | attccggcga | ttaaagattg gcaacaaccg | 900 |
| agtgacaatc | aaatgtcacg | gtggcggaat | tcaccattct | atatgcctgt agatgctcga | 960 |
| ccttggttcc | cacatgctga | tggctctgca | cacattgccg | cttatagttg tgtgactgct | 1020 |
| gacagctatt | gtcatattct | tttacaagaa | aacgtcttac | aagaacttgt tttgaaagaa | 1080 |
| acagtcttgc | aagataatga | cttaactgaa | agcaagcttc | agactcttga acaaaacaat | 1140 |
| ccagtagctg | atctgcgcac | taatggttac | tttgcatcga | gcgagttagc attaatcata | 1200 |
| gtacaaggta | atgacgaagc | acaattacgc | tgtgaattag | aaactattac agggcagtta | 1260 |
| agtactactg | gcataagtac | tatcagtatt | aaacagatcg | cagcagactg ttatgcccgt | 1320 |
| aatgatacta | acaaagccta | tagcgcagtg | cttattgccg | agactgctga agagttaagc | 1380 |
| aaagaaataa | ccttggcgtt | tgctggtatc | gctagcgtgt | ttaatgaaga tgctaaagaa | 1440 |
| tggaaaaccc | cgaagggcag | ttatttttacc | gcgcagcctg | caaataaaca ggctgctaac | 1500 |
| agcacacaga | atggtgtcac | cttcatgtac | ccaggtattg | tgctacata tgttggttta | 1560 |
| gggcgtgatc | tatttcatct | attcccacag | atttatcagc | ctgtagcggc tttagccgat | 1620 |
| gacattggcg | aaagtctaaa | agatactta | cttaatccac | gcagtattag tcgtcatagc | 1680 |
| tttaaagaac | tcaagcagtt | ggatctggac | ctgcgcggta | acttagccaa tatcgctgaa | 1740 |
| gccggtgtgg | gttttgcttg | tgtgtttacc | aaggtatttg | aagaagtctt tgccgttaaa | 1800 |
| gctgactttg | ctacaggtta | tagcatgggt | gaagtaagca | tgtatgcagc actaggctgc | 1860 |
| tggcagcaac | cgggattgat | gagtgctcgc | cttgcacaat | cgaataccTt taatcatcaa | 1920 |
| ctttgcggcg | agttaagaac | actacgtcag | cattgggca | tggatgatgt agctaacggt | 1980 |
| acgttcgagc | agatctggga | aacctatacc | attaaggcaa | cgattgaaca ggtcgaaatt | 2040 |
| gcctctgcag | atgaagatcg | tgtgtattgc | accattatca | atacacctga tagcttgttg | 2100 |
| ttagccggtt | atccagaagc | ctgtcagcga | gtcattaaga | attttaggtgt gcgtgcaatg | 2160 |
| gcattgaata | tggcgaacgc | aattcacagc | gcgccagctt | atgccgaata cgatcatatg | 2220 |
| gttgagctat | accatatgga | tgttactcca | cgtattaata | ccaagatgta ttcaagctca | 2280 |
| tgttatttac | cgattccaca | acgcagcaaa | gcgatttccc | acagtattgc taaatgtttg | 2340 |

-continued

```
tgtgatgtgg tggatttccc acgtttggtt aataccttac atgacaaagg tgcgcgggta      2400
ttcattgaaa tgggtccagg tcgttcgtta tgtagctggg tagataagat cttagttaat      2460
ggcgatggcg ataataaaaa gcaaagccaa catgtatctg ttcctgtgaa tgccaaaggc      2520
accagtgatg aacttactta tattcgtgcg attgctaagt taattagtca tggcgtgaat      2580
ttgaatttag atagcttgtt taacgggtca atcctggtta aagcaggcca tatagcaaac      2640
acgaacaaat ag                                                         2652
```

<210> SEQ ID NO 79
<211> LENGTH: 6057
<212> TYPE: DNA
<213> ORGANISM: Vibrio marinus

<400> SEQUENCE: 79

```
atggatttaa agagagtaat tatggaaaat attgcagtag taggtattgc taatttgttc       60
ccgggctcac aagcaccgga tcaattttgg cagcaattgc ttgaacaaca agattgccgc      120
agtaaggcga ccgctgttca atgggcgtt gatcctgcta aatataccgc caacaaaggt      180
gacacagata aattttactg tgtgcacggc ggttacatca gtgatttcaa ttttgatgct      240
tcaggttatc aactcgataa tgattatta gccggtttag atgaccttaa tcaatggggg      300
ctttatgtta cgaaacaagc ccttaccgat gcgggttatt gggcagtac tgcactagaa      360 aactgtggtg tgattttagg taatttgtca ttcccaacta aatcatctaa tcagctgttt      420
atgcctttgt atcatcaagt tgttgataat gccttaaagg cggtattaca tcctgatttt      480
caattaacgc attacacagc accgaaaaaa acacatgctg acaatgcatt agtagcaggt      540
tatccagctg cattgatcgc gcaagcggcg ggtcttggtg gttcacattt tgcactggat      600
gcggcttgtg cttcatcttg ttatagcgtt aagttagcgt gtgattacct gcatacgggt      660
aaagccaaca tgatgcttgc tggtgcggta tctgcagcag atcctatgtt cgtaaatatg      720
ggtttctcga tattccaagc ttacccagct aacaatgtac atgccccgtt tgaccaaaat      780
tcacaaggtc tatttgccgg tgaaggcgcg ggcatgatgg tattgaaacg tcaaagtgat      840
gcagtacgtg atggtgatca tatttacgcc attattaaag gcggcgcatt atcgaatgac      900
ggtaaaggcg agtttgtatt aagcccgaac accaagggcc aagtattagt atatgaacgt      960
gcttatgccg atgcagatgt tgacccgagt acagttgact atattgaatg tcatgcaacg     1020
ggcacaccta agggtgacaa tgttgaattg cgttcgatgg aaaccttttt cagtcgcgta     1080
aataacaaac cattactggg ctcggttaaa tctaaccttg gtcatttgtt aactgccgct     1140
ggtatgcctg gcatgaccaa agctatgtta gcgctaggta aggtcttat tcctgcaacg     1200 attaacttaa agcaaccact gcaatctaaa aacggttact ttactggcga gcaaatgcca     1260
acgacgactg tgtcttggcc aacaactccg ggtgccaagg cagataaacc gcgtaccgca     1320
ggtgtgagcg tatttggttt tggtggcagc aacgcccatt ggtattaca acagccaacg     1380 caaacactcg agactaattt tagtgttgct aaaccacgtg agcctttggc tattattggt     1440
atggacagcc attttggtag tgccagtaat ttagcgcagt tcaaaacctt attaaataat     1500
aatcaaaata ccttccgtga attaccagaa caacgctgga aaggcatgga agtaacgct      1560 aacgtcatgc agtcgttaca attacgcaaa gcgcctaaag cagttacgt tgaacagcta     1620 gatattgatt tcttgcgttt taaagtaccg cctaatgaaa aagattgctt gatcccgcaa     1680
cagttaatga tgatgcaagt ggcagacaat gctgcgaaaa acgaggtct agttgaaggt     1740 cgtaatgttg cggtattagt agcgatgggc atggaactgg aattacatca gtatcgtggt     1800
```

```
cgcgttaatc taaccaccca aattgaagac agcttattac agcaaggtat taacctgact    1860
gttgagcaac gtgaagaact gaccaatatt gctaaagacg gtgttgcctc ggctgcacag    1920
ctaaatcagt atacgagttt cattggtaat attatggcgt cacgtatttc ggcgttatgg    1980 gattttctg gtcctgctat taccgtatcg gctgaagaaa actctgttta tcgttgtgtt    2040
gaattagctg aaaatctatt tcaaaccagt gatgttgaag ccgttattat tgctgctgtt    2100
gatttgtctg gttcaattga aaacattact ttacgtcagc actacggtcc agttaatgaa    2160
aagggatctg taagtgaatg tggtccggtt aatgaaagca gttcagtaac caacaatatt    2220
cttgatcagc aacaatggct ggtgggtgaa ggcgcagcgg ctattgtcgt taaaccgtca    2280
tcgcaagtca ctgctgagca agtttatgcg cgtattgatg cggtgagttt tgcccctggt    2340
agcaatgcga aagcaattac gattgcagcg gataaagcat taacacttgc tggtatcagt    2400
gctgctgatg tagctagtgt tgaagcacat gcaagtggtt ttagtgccga aaataatgct    2460
gaaaaaaccg cgttaccgac tttataccca agcgcaagta tcagttcggt gaaagccaat    2520
attggtcata cgtttaatgc ctcgggtatg gcgagtatta ttaaaacggc gctgctgtta    2580
gatcagaata cgagtcaaga tcagaaaagc aaacatattg ctattaacgg tctaggtcgt    2640
gataacagct gcgcgcatct tatcttatcg agttcagcgc aagcgcatca agttgcacca    2700
gcgcctgtat ctggtatggc caagcaacgc ccacagttag ttaaaaccat caaactcggt    2760
ggtcagttaa ttagcaacgc gattgttaac agtgcgagtt catctttaca cgctattaaa    2820
gcgcagtttg ccggtaagca cttaaacaaa gttaaccagc cagtgatgat ggataacctg    2880
aagccccaag gtattagcgc tcatgcaacc aatgagtatg tggtgactgg agctgctaac    2940
actcaagctt ctaacattca agcatctcat gttcaagcgt caagtcatgc acaagagata    3000
gcaccaaacc aagttcaaaa tatgcaagct acagcagccg ctgtaagttc accccttcct    3060
caacatcaac acacagcgca gcccgtagcg gcaccgagcg ttgttggagt gactgtgaaa    3120
cataaagcaa gtaaccaaat tcatcagcaa gcgtctacgc ataaagcatt tttagaaagt    3180
cgtttagctg cacagaaaaa cctatcgcaa cttgttgaat tgcaaaccaa gctgtcaatc    3240
caaactggta gtgacaatac atctaacaat actgcgtcaa caagcaatac agtgctaaca    3300
aatcctgtat cagcaacgcc attaacactt gtgtctaatg cgcctgtagt agcgacaaac    3360
ctaaccagta cagaagcaaa agcgcaagca gctgctacac aagctggttt tcagataaaa    3420
ggacctgttg gttacaacta tccaccgctg cagttaattg aacgttataa taaaccagaa    3480
aacgtgattt acgatcaagc tgatttggtt gaattcgctg aaggtgatat tggtaaggta    3540
tttggtgctg aatacaatat tattgatggc tattcgcgtc gtgtacgtct gccaacctca    3600
gattacttgt tagtaacacg tgttactgaa cttgatgcca aggtgcatga atacaagaaa    3660
tcatacatgt gtactgaata tgatgtgcct gttgatgcac cgttcttaat tgatggtcag    3720
atcccttggt ctgttgccgt cgaatcaggc cagtgtgatt tgatgttgat ttcatatatc    3780
ggtattgatt ccaagcgaa aggcgaacgt gtttaccgtt tacttgattg tgaattaact    3840
ttccttgaag agatggcttt tggtggcgat actttacgtt acgagatcca cattgattcg    3900
tatgcacgta acggcgagca attattattc ttcttccatt acgattgtta cgtaggggat    3960
aagaaggtac ttatcatgcg taatggttgt gctggttct ttactgacga agaactttct    4020
gatggtaaag gcgttattca taacgacaaa gacaaagctg agtttagcaa tgctgttaaa    4080
tcatcattca cgccgttatt acaacataac cgtggtcaat acgattataa cgacatgatg    4140
```

| | | | |
|---|---|---|---|
| aagttggtta | atggtgatgt | tgccagttgt | tttggtccgc aatatgatca aggtggccgt | 4200 |
| aatccatcat | tgaaattctc | gtctgagaag | ttcttgatga ttgaacgtat taccaagata | 4260 |
| gacccaaccg | gtggtcattg | gggactaggc | ctgttagaag gtcagaaaga tttagaccct | 4320 |
| gagcattggt | atttcccttg | tcactttaaa | ggtgatcaag taatggctgg ttcgttgatg | 4380 |
| tcggaaggtt | gtggccaaat | ggcgatgttc | tcatgctgt ctcttggtat gcataccaat | 4440 |
| gtgaacaacg | ctcgtttcca | accactacca | ggtgaatcac aaacggtacg ttgtcgtggg | 4500 |
| caagtactgc | cacagcgcaa | taccttaact | taccgtatgg aagttactgc gatgggtatg | 4560 |
| catccacagc | cattcatgaa | agctaatatt | gatattttgc ttgacggtaa agtggttgtt | 4620 |
| gatttcaaaa | acttgagcgt | gatgatcagc | gaacaagatg agcattcaga ttaccctgta | 4680 |
| acactgccga | gtaatgtggc | gcttaaagcg | attactgcac ctgttgcgtc agtagcacca | 4740 |
| gcatcttcac | ccgctaacag | cgcggatcta | gacgaacgtg gtgttgaacc gtttaagttt | 4800 |
| cctgaacgtc | cgttaatgcg | tgttgagtca | gacttgtctg caccgaaaag caaaggtgtg | 4860 |
| acaccgatta | agcattttga | agcgcctgct | gttgctggtc atcatagagt gcctaaccaa | 4920 |
| gcaccgttta | caccttggca | tatgtttgag | tttgcgacgg gtaatatttc taactgtttc | 4980 |
| ggtcctgatt | ttgatgttta | tgaaggtcgt | attccacctc gtacaccttg tggcgattta | 5040 |
| caagttgtta | ctcaggttgt | agaagtgcag | ggcgaacgtc ttgatcttaa aaatccatca | 5100 |
| agctgtgtag | ctgaatacta | tgtaccggaa | gacgcttggt actttactaa aaacagccat | 5160 |
| gaaaactgga | tgccttattc | attaatcatg | gaaattgcat tgcaaccaaa tggctttatt | 5220 |
| tctggttaca | tgggcacgac | gcttaaatac | cctgaaaaag atctgttctt ccgtaacctt | 5280 |
| gatggtagcg | gcacgttatt | aaagcagatt | gatttacgcg gcaagaccat tgtgaataaa | 5340 |
| tcagtcttgg | ttagtacggc | tattgctggt | ggcgcgatta ttcaaagttt cacgtttgat | 5400 |
| atgtctgtag | atggcgagct | attttatact | ggtaaagctg tatttggtta ctttagtggt | 5460 |
| gaatcactga | ctaaccaact | gggcattgat | aacggtaaaa cgactaatgc gtggtttgtt | 5520 |
| gataacaata | cccccgcagc | gaatattgat | gtgtttgatt taactaatca gtcattggct | 5580 |
| ctgtataaag | cgcctgtgga | taaaccgcat | tataaattgg ctggtggtca gatgaacttt | 5640 |
| atcgatacag | tgtcagtggt | tgaaggcggt | ggtaaagcgg gcgtggctta tgtttatggc | 5700 |
| gaacgtacga | ttgatgctga | tgattggttc | ttccgttatc acttccacca agatccggtg | 5760 |
| atgccaggtt | cattaggtgt | tgaagctatt | attgagttga tgcagaccta tgcgcttaaa | 5820 |
| aatgatttgg | gtggcaagtt | tgctaaccca | cgtttcattg cgccgatgac gcaagttgat | 5880 |
| tggaaatacc | gtgggcaaat | tacgccgctg | aataaacaga tgtcactgga cgtgcatatc | 5940 |
| actgagatcg | tgaatgacgc | tggtgaagtg | cgaatcgttg gtgatgcgaa tctgtctaaa | 6000 |
| gatggtctgc | gtatttatga | agttaaaaac | atcgttttaa gtattgttga agcgtaa | 6057 |

<210> SEQ ID NO 80
<211> LENGTH: 1665
<212> TYPE: DNA
<213> ORGANISM: Vibrio marinus

<400> SEQUENCE: 80

| | | | |
|---|---|---|---|
| atgaatatag | taagtaatca | ttcggcagct | acaaaaaagg aattaagaat gtcgagttta | 60 |
| ggttttaaca | ataacaacgc | aattaactgg | gcttggaaag tagatccagc gtcagttcat | 120 |
| acacaagatg | cagaaattaa | agcagcttta | atggatctaa ctaaacctct ctatgtggcg | 180 |
| aataattcag | gcgtaactgg | tatagctaat | catacgtcag tagcaggtgc gatcagcaat | 240 |

-continued

```
aacatcgatg ttgatgtatt ggcgtttgcg caaaagttaa acccagaaga tctgggtgat    300
gatgcttaca agaaacagca cggcgttaaa tatgcttatc atggcggtgc gatggcaaat    360
ggtattgcct cggttgaatt ggttgttgcg ttaggtaaag cagggctgtt atgttcattt    420
ggtgctgcag gtctagtgcc tgatgcggtt aagatgcaa ttcgtcgtat tcaagctgaa    480
ttaccaaatg gcccttatgc ggttaacttg atccatgcac cagcagaaga agcattagag    540
cgtggcgcgg ttgaacgttt cctaaaactt ggcgtcaaga cggtagaggc ttcagcttac    600
cttggtttaa ctgaacacat tgtttggtat cgtgctgctg gtctaactaa aaacgcagat    660
ggcagtgtta atatcggtaa caaggttatc gctaaagtat cgcgtaccga agttggtcgc    720
cgctttatgg aacctgcacc gcaaaaatta ctggataagt tattagaaca aaataagatc    780 accctgaac aagctgcttt agcgttgctt gtacctatgg ctgatgatat tactggggaa    840
gcggattctg gtggtcatac agataaccgt ccgttttta cattattacc gacgattatt    900
ggtctgcgtg atgaagtgca agcgaagtat aacttctctc ctgcattacg tgttggtgct    960
ggtggtggta tcggaacgcc tgaagcagca ctcgctgcat ttaacatggg cgcggcttat   1020
atcgttctgg gttctgtgaa tcaggcgtgt gttgaagcgg gtgcatctga atatactcgt   1080
aaactgttat cgacagttga aatggctgat gtgactatgg cacctgctgc agatatgttt   1140
gaaatgggtg tgaagctgca agtattaaaa cgcggttcta tgttcgcgat gcgtgcgaag   1200
aaactgtatg acttgtatgt ggcttatgac tcgattgaag atatcccagc tgctgaacgt   1260
gagaagattg aaaaacaaat cttccgtgca aacctagacg agatttggga tggcactatc   1320
gctttcttta ctgaacgcga tccagaaatg ctagcccgtg caacgagtag tcctaaacgt   1380
aaaatggcac ttatcttccg ttggtatctt ggcctttctt cacgctggtc aaacacaggc   1440
gagaagggac gtgaaatgga ttatcagatt tgggcaggcc caagtttagg tgcattcaac   1500
agctgggtga aggttctta ccttgaagac tatacccgcc gtggcgctgt agatgttgct   1560
ttgcatatgc ttaaaggtgc tgcgtattta caacgtgtaa accagttgaa attgcaaggt   1620
gttagcttaa gtacagaatt ggcaagttat cgtacgagtg attaa                   1665
```

<210> SEQ ID NO 81
<211> LENGTH: 2910
<212> TYPE: DNA
<213> ORGANISM: Shewanella putrefaciens

<400> SEQUENCE: 81

```
atgagtatgt tttaaattc aaaactttcg cgctcagtca aacttgccat atccgcaggc     60
ttaacagcct cgctagctat gcctgttttt gcagaagaaa ctgctgctga gaacaaata    120 gaaagagtcg cagtgaccgg atcgcgaatc gctaaagcag agctaactca accagctcca    180
gtcgtcagcc tttcagccga agaactgaca aaatttggta atcaagattt aggtagcgta    240
ctagcagaat tacctgctat tggtgcaacc aacactatta ttggtaataa caatagcaac    300
tcaagcgcag tgttagctc agcagacttg cgtcgtctag gtgctaacag aaccttagta    360
ttagtcaacg gtaagcgcta cgttgccggc caaccgggct cagctgaggt agatttgtca    420
actataccaa ctagcatgat ctcgcgagtt gagattgtaa ccggcggtgc ttcagcaatt    480
tatggttcgg acgctgtatc aggtgttatc aacgttatcc ttaaagaaga ctttgaaggc    540
tttgagttta acgcacgtac tagcggttct actgaaagtg taggcactca agagcactct    600
tttgacattt tgggtggtgc aaacgttgca gatggacgtg gtaatgtaac cttctacgca    660
```

-continued

```
ggttatgaac gtacaaaaga agtcatggct accgacattc gccaattcga tgcttgggga      720
acaattaaaa acgaagccga tggtggtgaa gatgatggta ttccagacag actacgtgta      780
ccacgagttt attctgaaat gattaatgct accggtgtta tcaatgcatt tggtggtgga      840
attggtcgct caacctttga cagtaacggc aatcctattg cacaacaaga acgtgatggg      900
actaacagct ttgcatttgg ttcattccct aatggctgtg acacatgttt caacactgaa      960
gcatacgaaa actatattcc aggggtagaa agaataaacg ttggctcatc attcaacttt     1020
gattttaccg ataacattca attttacact gacttcagat atgtaaagtc agatattcag     1080
caacaatttc agccttcatt ccgttttggt aacattaata tcaatgttga agataacgcc     1140
tttttgaatg acgacttgcg tcagcaaatg ctcgatgcgg gtcaaaccaa tgctagtttt     1200
gccaagtttt ttgatgaatt aggaaatcgc tcagcagaaa ataaacgcga acttttccgt     1260
tacgtaggtg gctttaaagg tggctttgat attagcgaaa ccatatttga ttacgacctt     1320
tactatgttt atggcgagac taataaccgt cgtaaaaccc ttaatgacct aattcctgat     1380
aactttgtcg cagctgtcga ctctgttatt gatcctgata ctggcttagc agcgtgtcgc     1440
tcacaagtag caagcgctca aggcgatgac tatacagatc ccgcgtctgt aaatggtagc     1500
gactgtgttg cttataaccc atttggcatg gtcaagctt cagcagaagc ccgcgactgg      1560
gtttctgctg atgtgactcg tgaagacaaa ataactcaac aagtgattgg tggtactctc     1620
ggtaccgatt ctgaagaact atttgagctt caaggtggtg caatcgctat ggttgttggt     1680
tttgaatacc gtgaagaaac gtctggttca caaaccgatg aatttactaa agcaggtttc     1740
ttgacaagcg ctgcaacgcc agattcttat ggcgaatacg acgtgactga gtattttgtt     1800
gaggtgaaca tcccagtact aaaagaatta cctttttgcac atgagttgag ctttgacggt     1860
gcataccgta atgctgatta ctcacatgcc ggtaagactg aagcatggaa agctggtatg     1920
ttctactcac cattagagca acttgcatta cgtggtacgg taggtgaagc agtacgagca     1980
ccaaacattg cagaagcctt tagtccacgc tctcctggtt ttggccgcgt ttcagatcca     2040
tgtgatgcag ataacattaa tgacgatccg gatcgcgtgt caaactgtgc agcattgggg     2100
atccctccag gattccaagc taatgataac gtcagtgtag ataccttatc tggtggtaac     2160
ccagatctaa aacctgaaac atcaacatcc tttacaggtg gtcttgtttg gacaccaacg     2220
tttgctgaca atctatcatt cactgtcgat tattatgata ttcaaattga ggatgctatt     2280
ttgtcagtag ccacccagac tgtggctgat aactgtgttg actcaactgg cggacctgac     2340
accgacttct gtagtcaagt tgatcgtaat ccaacgacct atgatattga acttgttcgc     2400
tctggttatc taaatgccgc ggcattgaat accaaaggta ttgaatttca agctgcatac     2460
tcattagatc tagagtcttt caacgcgcct ggtgaactac gcttcaacct attggggaac     2520
caattacttg aactagaacg tcttgaattc caaaatcgtc ctgatgagat taatgatgaa     2580
aaaggcgaag taggtgatcc agagctgcag ttccgcctag gcatcgatta ccgtctagat     2640
gatctaagtg ttagctggaa cacgcgttat attgatagcg tagtaactta tgatgtctct     2700
gaaaatggtg gctctcctga agatttatat ccaggccaca taggctcaat gacaactcat     2760
gacttgagcg ctacatacta catcaatgag aacttcatga ttaacggtgg tgtacgtaac     2820
ctatttgacg cacttccacc tggatacact aacgatgcgc tatatgatct agttggtcgc     2880
cgtgcattcc taggtattaa ggtaatgatg                                       2910
```

<210> SEQ ID NO 82
<211> LENGTH: 864

-continued

```
<212> TYPE: DNA
<213> ORGANISM: Shewanella putrefaciens

<400> SEQUENCE: 82
atggcaaaaa taaatagtga acacttggat gaagctacta ttacttcgaa taagtgtacg      60
caaacagaga ctgaggctcg gcatagaaat gccactacaa cacctgagat gcgccgattc     120
atacaagagt cggatctcag tgttagccaa ctgtctaaaa tattaaatat cagtgaagct     180
accgtacgta agtggcgcaa gcgtgactct gtcgaaaact gtcctaatac cccgcaccat     240
ctcaatacca cgctaacccc tttgcaagaa tatgtggttg tgggcctgcg ttatcaattg     300
aaaatgccat tagacagatt gctcaaagca acccaagagt ttatcaatcc aaacgtgtcg     360
cgctcaggtt tagcaagatg tttgaagcgt atggcgtttt cacgggtgag tgatatccaa     420
agcccacacg taccaatgcg ctactttaat caaattccag tcactcaagg cagcgatgtg     480
caaacctaca ccctgcacta tgaaacgctg gcaaaaacct tagccttacc tagtaccgat     540
ggtgacaatg tggtgcaagt ggtgtctctc accattccac aaagttaac cgaagaagca     600 cccagttcaa ttttgctcgg cattgatcct catagcgact ggatctatct cgacatatac     660
caagatggca atacacaagc cacgaataga tatatggctt atgtgctaaa acacgggcca     720
ttccatttac gaaagttact cgtgcgtaac tatcacacct ttttacagcg ctttcctgga     780
gcgacgcaaa atcgccgccc ctctaaagat atgcctgaaa caatcaacaa gacgcctgaa     840
acacaggcac ccagtggaga ctca                                           864

<210> SEQ ID NO 83
<211> LENGTH: 8268
<212> TYPE: DNA
<213> ORGANISM: Shewanella putrefaciens

<400> SEQUENCE: 83
atgagccaga cctctaaacc tacaaactca gcaactgagc aagcacaaga ctcacaagct      60
gactctcgtt taaataaacg actaaagat atgccaattg ctattgttgg catggcgagt     120
atttttgcaa actctcgcta tttgaataag ttttgggact taatcagcga aaaaattgat     180
gcgattactg aattaccatc aactcactgg cagcctgaag aatattacga cgcagataaa     240
accgcagcag acaaaagcta ctgtaaacgt ggtggctttt tgccagatgt agacttcaac     300
ccaatggagt ttggcctgcc gccaaacatt ttggaactga ccgattcatc gcaactatta     360
tcactcatcg ttgctaaaga agtgttggct gatgctaact tacctgagaa ttacgaccgc     420
gataaaattg gtatcacctt aggtgtcggc ggtggtcaaa aaattagcca cagcctaaca     480
gcgcgtctgc aatacccagt attgaagaaa gtattcgcca atagcggcat tagtgacacc     540
gacagcgaaa tgcttatcaa gaaattccaa gaccaatatg tacactggga agaaaactcg     600
ttcccaggtt cacttggtaa cgttattgcg ggccgtatcg ccaaccgctt cgattttggc     660
ggcatgaact gtgtggttga tgctgcctgt gctggatcac ttgctgctat gcgtatggcg     720
ctaacagagc taactgaagg tcgctctgaa atgatgatca ccggtggtgt gtgtactgat     780
aactcaccct ctatgtatat gagcttttca aaaacgcccg cctttaccac taacgaaacc     840
attcagccat ttgatatcga ctcaaaaggc atgatgattg gtgaaggtat tggcatggtg     900
gcgctaaagc gtcttgaaga tgcagagcgc gatggcgacc gcatttactc tgtaattaaa     960
ggtgtgggtg catcatctga cggtaagttt aaatcaatct atgcccctcg cccatcaggc    1020
caagctaaag cacttaaccg tgcctatgat gacgcaggtt ttgcgccgca taccttaggt    1080
```

```
ctaattgaag ctcacggaac aggtactgca gcaggtgacg cggcagagtt tgccggcctt   1140
tgctcagtat ttgctgaagg caacgatacc aagcaacaca ttgcgctagg ttcagttaaa   1200
tcacaaattg gtcatactaa atcaactgca ggtacagcag gtttaattaa agctgctctt   1260
gctttgcatc acaaggtact gccgccgacc attaacgtta gtcagccaag ccctaaactt   1320
gatatcgaaa actcaccgtt ttatctaaac actgagactc gtccatggtt accacgtgtt   1380
gatggtacgc cgcgccgcgc gggtattagc tcatttggtt ttggtggcac taacttccat   1440
tttgtactag aagagtacaa ccaagaacac agccgtactg atagcgaaaa agctaagtat   1500
cgtcaacgcc aagtggcgca aagcttcctt gttagcgcaa gcgataaagc atcgctaatt   1560
aacgagttaa acgtactagc agcatctgca agccaagctg agtttatcct caaagatgca   1620
gcagcaaact atggcgtacg tgagcttgat aaaaatgcac cacggatcgg tttagttgca   1680
aacacagctg aagagttagc aggcctaatt aagcaagcac ttgccaaact agcagctagc   1740
gatgataacg catggcagct acctggtggc actagctacc gcgccgctgc agtagaaggt   1800
aaagttgccg cactgtttgc tggccaaggt tcacaatatc tcaatatggg ccgtgacctt   1860
acttgttatt acccagagat gcgtcagcaa tttgtaactg cagataaagt atttgccgca   1920
aatgataaaa cgccgttatc gcaaactctg tatccaaagc ctgtatttaa taaagatgaa   1980 ttaaggctc aagaagccat tttgaccaat accgccaatg cccaaagcgc aattggtgcg   2040
atttcaatgg gtcaatacga tttgtttact gcggctggct ttaatgccga catggttgca   2100
ggccatagct ttggtgagct aagtgcactg tgtgctgcag gtgttatttc agctgatgac   2160
tactacaagc tggcttttgc tcgtggtgag gctatggcaa caaaagcacc ggctaaagac   2220
ggcgttgaag cagatgcagg agcaatgttt gcaatcataa ccaagagtgc tgcagacctt   2280
gaaaccgttg aagccaccat cgctaaattt gatggggtga agtcgctaa ctataacgcg   2340 ccaacgcaat cagtaattgc aggcccaaca gcaactaccg ctgatgcggc taaagcgcta   2400
actgagcttg gttacaaagc gattaacctg ccagtatcag gtgcattcca cactgaactt   2460
gttggtcacg ctcaagcgcc atttgctaaa gcgattgacg cagccaaatt tactaaaaca   2520
agccgagcac tttactcaaa tgcaactggc ggactttatg aaagcactgc tgcaaagatt   2580
aaagcctcgt ttaagaaaca tatgcttcaa tcagtgcgct ttactagcca gctagaagcc   2640
atgtacaacg acggcgcccg tgtatttgtt gaatttggtc aaagaacat cttacaaaaa   2700 ttagttcaag gcacgcttgt caacactgaa aatgaagttt gcactatctc tatcaaccct   2760
aatcctaaag ttgatagtga tctgcagctt aagcaagcag caatgcagct agcggttact   2820
ggtgtggtac tcagtgaaat tgacccatac caagccgata ttgccgcacc agcgaaaaag   2880
tcgccaatga gcatttcgct taatgctgct aaccatatca gcaaagcaac tcgcgctaag   2940
atggccaagt ctttagagac aggtatcgtc acctcgcaaa tagaacatgt tattgaagaa   3000
aaaatcgttg aagttgagaa actggttgaa gtcgaaaaga tcgtcgaaaa agtggttgaa   3060
gtagagaaag ttgttgaggt tgaagctcct gttaattcag tgcaagccaa tgcaattcaa   3120
acccgttcag ttgtcgctcc agtaatagag aaccaagtcg tgtctaaaaa cagtaagcca   3180
gcagtccaga gcattagtgg tgatgcactc agcaacttttt ttgctgcaca gcagcaaacc   3240
gcacagttgc atcagcagtt cttagctatt ccgcagcaat atggtgagac gttcactacg   3300
ctgatgaccg agcaagctaa actggcaagt tctggtgttg caattccaga gagtctgcaa   3360
cgctcaatgg agcaattcca ccaactacaa gcgcaaacac tacaaagcca cacccagttc   3420
cttgagatgc aagcgggtag caacattgca gcgttaaacc tactcaatag cagccaagca   3480
```

```
acttacgctc cagccattca caatgaagcg attcaaagcc aagtggttca aagccaaact   3540
gcagtccagc cagtaatttc aacacaagtt aaccatgtgt cagagcagcc aactcaagct   3600
ccagctccaa aagcgcagcc agcacctgtg acaactgcag ttcaaactgc tccggcacaa   3660
gttgttcgtc aagccgcacc agttcaagcc gctattgaac cgattaatac aagtgttgcg   3720
actacaacgc cttcagcctt cagcgccgaa acagccctga gcgcaacaaa agtccaagcc   3780
actatgcttg aagtggttgc tgagaaaacc ggttacccaa ctgaaatgct agagcttgaa   3840
atggatatgg aagccgattt aggcatcgat tctatcaagc gtgtagaaat tcttggcaca   3900
gtacaagatg agctaccggg tctacctgag cttagccctg aagatctagc tgagtgtcga   3960
acgctaggcg aaatcgttga ctatatgggc agtaaactgc cggctgaagg ctctatgaat   4020
tctcagctgt ctacaggttc cgcagctgcg actcctgcag cgaatggtct ttctgcggag   4080
aaagttcaag cgactatgat gtctgtggtt gccgaaaaga ctggctaccc aactgaaatg   4140
ctagagcttg aaatggatat ggaagccgat ttaggcatag attctatcaa gcgcgttgaa   4200
attcttggca cagtacaaga tgagctaccg ggtctacctg agcttagccc tgaagatcta   4260
gctgagtgtc gtactctagg cgaaatcgtt gactatatga actctaaact cgctgacggc   4320
tctaagctgc cggctgaagg ctctatgaat tctcagctgt ctacaagtgc cgcagctgcg   4380
actcctgcag cgaatggtct ctctgcggag aaagttcaag cgactatgat gtctgtggtt   4440
gccgaaaaga ctggctaccc aactgaaatg ctagaacttg aaatggatat ggaagctgac   4500
cttggcatcg attcaatcaa gcgcgttgaa attcttggca cagtacaaga tgagctaccg   4560
ggtttacctg agctaaatcc agaagatttg gcagagtgtc gtactcttgg cgaaatcgtg   4620
acttatatga actctaaact cgctgacggc tctaagctgc cagctgaagg ctctatgcac   4680
tatcagctgt ctacaagtac cgctgctgcg actcctgtag cgaatggtct ctctgcagaa   4740
aaagttcaag cgaccatgat gtctgtagtt gcagataaaa ctggctaccc aactgaaatg   4800
cttgaacttg aaatggatat ggaagccgat ttaggtatcg attctatcaa gcgcgttgaa   4860
attcttggca cagtacaaga tgagctaccg ggtttacctg agctaaatcc agaagatcta   4920
gcagagtgtc gcaccctagg cgaaatcgtt gactatatgg gcagtaaact gccggctgaa   4980
ggctctgcta atacaagtgc cgctgcgtct cttaatgtta gtgccgttgc ggcgcctcaa   5040
gctgctgcga ctcctgtatc gaacggtctc tctgcagaga aagtgcaaag cactatgatg   5100
tcagtagttc agaaaagac cggctaccca actgaaatgc tagaacttgg catggatatg   5160
gaagccgatt taggtatcga ctcaattaaa cgcgttgaga ttcttggcac agtacaagat   5220
gagctaccgg gtctaccaga gcttaatcct gaagatttag ctgagtgccg tacgctgggc   5280
gaaatcgttg actatatgaa ctctaagctg gctgacggct ctaagcttcc agctgaaggc   5340
tctgctaata caagtgccac tgctgcgact cctgcagtga atggtctttc tgctgacaag   5400
gtacaggcga ctatgatgtc tgtagttgct gaaaagaccg gctacccaac tgaaatgcta   5460
gaacttggca tggatatgga agcagacctt ggtattgatt ctattaagcg cgttgaaatt   5520
cttggcacag tacaagatga gctcccaggt ttacctgagc ttaatcctga agatctcgct   5580
gagtgccgca cgcttggcga aatcgttagc tatatgaact ctcaactggc tgatggctct   5640
aaactttcta caagtgcggc tgaaggctct gctgatacaa gtgctgcaaa tgctgcaaag   5700
ccggcagcaa tttcggcaga accaagtgtt gagcttcctc ctcatagcga ggtagcgcta   5760
aaaaagctta atgcggcgaa caagctagaa aattgtttcg ccgcagacgc aagtgttgtg   5820
```

-continued

```
attaacgatg atggtcacaa cgcaggcgtt ttagctgaga aacttattaa acaaggccta      5880
aaagtagccg ttgtgcgttt accgaaaggt cagcctcaat cgccactttc aagcgatgtt      5940
gctagctttg agcttgcctc aagccaagaa tctgagcttg aagccagtat cactgcagtt      6000
atcgcgcaga ttgaaactca ggttggcgct attggtggct ttattcactt gcaaccagaa      6060
gcgaatacag aagagcaaac ggcagtaaac ctagatgcgc aaagttttac tcacgttagc      6120
aatgcgttct tgtgggccaa attattgcaa ccaaagctcg ttgctggagc agatgcgcgt      6180
cgctgttttg taacagtaag ccgtatcgac ggtggctttg gttacctaaa tactgacgcc      6240
ctaaaagatg ctgagctaaa ccaagcagca ttagctggtt taactaaaac cttaagccat      6300
gaatggccac aagtgttctg tcgcgcgcta gatattgcaa cagatgttga tgcaacccat      6360
cttgctgatg caatcaccag tgaactattt gatagccaag ctcagctacc tgaagtgggc      6420
ttaagcttaa ttgatggcaa agttaaccgc gtaactctag ttgctgctga agctgcagat      6480
aaaacagcaa aagcagagct taacagcaca gataaaatct tagtgactgg tggggcaaaa      6540
ggggtgacat ttgaatgtgc actggcatta gcatctcgca gccagtctca ctttatctta      6600
gctgggcgca gtgaattaca agcttttacca agctgggctg agggtaagca aactagcgag      6660
ctaaaatcag ctgcaatcgc acatattatt tctactggtc aaaagccaac gcctaagcaa      6720
gttgaagccg ctgtgtggcc agtgcaaagc agcattgaaa ttaatgccgc cctagccgcc      6780
tttaacaaag ttggcgcctc agctgaatac gtcagcatgg atgttaccga tagcgccgca      6840
atcacagcag cacttaatgg tcgctcaaat gagatcaccg gtcttattca tggcgcaggt      6900
gtactagccg acaagcatat tcaagacaag actcttgctg aacttgctaa agtttatggc      6960
actaaagtca acggcctaaa agcgctgctc gcggcacttg agccaagcaa aattaaatta      7020
cttgctatgt tctcatctgc agcaggtttt tacggtaata tcggccaaag cgattacgcg      7080
atgtcgaacg atattcttaa caaggcagcg ctgcagttca ccgctcgcaa cccacaagct      7140
aaagtcatga gctttaactg gggtccttgg gatggcggca tggttaaccc agcgcttaaa      7200
aagatgttta ccgagcgtgg tgtgtacgtt attccactaa aagcaggtgc agagctattt      7260
gccactcagc tattggctga aactggcgtg cagttgctca ttggtacgtc aatgcaaggt      7320
ggcagcgaca ctaaagcaac tgagactgct tctgtaaaaa agcttaatgc gggtgaggtg      7380
ctaagtgcat cgcatccgcg tgctggtgca caaaaaacac cactacaagc tgtcactgca      7440
acgcgtctgt taaccccaag tgccatggtc ttcattgaag atcaccgcat tggcggtaac      7500
agtgtgttgc caacggtatg cgccatcgac tggatgcgtg aagcggcaag cgacatgctt      7560
ggcgctcaag ttaaggtact tgattacaag ctattaaaag gcattgtatt tgagactgat      7620
gagccgcaag agttaacact tgagctaacg ccagacgatt cagacgaagc tacgctacaa      7680
gcattaatca gctgtaatgg gcgtccgcaa tacaaggcga cgcttatcag tgataatgcc      7740
gatattaagc aacttaacaa gcagtttgat ttaagcgcta aggcgattac cacagcaaaa      7800
gagctttata gcaacggcac cttgttccac ggtccgcgtc tacaagggat ccaatctgta      7860
gtgcagttcg atgatcaagg cttaattgct aaagtcgctc tgcctaaggt tgaacttagc      7920
gattgtggtg agttcttgcc gcaaacccac atgggtggca gtcaaccttt tgctgaggac      7980
ttgctattac aagctatgct ggtttgggct cgccttaaaa ctggctcggc aagtttgcca      8040
tcaagcattg gtgagtttac ctcataccaa ccaatggcct ttggtgaaac tggtaccata      8100
gagcttgaag tgattaagca caacaaacgc tcacttgaag cgaatgttgc gctatatcgt      8160
gacaacggcg agttaagtgc catgtttaag tcagctaaaa tcaccattag caaaagctta      8220
```

-continued aattcagcat ttttacctgc tgtcttagca aacgacagtg aggcgaat        8268

<210> SEQ ID NO 84
<211> LENGTH: 2313
<212> TYPE: DNA
<213> ORGANISM: Shewanella putrefaciens

<400> SEQUENCE: 84

| | | | | | |
|---|---|---|---|---|---|
| atgccgctgc | gcatcgcact | tatcttactg | ccaacaccgc | agtttgaagt | taactctgtc | 60 |
| gaccagtcag | tattagccag | ctatcaaaca | ctgcagcctg | agctaaatgc | cctgcttaat | 120 |
| agtgcgccga | cacctgaaat | gctcagcatc | actatctcag | atgatagcga | tgcaaacagc | 180 |
| tttgagtcgc | agctaaatgc | tgcgaccaac | gcaattaaca | atggctatat | cgtcaagctt | 240 |
| gctacggcaa | ctcacgcttt | gttaatgctg | cctgcattaa | aagcggcgca | aatgcggatc | 300 |
| catcctcatg | cgcagcttgc | cgctatgcag | caagctaaat | cgacgccaat | gagtcaagta | 360 |
| tctggtgagc | taaagcttgg | cgctaatgcg | ctaagcctag | ctcagactaa | tgcgctgtct | 420 |
| catgctttaa | gccaagccaa | gcgtaactta | actgatgtca | gcgtgaatga | gtgttttgag | 480 |
| aacctcaaaa | gtgaacagca | gttcacagag | gtttattcgc | ttattcagca | acttgctagc | 540 |
| cgcacccatg | tgagaaaaga | ggttaatcaa | ggtgtggaac | ttggccctaa | acaagccaaa | 600 |
| agccactatt | ggtttagcga | atttcaccaa | accgtgttg | ctgccatcaa | ctttattaat | 660 |
| ggccaacaag | caaccagcta | tgtgcttact | caaggttcag | gattgttagc | tgcgaaatca | 720 |
| atgctaaacc | agcaaagatt | aatgtttatc | ttgccgggta | acagtcagca | acaaataacc | 780 |
| gcatcaataa | ctcagttaat | gcagcaatta | gagcgtttgc | aggtaactga | ggttaatgag | 840 |
| ctttctctag | aatgccaact | agagctgctc | agcataatgt | atgacaactt | agtcaacgca | 900 |
| gacaaactca | ctactcgcga | tagtaagccc | gcttatcagg | ctgtgattca | agcaagctct | 960 |
| gttagcgctg | caaagcaaga | gttaagcgcg | cttaacgatg | cactcacagc | gctgtttgct | 1020 |
| gagcaaacaa | acgccacatc | aacgaataaa | ggcttaatcc | aatacaaaac | accggcgggc | 1080 |
| agttacttaa | ccctaacacc | gcttggcagc | aacaatgaca | acgcccaagc | gggtcttgct | 1140 |
| tttgtctatc | cgggtgtggg | aacggtttac | gccgatatgc | ttaatgagct | gcatcagtac | 1200 |
| ttccctgcgc | tttacgccaa | acttgagcgt | gaaggcgatt | taaaggcgat | gctacaagca | 1260 |
| gaagatatct | atcatcttga | ccctaaacat | gctgcccaaa | tgagcttagg | tgacttagcc | 1320 |
| attgctggcg | tggggagcag | ctacctgtta | actcagctgc | tcaccgatga | gtttaatatt | 1380 |
| aagcctaatt | ttgcattagg | ttactcaatg | ggtgaagcat | caatgtgggc | aagcttaggc | 1440 |
| gtatggcaaa | accgcatgc | gctgatcagc | aaaacccaaa | ccgacccgct | atttacttct | 1500 |
| gctatttccg | gcaaattgac | cgcggttaga | caagcttggc | agcttgatga | taccgcagcg | 1560 |
| gaaatccagt | ggaatagctt | tgtggttaga | agtgaagcag | cgccgattga | agccttgcta | 1620 |
| aaagattacc | cacacgctta | cctcgcgatt | attcaagggg | atacctgcgt | aatcgctggc | 1680 |
| tgtgaaatcc | aatgtaaagc | gctacttgca | gcactgggta | acgcgggtat | tgcagctaat | 1740 |
| cgtgtaacgg | cgatgcatac | gcagcctgcg | atgcaagagc | atcaaaatgt | gatggatttt | 1800 |
| tatctgcaac | cgttaaaagc | agagcttcct | agtgaaataa | gctttatcag | cgccgctgat | 1860 |
| ttaactgcca | agcaaacggt | gagtgagcaa | gcacttagca | gccaagtcgt | tgctcagtct | 1920 |
| attgccgaca | ccttctgcca | aaccttggac | tttaccgcgc | tagtacatca | cgcccaacat | 1980 |
| caaggcgcta | agctgtttgt | tgaaattggc | gcggatagac | aaaactgcac | cttgatagac | 2040 |

```
aagattgtta acaagatgg tgccagcagt gtacaacatc aaccttgttg cacagtgcct    2100
atgaacgcaa aaggtagcca agatattacc agcgtgatta aagcgcttgg ccaattaatt    2160
agccatcagg tgccattatc ggtgcaacca tttattgatg gactcaagcg cgagctaaca    2220
ctttgccaat tgaccagcca acagctggca gcacatgcaa atgttgacag caagtttgag    2280
tctaaccaag accatttact tcaaggggaa gtc                                 2313
```

<210> SEQ ID NO 85
<211> LENGTH: 6012
<212> TYPE: DNA
<213> ORGANISM: Shewanella putrefaciens

<400> SEQUENCE: 85

```
atgtcattac cagacaatgc ttctaaccac ctttctgcca accagaaagg cgcatctcag      60
gcaagtaaaa ccagtaagca aagcaaaatc gccattgtcg gtttagccac tctgtatcca     120
gacgctaaaa ccccgcaaga attttggcag aatttgctgg ataaacgcga ctctcgcagc     180
accttaacta cgaaaaact cggcgctaac agccaagatt atcaaggtgt gcaaggccaa      240
tctgaccgtt tttattgtaa taaaggcggc tacattgaga acttcagctt taatgctgca     300
ggctacaaat tgccggagca aagcttaaat ggcttggacg acagcttcct ttgggcgctc     360
gatactagcc gtaacgcact aattgatgct ggtattgata tcaacggcgc tgatttaagc     420
cgcgcaggtg tagtcatggg cgcgctgtcg ttcccaacta cccgctcaaa cgatctgttt     480
ttgccaattt atcacagcgc cgttgaaaaa gccctgcaag ataaactagg cgtaaaggca     540
tttaagctaa gcccaactaa tgctcatacc gctcgcgcgg caaatgagag cagcctaaat     600
gcagccaatg gtgccattgc ccataacagc tcaaaagtgg tggccgatgc acttggcctt     660
ggcggcgcac aactaagcct agatgctgcc tgtgctagtt cggtttactc attaaagctt     720
gcctgcgatt acctaagcac tggcaaagcc gatatcatgc tagcaggcgc agtatctggc     780
gcggatcctt tctttattaa tatgggattc tcaatcttcc acgcctaccc agaccatggt     840
atctcagtac cgtttgatgc cagcagtaaa ggtttgtttg ctggcgaagg cgctggcgta     900
ttagtgctta aacgtcttga agatgccgag cgcgacaatg acaaaatcta tgcggttgtt     960
agcggcgtag gtctatcaaa cgacggtaaa ggccagtttg tattaagccc taatccaaaa    1020
ggtcaggtga aggcctttga acgtgcttat gctgccagtg acattgagcc aaaagacatt    1080
gaagtgattg agtgccacgc aacaggcaca ccgcttggcg ataaaattga gctcacttca    1140
atggaaacct tctttgaaga caagctgcaa ggcaccgatg caccgttaat tggctcagct    1200
aagtctaact taggccacct attaactgca gcgcatgcgg ggatcatgaa gatgatcttc    1260
gccatgaaag aaggttacct gccgccaagt atcaatatta gtgatgctat cgcttcgccg    1320
aaaaaactct tcggtaaacc aaccctgcct agcatggttc aaggctggcc agataagcca    1380
tcgaataatc attttggtgt aagaacccgt cacgcaggcg tatcggtatt tggctttggt    1440
ggctgtaacg cccatctgtt gcttgagtca tacaacggca aaggaacagt aaaggcagaa    1500
gccactcaag taccgcgtca agctgagccg ctaaaagtgg ttggccttgc ctcgcacttt    1560
gggcctctta gcagcattaa tgcactcaac aatgctgtga cccaagatgg gaatggcttt    1620
atcgaactgc cgaaaaagcg ctggaaaggc cttgaaaagc acagtgaact gttagctgaa    1680
tttggcttag catctgcgcc aaaaggtgct tatgttgata acttcgagct ggactttta    1740 cgctttaaac tgccgccaaa cgaagatgac cgtttgatct cacagcagct aatgctaatg    1800
cgagtaacag acgaagccat tcgtgatgcc aagcttgagc cggggcaaaa agtagctgta    1860
```

-continued

```
ttagtggcaa tggaaactga gcttgaactg catcagttcc gcggccgggt taacttgcat      1920
actcaattag cgcaaagtct tgccgccatg ggcgtgagtt tatcaacgga tgaataccaa      1980
gcgcttgaag ccatcgccat ggacagcgtg cttgatgctg ccaagctcaa tcagtacacc      2040
agctttattg gtaatattat ggcgtcacgc gtggcgtcac tatgggactt taatggccca      2100
gccttcacta tttcagcagc agagcaatct gtgagccgct gtatcgatgt ggcgcaaaac      2160
ctcatcatgg aggataacct agatgcggtg gtgattgcag cggtcgatct ctctggtagc      2220
tttgagcaag tcattcttaa aaatgccatt gcacctgtag ccattgagcc aaacctcgaa      2280
gcaagcctta atccaacatc agcaagctgg aatgtcggtg aaggtgctgg cgcggtcgtg      2340
cttgttaaaa atgaagctac atcgggctgc tcatacggcc aaattgatgc acttggcttt      2400
gctaaaactg ccgaaacagc gttggctacc gacaagctac tgagccaaac tgccacagac      2460
tttaataagg ttaaagtgat tgaaactatg gcagcgcctg ctagccaaat tcaattagcg      2520
ccaatagtta gctctcaagt gactcacact gctgcagagc agcgtgttgg tcactgcttt      2580
gctgcagcgg gtatggcaag cctattacac ggcttactta acttaaatac tgtagcccaa      2640
accaataaag ccaattgcgc gcttatcaac aatatcagtg aaaaccaatt atcacagctg      2700
ttgattagcc aaacagcgag cgaacaacaa gcattaaccg cgcgtttaag caatgagctt      2760
aaatccgatg ctaaacacca actggttaag caagtcacct taggtggccg tgatatctac      2820
cagcatattg ttgatacacc gcttgcaagc cttgaaagca ttactcagaa attggcgcaa      2880
gcgacagcat cgacagtggt caaccaagtt aaacctatta aggccgctgg ctcagtcgaa      2940
atggctaact cattcgaaac ggaaagctca gcagagccac aaataacaat tgcagcacaa      3000
cagactgcaa acattggcgt caccgctcag gcaaccaaac gtgaattagg tacccccacca     3060 atgacaacaa ataccattgc taatacagca ataatttag acaagactct tgagactgtt       3120
gctggcaata ctgttgctag caaggttggc tctggcgaca tagtcaattt tcaacagaac      3180
caacaattgg ctcaacaagc tcacctcgcc tttcttgaaa gccgcagtgc gggtatgaag      3240
gtggctgatg ctttattgaa gcaacagcta gctcaagtaa caggccaaac tatcgataat      3300
caggccctcg atactcaagc cgtcgatact caaacaagcg agaatgtagc gattgccgca      3360
gaatcaccag ttcaagttac aacacctgtt caagttacaa cacctgttca aatcagtgtt      3420
gtggagttaa aaccagatca cgctaatgtg ccaccataca cgccgccagt gcctgcatta      3480
aagccgtgta tctggaacta tgccgattta gttgagtacg cagaaggcga tatcgccaag      3540
gtatttggca gtgattatgc cattatcgac agctactcgc gccgcgtacg tctaccgacc      3600
actgactacc tgttggtatc gcgcgtgacc aaacttgatg cgaccatcaa tcaatttaag      3660
ccatgctcaa tgaccactga gtacgacatc cctgttgatg cgccgtactt agtagacgga      3720
caaatccctt gggcggtagc agtagaatca ggccaatgtg acttgatgct tattagctat      3780
ctcggtatcg actttgagaa caaaggcgag cgggtttatc gactactcga ttgtaccctc      3840
accttcctag cgacttgcc acgtggcgga gataccctac gttacgacat taagatcaat      3900
aactatgctc gcaacggcga caccctgctg ttcttcttct cgtatgagtg ttttgttggc      3960
gacaagatga tcctcaagat ggatggcggc tgcgctggct tcttcactga tgaagagctt      4020
gccgacggta aggcgtgat tcgcacagaa gaagagatta agctcgcag cctagtgcaa       4080 aagcaacgct ttaatccgtt actagattgt cctaaaaccc aatttagtta tggtgatatt     4140
cataagctat taactgctga tattgagggt tgttttggcc caagccacag tggcgtccac     4200
```

```
cagccgtcac tttgtttcgc atctgaaaaa ttcttgatga ttgaacaagt cagcaaggtt    4260
gatcgcactg gcggtacttg gggacttggc ttaattgagg gtcataagca gcttgaagca    4320
gaccactggt acttcccatg tcatttcaag ggcgaccaag tgatggctgg ctcgctaatg    4380
gctgaaggtt gtggccagtt attgcagttc tatatgctgc accttggtat gcatacccaa    4440
actaaaaatg gtcgtttcca acctcttgaa aacgcctcac agcaagtacg ctgtcgcggt    4500
caagtgctgc cacaatcagg cgtgctaact taccgtatgg aagtgactga aatcggtttc    4560
agtccacgcc catatgctaa agctaacatc gatatcttgc ttaatggcaa agcggtagtg    4620
gatttccaaa acctagggt gatgataaaa gaggaagatg agtgtactcg ttatccactt    4680
ttgactgaat caacaacggc tagcactgca caagtaaacg ctcaaacaag tgcgaaaaag    4740
gtatacaagc cagcatcagt caatgcgcca ttaatggcac aaattcctga tctgactaaa    4800
gagccaaaca agggcgttat tccgatttcc catgttgaag caccaattac gccagactac    4860
ccgaaccgtg tacctgatac agtgccattc acgccgtatc acatgtttga gtttgctaca    4920
ggcaatatcg aaaactgttt cgggccagag ttctcaatct atcgcggcat gatcccacca    4980
cgtacaccat gcggtgactt acaagtgacc acacgtgtga ttgaagttaa cggtaagcgt    5040
ggcgacttta aaaagccatc atcgtgtatc gctgaatatg aagtgcctgc agatgcgtgg    5100
tatttcgata aaaacagcca cggcgcagtg atgccatatt caattttaat ggagatctca    5160
ctgcaaccta acggctttat ctcaggttac atgggcacaa ccctaggctt ccctggcctt    5220
gagctgttct tccgtaactt agacggtagc ggtgagttac tacgtgaagt agatttacgt    5280 ggtaaaaacca tccgtaacga ctcacgttta ttatcaacag tgatggccgg cactaacatc    5340
atccaaagct ttagcttcga gctaagcact gacggtgagc ctttctatcg cggcactgcg    5400
gtatttggct attttaaagg tgacgcactt aaagatcagc taggcctaga taacggtaaa    5460
gtcactcagc catggcatgt agctaacggc gttgctgcaa gcactaaggt gaacctgctt    5520
gataagagct gccgtcactt taatgcgcca gctaaccagc cacactatcg tctagccggt    5580
ggtcagctga actttatcga cagtgttgaa attgttgata tggcggcac cgaaggttta    5640 ggttacttgt atgccgagcg caccattgac ccaagtgatt ggttcttcca gttccacttc    5700
caccaagatc cggttatgcc aggctcctta ggtgttgaag caattattga aaccatgcaa    5760
gcttacgcta ttagtaaaga cttgggcgca gatttcaaaa atcctaagtt tggtcagatt    5820
ttatcgaaca tcaagtggaa gtatcgcggt caaatcaatc cgctgaacaa gcagatgtct    5880
atggatgtca gcattacttc aatcaaagat gaagacggta agaaagtcat cacaggtaat    5940
gccagcttga gtaaagatgg tctgcgcata tacgaggtct tcgatatagc tatcagcatc    6000
gaagaatctg ta                                                         6012
```

<210> SEQ ID NO 86
<211> LENGTH: 1629
<212> TYPE: DNA
<213> ORGANISM: Shewanella putrefaciens

<400> SEQUENCE: 86

```
atgaatccta cagcaactaa cgaaatgctt tctccgtggc catgggctgt gacagagtca      60
aatatcagtt ttgacgtgca agtgatggaa caacaactta agatttttag ccgggcatgt     120
tacgtggtca atcatgccga ccacggcttt ggtattgcgc aaactgccga tatcgtgact     180
gaacaagcgg caaacagcac agatttacct gttagtgctt ttactcctgc attaggtacc     240
gaaagcctag gcgacaataa tttccgccgc gttcacggcg ttaaatacgc ttattacgca     300
```

-continued

```
ggcgctatgg caaacggtat ttcatctgaa gagctagtga ttgccctagg tcaagctggc    360
attttgtgtg gttcgtttgg agcagccggt cttattccaa gtcgcgttga agcggcaatt    420
aaccgtattc aagcagcgct gccaaatggc ccttatatgt ttaaccttat ccatagtcct    480
agcgagccag cattagagcg tggcagcgta gagctatttt taaagcataa ggtacgcacc    540
gttgaagcat cagctttctt aggtctaaca ccacaaatcg tctattaccg tgcagcagga    600
ttgagccgag acgcacaagg taaagttgtg gttggtaaca aggttatcgc taaagtaagt    660
cgcaccgaaa tggctgaaaa gtttatgatg ccagcgcccg caaaaatgct acaaaaacta    720
gttgatgacg gttcaattac cgctgagcaa atggagctgg cgcaacttgt acctatggct    780
gacgacatca ctgcagaggc cgattcaggt ggccatactg ataaccgtcc attagtaaca    840
ttgctgccaa ccatttttagc gctgaaagaa gaaattcaag ctaaatacca atacgacact    900
cctattcgtg tcggttgtgg tggcggtgtg ggtacgcctg atgcagcgct ggcaacgttt    960
aacatgggcg cggcgtatat tgttaccggc tctatcaacc aagcttgtgt tgaagcgggc   1020
gcaagtgatc acactcgtaa attacttgcc accactgaaa tggccgatgt gactatggca   1080
ccagctgcag atatgttcga gatgggcgta aaactgcagg tggttaagcg cggcacgcta   1140
ttcccaatgc gcgctaacaa gctatatgag atctacaccc gttacgattc aatcgaagcg   1200
atcccattag acgagcgtga aaagcttgag aaacaagtat tccgctcaag cctagatgaa   1260
atatgggcag gtacagtggc gcactttaac gagcgcgacc ctaagcaaat cgaacgcgca   1320
gagggtaacc ctaagcgtaa aatggcattg attttccgtt ggtacttagg tctttctagt   1380
cgctggtcaa actcaggcga agtgggtcgt gaaatggatt atcaaatttg ggctggccct   1440
gctctcggtg catttaacca atgggcaaaa ggcagttact tagataacta tcaagaccga   1500
aatgccgtcg atttggcaaa gcacttaatg tacggcgcgg cttacttaaa tcgtattaac   1560
tcgctaacgg ctcaaggcgt taaagtgcca gcacagttac ttcgctggaa gccaaaccaa   1620
agaatggcc                                                          1629
```